(12) United States Patent
Shiku et al.

(10) Patent No.: US 12,344,674 B2
(45) Date of Patent: *Jul. 1, 2025

(54) BISPECIFIC ANTIBODY

(71) Applicants: MIE UNIVERSITY, Tsu (JP);
DAIICHI SANKYO COMPANY, LIMITED, Tokyo (JP)

(72) Inventors: Hiroshi Shiku, Tsu (JP); Yasushi Akahori, Tsu (JP); Kento Tanaka, Tokyo (JP); Ayaka Yatsu, Tokyo (JP); Junya Ichikawa, Tokyo (JP); Toshiaki Ohtsuka, Tokyo (JP); Shiho Kozuma, Tokyo (JP); Ryuji Hashimoto, Tokyo (JP); Makiko Nakayama, Tokyo (JP); Naoya Shinozaki, Tokyo (JP); Kensuke Nakamura, Tokyo (JP); Ichiro Watanabe, Tokyo (JP); Shinji Furuzono, Tokyo (JP)

(73) Assignees: MIE UNIVERSITY, Tsu (JP); DAIICHI SANKYO COMPANY, LIMITED, Tokyo (JP)

( * ) Notice: Subject to any disclaimer, the term of this patent is extended or adjusted under 35 U.S.C. 154(b) by 136 days.

This patent is subject to a terminal disclaimer.

(21) Appl. No.: 17/799,648

(22) PCT Filed: Mar. 29, 2021

(86) PCT No.: PCT/JP2021/013378
§ 371 (c)(1),
(2) Date: Aug. 12, 2022

(87) PCT Pub. No.: WO2021/200857
PCT Pub. Date: Oct. 7, 2021

(65) Prior Publication Data
US 2023/0348616 A1 Nov. 2, 2023

(30) Foreign Application Priority Data
Mar. 30, 2020 (JP) .................. 2020-061476

(51) Int. Cl.
C07K 16/30 (2006.01)
A61K 39/00 (2006.01)
A61P 35/00 (2006.01)
C07K 16/28 (2006.01)
C07K 16/32 (2006.01)
C07K 16/46 (2006.01)
C12N 5/0783 (2010.01)

(52) U.S. Cl.
CPC .............. *C07K 16/30* (2013.01); *A61P 35/00* (2018.01); *C07K 16/2809* (2013.01); *C07K 16/2833* (2013.01); *C07K 16/32* (2013.01); *C07K 16/468* (2013.01); *C12N 5/0636* (2013.01); *A61K 2039/505* (2013.01); *C07K 2317/31* (2013.01); *C07K 2317/52* (2013.01); *C07K 2317/522* (2013.01); *C07K 2317/524* (2013.01); *C07K 2317/526* (2013.01); *C07K 2317/528* (2013.01); *C07K 2317/53* (2013.01); *C07K 2317/55* (2013.01); *C07K 2317/56* (2013.01); *C07K 2317/565* (2013.01); *C07K 2317/622* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2007/0071675 A1 | 3/2007 | Wu et al. | |
| 2010/0015133 A1 | 1/2010 | Igawa et al. | |
| 2015/0232561 A1 | 8/2015 | Fenn et al. | |
| 2016/0102135 A1 | 4/2016 | Escobar-Cabrera | |
| 2019/0359712 A1 | 11/2019 | Takahashi et al. | |
| 2019/0382504 A1 | 12/2019 | Liu et al. | |

FOREIGN PATENT DOCUMENTS

| | | |
|---|---|---|
| CN | 107922471 A | 4/2018 |
| CN | 110256567 A | 9/2019 |
| JP | 2003-111595 A | 4/2003 |
| JP | 2016-520598 | 7/2016 |
| JP | 2018-525973 A | 9/2018 |

(Continued)

OTHER PUBLICATIONS

Fidler IJ. "Biological heterogeneity of cancer: implication to therapy", Hum Vaccin Immunother. Aug. 2012;8(8):1141-2. (Year: 2012).*

(Continued)

*Primary Examiner* — Amy E Juedes
*Assistant Examiner* — Peter Johansen
(74) *Attorney, Agent, or Firm* — Foley & Lardner LLP

(57) ABSTRACT

An antibody that can be used as an anti-tumor agent and an anti-tumor agent comprises a molecule containing such an antibody. Such an antibody or a binding fragment thereof comprises: a heavy chain CDRH1 consisting of SEQ ID NO: 54, a heavy chain CDRH2 consisting of SEQ ID NO: 55, a heavy chain CDRH3 consisting of SEQ ID NO: 56, a light chain CDRL1 consisting of SEQ ID NO: 57 or a light chain CDRL1 consisting of an amino acid sequence derived from SEQ ID NO: 57 in which amino acid 7 is W and/or amino acid 8 is K, a light chain CDRL2 consisting of SEQ ID NO: 58, and a light chain CDRL3 consisting of SEQ ID NO: 59 or a light chain CDRL3 consisting of an amino acid sequence derived from SEQ ID NO: 59 in which amino acid 2 is A or S.

18 Claims, 226 Drawing Sheets

Specification includes a Sequence Listing.

(56) References Cited

FOREIGN PATENT DOCUMENTS

| | | |
|---|---|---|
| RU | 2585091 C1 | 5/2016 |
| WO | WO-98/50431 A2 | 11/1998 |
| WO | WO-01/77342 A1 | 10/2001 |
| WO | WO-2005/113595 A2 | 12/2005 |
| WO | WO-2006/106905 A1 | 10/2006 |
| WO | WO-2010/106431 A2 | 9/2010 |
| WO | WO-2011/028952 A1 | 3/2011 |
| WO | WO-2011/131746 A2 | 10/2011 |
| WO | WO-2016/210365 A2 | 12/2016 |
| WO | WO-2017/109496 A1 | 6/2017 |
| WO | WO-2018/017786 A2 | 1/2018 |
| WO | WO-2018/117237 A1 | 6/2018 |
| WO | WO-2021/003357 A1 | 1/2021 |

OTHER PUBLICATIONS

The Merck Manuals Online Medical Library, [online]. Whitehouse Station, NJ: Merck Research Laboratories, 2006-2007. [retrieved on Oct. 19, 2020]. <URL: https://www.merckmanuals.com/professional/hematology-and-oncology/overview-of-cancer/cellular-and-molecular-basis-of-cancer> (Year: 2020).*

Thomas et al. "NY-ESO-1 Based Immunotherapy of Cancer: Current Perspectives", Front Immunol. May 1, 2018:9:947 (Year: 2018).*

McCormack et al. "Bi-specific TCR-anti CD3 redirected T-cell targeting of NY-ESO-1- and LAGE-1-positive tumors", Cancer Immunol Immunother. Apr. 2013;62(4):773-85 (Year: 2013).*

Casset et al., "A peptide mimetic of an anti-CD4 monoclonal antibody by rational design", BBRC, May 20, 2003, vol. 307, pp. 198-205.

Chen et al., "Selection and analysis of an optimized anti-VEGF antibody: crystal structure of an affinity-matured Fab in complex with antigen", J. Mol. Bio., Sep. 13, 1999, vol. 293, pp. 865-881.

Lamminmaki et al., "Crystal structure of a recombinant anti-estradiol Fab fragment in complex with 17beta-estradiol", JBC, Jul. 12, 2001, vol. 276, pp. 36687-36694.

MacCallum et al., "Antibody-antigen Interactions: Contact Analysis and Binding Site Topography", J. Mol. Biol., Jul. 30, 1996, vol. 262, pp. 732-745.

McCormack et al., "Bi-specific TCR-anti CD3 redirected T-cell targeting of NY-ESO-1- and LAGE-1-positive tumors", Cancer Immunol Immunother., Apr. 2013, vol. 62, pp. 773-785.

Padlan et al., "Structure of an antibody-antigen complex: crystal structure of the HyHEL-10 Fab-lysozyme complex", PNAS, Apr. 24, 1989, vol. 86, pp. 5938-5942.

Pascalis et al., "Grafting of "Abbreviated" Complementarity-Determining Regions Containing Specificity- Determining Residues Essential for Ligand Contact to Engineer a Less Immunogenic Humanized Monoclonal Antibody", The Journal of Immunology, Jul. 3, 2002, vol. 169, pp. 3076-3084.

Rudikoff et al., "Single amino acid substitution altering antigen-binding specificity", Proc Natl Acad Sci USA, 1982, vol. 79, p. 1979-1983.

Vajdos et al., "Comprehensive functional maps of the antigen-binding site of an anti-ErbB2 antibody obtained with shotgun scanning mutagenesis", J. Mol. Biol., Mar. 22, 2002, vol. 320, pp. 415-428.

Wu et al., "Humanization of a murine monoclonal antibody by simultaneous optimization of framework and CDR residues", J. Mol. Biol., Aug. 26, 1999, vol. 294, pp. 151-162.

European Extended Search Report issued in corresponding European Patent Application No. 21782349.1 dated Apr. 12, 2024 (9 pages).

Maruta et al., "Development of T-Cell Therapy By Exploiting Modified Antibodies Specific for A2/NY-ES0-1 for Refractory Myeloma", Blood, American Society of Hematology, vol. 130, Dec. 7, 2017, p. 1913, XP 086630705.

Chen, Y., et al., "A testicular antigen aberrantly expressed in human cancers detected by autologous antibody screening", Proc. Natl. Acad. Sci. U.S.A. vol. 94, pp. 1914-1918, 1997.

Goydos, J. et al., "NY-ESO-1 and CTp11 Expression May Correlate with Stage of Progression in Melanoma", Journal of Surgical Research, vol. 98, pp. 76-80, 2001.

Held, G., et al., "Dissecting cytotoxic T cell responses towards the NY-ES0-1 protein by peptide/MHC-specific antibody fragments", Eur. J. Immunol. 2004, vol. 34, pp. 2919-2929, abstract, item 2.

International Searching Authority, "International Search Report and Written Opinion", issued in connection with International Patent Application No. PCT/JP2021/013378, dated Jun. 15, 2021.

Jager, E., et al. Simultaneous Humoral and Cellular Immune Response against Cancer-Testis Antigen NY-ESO-1: Definition of Human Histocompatibility Leukocyte Antigen (HLA)-A2-binding Peptide Epitopes, J. Exp. Med., vol. 187, No. 2, pp. 265-270, Jan. 19, 1998.

Kurashige, T. et al., "NY-ESO-1 Expression and Immunogenicity Associated with Transitional Cell Carcinoma: Correlation with Tumor Grade", Cancer Research, pp. 4671-4674, Jun. 15, 2001.

Le Jeune, C. et al., "Potential for bispecific T-cell engagers: role of blinatumomab in acute lymphoblastic leukemia", Drug Des. Devel. Ther., pp. 757-765, 2016.

Lethe, B. et al., "LAGE-1, a New Gene With Tumor Specificity," Int. J. Cancer, vol. 76, pp. 903-908, 1998.

Maruda, M., et al., "A Novel for Multiple Myeloma Applied to A2/NY-ESO-I Specific Modified Antibodies", Abstracts of the 21st Annual Mtg. of the Japanese Assoc. of Cancer Immun. 013-4. p. 131.

Nicholaou, T. et al., "Directions in the immune targeting of cancer: Lessons learned from the cancer-testis Ag NY-ESO-1", Immunology and Cell Biology vol. 84, pp. 303-317, 2006.

Purbhoo, M. et al., "Quantifying and Imaging NY-ESO-1/LAGE-1-Derived Epitopes on Tumor Cells Using High Affinity T Cell Receptors", Journal of Immunology, vol. 176, pp. 7308-7316, 2006.

Staerz, U. et al., "Hybrid antibodies can target sites for attack by T cells", Nature, vol. 314, pp. 628-631, Apr. 18, 1985.

Staerz, U., et al. "Redirecting the Cellular Immune Response", Inter. Rev. Immunol. vol. 4, pp. 159-173, 1989.

Stewart-Jones, G. et al., Rational development of high-affinity T-cell receptor-like antibodies, PNAS, 2009, vol. 106, No. 14, pp. 5784-5788, abstract, p. 5785, right column, last paragraph. column, last paragraph.

Van Rhee, F., et al., "NY-ESO-1 is highly expressed in poor-prognosis multiple myeloma and induces spontaneous humoral and cellular immune responses", Blood, vol. 105, No. 10, pp. 3939-3944, May 15, 2005.

Office Action issued in corresponding Chinese Patent Application No. 202180009615.9 dated Oct. 31, 2023 (24 pages).

Xiong et al., "Anti-tumor immune mechanism of tumor-infiltrating CD4 + T lymphocytes", Journal of Clinical Laboratory Science, Dec. 2015, vol. 33, No. 12, 10 pages.

Badri et al., "Optimization of radiation dosing schedules for proneural glioblastoma", Mathematical Biology, Jun. 21, 2015, pp. 1-36.

Baylot et al., "TCTP Has a Crucial Role in the Different Stages of Prostate Cancer Malignant Progression", A. Telerman, R. Amson (eds.), TCTP/tpt1—Remodeling Signaling from Stem Cell to Disease, Results and Problems in Cell Differentiation, Nov. 18, 2017, vol. 64, pp. 255-261.

Muller et al., "Spliceosomal Peptide P140 for Immunotherapy of Systemic Lupus Erythematosus", American College of Rheumatology, Arthritis & Rheumatism, Dec. 2008, vol. 58, No. 12, pp. 3873-3883.

Office Action issued in corresponding Russian Patent Application No. 2022127963 dated May 31, 2024 (22 pages).

* cited by examiner

Fig. 1

| scFv | Substance added to T2 | | | | | | | | | | | |
|---|---|---|---|---|---|---|---|---|---|---|---|---|
| | Solvent | Peptide | | | | | | | | | | |
| | DMSO | NY-ESO | 1F | 2M | 3A | 4A | 5A | 6L | 7F | 8A | 9A | gp100 |
| NYA-0001 | 1.04 | 5.75 | 0.60 | 7.72 | 7.88 | 0.83 | 0.78 | 7.97 | 0.97 | 6.67 | 6.56 | 0.43 |
| NYA-1143 | 0.98 | 12.90 | 1.77 | 11.89 | 10.20 | 5.91 | 3.15 | 12.92 | 4.26 | 8.74 | 15.12 | 0.41 |
| NYA-1154 | 1.02 | 9.98 | 3.98 | 9.49 | 8.00 | 6.63 | 1.12 | 9.36 | 6.08 | 11.95 | 11.16 | 0.46 |
| NYA-1163 | 0.97 | 3.67 | 0.53 | 1.85 | 1.70 | 0.57 | 0.62 | 1.74 | 1.11 | 6.00 | 4.01 | 0.44 |
| NYA-2023 | 0.94 | 8.85 | 0.72 | 6.74 | 4.92 | 2.48 | 1.21 | 7.51 | 4.72 | 5.40 | 10.79 | 0.40 |
| NYA-2027 | 1.09 | 5.75 | 0.57 | 7.84 | 9.91 | 0.99 | 0.75 | 7.85 | 5.41 | 9.47 | 6.90 | 0.41 |
| NYA-2035 | 1.03 | 9.94 | 0.60 | 8.80 | 5.81 | 2.16 | 2.27 | 8.95 | 5.83 | 6.41 | 11.46 | 0.38 |
| NYA-2044 | 0.91 | 12.93 | 0.68 | 13.53 | 10.90 | 3.21 | 2.20 | 13.39 | 3.62 | 10.04 | 15.61 | 0.39 |
| NYA-2045 | 0.81 | 9.03 | 0.53 | 8.8 | 7.46 | 1.17 | 0.94 | 8.8 | 1.99 | 7.35 | 9.98 | 0.39 |
| NYA-2047 | 0.89 | 7.99 | 0.48 | 7.34 | 6.09 | 0.86 | 1.03 | 7.07 | 3.11 | 6.61 | 9.54 | 0.39 |
| NYA-2048 | 0.90 | 6.58 | 0.51 | 5.36 | 4.20 | 0.63 | 0.67 | 6.14 | 1.46 | 4.11 | 7.75 | 0.41 |
| NYA-2060 | 0.83 | 8.78 | 0.52 | 6.93 | 5.51 | 0.73 | 0.70 | 7.94 | 2.51 | 6.18 | 9.48 | 0.41 |
| NYA-2061 | 0.85 | 8.62 | 0.54 | 7.17 | 4.73 | 0.59 | 0.66 | 7.13 | 2.04 | 5.22 | 9.16 | 0.40 |
| NYA-2143 | 1.04 | 13.06 | 2.72 | 13.19 | 10.28 | 7.19 | 4.30 | 12.87 | 5.26 | 9.69 | 14.50 | 0.38 |
| NYC-0003 | 0.92 | 3.74 | 3.28 | 3.73 | 4.34 | 0.76 | 0.69 | 4.14 | 3.99 | 3.42 | 4.77 | 0.39 |
| NYC-0004 | 0.76 | 6.02 | 3.56 | 5.66 | 4.75 | 2.02 | 0.65 | 3.78 | 5.07 | 3.69 | 7.99 | 0.37 |

Fig. 2A

| Gene | Uniprot ID | Start position | Sequence | HLA-A0201 IC50 (nM) |
|---|---|---|---|---|
| DOLPP1 | Q86YN1 | 104 | SQFMWFFSV | 2.64 |
| IL20RB | Q6UXL0 | 14 | SLFMWFFYA | 2.95 |
| PRKD1 | Q15139 | 763 | SLDMWSVGV | 14.74 |
| PRKD3 | O94806 | 756 | SLDMWSVGV | 14.74 |
| PRKD2 | Q9BZL6 | 731 | SLDMWSVGV | 14.74 |
| CD163 | Q86VB7 | 885 | SIPMWVDNV | 145.66 |
| P2RY8 | Q86VZ1 | 186 | SVAMWAVFL | 212.86 |
| NY-ESO-1 | P78358 | 157 | SLLMWITQC | 363.83 |

Fig. 2B

| scFv | Substance added to T2 | | | | | | | |
|---|---|---|---|---|---|---|---|---|
| | Solvent | Peptide | | | | | | |
| | DMSO | NY-ESO | DOLPP1 | IL20RB | PRKD2 | CD163 | P2RY8 | gp100 |
| NYA-0001 | 0.92 | 5.12 | 0.37 | 0.42 | 0.33 | 0.48 | 0.73 | 0.31 |
| NYA-1143 | 0.94 | 13.44 | 0.37 | 0.42 | 0.32 | 0.46 | 0.69 | 0.30 |
| NYA-1154 | 1.01 | 13.76 | 0.46 | 0.51 | 2.72 | 0.54 | 0.65 | 0.31 |
| NYA-1163 | 0.88 | 4.21 | 0.36 | 0.41 | 0.31 | 0.46 | 0.69 | 0.30 |
| NYA-2023 | 0.88 | 10.11 | 0.42 | 0.42 | 0.42 | 0.48 | 0.70 | 0.30 |
| NYA-2027 | 0.96 | 7.25 | 0.39 | 0.42 | 0.32 | 0.51 | 0.70 | 0.31 |
| NYA-2035 | 0.97 | 11.14 | 0.38 | 0.41 | 0.33 | 0.48 | 0.69 | 0.29 |
| NYA-2044 | 0.95 | 14.28 | 0.38 | 0.43 | 0.33 | 0.47 | 0.72 | 0.32 |
| NYA-2045 | 0.96 | 13.84 | 0.43 | 0.47 | 0.34 | 0.48 | 0.58 | 0.30 |
| NYA-2047 | 0.98 | 10.25 | 0.40 | 0.43 | 0.35 | 0.47 | 0.72 | 0.30 |
| NYA-2048 | 0.90 | 8.82 | 0.44 | 0.48 | 0.35 | 0.52 | 0.69 | 0.34 |
| NYA-2060 | 0.85 | 11.17 | 0.42 | 0.45 | 0.33 | 0.47 | 0.62 | 0.32 |
| NYA-2061 | 0.82 | 10.37 | 0.40 | 0.46 | 0.33 | 0.48 | 0.57 | 0.32 |
| NYA-2143 | 0.90 | 13.48 | 0.38 | 0.42 | 0.32 | 0.46 | 0.69 | 0.31 |
| NYC-0003 | 1.00 | 5.22 | 0.38 | 0.43 | 1.53 | 1.08 | 2.01 | 0.32 |
| NYC-0004 | 1.01 | 9.19 | 0.39 | 0.43 | 3.41 | 0.49 | 1.98 | 0.32 |

Fig. 6B
(a)
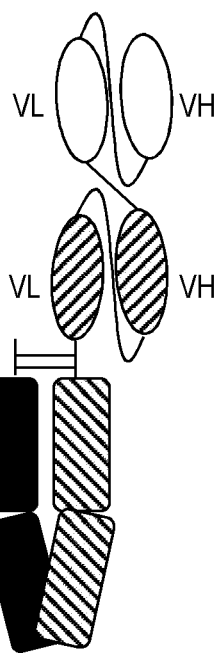
taFv-heterodimer Fc-type
(taFv-Fc-type)
(b)
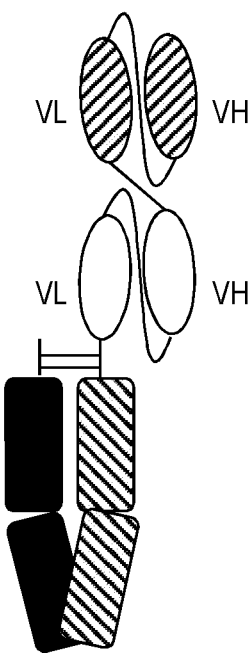
taFv (inversed)-heterodimer Fc-type
(taFv (inversed)-Fc-type)
(c)
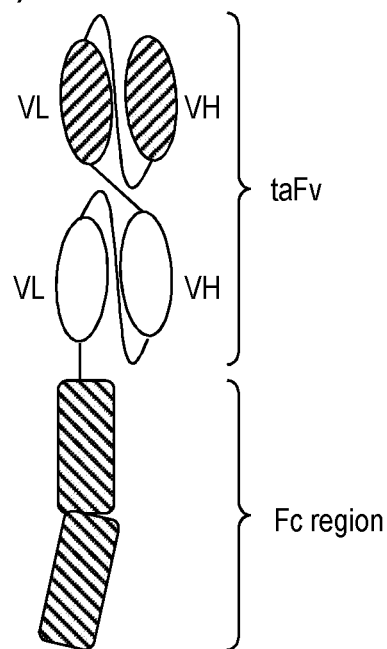
(d)

Fig. 8

```
NY-ESO Peptide
SLLMWITQC
(SEQ ID NO: 1)
```

Fig. 9

```
MAGEC-1 Peptide
ILFGISLREV
(SEQ ID NO: 2)
```

Fig. 10 scFv sequence analysis primer 1
CTCTTCGCTATTACGCCAGCTGGCGA
(SEQ ID NO: 3)

Fig. 11 scFv sequence analysis primer 2
ATAACAATTTCACACAGGAAACAGCTATGA
(SEQ ID NO: 4)

Fig. 12

NYA-0001 heavy chain variable region
GAGGTGCAGCTGGTGGAGTCTGGGGGAGGCGTGGTCCAGCCTGGGAGGTCCCTGAC
ACCCTCCTGTTCAGCGTCTGGATTCTCCATCCGTAGTTATGATATACACTGGGTCC
GCCAGGCTCCAGGCAAGGGGCTAGAGTGGGTGGCCACTATATCATATGATGGAAGT
CAGAAGTACTTCGCAGACTCCGTGAAGGGCCGATTTACCATCTTCAGAGACGAATC
GGAGAACATGGTGTATCTGCAAATGAGCGGCCTGAGAGTTGAGGACACGGCTGTTT
ATCACTGTGCGAGAGGGAGTAGTGGTCATTATGAGGCTTTTGATATCTGGGGCCAA
GGGACAATGGTCACCGTCTCTTCA
(SEQ ID NO: 5)

Fig. 13

NYA-0001 heavy chain variable region
EVQLVESGGGVVQPGRSLTPSCSASGFSIRSYDIHWVRQAPGKGLEWVATISYDGS
QKYFADSVKGRFTIFRDESENMVYLQMSGLRVEDTAVYHCARGSSGHYEAFDIWGQ
GTMVTVSS
(SEQ ID NO: 6)

Fig. 14

NYA-0001 light chain variable region
CAGTCTGTGTTGACGCAGCCGCCCTCAGTGTCTGCGGCCCCAGGACAGAAGGTCAC
CATCTCCTGCTCTGGAAGCAGCTCCAACATTGGGAATAATTATGTATCCTGGTACC
AGCAGCTCCCAGGAACAGCCCCCAAACTCCTCATTTATGACAATAATAAGCGACCC
TCAGGGATTCCTGACCGATTCTCTGGCTCCAAGTCTGGCACGTCAGCCACCCTGGG
CATCACCGGACTCCAGACTGGGGACGAGGCCGATTATTACTGCGGAACATGGGATA
GCAGCCTGAGTGCCCCTTGGGTGTTCGGCGGAGGGACCAAGGTCACCGTCCTA
(SEQ ID NO: 7)

Fig. 15

NYA-0001 light chain variable region
QSVLTQPPSVSAAPGQKVTISCSGSSSNIGNNYVSWYQQLPGTAPKLLIYDNNKRP
SGIPDRFSGSKSGTSATLGITGLQTGDEADYYCGTWDSSLSAPWVFGGGTKVTVL
(SEQ ID NO: 8)

Fig. 16

NYA-0060 heavy chain variable region
GAGGTGCAGCTGGTGGAGTCTGGGGGAGGCGTGGTCCAGCCTGGGAGGTCCCTGAC
ACCCTCCTGTTCAGCGTCTGGATTCTCCATCCGTAGCTATGATATACACTGGGTCC
GCCTGGCTCCAGGCAAGGGGCTAGAGTGGGTGGCCACTATATCATATGATGGAAGT
CAGAAGTACTTCGCAGACTCCGTGAAGGGCCGATTTACCATCTTCAGAGACGAATC
GGAGAACATGGTGTATCTGCAAATGAGCGGCCTGAGAGTTGAGGACACGGCTGTTT
ATCACTGTGCGAGAGGGAGTAGTGGTCATTATGAGGCTTTTGATATCTGGGGCCAA
GGGACAATGGTCACCGTCTCTTCA
(SEQ ID NO: 9)

Fig. 17

NYA-0060 heavy chain variable region
EVQLVESGGGVVQPGRSLTPSCSASGFSIRSYDIHWVRLAPGKGLEWVATISYDGS
QKYFADSVKGRFTIFRDESENMVYLQMSGLRVEDTAVYHCARGSSGHYEAFDIWGQ
GTMVTVSS
(SEQ ID NO: 10)

Fig. 18

NYA-0060 light chain variable region
CAGTCTGTGTTGACGCAGCCGCCCTCAGTGTCTGCGGCCCCAGGACAGAAGGTCAC
CATCTCCTGCTCTGGAAGCAGCTCCAACATTGGGAATAATTATGTATCCTGGTACC
AGCAGCTCCCAGGAACAGCCCCCAAACTCCTCATTTATGACAATAATAAGCGACCC
TCAGGGATTCCTGACCGATTCTCTGGCTCCAAGTCTGGCACGTCAGCCACCCTGGG
CATCACCGGACTCCAGACTGGGGACGAGGCCGATTATTACTGCGGAACATGGGATA
GCAGCCTGAGTGCCCCTTGGGTGTTCGGCGGAGGGACCAAGGTCACCGTCCTA
(SEQ ID NO: 11)

Fig. 19

NYA-0060 light chain variable region
QSVLTQPPSVSAAPGQKVTISCSGSSSNIGNNYVSWYQQLPGTAPKLLIYDNNKRP
SGIPDRFSGSKSGTSATLGITGLQTGDEADYYCGTWDSSLSAPWVFGGGTKVTVL
(SEQ ID NO: 12)

Fig. 20

NYA-0068 heavy chain variable region
GAGGTGCAGCTGGTGGAGTCTGGGGGAGGCGTGGTCCAGCCTGGGAGGTCCCTGAC
ACCCTCCTGTTCAGCGTCTGGATTCTCCATCCGTAGTTATGATATACACTGGGTCC
GCCAGGCTCCAGGCAAGGGGCTAGAGTGGGTGGCCACTATATCATATGATGGAAGT
CAGAAGTACTTCGCAGACTCCGTGAAGGGCCGATTTACCATCTTCAGAGACGAATC
GGAGAACATGGTGTATCTGCAAATGAGCGGCCTGAGAGTTGAGGACACGGCTGTTT
ATCACTGTGCGAGAGGGAGTAGTGGTCATTATGAGGCTTTTGATATCTGGGGCCAA
GGGACAATGGTCACCGTCTCTTCA
(SEQ ID NO: 13)

Fig. 21

NYA-0068 heavy chain variable region
EVQLVESGGGVVQPGRSLTPSCSASGFSIRSYDIHWVRQAPGKGLEWVATISYDGS
QKYFADSVKGRFTIFRDESENMVYLQMSGLRVEDTAVYHCARGSSGHYEAFDIWGQ
GTMVTVSS
(SEQ ID NO: 14)

Fig. 22

NYA-0068 light chain variable region
CAGTCTGTGTTGACGCAGCCGCCCTCAGTGTCTGCGGCCCCAGGACAGAAGGTCAC
CATCTCCTGCTCTGGAAGCAGCTCCAACATTGGGAATTGGTATGTATCCTGGTACC
AGCAGCTCCCAGGAACAGCCCCCAAACTCCTCATTTATGACAATAATAAGCGACCC
TCAGGGATTCCTGACCGATTCTCTGGCTCCAAGTCTGGCACGTCAGCCACCCTGGG
CATCACCGGACTCCAGACTGGGGACGAGGCCGATTATTACTGCGGAACATGGGATA
GCAGCCTGAGTGCCCCTTGGGTGTTCGGCGGAGGGACCAAGGTCACCGTCCTA
(SEQ ID NO: 15)

Fig. 23

NYA-0068 light chain variable region
QSVLTQPPSVSAAPGQKVTISCSGSSSNIGNWYVSWYQQLPGTAPKLLIYDNNKRP
SGIPDRFSGSKSGTSATLGITGLQTGDEADYYCGTWDSSLSAPWVFGGGTKVTVL
(SEQ ID NO: 16)

Fig. 24

NYA-0082 heavy chain variable region
GAGGTGCAGCTGGTGGAGTCTGGGGGAGGCGTGGTCCAGCCTGGGAGGTCCCTGAC
ACCCTCCTGTTCAGCGTCTGGATTCTCCATCCGTAGTTATGATATACACTGGGTCC
GCCAGGCTCCAGGCAAGGGGCTAGAGTGGGTGGCCACTATATCATATGATGGAAGT
CAGAAGTACTTCGCAGACTCCGTGAAGGGCCGATTTACCATCTTCAGAGACGAATC
GGAGAACATGGTGTATCTGCAAATGAGCGGCCTGAGAGTTGAGGACACGGCTGTTT
ATCACTGTGCGAGAGGGAGTAGTGGTCATTATGAGGCTTTTGATATCTGGGGCCAA
GGGACAATGGTCACCGTCTCTTCA
(SEQ ID NO: 17)

Fig. 25

NYA-0082 heavy chain variable region
EVQLVESGGGVVQPGRSLTPSCSASGFSIRSYDIHWVRQAPGKGLEWVATISYDGS
QKYFADSVKGRFTIFRDESENMVYLQMSGLRVEDTAVYHCARGSSGHYEAFDIWGQ
GTMVTVSS
(SEQ ID NO: 18)

Fig. 26

NYA-0082 light chain variable region
CAGTCTGTGTTGACGCAGCCGCCCTCAGTGTCTGCGGCCCCAGGACAGAAGGTCAC
CATCTCCTGCTCTGGAAGCAGCTCCAACATTGGGAATAATTATGTATCCTGGTACC
AGCGGCTCCCAGGAACAGCCCCCAAACTCCTCATTTATGACAATAATAAGCGACCC
TCAGGGATTCCTGACCGATTCTCTGGCTCCAAGTCTGGCACGTCAGCCACCCTGGG
CATCACCGGACTCCAGACTGGGGACGAGGCCGATTATTACTGCGGATCATGGGATA
GCAGCCTGAGTGCCCCTTGGGTGTTCGGCGGAGGGACCAAGGTCACCGTCCTA
(SEQ ID NO: 19)

Fig. 27

NYA-0082 light chain variable region
QSVLTQPPSVSAAPGQKVTISCSGSSSNIGNNYVSWYQRLPGTAPKLLIYDNNKRP
SGIPDRFSGSKSGTSATLGITGLQTGDEADYYCGSWDSSLSAPWVFGGGTKVTVL
(SEQ ID NO: 20)

Fig. 28

NYA-1163 tag adduct
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGCTATGATATACACTGG
GTCCGCCTGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCT
GTTTATCACTGTGCGAGAGGGAGTAGTGGTCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATAA
TTATGTATCCTGGTACCAGCAGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTATTA
CTGCGGAACATGGATAGCAGCCTGAGTGCCCTTGGGTGTTCGGCGGAGGGACCA
AGGTCACCGTCCTAGGCGCGGCCGCAGGTGCAGGTGGTGATTACAAAGATGATGAC
GATAAAGGTGCAGCGGCGCATCACCATCATCACCAC
(SEQ ID NO: 21), signal sequence (1-57), NYA-1163 (61-798), FLAG-His tag (799-876)

Fig. 29

NYA-2023 tag adduct
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGTTATGATATACACTGG
GTCCGCCAGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCT
GTTTATCACTGTGCGAGAGGGAGTAGTGGTCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATTG
GTATGTATCCTGGTACCAGCAGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTATTA
CTGCGGAACATGGGATAGCAGCCTGAGTGCCCCTTGGGTGTTCGGCGGAGGGACCA
AGGTCACCGTCCTAGGCGCGGCCGCAGGTGCAGGTGGTGATTACAAAGATGATGAC
GATAAAGGTGCAGCGGCGCATCACCATCATCACCAC
(SEQ ID NO: 22), signal sequence (1-57), NYA-2023 (61-
798), FLAG-His tag (799-876)

Fig. 30

NYA-2027 tag adduct
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGTTATGATATACACTGG
GTCCGCCAGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCT
GTTTATCACTGTGCGAGAGGGAGTAGTGGTCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATAA
TTATGTATCCTGGTACCAGCAGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTATTA
CTGCGGATCATGGGATAGCAGCCTGAGTGCCCTTGGGTGTTCGGCGGAGGGACCA
AGGTCACCGTCCTAGGCGCGGCCGCAGGTGCAGGTGGTGATTACAAAGATGATGAC
GATAAAGGTGCAGCGGCGCATCACCATCATCACCAC
(SEQ ID NO: 23), signal sequence (1-57), NYA-2027(61-
798), FLAG-His tag (799-876)

Fig. 31

NYA-1143 tag adduct
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGCTATGATATACACTGG
GTCCGCCTGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCT
GTTTATCACTGTGCGAGAGGGAGTAGTGGTCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATTG
GTATGTATCCTGGTACCAGCAGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTATTA
CTGCGGAACATGGGATAGCAGCCTGAGTGCCCCTTGGGTGTTCGGCGGAGGGACCA
AGGTCACCGTCCTAGGCGCGGCCGCAGGTGCAGGTGGTGATTACAAAGATGATGAC
GATAAAGGTGCAGCGGCGCATCACCATCATCACCAC
(SEQ ID NO: 24), signal sequence (1-57), NYA-1143 (61-798), FLAG-His tag (799-876)

Fig. 32

NYA-2143 tag adduct
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGCTATGATATACACTGG
GTCCGCCTGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCT
GTTTATCACTGTGCGAGAGGGAGTAGTGGTCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATTG
GTATGTATCCTGGTACCAGCGGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTATTA
CTGCGGAACATGGGATAGCAGCCTGAGTGCCCCTTGGGTGTTCGGCGGAGGGACCA
AGGTCACCGTCCTAGGCGCGGCCGCAGGTGCAGGTGGTGATTACAAAGATGATGAC
GATAAAGGTGCAGCGGCGCATCACCATCATCACCAC
(SEQ ID NO: 25), signal sequence (1-57), NYA-2143 (61-798), FLAG-His tag (799-876)

Fig. 33

NYA-1163 tag adduct
MKHLWFFLLLVAAPRWVLSGEVQLVESGGGVVQPGRSLTPSCSASGFSIRSYDIHW
VRLAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNNYVSWYQQLPGTAPKLLIYDNNKRPSGIPDRFSGSKSG
TSATLGITGLQTGDEADYYCGTWDSSLSAPWVFGGGTKVTVLGAAAGAGGDYKDDD
DKGAAAHHHHHH
(SEQ ID NO: 26), signal sequence (1-19), NYA-1163 (21-266), FLAG-His tag (267-292)

Fig. 34

NYA-2023 tag adduct
MKHLWFFLLLVAAPRWVLSGEVQLVESGGGVVQPGRSLTPSCSASGFSIRSYDIHW
VRQAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNWYVSWYQQLPGTAPKLLIYDNNKRPSGIPDRFSGSKSG
TSATLGITGLQTGDEADYYCGTWDSSLSAPWVFGGGTKVTVLGAAAGAGGDYKDDD
DKGAAAHHHHHH
(SEQ ID NO: 27), signal sequence (1-19), NYA-2023 (21-266), FLAG-His tag (267-292)

Fig. 35

NYA-2027 tag adduct
MKHLWFFLLLVAAPRWVLSGEVQLVESGGGVVQPGRSLTPSCSASGFSIRSYDIHW
VRQAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNNYVSWYQQLPGTAPKLLIYDNNKRPSGIPDRFSGSKSG
TSATLGITGLQTGDEADYYCGSWDSSLSAPWVFGGGTKVTVLGAAAGAGGDYKDDD
DKGAAAHHHHHH
(SEQ ID NO: 28), signal sequence (1-19), NYA-2027(21-266), FLAG-His tag (267-292)

Fig. 36

NYA-1143 tag adduct
MKHLWFFLLLVAAPRWVLSGEVQLVESGGGVVQPGRSLTPSCSASGFSIRSYDIHW
VRLAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNWYVSWYQQLPGTAPKLLIYDNNKRPSGIPDRFSGSKSG
TSATLGITGLQTGDEADYYCGTWDSSLSAPWVFGGGTKVTVLGAAAGAGGDYKDDD
DKGAAAHHHHHH
(SEQ ID NO: 29), signal sequence (1-19), NYA-1143 (21-266), FLAG-His tag (267-292)

Fig. 37

NYA-2143 tag adduct
MKHLWFFLLLVAAPRWVLSGEVQLVESGGGVVQPGRSLTPSCSASGFSIRSYDIHW
VRLAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNWYVSWYQRLPGTAPKLLIYDNNKRPSGIPDRFSGSKSG
TSATLGITGLQTGDEADYYCGTWDSSLSAPWVFGGGTKVTVLGAAAGAGGDYKDDD
DKGAAAHHHHHH
(SEQ ID NO: 30), signal sequence (1-19), NYA-2143 (21-266), FLAG-His tag (267-292)

Fig. 38

NYA-1154 tag adduct
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGTTATGATATGCACTGG
GTCCGCCAGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCC
GTTTATCACTGTGCGAGAGGGAGTAGTAATCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATAA
TTATGTATCCTGGTACCAGCGGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTACTA
CTGCGGAGCATGGGATAGCAGCCTGAGTGCCCCTTGGGTGTTCGGCGGAGGGACCA
AGGTCACCGTCCTAGGCGCGGCCGCAGGTGCAGGTGGTGATTACAAAGATGATGAC
GATAAAGGTGCAGCGGCGCATCACCATCATCACCAC
(SEQ ID NO: 31), signal sequence (1-57), NYA-1154(61-798), FLAG-His tag (799-876)

Fig. 39

NYA-1154 tag adduct
MKHLWFFLLLVAAPRWVLSGEVQLVESGGGVVQPGRSLTPSCSASGFSIRSYDMHW
VRQAPGKGLEWVATISYDGSQKYFADSVKGRFTIFRDESENMVYLQMSGLRVEDTA
VYHCARGSSNHYEAFDIWGQGTMVTVSSGGGGSGGGGSGGGGSQSVLTQPPSVSAA
PGQKVTISCSGSSSNIGNNYVSWYQRLPGTAPKLLIYDNNKRPSGIPDRFSGSKSG
TSATLGITGLQTGDEADYYCGAWDSSLSAPWVFGGGTKVTVLGAAAGAGGDYKDDD
DKGAAAHHHHHH
(SEQ ID NO: 32), signal sequence (1-19), NYA-1154(21-266), FLAG-His tag (267-292)

Fig. 40

HLA-A*0201 (GenBank:ASA47534.1) truncate
MSHSMRYFFTSVSRPGRGEPRFIAVGYVDDTQFVRFDSDAASQRMEPRAPWIEQEG
PEYWDGETRKVKAHSQTHRVDLGTLRGYYNQSEAGSHTVQRMYGCDVGSDWRFLRG
YHQYAYDGKDYIALKEDLRSWTAADMAAQTTKHKWEAAHVAEQLRAYLEGTCVEWL
RRYLENGKETLQRTDAPKTHMTHHAVSDHEATLRCWALSFYPAEITLTWQRDGEDQ
TQDTELVETRPAGDGTFQKWAAVVVPSGQEQRYTCHVQHEGLPKPLTLRWEGLNDI
FEAQKIEWHE
(SEQ ID NO: 33)

Fig. 41

β2-microglobulin
MIQRTPKIQVYSRHPAENGKSNFLNCYVSGFHPSDIEVDLLKNGERIEKVEHSDLS
FSKDWSFYLLYYTEFTPTEKDEYACRVNHVTLSQPKIVKWDRDM
(SEQ ID NO: 34)

Fig. 42

NYA-2035 tag adduct
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGCTATGATATACACTGG
GTCCGCCTGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCT
GTTTATCACTGTGCGAGAGGGAGTAGTGGTCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATTG
GAAGGTATCCTGGTACCAGCAGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTATTA
CTGCGGAACATGGGATAGCAGCCTGAGTGCCCCTTGGGTGTTCGGCGGAGGGACCA
AGGTCACCGTCCTAGGCGCGGCCGCAGGTGCAGGTGGTGATTACAAAGATGATGAC
GATAAAGGTGCAGCGGCGCATCACCATCATCACCAC
(SEQ ID NO: 35), signal sequence (1-57), NYA-2035 (61-798), FLAG-His tag (799-876)

Fig. 43

NYA-2035 tag adduct
MKHLWFFLLLVAAPRWVLSGEVQLVESGGGVVQPGRSLTPSCSASGFSIRSYDIHW
VRLAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNWKVSWYQQLPGTAPKLLIYDNNKRPSGIPDRFSGSKSG
TSATLGITGLQTGDEADYYCGTWDSSLSAPWVFGGGTKVTVLGAAAGAGGDYKDDD
DKGAAAHHHHHH
(SEQ ID NO: 36), signal sequence (1-19), NYA-2035 (21-266), FLAG-His tag (267-292)

Fig. 44

NYA-1143-VH01
EVQLVESGGGLVQPGGSLRLSCAASGFSIRSYDIHWVRLAPGKGLEWVATISYDGS
QKYYADSVKGRFTISRDESKNTLYLQMNSLRAEDTAVYHCARGSSGHYEAFDIWGQ
GTLVTVSS
(SEQ ID NO: 37)

Fig. 45

NYA-1143-VH02
QVQLVESGGGVVQPGRSLRLSCAASGFSIRSYDMHWVRQAPGKGLEWVATISYDGS
QKYYADSVKGRFTISRDNSKNTLYLQMSSLRAEDTAVYHCARGSSGHYEAFDIWGQ
GTLVTVSS
(SEQ ID NO: 38)

Fig. 46

NYA-1143-VH03
EVQLVESGGGLVQPGGSLRLSCAASGFSIRSYDIHWVRQAPGKGLEWVATISYDGS
QKYYADSVKGRFTISRDESKNTLYLQMNSLRAEDTAVYHCARGSSGHYEAFDIWGQ
GTLVTVSS
(SEQ ID NO: 39)

Fig. 47

NYA-1143-VL01
QSVLTQPPSASGTPGQRVTISCSGSSSNIGNWYVSWYQQLPGTAPKLLIYDNNKRP
SGVPDRFSGSKSGTSASLAISGLQSEDEADYYCGTWDSSLSAPWVFGGGTKLTVL
(SEQ ID NO: 40)

Fig. 48

NYA-2044 tag adduct
ATGAAACACCTGTGGTTCTTCCTCCTGCTGGTGGCAGCTCCCAGATGGGTGCTGAG
CGGTGAGGTACAGCTGGTGGAATCCGGTGGAGGCCTTGTGCAACCGGGAGGCTCCC
TGCGACTCTCTTGCGCCGCATCTGGCTTTTCCATACGATCCTACGATATTCATTGG
GTCCGACTCGCCCCTGGCAAAGGTCTTGAATGGGTTGCCACTATCTCCTACGACGG
GTCTCAGAAATATTATGCGGATTCAGTGAAGGGGCGGTTCACAATTTCACGAGACG
AGTCAAAGAATACACTGTACCTCCAAATGAATTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTCAATCCGTTCTGACTCAGCCACCCTCCGTGAGTGCAGCG
CCTGGACAGAAGGTCACAATATCATGTTCTGGCTCTTCAAGCAACATCGGAAACTG
GTACGTGAGCTGGTACCAGCAGCTCCCCGGCACGGCGCCCAAGCTTCTGATATATG
ACAACAACAAACGGCCCAGTGGAATCCCTGACAGATTCAGTGGGTCTAAAAGTGGT
ACAAGCGCTACCCTGGGTATCACCGGATTGCAGACCGGAGATGAGGCGGACTATTA
TTGCGGAACCTGGGACTCCAGCCTGAGCGCTCCCTGGGTTTTCGGCGGAGGTACTA
AGGTTACCGTCTTGGGCGCGGCCGCAGGTGCAGGTGGTGATTACAAAGATGATGAC
GATAAAGGTGCAGCGGCGCATCACCATCATCACCAC
(SEQ ID NO: 41), signal sequence (1-57), NYA-2044(61-
798), FLAG-His tag (799-876)

Fig. 49

NYA-2045 tag adduct
ATGAAACACCTGTGGTTCTTCCTCCTGCTGGTGGCAGCTCCCAGATGGGTGCTGAG
CGGTGAGGTACAGCTGGTGGAATCCGGTGGAGGCCTTGTGCAACCGGGAGGCTCCC
TGCGACTCTCTTGCGCCGCATCTGGCTTTTCCATACGATCCTACGATATTCATTGG
GTCCGACTCGCCCCTGGCAAAGGTCTTGAATGGGTTGCCACTATCTCCTACGACGG
GTCTCAGAAATATTATGCGGATTCAGTGAAGGGGCGGTTCACAATTTCACGAGACG
AGTCAAAGAATACACTGTACCTCCAAATGAATTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTCAATCCGTTCTGACTCAGCCACCCTCCGCCTCTGGCACC
CCGGGCCAACGGGTCACAATATCATGTTCTGGCTCTTCAAGCAACATCGGAAACTG
GTACGTGAGCTGGTACCAGCAGCTCCCCGGCACGGCGCCCAAGCTTCTGATATATG
ACAACAACAAACGGCCCAGTGGAGTTCCTGACAGATTCAGTGGGTCTAAAAGTGGT
ACAAGCGCTAGCCTGGCCATAAGTGGTCTGCAGAGTGAAGATGAGGCGGACTATTA
TTGCGGAACCTGGGACTCCAGCCTGAGCGCTCCCTGGGTTTTCGGCGGAGGTACTA
AGCTGACCGTCTTGGGCGCGGCCGCAGGTGCAGGTGGTGATTACAAAGATGATGAC
GATAAAGGTGCAGCGGCGCATCACCATCATCACCAC
(SEQ ID NO: 42), signal sequence (1-57), NYA-2045 (61-798), FLAG-His tag (799-876)

Fig. 50

NYA-2047 tag adduct
ATGAAACACCTGTGGTTCTTCCTCCTGCTGGTGGCAGCTCCCAGATGGGTGCTGAG
CGGTCAAGTACAGCTGGTGGAATCCGGTGGAGGCGTGGTCCAGCCGGGACGCAGCT
TGAGACTGTCCTGCGCTGCATCTGGCTTTTCCATACGATCCTACGATATGCACTGG
GTTCGCCAAGCCCCTGGCAAAGGTCTTGAATGGGTTGCCACTATCTCCTACGACGG
GTCTCAGAAATATTACGCGGATTCAGTGAAGGGGCGGTTCACAATTTCACGGGACA
ATTCAAAGAATACCTTGTATCTCCAGATGTCTTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTCAATCCGTTCTGACTCAGCCACCCTCCGTGAGTGCAGCG
CCTGGACAGAAGGTCACAATATCATGTTCTGGCTCTTCAAGCAACATCGGAAACTG
GTACGTGAGCTGGTACCAGCAGCTCCCCGGCACGGCGCCCAAGCTTCTGATATATG
ACAACAACAAACGGCCCAGTGGAATCCCTGACAGATTCAGTGGGTCTAAAAGTGGT
ACAAGCGCTACCCTGGGTATCACCGGATTGCAGACCGGAGATGAGGCGGACTATTA
TTGCGGAACCTGGGACTCCAGCCTGAGCGCTCCCTGGGTTTTCGGCGGAGGTACTA
AGGTTACCGTCTTGGGCGCGGCCGCAGGTGCAGGTGGTGATTACAAAGATGATGAC
GATAAAGGTGCAGCGGCGCATCACCATCATCACCAC
(SEQ ID NO: 43), signal sequence (1-57), NYA-2047(61-
798), FLAG-His tag (799-876)

Fig. 51

NYA-2048 tag adduct
ATGAAACACCTGTGGTTCTTCCTCCTGCTGGTGGCAGCTCCCAGATGGGTGCTGAG
CGGACAAGTTCAACTCGTGGAATCTGGTGGAGGGGTGGTACAACCAGGCCGGTCAC
TTAGACTGTCCTGCGCTGCGAGTGGATTTTCCATCAGATCTTACGACATGCACTGG
GTTCGCCAAGCACCCGGAAAGGGTTTGGAATGGGTGGCTACGATCTCCTACGATGG
ATCCCAGAAGTATTACGCCGACAGCGTCAAGGGCCGATTTACAATATCACGGGACA
ATTCAAAGAATACCTTGTATCTCCAGATGTCTTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTCAATCCGTTCTGACTCAGCCACCCTCCGCCTCTGGCACC
CCGGGCCAACGGGTCACAATATCATGTTCTGGCTCTTCAAGCAACATCGGAAACTG
GTACGTGAGCTGGTACCAGCAGCTCCCCGGCACGGCGCCCAAGCTTCTGATATATG
ACAACAACAAACGGCCCAGTGGAGTTCCTGACAGATTCAGTGGGTCTAAAAGTGGT
ACAAGCGCTAGCCTGGCCATAAGTGGTCTGCAGAGTGAAGATGAGGCGGACTATTA
TTGCGGAACCTGGGACTCCAGCCTGAGCGCTCCCTGGGTTTTCGGCGGAGGTACTA
AGCTGACCGTCTTGGGCGCGGCCGCAGGTGCAGGTGGTGATTACAAAGATGATGAC
GATAAAGGTGCAGCGGCGCATCACCATCATCACCAC
(SEQ ID NO: 44), signal sequence (1-57), NYA-2048(61-
798), FLAG-His tag (799-876)

Fig. 52

NYA-2060 tag adduct
ATGAAACACCTGTGGTTCTTCCTCCTGCTGGTGGCAGCTCCCAGATGGGTGCTGAG
CGGTGAGGTACAGCTGGTGGAATCCGGTGGAGGCCTTGTGCAACCGGGAGGCTCCC
TGCGACTCTCTTGCGCCGCATCTGGCTTTTCCATACGATCCTACGATATTCATTGG
GTCCGACAAGCCCCTGGCAAAGGTCTTGAATGGGTTGCCACTATCTCCTACGACGG
GTCTCAGAAATATTATGCGGATTCAGTGAAGGGGCGGTTCACAATTTCACGAGACG
AGTCAAAGAATACACTGTACCTCCAAATGAATTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTCAATCCGTTCTGACTCAGCCACCCTCCGTGAGTGCAGCG
CCTGGACAGAAGGTCACAATATCATGTTCTGGCTCTTCAAGCAACATCGGAAACTG
GTACGTGAGCTGGTACCAGCAGCTCCCCGGCACGGCGCCCAAGCTTCTGATATATG
ACAACAACAAACGGCCCAGTGGAATCCCTGACAGATTCAGTGGGTCTAAAAGTGGT
ACAAGCGCTACCCTGGGTATCACCGGATTGCAGACCGGAGATGAGGCGGACTATTA
TTGCGGAACCTGGGACTCCAGCCTGAGCGCTCCCTGGGTTTTCGGCGGAGGTACTA
AGGTTACCGTCTTGGGCGCGGCCGCAGGTGCAGGTGGTGATTACAAAGATGATGAC
GATAAGGTGCAGCGGCGCATCACCATCATCACCAC
(SEQ ID NO: 45), signal sequence (1-57), NYA-2060(61-
798), FLAG-His tag (799-876)

Fig. 53

NYA-2061 tag adduct
ATGAAACACCTGTGGTTCTTCCTCCTGCTGGTGGCAGCTCCCAGATGGGTGCTGAG
CGGTGAGGTACAGCTGGTGGAATCCGGTGGAGGCCTTGTGCAACCGGGAGGCTCCC
TGCGACTCTCTTGCGCCGCATCTGGCTTTTCCATACGATCCTACGATATTCATTGG
GTCCGACAAGCCCCTGGCAAAGGTCTTGAATGGGTTGCCACTATCTCCTACGACGG
GTCTCAGAAATATTATGCGGATTCAGTGAAGGGGCGGTTCACAATTTCACGAGACG
AGTCAAAGAATACACTGTACCTCCAAATGAATTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTCAATCCGTTCTGACTCAGCCACCCTCCGCCTCTGGCACC
CCGGGCCAACGGGTCACAATATCATGTTCTGGCTCTTCAAGCAACATCGGAAACTG
GTACGTGAGCTGGTACCAGCAGCTCCCCGGCACGGCGCCCAAGCTTCTGATATATG
ACAACAACAAACGGCCCAGTGGAGTTCCTGACAGATTCAGTGGGTCTAAAAGTGGT
ACAAGCGCTAGCCTGGCCATAAGTGGTCTGCAGAGTGAAGATGAGGCGGACTATTA
TTGCGGAACCTGGGACTCCAGCCTGAGCGCTCCCTGGGTTTTCGGCGGAGGTACTA
AGCTGACCGTCTTGGGCGCGGCCGCAGGTGCAGGTGGTGATTACAAAGATGATGAC
GATAAAGGTGCAGCGGCGCATCACCATCATCACCAC
(SEQ ID NO: 46), signal sequence (1-57), NYA-2061 (61-798), FLAG-His tag (799-876)

Fig. 54

NYA-2044 tag adduct
MKHLWFFLLLVAAPRWVLSGEVQLVESGGGLVQPGGSLRLSCAASGFSIRSYDIHW
VRLAPGKGLEWVATISYDGSQKYYADSVKGRFTISRDESKNTLYLQMNSLRAEDTA
VYHCARGSSGHYEAFDIWGQGTLVTVSSGGGGSGGGGSGGGGSQSVLTQPPSVSAA
PGQKVTISCSGSSSNIGNWYVSWYQQLPGTAPKLLIYDNNKRPSGIPDRFSGSKSG
TSATLGITGLQTGDEADYYCGTWDSSLSAPWVFGGGTKVTVLGAAAGAGGDYKDDD
DKGAAAHHHHHH
(SEQ ID NO: 47), signal sequence (1-19), NYA-2044 (21-266), FLAG-His tag (267-292)

Fig. 55

NYA-2045 tag adduct
MKHLWFFLLLVAAPRWVLSGEVQLVESGGGLVQPGGSLRLSCAASGFSIRSYDIHW
VRLAPGKGLEWVATISYDGSQKYYADSVKGRFTISRDESKNTLYLQMNSLRAEDTA
VYHCARGSSGHYEAFDIWGQGTLVTVSSGGGGSGGGGSGGGGSQSVLTQPPSASGT
PGQRVTISCSGSSSNIGNWYVSWYQQLPGTAPKLLIYDNNKRPSGVPDRFSGSKSG
TSASLAISGLQSEDEADYYCGTWDSSLSAPWVFGGGTKLTVLGAAAGAGGDYKDDD
DKGAAAHHHHHH
(SEQ ID NO: 48), signal sequence (1-19), NYA-2045 (21-266), FLAG-His tag (267-292)

Fig. 56

NYA-0082
EVQLVESGGGVVQPGRSLTPSCSASGFSIRSYDIHWVRQAPGKGLEWVATISYDGS
QKYFADSVKGRFTIFRDESENMVYLQMSGLRVEDTAVYHCARGSSGHYEAFDIWGQ
GTMVTVSSGGGGSGGGGSGGGGSQSVLTQPPSVSAAPGQKVTISCSGSSSNIGNNY
VSWYQRLPGTAPKLLIYDNNKRPSGIPDRFSGSKSGTSATLGITGLQTGDEADYYC
GSWDSSLSAPWVFGGGTKVTVL
(SEQ ID NO: 49)

Fig. 57

NYA-2047 tag adduct
MKHLWFFLLLVAAPRWVLSGQVQLVESGGGVVQPGRSLRLSCAASGFSIRSYDMHW
VRQAPGKGLEWVATISYDGSQKYYADSVKGRFTISRDNSKNTLYLQMSSLRAEDTA
VYHCARGSSGHYEAFDIWGQGTLVTVSSGGGGSGGGGSGGGGSQSVLTQPPSVSAA
PGQKVTISCSGSSSNIGNWYVSWYQQLPGTAPKLLIYDNNKRPSGIPDRFSGSKSG
TSATLGITGLQTGDEADYYCGTWDSSLSAPWVFGGGTKVTVLGAAAGAGGDYKDDD
DKGAAAHHHHHH
(SEQ ID NO: 50), signal sequence (1-19), NYA-2047(21-266), FLAG-His tag (267-292)

Fig. 58

NYA-2048 tag adduct
MKHLWFFLLLVAAPRWVLSGQVQLVESGGGVVQPGRSLRLSCAASGFSIRSYDMHW
VRQAPGKGLEWVATISYDGSQKYYADSVKGRFTISRDNSKNTLYLQMSSLRAEDTA
VYHCARGSSGHYEAFDIWGQGTLVTVSSGGGGSGGGGSGGGGSQSVLTQPPSASGT
PGQRVTISCSGSSSNIGNWYVSWYQQLPGTAPKLLIYDNNKRPSGVPDRFSGSKSG
TSASLAISGLQSEDEADYYCGTWDSSLSAPWVFGGGTKLTVLGAAAGAGGDYKDDD
DKGAAAHHHHHH
(SEQ ID NO: 51), signal sequence (1-19), NYA-2048 (21-266), FLAG-His tag (267-292)

Fig. 59

NYA-2060 tag adduct
MKHLWFFLLLVAAPRWVLSGEVQLVESGGGLVQPGGSLRLSCAASGFSIRSYDIHW
VRQAPGKGLEWVATISYDGSQKYYADSVKGRFTISRDESKNTLYLQMNSLRAEDTA
VYHCARGSSGHYEAFDIWGQGTLVTVSSGGGGSGGGGSGGGGSQSVLTQPPSVSAA
PGQKVTISCSGSSSNIGNWYVSWYQQLPGTAPKLLIYDNNKRPSGIPDRFSGSKSG
TSATLGITGLQTGDEADYYCGTWDSSLSAPWVFGGGTKVTVLGAAAGAGGDYKDDD
DKGAAAHHHHHH
(SEQ ID NO: 52), signal sequence (1-19), NYA-2060(21-266), FLAG-His tag (267-292)

Fig. 60

NYA-2061 tag adduct
MKHLWFFLLLVAAPRWVLSGEVQLVESGGGLVQPGGSLRLSCAASGFSIRSYDIHW
VRQAPGKGLEWVATISYDGSQKYYADSVKGRFTISRDESKNTLYLQMNSLRAEDTA
VYHCARGSSGHYEAFDIWGQGTLVTVSSGGGGSGGGGSGGGGSQSVLTQPPSASGT
PGQRVTISCSGSSSNIGNWYVSWYQQLPGTAPKLLIYDNNKRPSGVPDRFSGSKSG
TSASLAISGLQSEDEADYYCGTWDSSLSAPWVFGGGTKLTVLGAAAGAGGDYKDDD
DKGAAAHHHHHH
(SEQ ID NO: 53), signal sequence (1-19), NYA-2061 (21-266), FLAG-His tag (267-292)

Fig. 61

| | |
|---|---|
| NYA-0001-CDRH1 | GFSIRSYD |
| NYA-0001-CDRH2 | ISYDGSQK |
| NYA-0001-CDRH3 | ARGSSGHYEAFDI |
| NYA-0001-CDRL1 | SSNIGNNY |
| NYA-0001-CDRL2 | DNN |
| NYA-0001-CDRL3 | GTWDSSLSAPWV |

(SEQ ID NOs: 54 to 59)

Fig. 62

NYA-2023-CDRL1
SSNIGNWY
(SEQ ID NO: 60)

Fig. 63

NYA-2027-CDRL3
GSWDSSLSAPWV
(SEQ ID NO: 61)

Fig. 64

```
NYA-1154-CDRH3      ARGSSNHYEAFDI
NYA-1154-CDRL3      GAWDSSLSAPWV
(SEQ ID NOs: 62 and 63)
```

Fig. 65

NYA-0035-CDRL1
SSNIGNWK
(SEQ ID NO: 64)

Fig. 66

NYC-0003 tag adduct
ATGAAACACCTGTGGTTCTTCCTCCTGCTGGTGGCAGCTCCCAGATGGGTGCTGAG
CGGCGAAGTCCAGCTGTTGGAGTCAGGTGGCGGATTGGTGCAACCTGGCGGGTCAC
TGAGGCTGAGTTGTGCAGCTAGCGGCTTCACATTCTCTACGTATCAGATGAGCTGG
GTGAGACAGGCTCCAGGAAAGGGTCTGGAATGGGTCAGCGGGATTGTGTCTAGCGG
TGGCTCCACTGCCTATGCCGATAGCGTAAAAGGCCGCTTTACGATCTCTCGGGACA
ACTCTAAGAACACACTCTATCTGCAGATGAATTCCCTTAGAGCCGAAGATACCGCC
GTGTACTACTGTGCTGGGGAACTGCTCCCGTATTACGGTATGGACGTTTGGGGCCA
AGGCACCACTGTCACAGTGAGTTCCGGTGGAGGCGGGTCAGGCGGAGGCGGTAGTG
GAGGTGGAGGATCACAAAGCGAGCTGACACAGCCTAGGTCCGTATCCGGAAGTCCA
GGGCAGAGCGTCACCATCAGCTGCACTGGCACCTCTCGAGATGTCGGCGGATACAA
CTACGTGTCTTGGTATCAGCAGCATCCCGGCAAAGCGCCCAAACTCATCATACACG
ACGTGATTGAGCGGTCCAGTGGGGTTCCCGATCGTTTCAGCGGGTCAAAGTCCGGA
AATACCGCAAGCCTGACCATTTCTGGGCTTCAGGCAGAGGATGAGGCTGACTACTA
CTGCTGGTCCTTTGCCGGGAGCTATTACGTGTTTGGGACAGGGACTGACGTGACTG
TTCTGGGCGCGGCCGCAGGTGCAGGTGGTGATTACAAAGATGATGACGATAAAGGT
GCAGCGGCGCATCACCATCATCACCAC
(SEQ ID NO: 65), signal sequence (1-57), NYC-0003 (61-789), FLAG-His tag (789-867)

Fig. 67

NYC-0004 tag adduct
ATGAAACACCTGTGGTTCTTCCTCCTGCTGGTGGCAGCTCCCAGATGGGTGCTGAG
CGGCGAAGTCCAGCTGTTGGAGTCAGGTGGCGGATTGGTGCAACCTGGCGGGTCAC
TGAGGCTGAGTTGTGCAGCTAGCGGCTTCACATTCTCTACGTATCAGATGAGCTGG
GTGAGACAGGCTCCAGGAAAGGGTCTGGAATGGGTCAGCGGGATTGTGTCTAGCGG
TGGCTCCACTGCCTATGCCGATAGCGTAAAAGGCCGCTTTACGATCTCTCGGGACA
ACTCTAAGAACACACTCTATCTGCAGATGAATTCCCTTAGAGCCGAAGATACCGCC
GTGTACTACTGTGCTGGGGAACTGCTCCCGTATTACGGTATGGACGTTTGGGGCCA
AGGCACCACTGTCACAGTGAGTTCCGGTGGAGGCGGGTCAGGCGGAGGCGGTAGTG
GAGGTGGAGGATCACAAAGCGAGCTGACACAGCCTAGGTCCGTATCCGGAAGTCCA
GGGCAGAGCGTCACCATCAGCTGCACTGGCACCGAGCGAGATGTCGGCGGATACAA
CTACGTGTCTTGGTATCAGCAGCATCCCGGCAAAGCGCCCAAACTCATCATACACG
ACGTGATTGAGCGGTCCAGTGGGGTTCCCGATCGTTTCAGCGGGTCAAAGTCCGGA
ATACCGCAAGCCTGACCATTTCTGGGCTTCAGGCAGAGGATGAGGCTGACTACTA
CTGCTGGTCCTTTGCCGGGGGCTATTACGTGTTTGGACAGGGACTGACGTGACTG
TTCTGGGCGCGGCCGCAGGTGCAGGTGGTGATTACAAAGATGATGACGATAAAGGT
GCAGCGGCGCATCACCATCATCACCAC
(SEQ ID NO: 66), signal sequence (1-57), NYC-0004(61-789), FLAG-His tag (789-867)

Fig. 68

NYC-0003 tag adduct
MKHLWFFLLLVAAPRWVLSGEVQLLESGGGLVQPGGSLRLSCAASGFTFSTYQMSW
VRQAPGKGLEWVSGIVSSGGSTAYADSVKGRFTISRDNSKNTLYLQMNSLRAEDTA
VYYCAGELLPYYGMDVWGQGTTVTVSSGGGGSGGGGSGGGGSQSELTQPRSVSGSP
GQSVTISCTGTSRDVGGYNYVSWYQQHPGKAPKLIIHDVIERSSGVPDRFSGSKSG
NTASLTISGLQAEDEADYYCWSFAGSYYVFGTGTDVTVLGAAAGAGGDYKDDDDKG
AAAHHHHHH
(SEQ ID NO: 67), signal sequence (1-19), NYC-0003 (21-263), FLAG-His tag (264-289)

Fig. 69

NYC-0004 tag adduct
MKHLWFFLLLVAAPRWVLSGEVQLLESGGGLVQPGGSLRLSCAASGFTFSTYQMSW
VRQAPGKGLEWVSGIVSSGGSTAYADSVKGRFTISRDNSKNTLYLQMNSLRAEDTA
VYYCAGELLPYYGMDVWGQGTTVTVSSGGGGSGGGGSGGGGSQSELTQPRSVSGSP
GQSVTISCTGTERDVGGYNYVSWYQQHPGKAPKLIIHDVIERSSGVPDRFSGSKSG
NTASLTISGLQAEDEADYYCWSFAGGYYVFGTGTDVTVLGAAAGAGGDYKDDDDKG
AAAHHHHHH
(SEQ ID NO: 68), signal sequence (1-19), NYC-0004(21-263), FLAG-His tag (264-289)

Fig. 70

NYA-0001 tag adduct
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGTTATGATATACACTGG
GTCCGCCAGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCT
GTTTATCACTGTGCGAGAGGGAGTAGTGGTCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATAA
TTATGTATCCTGGTACCAGCAGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTATTA
CTGCGGAACATGGGATAGCAGCCTGAGTGCCCCTTGGGTGTTCGGCGGAGGGACCA
AGGTCACCGTCCTAGGCGCGGCCGCAGGTGCAGGTGGTGATTACAAAGATGATGAC
GATAAAGGTGCAGCGGCGCATCACCATCATCACCAC
(SEQ ID NO: 69), signal sequence (1-57), NYA-0001 (61-798), FLAG-His tag (799-876)

Fig. 71

NYA-0001 tag adduct
MKHLWFFLLLVAAPRWVLSGEVQLVESGGGVVQPGRSLTPSCSASGFSIRSYDIHW
VRQAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNNYVSWYQQLPGTAPKLLIYDNNKRPSGIPDRFSGSKSG
TSATLGITGLQTGDEADYYCGTWDSSLSAPWVFGGGTKVTVLGAAAGAGGDYKDDD
DKGAAAHHHHHH
(SEQ ID NO: 70), signal sequence (1-19), NYA-0001 (21-266), FLAG-His tag (267-292)

Fig. 72

HC1
ATGAAACACCTGTGGTTCTTCCTCCTGCTGGTGGCAGCTCCCAGATGGGTGCTGAG
CGACAAAACTCACACATGCCCACCCTGCCCAGCACCTGAAGCCGCAGGGGGACCCT
CAGTCTTCCTCTTCCCCCCAAAACCCAAGGACACCCTCATGATCTCCCGGACCCCT
GAGGTCACATGCGTGGTGGTGTCAGTGAGCCACGAAGACCCTGAGGTCAAGTTCAA
CTGGTACGTGGACGGCGTGGAGGTGCATAATGCCAAGACAAAGCCCCGGGAGGAGC
AGTACAACAGCACGTACCGGGTGGTCAGCGTCCTCACCGTCCTGCACCAGGACTGG
CTGAATGGCAAGGAGTACAAGTGCAAGGTCTCCAACAAAGCCCTCCCAGCCCCCAT
CGAGAAAACCATCTCCAAAGCCAAAGGCCAGCCCCGGGAACCACAGGTGTACGTGC
TGCCCCCATCCCGGGACGAGCTGACCAAGAACCAGGTCAGCCTGCTGTGCCTGGTC
AAAGGCTTCTATCCCAGCGACATCGCCGTGGAGTGGGAGAGCAATGGCCAGCCCGA
GAACAACTACCTGACCTGGCCTCCCGTGCTGGACTCCGACGGCTCCTTCTTCCTCT
ACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTC
TCCCGGCAAG
(SEQ ID NO: 71), signal sequence (1-57), hinge (58-87),
CH2 (88-417), CH3 (418-738)

Fig. 73

NYF-0016-HC2
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGCTATGATATACACTGG
GTCCGCCTGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCT
GTTTATCACTGTGCGAGAGGGAGTAGTGGTCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATTG
GTATGTATCCTGGTACCAGCAGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTATTA
CTGCGGAACATGGGATAGCAGCCTGAGTGCCCCTTGGGTGTTCGGCGGAGGGACCA
AGGTCACCGTCCTAGGGGGAGGCGGTTCAGAAGTGCAGCTGGTGGAATCCGGGGGG
GGCCTGGTGCAGCCTGGGGGGAGCCTGAGACTGAGTTGTGCCGCCTCTGGGGTGAC
ATTTAACTACTATGGCATGTCTTGGATCCGCCAGGCACCTGGAAAGGGCCTGGAGT
GGGTGGCCAGCATCACTAGGTCCGGCGGGCGAATCTACTATCCCGACAGCGTCAAG
GGCAGGTTCACAATTTCCCGCGAGAACACACAGAAAACTCTGTACCTGCAGATGAA
TAGCCTGAGAGCCGAAGATACAGCTGTGTACTATTGCACTCTGGACGGCAGGGATG
GGTGGGTCGCCTATTGGGGCAGGGAACCCTGGTGACAGTCAGCTCCGGAGGAGGA
GGATCTGGCGGAGGAGGCAGTGGGGGAGGCGGGTCAAACTTTATGCTCACTCAGCC
GTCCTCTGTTTCTGGCGTACCTGGCCAACGGGTGACCATTAGCTGTACGGGTAATA
CCGGGAATATCGGGTCTAACTACGTGAACTGGTATCAGCAGCTTCCAGGGACAGCT
CCCAAGTTGCTGATCTATCGCGACGACAAAGACCCTCAGGGGTCCCTGACCGATT
TAGTGGCAGCAAAAGCGGTACTTCCGCTTCCCTGGCGATAACCGGCTTTCAGGCCG
AAGATGAGGCAGACTACTATTGCCAGTCATATTCCAGCGGCTTCATCTTCGGAGGC
GGAACTAAGCTGACAGTGTTGGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCGGCAAG
(SEQ ID NO: 72), signal sequence (1-57), NYA-1143 (61-798), linker (799-813), C3E-7085 (814-1533), linker (1534-1539), hinge (1540-1584), CH2 (1585-1914), CH3 (1915-2235)

Fig. 74

NYF-0019-HC2
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGCTATGATATACACTGG
GTCCGCCTGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCT
GTTTATCACTGTGCGAGAGGGAGTAGTGGTCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATTG
GTATGTATCCTGGTACCAGCGGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTATTA
CTGCGGAACATGGGATAGCAGCCTGAGTGCCCCTTGGGTGTTCGGCGGAGGGACCA
AGGTCACCGTCCTAGGGGAGGCGGTTCAGAAGTGCAGCTGGTGGAATCCGGGGGG
GGCCTGGTGCAGCCTGGGGGGAGCCTGAGACTGAGTTGTGCCGCCTCTGGGGTGAC
ATTTAACTACTATGGCATGTCTTGGATCCGCCAGGCACCTGGAAAGGGCCTGGAGT
GGGTGGCCAGCATCACTAGGTCCGGCGGGCGAATCTACTATCCCGACAGCGTCAAG
GGCAGGTTCACAATTTCCCGCGAGAACACACAGAAAACTCTGTACCTGCAGATGAA
TAGCCTGAGAGCCGAAGATACAGCTGTGTACTATTGCACTCTGGACGGCAGGGATG
GGTGGGTCGCCTATTGGGGCAGGGAACCCTGGTGACAGTCAGCTCCGGAGGAGGA
GGATCTGGCGGAGGAGGCAGTGGGGAGGCGGGTCAAACTTTATGCTCACTCAGCC
GTCCTCTGTTTCTGGCGTACCTGGCCAACGGGTGACCATTAGCTGTACGGGTAATA
CCGGGAATATCGGGTCTAACTACGTGAACTGGTATCAGCAGCTTCCAGGGACAGCT
CCCAAGTTGCTGATCTATCGCGACGACAAAAGACCCTCAGGGGTCCCTGACCGATT
TAGTGGCAGCAAAAGCGGTACTTCCGCTTCCCTGGCGATAACCGGCTTTCAGGCCG
AAGATGAGGCAGACTACTATTGCCAGTCATATTCCAGCGGCTTCATCTTCGGAGGC
GGAACTAAGCTGACAGTGTTGGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCATCGAGAAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCGGCAAG
(SEQ ID NO: 73), signal sequence (1-57), NYA-2143 (61-798), linker (799-813), C3E-7085 (814-1533), linker (1534-1539), hinge (1540-1584), CH2 (1585-1914), CH3 (1915-2235)

Fig. 75

NYF-0022-HC2
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGCTATGATATACACTGG
GTCCGCCTGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCT
GTTTATCACTGTGCGAGAGGGAGTAGTGGTCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATAA
TTATGTATCCTGGTACCAGCAGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTATTA
CTGCGGAACATGGGATAGCAGCCTGAGTGCCCCTTGGGTGTTCGGCGGAGGGACCA
AGGTCACCGTCCTAGGGGGAGGCGGTTCAGAAGTGCAGCTGGTGGAATCCGGGGGG
GGCCTGGTGCAGCCTGGGGGGAGCCTGAGACTGAGTTGTGCCGCCTCTGGGGTGAC
ATTTAACTACTATGGCATGTCTTGGATCCGCCAGGCACCTGGAAAGGGCCTGGAGT
GGGTGGCCAGCATCACTAGGTCCGGCGGGCGAATCTACTATCCCGACAGCGTCAAG
GGCAGGTTCACAATTTCCCGCGAGAACACACAGAAACTCTGTACCTGCAGATGAA
TAGCCTGAGAGCCGAAGATACAGCTGTGTACTATTGCACTCTGGACGGCAGGGATG
GGTGGGTCGCCTATTGGGGCAGGGAACCCTGGTGACAGTCAGCTCCGGAGGAGGA
GGATCTGGCGGAGGAGGCAGTGGGGAGGCGGGTCAAACTTTATGCTCACTCAGCC
GTCCTCTGTTTCTGGCGTACCTGGCCAACGGGTGACCATTAGCTGTACGGGTAATA
CCGGGAATATCGGGTCTAACTACGTGAACTGGTATCAGCAGCTTCCAGGGACAGCT
CCCAAGTTGCTGATCTATCGCGACGACAAAAGACCCTCAGGGGTCCCTGACCGATT
TAGTGGCAGCAAAAGCGGTACTTCCGCTTCCCTGGCGATAACCGGCTTTCAGGCCG
AAGATGAGGCAGACTACTATTGCCAGTCATATTCCAGCGGCTTCATCTTCGGAGGC
GGAACTAAGCTGACAGTGTTGGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCGGCAAG
(SEQ ID NO: 74), signal sequence (1-57), NYA-1163 (61-798), linker (799-813), C3E-7085 (814-1533), linker (1534-1539), hinge (1540-1584), CH2 (1585-1914), CH3 (1915-2235)

Fig. 76

NYF-0023-HC2
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGTTATGATATACACTGG
GTCCGCCAGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCT
GTTTATCACTGTGCGAGAGGGAGTAGTGGTCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATTG
GTATGTATCCTGGTACCAGCAGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTATTA
CTGCGGAACATGGGATAGCAGCCTGAGTGCCCCTTGGGTGTTCGGCGGAGGGACCA
AGGTCACCGTCCTAGGGGGAGGCGGTTCAGAAGTGCAGCTGGTGGAATCCGGGGGG
GGCCTGGTGCAGCCTGGGGGGAGCCTGAGACTGAGTTGTGCCGCCTCTGGGGTGAC
ATTTAACTACTATGGCATGTCTTGGATCCGCCAGGCACCTGGAAAGGGCCTGGAGT
GGGTGGCCAGCATCACTAGGTCCGGCGGGCGAATCTACTATCCCGACAGCGTCAAG
GGCAGGTTCACAATTTCCCGCGAGAACACACAGAAAACTCTGTACCTGCAGATGAA
TAGCCTGAGAGCCGAAGATACAGCTGTGTACTATTGCACTCTGGACGGCAGGGATG
GGTGGGTCGCCTATTGGGGCAGGGAACCCTGGTGACAGTCAGCTCCGGAGGAGGA
GGATCTGGCGGAGGAGGCAGTGGGGGAGGCGGGTCAAACTTTATGCTCACTCAGCC
GTCCTCTGTTTCTGGCGTACCTGGCCAACGGGTGACCATTAGCTGTACGGGTAATA
CCGGGAATATCGGGTCTAACTACGTGAACTGGTATCAGCAGCTTCCAGGGACAGCT
CCCAAGTTGCTGATCTATCGCGACGACAAAAGACCCTCAGGGGTCCCTGACCGATT
TAGTGGCAGCAAAAGCGGTACTTCCGCTTCCCTGGCGATAACCGGCTTTCAGGCCG
AAGATGAGGCAGACTACTATTGCCAGTCATATTCCAGCGGCTTCATCTTCGGAGGC
GGAACTAAGCTGACAGTGTTGGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCGGCAAG
(SEQ ID NO: 75), signal sequence (1-57), NYA-2023 (61-798), linker (799-813), C3E-7085 (814-1533), linker (1534-1539), hinge (1540-1584), CH2 (1585-1914), CH3 (1915-2235)

Fig. 77

NYF-0027-HC2
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGTTATGATATACACTGG
GTCCGCCAGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCT
GTTTATCACTGTGCGAGAGGGAGTAGTGGTCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATAA
TTATGTATCCTGGTACCAGCAGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTATTA
CTGCGGATCATGGGATAGCAGCCTGAGTGCCCCTTGGGTGTTCGGCGGAGGGACCA
AGGTCACCGTCCTAGGGGAGGCGGTTCAGAAGTGCAGCTGGTGGAATCCGGGGGG
GGCCTGGTGCAGCCTGGGGGGAGCCTGAGACTGAGTTGTGCCGCCTCTGGGGTGAC
ATTTAACTACTATGGCATGTCTTGGATCCGCCAGGCACCTGGAAAGGGCCTGGAGT
GGGTGGCCAGCATCACTAGGTCCGGCGGGCGAATCTACTATCCCGACAGCGTCAAG
GGCAGGTTCACAATTTCCCGCGAGAACACACAGAAAACTCTGTACCTGCAGATGAA
TAGCCTGAGAGCCGAAGATACAGCTGTGTACTATTGCACTCTGGACGGCAGGGATG
GGTGGGTCGCCTATTGGGGCAGGGAACCCTGGTGACAGTCAGCTCCGGAGGAGGA
GGATCTGGCGGAGGAGGCAGTGGGGGAGGCGGGTCAAACTTTATGCTCACTCAGCC
GTCCTCTGTTTCTGGCGTACCTGGCCAACGGGTGACCATTAGCTGTACGGGTAATA
CCGGGAATATCGGGTCTAACTACGTGAACTGGTATCAGCAGCTTCCAGGGACAGCT
CCCAAGTTGCTGATCTATCGCGACGACAAAGACCCTCAGGGGTCCCTGACCGATT
TAGTGGCAGCAAAAGCGGTACTTCCGCTTCCCTGGCGATAACCGGCTTTCAGGCCG
AAGATGAGGCAGACTACTATTGCCAGTCATATTCCAGCGGCTTCATCTTCGGAGGC
GGAACTAAGCTGACAGTGTTGGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCGGCAAG
(SEQ ID NO: 76), signal sequence (1-57), NYA-2027(61-798), linker (799-813), C3E-7085 (814-1533), linker (1534-1539), hinge (1540-1584), CH2 (1585-1914), CH3 (1915-2235)

Fig. 78

NYF-0035-HC2
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGCTATGATATACACTGG
GTCCGCCTGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCT
GTTTATCACTGTGCGAGAGGGAGTAGTGGTCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATTG
GAAGGTATCCTGGTACCAGCAGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTATTA
CTGCGGAACATGGGATAGCAGCCTGAGTGCCCCTTGGGTGTTCGGCGGAGGGACCA
AGGTCACCGTCCTAGGGGAGGCGGTTCAGAAGTGCAGCTGGTGGAATCCGGGGGG
GGCCTGGTGCAGCCTGGGGGGAGCCTGAGACTGAGTTGTGCCGCCTCTGGGGTGAC
ATTTAACTACTATGGCATGTCTTGGATCCGCCAGGCACCTGGAAAGGGCCTGGAGT
GGGTGGCCAGCATCACTAGGTCCGGCGGGCGAATCTACTATCCCGACAGCGTCAAG
GGCAGGTTCACAATTTCCCGCGAGAACACACAGAAAACTCTGTACCTGCAGATGAA
TAGCCTGAGAGCCGAAGATACAGCTGTGTACTATTGCACTCTGGACGGCAGGGATG
GGTGGGTCGCCTATTGGGGCAGGGAACCCTGGTGACAGTCAGCTCCGGAGGAGGA
GGATCTGGCGGAGGAGGCAGTGGGGAGGCGGGTCAAACTTTATGCTCACTCAGCC
GTCCTCTGTTTCTGGCGTACCTGGCCAACGGGTGACCATTAGCTGTACGGGTAATA
CCGGGAATATCGGGTCTAACTACGTGAACTGGTATCAGCAGCTTCCAGGGACAGCT
CCCAAGTTGCTGATCTATCGCGACGACAAAGACCCTCAGGGGTCCCTGACCGATT
TAGTGGCAGCAAAAGCGGTACTTCCGCTTCCCTGGCGATAACCGGCTTTCAGGCCG
AAGATGAGGCAGACTACTATTGCCAGTCATATTCCAGCGGCTTCATCTTCGGAGGC
GGAACTAAGCTGACAGTGTTGGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCGGCAAG
(SEQ ID NO: 77), signal sequence (1-57), NYA-2035 (61-798), linker (799-813), C3E-7085 (814-1533), linker (1534-1539), hinge (1540-1584), CH2 (1585-1914), CH3 (1915-2235)

Fig. 79

NYF-0044-HC2
ATGAAACACCTGTGGTTCTTCCTCCTGCTGGTGGCAGCTCCCAGATGGGTGCTGAG
CGGTGAGGTACAGCTGGTGGAATCCGGTGGAGGCCTTGTGCAACCGGGAGGCTCCC
TGCGACTCTCTTGCGCCGCATCTGGCTTTTCCATACGATCCTACGATATTCATTGG
GTCCGACTCGCCCCTGGCAAAGGTCTTGAATGGGTTGCCACTATCTCCTACGACGG
GTCTCAGAAATATTATGCGGATTCAGTGAAGGGGCGGTTCACAATTTCACGAGACG
AGTCAAAGAATACACTGTACCTCCAAATGAATTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTCAATCCGTTCTGACTCAGCCACCCTCCGTGAGTGCAGCG
CCTGGACAGAAGGTCACAATATCATGTTCTGGCTCTTCAAGCAACATCGGAAACTG
GTACGTGAGCTGGTACCAGCAGCTCCCCGGCACGGCGCCCAAGCTTCTGATATATG
ACAACAACAAACGGCCCAGTGGAATCCCTGACAGATTCAGTGGGTCTAAAAGTGGT
ACAAGCGCTACCCTGGGTATCACCGGATTGCAGACCGGAGATGAGGCGGACTATTA
TTGCGGAACCTGGGACTCCAGCCTGAGCGCTCCCTGGGTTTTCGGCGGAGGTACTA
AGGTTACCGTCTTGGGAGGAGGCGGTTCAGAAGTGCAGCTGGTGGAATCCGGGGGG
GGCCTGGTGCAGCCTGGGGGGAGCCTGAGACTGAGTTGTGCCGCCTCTGGGGTGAC
ATTTAACTACTATGGCATGTCTTGGATCCGCCAGGCACCTGGAAAGGGCCTGGAGT
GGGTGGCCAGCATCACTAGGTCCGGCGGGCGAATCTACTATCCCGACAGCGTCAAG
GGCAGGTTCACAATTTCCCGCGAGAACACACAGAAAACTCTGTACCTGCAGATGAA
TAGCCTGAGAGCCGAAGATACAGCTGTGTACTATTGCACTCTGGACGGCAGGGATG
GGTGGGTCGCCTATTGGGGCAGGGAACCCTGGTGACAGTCAGCTCCGGAGGAGGA
GGATCTGGCGGAGGAGGCAGTGGGGGAGGCGGGTCAAACTTTATGCTCACTCAGCC
GTCCTCTGTTTCTGGCGTACCTGGCCAACGGGTGACCATTAGCTGTACGGGTAATA
CCGGGAATATCGGGTCTAACTACGTGAACTGGTATCAGCAGCTTCCAGGGACAGCT
CCCAAGTTGCTGATCTATCGCGACGACAAAGACCCTCAGGGGTCCCTGACCGATT
TAGTGGCAGCAAAAGCGGTACTTCCGCTTCCCTGGCGATAACCGGCTTTCAGGCCG
AAGATGAGGCAGACTACTATTGCCAGTCATATTCCAGCGGCTTCATCTTCGGAGGC
GGAACTAAGCTGACAGTGTTGGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCGGCAAG
(SEQ ID NO: 78), signal sequence (1-57), NYA-2044 (61-798), linker (799-813), C3E-7085 (814-1533), linker (1534-1539), hinge (1540-1584), CH2 (1585-1914), CH3 (1915-2235)

Fig. 80

NYF-0045-HC2
ATGAAACACCTGTGGTTCTTCCTCCTGCTGGTGGCAGCTCCCAGATGGGTGCTGAG
CGGTGAGGTACAGCTGGTGGAATCCGGTGGAGGCCTTGTGCAACCGGGAGGCTCCC
TGCGACTCTCTTGCGCCGCATCTGGCTTTTCCATACGATCCTACGATATTCATTGG
GTCCGACTCGCCCCTGGCAAAGGTCTTGAATGGGTTGCCACTATCTCCTACGACGG
GTCTCAGAAATATTATGCGGATTCAGTGAAGGGGCGGTTCACAATTTCACGAGACG
AGTCAAAGAATACACTGTACCTCCAAATGAATTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTCAATCCGTTCTGACTCAGCCACCCTCCGCCTCTGGCACC
CCGGGCCAACGGGTCACAATATCATGTTCTGGCTCTTCAAGCAACATCGGAAACTG
GTACGTGAGCTGGTACCAGCAGCTCCCCGGCACGGCGCCCAAGCTTCTGATATATG
ACAACAACAAACGGCCCAGTGGAGTTCCTGACAGATTCAGTGGGTCTAAAAGTGGT
ACAAGCGCTAGCCTGGCCATAAGTGGTCTGCAGAGTGAAGATGAGGCGGACTATTA
TTGCGGAACCTGGGACTCCAGCCTGAGCGCTCCCTGGGTTTTCGGCGGAGGTACTA
AGCTGACCGTCTTGGGAGGAGGCGGTTCAGAAGTGCAGCTGGTGGAATCCGGGGGG
GGCCTGGTGCAGCCTGGGGGGAGCCTGAGACTGAGTTGTGCCGCCTCTGGGGTGAC
ATTTAACTACTATGGCATGTCTTGGATCCGCCAGGCACCTGGAAAGGGCCTGGAGT
GGGTGGCCAGCATCACTAGGTCCGGCGGGCGAATCTACTATCCCGACAGCGTCAAG
GGCAGGTTCACAATTTCCCGCGAGAACACACAGAAAACTCTGTACCTGCAGATGAA
TAGCCTGAGAGCCGAAGATACAGCTGTGTACTATTGCACTCTGGACGGCAGGGATG
GGTGGGTCGCCTATTGGGGCAGGGAACCCTGGTGACAGTCAGCTCCGGAGGAGGA
GGATCTGGCGGAGGAGGCAGTGGGGGAGGCGGGTCAAACTTTATGCTCACTCAGCC
GTCCTCTGTTTCTGGCGTACCTGGCCAACGGGTGACCATTAGCTGTACGGGTAATA
CCGGGAATATCGGGTCTAACTACGTGAACTGGTATCAGCAGCTTCCAGGGACAGCT
CCCAAGTTGCTGATCTATCGCGACGACAAAGACCCTCAGGGGTCCCTGACCGATT
TAGTGGCAGCAAAAGCGGTACTTCCGCTTCCCTGGCGATAACCGGCTTTCAGGCCG
AAGATGAGGCAGACTACTATTGCCAGTCATATTCCAGCGGCTTCATCTTCGGAGGC
GGAACTAAGCTGACAGTGTTGGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCGGCAAG
(SEQ ID NO: 79), signal sequence (1-57), NYA-2045 (61-798), linker (799-813), C3E-7085 (814-1533), linker (1534-1539), hinge (1540-1584), CH2 (1585-1914), CH3 (1915-2235)

Fig. 81

NYF-0047-HC2
ATGAAACACCTGTGGTTCTTCCTCCTGCTGGTGGCAGCTCCCAGATGGGTGCTGAG
CGGTCAAGTACAGCTGGTGGAATCCGGTGGAGGCGTGGTCCAGCCGGGACGCAGCT
TGAGACTGTCCTGCGCTGCATCTGGCTTTTCCATACGATCCTACGATATGCACTGG
GTTCGCCAAGCCCCTGGCAAAGGTCTTGAATGGGTTGCCACTATCTCCTACGACGG
GTCTCAGAAATATTACGCGGATTCAGTGAAGGGGCGGTTCACAATTTCACGGGACA
ATTCAAAGAATACCTTGTATCTCCAGATGTCTTCACTGAGAGCCGAGGATACTGCA
GTCTATCATTGTCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTCAATCCGTTCTGACTCAGCCACCCTCCGTGAGTGCAGCG
CCTGGACAGAAGGTCACAATATCATGTTCTGGCTCTTCAAGCAACATCGGAAACTG
GTACGTGAGCTGGTACCAGCAGCTCCCCGGCACGGCGCCCAAGCTTCTGATATATG
ACAACAACAAACGGCCCAGTGGAATCCCTGACAGATTCAGTGGGTCTAAAAGTGGT
ACAAGCGCTACCCTGGGTATCACCGGATTGCAGACCGGAGATGAGGCGGACTATTA
TTGCGGAACCTGGGACTCCAGCCTGAGCGCTCCCTGGGTTTTCGGCGGAGGTACTA
AGGTTACCGTCTTGGGAGGAGGCGGTTCAGAAGTGCAGCTGGTGGAATCCGGGGGG
GGCCTGGTGCAGCCTGGGGGGAGCCTGAGACTGAGTTGTGCCGCCTCTGGGGTGAC
ATTTAACTACTATGGCATGTCTTGGATCCGCCAGGCACCTGGAAAGGGCCTGGAGT
GGGTGGCCAGCATCACTAGGTCCGGCGGGCGAATCTACTATCCCGACAGCGTCAAG
GGCAGGTTCACAATTTCCCGCGAGAACACACAGAAAACTCTGTACCTGCAGATGAA
TAGCCTGAGAGCCGAAGATACAGCTGTGTACTATTGCACTCTGGACGGCAGGGATG
GGTGGGTCGCCTATTGGGGCAGGGAACCCTGGTGACAGTCAGCTCCGGAGGAGGA
GGATCTGGCGGAGGAGGCAGTGGGGGAGGCGGGTCAAACTTTATGCTCACTCAGCC
GTCCTCTGTTTCTGGCGTACCTGGCCAACGGGTGACCATTAGCTGTACGGGTAATA
CCGGGAATATCGGGTCTAACTACGTGAACTGGTATCAGCAGCTTCCAGGGACAGCT
CCCAAGTTGCTGATCTATCGCGACGACAAAGACCCTCAGGGGTCCCTGACCGATT
TAGTGGCAGCAAAAGCGGTACTTCCGCTTCCCTGGCGATAACCGGCTTTCAGGCCG
AAGATGAGGCAGACTACTATTGCCAGTCATATTCCAGCGGCTTCATCTTCGGAGGC
GGAACTAAGCTGACAGTGTTGGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCGGCAAG
(SEQ ID NO: 80), signal sequence (1-57), NYA-2047(61-798), linker (799-813), C3E-7085 (814-1533), linker (1534-1539), hinge (1540-1584), CH2 (1585-1914), CH3 (1915-2235)

Fig. 82

NYF-0048-HC2
ATGAAACACCTGTGGTTCTTCCTCCTGCTGGTGGCAGCTCCCAGATGGGTGCTGAG
CGGACAAGTTCAACTCGTGGAATCTGGTGGAGGGGTGGTACAACCAGGCCGGTCAC
TTAGACTGTCCTGCGCTGCGAGTGGATTTTCCATCAGATCTTACGACATGCACTGG
GTTCGCCAAGCACCCGGAAAGGGTTTGGAATGGGTGGCTACGATCTCCTACGATGG
ATCCCAGAAGTATTACGCCGACAGCGTCAAGGGCCGATTTACAATATCACGGGACA
ATTCAAAGAATACCTTGTATCTCCAGATGTCTTCACTGAGAGCCGAGGATACTGCA
GTCTATCATTGTCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTCAATCCGTTCTGACTCAGCCACCCTCCGCCTCTGGCACC
CCGGGCCAACGGGTCACAATATCATGTTCTGGCTCTTCAAGCAACATCGGAAACTG
GTACGTGAGCTGGTACCAGCAGCTCCCCGGCACGGCGCCCAAGCTTCTGATATATG
ACAACAACAAACGGCCCAGTGGAGTTCCTGACAGATTCAGTGGGTCTAAAAGTGGT
ACAAGCGCTAGCCTGGCCATAAGTGGTCTGCAGAGTGAAGATGAGGCGGACTATTA
TTGCGGAACCTGGGACTCCAGCCTGAGCGCTCCCTGGGTTTTCGGCGGAGGTACTA
AGCTGACCGTCTTGGGAGGAGGCGGTTCAGAAGTGCAGCTGGTGGAATCCGGGGGG
GGCCTGGTGCAGCCTGGGGGGAGCCTGAGACTGAGTTGTGCCGCCTCTGGGGTGAC
ATTTAACTACTATGGCATGTCTTGGATCCGCCAGGCACCTGGAAAGGGCCTGGAGT
GGGTGGCCAGCATCACTAGGTCCGGCGGGCGAATCTACTATCCCGACAGCGTCAAG
GGCAGGTTCACAATTTCCCGCGAGAACACACAGAAAACTCTGTACCTGCAGATGAA
TAGCCTGAGAGCCGAAGATACAGCTGTGTACTATTGCACTCTGGACGGCAGGGATG
GGTGGGTCGCCTATTGGGGCAGGGAACCCTGGTGACAGTCAGCTCCGGAGGAGGA
GGATCTGGCGGAGGAGGCAGTGGGGAGGCGGGTCAAACTTTATGCTCACTCAGCC
GTCCTCTGTTTCTGGCGTACCTGGCCAACGGGTGACCATTAGCTGTACGGGTAATA
CCGGGAATATCGGGTCTAACTACGTGAACTGGTATCAGCAGCTTCCAGGGACAGCT
CCCAAGTTGCTGATCTATCGCGACGACAAAAGACCCTCAGGGGTCCCTGACCGATT
TAGTGGCAGCAAAAGCGGTACTTCCGCTTCCCTGGCGATAACCGGCTTTCAGGCCG
AAGATGAGGCAGACTACTATTGCCAGTCATATTCCAGCGGCTTCATCTTCGGAGGC
GGAACTAAGCTGACAGTGTTGGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCGGCAAG
(SEQ ID NO: 81), signal sequence (1-57), NYA-2048(61-798), linker (799-813), C3E-7085 (814-1533), linker (1534-1539), hinge (1540-1584), CH2 (1585-1914), CH3 (1915-2235)

Fig. 83

NYF-0060-HC2
ATGAAACACCTGTGGTTCTTCCTCCTGCTGGTGGCAGCTCCCAGATGGGTGCTGAG
CGGTGAGGTACAGCTGGTGGAATCCGGTGGAGGCCTTGTGCAACCGGGAGGCTCCC
TGCGACTCTCTTGCGCCGCATCTGGCTTTTCCATACGATCCTACGATATTCATTGG
GTCCGACAAGCCCCTGGCAAGGTCTTGAATGGGTTGCCACTATCTCCTACGACGG
GTCTCAGAAATATTATGCGGATTCAGTGAAGGGGCGGTTCACAATTTCACGAGACG
AGTCAAAGAATACACTGTACCTCCAAATGAATTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTCAATCCGTTCTGACTCAGCCACCCTCCGTGAGTGCAGCG
CCTGGACAGAAGGTCACAATATCATGTTCTGGCTCTTCAAGCAACATCGGAAACTG
GTACGTGAGCTGGTACCAGCAGCTCCCCGGCACGGCGCCCAAGCTTCTGATATATG
ACAACAACAAACGGCCCAGTGGAATCCCTGACAGATTCAGTGGGTCTAAAAGTGGT
ACAAGCGCTACCCTGGGTATCACCGGATTGCAGACCGGAGATGAGGCGGACTATTA
TTGCGGAACCTGGGACTCCAGCCTGAGCGCTCCCTGGGTTTTCGGCGGAGGTACTA
AGGTTACCGTCTTGGGAGGAGGCGGTTCAGAAGTGCAGCTGGTGGAATCCGGGGGG
GGCCTGGTGCAGCCTGGGGGGAGCCTGAGACTGAGTTGTGCCGCCTCTGGGGTGAC
ATTTAACTACTATGGCATGTCTTGGATCCGCCAGGCACCTGGAAAGGGCCTGGAGT
GGGTGGCCAGCATCACTAGGTCCGGCGGGCGAATCTACTATCCCGACAGCGTCAAG
GGCAGGTTCACAATTTCCCGCGAGAACACACAGAAAACTCTGTACCTGCAGATGAA
TAGCCTGAGAGCCGAAGATACAGCTGTGTACTATTGCACTCTGGACGGCAGGGATG
GGTGGGTCGCCTATTGGGGCAGGGAACCCTGGTGACAGTCAGCTCCGGAGGAGGA
GGATCTGGCGGAGGAGGCAGTGGGGAGGCGGGTCAAACTTTATGCTCACTCAGCC
GTCCTCTGTTTCTGGCGTACCTGGCCAACGGGTGACCATTAGCTGTACGGGTAATA
CCGGGAATATCGGGTCTAACTACGTGAACTGGTATCAGCAGCTTCCAGGGACAGCT
CCCAAGTTGCTGATCTATCGCGACGACAAAAGACCCTCAGGGGTCCCTGACCGATT
TAGTGGCAGCAAAAGCGGTACTTCCGCTTCCCTGGCGATAACCGGCTTTCAGGCCG
AAGATGAGGCAGACTACTATTGCCAGTCATATTCCAGCGGCTTCATCTTCGGAGGC
GGAACTAAGCTGACAGTGTTGGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCGGCAAG
(SEQ ID NO: 82), signal sequence (1-57), NYA-2060(61-798), linker (799-813), C3E-7085 (814-1533), linker (1534-1539), hinge (1540-1584), CH2 (1585-1914), CH3 (1915-2235)

Fig. 84

NYF-0061-HC2
ATGAAACACCTGTGGTTCTTCCTCCTGCTGGTGGCAGCTCCCAGATGGGTGCTGAG
CGGTGAGGTACAGCTGGTGGAATCCGGTGGAGGCCTTGTGCAACCGGGAGGCTCCC
TGCGACTCTCTTGCGCCGCATCTGGCTTTTCCATACGATCCTACGATATTCATTGG
GTCCGACAAGCCCCTGGCAAGGTCTTGAATGGGTTGCCACTATCTCCTACGACGG
GTCTCAGAAATATTATGCGGATTCAGTGAAGGGGCGGTTCACAATTTCACGAGACG
AGTCAAAGAATACACTGTACCTCCAAATGAATTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTCAATCCGTTCTGACTCAGCCACCCTCCGCCTCTGGCACC
CCGGGCCAACGGGTCACAATATCATGTTCTGGCTCTTCAAGCAACATCGGAAACTG
GTACGTGAGCTGGTACCAGCAGCTCCCCGGCACGGCGCCCAAGCTTCTGATATATG
ACAACAACAAACGGCCCAGTGGAGTTCCTGACAGATTCAGTGGGTCTAAAAGTGGT
ACAAGCGCTAGCCTGGCCATAAGTGGTCTGCAGAGTGAAGATGAGGCGGACTATTA
TTGCGGAACCTGGGACTCCAGCCTGAGCGCTCCCTGGGTTTTCGGCGGAGGTACTA
AGCTGACCGTCTTGGGAGGAGGCGGTTCAGAAGTGCAGCTGGTGGAATCCGGGGGG
GGCCTGGTGCAGCCTGGGGGGAGCCTGAGACTGAGTTGTGCCGCCTCTGGGGTGAC
ATTTAACTACTATGGCATGTCTTGGATCCGCCAGGCACCTGGAAAGGGCCTGGAGT
GGGTGGCCAGCATCACTAGGTCCGGCGGGCGAATCTACTATCCCGACAGCGTCAAG
GGCAGGTTCACAATTTCCCGCGAGAACACACAGAAACTCTGTACCTGCAGATGAA
TAGCCTGAGAGCCGAAGATACAGCTGTGTACTATTGCACTCTGGACGGCAGGGATG
GGTGGGTCGCCTATTGGGGCAGGGAACCCTGGTGACAGTCAGCTCCGGAGGAGGA
GGATCTGGCGGAGGAGGCAGTGGGGGAGGCGGGTCAAACTTTATGCTCACTCAGCC
GTCCTCTGTTTCTGGCGTACCTGGCCAACGGGTGACCATTAGCTGTACGGGTAATA
CCGGGAATATCGGGTCTAACTACGTGAACTGGTATCAGCAGCTTCCAGGGACAGCT
CCCAAGTTGCTGATCTATCGCGACGACAAAAGACCCTCAGGGGTCCCTGACCGATT
TAGTGGCAGCAAAAGCGGTACTTCCGCTTCCCTGGCGATAACCGGCTTTCAGGCCG
AAGATGAGGCAGACTACTATTGCCAGTCATATTCCAGCGGCTTCATCTTCGGAGGC
GGAACTAAGCTGACAGTGTTGGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCGGCAAG
(SEQ ID NO: 83), signal sequence (1-57), NYA-2061 (61-798), linker (799-813), C3E-7085 (814-1533), linker (1534-1539), hinge (1540-1584), CH2 (1585-1914), CH3 (1915-2235)

Fig. 85

HC1
MKHLWFFLLLVAAPRWVLSDKTHTCPPCPAPEAAGGPSVFLFPPKPKDTLMISRTP
EVTCVVVSVSHEDPEVKFNWYVDGVEVHNAKTKPREEQYNSTYRVVSVLTVLHQDW
LNGKEYKCKVSNKALPAPIEKTISKAKGQPREPQVYVLPPSRDELTKNQVSLLCLV
KGFYPSDIAVEWESNGQPENNYLTWPPVLDSDGSFFLYSKLTVDKSRWQQGNVFSC
SVMHEALHNHYTQKSLSLSPGK
(SEQ ID NO: 84), signal sequence (1-19), hinge (20-29),
CH2 (30-139), CH3 (140-246)

Fig. 86

NYF-0016-HC
MKHLWFFLLLVAAPRWVLSGEVQLVESGGGVVQPGRSLTPSCSASGFSIRSYDIHW
VRLAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNWYVSWYQQLPGTAPKLLIYDNNKRPSGIPDRFSGSKSG
TSATLGITGLQTGDEADYYCGTWDSSLSAPWVFGGGTKVTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSGGG
GSGGGGSGGGGSNFMLTQPSSVSGVPGQRVTISCTGNTGNIGSNYVNWYQQLPGTA
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPGK
(SEQ ID NO: 85), signal sequence (1-19), NYA-1143 (21-266), linker (267-271), C3E-7085 (272-511), linker (512-513), hinge (514-528), CH2 (529-638), CH3 (639-745)

Fig. 87

NYF-0019-HC2
MKHLWFFLLLVAAPRWVLSGEVQLVESGGGVVQPGRSLTPSCSASGFSIRSYDIHW
VRLAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNWYVSWYQRLPGTAPKLLIYDNNKRPSGIPDRFSGSKSG
TSATLGITGLQTGDEADYYCGTWDSSLSAPWVFGGGTKVTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSGGG
GSGGGGSGGGGSNFMLTQPSSVSGVPGQRVTISCTGNTGNIGSNYVNWYQQLPGTA
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPGK
(SEQ ID NO: 86), signal sequence (1-19), NYA-2143 (21-266), linker (267-271), C3E-7085 (272-511), linker (512-513), hinge (514-528), CH2 (529-638), CH3 (639-745)

Fig. 88

NYF-0022-HC2
MKHLWFFLLLVAAPRWVLSGEVQLVESGGGVVQPGRSLTPSCSASGFSIRSYDIHW
VRLAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNNYVSWYQQLPGTAPKLLIYDNNKRPSGIPDRFSGSKSG
TSATLGITGLQTGDEADYYCGTWDSSLSAPWVFGGGTKVTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSGGG
GSGGGGSGGGGSNFMLTQPSSVSGVPGQRVTISCTGNTGNIGSNYVNWYQQLPGTA
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPGK
(SEQ ID NO: 87), signal sequence (1-19), NYA-1163 (21-266), linker (267-271), C3E-7085 (272-511), linker (512-513), hinge (514-528), CH2 (529-638), CH3 (639-745)

Fig. 89

NYF-0023-HC2
MKHLWFFLLLVAAPRWVLSGEVQLVESGGGVVQPGRSLTPSCSASGFSIRSYDIHW
VRQAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNWYVSWYQQLPGTAPKLLIYDNNKRPSGIPDRFSGSKSG
TSATLGITGLQTGDEADYYCGTWDSSLSAPWVFGGGTKVTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSGGG
GSGGGGSGGGGSNFMLTQPSSVSGVPGQRVTISCTGNTGNIGSNYVNWYQQLPGTA
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPGK
(SEQ ID NO: 88), signal sequence (1-19), NYA-2023 (21-266), linker (267-271), C3E-7085 (272-511), linker (512-513), hinge (514-528), CH2 (529-638), CH3 (639-745)

Fig. 90

NYF-0027-HC2
MKHLWFFLLLVAAPRWVLSGEVQLVESGGGVVQPGRSLTPSCSASGFSIRSYDIHW
VRQAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNNYVSWYQQLPGTAPKLLIYDNNKRPSGIPDRFSGSKSG
TSATLGITGLQTGDEADYYCGSWDSSLSAPWVFGGGTKVTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSGGG
GSGGGGSGGGGSNFMLTQPSSVSGVPGQRVTISCTGNTGNIGSNYVNWYQQLPGTA
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPGK
(SEQ ID NO: 89), signal sequence (1-19), NYA-2027(21-266), linker (267-271), C3E-7085 (272-511), linker (512-513), hinge (514-528), CH2 (529-638), CH3 (639-745)

Fig. 91

NYF-0035-HC2
MKHLWFFLLLVAAPRWVLSGEVQLVESGGGVVQPGRSLTPSCSASGFSIRSYDIHW
VRLAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNWKVSWYQQLPGTAPKLLIYDNNKRPSGIPDRFSGSKSG
TSATLGITGLQTGDEADYYCGTWDSSLSAPWVFGGGTKVTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSGGG
GSGGGGSGGGGSNFMLTQPSSVSGVPGQRVTISCTGNTGNIGSNYVNWYQQLPGTA
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPGK
(SEQ ID NO: 90), signal sequence (1-19), NYA-2035 (21-266), linker (267-271), C3E-7085 (272-511), linker (512-513), hinge (514-528), CH2 (529-638), CH3 (639-745)

Fig. 92

NYF-0044-HC2
MKHLWFFLLLVAAPRWVLSGEVQLVESGGGLVQPGGSLRLSCAASGFSIRSYDIHW
VRLAPGKGLEWVATISYDGSQKYYADSVKGRFTISRDESKNTLYLQMNSLRAEDTA
VYHCARGSSGHYEAFDIWGQGTLVTVSSGGGGSGGGGSGGGGSQSVLTQPPSVSAA
PGQKVTISCSGSSSNIGNWYVSWYQQLPGTAPKLLIYDNNKRPSGIPDRFSGSKSG
TSATLGITGLQTGDEADYYCGTWDSSLSAPWVFGGGTKVTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSGGG
GSGGGGSGGGGSNFMLTQPSSVSGVPGQRVTISCTGNTGNIGSNYVNWYQQLPGTA
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPGK
(SEQ ID NO: 91), signal sequence (1-19), NYA-2044(21-
266), linker (267-271), C3E-7085 (272-511), linker (512-
513), hinge (514-528), CH2 (529-638), CH3 (639-745)

Fig. 93

NYF-0045-HC2
MKHLWFFLLLVAAPRWVLSGEVQLVESGGGLVQPGGSLRLSCAASGFSIRSYDIHW
VRLAPGKGLEWVATISYDGSQKYYADSVKGRFTISRDESKNTLYLQMNSLRAEDTA
VYHCARGSSGHYEAFDIWGQGTLVTVSSGGGGSGGGGSGGGGSQSVLTQPPSASGT
PGQRVTISCSGSSSNIGNWYVSWYQQLPGTAPKLLIYDNNKRPSGVPDRFSGSKSG
TSASLAISGLQSEDEADYYCGTWDSSLSAPWVFGGGTKLTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSGGG
GSGGGGSGGGGSNFMLTQPSSVSGVPGQRVTISCTGNTGNIGSNYVNWYQQLPGTA
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPGK
(SEQ ID NO: 92), signal sequence (1-19), NYA-2045 (21-
266), linker (267-271), C3E-7085 (272-511), linker (512-
513), hinge (514-528), CH2 (529-638), CH3 (639-745)

Fig. 94

NYF-0047-HC2
MKHLWFFLLLVAAPRWVLSGQVQLVESGGGVVQPGRSLRLSCAASGFSIRSYDMHW
VRQAPGKGLEWVATISYDGSQKYYADSVKGRFTISRDNSKNTLYLQMSSLRAEDTA
VYHCARGSSGHYEAFDIWGQGTLVTVSSGGGGSGGGGSGGGGSQSVLTQPPSVSAA
PGQKVTISCSGSSSNIGNWYVSWYQQLPGTAPKLLIYDNNKRPSGIPDRFSGSKSG
TSATLGITGLQTGDEADYYCGTWDSSLSAPWVFGGGTKVTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSGGG
GSGGGGSGGGGSNFMLTQPSSVSGVPGQRVTISCTGNTGNIGSNYVNWYQQLPGTA
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPGK
(SEQ ID NO: 93), signal sequence (1-19), NYA-2047(21-
266), linker (267-271), C3E-7085 (272-511), linker (512-
513), hinge (514-528), CH2 (529-638), CH3 (639-745)

Fig. 95

NYF-0048-HC2
MKHLWFFLLLVAAPRWVLSGQVQLVESGGGVVQPGRSLRLSCAASGFSIRSYDMHW
VRQAPGKGLEWVATISYDGSQKYYADSVKGRFTISRDNSKNTLYLQMSSLRAEDTA
VYHCARGSSGHYEAFDIWGQGTLVTVSSGGGGSGGGGSGGGGSQSVLTQPPSASGT
PGQRVTISCSGSSSNIGNWYVSWYQQLPGTAPKLLIYDNNKRPSGVPDRFSGSKSG
TSASLAISGLQSEDEADYYCGTWDSSLSAPWVFGGGTKLTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSGGG
GSGGGGSGGGGSNFMLTQPSSVSGVPGQRVTISCTGNTGNIGSNYVNWYQQLPGTA
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPGK
(SEQ ID NO: 94), signal sequence (1-19), NYA-2048(21-
266), linker (267-271), C3E-7085 (272-511), linker (512-
513), hinge (514-528), CH2 (529-638), CH3 (639-745)

Fig. 96

NYF-0060-HC2
MKHLWFFLLLVAAPRWVLSGEVQLVESGGGLVQPGGSLRLSCAASGFSIRSYDIHW
VRQAPGKGLEWVATISYDGSQKYYADSVKGRFTISRDESKNTLYLQMNSLRAEDTA
VYHCARGSSGHYEAFDIWGQGTLVTVSSGGGGSGGGGSGGGGSQSVLTQPPSVSAA
PGQKVTISCSGSSSNIGNWYVSWYQQLPGTAPKLLIYDNNKRPSGIPDRFSGSKSG
TSATLGITGLQTGDEADYYCGTWDSSLSAPWVFGGGTKVTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSGGG
GSGGGGSGGGGSNFMLTQPSSVSGVPGQRVTISCTGNTGNIGSNYVNWYQQLPGTA
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPGK
(SEQ ID NO: 95), signal sequence (1-19), NYA-2060(21-266), linker (267-271), C3E-7085 (272-511), linker (512-513), hinge (514-528), CH2 (529-638), CH3 (639-745)

Fig. 97

NYF-0061-HC2
MKHLWFFLLLVAAPRWVLSGEVQLVESGGGLVQPGGSLRLSCAASGFSIRSYDIHW
VRQAPGKGLEWVATISYDGSQKYYADSVKGRFTISRDESKNTLYLQMNSLRAEDTA
VYHCARGSSGHYEAFDIWGQGTLVTVSSGGGGSGGGGSGGGGSQSVLTQPPSASGT
PGQRVTISCSGSSSNIGNWYVSWYQQLPGTAPKLLIYDNNKRPSGVPDRFSGSKSG
TSASLAISGLQSEDEADYYCGTWDSSLSAPWVFGGGTKLTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSGGG
GSGGGGSGGGGSNFMLTQPSSVSGVPGQRVTISCTGNTGNIGSNYVNWYQQLPGTA
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPGK
(SEQ ID NO: 96), signal sequence (1-19), NYA-2061 (21-
266), linker (267-271), C3E-7085 (272-511), linker (512-
513), hinge (514-528), CH2 (529-638), CH3 (639-745)

Fig. 98

NYA-0001-Fab-HC1-k delete
ATGAAACACCTGTGGTTCTTCCTCCTGCTGGTGGCAGCTCCCAGATGGGTGCTGAG
CGAGGTGCAGCTGGTGGAGTCTGGGGGAGGCGTGGTCCAGCCTGGGAGGTCCCTGA
CACCCTCCTGTTCAGCGTCTGGATTCTCCATCCGTAGTTATGATATACACTGGGTC
CGCCAGGCTCCAGGCAAGGGGCTAGAGTGGGTGGCCACTATATCATATGATGGAAG
TCAGAAGTACTTCGCAGACTCCGTGAAGGGCCGATTTACCATCTTCAGAGACGAAT
CGGAGAACATGGTGTATCTGCAAATGAGCGGCCTGAGAGTTGAGGACACGGCTGTT
TATCACTGTGCGAGAGGGAGTAGTGGTCATTATGAGGCTTTTGATATCTGGGGCCA
AGGGACAATGGTCACCGTCTCTTCAGCCTCCACCAAGGGCCCAAGCGTCTTCCCCC
TGGCACCCTCCTCCAAGAGCACCTCTGGCGGCACAGCCGCCCTGGGCTGCCTGGTC
AAGGACTACTTCCCCGAACCCGTGACCGTGAGCTGGAACTCAGGCGCCCTGACCAG
CGGCGTGCACACCTTCCCCGCTGTCCTGCAGTCCTCAGGACTCTACTCCCTCAGCA
GCGTGGTGACCGTGCCCTCCAGCAGCTTGGGCACCCAGACCTACATCTGCAACGTG
AATCACAAGCCCAGCAACACCAAGGTGGACAAGAGAGTTGAGCCCAAATCTTGTGA
CAAAACTCACACATGCCCACCCTGCCCAGCACCTGAAGCCGCAGGGGGACCCTCAG
TCTTCCTCTTCCCCCCAAAACCCAAGGACACCCTCATGATCTCCCGGACCCCTGAG
GTCACATGCGTGGTGGTGTCAGTGAGCCACGAAGACCCTGAGGTCAAGTTCAACTG
GTACGTGGACGGCGTGGAGGTGCATAATGCCAAGACAAAGCCCCGGGAGGAGCAGT
ACAACAGCACGTACCGGGTGGTCAGCGTCCTCACCGTCCTGCACCAGGACTGGCTG
AATGGCAAGGAGTACAAGTGCAAGGTCTCCAACAAAGCCCTCCCAGCCCCCATCGA
GAAAACCATCTCCAAAGCCAAAGGCCAGCCCCGGGAACCACAGGTGTACGTGCTGC
CCCCATCCCGGGACGAGCTGACCAAGAACCAGGTCAGCCTGCTGTGCCTGGTCAAA
GGCTTCTATCCCAGCGACATCGCCGTGGAGTGGGAGAGCAATGGCCAGCCCGAGAA
CAACTACCTGACCTGGCCTCCCGTGCTGGACTCCGACGGCTCCTTCTTCCTCTACA
GCAAGCTCACCGTGGACAAGAGCAGGTGGCAGCAGGGCAACGTCTTCTCATGCTCC
GTGATGCATGAGGCTCTGCACAACCACTACACCCAGAAGAGCCTCTCCCTGTCTCC
CGGC
(SEQ ID NO: 97), signal sequence (1-57), NYA-0001_VH
(58-417), CH1 (418-711), hinge (712-756), CH2 (757-1086),
CH3 (1087-1404)

Fig. 99

NYA-0001-LC
ATGGTGCTGCAGACCCAGGTGTTCATCTCCCTGCTGCTGTGGATCTCCGGCGCGTA
CGGCCAGTCTGTGTTGACGCAGCCGCCCTCAGTGTCTGCGGCCCCAGGACAGAAGG
TCACCATCTCCTGCTCTGGAAGCAGCTCCAACATTGGGAATAATTATGTATCCTGG
TACCAGCAGCTCCCAGGAACAGCCCCCAAACTCCTCATTTATGACAATAATAAGCG
ACCCTCAGGGATTCCTGACCGATTCTCTGGCTCCAAGTCTGGCACGTCAGCCACCC
TGGGCATCACCGGACTCCAGACTGGGGACGAGGCCGATTATTACTGCGGAACATGG
GATAGCAGCCTGAGTGCCCCTTGGGTGTTCGGCGGAGGGACCAAGGTCACCGTCCT
AGGCCAGCCTAAGGCTGCCCCTAGCGTGACCCTGTTCCCTCCTTCCAGCGAGGAGC
TTCAAGCTAACAAGGCCACCCTGGTGTGTCTTATCTCTGACTTCTACCCTGGCGCT
GTGACCGTGGCCTGGAAGGCTGACAGCTCCCTGTGAAGGCCGGAGTGGAGACCAC
CACACCTAGCAAGCAGTCTAACAACAAGTACGCTGCCAGCTCCTACCTGAGCCTTA
CCCCTGAGCAGTGGAAGTCTCACAGAAGCTACTCCTGTCAAGTGACCCACGAGGGC
AGCACCGTGGAGAAGACCGTGGCTCCTACCGAGTGTTCC
(SEQ ID NO: 98), signal sequence (1-60), NYA-0001_VL
(61-393), CL (394-711)

Fig. 100

NYA-0001-Fab-HC1-k delete
MKHLWFFLLLVAAPRWVLSEVQLVESGGGVVQPGRSLTPSCSASGFSIRSYDIHWV
RQAPGKGLEWVATISYDGSQKYFADSVKGRFTIFRDESENMVYLQMSGLRVEDTAV
YHCARGSSGHYEAFDIWGQGTMVTVSSASTKGPSVFPLAPSSKSTSGGTAALGCLV
KDYFPEPVTVSWNSGALTSGVHTFPAVLQSSGLYSLSSVVTVPSSSLGTQTYICNV
NHKPSNTKVDKRVEPKSCDKTHTCPPCPAPEAAGGPSVFLFPPKPKDTLMISRTPE
VTCVVVSVSHEDPEVKFNWYVDGVEVHNAKTKPREEQYNSTYRVVSVLTVLHQDWL
NGKEYKCKVSNKALPAPIEKTISKAKGQPREPQVYVLPPSRDELTKNQVSLLCLVK
GFYPSDIAVEWESNGQPENNYLTWPPVLDSDGSFFLYSKLTVDKSRWQQGNVFSCS
VMHEALHNHYTQKSLSLSPG
(SEQ ID NO: 99), signal sequence (1-19), NYA-0001_VH
(20-139), CH1 (140-237), hinge (238-252), CH2 (253-362),
CH3 (363-468)

Fig. 101

NYA-0001-LC
MVLQTQVFISLLLWISGAYGQSVLTQPPSVSAAPGQKVTISCSGSSSNIGNNYVSW
YQQLPGTAPKLLIYDNNKRPSGIPDRFSGSKSGTSATLGITGLQTGDEADYYCGTW
DSSLSAPWVFGGGTKVTVLGQPKAAPSVTLFPPSSEELQANKATLVCLISDFYPGA
VTVAWKADSSPVKAGVETTTPSKQSNNKYAASSYLSLTPEQWKSHRSYSCQVTHEG
STVEKTVAPTECS
(SEQ ID NO: 100), signal sequence (1-20), NYA-0001_VL
(21-131), CL (132-237)

Fig. 102

NYA-1143-Fab-HC1-k delete
ATGAAACACCTGTGGTTCTTCCTCCTGCTGGTGGCAGCTCCCAGATGGGTGCTGAG
CGAGGTGCAGCTGGTGGAGTCTGGGGGAGGCGTGGTCCAGCCTGGGAGGTCCCTGA
CACCCTCCTGTTCAGCGTCTGGATTCTCCATCCGTAGCTATGATATACACTGGGTC
CGCCTGGCTCCAGGCAAGGGGCTAGAGTGGGTGGCCACTATATCATATGATGGAAG
TCAGAAGTACTTCGCAGACTCCGTGAAGGGCCGATTTACCATCTTCAGAGACGAAT
CGGAGAACATGGTGTATCTGCAAATGAGCGGCCTGAGAGTTGAGGACACGGCTGTT
TATCACTGTGCGAGAGGGAGTAGTGGTCATTATGAGGCTTTTGATATCTGGGGCCA
AGGGACAATGGTCACCGTCTCTTCAGCCTCCACCAAGGGCCCAAGCGTCTTCCCCC
TGGCACCCTCCTCCAAGAGCACCTCTGGCGGCACAGCCGCCCTGGGCTGCCTGGTC
AAGGACTACTTCCCCGAACCCGTGACCGTGAGCTGGAACTCAGGCGCCCTGACCAG
CGGCGTGCACACCTTCCCCGCTGTCCTGCAGTCCTCAGGACTCTACTCCCTCAGCA
GCGTGGTGACCGTGCCCTCCAGCAGCTTGGGCACCCAGACCTACATCTGCAACGTG
AATCACAAGCCCAGCAACACCAAGGTGGACAAGAGAGTTGAGCCCAAATCTTGTGA
CAAAACTCACACATGCCCACCCTGCCCAGCACCTGAAGCCGCAGGGGGACCCTCAG
TCTTCCTCTTCCCCCCAAAACCCAAGGACACCCTCATGATCTCCCGGACCCCTGAG
GTCACATGCGTGGTGGTGTCAGTGAGCCACGAAGACCCTGAGGTCAAGTTCAACTG
GTACGTGGACGGCGTGGAGGTGCATAATGCCAAGACAAAGCCCCGGGAGGAGCAGT
ACAACAGCACGTACCGGGTGGTCAGCGTCCTCACCGTCCTGCACCAGGACTGGCTG
AATGGCAAGGAGTACAAGTGCAAGGTCTCCAACAAAGCCCTCCCAGCCCCCATCGA
GAAAACCATCTCCAAAGCCAAAGGCCAGCCCCGGGAACCACAGGTGTACGTGCTGC
CCCCATCCCGGGACGAGCTGACCAAGAACCAGGTCAGCCTGCTGTGCCTGGTCAAA
GGCTTCTATCCCAGCGACATCGCCGTGGAGTGGGAGAGCAATGGCCAGCCCGAGAA
CAACTACCTGACCTGGCCTCCCGTGCTGGACTCCGACGGCTCCTTCTTCCTCTACA
GCAAGCTCACCGTGGACAAGAGCAGGTGGCAGCAGGGCAACGTCTTCTCATGCTCC
GTGATGCATGAGGCTCTGCACAACCACTACACCCAGAAGAGCCTCTCCCTGTCTCC
CGGC
(SEQ ID NO: 101), signal sequence (1-57), NYA-1143_VH
(58-417), CH1 (418-711), hinge (712-756), CH2 (757-1086),
CH3 (1087-1404)

Fig. 103

NYA-1143-LC
ATGGTGCTGCAGACCCAGGTGTTCATCTCCCTGCTGCTGTGGATCTCCGGCGCGTA
CGGCCAGTCTGTGTTGACGCAGCCGCCCTCAGTGTCTGCGGCCCCAGGACAGAAGG
TCACCATCTCCTGCTCTGGAAGCAGCTCCAACATTGGGAATTGGTATGTATCCTGG
TACCAGCAGCTCCCAGGAACAGCCCCCAAACTCCTCATTTATGACAATAATAAGCG
ACCCTCAGGGATTCCTGACCGATTCTCTGGCTCCAAGTCTGGCACGTCAGCCACCC
TGGGCATCACCGGACTCCAGACTGGGGACGAGGCCGATTATTACTGCGGAACATGG
GATAGCAGCCTGAGTGCCCCTTGGGTGTTCGGCGGAGGGACCAAGGTCACCGTCCT
AGGCCAGCCTAAGGCTGCCCCTAGCGTGACCCTGTTCCCTCCTTCCAGCGAGGAGC
TTCAAGCTAACAAGGCCACCCTGGTGTGTCTTATCTCTGACTTCTACCCTGGCGCT
GTGACCGTGGCCTGGAAGGCTGACAGCTCCCTGTGAAGGCCGGAGTGGAGACCAC
CACACCTAGCAAGCAGTCTAACAACAAGTACGCTGCCAGCTCCTACCTGAGCCTTA
CCCCTGAGCAGTGGAAGTCTCACAGAAGCTACTCCTGTCAAGTGACCCACGAGGGC
AGCACCGTGGAGAAGACCGTGGCTCCTACCGAGTGTTCC
(SEQ ID NO: 102), signal sequence (1-60), NYA-1143_VL
(61-393), CL (394-711)

Fig. 104

C3E-7085-HC2-k delete
ATGAAACACCTGTGGTTCTTCCTCCTGCTGGTGGCAGCTCCCAGATGGGTGCTGAG
CGGAGAAGTGCAGCTGGTGGAATCCGGGGGGGGCCTGGTGCAGCCTGGGGGGAGCC
TGAGACTGAGTTGTGCCGCCTCTGGGGTGACATTTAACTACTATGGCATGTCTTGG
ATCCGCCAGGCACCTGGAAAGGGCCTGGAGTGGGTGGCCAGCATCACTAGGTCCGG
CGGGCGAATCTACTATCCCGACAGCGTCAAGGGCAGGTTCACAATTTCCCGCGAGA
ACACACAGAAAACTCTGTACCTGCAGATGAATAGCCTGAGAGCCGAAGATACAGCT
GTGTACTATTGCACTCTGGACGGCAGGGATGGGTGGTCGCCTATTGGGGCAGGG
AACCCTGGTGACAGTCAGCTCCGGAGGAGGAGGATCTGGCGGAGGAGGCAGTGGGG
GAGGCGGGTCAAACTTTATGCTCACTCAGCCGTCCTCTGTTTCTGGCGTACCTGGC
CAACGGGTGACCATTAGCTGTACGGGTAATACCGGGAATATCGGGTCTAACTACGT
GAACTGGTATCAGCAGCTTCCAGGGACAGCTCCCAAGTTGCTGATCTATCGCGACG
ACAAAAGACCCTCAGGGGTCCCTGACCGATTTAGTGGCAGCAAAAGCGGTACTTCC
GCTTCCCTGGCGATAACCGGCTTTCAGGCCGAAGATGAGGCAGACTACTATTGCCA
GTCATATTCCAGCGGCTTCATCTTCGGAGGCGGAACTAAGCTGACAGTGTTGGCAG
CCGAGCCCAAATCTTCTGACAAAACTCACACATGCCCACCCTGCCCAGCACCTGAA
GCCGCAGGGGGACCCTCAGTCTTCCTCTTCCCCCCAAAACCCAAGGACACCCTCAT
GATCTCCCGGACCCCTGAGGTCACATGCGTGGTGGTGTCAGTGAGCCACGAAGACC
CTGAGGTCAAGTTCAACTGGTACGTGGACGGCGTGGAGGTGCATAATGCCAAGACA
AAGCCCCGGGAGGAGCAGTACAACAGCACGTACCGGGTGGTCAGCGTCCTCACCGT
CCTGCACCAGGACTGGCTGAATGGCAAGGAGTACAAGTGCAAGGTCTCCAACAAAG
CCCTCCCAGCCCCCATCGAGAAAACCATCTCCAAAGCCAAAGGCCAGCCCCGGGAA
CCACAGGTGTACGTGTACCCCCCATCCCGGGACGAGCTGACCAAGAACCAGGTCAG
CCTGACCTGCCTGGTCAAAGGCTTCTATCCCAGCGACATCGCCGTGGAGTGGGAGA
GCAATGGCCAGCCCGAGAACAACTACAAGACCACCCCTCCCGTGCTGGACTCCGAC
GGCTCCTTCGCCCTCGTGAGCAAGCTCACCGTGGACAAGAGCAGGTGGCAGCAGGG
CAACGTCTTCTCATGCTCCGTGATGCATGAGGCTCTGCACAACCACTACACCCAGA
AGAGCCTCTCCCTGTCTCCC
(SEQ ID NO: 103), signal sequence (1-57), C3E-7085 (61-
780), linker (781-786), hinge (787-831), CH2 (832-1161),
CH3 (1162-1479)

Fig. 105

NYA-1143-Fab-HC1-k delete
MKHLWFFLLLVAAPRWVLSEVQLVESGGGVVQPGRSLTPSCSASGFSIRSYDIHWV
RLAPGKGLEWVATISYDGSQKYFADSVKGRFTIFRDESENMVYLQMSGLRVEDTAV
YHCARGSSGHYEAFDIWGQGTMVTVSSASTKGPSVFPLAPSSKSTSGGTAALGCLV
KDYFPEPVTVSWNSGALTSGVHTFPAVLQSSGLYSLSSVVTVPSSSLGTQTYICNV
NHKPSNTKVDKRVEPKSCDKTHTCPPCPAPEAAGGPSVFLFPPKPKDTLMISRTPE
VTCVVVSVSHEDPEVKFNWYVDGVEVHNAKTKPREEQYNSTYRVVSVLTVLHQDWL
NGKEYKCKVSNKALPAPIEKTISKAKGQPREPQVYVLPPSRDELTKNQVSLLCLVK
GFYPSDIAVEWESNGQPENNYLTWPPVLDSDGSFFLYSKLTVDKSRWQQGNVFSCS
VMHEALHNHYTQKSLSLSPG
(SEQ ID NO: 104), signal sequence (1-19), NYA-1143_VH
(20-139), CH1 (140-237), hinge (238-252), CH2 (253-362),
CH3 (363-468)

Fig. 106

NYA-1143-LC
MVLQTQVFISLLLWISGAYGQSVLTQPPSVSAAPGQKVTISCSGSSSNIGNWYVSW
YQQLPGTAPKLLIYDNNKRPSGIPDRFSGSKSGTSATLGITGLQTGDEADYYCGTW
DSSLSAPWVFGGGTKVTVLGQPKAAPSVTLFPPSSEELQANKATLVCLISDFYPGA
VTVAWKADSSPVKAGVETTTPSKQSNNKYAASSYLSLTPEQWKSHRSYSCQVTHEG
STVEKTVAPTECS
(SEQ ID NO: 105), signal sequence (1-20), NYA-1143_VL
(21-131), CL (132-237)

Fig. 107

C3E-7085-HC2-k delete
MKHLWFFLLLVAAPRWVLSGEVQLVESGGGLVQPGGSLRLSCAASGVTFNYYGMSW
IRQAPGKGLEWVASITRSGGRIYYPDSVKGRFTISRENTQKTLYLQMNSLRAEDTA
VYYCTLDGRDGWVAYWGQGTLVTVSSGGGGSGGGGSGGGGSNFMLTQPSSVSGVPG
QRVTISCTGNTGNIGSNYVNWYQQLPGTAPKLLIYRDDKRPSGVPDRFSGSKSGTS
ASLAITGFQAEDEADYYCQSYSSGFIFGGGTKLTVLAAEPKSSDKTHTCPPCPAPE
AAGGPSVFLFPPKPKDTLMISRTPEVTCVVVSVSHEDPEVKFNWYVDGVEVHNAKT
KPREEQYNSTYRVVSVLTVLHQDWLNGKEYKCKVSNKALPAPIEKTISKAKGQPRE
PQVYVYPPSRDELTKNQVSLTCLVKGFYPSDIAVEWESNGQPENNYKTTPPVLDSD
GSFALVSKLTVDKSRWQQGNVFSCSVMHEALHNHYTQKSLSLSPG
(SEQ ID NO: 106), signal sequence (1-19), C3E-7085 (21-
260), linker (261-262), hinge (263-277), CH2 (278-387),
CH3 (388-493)

Fig. 108

NYA-1143-HC1-k delete
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGCTATGATATACACTGG
GTCCGCCTGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCT
GTTTATCACTGTGCGAGAGGGAGTAGTGGTCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATTG
GTATGTATCCTGGTACCAGCAGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTATTA
CTGCGGAACATGGGATAGCAGCCTGAGTGCCCCTTGGGTGTTCGGCGGAGGGACCA
AGGTCACCGTCCTAGCAGCCGAGCCCAAATCTTCTGACAAAACTCACACATGCCCA
CCCTGCCCAGCACCTGAAGCCGCAGGGGGACCCTCAGTCTTCCTCTTCCCCCCAAA
ACCCAAGGACACCCTCATGATCTCCCGGACCCCTGAGGTCACATGCGTGGTGGTGT
CAGTGAGCCACGAAGACCCTGAGGTCAAGTTCAACTGGTACGTGGACGGCGTGGAG
GTGCATAATGCCAAGACAAAGCCCCGGGAGGAGCAGTACAACAGCACGTACCGGGT
GGTCAGCGTCCTCACCGTCCTGCACCAGGACTGGCTGAATGGCAAGGAGTACAAGT
GCAAGGTCTCCAACAAAGCCCTCCCAGCCCCCATCGAGAAAACCATCTCCAAAGCC
AAAGGCCAGCCCCGGGAACCACAGGTGTACGTGCTGCCCCCATCCCGGGACGAGCT
GACCAAGAACCAGGTCAGCCTGCTGTGCCTGGTCAAAGGCTTCTATCCCAGCGACA
TCGCCGTGGAGTGGGAGAGCAATGGCCAGCCCGAGAACAACTACCTGACCTGGCCT
CCCGTGCTGGACTCCGACGGCTCCTTCTTCCTCTACAGCAAGCTCACCGTGGACAA
GAGCAGGTGGCAGCAGGGCAACGTCTTCTCATGCTCCGTGATGCATGAGGCTCTGC
ACAACCACTACACCCAGAAGAGCCTCTCCCTGTCTCCCGGC
(SEQ ID NO: 107), signal sequence (1-57), NYA-1143 (61-798), linker799-800), hinge (801-849), CH2 (850-1179), CH3 (1180-1497)

Fig. 109

NYA-1143-HC1-k delete
MKHLWFFLLLVAAPRWVLSGEVQLVESGGGVVQPGRSLTPSCSASGFSIRSYDIHW
VRLAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNWYVSWYQQLPGTAPKLLIYDNNKRPSGIPDRFSGSKSG
TSATLGITGLQTGDEADYYCGTWDSSLSAPWVFGGGTKVTVLAAEPKSSDKTHTCP
PCPAPEAAGGPSVFLFPPKPKDTLMISRTPEVTCVVVSVSHEDPEVKFNWYVDGVE
VHNAKTKPREEQYNSTYRVVSVLTVLHQDWLNGKEYKCKVSNKALPAPIEKTISKA
KGQPREPQVYVLPPSRDELTKNQVSLLCLVKGFYPSDIAVEWESNGQPENNYLTWP
PVLDSDGSFFLYSKLTVDKSRWQQGNVFSCSVMHEALHNHYTQKSLSLSPG
(SEQ ID NO: 108), signal sequence (1-19), NYA-1143 (21-
266), linker (267-268), hinge (269-283), CH2 (284-393),
CH3 (394-499)

Fig. 110

C3E-7085-NYA-1154-Fab-HC2-k delete
ATGAAACACCTGTGGTTCTTCCTCCTGCTGGTGGCAGCTCCCAGATGGGTGCTGAG
CGGAGAAGTGCAGCTGGTGGAATCCGGGGGGGGCCTGGTGCAGCCTGGGGGGAGCC
TGAGACTGAGTTGTGCCGCCTCTGGGGTGACATTAACTACTATGGCATGTCTTGG
ATCCGCCAGGCACCTGGAAAGGGCCTGGAGTGGGTGGCCAGCATCACTAGGTCCGG
CGGGCGAATCTACTATCCCGACAGCGTCAAGGGCAGGTTCACAATTTCCGCGAGA
ACACACAGAAAACTCTGTACCTGCAGATGAATAGCCTGAGAGCCGAAGATACAGCT
GTGTACTATTGCACTCTGGACGGCAGGGATGGGTGGGTCGCCTATTGGGGCAGGG
AACCCTGGTGACAGTCAGCTCCGGAGGAGGAGGATCTGGCGGAGGAGGCAGTGGGG
GAGGCGGGTCAAACTTTATGCTCACTCAGCCGTCCTCTGTTTCTGGCGTACCTGGC
CAACGGGTGACCATTAGCTGTACGGGTAATACCGGAATATCGGGTCTAACTACGT
GAACTGGTATCAGCAGCTTCCAGGGACAGCTCCCAAGTTGCTGATCTATCGCGACG
ACAAAAGACCCTCAGGGGTCCCTGACCGATTTAGTGGCAGCAAAAGCGGTACTTCC
GCTTCCCTGGCGATAACCGGCTTTCAGGCCGAAGATGAGGCAGACTACTATTGCCA
GTCATATTCCAGCGGCTTCATCTTCGGAGGCGGAACTAAGCTGACAGTGTTGGGGG
GAGGCGGTTCAGAGGTGCAGCTGGTGGAGTCTGGGGGAGGCGTGGTCCAGCCTGGG
AGGTCCCTGACACCCTCCTGTTCAGCGTCTGGATTCTCCATCCGTAGTTATGATAT
GCACTGGGTCCGCCAGGCTCCAGGCAAGGGGCTAGAGTGGGTGGCCACTATATCAT
ATGATGGAAGTCAGAAGTACTTCGCAGACTCCGTGAAGGGCCGATTTACCATCTTC
AGAGACGAATCGGAGAACATGGTGTATCTGCAAATGAGCGGCCTGAGAGTTGAGGA
CACGGCCGTTTATCACTGTGCGAGAGGGAGTAGTAATCATTATGAGGCTTTTGATA
TCTGGGGCCAAGGGACAATGGTCACCGTCTCTTCAGCCTCCACCAAGGGCCCAAGC
GTCTTCCCCCTGGCACCCTCCTCCAAGAGCACCTCTGGCGGCACAGCCGCCCTGGG
CTGCCTGGTCAAGGACTACTTCCCCGAACCCGTGACCGTGAGCTGGAACTCAGGCG
CCCTGACCAGCGGCGTGCACACCTTCCCCGCTGTCCTGCAGTCCTCAGGACTCTAC
TCCCTCAGCAGCGTGGTGACCGTGCCCTCCAGCAGCTTGGGCACCCAGACCTACAT
CTGCAACGTGAATCACAAGCCCAGCAACACCAAGGTGGACAAGAGAGTTGAGCCCA
AATCTTGTGACAAAACTCACACATGCCCACCCTGCCCAGCACCTGAAGCCGCAGGG
GGACCCTCAGTCTTCCTCTTCCCCCCAAAACCCAAGGACACCCTCATGATCTCCCG
GACCCCTGAGGTCACATGCGTGGTGGTGTCAGTGAGCCACGAAGACCCTGAGGTCA
AGTTCAACTGGTACGTGGACGGCGTGGAGGTGCATAATGCCAAGACAAAGCCCCGG
GAGGAGCAGTACAACAGCACGTACCGGGTGGTCAGCGTCCTCACCGTCCTGCACCA
GGACTGGCTGAATGGCAAGGAGTACAAGTGCAAGGTCTCCAACAAAGCCCTCCCAG
CCCCCATCGAGAAACCATCTCCAAAGCCAAAGGCCAGCCCCGGGAACCACAGGTG
TACGTGTACCCCCCATCCCGGGACGAGCTGACCAAGAACCAGGTCAGCCTGACCTG
CCTGGTCAAAGGCTTCTATCCCAGCGACATCGCCGTGGAGTGGGAGAGCAATGGCC
AGCCCGAGAACAACTACAAGACCACCCCTCCCGTGCTGGACTCCGACGGCTCCTTC
GCCCTCGTGAGCAAGCTCACCGTGGACAAGAGCAGGTGGCAGCAGGGCAACGTCTT
CTCATGCTCCGTGATGCATGAGGCTCTGCACAACCACTACACCCAGAAGAGCCTCT
CCCTGTCTCCCGGC
(SEQ ID NO: 109), signal sequence (1-57), C3E-7085 (61-780), linker (781-795), NYA-1154-VH (796-1155), CH1 (1156-1470), hinge (1471-1500), CH2 (1501-1830), CH3 (1831-2142)

Fig. 111

NYA-1154-LC
ATGGTGCTGCAGACCCAGGTGTTCATCTCCCTGCTGCTGTGGATCTCCGGCGCGTA
CGGCCAGTCTGTGTTGACGCAGCCGCCCTCAGTGTCTGCGGCCCCAGGACAGAAGG
TCACCATCTCCTGCTCTGGAAGCAGCTCCAACATTGGGAATAATTATGTATCCTGG
TACCAGCGGCTCCCAGGAACAGCCCCCAAACTCCTCATTTATGACAATAATAAGCG
ACCCTCAGGGATTCCTGACCGATTCTCTGGCTCCAAGTCTGGCACGTCAGCCACCC
TGGGCATCACCGGACTCCAGACTGGGGACGAGGCCGATTACTACTGCGGAGCATGG
GATAGCAGCCTGAGTGCCCCTTGGGTGTTCGGCGGAGGGACCAAGGTCACCGTCCT
AGGCCAGCCTAAGGCTGCCCCTAGCGTGACCCTGTTCCCTCCTTCCAGCGAGGAGC
TTCAAGCTAACAAGGCCACCCTGGTGTGTCTTATCTCTGACTTCTACCCTGGCGCT
GTGACCGTGGCCTGGAAGGCTGACAGCTCCCTGTGAAGGCCGGAGTGGAGACCAC
CACACCTAGCAAGCAGTCTAACAACAAGTACGCTGCCAGCTCCTACCTGAGCCTTA
CCCCTGAGCAGTGGAAGTCTCACAGAAGCTACTCCTGTCAAGTGACCCACGAGGGC
AGCACCGTGGAGAAGACCGTGGCTCCTACCGAGTGTTCC
(SEQ ID NO: 110), signal sequence (1-60), NYA-1154_VL
(61-393), CL (394-711)

Fig. 112

OAA-HC1-k delete
ATGAAACACCTGTGGTTCTTCCTCCTGCTGGTGGCAGCTCCCAGATGGGTGCTGAG
CGACAAAACTCACACATGCCCACCCTGCCCAGCACCTGAAGCCGCAGGGGGACCCT
CAGTCTTCCTCTTCCCCCCAAAACCCAAGGACACCCTCATGATCTCCCGGACCCCT
GAGGTCACATGCGTGGTGGTGTCAGTGAGCCACGAAGACCCTGAGGTCAAGTTCAA
CTGGTACGTGGACGGCGTGGAGGTGCATAATGCCAAGACAAAGCCCCGGGAGGAGC
AGTACAACAGCACGTACCGGGTGGTCAGCGTCCTCACCGTCCTGCACCAGGACTGG
CTGAATGGCAAGGAGTACAAGTGCAAGGTCTCCAACAAAGCCCTCCCAGCCCCCAT
CGAGAAAACCATCTCCAAAGCCAAAGGCCAGCCCCGGGAACCACAGGTGTACGTGC
TGCCCCCATCCCGGGACGAGCTGACCAAGAACCAGGTCAGCCTGCTGTGCCTGGTC
AAAGGCTTCTATCCCAGCGACATCGCCGTGGAGTGGGAGAGCAATGGCCAGCCCGA
GAACAACTACCTGACCTGGCCTCCCGTGCTGGACTCCGACGGCTCCTTCTTCCTCT
ACAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTC
TCCCGGC
(SEQ ID NO: 111), signal sequence (1-57), hinge (58-87),
CH2 (88-417), CH3 (418-735)

Fig. 113

C3E-7085-NYA-1154-Fab-HC2-k delete
MKHLWFFLLLVAAPRWVLSGEVQLVESGGGLVQPGGSLRLSCAASGVTFNYYGMSW
IRQAPGKGLEWVASITRSGGRIYYPDSVKGRFTISRENTQKTLYLQMNSLRAEDTA
VYYCTLDGRDGWVAYWGQGTLVTVSSGGGGSGGGGSGGGGSNFMLTQPSSVSGVPG
QRVTISCTGNTGNIGSNYVNWYQQLPGTAPKLLIYRDDKRPSGVPDRFSGSKSGTS
ASLAITGFQAEDEADYYCQSYSSGFIFGGGTKLTVLGGGGSEVQLVESGGGVVQPG
RSLTPSCSASGFSIRSYDMHWVRQAPGKGLEWVATISYDGSQKYFADSVKGRFTIF
RDESENMVYLQMSGLRVEDTAVYHCARGSSNHYEAFDIWGQGTMVTVSSASTKGPS
VFPLAPSSKSTSGGTAALGCLVKDYFPEPVTVSWNSGALTSGVHTFPAVLQSSGLY
SLSSVVTVPSSSLGTQTYICNVNHKPSNTKVDKRVEPKSCDKTHTCPPCPAPEAAG
GPSVFLFPPKPKDTLMISRTPEVTCVVVSVSHEDPEVKFNWYVDGVEVHNAKTKPR
EEQYNSTYRVVSVLTVLHQDWLNGKEYKCKVSNKALPAPIEKTISKAKGQPREPQV
YVYPPSRDELTKNQVSLTCLVKGFYPSDIAVEWESNGQPENNYKTTPPVLDSDGSF
ALVSKLTVDKSRWQQGNVFSCSVMHEALHNHYTQKSLSLSPG
(SEQ ID NO: 112), signal sequence (1-19), C3E-7085 (21-
260), linker (261-265), NYA-1154-VH (266-385), CH1 (386-
490), hinge (491-500), CH2 (501-610), CH3 (611-714)

Fig. 114

NYA-1154-LC
MVLQTQVFISLLLWISGAYGQSVLTQPPSVSAAPGQKVTISCSGSSSNIGNNYVSW
YQRLPGTAPKLLIYDNNKRPSGIPDRFSGSKSGTSATLGITGLQTGDEADYYCGAW
DSSLSAPWVFGGGTKVTVLGQPKAAPSVTLFPPSSEELQANKATLVCLISDFYPGA
VTVAWKADSSPVKAGVETTTPSKQSNNKYAASSYLSLTPEQWKSHRSYSCQVTHEG
STVEKTVAPTECS
(SEQ ID NO: 113), signal sequence (1-20), NYA-1154_VL
(21-131), CL (132-237)

Fig. 115

OAA-HC1-k delete
MKHLWFFLLLVAAPRWVLSDKTHTCPPCPAPEAAGGPSVFLFPPKPKDTLMISRTP
EVTCVVVSVSHEDPEVKFNWYVDGVEVHNAKTKPREEQYNSTYRVVSVLTVLHQDW
LNGKEYKCKVSNKALPAPIEKTISKAKGQPREPQVYVLPPSRDELTKNQVSLLCLV
KGFYPSDIAVEWESNGQPENNYLTWPPVLDSDGSFFLYSKLTVDKSRWQQGNVFSC
SVMHEALHNHYTQKSLSLSPG
(SEQ ID NO: 114), signal sequence (1-19), hinge (20-29),
CH2 (30-139), CH3 (140-245)

Fig. 116

NYF-0010-HC2-k delete
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGTTATGATATGCACTGG
GTCCGCCAGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCC
GTTTATCACTGTGCGAGAGGGAGTAGTAATCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATAA
TTATGTATCCTGGTACCAGCGGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTACTA
CTGCGGAGCATGGGATAGCAGCCTGAGTGCCCCTTGGGTGTTCGGCGGAGGGACCA
AGGTCACCGTCCTAGGGGAGGCGGTTCAGAAGTGCAGCTGGTGGAATCCGGGGGG
GGCCTGGTGCAGCCTGGGGGGAGCCTGAGACTGAGTTGTGCCGCCTCTGGGGTGAC
ATTTAACTACTATGGCATGTCTTGGATCCGCCAGGCACCTGGAAAGGGCCTGGAGT
GGGTGGCCAGCATCACTAGGTCCGGCGGGCGAATCTACTATCCCGACAGCGTCAAG
GGCAGGTTCACAATTTCCCGCGAGAACACACAGAAAACTCTGTACCTGCAGATGAA
TAGCCTGAGAGCCGAAGATACAGCTGTGTACTATTGCACTCTGGACGGCAGGGATG
GGTGGGTCGCCTATTGGGGCAGGGAACCCTGGTGACAGTCAGCTCCGGAGGAGGA
GGATCTGGCGGAGGAGGCAGTGGGGAGGCGGGTCAAACTTTATGCTCACTCAGCC
GTCCTCTGTTTCTGGCGTACCTGGCCAACGGGTGACCATTAGCTGTACGGGTAATA
CCGGGAATATCGGGTCTAACTACGTGAACTGGTATCAGCAGCTTCCAGGGACAGCT
CCCAAGTTGCTGATCTATCGCGACGACAAAGACCCTCAGGGGTCCCTGACCGATT
TAGTGGCAGCAAAAGCGGTACTTCCGCTTCCCTGGCGATAACCGGCTTTCAGGCCG
AAGATGAGGCAGACTACTATTGCCAGTCATATTCCAGCGGCTTCATCTTCGGAGGC
GGAACTAAGCTGACAGTGTTGGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCCGGC
(SEQ ID NO: 115), signal sequence (1-57), NYA-1154(61-798), linker (799-813), C3E-7085 (814-1533), linker (1534-1539), hinge (1540-1584), CH2 (1585-1914), CH3 (1915-2232)

Fig. 117

NYF-0004-HC2-k delete
ATGAAACACCTGTGGTTCTTCCTCCTGCTGGTGGCAGCTCCCAGATGGGTGCTGAG
CGGAGAAGTGCAGCTGGTGGAATCCGGGGGGGGCCTGGTGCAGCCTGGGGGGAGCC
TGAGACTGAGTTGTGCCGCCTCTGGGGTGACATTAACTACTATGGCATGTCTTGG
ATCCGCCAGGCACCTGGAAAGGGCCTGGAGTGGGTGGCCAGCATCACTAGGTCCGG
CGGGCGAATCTACTATCCCGACAGCGTCAAGGGCAGGTTCACAATTTCCCGCGAGA
ACACACAGAAAACTCTGTACCTGCAGATGAATAGCCTGAGAGCCGAAGATACAGCT
GTGTACTATTGCACTCTGGACGGCAGGGATGGGTGGTCGCCTATTGGGGCAGGG
AACCCTGGTGACAGTCAGCTCCGGAGGAGGAGGATCTGGCGGAGGAGGCAGTGGGG
GAGGCGGGTCAAACTTTATGCTCACTCAGCCGTCCTCTGTTTCTGGCGTACCTGGC
CAACGGGTGACCATTAGCTGTACGGGTAATACCGGGAATATCGGGTCTAACTACGT
GAACTGGTATCAGCAGCTTCCAGGGACAGCTCCCAAGTTGCTGATCTATCGCGACG
ACAAAAGACCCTCAGGGGTCCCTGACCGATTTAGTGGCAGCAAAAGCGGTACTTCC
GCTTCCCTGGCGATAACCGGCTTTCAGGCCGAAGATGAGGCAGACTACTATTGCCA
GTCATATTCCAGCGGCTTCATCTTCGGAGGCGGAACTAAGCTGACAGTGTTGGGGG
GAGGCGGTTCAGAGGTGCAGCTGGTGGAGTCTGGGGGAGGCGTGGTCCAGCCTGGG
AGGTCCCTGACACCCTCCTGTTCAGCGTCTGGATTCTCCATCCGTAGTTATGATAT
GCACTGGGTCCGCCAGGCTCCAGGCAAGGGGCTAGAGTGGGTGGCCACTATATCAT
ATGATGGAAGTCAGAAGTACTTCGCAGACTCCGTGAAGGGCCGATTTACCATCTTC
AGAGACGAATCGGAGAACATGGTGTATCTGCAAATGAGCGGCCTGAGAGTTGAGGA
CACGGCCGTTTATCACTGTGCGAGAGGGAGTAGTAATCATTATGAGGCTTTTGATA
TCTGGGGCCAAGGGACAATGGTCACCGTCTCTTCAGGTGGAGGCGGTTCAGGCGGA
GGTGGCAGCGGCGGTGGCGGGAGTCAGTCTGTGTTGACGCAGCCGCCCTCAGTGTC
TGCGGCCCCAGGACAGAAGGTCACCATCTCCTGCTCTGGAAGCAGCTCCAACATTG
GGAATAATTATGTATCCTGGTACCAGCGGCTCCCAGGAACAGCCCCCAAACTCCTC
ATTTATGACAATAATAAGCGACCCTCAGGGATTCCTGACCGATTCTCTGGCTCCAA
GTCTGGCACGTCAGCCACCCTGGGCATCACCGGACTCCAGACTGGGGACGAGGCCG
ATTACTACTGCGGAGCATGGGATAGCAGCCTGAGTGCCCCTTGGGTGTTCGGCGGA
GGGACCAAGGTCACCGTCCTAGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCCGGC
(SEQ ID NO: 116), signal sequence (1-57), C3E-7085 (61-780), linker (781-795), NYA-1154(796-1533), linker (1534-1539), hinge (1540-1584), CH2 (1585-1914), CH3 (1915-2232)

Fig. 118

NYF-0011-HC2-k delete
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGCTATGATATACACTGG
GTCCGCCTGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCT
GTTTATCACTGTGCGAGAGGGAGTAGTGGTCATTATGAGGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATTG
GTATGTATCCTGGTACCAGCAGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTATTA
CTGCGGAACATGGGATAGCAGCCTGAGTGCCCCTTGGGTGTTCGGCGGAGGGACCA
AGGTCACCGTCCTAGGGGAGGCGGTTCAGAAGTGCAGCTGGTGGAATCCGGGGGG
GGCCTGGTGCAGCCTGGGGGGAGCCTGAGACTGAGTTGTGCCGCCTCTGGGGTGAC
ATTTAACTACTATGGCATGTCTTGGATCCGCCAGGCACCTGGAAAGGGCCTGGAGT
GGGTGGCCAGCATCACTAGGTCCGGCGGGCGAATCTACTATCCCGACAGCGTCAAG
GGCAGGTTCACAATTTCCCGCGAGAACACACAGAAAACTCTGTACCTGCAGATGAA
TAGCCTGAGAGCCGAAGATACAGCTGTGTACTATTGCACTCTGGACGGCAGGGATG
GGTGGGTCGCCTATTGGGGCAGGGAACCCTGGTGACAGTCAGCTCCGGAGGAGGA
GGATCTGGCGGAGGAGGCAGTGGGGAGGCGGGTCAAACTTTATGCTCACTCAGCC
GTCCTCTGTTTCTGGCGTACCTGGCCAACGGGTGACCATTAGCTGTACGGGTAATA
CCGGGAATATCGGGTCTAACTACGTGAACTGGTATCAGCAGCTTCCAGGGACAGCT
CCCAAGTTGCTGATCTATCGCGACGACAAAGACCCTCAGGGGTCCCTGACCGATT
TAGTGGCAGCAAAAGCGGTACTTCCGCTTCCCTGGCGATAACCGGCTTTCAGGCCG
AAGATGAGGCAGACTACTATTGCCAGTCATATTCCAGCGGCTTCATCTTCGGAGGC
GGAACTAAGCTGACAGTGTTGGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCATCGAGAAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCGGC
(SEQ ID NO: 117), signal sequence (1-57), NYA-1143 (61-798), linker (799-813), C3E-7085 (814-1533), linker (1534-1539), hinge (1540-1584), CH2 (1585-1914), CH3 (1915-2232)

Fig. 119

NYF-0010-HC2-k delete
MKHLWFFLLLVAAPRWVLSGEVQLVESGGGVVQPGRSLTPSCSASGFSIRSYDMHW
VRQAPGKGLEWVATISYDGSQKYFADSVKGRFTIFRDESENMVYLQMSGLRVEDTA
VYHCARGSSNHYEAFDIWGQGTMVTVSSGGGGSGGGGSGGGGSQSVLTQPPSVSAA
PGQKVTISCSGSSSNIGNNYVSWYQRLPGTAPKLLIYDNNKRPSGIPDRFSGSKSG
TSATLGITGLQTGDEADYYCGAWDSSLSAPWVFGGGTKVTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSGGG
GSGGGGSGGGGSNFMLTQPSSVSGVPGQRVTISCTGNTGNIGSNYVNWYQQLPGTA
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPG
(SEQ ID NO: 118), signal sequence (1-19), NYA-1154(21-
266), linker (267-271), C3E-7085 (272-511), linker (512-
513), hinge (514-528), CH2 (529-638), CH3 (639-744)

Fig. 120

NYF-0004-HC2-k delete
MKHLWFFLLLVAAPRWVLSGEVQLVESGGGLVQPGGSLRLSCAASGVTFNYYGMSW
IRQAPGKGLEWVASITRSGGRIYYPDSVKGRFTISRENTQKTLYLQMNSLRAEDTA
VYYCTLDGRDGWVAYWGQGTLVTVSSGGGGSGGGGSGGGGSNFMLTQPSSVSGVPG
QRVTISCTGNTGNIGSNYVNWYQQLPGTAPKLLIYRDDKRPSGVPDRFSGSKSGTS
ASLAITGFQAEDEADYYCQSYSSGFIFGGGTKLTVLGGGGSEVQLVESGGGVVQPG
RSLTPSCSASGFSIRSYDMHWVRQAPGKGLEWVATISYDGSQKYFADSVKGRFTIF
RDESENMVYLQMSGLRVEDTAVYHCARGSSNHYEAFDIWGQGTMVTVSSGGGGSGG
GGSGGGGSQSVLTQPPSVSAAPGQKVTISCSGSSSNIGNNYVSWYQRLPGTAPKLL
IYDNNKRPSGIPDRFSGSKSGTSATLGITGLQTGDEADYYCGAWDSSLSAPWVFGG
GTKVTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPG
(SEQ ID NO: 119), signal sequence (1-19), C3E-7085 (21-260), linker (261-265), NYA-1154 (272-511), linker (512-513), hinge (514-528), CH2 (529-638), CH3 (639-744)

Fig. 121

NYF-0011-HC2-k delete
MKHLWFFLLLVAAPRWVLSGEVQLVESGGGVVQPGRSLTPSCSASGFSIRSYDIHW
VRLAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNWYVSWYQQLPGTAPKLLIYDNNKRPSGIPDRFSGSKSG
TSATLGITGLQTGDEADYYCGTWDSSLSAPWVFGGGTKVTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSGGG
GSGGGGSGGGGSNFMLTQPSSVSGVPGQRVTISCTGNTGNIGSNYVNWYQQLPGTA
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPG
(SEQ ID NO: 120), signal sequence (1-19), NYA-1143 (21-266), linker (267-271), C3E-7085 (272-511), linker (512-513), hinge (514-528), CH2 (529-638), CH3 (639-744)

Fig. 122

Point mutant NY-ESO peptide 1F
FLLMWITQC
(SEQ ID NO: 121)

Fig. 123

```
Point mutant NY-ESO peptide 2M
SMLMWITQC
(SEQ ID NO: 122)
```

Fig. 124

Point mutant NY-ESO peptide 3A
SLAMWITQC
(SEQ ID NO: 123)

Fig. 125

```
Point mutant NY-ESO peptide 4A
SLLAWITQC
(SEQ ID NO: 124)
```

Fig. 126

Point mutant NY-ESO peptide 5A
SLLMAITQC
(SEQ ID NO: 125)

Fig. 127

Point mutant NY-ESO peptide 6L
SLLMWLTQC
(SEQ ID NO: 126)

Fig. 128

Point mutant NY-ESO peptide 7F
SLLMWIFQC
(SEQ ID NO: 127)

Fig. 129

Point mutant NY-ESO peptide 8A
SLLMWITAC
(SEQ ID NO: 128)

Fig. 130

Point mutant NY-ESO peptide 9A
SLLMWITQA
(SEQ ID NO: 129)

Fig. 131 gp100 Peptide
IMDQVPFSV
(SEQ ID NO: 130)

Fig. 132

Homologous peptide DOLPP1
SQFMWFFSV
(SEQ ID NO: 131)

Fig. 133

```
Homologous peptide IL20RB
SLFMWFFYA
(SEQ ID NO: 132)
```

Fig. 134

```
Homologous peptide PRKD2
SLDMWSVGV
(SEQ ID NO: 133)
```

Fig. 135

```
Homologous peptide CD163
SIPMWVDNV
(SEQ ID NO: 134)
```

Fig. 136

```
Homologous peptide P2RY8
SVAMWAVFL
(SEQ ID NO: 135)
```

Fig. 137

C3E-7034
GEVQLVESGGGLVQPGGSLRLSCAASGVTFNYYGMSWIRQAPGKGLEWVASITNSG
GRIYYPDSVKGRFTISRENTQKTLYLQMNSLRAEDTAVYYCTLDGRDGWVAYWGQG
TLVTVSSGGGGSGGGGSGGGGSNFMLTQPHSVSESPGKTVTISCKRNTGNIGSNYV
NWYQQHEGSSPTTIIYRDDKRPDGVSDRFSGSIDRSSKSASLTISNLKTEDEADYF
CQSYSSGFIFGGGTKLTVLGAAAGAGGDYKDDDDKGAAAHHHHHH
(SEQ ID NO: 136), C3E-7034 (1-269), C3E-7034 scFv (2-243), FLAG-His tag (244-269)

Fig. 138

C3E-7036
GEVQLVESGGGLVQPGGSLRLSCAASGVTFNYYGMSWIRQAPGKGLEWVASITNSG
GRIYYPDSVKGRFTISRENTQKTLYLQMNSLRAEDTAVYYCTLDGRDGWVAYWGQG
TLVTVSSGGGGSGGGGSGGGGSNFMLTQPSSVSGVPGQRVTISCTGNTGNIGSNYV
NWYQQLPGTAPKLLIYRDDKRPSGVPDRFSGSKSGTSASLAITGFQAEDEADYYCQ
SYSSGFIFGGGTKLTVLGAAAGAGGDYKDDDDKGAAAHHHHHH
(SEQ ID NO: 137), C3E-7036 (1-267), C3E-7036 scFv (2-241), FLAG-His tag (242-267)

Fig. 139

C3E-7085
GEVQLVESGGGLVQPGGSLRLSCAASGVTFNYYGMSWIRQAPGKGLEWVASITRSG
GRIYYPDSVKGRFTISRENTQKTLYLQMNSLRAEDTAVYYCTLDGRDGWVAYWGQG
TLVTVSSGGGGSGGGGSGGGGSNFMLTQPSSVSGVPGQRVTISCTGNTGNIGSNYV
NWYQQLPGTAPKLLIYRDDKRPSGVPDRFSGSKSGTSASLAITGFQAEDEADYYCQ
SYSSGFIFGGGTKLTVLGAAAGAGGDYKDDDDKGAAAHHHHHH
(SEQ ID NO: 138), C3E-7085 (1-267), C3E-7085 scFv (2-241), FLAG-His tag (242-267)

Fig. 140

C3E-7088
GEVQLVESGGGLVQPGGSLRLSCAASGVTFNYYGMSWIRQAPGKGLEWVASITRSG
GRIYYPDSVKGRFTISRENTQKTLYLQMNSLRAEDTAVYYCTLDGRDGWVAYWGQG
TLVTVSSGGGGSGGGGSGGGGSNFMLTQPHSVSESPGKTVTISCKRNTGNIGSNYV
NWYQQHEGSSPTTIIYRNDKRPDGVSDRFSGSIDRSSKSASLTISNLKTEDEADYF
CQSYSSGFIFGGGTKLTVLGAAAGAGGDYKDDDDKGAAAHHHHHH
(SEQ ID NO: 139), C3E-7088(1-269), C3E-7088 scFv (2-243),
FLAG-His tag (244-269)

Fig. 141

C3E-7093
GEVQLVESGGGLVQPGGSLRLSCAASGVTFNYYGMSWIRQAPGKGLEWVASITSSG
GRIYYPDSVKGRFTISRENTQKTLYLQMNSLRAEDTAVYYCTLDGRDGWVAYWGQG
TLVTVSSGGGGSGGGGSGGGGSNFMLTQPHSVSESPGKTVTISCKRNTGNIGSNYV
NWYQQHEGSSPTTIIYRNDKRPDGVSDRFSGSIDRSSKSASLTISNLKTEDEADYF
CQSYSSGFIFGGGTKLTVLGAAAGAGGDYKDDDDKGAAAHHHHHH
(SEQ ID NO: 140), C3E-7093 (1-269), C3E-7093 scFv (2-243), FLAG-His tag (244-269)

Fig. 142

C3E-7085 heavy chain CDRH1    GVTFNYYG
C3E-7085 heavy chain CDRH2    ITRSGGRI
C3E-7085 heavy chain CDRH3    TLDGRDGWVAY
C3E-7085 light chain CDRL1    TGNIGSNY
C3E-7085 light chain CDRL2    RDD
C3E-7085 light chain CDRL3    QSYSSGFI
(SEQ ID NOs: 141 to 146)

Fig. 143

C3E-7078
GEVQLVESGGGLVQPGGSLRLSCAASGVTFNYYGMSWIRQAPGKGLEWVASITRSG
GRIYYPDSVKGRFTISRENTQKTLYLQMNSLRAEDTAVYYCTLDGRDGWVAYWGQG
TLVTVSSGGGGSGGGGSGGGGSNFMLTQPHSVSESPGKTVTISCKRNTGNIGSNYV
NWYQQHEGSSPTTIIYRDDKRPDGVSDRFSGSIDRSSKSASLTISNLKTEDEADYF
CQSYSSGFIFGGGTKLTVLGAAAGAGGDYKDDDDKGAAAHHHHHH
(SEQ ID NO: 147), C3E-7078(1-269), C3E-7078 scFv (2-243),
FLAG-His tag (244-269)

Fig. 144

NYF-0014-HC2
ATGAAACACCTGTGGTTCTTCCTCCTGCTGGTGGCAGCTCCCAGATGGGTGCTGAG
CGGAGAGGTGCAGCTGGTGGAGTCTGGGGGAGGCGTGGTCCAGCCTGGGAGGTCCC
TGACACCCTCCTGTTCAGCGTCTGGATTCTCCATCCGTAGTTATGATATACACTGG
GTCCGCCAGGCTCCAGGCAAGGGGCTAGAGTGGGTGGCCACTATATCATATGATGG
AAGTCAGAAGTACTTCGCAGACTCCGTGAAGGGCCGATTTACCATCTTCAGAGACG
AATCGGAGAACATGGTGTATCTGCAAATGAGCGGCCTGAGAGTTGAGGACACGGCT
GTTTATCACTGTGCGAGAGGGAGTAGTGGTCATTATGAGCTTTTGATATCTGGGG
CCAAGGGACAATGGTCACCGTCTCTTCAGGTGGAGGCGGTTCAGGCGGAGGTGGCA
GCGGCGGTGGCGGGAGTCAGTCTGTGTTGACGCAGCCGCCCTCAGTGTCTGCGGCC
CCAGGACAGAAGGTCACCATCTCCTGCTCTGGAAGCAGCTCCAACATTGGGAATAA
TTATGTATCCTGGTACCAGCAGCTCCCAGGAACAGCCCCCAAACTCCTCATTTATG
ACAATAATAAGCGACCCTCAGGGATTCCTGACCGATTCTCTGGCTCCAAGTCTGGC
ACGTCAGCCACCCTGGGCATCACCGGACTCCAGACTGGGGACGAGGCCGATTATTA
CTGCGGAACATGGGATAGCAGCCTGAGTGCCCCTTGGGTGTTCGGCGGAGGGACCA
AGGTCACCGTCCTAGGGGAGGCGGTTCAGAAGTGCAGCTGGTGGAATCCGGGGGG
GGCCTGGTGCAGCCTGGGGGAGCCTGAGACTGAGTTGTGCCGCCTCTGGGGTGAC
ATTTAACTACTATGGCATGTCTTGGATCCGCCAGGCACCTGGAAAGGGCCTGGAGT
GGGTGGCCAGCATCACTAGGTCCGGCGGGCGAATCTACTATCCCGACAGCGTCAAG
GGCAGGTTCACAATTTCCCGCGAGAACACACAGAAAACTCTGTACCTGCAGATGAA
TAGCCTGAGAGCCGAAGATACAGCTGTGTACTATTGCACTCTGGACGGCAGGGATG
GGTGGGTCGCCTATTGGGGGCAGGGAACCCTGGTGACAGTCAGCTCCGGAGGAGGA
GGATCTGGCGGAGGAGGCAGTGGGGAGGCGGGTCAAACTTTATGCTCACTCAGCC
GTCCTCTGTTTCTGGCGTACCTGGCCAACGGGTGACCATTAGCTGTACGGGTAATA
CCGGGAATATCGGGTCTAACTACGTGAACTGGTATCAGCAGCTTCCAGGGACAGCT
CCCAAGTTGCTGATCTATCGCGACGACAAAAGACCCTCAGGGGTCCCTGACCGATT
TAGTGGCAGCAAAAGCGGTACTTCCGCTTCCCTGGCGATAACCGGCTTTCAGGCCG
AAGATGAGGCAGACTACTATTGCCAGTCATATTCCAGCGGCTTCATCTTCGGAGGC
GGAACTAAGCTGACAGTGTTGGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCGGCAAG
(SEQ ID NO: 148), signal sequence (1-57), NYA-0001 (61-798), linker (799-813), C3E-7085 (814-1533), linker (1534-1539), hinge (1540-1584), CH2 (1585-1914), CH3 (1915-2235)

Fig. 145

NYF-0014-HC2
MKHLWFFLLLVAAPRWVLSGEVQLVESGGGVVQPGRSLTPSCSASGFSIRSYDIHW
VRQAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNNYVSWYQQLPGTAPKLLIYDNNKRPSGIPDRFSGSKSG
TSATLGITGLQTGDEADYYCGTWDSSLSAPWVFGGGTKVTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSGGG
GSGGGGSGGGGSNFMLTQPSSVSGVPGQRVTISCTGNTGNIGSNYVNWYQQLPGTA
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPGK
(SEQ ID NO: 149), signal sequence (1-19), NYA-0001 (21-266), linker (267-271), C3E-7085 (272-511), linker (512-513), hinge (514-528), CH2 (529-638), CH3 (639-745)

Fig. 146

NYF-0082-HC2
MKHLWFFLLLVAAPRWVLSGEVQLVESGGGVVQPGRSLTPSCSASGFSIRSYDIHW
VRQAPGKGLEWVATISYDGSQKYFADSVKGRFTIFRDESENMVYLQMSGLRVEDTA
VYHCARGSSGHYEAFDIWGQGTMVTVSSGGGGSGGGGSGGGGSQSVLTQPPSVSAA
PGQKVTISCSGSSSNIGNNYVSWYQRLPGTAPKLLIYDNNKRPSGIPDRFSGSKSG
TSATLGITGLQTGDEADYYCGSWDSSLSAPWVFGGGTKVTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSGGG
GSGGGGSGGGGSNFMLTQPSSVSGVPGQRVTISCTGNTGNIGSNYVNWYQQLPGTA
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPGK
(SEQ ID NO: 150), signal sequence (1-19), NYA-0082 (21-266), linker (267-271), C3E-7085 (272-511), linker (512-513), hinge (514-528), CH2 (529-638), CH3 (639-745)

Fig. 147

Human CD3ε amino acid sequence
MQSGTHWRVLGLCLLSVGVWGQDGNEEMGGITQTPYKVSISGTTVILTCPQYPGSE
ILWQHNDKNIGGDEDDKNIGSDEDHLSLKEFSELEQSGYYVCYPRGSKPEDANFYL
YLRARVCENCMEMDVMSVATIVIVDICITGGLLLLVYYWSKNRKAKAKPVTRGAGA
GGRQRGQNKERPPPVPNPDYEPIRKGQRDLYSGLNQRRI
(SEQ ID NO: 151: NCBI Reference Sequence: NP_000724.1)

Fig. 148

NYZ-0038-HC2
ATGAAACACCTGTGGTTCTTCCTCCTGCTGGTGGCAGCTCCCAGATGGGTGCTGAG
CGGTGAGGTACAGCTGGTGGAATCCGGTGGAGGCCTTGTGCAACCGGGAGGCTCCC
TGCGACTCTCTTGCGCCGCATCTGGCTTTTCCATACGATCCTACGATATTCATTGG
GTCCGACAAGCCCCTGGCAAAGGTCTTGAATGGGTTGCCACTATCTCCTACGACGG
GTCTCAGAATATTATGCGGATTCAGTGAAGGGGCGGTTCACAATTTCACGAGACG
AGTCAAAGAATACACTGTACCTCCAAATGAATTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTCAATCCGTTCTGACTCAGCCACCCTCCGCCTCTGGCACC
CCGGGCCAACGGGTCACAATATCATGTTCTGGCTCTTCAAGCAACATCGGAAACTG
GTACGTGAGCTGGTACCAGCAGCTCCCCGGCACGGCGCCCAAGCTTCTGATATATG
ACAACAACAAACGGCCCAGTGGAGTTCCTGACAGATTCAGTGGGTCTAAAAGTGGT
ACAAGCGCTAGCCTGGCCATAAGTGGTCTGCAGAGTGAAGATGAGGCGGACTATTA
TTGCGGAACCTGGGACTCCAGCCTGAGCGCTCCCTGGGTTTTCGGCGGAGGTACTA
AGCTGACCGTCTTGGGAGGAGGCGGTTCAGAAGTGCAGCTGGTGGAATCCGGGGGG
GGCCTGGTGCAGCCTGGGGGGAGCCTGAGACTGAGTTGTGCCGCCTCTGGGGTGAC
ATTTAACTACTATGGCATGTCTTGGATCCGCCAGGCACCTGGAAAGGGCCTGGAGT
GGGTGGCCAGCATCACTAGGTCCGGCGGGCGAATCTACTATCCCGACAGCGTCAAG
GGCAGGTTCACAATTTCCCGCGAGAACACACAGAAACTCTGTACCTGCAGATGAA
TAGCCTGAGAGCCGAAGATACAGCTGTGTACTATTGCACTCTGGACGGCAGGGATG
GGTGGGTCGCCTATTGGGGGTGTGGAACCCTGGTGACAGTCAGCTCCGGAGGAGGA
GGATCTGGCGGAGGAGGCAGTGGGGGAGGCGGGTCAAACTTTATGCTCACTCAGCC
GTCCTCTGTTTCTGGCGTACCTGGCCAACGGGTGACCATTAGCTGTACGGGTAATA
CCGGGAATATCGGGTCTAACTACGTGAACTGGTATCAGCAGCTTCCAGGGACATGT
CCCAAGTTGCTGATCTATCGCGACGACAAAAGACCCTCAGGGGTCCCTGACCGATT
TAGTGGCAGCAAAAGCGGTACTTCCGCTTCCCTGGCGATAACCGGCTTTCAGGCCG
AAGATGAGGCAGACTACTATTGCCAGTCATATTCCAGCGGCTTCATCTTCGGAGGC
GGAACTAAGCTGACAGTGTTGGCAGCCGAGCCCAAATCTTCTGACAAAACTCACAC
ATGCCCACCCTGCCCAGCACCTGAAGCCGCAGGGGACCCTCAGTCTTCCTCTTCC
CCCCAAAACCCAAGGACACCCTCATGATCTCCCGGACCCCTGAGGTCACATGCGTG
GTGGTGTCAGTGAGCCACGAAGACCCTGAGGTCAAGTTCAACTGGTACGTGGACGG
CGTGGAGGTGCATAATGCCAAGACAAAGCCCCGGGAGGAGCAGTACAACAGCACGT
ACCGGGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTC
CAAAGCCAAAGGCCAGCCCCGGGAACCACAGGTGTACGTGTACCCCCCATCCCGGG
ACGAGCTGACCAAGAACCAGGTCAGCCTGACCTGCCTGGTCAAAGGCTTCTATCCC
AGCGACATCGCCGTGGAGTGGGAGAGCAATGGCCAGCCCGAGAACAACTACAAGAC
CACCCCTCCCGTGCTGGACTCCGACGGCTCCTTCGCCCTCGTGAGCAAGCTCACCG
TGGACAAGAGCAGGTGGCAGCAGGGCAACGTCTTCTCATGCTCCGTGATGCATGAG
GCTCTGCACAACCACTACACCCAGAAGAGCCTCTCCCTGTCTCCGGCAAG
(SEQ ID NO: 152), signal sequence (1-57), NYA-2061 (61-798), linker (799-813), C3E-7096(814-1533), linker (1534-1539), hinge (1540-1584), CH2 (1585-1914), CH3 (1915-2235)

Fig. 149

NYZ-0082-HC2
ATGAAACACCTGTGGTTCTTCCTCCTGCTGGTGGCAGCTCCCAGATGGGTGCTGAG
CGGTGAGGTACAGCTGGTGGAATCCGGTGGAGGCCTTGTGCAACCGGGAGGCTCCC
TGCGACTCTCTTGCGCCGCATCTGGCTTTTCCATACGATCCTACGATATTCATTGG
GTCCGACAAGCCCCTGGCAAAGGTCTTGAATGGGTTGCCACTATCTCCTACGACGG
GTCTCAGAAATATTATGCGGATTCAGTGAAGGGGCGGTTCACAATTTCACGAGACG
AGTCAAGAATACACTGTACCTCCAAATGAATTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTGGAGGAGGTGGATCTCAATCCGTTCTGACTCAGCCACCC
TCCGCCTCTGGCACCCCGGGCCAACGGGTCACAATATCATGTTCTGGCTCTTCAAG
CAACATCGGAAACTGGTACGTGAGCTGGTACCAGCAGCTCCCCGGCACGGCGCCCA
AGCTTCTGATATATGACAACAACAAACGGCCCAGTGGAGTTCCTGACAGATTCAGT
GGGTCTAAAAGTGGTACAAGCGCTAGCCTGGCCATAAGTGGTCTGCAGAGTGAAGA
TGAGGCGGACTATTATTGCGGAACCTGGGACTCCAGCCTGAGCGCTCCCTGGGTTT
TCGGCGGAGGTACTAAGCTGACCGTCTTGGGAGGAGGCGGTTCAGAAGTGCAGCTG
GTGGAATCCGGGGGGGCCTGGTGCAGCCTGGGGGAGCCTGAGACTGAGTTGTGC
CGCCTCTGGGGTGACATTTAACTACTATGGCATGTCTTGGATCCGCCAGGCACCTG
GAAAGGGCCTGGAGTGGGTGGCCAGCATCACTAGGTCCGGCGGGCGAATCTACTAT
CCCGACAGCGTCAAGGGCAGGTTCACAATTTCCCGCGAGAACACACAGAAAACTCT
GTACCTGCAGATGAATAGCCTGAGAGCCGAAGATACAGCTGTGTACTATTGCACTC
TGGACGGCAGGGATGGGTGGGTCGCCTATTGGGGGTGTGGAACCCTGGTGACAGTC
AGCTCCGGAGGAGGAGGATCTGGCGGAGGAGGCAGTGGGGGAGGCGGGTCAAACTT
TATGCTCACTCAGCCGTCCTCTGTTTCTGGCGTACCTGGCCAACGGGTGACCATTA
GCTGTACGGGTAATACCGGGAATATCGGGTCTAACTACGTGAACTGGTATCAGCAG
CTTCCAGGGACATGTCCCAAGTTGCTGATCTATCGCGACGACAAAAGACCCTCAGG
GGTCCCTGACCGATTTAGTGGCAGCAAAAGCGGTACTTCCGCTTCCCTGGCGATAA
CCGGCTTTCAGGCCGAAGATGAGGCAGACTACTATTGCCAGTCATATTCCAGCGGC
TTCATCTTCGGAGGCGGAACTAAGCTGACAGTGTTGGCAGCCGAGCCCAAATCTTC
TGACAAAACTCACACATGCCCACCCTGCCCAGCACCTGAAGCCGCAGGGGACCCT
CAGTCTTCCTCTTCCCCCCAAAACCCAAGGACACCCTCATGATCTCCCGGACCCCT
GAGGTCACATGCGTGGTGGTGTCAGTGAGCCACGAAGACCCTGAGGTCAAGTTCAA
CTGGTACGTGGACGGCGTGGAGGTGCATAATGCCAAGACAAAGCCCCGGGAGGAGC
AGTACAACAGCACGTACCGGGTGGTCAGCGTCCTCACCGTCCTGCACCAGGACTGG
CTGAATGGCAAGGAGTACAAGTGCAAGGTCTCCAACAAAGCCCTCCCAGCCCCCAT
CGAGAAAACCATCTCCAAAGCCAAAGGCCAGCCCCGGGAACCACAGGTGTACGTGT
ACCCCCCATCCCGGGACGAGCTGACCAAGAACCAGGTCAGCCTGACCTGCCTGGTC
AAAGGCTTCTATCCCAGCGACATCGCCGTGGAGTGGGAGAGCAATGGCCAGCCCGA
GAACAACTACAAGACCACCCCTCCCGTGCTGGACTCCGACGGCTCCTTCGCCCTCG
TGAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTC
TCCCGGCAAG
(SEQ ID NO: 153), signal sequence (1-57), NYA-3061 (61-813), linker (814-828), C3E-7096(829-1548), linker (1549-1554), hinge (1555-1599), CH2 (1600-1929), CH3 (1930-2250)

Fig. 150

```
NYZ-0083-HC2
ATGAAACACCTGTGGTTCTTCCTCCTGCTGGTGGCAGCTCCCAGATGGGTGCTGAG
CGGTGAGGTACAGCTGGTGGAATCCGGTGGAGGCCTTGTGCAACCGGGAGGCTCCC
TGCGACTCTCTTGCGCCGCATCTGGCTTTTCCATACGATCCTACGATATTCATTGG
GTCCGACAAGCCCCTGGCAAAGGTCTTGAATGGGTTGCCACTATCTCCTACGACGG
GTCTCAGAAATATTATGCGGATTCAGTGAAGGGGCGGTTCACAATTTCACGAGACG
AGTCAAGAATACACTGTACCTCCAAATGAATTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTGGAGGAGGTGGATCTCAATCCGTTCTGACTCAGCCACCC
TCCGCCTCTGGCACCCCGGGCCAACGGGTCACAATATCATGTTCTGGCTCTTCAAG
CAACATCGGAAACTGGTACGTGAGCTGGTACCAGCAGCTCCCCGGCACGGCGCCCA
AGCTTCTGATATATGACAACAACAAACGGCCCAGTGGAGTTCCTGACAGATTCAGT
GGGTCTAAAAGTGGTACAAGCGCTAGCCTGGCCATAAGTGGTCTGCAGAGTGAAGA
TGAGGCGGACTATTATTGCGGAACCTGGGACTCCAGCCTGAGCGCTCCCTGGGTTT
TCGGCGGAGGTACTAAGCTGACCGTCTTGGGAGGAGGCGGTTCAGAAGTGCAGCTG
GTGGAATCCGGGGGGGCCTGGTGCAGCCTGGGGGAGCCTGAGACTGAGTTGTGC
CGCCTCTGGGGTGACATTTAACTACTATGGCATGTCTTGGATCCGCCAGGCACCTG
GAAAGTGTCTGGAGTGGGTGGCCAGCATCACTAGGTCCGGCGGGCGAATCTACTAT
CCCGACAGCGTCAAGGGCAGGTTCACAATTTCCCGCGAGAACACACAGAAACTCT
GTACCTGCAGATGAATAGCCTGAGAGCCGAAGATACAGCTGTGTACTATTGCACTC
TGGACGGCAGGGATGGGTGGGTCGCCTATTGGGGCAGGGAACCCTGGTGACAGTC
AGCTCCGGAGGAGGAGGATCTGGCGGAGGAGGCAGTGGGGGAGGCGGGTCAAACTT
TATGCTCACTCAGCCGTCCTCTGTTTCTGGCGTACCTGGCCAACGGGTGACCATTA
GCTGTACGGGTAATACCGGGAATATCGGGTCTAACTACGTGAACTGGTATCAGCAG
CTTCCAGGGACAGCTCCCAAGTTGCTGATCTATCGCGACGACAAAAGACCCTCAGG
GGTCCCTGACCGATTTAGTGGCAGCAAAAGCGGTACTTCCGCTTCCCTGGCGATAA
CCGGCTTTCAGGCCGAAGATGAGGCAGACTACTATTGCCAGTCATATTCCAGCGGC
TTCATCTTCGGATGTGGAACTAAGCTGACAGTGTTGGCAGCCGAGCCCAAATCTTC
TGACAAAACTCACACATGCCCACCCTGCCCAGCACCTGAAGCCGCAGGGGGACCCT
CAGTCTTCCTCTTCCCCCCAAAACCCAAGGACACCCTCATGATCTCCCGGACCCCT
GAGGTCACATGCGTGGTGGTGCAGTGAGCCACGAAGACCCTGAGGTCAAGTTCAA
CTGGTACGTGGACGGCGTGGAGGTGCATAATGCCAAGACAAAGCCCCGGGAGGAGC
AGTACAACAGCACGTACCGGGTGGTCAGCGTCCTCACCGTCCTGCACCAGGACTGG
CTGAATGGCAAGGAGTACAAGTGCAAGGTCTCCAACAAAGCCCTCCCAGCCCCCAT
CGAGAAACCATCTCCAAAGCCAAAGGCCAGCCCCGGGAACCACAGGTGTACGTGT
ACCCCCCATCCCGGGACGAGCTGACCAAGAACCAGGTCAGCCTGACCTGCCTGGTC
AAAGGCTTCTATCCCAGCGACATCGCCGTGGAGTGGGAGAGCAATGGCCAGCCCGA
GAACAACTACAAGACCACCCCTCCCGTGCTGGACTCCGACGGCTCCTTCGCCCTCG
TGAGCAAGCTCACCGTGGACAAGAGCAGGTGGCAGCAGGGCAACGTCTTCTCATGC
TCCGTGATGCATGAGGCTCTGCACAACCACTACACCCAGAAGAGCCTCTCCCTGTC
TCCCGGCAAG
```

(SEQ ID NO: 154), signal sequence (1-57), NYA-3061 (61-813), linker (814-828), C3E-7097(829-1548), linker (1549-1554), hinge (1555-1599), CH2 (1600-1929), CH3 (1930-2250)

Fig. 151

NYZ-0038-HC2
MKHLWFFLLLVAAPRWVLSGEVQLVESGGGLVQPGGSLRLSCAASGFSIRSYDIHW
VRQAPGKGLEWVATISYDGSQKYYADSVKGRFTISRDESKNTLYLQMNSLRAEDTA
VYHCARGSSGHYEAFDIWGQGTLVTVSSGGGGSGGGGSGGGGSQSVLTQPPSASGT
PGQRVTISCSGSSSNIGNWYVSWYQQLPGTAPKLLIYDNNKRPSGVPDRFSGSKSG
TSASLAISGLQSEDEADYYCGTWDSSLSAPWVFGGGTKLTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGCGTLVTVSSGGG
GSGGGGSGGGGSNFMLTQPSSVSGVPGQRVTISCTGNTGNIGSNYVNWYQQLPGTC
PKLLIYRDDKRPSGVPDRFSGSKSGTSASLAITGFQAEDEADYYCQSYSSGFIFGG
GTKLTVLAAEPKSSDKTHTCPPCPAPEAAGGPSVFLFPPKPKDTLMISRTPEVTCV
VVSVSHEDPEVKFNWYVDGVEVHNAKTKPREEQYNSTYRVVSVLTVLHQDWLNGKE
YKCKVSNKALPAPIEKTISKAKGQPREPQVYVYPPSRDELTKNQVSLTCLVKGFYP
SDIAVEWESNGQPENNYKTTPPVLDSDGSFALVSKLTVDKSRWQQGNVFSCSVMHE
ALHNHYTQKSLSLSPGK
(SEQ ID NO: 155), signal sequence (1-19), NYA-2061 (21-266), linker (267-271), C3E-7096(272-511), linker (512-513), hinge (514-528), CH2 (529-638), CH3 (639-745)

Fig. 152

NYZ-0082-HC2
MKHLWFFLLLVAAPRWVLSGEVQLVESGGGLVQPGGSLRLSCAASGFSIRSYDIHW
VRQAPGKGLEWVATISYDGSQKYYADSVKGRFTISRDESKNTLYLQMNSLRAEDTA
VYHCARGSSGHYEAFDIWGQGTLVTVSSGGGGSGGGGSGGGGSGGGGSQSVLTQPP
SASGTPGQRVTISCSGSSSNIGNWYVSWYQQLPGTAPKLLIYDNNKRPSGVPDRFS
GSKSGTSASLAISGLQSEDEADYYCGTWDSSLSAPWVFGGGTKLTVLGGGGSEVQL
VESGGGLVQPGGSLRLSCAASGVTFNYYGMSWIRQAPGKGLEWVASITRSGGRIYY
PDSVKGRFTISRENTQKTLYLQMNSLRAEDTAVYYCTLDGRDGWVAYWGCGTLVTV
SSGGGGSGGGGSGGGGSNFMLTQPSSVSGVPGQRVTISCTGNTGNIGSNYVNWYQQ
LPGTCPKLLIYRDDKRPSGVPDRFSGSKSGTSASLAITGFQAEDEADYYCQSYSSG
FIFGGGTKLTVLAAEPKSSDKTHTCPPCPAPEAAGGPSVFLFPPKPKDTLMISRTP
EVTCVVVSVSHEDPEVKFNWYVDGVEVHNAKTKPREEQYNSTYRVVSVLTVLHQDW
LNGKEYKCKVSNKALPAPIEKTISKAKGQPREPQVYVYPPSRDELTKNQVSLTCLV
KGFYPSDIAVEWESNGQPENNYKTTPPVLDSDGSFALVSKLTVDKSRWQQGNVFSC
SVMHEALHNHYTQKSLSLSPGK
(SEQ ID NO: 156), signal sequence (1-19), NYA-3061 (21-
271), linker (272-276), C3E-7096(277-516), linker (517-
518), hinge (519-533), CH2 (534-643), CH3 (644-750)

Fig. 153

NYZ-0083-HC2
MKHLWFFLLLVAAPRWVLSGEVQLVESGGGLVQPGGSLRLSCAASGFSIRSYDIHW
VRQAPGKGLEWVATISYDGSQKYYADSVKGRFTISRDESKNTLYLQMNSLRAEDTA
VYHCARGSSGHYEAFDIWGQGTLVTVSSGGGGSGGGGSGGGGSGGGGSQSVLTQPP
SASGTPGQRVTISCSGSSSNIGNWYVSWYQQLPGTAPKLLIYDNNKRPSGVPDRFS
GSKSGTSASLAISGLQSEDEADYYCGTWDSSLSAPWVFGGGTKLTVLGGGGSEVQL
VESGGGLVQPGGSLRLSCAASGVTFNYYGMSWIRQAPGKCLEWVASITRSGGRIYY
PDSVKGRFTISRENTQKTLYLQMNSLRAEDTAVYYCTLDGRDGWVAYWGQGTLVTV
SSGGGGSGGGGSGGGGSNFMLTQPSSVSGVPGQRVTISCTGNTGNIGSNYVNWYQQ
LPGTAPKLLIYRDDKRPSGVPDRFSGSKSGTSASLAITGFQAEDEADYYCQSYSSG
FIFGCGTKLTVLAAEPKSSDKTHTCPPCPAPEAAGGPSVFLFPPKPKDTLMISRTP
EVTCVVVSVSHEDPEVKFNWYVDGVEVHNAKTKPREEQYNSTYRVVSVLTVLHQDW
LNGKEYKCKVSNKALPAPIEKTISKAKGQPREPQVYVYPPSRDELTKNQVSLTCLV
KGFYPSDIAVEWESNGQPENNYKTTPPVLDSDGSFALVSKLTVDKSRWQQGNVFSC
SVMHEALHNHYTQKSLSLSPGK
(SEQ ID NO: 157), signal sequence (1-19), NYA-3061 (21-
271), linker (272-276), C3E-7097(277-516), linker (517-
518), hinge (519-533), CH2 (534-643), CH3 (644-750)

Fig. 154

NYZ-1010-HC2
ATGAAACACCTGTGGTTCTTCCTCCTGCTGGTGGCAGCTCCCAGATGGGTGCTGAG
CGGTGAGGTACAGCTGGTGGAATCCGGTGGAGGCCTTGTGCAACCGGGAGGCTCCC
TGCGACTCTCTTGCGCCGCATCTGGCTTTTCCATACGATCCTACGATATTCATTGG
GTCCGACAAGCCCCTGGCAAAGGTCTTGAATGGGTTGCCACTATCTCCTACGACGG
GTCTCAGAAATATTATGCGGATTCAGTGAAGGGGCGGTTCACAATTTCACGAGACG
AGTCAAAGAATACACTGTACCTCCAAATGAATTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTGGAGGAGGTGGATCTCAATCCGTTCTGACTCAGCCACCC
TCCGCCTCTGGCACCCCGGGCCAACGGGTCACAATATCATGTTCTGGCTCTTCAAG
CAACATCGGAAACTGGTACGTGAGCTGGTACCAGCAGCTCCCGGCACGGCGCCCA
AGCTTCTGATATATGACAACAACAAACGGCCCAGTGGAGTTCCTGACAGATTCAGT
GGGTCTAAAAGTGGTACAAGCGCTAGCCTGGCCATAAGTGGTCTGCAGAGTGAAGA
TGAGGCGGACTATTATTGCGGAACCTGGGACTCCAGCCTGAGCGCTCCCTGGGTTT
TCGGCGGAGGTACTAAGCTGACCGTCTTGGAGGAGGCGGTTCAGAAGTGCAGCTG
GTGGAATCCGGGGGGGCCTGGTGCAGCCTGGGGGAGCCTGAGACTGAGTTGTGC
CGCCTCTGGGGTGACATTTAACTACTATGGCATGTCTTGGATCCGCCAGGCACCTG
GAAAGGGCCTGGAGTGGGTGGCCAGCATCACTAGGTCCGGCGGGCGAATCTACTAT
CCCGACAGCGTCAAGGGCAGGTTCACAATTTCCCGCGAGAACACACAGAAAACTCT
GTACCTGCAGATGAATAGCCTGAGAGCCGAAGATACAGCTGTGTACTATTGCACTC
TGGACGGCAGGGATGGGTGGGTCGCCTATTGGGGTCAGGGAACCCTGGTGACAGTC
AGCTCCGCCTCCACCAAGGGCCCAAGCGTCTTCCCCCTGGCACCCTCCTCCAAGAG
CACCTCTGGCGGCACAGCCGCCCTGGGCTGCCTGGTCAAGGACTACTTCCCCGAAC
CCGTGACCGTGAGCTGGAACTCAGGCGCCCTGACCAGCGGCGTGCACACCTTCCCC
GCTGTCCTGCAGTCCTCAGGACTCTACTCCCTCAGCAGCGTGGTGACCGTGCCCTC
CAGCAGCTTGGGCACCCAGACCTACATCTGCAACGTGAATCACAAGCCCAGCAACA
CCAAGGTGGACAAGAGAGTTGAGCCCAAGTCTTGCGACAAAACTCACACATGCCCA
CCCTGCCCAGCACCTGAAGCCGCAGGGGGACCCTCAGTCTTCCTCTTCCCCCCAAA
ACCCAAGGACACCCTCATGATCTCCCGGACCCCTGAGGTCACATGCGTGGTGGTGT
CAGTGAGCCACGAAGACCCTGAGGTCAAGTTCAACTGGTACGTGGACGGCGTGGAG
GTGCATAATGCCAAGACAAAGCCCCGGGAGGAGCAGTACAACAGCACGTACCGGGT
GGTCAGCGTCCTCACTGTCCTGCACCAGGACTGGCTGAATGGCAAGGAGTACAAGT
GCAAGGTCTCCAACAAAGCCCTCCCAGCCCCATCGAGAAAACCATCTCCAAAGCC
AAAGGCCAGCCCCGGGAACCACAGGTGTACGTGTACCCCCCATCCCGGGACGAGCT
GACCAAGAACCAGGTCAGCCTGACCTGCCTGGTCAAAGGCTTCTATCCCAGCGACA
TCGCCGTGGAGTGGGAGAGCAATGGCCAGCCCGAGAACAACTACAAGACCACCCCT
CCCGTGCTGGACTCCGACGGCTCCTTCGCCCTCGTGAGCAAGCTCACCGTGGACAA
GAGCAGGTGGCAGCAGGGCAACGTCTTCTCATGCTCCGTGATGCATGAGGCTCTGC
ACAACCACTACACCCAGAAGAGCCTCTCCCTGTCTCCGGCAAG (SEQ ID NO: 158), signal sequence (1-57), NYA-3061 (61-813), linker (814-828), C3E-7085-VH (829-1182), CH1 (1183-1476), hinge (1477-1521), CH2 (1522-1851), CH3 (1831-2172)

Fig. 155

C3E-7085-LC
ATGGTGCTGCAGACCCAGGTGTTCATCTCCCTGCTGCTGTGGATCTCCGGCGCGTA
CGGCAACTTTATGCTCACTCAGCCGTCCTCTGTTTCTGGCGTACCTGGCCAACGGG
TGACCATTAGCTGTACGGGTAATACCGGGAATATCGGGTCTAACTACGTGAACTGG
TATCAGCAGCTTCCAGGGACAGCTCCCAAGTTGCTGATCTATCGCGACGACAAAAG
ACCCTCAGGGGTCCCTGACCGATTTAGTGGCAGCAAAAGCGGTACTTCCGCTTCCC
TGGCGATAACCGGCTTTCAGGCCGAAGATGAGGCAGACTACTATTGCCAGTCATAT
TCCAGCGGCTTCATCTTCGGAGGCGGAACTAAGCTGACAGTGCTGGGCCAGCCTAA
GGCTGCCCCTAGCGTGACCCTGTTCCCTCCTTCCAGCGAGGAGCTTCAAGCTAACA
AGGCCACCCTGGTGTGTCTTATCTCTGACTTCTACCCTGGCGCTGTGACCGTGGCC
TGGAAGGCTGACAGCTCCCCTGTGAAGGCCGGAGTGGAGACCACCACACCTAGCAA
GCAGTCTAACAACAAGTACGCTGCCAGCTCCTACCTGAGCCTTACCCCTGAGCAGT
GGAAGTCTCACAGAAGCTACTCCTGTCAAGTGACCCACGAGGGCAGCACCGTGGAG
AAGACCGTGGCTCCTACCGAGTGTTCC
(SEQ ID NO: 159), signal sequence (1-60), C3E-7085_VL
(61-381), CL (382-699)

Fig. 156

NYZ-1010-HC2
MKHLWFFLLLVAAPRWVLSGEVQLVESGGGLVQPGGSLRLSCAASGFSIRSYDIHW
VRQAPGKGLEWVATISYDGSQKYYADSVKGRFTISRDESKNTLYLQMNSLRAEDTA
VYHCARGSSGHYEAFDIWGQGTLVTVSSGGGGSGGGGSGGGGSGGGGSQSVLTQPP
SASGTPGQRVTISCSGSSSNIGNWYVSWYQQLPGTAPKLLIYDNNKRPSGVPDRFS
GSKSGTSASLAISGLQSEDEADYYCGTWDSSLSAPWVFGGGTKLTVLGGGGSEVQL
VESGGGLVQPGGSLRLSCAASGVTFNYYGMSWIRQAPGKGLEWVASITRSGGRIYY
PDSVKGRFTISRENTQKTLYLQMNSLRAEDTAVYYCTLDGRDGWVAYWGQGTLVTV
SSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKRVEPKSCDKTHTCP
PCPAPEAAGGPSVFLFPPKPKDTLMISRTPEVTCVVVSVSHEDPEVKFNWYVDGVE
VHNAKTKPREEQYNSTYRVVSVLTVLHQDWLNGKEYKCKVSNKALPAPIEKTISKA
KGQPREPQVYVYPPSRDELTKNQVSLTCLVKGFYPSDIAVEWESNGQPENNYKTTP
PVLDSDGSFALVSKLTVDKSRWQQGNVFSCSVMHEALHNHYTQKSLSLSPGK
(SEQ ID NO: 160), signal sequence (1-19), NYA-3061 (21-
271), linker (272-276), C3E-7085-VH (277-394), CH1 (395-
492), hinge (493-507), CH2 (508-617), CH3 (618-724)

Fig. 157

C3E-7085-LC
MVLQTQVFISLLLWISGAYGNFMLTQPSSVSGVPGQRVTISCTGNTGNIGSNYVNW
YQQLPGTAPKLLIYRDDKRPSGVPDRFSGSKSGTSASLAITGFQAEDEADYYCQSY
SSGFIFGGGTKLTVLGQPKAAPSVTLFPPSSEELQANKATLVCLISDFYPGAVTVA
WKADSSPVKAGVETTTPSKQSNNKYAASSYLSLTPEQWKSHRSYSCQVTHEGSTVE
KTVAPTECS
(SEQ ID NO: 161), signal sequence (1-20), C3E-7085_VL
(21-127), CL (128-233)

Fig. 158A

| Antibody | Substance added to T2 | | | | | | | | | | | |
|---|---|---|---|---|---|---|---|---|---|---|---|---|
| | Solvent | Peptide | | | | | | | | | | |
| | DMSO | NY-ESO | 1F | 2M | 3A | 4A | 5A | 6L | 7F | 8A | 9A | gp100 |
| NYZ-0038 | 1.02 | 57.13 | 0.66 | 45.71 | 29.72 | 1.39 | 1.13 | 47.00 | 5.56 | 19.15 | 58.37 | 0.37 |
| NYZ-0082 | 1.02 | 54.49 | 0.79 | 41.13 | 27.09 | 2.26 | 1.74 | 45.35 | 10.08 | 19.93 | 58.10 | 0.36 |
| NYZ-0083 | 1.01 | 53.60 | 0.96 | 41.34 | 28.94 | 3.05 | 2.15 | 45.85 | 12.76 | 22.46 | 56.72 | 0.34 |
| NYZ-1010 | 1.15 | 43.32 | 0.86 | 39.52 | 21.30 | 1.05 | 1.02 | 37.59 | 3.86 | 17.38 | 51.90 | 0.53 |

Fig. 158B

| Antibody | Substance added to T2 | | | | | | | |
|---|---|---|---|---|---|---|---|---|
| | Solvent | Peptide | | | | | | |
| | DMSO | NY-ESO | DOLPP1 | IL20RB | PRKD2 | CD163 | P2RY8 | gp100 |
| NYZ-0038 | 1.07 | <u>51.65</u> | 0.71 | 0.70 | 0.41 | 0.66 | 0.89 | 0.44 |
| NYZ-0082 | 1.11 | <u>47.54</u> | 0.69 | 0.69 | 0.40 | 0.62 | 0.87 | 0.42 |
| NYZ-0083 | 1.01 | <u>47.17</u> | 0.63 | 0.62 | 0.37 | 0.55 | 0.76 | 0.38 |
| NYZ-1010 | 1.19 | <u>44.35</u> | 0.70 | 0.88 | 0.54 | 0.67 | 0.95 | 0.54 |

Fig. 161

GGGGS linker
GGGGS
(SEQ ID NO: 162)

Fig. 164

NYA-3061
ATGAAACACCTGTGGTTCTTCCTCCTGCTGGTGGCAGCTCCCAGATGGGTGCTGAG
CGGTGAGGTACAGCTGGTGGAATCCGGTGGAGGCCTTGTGCAACCGGGAGGCTCCC
TGCGACTCTCTTGCGCCGCATCTGGCTTTTCCATACGATCCTACGATATTCATTGG
GTCCGAcaaGCCCCTGGCAAAGGTCTTGAATGGGTTGCCACTATCTCCTACGACGG
GTCTCAGAAATATTATGCGGATTCAGTGAAGGGGCGGTTCACAATTTCACGAGACG
AGTCAAAGAATACACTGTACCTCCAAATGAATTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTGGAGGAGGTGGATCTCAATCCGTTCTGACTCAGCCACCC
TCCGCCTCTGGCACCCCGGGCCAACGGGTCACAATATCATGTTCTGGCTCTTCAAG
CAACATCGGAAACTGGTACGTGAGCTGGTACCAGCAGCTCCCCGGCACGGCGCCCA
AGCTTCTGATATATGACAACAACAAACGGCCCAGTGGAGTTCCTGACAGATTCAGT
GGGTCTAAAAGTGGTACAAGCGCTAGCCTGGCCATAAGTGGTCTGCAGAGTGAAGA
TGAGGCGGACTATTATTGCGGAACCTGGGACTCCAGCCTGAGCGCTCCCTGGGTTT
TCGGCGGAGGTACTAAGCTGACCGTCTTGGGCGCGGCCGCAGGTGCAGGTGGTGAT
TACAAAGATGATGACGATAAAGGTGCAGCGGCGCATCACCATCATCACCAC
(SEQ ID NO: 163), signal sequence (1-57), NYA-3061 (61-813), FLAG-His tag (814-891)

Fig. 165

NYA-3061
MKHLWFFLLLVAAPRWVLSGEVQLVESGGGLVQPGGSLRLSCAASGFSIRSYDIHW
VRQAPGKGLEWVATISYDGSQKYYADSVKGRFTISRDESKNTLYLQMNSLRAEDTA
VYHCARGSSGHYEAFDIWGQGTLVTVSSGGGGSGGGGSGGGGSGGGGSQSVLTQPP
SASGTPGQRVTISCSGSSSNIGNWYVSWYQQLPGTAPKLLIYDNNKRPSGVPDRFS
GSKSGTSASLAISGLQSEDEADYYCGTWDSSLSAPWVFGGGTKLTVLGAAAGAGGD
YKDDDDKGAAAHHHHHH
(SEQ ID NO: 164), signal sequence (1-19), NYA-3061 (21-271), FLAG-His tag (272-297)

Fig. 166

NYC-0005
ATGAAGCACCTGTGGTTCTTTCTGCTGCTGGTGGCCGCTCCTAGATGGGTGTTGTC
TGGCGAAGTGCAGCTGGTGGAATCTGGTGGCGGAGTTGTTCAGCCTGGCGGCTCTC
TGAGACTGAGCTGTGTGGCCAGCGGCTTCACCTTCGACGACTACGCCATGTACTGG
GTCCGACAGGTGCCAGGCAAGGACCTGGAATGGGTGTCCCTGATTTCTGGCGACGG
CGACATCACCTACTACGTGGACTCTGTGAAGGGCAGATTCACCGTGTCCAGAGACA
ACAACAAGAACAGCCTGTACCTGCAGATGAAGTCCCTGCGCGTGGAAGATACAGCC
CTGTACTACTGCGCCAAGGACATGATCTACTACGCCTCTTGGAGCGGCTACGGCAG
CAGCGATTACTACTACTATGTGATGGACGTGTGGGGCCAGGGCACCACCGTTACAG
TTTCTAGCGGAGGCGGAGGAAGTGGCGGCGGAGGATCTGGCGGTGGTGGTTCTGAT
ATCCAGATGACACAGAGCCCCAGCAGCCTGTCTGCCTCTGTGGGAGACAGAGTGAC
CATCACCTGTAGAGCCAGCCAGAGCATCAGCAGCTACCTGAACTGGTATCAGCAGA
AGCCCGGCAAGGCCCCTAAACTGCTGATCTATGCCGCCTCCAGTCTGCAGAGCGGA
GTGCCTAGCAGATTTCTGGCAGCGGCTCCGGCACCGATTTCACCCTGACCATATC
TAGCCTGCAGCCTGAGGACTTCGCCACCTACTATTGCCAGCAGAGCTACAGCACCC
CTCCTATCACCTTTGGCCAGGGAACCAGACTGGAAATCAAAGGCGCTGCTGCAGGC
GCTGGCGGCGACTACAAAGACGATGATGATAAGGGCGCTGCCGCTCACCACCACCA
TCACCAT
(SEQ ID NO: 165), signal sequence (1-57), NYC-0005 (61-825), FLAG-His tag (826-903)

Fig. 167

NYC-0005
MKHLWFFLLLVAAPRWVLSGEVQLVESGGGVVQPGGSLRLSCVASGFTFDDYAMYW
VRQVPGKDLEWVSLISGDGDITYYVDSVKGRFTVSRDNNKNSLYLQMKSLRVEDTA
LYYCAKDMIYYASWSGYGSSDYYYYVMDVWGQGTTVTVSSGGGGSGGGGSGGGGSD
IQMTQSPSSLSASVGDRVTITCRASQSISSYLNWYQQKPGKAPKLLIYAASSLQSG
VPSRFSGSGSGTDFTLTISSLQPEDFATYYCQQSYSTPPITFGQGTRLEIKGAAAG
AGGDYKDDDDKGAAAHHHHHH
(SEQ ID NO: 166), signal sequence (1-19), NYC-0005 (21-275), FLAG-His tag (276-301)

Fig. 168

NYC-0006
ATGAAGCACCTGTGGTTCTTTCTGCTGCTGGTGGCCGCTCCTAGATGGGTGTTGTC
TGGCGAAGTGCAGCTGGTGGAATCTGGTGGCGGAGTTGTTCAGCCTGGCGGCTCTC
TGAGACTGTCTTGTGCCGCCAGCGGCTTCACCTTCGACGACTACGCCATGTACTGG
GTCCGACAGGCCCCTGGCAAAGGCCTTGAATGGGTGTCCCTGATCAGCGGAGATGG
CGGCAGCATGTACTACGCCGATAGCGTGAAGGGCAGATTCACCATCAGCCGGGACA
ACAGCAAGAACAGCCTGTACCTGCAGATGAACTCCCTGCGGACCGAGGACACAGCC
CTGTACTACTGCGCCAAGGATATGATCTTCTACGCCTTTTGGAGCGGCTACGGCAG
CAGCGATTACTACTACTACGTGATGGACGTGTGGGGCCAGGGCACCACAGTGACAG
TTTATTCTGGCGGCGGAGGATCTGGCGGAGGTGGAAGCGGAGGCGGTGGATCTGAT
ATCCAGATGACACAGAGCCCCAGCAGCCTGTCTGCCTCTGTGGGAGACAGAGTGAC
CATCACCTGTCGGGCCAGCCAGAGAATCAGCACCTACCTGAACTGGTATCAGCAGA
AGCCCGGCAAGGCCCCTAAGCTGCTGATCTATGCTGCCTCCAGTCTGCAGAGCGGC
GTGCCAAGCAGATTTCTGGCAGCGGCTCTGGCACCGACTTCACCCTGACCATATC
TAGCCTGCAGCCTGAGGACTTCGCCACCTACTACTGCCAGCAGAGCTACAGCACCC
CTCCTATCACCTTTGGCCAGGGAACCAGACTGGAAATCAAAGGCGCTGCTGCAGGC
GCAGGCGGCGACTACAAAGACGATGATGATAAGGGCGCTGCCGCTCACCACCACCA
TCACCAT
(SEQ ID NO: 167), signal sequence (1-57), NYC-0006(61-825), FLAG-His tag (826-903)

Fig. 169

NYC-0006
MKHLWFFLLLVAAPRWVLSGEVQLVESGGGVVQPGGSLRLSCAASGFTFDDYAMYW
VRQAPGKGLEWVSLISGDGGSMYYADSVKGRFTISRDNSKNSLYLQMNSLRTEDTA
LYYCAKDMIFYAFWSGYGSSDYYYYVMDVWGQGTTVTVYSGGGGSGGGGSGGGGSD
IQMTQSPSSLSASVGDRVTITCRASQRISTYLNWYQQKPGKAPKLLIYAASSLQSG
VPSRFSGSGSGTDFTLTISSLQPEDFATYYCQQSYSTPPITFGQGTRLEIKGAAAG
AGGDYKDDDDKGAAAHHHHHH
(SEQ ID NO: 168), signal sequence (1-19), NYC-0006(21-275), FLAG-His tag (276-301)

Fig. 170

NYC-0007
ATGAAGCACCTGTGGTTCTTTCTGCTGCTGGTGGCCGCTCCTAGATGGGTGTTGTC
TGGCGAAGTGCAGCTGGTGGAATCTGGTGGCGGAGTTGTTCAGCCTGGCGGCTCTC
TGAGACTGTCTTGTGCCGCCAGCGGCTTCACCTTCGACGATTATGCCATGCACTGG
GTCCGACAGGCCCCTGGCAAGGACTTGAATGGGTGTCCCTGATCAGCGGCGACGG
CGACAATACCTACTACGCCGATAGCGTGAAGGGCAGATTCACCATCAGCCGGGACA
ACAACAAGAACAGCCTGTACCTGCAGATGAACTCCCTGCGGACCGAGGACACCGCC
TTCTACTACTGTGCCAAAGAGCTGATCTTCGGCAAGGTGCTGCACGACTTTTACTA
CTACGTGATGGACGTGTGGGGCCAGGGCACCACAGTGACAGTTTCTAGCGGAGGCG
GAGGAAGTGGCGGCGGAGGATCTGGCGGTGGTGGTTCTGATATCCAGATGACACAG
AGCCCCAGCAGCCTGTCTGCCTCTGTGGGAGACAGAGTGACCATCACCTGTAGAGC
CAGCCAGAGCATCAGCAGCTACCTGAACTGGTATCAGCAGAAGCCCGGCAAGGCCC
CTAAACTGCTGATCTATGCCGCCTCCAGTCTGCAGAGCGGAGTGCCTAGCAGATTT
TCTGGCAGCGGCTCCGGCACCGATTTCACCCTGACCATATCTAGCCTGCAGCCTGA
GGACTTCGCCACCTACTACTGCCAGCAGAGCTACAGCACCCCTCCTATCACCTTTG
GCCAGGGAACCAGACTGGAAATCAAAGGCGCTGCTGCAGGCGCAGGCGGCGACTAC
AAAGACGATGATGATAAGGGCGCTGCCGCTCACCACCACCATCACCAT
(SEQ ID NO: 169), signal sequence (1-57), NYC-0007(61-
810), FLAG-His tag (811-888)

Fig. 171

NYC-0007
MKHLWFFLLLVAAPRWVLSGEVQLVESGGGVVQPGGSLRLSCAASGFTFDDYAMHW
VRQAPGKGLEWVSLISGDGDNTYYADSVKGRFTISRDNNKNSLYLQMNSLRTEDTA
FYYCAKELIFGKVLHDFYYYVMDVWGQGTTVTVSSGGGGSGGGGSGGGGSDIQMTQ
SPSSLSASVGDRVTITCRASQSISSYLNWYQQKPGKAPKLLIYAASSLQSGVPSRF
SGSGSGTDFTLTISSLQPEDFATYYCQQSYSTPPITFGQGTRLEIKGAAAGAGGDY
KDDDDKGAAAHHHHHH
(SEQ ID NO: 170), signal sequence (1-19), NYC-0007(21-270), FLAG-His tag (271-296)

Fig. 172

NYC-0008
ATGAAGCACCTGTGGTTCTTTCTGCTGCTGGTGGCCGCTCCTAGATGGGTGTTGTC
TGGCGAAGTGCAGCTGGTGGAATCTGGTGGCGGAGTTGTTCAGCCTGGCGGCTCTC
TGAGACTGAGCTGTGAAGCCTCCGGCTTCATCTTCGACGACTACGCCATGCACTGG
GTCCGACAGGCACCTGGCAAGGCCTTGAATGGGTGTCCCTGATCTCTGGCGACGG
CGACATCATCTACTACGCCGACTCTGTGAAGGGCAGATTCACCATCAGCCGGGACA
ACAGCAAGAACAGCCTGTACCTGCAGATGAACTCCCTGATCATCGAGGACACAGCC
CTGTACTACTGCGCCAAGGATTGGGTGTTCGGCGTCGTGATGACCCACTACTGGTA
CTTCGGCCTGGATGTGTGGGGCCAGGGAACCACAGTGACAGTTTCTAGCGGAGGCG
GAGGAAGTGGCGGCGGAGGATCTGGCGGTGGTGGTTCTGATATCCAGATGACACAG
AGCCCCAGCAGCCTGTCTGCCTCTGAAGGCGACAGAGTGACCATCACCTGTAGAGC
CAGCCAGAGCATCAGCACCTACCTGAACTGGTATCAGCAGAAGCCCGGCAAGGCCC
CTAAGCTGCTGATCTATGGTGCCTCCAGTCTGCAGAGCGGCGTGCCAAGCAGATTT
TCTGGCAGCGGCTCTGGCACCGACTTCACCCTGACCATATCTAGCCTGCAGCCTGA
GGACTTCGCCACCTACTACTGCCAGCAGTCCTACAGCACCCCTCCTATCACATTTG
GCCAGGGCACCAAGGTGGAAATCAAAGGCGCTGCTGCAGGCGCTGGCGGCGACTAC
AAAGACGATGATGATAAGGGCGCTGCCGCTCACCACCACCATCACCAT
(SEQ ID NO: 171), signal sequence (1-57), NYC-0008(61-
810), FLAG-His tag (811-888)

Fig. 173

NYC-0008
MKHLWFFLLLVAAPRWVLSGEVQLVESGGGVVQPGGSLRLSCEASGFIFDDYAMHW
VRQAPGKGLEWVSLISGDGDIIYYADSVKGRFTISRDNSKNSLYLQMNSLIIEDTA
LYYCAKDWVFGVVMTHYWYFGLDVWGQGTTVTVSSGGGGSGGGGSGGGGSDIQMTQ
SPSSLSASEGDRVTITCRASQSISTYLNWYQQKPGKAPKLLIYGASSLQSGVPSRF
SGSGSGTDFTLTISSLQPEDFATYYCQQSYSTPPITFGQGTKVEIKGAAAGAGGDY
KDDDDKGAAAHHHHHH
(SEQ ID NO: 172), signal sequence (1-19), NYC-0008(21-270), FLAG-His tag (271-296)

Fig. 174

NYC-0009
ATGAAGCACCTGTGGTTCTTTCTGCTGCTGGTGGCCGCTCCTAGATGGGTGTTGTC
TGGCGAAGTGCAGCTGGTGGAATCTGGTGGCGGAGTTGTTCAGCCTGGCGGCTCTC
TGAGACTGTCTTGTGCCGCCAGCGGCTTCACCTTCGACGATTATGCCATGCACTGG
GTCCGACAGGCCCCTGGCAAGGACTTGAATGGGTGTCCCTGATCTCTGGCGGAGG
CGGCGGAACCTACTACAGCGATTCTGTGAAGGGCAGATTCACCATCAGCCGGGACA
CCAGCAAGGACAGCCTGTACCTGCAGATGAACAGCCTGCGGACCGAGGACACAGCC
CTGTACTACTGCGCCAAGGACATGGTGTTCGGCGTGGTCACCCCTTACTACTACTT
CGCCCTGGATGTGTGGGGCCAGGGCACAACAGTGACAGTCTCTTCTGGCGGCGGAG
GAAGCGGAGGCGGAGGATCCGGTGGTGGTGGATCTGACATCCAGATGACACAGAGC
CCCAGCAGCCTGTCTGCCTCTGTGGGAGACAGAGTGACCATCACCTGTAGAGCCAG
CCAGAGCATCAACAGCTACCTGAACTGGTATCAGCAGAAGCCCGGCAAGGCCCCTA
AGCTGCTGATCTATGCTGCCTCCAGTCTGCAGAGCGGCGTGCCAAGCAGATTTTCT
GGCAGCGGCTCTGGCACCGACTTCACCCTGACCATATCTAGCCTGCAGCCTGAGGA
CTTCGCCACCTACTACTGCCAGCAGAGCTACAGCGCCCCTCCTATCACATTTGGCC
AGGGAACCAGACTGGAAATCAAAGGCGCTGCTGCAGGCGCAGGCGGCGACTACAAA
GACGATGATGATAAGGGCGCTGCCGCTCACCACCATCACCATCAT
(SEQ ID NO: 173), signal sequence (1-57), NYC-0009(61-
807), FLAG-His tag (808-885)

Fig. 175

NYC-0009
MKHLWFFLLLVAAPRWVLSGEVQLVESGGGVVQPGGSLRLSCAASGFTFDDYAMHW
VRQAPGKGLEWVSLISGGGGGTYYSDSVKGRFTISRDTSKDSLYLQMNSLRTEDTA
LYYCAKDMVFGVVTPYYYFALDVWGQGTTVTVSSGGGGSGGGGSGGGGSDIQMTQS
PSSLSASVGDRVTITCRASQSINSYLNWYQQKPGKAPKLLIYAASSLQSGVPSRFS
GSGSGTDFTLTISSLQPEDFATYYCQQSYSAPPITFGQGTRLEIKGAAAGAGGDYK
DDDDKGAAAHHHHHH
(SEQ ID NO: 174), signal sequence (1-19), NYC-0009(21-
269), FLAG-His tag (270-295)

Fig. 176

NYC-0010
ATGAAGCACCTGTGGTTCTTTCTGCTGCTGGTGGCCGCTCCTAGATGGGTGTTGTC
TGGCGAAGTGCAGCTGGTGGAATCTGGTGGCGGAGTTGTTCAGCCTGGCGGCTCTC
TGAGACTGAGCTGTGCTGTGTCCGGCTTCACCTTCGACGACTACGCCATGCACTGG
GTCCGACAGGCACCTGGCAAGGCCTTGAATGGGTGTCCCTGATCAGCGGAGATGG
CGGCAGCACACACTACGCCGATTCTGTGAAGGGCAGATTCACCATCAGCCGGGACA
ACAGCAAGAACAGCCTGTACCTGCAGATGAACTCCCTGCGGACAGGCGACACAGCC
CTGTACTACTGCGCCAAGGACATGATCTTCGCCGTGGTCATCACCGACTACCACTA
CTACGGCATGGACGTGTGGGGCCAGGGAACCACAGTGACAGTTTCTAGCGGAGGCG
GAGGAAGTGGCGGCGGAGGATCTGGCGGTGGTGGTTCTGATATCCAGATGACACAG
AGCCCCAGCAGCCTGTCTGCCTCTGTGGGAGACAGAGTGACCATCACCTGTAGAGC
CAGCCAGAGCATCAGCAGCTACCTGAACTGGTATCAGCAGAAGCCCGGCAAGGCCC
CTAAACTGCTGATCTATGCCGCCTCCAGTCTGCAGAGCGGAGTGCCTAGCAGATTT
TCTGGCAGCGGCTCCGGCACCGATTTCACCCTGACCATATCTAGCCTGCAGCCTGA
GGACTTCGCCACCTACTACTGCCAGCAGAGCTACAGCACCCCTCCTATCACCTTTG
GCCAGGGCACCAGACTGGAAATCAAAGGCGCTGCTGCAGGCGCTGGCGGCGACTAC
AAAGACGATGATGATAAGGGCGCTGCCGCTCACCACCACCATCACCAT
(SEQ ID NO: 175), signal sequence (1-57), NYC-0010(61-810), FLAG-His tag (811-888)

Fig. 177

NYC-0010
MKHLWFFLLLVAAPRWVLSGEVQLVESGGGVVQPGGSLRLSCAVSGFTFDDYAMHW
VRQAPGKGLEWVSLISGDGGSTHYADSVKGRFTISRDNSKNSLYLQMNSLRTGDTA
LYYCAKDMIFAVVITDYHYYGMDVWGQGTTVTVSSGGGGSGGGGSGGGGSDIQMTQ
SPSSLSASVGDRVTITCRASQSISSYLNWYQQKPGKAPKLLIYAASSLQSGVPSRF
SGSGSGTDFTLTISSLQPEDFATYYCQQSYSTPPITFGQGTRLEIKGAAAGAGGDY
KDDDDKGAAAHHHHHH
(SEQ ID NO: 176), signal sequence (1-19), NYC-0010(21-270), FLAG-His tag (271-296)

Fig. 178

HC-h
ATGAAACACCTGTGGTTCTTCCTCCTGCTGGTGGCAGCTCCCAGATGGGTGCTGAG
CGACAAAACTCACACATGCCCACCCTGCCCAGCACCTGAAGCCGCCGGCGGACCCT
CAGTCTTCCTCTTCCCCCCAAAACCCAAGGACACCCTCATGATCTCCCGGACCCCT
GAGGTCACATGCGTGGTGGTGGACGTGAGCCACGAAGACCCTGAGGTCAAGTTCAA
CTGGTACGTGGACGGCGTGGAGGTGCATAATGCCAAGACCAAGCCTAGAGAGGAAC
AGTACAACAGCACCTACCGGGTGGTGTCCGTGCTGACAGTGCTGCACCAGGACTGG
CTGAACGGCAAAGAGTACAAGTGCAAGGTGTCCAACAAGGCCCTGCCTGCCCCCAT
CGAGAAAACCATCAGCAAGGCCAAGGGCCAGCCCCGCGAACCTCAAGTGTGCACCC
TGCCACCCTCCCGGGATGAGCTGACCAAGAACCAGGTGTCCCTGAGCTGTGCCGTG
AAGGGCTTCTACCCCTCCGATATCGCCGTGGAATGGGAGAGCAACGGCCAGCCCGA
GAACAACTACAAGACCACCCCCCCTGTGCTGGACAGCGACGGCTCATTCTTCCTGG
TGTCCAAGCTGACCGTGGACAAGTCCAGATGGCAGCAGGGCAACGTCTTCTCATGC
TCCGTGATGCATGAGGCTCTGCACAACCACTACACCCAGAAGAGCCTCTCCCTGTC
TCCCGGCAAA
(SEQ ID NO: 177), signal sequence (1-57), constant
region (58-738)

Fig. 179

HC-h
MKHLWFFLLLVAAPRWVLSDKTHTCPPCPAPEAAGGPSVFLFPPKPKDTLMISRTP
EVTCVVVDVSHEDPEVKFNWYVDGVEVHNAKTKPREEQYNSTYRVVSVLTVLHQDW
LNGKEYKCKVSNKALPAPIEKTISKAKGQPREPQVCTLPPSRDELTKNQVSLSCAV
KGFYPSDIAVEWESNGQPENNYKTTPPVLDSDGSFFLVSKLTVDKSRWQQGNVFSC
SVMHEALHNHYTQKSLSLSPGK
(SEQ ID NO: 178), signal sequence (1-19), constant
region (20-246)

Fig. 180

```
NYD-2047-HC-k
ATGAAGCACCTGTGGTTCTTTCTGCTGCTGGTGGCCGCTCCTAGATGGGTGCTGTC
TGGTCAAGTACAGCTGGTGGAATCCGGTGGAGGCGTGGTCCAGCCGGGACGCAGCT
TGAGACTGTCCTGCGCTGCATCTGGCTTTTCCATACGATCCTACGATATGCACTGG
GTTCGCCAAGCCCCTGGCAAAGGTCTTGAATGGGTTGCCACTATCTCCTACGACGG
GTCTCAGAAATATTACGCGGATTCAGTGAAGGGGCGGTTCACAATTTCACGGGACA
ATTCAAAGAATACCTTGTATCTCCAGATGTCTTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTCAATCCGTTCTGACTCAGCCACCCTCCGTGAGTGCAGCG
CCTGGACAGAAGGTCACAATATCATGTTCTGGCTCTTCAAGCAACATCGGAAACTG
GTACGTGAGCTGGTACCAGCAGCTCCCCGGCACGGCGCCCAAGCTTCTGATATATG
ACAACAACAAACGGCCCAGTGGAATCCCTGACAGATTCAGTGGGTCTAAAAGTGGT
ACAAGCGCTACCCTGGGTATCACCGGATTGCAGACCGGAGATGAGGCGGACTATTA
TTGCGGAACCTGGGACTCCAGCCTGAGCGCTCCCTGGGTTTTCGGCGGAGGTACTA
AGGTTACCGTCTTGGGCGGAGAACCCAAGAGCgcaGACAAGACCCACACCTGTCCT
CCATGTCCTGCTCCAGAAGCTGCAGGCGGCCCTTCCGTGTTTCTGTTCCCTCCAAA
GCCTAAGGACACCCTGATGATCAGCCGGACACCTGAAGTGACCTGCGTGGTGGTGG
ATGTGTCCCACGAGGATCCCGAAGTGAAGTTCAATTGGTACGTGGACGGCGTGGAA
GTGCACAACGCCAAGACCAAGCCTAGAGAGGAACAGTACAACAGCACCTACAGAGT
GGTGTCTGTGCTGACAGTGCTGCACCAGGACTGGCTGAACGGCAAAGAGTACAAGT
GCAAGGTGTCCAACAAGGCCCTGCCTGCTCCTATCGAGAAAACCATCAGCAAGGCC
AAGGGCCAGCCTAGGGAACCCCAGGTTTACACCCTGCCTCCATGCAGGGATGAGCT
GACCAAGAACCAGGTGTCCCTGTGGTGCCTGGTTAAGGGCTTCTACCCCTCCGATA
TCGCCGTGGAATGGGAGAGCAATGGCCAGCCAGAGAACAACTACAAGACAACCCCT
CCTGTGCTGGACTCCGACGGCTCATTCTTCCTGTACAGCAAGCTGACCGTGGACAA
GAGCAGATGGCAGCAGGGCAACGTGTTCAGCTGCAGCGTGATGCACGAGGCCCTGC
ACAACCACTACACACAGAAGTCCCTGTCTCTGAGCCCCGGCAAA
(SEQ ID NO: 179), signal sequence (1-57), NYA-2047(61-
798), linker (799-804), constant region (805-1500)
```

Fig. 181

NYD-2047-HC-k
MKHLWFFLLLVAAPRWVLSGQVQLVESGGGVVQPGRSLRLSCAASGFSIRSYDMHW
VRQAPGKGLEWVATISYDGSQKYYADSVKGRFTISRDNSKNTLYLQMSSLRAEDTA
VYHCARGSSGHYEAFDIWGQGTLVTVSSGGGGSGGGGSGGGGSQSVLTQPPSVSAA
PGQKVTISCSGSSSNIGNWYVSWYQQLPGTAPKLLIYDNNKRPSGIPDRFSGSKSG
TSATLGITGLQTGDEADYYCGTWDSSLSAPWVFGGGTKVTVLGGEPKSADKTHTCP
PCPAPEAAGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKA
KGQPREPQVYTLPPCRDELTKNQVSLWCLVKGFYPSDIAVEWESNGQPENNYKTTP
PVLDSDGSFFLYSKLTVDKSRWQQGNVFSCSVMHEALHNHYTQKSLSLSPGK
(SEQ ID NO: 180), signal sequence (1-19), NYA-2047(21-
266), linker (267-268), constant region (269-500)

Fig. 182

```
NYD-2061-HC-k
ATGAAGCACCTGTGGTTCTTTCTGCTGCTGGTGGCCGCTCCTAGATGGGTGCTGTC
TGGTGAGGTACAGCTGGTGGAATCCGGTGGAGGCCTTGTGCAACCGGGAGGCTCCC
TGCGACTCTCTTGCGCCGCATCTGGCTTTTCCATACGATCCTACGATATTCATTGG
GTCCGAcaaGCCCCTGGCAAAGGTCTTGAATGGGTTGCCACTATCTCCTACGACGG
GTCTCAGAAATATTATGCGGATTCAGTGAAGGGGCGGTTCACAATTTCACGAGACG
AGTCAAAGAATACACTGTACCTCCAAATGAATTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTCAATCCGTTCTGACTCAGCCACCCTCCGCCTCTGGCACC
CCGGGCCAACGGGTCACAATATCATGTTCTGGCTCTTCAAGCAACATCGGAAACTG
GTACGTGAGCTGGTACCAGCAGCTCCCCGGCACGGCGCCCAAGCTTCTGATATATG
ACAACAACAAACGGCCCAGTGGAGTTCCTGACAGATTCAGTGGGTCTAAAAGTGGT
ACAAGCGCTAGCCTGGCCATAAGTGGTCTGCAGAGTGAAGATGAGGCGGACTATTA
TTGCGGAACCTGGGACTCCAGCCTGAGCGCTCCCTGGGTTTTCGGCGGAGGTACTA
AGCTGACCGTCTTGGGCGGAGAACCCAAGAGCgcaGACAAGACCCACACCTGTCCT
CCATGTCCTGCTCCAGAAGCTGCAGGCGGCCCTTCCGTGTTTCTGTTCCCTCCAAA
GCCTAAGGACACCCTGATGATCAGCCGGACACCTGAAGTGACCTGCGTGGTGGTGG
ATGTGTCCCACGAGGATCCCGAAGTGAAGTTCAATTGGTACGTGGACGGCGTGGAA
GTGCACAACGCCAAGACCAAGCCTAGAGAGGAACAGTACAACAGCACCTACAGAGT
GGTGTCTGTGCTGACAGTGCTGCACCAGGACTGGCTGAACGGCAAAGAGTACAAGT
GCAAGGTGTCCAACAAGGCCCTGCCTGCTCCTATCGAGAAAACCATCAGCAAGGCC
AAGGGCCAGCCTAGGGAACCCCAGGTTTACACCCTGCCTCCATGCAGGGATGAGCT
GACCAAGAACCAGGTGTCCCTGTGGTGCCTGGTTAAGGGCTTCTACCCCTCCGATA
TCGCCGTGGAATGGGAGAGCAATGGCCAGCCAGAGAACAACTACAAGACAACCCCT
CCTGTGCTGGACTCCGACGGCTCATTCTTCCTGTACAGCAAGCTGACCGTGGACAA
GAGCAGATGGCAGCAGGGCAACGTGTTCAGCTGCAGCGTGATGCACGAGGCCCTGC
ACAACCACTACACACAGAAGTCCCTGTCTCTGAGCCCCGGCAAA
(SEQ ID NO: 181), signal sequence (1-57), NYA-2061 (61-
798), linker (799-804), constant region (805-1500)
```

Fig. 183

```
NYD-2061-HC-k
MKHLWFFLLLVAAPRWVLSGEVQLVESGGGLVQPGGSLRLSCAASGFSIRSYDIHW
VRQAPGKGLEWVATISYDGSQKYYADSVKGRFTISRDESKNTLYLQMNSLRAEDTA
VYHCARGSSGHYEAFDIWGQGTLVTVSSGGGGSGGGGSGGGGSQSVLTQPPSASGT
PGQRVTISCSGSSSNIGNWYVSWYQQLPGTAPKLLIYDNNKRPSGVPDRFSGSKSG
TSASLAISGLQSEDEADYYCGTWDSSLSAPWVFGGGTKLTVLGGEPKSADKTHTCP
PCPAPEAAGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKA
KGQPREPQVYTLPPCRDELTKNQVSLWCLVKGFYPSDIAVEWESNGQPENNYKTTP
PVLDSDGSFFLYSKLTVDKSRWQQGNVFSCSVMHEALHNHYTQKSLSLSPGK
(SEQ ID NO: 182), signal sequence (1-19), NYA-2061 (21-
266), linker (267-268), constant region (269-500)
```

Fig. 184

NYD-3061-HC-k
ATGAAGCACCTGTGGTTCTTTCTGCTGCTGGTGGCCGCTCCTAGATGGGTGCTGTC
TGGTGAGGTACAGCTGGTGGAATCCGGTGGAGGCCTTGTGCAACCGGGAGGCTCCC
TGCGACTCTCTTGCGCCGCATCTGGCTTTTCCATACGATCCTACGATATTCATTGG
GTCCGAcaaGCCCCTGGCAAAGGTCTTGAATGGGTTGCCACTATCTCCTACGACGG
GTCTCAGAAATATTATGCGGATTCAGTGAAGGGGCGGTTCACAATTTCACGAGACG
AGTCAAAGAATACACTGTACCTCCAAATGAATTCACTGAGAGCCGAGGATACTGCA
GTCTATCATTGTGCAAGAGGGTCCTCAGGCCACTACGAGGCCTTTGATATATGGGG
CCAAGGCACCTTGGTAACCGTTAGTAGCGGAGGTGGAGGAAGCGGAGGCGGCGGTT
CCGGAGGAGGTGGAAGTGGAGGAGGTGGATCTCAATCCGTTCTGACTCAGCCACCC
TCCGCCTCTGGCACCCCGGGCCAACGGGTCACAATATCATGTTCTGGCTCTTCAAG
CAACATCGGAAACTGGTACGTGAGCTGGTACCAGCAGCTCCCCGGCACGGCGCCCA
AGCTTCTGATATATGACAACAACAAACGGCCCAGTGGAGTTCCTGACAGATTCAGT
GGGTCTAAAAGTGGTACAAGCGCTAGCCTGGCCATAAGTGGTCTGCAGAGTGAAGA
TGAGGCGGACTATTATTGCGGAACCTGGGACTCCAGCCTGAGCGCTCCCTGGGTTT
TCGGCGGAGGTACTAAGCTGACCGTCTTGGGCGGAGAACCCAAGAGCGCAGACAAG
ACCCACACCTGTCCTCCATGTCCTGCTCCAGAAGCTGCAGGCGGCCCTTCCGTGTT
TCTGTTCCCTCCAAAGCCTAAGGACACCCTGATGATCAGCCGGACACCTGAAGTGA
CCTGCGTGGTGGTGGATGTGTCCCACGAGGATCCCGAAGTGAAGTTCAATTGGTAC
GTGGACGGCGTGGAAGTGCACAACGCCAAGACCAAGCCTAGAGAGGAACAGTACAA
CAGCACCTACAGAGTGGTGTCTGTGCTGACAGTGCTGCACCAGGACTGGCTGAACG
GCAAAGAGTACAAGTGCAAGGTGTCCAACAAGGCCCTGCCTGCTCCTATCGAGAAA
ACCATCAGCAAGGCCAAGGGCCAGCCTAGGGAACCCCAGGTTTACACCCTGCCTCC
ATGCAGGGATGAGCTGACCAAGAACCAGGTGTCCCTGTGGTGCCTGGTTAAGGGCT
TCTACCCCTCCGATATCGCCGTGGAATGGGAGAGCAATGGCCAGCCAGAGAACAAC
TACAAGACAACCCCTCCTGTGCTGGACTCCGACGGCTCATTCTTCCTGTACAGCAA
GCTGACCGTGGACAAGAGCAGATGGCAGCAGGGCAACGTGTTCAGCTGCAGCGTGA
TGCACGAGGCCCTGCACAACCACTACACACAGAAGTCCCTGTCTCTGAGCCCCGGC
AAA
(SEQ ID NO: 183), signal sequence (1-57), NYA-3061 (61-813), linker (814-819), constant region (820-1515)

Fig. 185

NYD-3061-HC-k
MKHLWFFLLLVAAPRWVLSGEVQLVESGGGLVQPGGSLRLSCAASGFSIRSYDIHW
VRQAPGKGLEWVATISYDGSQKYYADSVKGRFTISRDESKNTLYLQMNSLRAEDTA
VYHCARGSSGHYEAFDIWGQGTLVTVSSGGGGSGGGGSGGGGSGGGGSQSVLTQPP
SASGTPGQRVTISCSGSSSNIGNWYVSWYQQLPGTAPKLLIYDNNKRPSGVPDRFS
GSKSGTSASLAISGLQSEDEADYYCGTWDSSLSAPWVFGGGTKLTVLGGEPKSADK
THTCPPCPAPEAAGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEK
TISKAKGQPREPQVYTLPPCRDELTKNQVSLWCLVKGFYPSDIAVEWESNGQPENN
YKTTPPVLDSDGSFFLYSKLTVDKSRWQQGNVFSCSVMHEALHNHYTQKSLSLSPG
K
(SEQ ID NO: 184), signal sequence (1-19), NYA-3061 (21-271), linker (272-273), constant region (274-505)

Fig. 186

NYC-0011-HC-k
ATGAAGCACCTGTGGTTCTTTCTGCTGCTGGTGGCCGCTCCTAGATGGGTGCTGTC
TGGCGAAGTGCAGCTGGTGGAATCTGGTGGCGGAGTTGTTCAGCCTGGCGGCTCTC
TGAGACTGAGCTGTGTGGCCAGCGGCTTCACCTTCGACGACTACGCCATGTACTGG
GTCCGACAGGTGCCAGGCAAGGACCTGGAATGGGTGTCCCTGATTTCTGGCGACGG
CGACATCACCTACTACGTGGACTCTGTGAAGGGCAGATTCACCGTGTCCAGAGACA
ACAACAAGAACAGCCTGTACCTGCAGATGAAGTCCCTGCGCGTGGAAGATACAGCC
CTGTACTACTGCGCCAAGGACATGATCTACTACGCCTCTTGGAGCGGCTACGGCAG
CAGCGATTACTACTACTATGTGATGGACGTGTGGGGCCAGGGCACCACCGTTACAG
TTTCTAGCGGAGGCGGAGGAAGTGGCGGCGGAGGATCTGGCGGTGGTGGTTCTGAT
ATCCAGATGACACAGAGCCCCAGCAGCCTGTCTGCCTCTGTGGGAGACAGAGTGAC
CATCACCTGTAGAGCCAGCCAGAGCATCAGCAGCTACCTGAACTGGTATCAGCAGA
AGCCCGGCAAGGCCCCTAAACTGCTGATCTATGCCGCCTCCAGTCTGCAGAGCGGA
GTGCCTAGCAGATTTTCTGGCAGCGGCTCCGGCACCGATTTCACCCTGACCATATC
TAGCCTGCAGCCTGAGGACTTCGCCACCTACTATTGCCAGCAGAGCTACAGCACCC
CTCCTATCACCTTTGGCCAGGGAACCAGACTGGAAATCAAAGGCGGAGAACCCAAG
AGCgcaGACAAGACCCACACCTGTCCTCCATGTCCTGCTCCAGAAGCTGCAGGCGG
CCCTTCCGTGTTTCTGTTCCCTCCAAAGCCTAAGGACACCCTGATGATCAGCCGGA
CACCTGAAGTGACCTGCGTGGTGGTGGATGTGTCCCACGAGGATCCCGAAGTGAAG
TTCAATTGGTACGTGGACGGCGTGGAAGTGCACAACGCCAAGACCAAGCCTAGAGA
GGAACAGTACAACAGCACCTACAGAGTGGTGTCTGTGCTGACAGTGCTGCACCAGG
ACTGGCTGAACGGCAAAGAGTACAAGTGCAAGGTGTCCAACAAGGCCCTGCCTGCT
CCTATCGAGAAAACCATCAGCAAGGCCAAGGGCCAGCCTAGGGAACCCCAGGTTTA
CACCCTGCCTCCATGCAGGGATGAGCTGACCAAGAACCAGGTGTCCCTGTGGTGCC
TGGTTAAGGGCTTCTACCCCTCCGATATCGCCGTGGAATGGGAGAGCAATGGCCAG
CCAGAGAACAACTACAAGACAACCCCTCCTGTGCTGGACTCCGACGGCTCATTCTT
CCTGTACAGCAAGCTGACCGTGGACAAGAGCAGATGGCAGCAGGGCAACGTGTTCA
GCTGCAGCGTGATGCACGAGGCCCTGCACAACCACTACACACAGAAGTCCCTGTCT
CTGAGCCCCGGCAAA
(SEQ ID NO: 185), signal sequence (1-57), NYC-0005 (61-
825), linker (826-831), constant region (832-1527)

Fig. 187

NYC-0011-HC-k
MKHLWFFLLLVAAPRWVLSGEVQLVESGGGVVQPGGSLRLSCVASGFTFDDYAMYW
VRQVPGKDLEWVSLISGDGDITYYVDSVKGRFTVSRDNNKNSLYLQMKSLRVEDTA
LYYCAKDMIYYASWSGYGSSDYYYYVMDVWGQGTTVTVSSGGGGSGGGGSGGGGSD
IQMTQSPSSLSASVGDRVTITCRASQSISSYLNWYQQKPGKAPKLLIYAASSLQSG
VPSRFSGSGSGTDFTLTISSLQPEDFATYYCQQSYSTPPITFGQGTRLEIKGGEPK
SADKTHTCPPCPAPEAAGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPA
PIEKTISKAKGQPREPQVYTLPPCRDELTKNQVSLWCLVKGFYPSDIAVEWESNGQ
PENNYKTTPPVLDSDGSFFLYSKLTVDKSRWQQGNVFSCSVMHEALHNHYTQKSLS
LSPGK
(SEQ ID NO: 186), signal sequence (1-19), NYC-0005 (21-
275), linker (276-277), constant region (278-509)

Fig. 188

NYC-0012-HC-k
ATGAAGCACCTGTGGTTCTTTCTGCTGCTGGTGGCCGCTCCTAGATGGGTGCTGTC
TGGCGAAGTGCAGCTGGTGGAATCTGGTGGCGGAGTTGTTCAGCCTGGCGGCTCTC
TGAGACTGTCTTGTGCCGCCAGCGGCTTCACCTTCGACGACTACGCCATGTACTGG
GTCCGACAGGCCCCTGGCAAAGGCCTTGAATGGGTGTCCCTGATCAGCGGAGATGG
CGGCAGCATGTACTACGCCGATAGCGTGAAGGGCAGATTCACCATCAGCCGGGACA
ACAGCAAGAACAGCCTGTACCTGCAGATGAACTCCCTGCGGACCGAGGACACAGCC
CTGTACTACTGCGCCAAGGATATGATCTTCTACGCCTTTTGGAGCGGCTACGGCAG
CAGCGATTACTACTACTACGTGATGGACGTGTGGGGCCAGGGCACCACAGTGACAG
TTTATTCTGGCGGCGGAGGATCTGGCGGAGGTGGAAGCGGAGGCGGTGGATCTGAT
ATCCAGATGACACAGAGCCCCAGCAGCCTGTCTGCCTCTGTGGGAGACAGAGTGAC
CATCACCTGTCGGGCCAGCCAGAGAATCAGCACCTACCTGAACTGGTATCAGCAGA
AGCCCGGCAAGGCCCCTAAGCTGCTGATCTATGCTGCCTCCAGTCTGCAGAGCGGC
GTGCCAAGCAGATTTTCTGGCAGCGGCTCTGGCACCGACTTCACCCTGACCATATC
TAGCCTGCAGCCTGAGGACTTCGCCACCTACTACTGCCAGCAGAGCTACAGCACCC
CTCCTATCACCTTTGGCCAGGGAACCAGACTGGAAATCAAAGGCGGAGAACCCAAG
AGCgcaGACAAGACCCACACCTGTCCTCCATGTCCTGCTCCAGAAGCTGCAGGCGG
CCCTTCCGTGTTTCTGTTCCCTCCAAAGCCTAAGGACACCCTGATGATCAGCCGGA
CACCTGAAGTGACCTGCGTGGTGGTGGATGTGTCCCACGAGGATCCCGAAGTGAAG
TTCAATTGGTACGTGGACGGCGTGGAAGTGCACAACGCCAAGACCAAGCCTAGAGA
GGAACAGTACAACAGCACCTACAGAGTGGTGTCTGTGCTGACAGTGCTGCACCAGG
ACTGGCTGAACGGCAAAGAGTACAAGTGCAAGGTGTCCAACAAGGCCCTGCCTGCT
CCTATCGAGAAAACCATCAGCAAGGCCAAGGGCCAGCCTAGGGAACCCCAGGTTTA
CACCCTGCCTCCATGCAGGGATGAGCTGACCAAGAACCAGGTGTCCCTGTGGTGCC
TGGTTAAGGGCTTCTACCCCTCCGATATCGCCGTGGAATGGGAGAGCAATGGCCAG
CCAGAGAACAACTACAAGACAACCCCTCCTGTGCTGGACTCCGACGGCTCATTCTT
CCTGTACAGCAAGCTGACCGTGGACAAGAGCAGATGGCAGCAGGGCAACGTGTTCA
GCTGCAGCGTGATGCACGAGGCCCTGCACAACCACTACACACAGAAGTCCCTGTCT
CTGAGCCCCGGCAAA
(SEQ ID NO: 187), signal sequence (1-57), NYC-0006 (61-825), linker (826-831), constant region (832-1527)

Fig. 189

NYC-0012-HC-k
MKHLWFFLLLVAAPRWVLSGEVQLVESGGGVVQPGGSLRLSCAASGFTFDDYAMYW
VRQAPGKGLEWVSLISGDGGSMYYADSVKGRFTISRDNSKNSLYLQMNSLRTEDTA
LYYCAKDMIFYAFWSGYGSSDYYYYVMDVWGQGTTVTVYSGGGGSGGGGSGGGGSD
IQMTQSPSSLSASVGDRVTITCRASQRISTYLNWYQQKPGKAPKLLIYAASSLQSG
VPSRFSGSGSGTDFTLTISSLQPEDFATYYCQQSYSTPPITFGQGTRLEIKGGEPK
SADKTHTCPPCPAPEAAGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPA
PIEKTISKAKGQPREPQVYTLPPCRDELTKNQVSLWCLVKGFYPSDIAVEWESNGQ
PENNYKTTPPVLDSDGSFFLYSKLTVDKSRWQQGNVFSCSVMHEALHNHYTQKSLS
LSPGK
(SEQ ID NO: 188), signal sequence (1-19), NYC-0006 (21-
275), linker (276-277), constant region (278-509)

Fig. 190

NYC-0013-HC-k
ATGAAGCACCTGTGGTTCTTTCTGCTGCTGGTGGCCGCTCCTAGATGGGTGCTGTC
TGGCGAAGTGCAGCTGGTGGAATCTGGTGGCGGAGTTGTTCAGCCTGGCGGCTCTC
TGAGACTGTCTTGTGCCGCCAGCGGCTTCACCTTCGACGATTATGCCATGCACTGG
GTCCGACAGGCCCCTGGCAAGGACTTGAATGGGTGTCCCTGATCAGCGGCGACGG
CGACAATACCTACTACGCCGATAGCGTGAAGGGCAGATTCACCATCAGCCGGGACA
ACAACAAGAACAGCCTGTACCTGCAGATGAACTCCCTGCGGACCGAGGACACCGCC
TTCTACTACTGTGCCAAAGAGCTGATCTTCGGCAAGGTGCTGCACGACTTTTACTA
CTACGTGATGGACGTGTGGGGCCAGGGCACCACAGTGACAGTTTCTAGCGGAGGCG
GAGGAAGTGGCGGCGGAGGATCTGGCGGTGGTGGTTCTGATATCCAGATGACACAG
AGCCCCAGCAGCCTGTCTGCCTCTGTGGGAGACAGAGTGACCATCACCTGTAGAGC
CAGCCAGAGCATCAGCAGCTACCTGAACTGGTATCAGCAGAAGCCCGGCAAGGCCC
CTAAACTGCTGATCTATGCCGCCTCCAGTCTGCAGAGCGGAGTGCCTAGCAGATTT
TCTGGCAGCGGCTCCGGCACCGATTTCACCCTGACCATATCTAGCCTGCAGCCTGA
GGACTTCGCCACCTACTACTGCCAGCAGAGCTACAGCACCCCTCCTATCACCTTTG
GCCAGGGAACCAGACTGGAAATCAAAGGCGGAGAACCCAAGAGCgcaGACAAGACC
CACACCTGTCCTCCATGTCCTGCTCCAGAAGCTGCAGGCGGCCCTTCCGTGTTTCT
GTTCCCTCCAAAGCCTAAGGACACCCTGATGATCAGCCGGACACCTGAAGTGACCT
GCGTGGTGGTGGATGTGTCCCACGAGGATCCCGAAGTGAAGTTCAATTGGTACGTG
GACGGCGTGGAAGTGCACAACGCCAAGACCAAGCCTAGAGAGGAACAGTACAACAG
CACCTACAGAGTGGTGTCTGTGCTGACAGTGCTGCACCAGGACTGGCTGAACGGCA
AAGAGTACAAGTGCAAGGTGTCCAACAAGGCCCTGCCTGCTCCTATCGAGAAAACC
ATCAGCAAGGCCAAGGGCCAGCCTAGGGAACCCCAGGTTTACACCCTGCCTCCATG
CAGGGATGAGCTGACCAAGAACCAGGTGTCCCTGTGGTGCCTGGTTAAGGGCTTCT
ACCCCTCCGATATCGCCGTGGAATGGGAGAGCAATGGCCAGCCAGAGAACAACTAC
AAGACAACCCCTCCTGTGCTGGACTCCGACGGCTCATTCTTCCTGTACAGCAAGCT
GACCGTGGACAAGAGCAGATGGCAGCAGGGCAACGTGTTCAGCTGCAGCGTGATGC
ACGAGGCCCTGCACAACCACTACACACAGAAGTCCCTGTCTCTGAGCCCCGGCAAA
(SEQ ID NO: 189), signal sequence (1-57), NYC-0007 (61-
810), linker (811-816), constant region (817-1512)

Fig. 191

```
NYC-0013-HC-k
MKHLWFFLLLVAAPRWVLSGEVQLVESGGGVVQPGGSLRLSCAASGFTFDDYAMHW
VRQAPGKGLEWVSLISGDGDNTYYADSVKGRFTISRDNNKNSLYLQMNSLRTEDTA
FYYCAKELIFGKVLHDFYYYVMDVWGQGTTVTVSSGGGGSGGGGSGGGGSDIQMTQ
SPSSLSASVGDRVTITCRASQSISSYLNWYQQKPGKAPKLLIYAASSLQSGVPSRF
SGSGSGTDFTLTISSLQPEDFATYYCQQSYSTPPITFGQGTRLEIKGGEPKSADKT
HTCPPCPAPEAAGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKT
ISKAKGQPREPQVYTLPPCRDELTKNQVSLWCLVKGFYPSDIAVEWESNGQPENNY
KTTPPVLDSDGSFFLYSKLTVDKSRWQQGNVFSCSVMHEALHNHYTQKSLSLSPGK
(SEQ ID NO: 190), signal sequence (1-19), NYC-0007 (21-
270), linker (271-272), constant region (273-504)
```

Fig. 192

NYC-0014-HC-k
ATGAAGCACCTGTGGTTCTTTCTGCTGCTGGTGGCCGCTCCTAGATGGGTGCTGTC
TGGCGAAGTGCAGCTGGTGGAATCTGGTGGCGGAGTTGTTCAGCCTGGCGGCTCTC
TGAGACTGAGCTGTGAAGCCTCCGGCTTCATCTTCGACGACTACGCCATGCACTGG
GTCCGACAGGCACCTGGCAAAGGCCTTGAATGGGTGTCCCTGATCTCTGGCGACGG
CGACATCATCTACTACGCCGACTCTGTGAAGGGCAGATTCACCATCAGCCGGGACA
ACAGCAAGAACAGCCTGTACCTGCAGATGAACTCCCTGATCATCGAGGACACAGCC
CTGTACTACTGCGCCAAGGATTGGGTGTTCGGCGTCGTGATGACCCACTACTGGTA
CTTCGGCCTGGATGTGTGGGGCCAGGGAACCACAGTGACAGTTTCTAGCGGAGGCG
GAGGAAGTGGCGGCGGAGGATCTGGCGGTGGTGGTTCTGATATCCAGATGACACAG
AGCCCCAGCAGCCTGTCTGCCTCTGAAGGCGACAGAGTGACCATCACCTGTAGAGC
CAGCCAGAGCATCAGCACCTACCTGAACTGGTATCAGCAGAAGCCCGGCAAGGCCC
CTAAGCTGCTGATCTATGGTGCCTCCAGTCTGCAGAGCGGCGTGCCAAGCAGATTT
TCTGGCAGCGGCTCTGGCACCGACTTCACCCTGACCATATCTAGCCTGCAGCCTGA
GGACTTCGCCACCTACTACTGCCAGCAGTCCTACAGCACCCCTCCTATCACATTTG
GCCAGGGCACCAAGGTGGAAATCAAAGGCGGAGAACCCAAGAGCgcaGACAAGACC
CACACCTGTCCTCCATGTCCTGCTCCAGAAGCTGCAGGCGGCCCTTCCGTGTTTCT
GTTCCCTCCAAAGCCTAAGGACACCCTGATGATCAGCCGGACACCTGAAGTGACCT
GCGTGGTGGTGGATGTGTCCCACGAGGATCCCGAAGTGAAGTTCAATTGGTACGTG
GACGGCGTGGAAGTGCACAACGCCAAGACCAAGCCTAGAGAGGAACAGTACAACAG
CACCTACAGAGTGGTGTCTGTGCTGACAGTGCTGCACCAGGACTGGCTGAACGGCA
AAGAGTACAAGTGCAAGGTGTCCAACAAGGCCCTGCCTGCTCCTATCGAGAAAACC
ATCAGCAAGGCCAAGGGCCAGCCTAGGGAACCCCAGGTTTACACCCTGCCTCCATG
CAGGGATGAGCTGACCAAGAACCAGGTGTCCCTGTGGTGCCTGGTTAAGGGCTTCT
ACCCCTCCGATATCGCCGTGGAATGGGAGAGCAATGGCCAGCCAGAGAACAACTAC
AAGACAACCCCTCCTGTGCTGGACTCCGACGGCTCATTCTTCCTGTACAGCAAGCT
GACCGTGGACAAGAGCAGATGGCAGCAGGGCAACGTGTTCAGCTGCAGCGTGATGC
ACGAGGCCCTGCACAACCACTACACACAGAAGTCCCTGTCTCTGAGCCCCGGCAAA
(SEQ ID NO: 191), signal sequence (1-57), NYC-0008 (61-
810), linker (811-816), constant region (817-1512)

Fig. 193

```
NYC-0014-HC-k
MKHLWFFLLLVAAPRWVLSGEVQLVESGGGVVQPGGSLRLSCEASGFIFDDYAMHW
VRQAPGKGLEWVSLISGDGDIIYYADSVKGRFTISRDNSKNSLYLQMNSLIIEDTA
LYYCAKDWVFGVVMTHYWYFGLDVWGQGTTVTVSSGGGGSGGGGSGGGGSDIQMTQ
SPSSLSASEGDRVTITCRASQSISTYLNWYQQKPGKAPKLLIYGASSLQSGVPSRF
SGSGSGTDFTLTISSLQPEDFATYYCQQSYSTPPITFGQGTKVEIKGGEPKSADKT
HTCPPCPAPEAAGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKT
ISKAKGQPREPQVYTLPPCRDELTKNQVSLWCLVKGFYPSDIAVEWESNGQPENNY
KTTPPVLDSDGSFFLYSKLTVDKSRWQQGNVFSCSVMHEALHNHYTQKSLSLSPGK
(SEQ ID NO: 192), signal sequence (1-19), NYC-0008 (21-
270), linker (271-272), constant region (273-504)
```

Fig. 194

```
NYC-0015-HC-k
ATGAAGCACCTGTGGTTCTTTCTGCTGCTGGTGGCCGCTCCTAGATGGGTGCTGTC
TGGCGAAGTGCAGCTGGTGGAATCTGGTGGCGGAGTTGTTCAGCCTGGCGGCTCTC
TGAGACTGTCTTGTGCCGCCAGCGGCTTCACCTTCGACGATTATGCCATGCACTGG
GTCCGACAGGCCCCTGGCAAGGACTTGAATGGGTGTCCCTGATCTCTGGCGGAGG
CGGCGGAACCTACTACAGCGATTCTGTGAAGGGCAGATTCACCATCAGCCGGGACA
CCAGCAAGGACAGCCTGTACCTGCAGATGAACAGCCTGCGGACCGAGGACACAGCC
CTGTACTACTGCGCCAAGGACATGGTGTTCGGCGTGGTCACCCCTTACTACTACTT
CGCCCTGGATGTGTGGGGCCAGGGCACAACAGTGACAGTCTCTTCTGGCGGCGGAG
GAAGCGGAGGCGGAGGATCCGGTGGTGGTGGATCTGACATCCAGATGACACAGAGC
CCCAGCAGCCTGTCTGCCTCTGTGGGAGACAGAGTGACCATCACCTGTAGAGCCAG
CCAGAGCATCAACAGCTACCTGAACTGGTATCAGCAGAAGCCCGGCAAGGCCCCTA
AGCTGCTGATCTATGCTGCCTCCAGTCTGCAGAGCGGCGTGCCAAGCAGATTTTCT
GGCAGCGGCTCTGGCACCGACTTCACCCTGACCATATCTAGCCTGCAGCCTGAGGA
CTTCGCCACCTACTACTGCCAGCAGAGCTACAGCGCCCCTCCTATCACATTTGGCC
AGGGAACCAGACTGGAAATCAAAGGCGGAGAACCCAAGAGCgcaGACAAGACCCAC
ACCTGTCCTCCATGTCCTGCTCCAGAAGCTGCAGGCGGCCCTTCCGTGTTTCTGTT
CCCTCCAAAGCCTAAGGACACCCTGATGATCAGCCGGACACCTGAAGTGACCTGCG
TGGTGGTGGATGTGTCCCACGAGGATCCCGAAGTGAAGTTCAATTGGTACGTGGAC
GGCGTGGAAGTGCACAACGCCAAGACCAAGCCTAGAGAGGAACAGTACAACAGCAC
CTACAGAGTGGTGTCTGTGCTGACAGTGCTGCACCAGGACTGGCTGAACGGCAAAG
AGTACAAGTGCAAGGTGTCCAACAAGGCCCTGCCTGCTCCTATCGAGAAAACCATC
AGCAAGGCCAAGGGCCAGCCTAGGGAACCCCAGGTTTACACCCTGCCTCCATGCAG
GGATGAGCTGACCAAGAACCAGGTGTCCCTGTGGTGCCTGGTTAAGGGCTTCTACC
CCTCCGATATCGCCGTGGAATGGGAGAGCAATGGCCAGCCAGAGAACAACTACAAG
ACAACCCCTCCTGTGCTGGACTCCGACGGCTCATTCTTCCTGTACAGCAAGCTGAC
CGTGGACAAGAGCAGATGGCAGCAGGGCAACGTGTTCAGCTGCAGCGTGATGCACG
AGGCCCTGCACAACCACTACACACAGAAGTCCCTGTCTCTGAGCCCCGGCAAA
```
(SEQ ID NO: 193), signal sequence (1-57), NYC-0009 (61-807), linker (808-813), constant region (814-1509)

Fig. 195

NYC-0015-HC-k
MKHLWFFLLLVAAPRWVLSGEVQLVESGGGVVQPGGSLRLSCAASGFTFDDYAMHW
VRQAPGKGLEWVSLISGGGGGTYYSDSVKGRFTISRDTSKDSLYLQMNSLRTEDTA
LYYCAKDMVFGVVTPYYYFALDVWGQGTTVTVSSGGGGSGGGGSGGGGSDIQMTQS
PSSLSASVGDRVTITCRASQSINSYLNWYQQKPGKAPKLLIYAASSLQSGVPSRFS
GSGSGTDFTLTISSLQPEDFATYYCQQSYSAPPITFGQGTRLEIKGGEPKSADKTH
TCPPCPAPEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPAPIEKTI
SKAKGQPREPQVYTLPPCRDELTKNQVSLWCLVKGFYPSDIAVEWESNGQPENNYK
TTPPVLDSDGSFFLYSKLTVDKSRWQQGNVFSCSVMHEALHNHYTQKSLSLSPGK
(SEQ ID NO: 194), signal sequence (1-19), NYC-0009 (21-
269), linker (270-271), constant region (272-503)

Fig. 196

NYC-0016-HC-k
ATGAAGCACCTGTGGTTCTTTCTGCTGCTGGTGGCCGCTCCTAGATGGGTGCTGTC
TGGCGAAGTGCAGCTGGTGGAATCTGGTGGCGGAGTTGTTCAGCCTGGCGGCTCTC
TGAGACTGAGCTGTGCTGTGTCCGGCTTCACCTTCGACGACTACGCCATGCACTGG
GTCCGACAGGCACCTGGCAAAGGCCTTGAATGGGTGTCCCTGATCAGCGGAGATGG
CGGCAGCACACACTACGCCGATTCTGTGAAGGGCAGATTCACCATCAGCCGGGACA
ACAGCAAGAACAGCCTGTACCTGCAGATGAACTCCCTGCGGACAGGCGACACAGCC
CTGTACTACTGCGCCAAGGACATGATCTTCGCCGTGGTCATCACCGACTACCACTA
CTACGGCATGGACGTGTGGGGCCAGGGAACCACAGTGACAGTTTCTAGCGGAGGCG
GAGGAAGTGGCGGCGGAGGATCTGGCGGTGGTGGTTCTGATATCCAGATGACACAG
AGCCCCAGCAGCCTGTCTGCCTCTGTGGGAGACAGAGTGACCATCACCTGTAGAGC
CAGCCAGAGCATCAGCAGCTACCTGAACTGGTATCAGCAGAAGCCCGGCAAGGCCC
CTAAACTGCTGATCTATGCCGCCTCCAGTCTGCAGAGCGGAGTGCCTAGCAGATTT
TCTGGCAGCGGCTCCGGCACCGATTTCACCCTGACCATATCTAGCCTGCAGCCTGA
GGACTTCGCCACCTACTACTGCCAGCAGAGCTACAGCACCCCTCCTATCACCTTTG
GCCAGGGCACCAGACTGGAAATCAAAGGCGGAGAACCCAAGAGCgcaGACAAGACC
CACACCTGTCCTCCATGTCCTGCTCCAGAAGCTGCAGGCGGCCCTTCCGTGTTTCT
GTTCCCTCCAAAGCCTAAGGACACCCTGATGATCAGCCGGACACCTGAAGTGACCT
GCGTGGTGGTGGATGTGTCCCACGAGGATCCGAAGTGAAGTTCAATTGGTACGTG
GACGGCGTGGAAGTGCACAACGCCAAGACCAAGCCTAGAGAGGAACAGTACAACAG
CACCTACAGAGTGGTGTCTGTGCTGACAGTGCTGCACCAGGACTGGCTGAACGGCA
AAGAGTACAAGTGCAAGGTGTCCAACAAGGCCCTGCCTGCTCCTATCGAGAAAACC
ATCAGCAAGGCCAAGGGCCAGCCTAGGGAACCCCAGGTTTACACCCTGCCTCCATG
CAGGGATGAGCTGACCAAGAACCAGGTGTCCCTGTGGTGCCTGGTTAAGGGCTTCT
ACCCCTCCGATATCGCCGTGGAATGGGAGAGCAATGGCCAGCCAGAGAACAACTAC
AAGACAACCCCTCCTGTGCTGGACTCCGACGGCTCATTCTTCCTGTACAGCAAGCT
GACCGTGGACAAGAGCAGATGGCAGCAGGGCAACGTGTTCAGCTGCAGCGTGATGC
ACGAGGCCCTGCACAACCACTACACACAGAAGTCCCTGTCTCTGAGCCCCGGCAAA
(SEQ ID NO: 195), signal sequence (1-57), NYC-0010 (61-
810), linker (811-816), constant region (817-1512)

Fig. 197

```
NYC-0016-HC-k
MKHLWFFLLLVAAPRWVLSGEVQLVESGGGVVQPGGSLRLSCAVSGFTFDDYAMHW
VRQAPGKGLEWVSLISGDGGSTHYADSVKGRFTISRDNSKNSLYLQMNSLRTGDTA
LYYCAKDMIFAVVITDYHYYGMDVWGQGTTVTVSSGGGGSGGGGSGGGGSDIQMTQ
SPSSLSASVGDRVTITCRASQSISSYLNWYQQKPGKAPKLLIYAASSLQSGVPSRF
SGSGSGTDFTLTISSLQPEDFATYYCQQSYSTPPITFGQGTRLEIKGGEPKSADKT
HTCPPCPAPEAAGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALPAPIEKT
ISKAKGQPREPQVYTLPPCRDELTKNQVSLWCLVKGFYPSDIAVEWESNGQPENNY
KTTPPVLDSDGSFFLYSKLTVDKSRWQQGNVFSCSVMHEALHNHYTQKSLSLSPGK
(SEQ ID NO: 196), signal sequence (1-19), NYC-0010 (21-
270), linker (271-272), constant region (273-504)
```

Fig. 198

```
NYZ-1007-HC2
MKHLWFFLLLVAAPRWVLSGEVQLVESGGGLVQPGGSLRLSCAASGFSIRSYDIHW
VRQAPGKGLEWVATISYDGSQKYYADSVKGRFTISRDESKNTLYLQMNSLRAEDTA
VYHCARGSSGHYEAFDIWGQGTLVTVSSGGGGSGGGGSGGGGSQSVLTQPPSASGT
PGQRVTISCSGSSSNIGNWYVSWYQQLPGTAPKLLIYDNNKRPSGVPDRFSGSKSG
TSASLAISGLQSEDEADYYCGTWDSSLSAPWVFGGGTKLTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSAST
KGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKRVEPKSCDKTHTCPPCPAP
EAAGGPSVFLFPPKPKDTLMISRTPEVTCVVVSVSHEDPEVKFNWYVDGVEVHNAK
TKPREEQYNSTYRVVSVLTVLHQDWLNGKEYKCKVSNKALPAPIEKTISKAKGQPR
EPQVYVYPPSRDELTKNQVSLTCLVKGFYPSDIAVEWESNGQPENNYKTTPPVLDS
DGSFALVSKLTVDKSRWQQGNVFSCSVMHEALHNHYTQKSLSLSPGK
(SEQ ID NO: 197), signal sequence (1-19), NYA-2061 (21-
266), linker (267-271), C3E-7085-VH (272-389), CH1 (390-
487), hinge (488-502), CH2 (503-612), CH3 (613-719)
```

Fig. 199

```
NYZ-1017-HC2
MKHLWFFLLLVAAPRWVLSGQVQLVESGGGVVQPGRSLRLSCAASGFSIRSYDMHW
VRQAPGKGLEWVATISYDGSQKYYADSVKGRFTISRDNSKNTLYLQMSSLRAEDTA
VYHCARGSSGHYEAFDIWGQGTLVTVSSGGGGSGGGGSGGGGSQSVLTQPPSVSAA
PGQKVTISCSGSSSNIGNWYVSWYQQLPGTAPKLLIYDNNKRPSGIPDRFSGSKSG
TSATLGITGLQTGDEADYYCGTWDSSLSAPWVFGGGTKVTVLGGGGSEVQLVESGG
GLVQPGGSLRLSCAASGVTFNYYGMSWIRQAPGKGLEWVASITRSGGRIYYPDSVK
GRFTISRENTQKTLYLQMNSLRAEDTAVYYCTLDGRDGWVAYWGQGTLVTVSSAST
KGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKRVEPKSCDKTHTCPPCPAP
EAAGGPSVFLFPPKPKDTLMISRTPEVTCVVVSVSHEDPEVKFNWYVDGVEVHNAK
TKPREEQYNSTYRVVSVLTVLHQDWLNGKEYKCKVSNKALPAPIEKTISKAKGQPR
EPQVYVYPPSRDELTKNQVSLTCLVKGFYPSDIAVEWESNGQPENNYKTTPPVLDS
DGSFALVSKLTVDKSRWQQGNVFSCSVMHEALHNHYTQKSLSLSPGK
  (SEQ ID NO: 198), signal sequence (1-19), NYA-2047  (21-
266), linker (267-271), C3E-7085-VH (272-389) , CH1
(390-487), hinge (488-502), CH2 (503-612), CH3 (613-719)
```

BISPECIFIC ANTIBODY

CROSS-REFERENCE TO RELATED APPLICATIONS

The present application claims priority under 37 U.S.C. § 371 to International Patent Application No. PCT/JP2021/013378, filed Mar. 29, 2021, which claims priority to and the benefit of Japanese Patent Application No. 2020-061476, filed on Mar. 30, 2020. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, is named 127565-0103_SL.txt and is 456 kb in size.

TECHNICAL FIELD

The present invention relates to an antibody, a bispecific antibody, and the like that are useful for the treatment of tumors.

BACKGROUND ART

NY-ESO-1 is a molecule that has been identified in esophageal cancer by a method of serological analysis of recombinant cDNA expression libraries (SEREX) (Non-Patent Literature 1), and LAGE-1 is also referred to as "NY-ESO-2," which is a molecule identified via representational difference analysis of the tumor cDNA library (Non-Patent Literature 2). While expression of such molecules is known to be localized in the testis in the case of normal tissue, the mechanism thereof remains unknown. Since expression of NY-ESO-1 and LAGE-1 has been reported to occur in a wide variety of cancer species, such as melanoma, lung cancer, bladder cancer, ovarian cancer, soft-tissue sarcoma, and myeloma (Non-Patent Literature 3), association thereof with cancer is also suggested. In addition, reports have been made concerning the correlation with the degree of malignancy. For example, the NY-ESO-1 expression level is higher in the metastatic focus of melanoma than in the primary focus thereof (Non-Patent Literature 4), the NY-ESO-1 and LAGE-1 expression levels are higher in the advanced urothelial carcinoma than in the early stage urothelial carcinoma (Non-Patent Literature 5), and the NY-ESO-1 expression level is higher in high-risk myeloma with chromosomal abnormalities than in myeloma without chromosomal abnormalities (Non-Patent Literature 6). On the basis of such information, NY-ESO-1 and LAGE-1 have drawn attention as molecules with high cancer-specificity, and a great deal of research and development has been made aimed at drug discovery in cancer vaccine therapy. To date, however, there have been no pharmaceutical products approved in this respect.

The 9-mer NY-ESO peptides of NY-ESO-1 and of LAGE-1 each comprising residues 157 to 165 (i.e., SLLMWITQC) are known to form a complex with HLA (histocompatibility leukocyte antigen)-A2 (i.e., the HLA/NY-ESO peptide complex) and present the complex extracellularly (Non-Patent Literature 7). As described above, expression of NY-ESO-1 and LAGE-1 is cancer-specific. This indicates that the HLA/NY-ESO peptide complex is a therapeutic target specific to cancer that is selectively present on HLA-A2-positive and NY-ESO-1- or LAGE-1-positive cancer cells (Non-Patent Literature 8). In addition, molecules that bind to the HLA/NY-ESO peptide complex, such as TCR (Patent Literature 1 and Patent Literature 2) and antibodies (Patent Literature 3 and Patent Literature 8) have been reported.

An application of a molecule binding to a cancer-targeting molecule is a CD3 bispecific antibody that functions on the basis of the T cell redirecting mechanism whereby it recruits T cells to cancer cells and thereby exerts antitumor effects by cytotoxicity (Non-Patent Literature 9 and Non-Patent Literature 10). An example of a currently available CD3 bispecific antibody medicine is Blinatumomab, which is a CD19 bispecific T-cell engager (BiTE). Such antibody medicine is approved for acute lymphoblastic leukemia (ALL), and clinical trials targeting other blood cancers have been in progress. However, the bispecific antibody format thereof is tandem scFv (taFv) without the Fc region, and the blood half-life upon administration thereof to a patient is significantly shorter than that attained with the use of the IgG type antibody that is commonly used as a therapeutic antibody (Non-Patent Literature 11).

Concerning bispecific antibodies having the heterodimer Fc region exhibiting the blood half-life equivalent to that of the IgG type antibody, research and clinical trials on CD3 bispecific antibodies with a variety of antibody formats, such as knobs-into-holes, CrossMAb, and DuoBody® (Patent Literatures 4, 5, 6, and 7), have been in progress, and a CD3 bispecific antibody utilizing an antibody against the HLA/NY-ESO peptide complex is reported (Non-Patent Literature 12).

CITATION LIST

Patent Literature

Patent Literature 1: WO 2005/113595
Patent Literature 2: WO 2017/109496
Patent Literature 3: WO 2010/106431
Patent Literature 4: WO 1998/050431
Patent Literature 5: WO 2006/106905
Patent Literature 6: WO 2011/028952
Patent Literature 7: WO 2011/131746
Patent Literature 8: WO 2021/003357

Non-Patent Literature

Non-Patent Literature 1: Proc. Natl. Acad. Sci., U.S.A., 94 (5), 1914-8, 1997
Non-Patent Literature 2: Int. J. Cancer, 76 (6), 903-8, 1998
Non-Patent Literature 3: Immunol. Cell Biol., 84 (3), 303-17, 2006
Non-Patent Literature 4: J. Surg. Res., 98 (2), 76-80, 2001
Non-Patent Literature 5: Cancer Res., 61 (12), 4671-4, 2001
Non-Patent Literature 6: Blood, 105 (10), 3939-44, 2005
Non-Patent Literature 7: J. Exp. Med., 187 (2), 265-70, 1998
Non-Patent Literature 8: J. Immunol., 176 (12), 7308-16, 2006
Non-Patent Literature 9: Nature, 314 (6012), 628-31, 1985
Non-Patent Literature 10: Int. Rev. Immunol., 4 (2), 159-73, 1989
Non-Patent Literature 11: Drug Des. Devel. Ther., 10, 757-765, 2016
Non-Patent Literature 12: Abstracts of the 21st Annual Meeting of the Japanese Association of Cancer Immunology, O13-4

SUMMARY OF INVENTION

Technical Problem

The present invention provides a novel anti-HLA-A2/NY-ESO antibody that can be used as an anti-tumor agent and an anti-tumor agent comprising, as an active ingredient, a molecule that binds to HLA-A2/NY-ESO comprising such antibody and the like.

Solution to Problem

The present inventors have conducted concentrated studies in order to solve the above problem. As a result, they discovered a novel anti-HLA-A2/NY-ESO antibody and a molecule that binds to HLA-A2/NY-ESO comprising such an antibody and the like. This has led to the completion of the present invention.

Specifically, the present invention includes the following.

[1] An antibody that binds specifically to human HLA/NY-ESO or a binding fragment thereof comprising:
  a heavy chain CDRH1 consisting of the amino acid sequence as shown in SEQ ID NO: 54,
  a heavy chain CDRH2 consisting of the amino acid sequence as shown in SEQ ID NO: 55,
  a heavy chain CDRH3 consisting of the amino acid sequence as shown in SEQ ID NO: 56,
  a light chain CDRL1 consisting of the amino acid sequence as shown in SEQ ID NO: 57 or a light chain CDRL1 consisting of an amino acid sequence derived from the amino acid sequence as shown in SEQ ID NO: 57 in which amino acid 7 is W and/or amino acid 8 is K,
  a light chain CDRL2 consisting of the amino acid sequence as shown in SEQ ID NO: 58, and
  a light chain CDRL3 consisting of the amino acid sequence as shown in SEQ ID NO: 59 or a light chain CDRL3 consisting of an amino acid sequence derived from the amino acid sequence as shown in SEQ ID NO: 59 in which amino acid 2 is A or S.

[2] The antibody according to [1] comprising CDRH1 to CDRH3 and CDRL1 to CDRL3 of one or more groups selected from the group consisting of the groups (i) to (v) below or a binding fragment thereof:
  (i) a heavy chain CDRH1 consisting of the amino acid sequence as shown in SEQ ID NO: 54,
  a heavy chain CDRH2 consisting of the amino acid sequence as shown in SEQ ID NO: 55,
  a heavy chain CDRH3 consisting of the amino acid sequence as shown in SEQ ID NO: 56,
  a light chain CDRL1 consisting of the amino acid sequence as shown in SEQ ID NO: 57,
  a light chain CDRL2 consisting of the amino acid sequence as shown in SEQ ID NO: 58, and
  a light chain CDRL3 consisting of the amino acid sequence as shown in SEQ ID NO: 59;
  (ii) a heavy chain CDRH1 consisting of the amino acid sequence as shown in SEQ ID NO: 54,
  a heavy chain CDRH2 consisting of the amino acid sequence as shown in SEQ ID NO: 55,
  a heavy chain CDRH3 consisting of the amino acid sequence as shown in SEQ ID NO: 56,
  a light chain CDRL1 consisting of an amino acid sequence derived from the amino acid sequence as shown in SEQ ID NO: 57 in which amino acid 7 is W,
  a light chain CDRL2 consisting of the amino acid sequence as shown in SEQ ID NO: 58, and
  a light chain CDRL3 consisting of the amino acid sequence as shown in SEQ ID NO: 59;
  (iii) a heavy chain CDRH1 consisting of the amino acid sequence as shown in SEQ ID NO: 54,
  a heavy chain CDRH2 consisting of the amino acid sequence as shown in SEQ ID NO: 55,
  a heavy chain CDRH3 consisting of the amino acid sequence as shown in SEQ ID NO: 56,
  a light chain CDRL1 consisting of the amino acid sequence as shown in SEQ ID NO: 57,
  a light chain CDRL2 consisting of the amino acid sequence as shown in SEQ ID NO: 58, and
  a light chain CDRL3 consisting of an amino acid sequence derived from the amino acid sequence as shown in SEQ ID NO: 59 in which amino acid 2 is A;
  (iv) a heavy chain CDRH1 consisting of the amino acid sequence as shown in SEQ ID NO: 54,
  a heavy chain CDRH2 consisting of the amino acid sequence as shown in SEQ ID NO: 55,
  a heavy chain CDRH3 consisting of the amino acid sequence as shown in SEQ ID NO: 56,
  a light chain CDRL1 consisting of the amino acid sequence as shown in SEQ ID NO: 57,
  a light chain CDRL2 consisting of the amino acid sequence as shown in SEQ ID NO: 58, and
  a light chain CDRL3 consisting of an amino acid sequence derived from the amino acid sequence as shown in SEQ ID NO: 59 in which amino acid 2 is S; and
  (v) a heavy chain CDRH1 consisting of the amino acid sequence as shown in SEQ ID NO: 54,
  a heavy chain CDRH2 consisting of the amino acid sequence as shown in SEQ ID NO: 55,
  a heavy chain CDRH3 consisting of the amino acid sequence as shown in SEQ ID NO: 56,
  a light chain CDRL1 consisting of an amino acid sequence derived from the amino acid sequence as shown in SEQ ID NO: 57 in which amino acid 7 is W and amino acid 8 is K,
  a light chain CDRL2 consisting of the amino acid sequence as shown in SEQ ID NO: 58, and
  a light chain CDRL3 consisting of the amino acid sequence as shown in SEQ ID NO: 59.

[3] The antibody or the binding fragment thereof according to [1] comprising a heavy chain variable region consisting of an amino acid sequence having 95% or higher sequence identity to an amino acid sequence of amino acids 21 to 140 of the amino acid sequence as shown in SEQ ID NO: 27 or the amino acid sequence as shown in SEQ ID NO: 38 or 39 and a light chain variable region consisting of an amino acid sequence having 95% or higher sequence identity to an amino acid sequence of amino acids 156 to 266 of the amino acid sequence as shown in SEQ ID NO: 27 or SEQ ID NO: 52 or the amino acid sequence as shown in SEQ ID NO: 40.

[4] The antibody or the binding fragment thereof according to [1] comprising:
  (H1) a heavy chain variable region consisting of the amino acid sequence as shown in SEQ ID NO: 6,
  (H2) a heavy chain variable region consisting of the amino acid sequence as shown in SEQ ID NO: 18,
  (H3) a heavy chain variable region consisting of an amino acid sequence of amino acids 21 to 140 of the amino acid sequence as shown in SEQ ID NO: 29,
  (H4) a heavy chain variable region consisting of an amino acid sequence of amino acids 21 to 140 of the amino acid sequence as shown in SEQ ID NO: 26, (H5) a heavy chain variable region consisting of an amino acid sequence of amino acids 21 to 140 of the amino acid sequence as shown in SEQ ID NO: 27,
(H6) a heavy chain variable region consisting of an amino acid sequence of amino acids 21 to 140 of the amino acid sequence as shown in SEQ ID NO: 28,
(H7) a heavy chain variable region consisting of an amino acid sequence of amino acids 21 to 140 of the amino acid sequence as shown in SEQ ID NO: 36,
(H8) a heavy chain variable region consisting of an amino acid sequence of amino acids 21 to 140 of the amino acid sequence as shown in SEQ ID NO: 47,
(H9) a heavy chain variable region consisting of an amino acid sequence of amino acids 21 to 140 of the amino acid sequence as shown in SEQ ID NO: 48,
(H10) a heavy chain variable region consisting of an amino acid sequence of amino acids 21 to 140 of the amino acid sequence as shown in SEQ ID NO: 50;
(H11) a heavy chain variable region consisting of an amino acid sequence of amino acids 21 to 140 of the amino acid sequence as shown in SEQ ID NO: 51,
(H12) a heavy chain variable region consisting of an amino acid sequence of amino acids 21 to 140 of the amino acid sequence as shown in SEQ ID NO: 52,
(H13) a heavy chain variable region consisting of an amino acid sequence of amino acids 21 to 140 of the amino acid sequence as shown in SEQ ID NO: 53,
(H14) a heavy chain variable region consisting of an amino acid sequence of amino acids 21 to 140 of the amino acid sequence as shown in SEQ ID NO: 30; or
(H15) a heavy chain variable region consisting of an amino acid sequence of amino acids 21 to 140 of the amino acid sequence as shown in SEQ ID NO: 156; and
(L1) a light chain variable region consisting of the amino acid sequence as shown in SEQ ID NO: 8,
(L2) a light chain variable region consisting of the amino acid sequence as shown in SEQ ID NO: 20,
(L3) a light chain variable region consisting of an amino acid sequence of amino acids 156 to 266 of the amino acid sequence as shown in SEQ ID NO: 29,
(L4) a light chain variable region consisting of an amino acid sequence of amino acids 156 to 266 of the amino acid sequence as shown in SEQ ID NO: 26,
(L5) a light chain variable region consisting of an amino acid sequence of amino acids 156 to 266 of the amino acid sequence as shown in SEQ ID NO: 27,
(L6) a light chain variable region consisting of an amino acid sequence of amino acids 156 to 266 of the amino acid sequence as shown in SEQ ID NO: 28,
(L7) a light chain variable region consisting of an amino acid sequence of amino acids 156 to 266 of the amino acid sequence as shown in SEQ ID NO: 36,
(L8) a light chain variable region consisting of an amino acid sequence of amino acids 156 to 266 of the amino acid sequence as shown in SEQ ID NO: 47,
(L9) a light chain variable region consisting of an amino acid sequence of amino acids 156 to 266 of the amino acid sequence as shown in SEQ ID NO: 48,
(L10) a light chain variable region consisting of an amino acid sequence of amino acids 156 to 266 of the amino acid sequence as shown in SEQ ID NO: 50,
(L11) a light chain variable region consisting of an amino acid sequence of amino acids 156 to 266 of the amino acid sequence as shown in SEQ ID NO: 51,
(L12) a light chain variable region consisting of an amino acid sequence of amino acids 156 to 266 of the amino acid sequence as shown in SEQ ID NO: 52,
(L13) a light chain variable region consisting of an amino acid sequence of amino acids 156 to 266 of the amino acid sequence as shown in SEQ ID NO: 53,
(L14) a light chain variable region consisting of an amino acid sequence of amino acids 156 to 266 of the amino acid sequence as shown in SEQ ID NO: 30; or
(L15) a light chain variable region consisting of an amino acid sequence of amino acids 161 to 271 of the amino acid sequence as shown in SEQ ID NO: 156.
[5] The antibody or the binding fragment thereof according to [4] comprising:
(H1L1) a heavy chain variable region consisting of the amino acid sequence as shown in SEQ ID NO: 6 and a light chain variable region consisting of the amino acid sequence as shown in SEQ ID NO: 8,
(H2L2) a heavy chain variable region consisting of the amino acid sequence as shown in SEQ ID NO: 18 and a light chain variable region consisting of the amino acid sequence as shown in SEQ ID NO: 20,
(H3L3) a heavy chain variable region consisting of an amino acid sequence of amino acids 21 to 140 of the amino acid sequence as shown in SEQ ID NO: 29 and a light chain variable region consisting of an amino acid sequence of amino acids 156 to 266 of the amino acid sequence as shown in SEQ ID NO: 29,
(H4L4) a heavy chain variable region consisting of an amino acid sequence of amino acids 21 to 140 of the amino acid sequence as shown in SEQ ID NO: 26 and a light chain variable region consisting of an amino acid sequence of amino acids 156 to 266 of the amino acid sequence as shown in SEQ ID NO: 26,
(H5L5) a heavy chain variable region consisting of an amino acid sequence of amino acids 21 to 140 of the amino acid sequence as shown in SEQ ID NO: 27 and a light chain variable region consisting of an amino acid sequence of amino acids 156 to 266 of the amino acid sequence as shown in SEQ ID NO: 27,
(H6L6) a heavy chain variable region consisting of an amino acid sequence of amino acids 21 to 140 of the amino acid sequence as shown in SEQ ID NO: 28 and a light chain variable region consisting of an amino acid sequence of amino acids 156 to 266 of the amino acid sequence as shown in SEQ ID NO: 28,
(H7L7) a heavy chain variable region consisting of an amino acid sequence of amino acids 21 to 140 of the amino acid sequence as shown in SEQ ID NO: 36 and a light chain variable region consisting of an amino acid sequence of amino acids 156 to 266 of the amino acid sequence as shown in SEQ ID NO: 36,
(H8L8) a heavy chain variable region consisting of an amino acid sequence of amino acids 21 to 140 of the amino acid sequence as shown in SEQ ID NO: 47 and a light chain variable region consisting of an amino acid sequence of amino acids 156 to 266 of the amino acid sequence as shown in SEQ ID NO: 47,
(H9L9) a heavy chain variable region consisting of an amino acid sequence of amino acids 21 to 140 of the amino acid sequence as shown in SEQ ID NO: 48 and a light chain variable region consisting of an amino acid sequence of amino acids 156 to 266 of the amino acid sequence as shown in SEQ ID NO: 48,
(H10L10) a heavy chain variable region consisting of an amino acid sequence of amino acids 21 to 140 of the amino acid sequence as shown in SEQ ID NO: 50 and a light chain variable region consisting of an amino acid sequence of amino acids 156 to 266 of the amino acid sequence as shown in SEQ ID NO: 50, (H11L11) a heavy chain variable region consisting of an amino acid sequence of amino acids 21 to 140 of the amino acid sequence as shown in SEQ ID NO: 51 and a light chain variable region consisting of an amino acid sequence of amino acids 156 to 266 of the amino acid sequence as shown in SEQ ID NO: 51, (H12L12) a heavy chain variable region consisting of an amino acid sequence of amino acids 21 to 140 of the amino acid sequence as shown in SEQ ID NO: 52 and a light chain variable region consisting of an amino acid sequence of amino acids 156 to 266 of the amino acid sequence as shown in SEQ ID NO: 52, (H13L13) a heavy chain variable region consisting of an amino acid sequence of amino acids 21 to 140 of the amino acid sequence as shown in SEQ ID NO: 53 and a light chain variable region consisting of an amino acid sequence of amino acids 156 to 266 of the amino acid sequence as shown in SEQ ID NO: 53, (H14L14) a heavy chain variable region consisting of an amino acid sequence of amino acids 21 to 140 of the amino acid sequence as shown in SEQ ID NO: 30 and a light chain variable region consisting of an amino acid sequence of amino acids 156 to 266 of the amino acid sequence as shown in SEQ ID NO: 30, or (H15L15) a heavy chain variable region consisting of an amino acid sequence of amino acids 21 to 140 of the amino acid sequence as shown in SEQ ID NO: 156 and a light chain variable region consisting of an amino acid sequence of amino acids 161 to 271 of the amino acid sequence as shown in SEQ ID NO: 156.

[6] The antibody or the binding fragment thereof according to any of [1] to [5], which is scFv.

[7] The antibody or the binding fragment thereof according to [6], which is (s1) scFv consisting of an amino acid sequence of amino acids 21 to 266 of the amino acid sequence as shown in SEQ ID NO: 70, (s2) scFv comprising a heavy chain variable region consisting of the amino acid sequence as shown in SEQ ID NO: 18 and a light chain variable region consisting of the amino acid sequence as shown in SEQ ID NO: 20, (s3) scFv consisting of an amino acid sequence of amino acids 21 to 266 of the amino acid sequence as shown in SEQ ID NO: 29, (s4) scFv consisting of an amino acid sequence of amino acids 21 to 266 of the amino acid sequence as shown in SEQ ID NO: 26, (s5) scFv consisting of an amino acid sequence of amino acids 21 to 266 of the amino acid sequence as shown in SEQ ID NO: 27, (s6) scFv consisting of an amino acid sequence of amino acids 21 to 266 of the amino acid sequence as shown in SEQ ID NO: 28, (s7) scFv consisting of an amino acid sequence of amino acids 21 to 266 of the amino acid sequence as shown in SEQ ID NO: 36, (s8) scFv consisting of an amino acid sequence of amino acids 21 to 266 of the amino acid sequence as shown in SEQ ID NO: 47, (s9) scFv consisting of an amino acid sequence of amino acids 21 to 266 of the amino acid sequence as shown in SEQ ID NO: 48, (s10) scFv consisting of an amino acid sequence of amino acids 21 to 266 of the amino acid sequence as shown in SEQ ID NO: 50, (s11) scFv consisting of an amino acid sequence of amino acids 21 to 266 of the amino acid sequence as shown in SEQ ID NO: 51, (s12) scFv consisting of an amino acid sequence of amino acids 21 to 266 of the amino acid sequence as shown in SEQ ID NO: 52, (s13) scFv consisting of an amino acid sequence of amino acids 21 to 266 of the amino acid sequence as shown in SEQ ID NO: 53, (s14) scFv consisting of an amino acid sequence of amino acids 21 to 266 of the amino acid sequence as shown in SEQ ID NO: 30, or (s15) scFv consisting of an amino acid sequence of amino acids 21 to 271 of the amino acid sequence as shown in SEQ ID NO: 156.

[8] A polynucleotide encoding the antibody or the binding fragment thereof according to any of [1] to [7].

[9] A vector comprising the polynucleotide according to [8].

[10] A host cell comprising the polynucleotide according to [8] or the vector according to [9].

[11] A method for producing an antibody that binds specifically to human HLA/NY-ESO or a binding fragment thereof comprising: (i) a step of culturing the host cell according to [10]; and (ii) a step of purifying an antibody or a binding fragment thereof from the culture product obtained in step (i).

[12] An antibody that binds specifically to human HLA/NY-ESO or a binding fragment thereof, which is obtained by the method according to [11].

[13] An antibody that has the properties (i) or (ii) below and binds to HLA-A2/NY-ESO or a binding fragment thereof:
 (i) binding to a site on HLA-A2/NY-ESO recognized by the antibody or the binding fragment thereof according to [7]; or
 (ii) binding to human HLA-A2/NY-ESO competitively with the antibody or the binding fragment thereof according to [7].

[14] A pharmaceutical composition comprising, as an active ingredient, the antibody or the binding fragment thereof according to any of [1] to [7], [12], and [13], the polynucleotide according to [8], the vector according to [9], or the cell according to [10].

[15] A molecule that binds specifically to human HLA/NY-ESO comprising the antibody or the binding fragment thereof according to any of [1] to [7], [12], and [13].

[16] The molecule according to [15], which is a multispecific antibody.

[17] The molecule according to [15], which is a bispecific antibody.

[18] The molecule according to any of [15] to [17], which comprises an antibody that binds specifically to CD3 or a binding fragment thereof.

[19] The molecule according to [18], wherein the antibody that binds specifically to CD3 or the binding fragment thereof comprises:
 (CCH1) a heavy chain CDRH1 consisting of the amino acid sequence as shown in SEQ ID NO: 141;
 (CCH2) a heavy chain CDRH2 consisting of the amino acid sequence as shown in SEQ ID NO: 142 or a heavy chain CDRH2 consisting of an amino acid sequence derived from the amino acid sequence as shown in SEQ ID NO: 142 in which amino acid 3 is N or S;
 (CCH3) a heavy chain CDRH3 consisting of the amino acid sequence as shown in SEQ ID NO: 143;
 (CCL1) a light chain CDRL1 consisting of the amino acid sequence as shown in SEQ ID NO: 144;

(CCL2) a light chain CDRL2 consisting of the amino acid sequence as shown in SEQ ID NO: 145 or a light chain CDRL2 consisting of an amino acid sequence derived from the amino acid sequence as shown in SEQ ID NO: 145 in which amino acid 2 is N; and (CCL3) a light chain CDRL3 consisting of the amino acid sequence as shown in SEQ ID NO: 146.

[20] The molecule according to [19], wherein the antibody that binds specifically to CD3 or the binding fragment thereof comprises:

(CH1) a heavy chain variable region consisting of an amino acid sequence of amino acids 2 to 119 of the amino acid sequence as shown in SEQ ID NO: 136, (CH2) a heavy chain variable region consisting of an amino acid sequence of amino acids 2 to 119 of the amino acid sequence as shown in SEQ ID NO: 137, (CH3) a heavy chain variable region consisting of an amino acid sequence of amino acids 2 to 119 of the amino acid sequence as shown in SEQ ID NO: 147, (CH4) a heavy chain variable region consisting of an amino acid sequence of amino acids 2 to 119 of the amino acid sequence as shown in SEQ ID NO: 138, (CH5) a heavy chain variable region consisting of an amino acid sequence of amino acids 2 to 119 of the amino acid sequence as shown in SEQ ID NO: 139, (CH6) a heavy chain variable region consisting of an amino acid sequence of amino acids 2 to 119 of the amino acid sequence as shown in SEQ ID NO: 140, (CH7) a heavy chain variable region consisting of an amino acid sequence of amino acids 272 to 389 of the amino acid sequence as shown in SEQ ID NO: 155, (CH8) a heavy chain variable region consisting of an amino acid sequence of amino acids 277 to 394 of the amino acid sequence as shown in SEQ ID NO: 156; or (CH9) a heavy chain variable region consisting of an amino acid sequence of amino acids 277 to 394 of the amino acid sequence as shown in SEQ ID NO: 157; and (CL1) a light chain variable region consisting of an amino acid sequence of amino acids 135 to 243 of the amino acid sequence as shown in SEQ ID NO: 136, (CL2) a light chain variable region consisting of an amino acid sequence of amino acids 135 to 241 of the amino acid sequence as shown in SEQ ID NO: 137, (CL3) a light chain variable region consisting of an amino acid sequence of amino acids 135 to 243 of the amino acid sequence as shown in SEQ ID NO: 147, (CL4) a light chain variable region consisting of an amino acid sequence of amino acids 135 to 241 of the amino acid sequence as shown in SEQ ID NO: 138, (CL5) a light chain variable region consisting of an amino acid sequence of amino acids 135 to 243 of the amino acid sequence as shown in SEQ ID NO: 139, (CL6) a light chain variable region consisting of an amino acid sequence of amino acids 135 to 243 of the amino acid sequence as shown in SEQ ID NO: 140, (CL7) a light chain variable region consisting of an amino acid sequence of amino acids 405 to 511 of the amino acid sequence as shown in SEQ ID NO: 155, (CL8) a light chain variable region consisting of an amino acid sequence of amino acids 410 to 516 of the amino acid sequence as shown in SEQ ID NO: 156, or (CL9) a light chain variable region consisting of an amino acid sequence of amino acids 410 to 516 of the amino acid sequence as shown in SEQ ID NO: 157.

[21] The molecule according to [20], wherein the antibody that binds specifically to CD3 or the binding fragment thereof comprises:

(CH1CL1) a heavy chain variable region consisting of an amino acid sequence of amino acids 2 to 119 of the amino acid sequence as shown in SEQ ID NO: 136 and a light chain variable region consisting of an amino acid sequence of amino acids 135 to 243 of the amino acid sequence as shown in SEQ ID NO: 136;

(CH2CL2) a heavy chain variable region consisting of an amino acid sequence of amino acids 2 to 119 of the amino acid sequence as shown in SEQ ID NO: 137 and a light chain variable region consisting of an amino acid sequence of amino acids 135 to 241 of the amino acid sequence as shown in SEQ ID NO: 137;

(CH3CL3) a heavy chain variable region consisting of an amino acid sequence of amino acids 2 to 119 of the amino acid sequence as shown in SEQ ID NO: 147 and a light chain variable region consisting of an amino acid sequence of amino acids 135 to 243 of the amino acid sequence as shown in SEQ ID NO: 147;

(CH4CL4) a heavy chain variable region consisting of an amino acid sequence of amino acids 2 to 119 of the amino acid sequence as shown in SEQ ID NO: 138 and a light chain variable region consisting of an amino acid sequence of amino acids 135 to 241 of the amino acid sequence as shown in SEQ ID NO: 138;

(CH5CL5) a heavy chain variable region consisting of an amino acid sequence of amino acids 2 to 119 of the amino acid sequence as shown in SEQ ID NO: 139 and a light chain variable region consisting of an amino acid sequence of amino acids 135 to 243 of the amino acid sequence as shown in SEQ ID NO: 139;

(CH6CL6) a heavy chain variable region consisting of an amino acid sequence of amino acids 2 to 119 of the amino acid sequence as shown in SEQ ID NO: 140 and a light chain variable region consisting of an amino acid sequence of amino acids 135 to 243 of the amino acid sequence as shown in SEQ ID NO: 140;

(CH7CL7) a heavy chain variable region consisting of an amino acid sequence of amino acids 272 to 389 of the amino acid sequence as shown in SEQ ID NO: 155 and a light chain variable region consisting of an amino acid sequence of amino acids 272 to 389 of the amino acid sequence as shown in SEQ ID NO: 155;

(CH8CL8) a heavy chain variable region consisting of an amino acid sequence of amino acids 277 to 394 of the amino acid sequence as shown in SEQ ID NO: 156 and a light chain variable region consisting of an amino acid sequence of amino acids 410 to 516 of the amino acid sequence as shown in SEQ ID NO: 156; or (CH9CL9) a heavy chain variable region consisting of an amino acid sequence of amino acids 277 to 394 of the amino acid sequence as shown in SEQ ID NO: 157 and a light chain variable region consisting of an amino acid sequence of amino acids 410 to 516 of the amino acid sequence as shown in SEQ ID NO: 157.

[22] The molecule according to any of [18] to [21], wherein the antibody that binds specifically to CD3 or the binding fragment thereof is scFv.

[23] The molecule according to [22], wherein scFv comprises:

(CS1) scFv consisting of an amino acid sequence of amino acids 2 to 243 of the amino acid sequence as shown in SEQ ID NO: 136;

(CS2) scFv consisting of an amino acid sequence of amino acids 2 to 241 of the amino acid sequence as shown in SEQ ID NO: 137;

(CS3) scFv consisting of an amino acid sequence of amino acids 2 to 243 of the amino acid sequence as shown in SEQ ID NO: 147;

(CS4) scFv consisting of an amino acid sequence of amino acids 2 to 241 of the amino acid sequence as shown in SEQ ID NO: 138;

(CS5) scFv consisting of an amino acid sequence of amino acids 2 to 243 of the amino acid sequence as shown in SEQ ID NO: 139;

(CS6) scFv consisting of an amino acid sequence of amino acids 2 to 243 of the amino acid sequence as shown in SEQ ID NO: 140;

(CS7) scFv consisting of an amino acid sequence of amino acids 272 to 511 of the amino acid sequence as shown in SEQ ID NO: 155;

(CS8) scFv consisting of an amino acid sequence of amino acids 277 to 516 of the amino acid sequence as shown in SEQ ID NO: 156; or (CS9) scFv consisting of an amino acid sequence of amino acids 277 to 516 of the amino acid sequence as shown in SEQ ID NO: 157.

[24] The molecule according to any of [18] to [23] comprising: a first polypeptide comprising scFv that binds specifically to human HLA/NY-ESO, scFv that binds specifically to CD3, and an Fc region (i) in that order from the N terminus toward the C terminus; and a second polypeptide comprising an Fc region (ii), wherein the first polypeptide is preferably associated with the second polypeptide at the Fc region (i) and the Fc region (ii).

[25] The molecule according to [24], wherein the scFv that binds specifically to human HLA/NY-ESO is the antibody that binds specifically to human HLA/NY-ESO or the binding fragment thereof according to [1], which is scFv.

[26] The molecule according to [24], wherein the scFv that binds specifically to human HLA/NY-ESO is the antibody that binds specifically to human HLA/NY-ESO or the binding fragment thereof according to [2], which is scFv.

[27] The molecule according to [24], wherein the scFv that binds specifically to human HLA/NY-ESO is the antibody that binds specifically to human HLA/NY-ESO or the binding fragment thereof according to [3], which is scFv.

[28] The molecule according to [24], wherein the scFv that binds specifically to human HLA/NY-ESO is the antibody that binds specifically to human HLA/NY-ESO or the binding fragment thereof according to [4], which is scFv.

[29] The molecule according to [24], wherein the scFv that binds specifically to human HLA/NY-ESO is the antibody that binds specifically to human HLA/NY-ESO or the binding fragment thereof according to [5], which is scFv.

[30] The molecule according to any of [19] to [24], wherein the scFv that binds specifically to CD3 is the antibody that binds specifically to CD3 or the binding fragment thereof according to [18], which is scFv.

[31] The molecule according to any of [19] to [24], wherein the scFv that binds specifically to CD3 is the antibody that binds specifically to CD3 or the binding fragment thereof according to [19], which is scFv.

[32] The molecule according to any of [19] to [24], wherein the scFv that binds specifically to CD3 is the antibody that binds specifically to CD3 or the binding fragment thereof according to [20] or [21], which is scFv.

[33] The molecule according to any of [19] to [24], wherein the scFv that binds specifically to CD3 is the antibody that binds specifically to CD3 or the binding fragment thereof according to [23], which is scFv.

[34] The molecule according to any of [24] to [33] comprising an amino acid sequence selected from the group consisting of an amino acid sequence of amino acids 21 to 511 of the amino acid sequence as shown in SEQ ID NO: 85, an amino acid sequence of amino acids 21 to 511 of the amino acid sequence as shown in SEQ ID NO: 87, an amino acid sequence of amino acids 21 to 511 of the amino acid sequence as shown in SEQ ID NO: 88, an amino acid sequence of amino acids 21 to 511 of the amino acid sequence as shown in SEQ ID NO: 89, an amino acid sequence of amino acids 21 to 511 of the amino acid sequence as shown in SEQ ID NO: 90, an amino acid sequence of amino acids 21 to 511 of the amino acid sequence as shown in SEQ ID NO: 91, an amino acid sequence of amino acids 21 to 511 of the amino acid sequence as shown in SEQ ID NO: 92, an amino acid sequence of amino acids 21 to 511 of the amino acid sequence as shown in SEQ ID NO: 93, an amino acid sequence of amino acids 21 to 511 of the amino acid sequence as shown in SEQ ID NO: 94, an amino acid sequence of amino acids 21 to 511 of the amino acid sequence as shown in SEQ ID NO: 95, an amino acid sequence of amino acids 21 to 511 of the amino acid sequence as shown in SEQ ID NO: 96, an amino acid sequence of amino acids 21 to 511 of the amino acid sequence as shown in SEQ ID NO: 86, an amino acid sequence of amino acids 21 to 511 of the amino acid sequence as shown in SEQ ID NO: 149, and an amino acid sequence of amino acids 21 to 511 of the amino acid sequence as shown in SEQ ID NO: 150.

[35] The molecule according to any of [24] to [33], which comprises an amino acid sequence selected from the group consisting of an amino acid sequence of amino acids 21 to 511 of the amino acid sequence as shown in SEQ ID NO: 155, an amino acid sequence of amino acids 21 to 516 of the amino acid sequence as shown in SEQ ID NO: 156, and an amino acid sequence of amino acids 21 to 516 of the amino acid sequence as shown in SEQ ID NO: 157.

[36] The molecule according to any of [24] to [34], wherein the first polypeptide comprises an amino acid sequence of amino acids 529 to 745 of the amino acid sequence as shown in SEQ ID NO: 85, 87, 88, 89, 90, 91, 92, 93, 94, 95, 96, 86, 149, or 150.

[37] The molecule according to any of [24] to [33] and [35], wherein the first polypeptide comprises an amino acid sequence of amino acids 529 to 745 of the amino acid sequence as shown in SEQ ID NO: 155, an amino acid sequence of amino acids 534 to 750 of the amino acid sequence as shown in SEQ ID NO: 156, or an amino acid sequence of amino acids 534 to 750 of the amino acid sequence as shown in SEQ ID NO: 157.

[38] The molecule according to [34] or [36], wherein the first polypeptide consists of an amino acid sequence selected from the group consisting of an amino acid sequence of amino acids 20 to 745 of the amino acid sequence as shown in SEQ ID NO: 85, an amino acid sequence of amino acids 20 to 745 of the amino acid sequence as shown in SEQ ID NO: 87, an amino acid sequence of amino acids 20 to 745 of the amino acid sequence as shown in SEQ ID NO: 88, an amino acid sequence of amino acids 20 to 745 of the amino acid sequence as shown in SEQ ID NO: 89, an amino acid sequence of amino acids 20 to 745 of the amino acid sequence as shown in SEQ ID NO: 90, an amino acid sequence of amino acids 20 to 745 of the amino acid sequence as shown in SEQ ID NO: 91, an amino acid sequence of amino acids 20 to 745 of the amino acid sequence as shown in SEQ ID NO: 92, an amino acid sequence of amino acids 20 to 745 of the amino acid sequence as shown in SEQ ID NO: 93, an amino acid sequence of amino acids 20 to 745 of the amino acid sequence as shown in SEQ ID NO: 94, an amino acid sequence of amino acids 20 to 745 of the amino acid sequence as shown in SEQ ID NO: 95, an amino acid sequence of amino acids 20 to 745 of the amino acid sequence as shown in SEQ ID NO: 96, an amino acid sequence of amino acids 20 to 745 of the amino acid sequence as shown in SEQ ID NO: 86, an amino acid sequence of amino acids 20 to 745 of the amino acid sequence as shown in SEQ ID NO: 149, and an amino acid sequence of amino acids 20 to 745 of the amino acid sequence as shown in SEQ ID NO: 150.

[39] The molecule according to [35] or [37], wherein the first polypeptide consists of an amino acid sequence selected from the group consisting of an amino acid sequence of amino acids 20 to 745 of the amino acid sequence as shown in SEQ ID NO: 155, an amino acid sequence of amino acids 20 to 750 of the amino acid sequence as shown in SEQ ID NO: 156, and an amino acid sequence of amino acids 20 to 750 of the amino acid sequence as shown in SEQ ID NO: 157.

[40] The molecule according to any of [24] to [39], wherein the second polypeptide comprises an amino acid sequence of amino acids 20 to 246 of the amino acid sequence as shown in SEQ ID NO: 84.

[41] The molecule according to any of [18] to [23] comprising a first polypeptide, a second polypeptide, and a third polypeptide, wherein
the first polypeptide comprises scFv that binds specifically to human HLA/NY-ESO, scFv that binds specifically to CD3, and an Fc region (i) in that order from the N terminus toward the C terminus,
the second polypeptide comprises an immunoglobulin heavy chain comprising an Fc region (ii), and
the third polypeptide comprises an immunoglobulin light chain; and
the second polypeptide is preferably associated with the third polypeptide, and
the first polypeptide is preferably associated with the second polypeptide in the Fc regions.

[42] The molecule according to [41], wherein the scFv that binds specifically to human HLA/NY-ESO is the antibody that binds specifically to human HLA/NY-ESO or the binding fragment thereof according to [1], which is scFv.

[43] The molecule according to [41], wherein the scFv that binds specifically to human HLA/NY-ESO is the antibody that binds specifically to human HLA/NY-ESO or the binding fragment thereof according to [2], which is scFv.

[44] The molecule according to [41], wherein the scFv that binds specifically to human HLA/NY-ESO is the antibody that binds specifically to human HLA/NY-ESO or the binding fragment thereof according to [3], which is scFv.

[45] The molecule according to [41], wherein the scFv that binds specifically to human HLA/NY-ESO is the antibody that binds specifically to human HLA/NY-ESO or the binding fragment thereof according to [4], which is scFv.

[46] The molecule according to [41], wherein the scFv that binds specifically to human HLA/NY-ESO is the antibody that binds specifically to human HLA/NY-ESO or the binding fragment thereof according to [5], which is scFv.

[47] The molecule according to any of [42] to [46], wherein the scFv that binds specifically to CD3 is the antibody that binds specifically to CD3 or the binding fragment thereof according to [18], which is scFv.

[48] The molecule according to any of [42] to [46], wherein the scFv that binds specifically to CD3 is the antibody that binds specifically to CD3 or the binding fragment thereof according to [19], which is scFv.

[49] The molecule according to any of [42] to [46], wherein the scFv that binds specifically to CD3 is the antibody that binds specifically to CD3 or the binding fragment thereof according to [20] or [21], which is scFv.

[50] The molecule according to any of [42] to [46], wherein the scFv that binds specifically to CD3 is the antibody that binds specifically to CD3 or the binding fragment thereof according to [23], which is scFv.

[51] The molecule according to any of [41] to [50], wherein the second polypeptide comprises an amino acid sequence of amino acids 20 to 242 of the amino acid sequence as shown in SEQ ID NO: 99.

[52] The molecule according to any of [41] to [51], wherein the third polypeptide comprises the amino acid sequence as shown in SEQ ID NO: 100.

[53] The molecule according to any of [41] to [52], wherein the first polypeptide comprises an amino acid sequence selected from the group consisting of an amino acid sequence of amino acids 21 to 511 of the amino acid sequence as shown in SEQ ID NO: 85, an amino acid sequence of amino acids 21 to 511 of the amino acid sequence as shown in SEQ ID NO: 87, an amino acid sequence of amino acids 21 to 511 of the amino acid sequence as shown in SEQ ID NO: 88, an amino acid sequence of amino acids 21 to 511 of the amino acid sequence as shown in SEQ ID NO: 89, an amino acid sequence of amino acids 21 to 511 of the amino acid sequence as shown in SEQ ID NO: 90, an amino acid sequence of amino acids 21 to 511 of the amino acid sequence as shown in SEQ ID NO: 91, an amino acid sequence of amino acids 21 to 511 of the amino acid sequence as shown in SEQ ID NO: 92, an amino acid sequence of amino acids 21 to 511 of the amino acid sequence as shown in SEQ ID NO: 93, an amino acid sequence of amino acids 21 to 511 of the amino acid sequence as shown in SEQ ID NO: 94, an amino acid sequence of amino acids 21 to 511 of the amino acid sequence as shown in SEQ ID NO: 95, an amino acid sequence of amino acids 21 to 511 of the amino acid sequence as shown in SEQ ID NO: 96, an amino acid sequence of amino acids 21 to 511 of the amino acid sequence as shown in SEQ ID NO: 86, an amino acid sequence of amino acids 21 to 511 of the amino acid sequence as shown in SEQ ID NO: 149, and an amino acid sequence of amino acids 21 to 511 of the amino acid sequence as shown in SEQ ID NO: 150.

[54] The molecule according to any of [41] to [53], wherein the first polypeptide consists of an amino acid sequence selected from the group consisting of an amino acid sequence of amino acids 20 to 745 of the amino acid sequence as shown in SEQ ID NO: 85, an amino acid sequence of amino acids 20 to 745 of the amino acid sequence as shown in SEQ ID NO: 87, an amino acid sequence of amino acids 20 to 745 of the amino acid sequence as shown in SEQ ID NO: 88, an amino acid sequence of amino acids 20 to 745 of the amino acid sequence as shown in SEQ ID NO: 89, an amino acid sequence of amino acids 20 to 745 of the amino acid sequence as shown in SEQ ID NO: 90, an amino acid sequence of amino acids 20 to 745 of the amino acid sequence as shown in SEQ ID NO: 91, an amino acid sequence of amino acids 20 to 745 of the amino acid sequence as shown in SEQ ID NO: 92, an amino acid sequence of amino acids 20 to 745 of the amino acid sequence as shown in SEQ ID NO: 93, an amino acid sequence of amino acids 20 to 745 of the amino acid sequence as shown in SEQ ID NO: 94, an amino acid sequence of amino acids 20 to 745 of the amino acid sequence as shown in SEQ ID NO: 95, an amino acid sequence of amino acids 20 to 745 of the amino acid sequence as shown in SEQ ID NO: 96, an amino acid sequence of amino acids 20 to 745 of the amino acid sequence as shown in SEQ ID NO: 86, an amino acid sequence of amino acids 20 to 745 of the amino acid sequence as shown in SEQ ID NO: 149, and an amino acid sequence of amino acids 20 to 745 of the amino acid sequence as shown in SEQ ID NO: 150.

[55] The molecule according to any one of [18] to [23] comprising a first polypeptide that comprises scFv that binds specifically to human HLA/NY-ESO, a heavy chain variable region and constant region CH1 of the antibody that binds specifically to CD3, and an immunoglobulin Fc region (i) in that order from the N terminus toward the C terminus, a second polypeptide that comprises a hinge region and an Fc region (ii) of the immunoglobulin, and a third polypeptide that comprises an antibody light chain consisting of a variable region and a constant region, wherein the first polypeptide is preferably associated with the second polypeptide at the Fc region (i) and the Fc region (ii), and the first polypeptide is preferably associated with the third polypeptide in the heavy chain variable region and the constant region CH1 of the antibody.

[56] The molecule according to [55], wherein the scFv that binds specifically to human HLA/NY-ESO is the antibody that binds specifically to human HLA/NY-ESO or the binding fragment thereof according to [1], which is scFv.

[57] The molecule according to [55], wherein the scFv that binds specifically to human HLA/NY-ESO is the antibody that binds specifically to human HLA/NY-ESO or the binding fragment thereof according to [2], which is scFv.

[58] The molecule according to [55], wherein the scFv that binds specifically to human HLA/NY-ESO is the antibody that binds specifically to human HLA/NY-ESO or the binding fragment thereof according to [3], which is scFv.

[59] The molecule according to [55], wherein the scFv that binds specifically to human HLA/NY-ESO is the antibody that binds specifically to human HLA/NY-ESO or the binding fragment thereof according to [4], which is scFv.

[60] The molecule according to [55], wherein the scFv that binds specifically to human HLA/NY-ESO is the antibody that binds specifically to human HLA/NY-ESO or the binding fragment thereof according to [5], which is scFv.

[61] The molecule according to any of [18] to [21], wherein the antibody that binds specifically to CD3 or the binding fragment thereof is Fab.

[62] The molecule according to any of [56] to [61], wherein the Fab that binds specifically to CD3 is the antibody that binds specifically to CD3 or the binding fragment thereof according to [18], which is Fab.

[63] The molecule according to any of [56] to [61], wherein the Fab that binds specifically to CD3 is the antibody that binds specifically to CD3 or the binding fragment thereof according to [19], which is Fab.

[64] The molecule according to any of [56] to [61], wherein the Fab that binds specifically to CD3 is the antibody that binds specifically to CD3 or the binding fragment thereof according to [20] or [21], which is Fab.

[65] The molecule according to any of [55] to [64], wherein the first polypeptide comprises an amino acid sequence of amino acids 21 to 394 of the amino acid sequence as shown in SEQ ID NO: 160.

[66] The molecule according to any of [55] to [65], wherein the first polypeptide comprises the amino acid sequence according to any one of (i) to (iii) below:
(i) an amino acid sequence of amino acids 20 to 724 of the amino acid sequence as shown in SEQ ID NO: 160;
(ii) an amino acid sequence of amino acids 20 to 719 of the amino acid sequence as shown in SEQ ID NO: 197; and
(iii) an amino acid sequence of amino acids 20 to 719 of the amino acid sequence as shown in SEQ ID NO: 198.

[67] The molecule according to any of [55] to [66], wherein the second polypeptide comprises an amino acid sequence of amino acids 20 to 246 of the amino acid sequence as shown in SEQ ID NO: 84.

[68] The molecule according to any of [56] to [67], wherein the third polypeptide comprises an amino acid sequence of amino acids 21 to 127 of the amino acid sequence as shown in SEQ ID NO: 161.

[69] The molecule according to any of [56] to [68], wherein the third polypeptide comprises an amino acid sequence of amino acids 21 to 233 of the amino acid sequence as shown in SEQ ID NO: 161.

[70] The molecule according to any of [15] to [69], wherein 1 or 2 amino acids are deleted from the carboxyl terminus of the amino acid sequence of at least one polypeptide included in the molecule.

[71] A polynucleotide comprising a nucleotide sequence encoding an amino acid sequence included in the molecule according to any of [15] to [70].

[72] A vector comprising the polynucleotide according to [71].

[73] A host cell comprising the polynucleotide according to [71] or the vector according to [72].

[74] A method for producing a molecule that binds specifically to human HLA/NY-ESO and human CD3 comprising: (i) a step of culturing the host cell according to [73]; and (ii) a step of purifying an antibody or a binding fragment thereof from the culture product obtained in the step (i).

[75] A molecule that binds specifically to human HLA/NY-ESO and human CD3, which is obtained by the method according to [74].

[76] A pharmaceutical composition comprising, as an active ingredient, the molecule according to any of [15] to [70] and [75], the polynucleotide according to [71], the vector according to [72], or the host cell according to [73].

[77] The pharmaceutical composition according to [14] or [76], which is an anti-cancer agent.

[78] The pharmaceutical composition according to [77], wherein cancer is one or more cancers selected from the group consisting of renal cancer, melanoma, squamous cell carcinoma, basal cell cancer, conjunctival cancer, oral cavity cancer, laryngeal cancer, pharyngeal cancer, thyroid gland cancer, lung cancer (non-small cell lung cancer (adenocarcinoma, epidermoid cancer, large cell cancer), and small cell lung cancer), breast cancer, esophageal cancer, gastric cancer, duodenal carcinoma, small bowel cancer, large bowel cancer, rectal cancer, appendiceal cancer, anal cancer, liver cancer, gallbladder cancer, bile duct cancer, pancreatic cancer, adrenal cancer, bladder cancer, prostate cancer, uterine cancer, vaginal cancer, liposarcoma, angiosarcoma, chondrosarcoma, rhabdomyosarcoma, Ewing's sarcoma, osteosarcoma, undifferentiated pleomorphic sarcoma, myxofibrosarcoma, malignant peripheral nerve sheath tumor, retroperitoneal sarcoma, synovial sarcoma, uterine sarcoma, gastrointestinal stromal tumor, leiomyosarcoma, epithelioid sarcoma, B cell lymphoma, T/NK-cell lymphoma, Hodgkin's lymphoma, myelogenic leukemia, lymphatic leukemia, myeloproliferative disorder, myelodysplastic syndrome, multiple myeloma, testicular carcinoma, and ovarian cancer.

[79] The pharmaceutical composition according to any of [76] to [78], which is used in combination with another agent.

Advantageous Effects of Invention

According to the present invention, an antibody that binds to HLA-A2/NY-ESO and a novel bispecific antibody (bispecific molecule) that binds to HLA-A2/NY-ESO and to CD3 is obtained. Also, a novel pharmaceutical composition comprising, as an active ingredient, such an antibody (molecule) is obtained. Such antibody or molecule has cytotoxicity and is thus useful as an agent for treatment or prevention of cancer and the like.

BRIEF DESCRIPTION OF DRAWINGS

FIG. 1 shows a table demonstrating standardized gMFI of anti-HLA/NY-ESO scFv: NYA-0001, NYA-1143, NYA-1154, NYA-1163, NYA-2023, NYA-2027, NYA-2035, NYA-2044, NYA-2045, NYA-2047, NYA-2048, NYA-2060, NYA-2061, NYA-2143, NYC-0003, and NYC-0004, relative to T2 cells supplemented with various point-mutant peptides. *Each underlined value indicates a half or lower than the standardized gMFI of each scFv relative to that of T2 cells supplemented with the NY-ESO peptide.

FIG. 2A shows a table demonstrating information concerning the selected homologous peptides. Binding affinity to HLA-A0201 predicted using NetMHCPan2.8 is indicated in terms of the 50% inhibitory concentration ($IC_{50}$).

FIG. 2B shows a table demonstrating standardized gMFI of anti-HLA/NY-ESO scFv: NYA-0001, NYA-1143, NYA-1154, NYA-1163, NYA-2023, NYA-2027, NYA-2035, NYA-2044, NYA-2045, NYA-2047, NYA-2048, NYA-2060, NYA-2061, NYA-2143, NYC-0003, and NYC-0004, relative to T2 cells supplemented with various homologous peptides. *Each underlined value indicates a value larger than the standardized gMFI of each scFv relative to that of T2 cells supplemented with DMSO.

FIG. 6B shows antibody formats described in the examples. (a): taFv-heterodimer Fc-type format: the same as FIG. 3 (d); Fc (negative slopes) comprising a heterodimer-forming mutation is added to the C terminal region of taFv and heterologously associated with another Fc (solid). In the example, the taFv-heterodimer Fc-type comprising anti-HLA-A2/NY-ESO scFv and anti-CD3 scFv was used for evaluation. (b): taFv (inversed)-heterodimer Fc-type format: the order of the two scFv constructs is inverted in the taFv-heterodimer Fc-type format. In the example, taFv (inversed)-heterodimer Fc-type comprising anti-CD3 scFv and anti-HLA-A2/NY-ESO scFv was used for evaluation. (c) shows the first polypeptide of the taFv (inversed)-heterodimer Fc-type. The first polypeptide comprises scFv that binds specifically to CD3, scFv that binds specifically to human HLA/NY-ESO, and the Fc region (i) in that order from the N terminus toward the C terminus. (d) shows the second polypeptide of the taFv (inversed)-heterodimer Fc-type. The second polypeptide comprises a hinge region and the Fc region (ii).

FIG. 8 The amino acid sequence of the peptide in NY-ESO (SEQ ID NO: 1)

FIG. 9 The amino acid sequence of the peptide in MAGEC-1 (SEQ ID NO: 2)

FIG. 10 The scFv sequence analysis primer 1 (SEQ ID NO: 3)

FIG. 11 The scFv sequence analysis primer 2 (SEQ ID NO: 4)

FIG. 12 The nucleotide sequence of the heavy chain variable region of NYA-0001 (SEQ ID NO: 5)

FIG. 13 The amino acid sequence of the heavy chain variable region of NYA-0001 (SEQ ID NO: 6)

FIG. 14 The nucleotide sequence of the light chain variable region of NYA-0001 (SEQ ID NO: 7)

FIG. 15 The amino acid sequence of the light chain variable region of NYA-0001 (SEQ ID NO: 8)

FIG. 16 The nucleotide sequence of the heavy chain variable region of NYA-0060 (SEQ ID NO: 9)

FIG. 17 The amino acid sequence of the heavy chain variable region of NYA-0060 (SEQ ID NO: 10)

FIG. 18 The nucleotide sequence of the light chain variable region of NYA-0060 (SEQ ID NO: 11)

FIG. 19 The amino acid sequence of the light chain variable region of NYA-0060 (SEQ ID NO: 12)

FIG. 20 The nucleotide sequence of the heavy chain variable region of NYA-0068 (SEQ ID NO: 13)

FIG. 21 The amino acid sequence of the heavy chain variable region of NYA-0068 (SEQ ID NO: 14)

FIG. 22 The nucleotide sequence of the light chain variable region of NYA-0068 (SEQ ID NO: 15)

FIG. 23 The amino acid sequence of the light chain variable region of NYA-0068 (SEQ ID NO: 16)

FIG. 24 The nucleotide sequence of the heavy chain variable region of NYA-0082 (SEQ ID NO: 17)

FIG. 25 The amino acid sequence of the heavy chain variable region of NYA-0082 (SEQ ID NO: 18)

FIG. 26 The nucleotide sequence of the light chain variable region of NYA-0082 (SEQ ID NO: 19)

FIG. 27 The amino acid sequence of the light chain variable region of NYA-0082 (SEQ ID NO: 20)

FIG. 28 The nucleotide sequence of the NYA-1163 tag adduct (SEQ ID NO: 21)

FIG. 29 The nucleotide sequence of the NYA-2023 tag adduct (SEQ ID NO: 22)

FIG. 30 The nucleotide sequence of the NYA-2027 tag adduct (SEQ ID NO: 23)

FIG. 31 The nucleotide sequence of the NYA-1143 tag adduct (SEQ ID NO: 24)

FIG. 32 The nucleotide sequence of the NYA-2143 tag adduct (SEQ ID NO: 25)

FIG. 33 The amino acid sequence of the NYA-1163 tag adduct (SEQ ID NO: 26); NYA-1163: amino acids 21 to 266

FIG. 34 The amino acid sequence of the NYA-2023 tag adduct (SEQ ID NO: 27); NYA-2023: amino acids 21 to 266

FIG. 35 The amino acid sequence of the NYA-2027 tag adduct (SEQ ID NO: 28); NYA-2027: amino acids 21 to 266

FIG. 36 The amino acid sequence of the NYA-1143 tag adduct (SEQ ID NO: 29); NYA-1143: amino acids 21 to 266

FIG. 37 The amino acid sequence of the NYA-2143 tag adduct (SEQ ID NO: 30); NYA-2143: amino acids 21 to 266

FIG. 38 The nucleotide sequence of the NYA-1154 tag adduct (SEQ ID NO: 31)

FIG. 39 The amino acid sequence of the NYA-1154 tag adduct (SEQ ID NO: 32); NYA-1154: amino acids 21 to 266

FIG. 40 The amino acid sequence of HLA-A*0201 (GenBank: ASA47534.1) truncate (SEQ ID NO: 33)

FIG. 41 The amino acid sequence of β2-microglobulin (SEQ ID NO: 34)

FIG. 42 The nucleotide sequence of the NYA-2035 tag adduct (SEQ ID NO: 35)

FIG. 43 The amino acid sequence of the NYA-2035 tag adduct (SEQ ID NO: 36); NYA-2035: amino acids 21 to 266

FIG. 44 The amino acid sequence of NYA-1143-VH01 (SEQ ID NO: 37)

FIG. 45 The amino acid sequence of NYA-1143-VH02 (SEQ ID NO: 38)

FIG. 46 The amino acid sequence of NYA-1143-VH03 (SEQ ID NO: 39)

FIG. 47 The amino acid sequence of NYA-1143-VL01 (SEQ ID NO: 40)

FIG. 48 The nucleotide sequence of the NYA-2044 tag adduct (SEQ ID NO: 41)

FIG. 49 The nucleotide sequence of the NYA-2045 tag adduct (SEQ ID NO: 42)

FIG. 50 The nucleotide sequence of the NYA-2047 tag adduct (SEQ ID NO: 43)

FIG. 51 The nucleotide sequence of the NYA-2048 tag adduct (SEQ ID NO: 44)

FIG. 52 The nucleotide sequence of the NYA-2060 tag adduct (SEQ ID NO: 45)

FIG. 53 The nucleotide sequence of the NYA-2061 tag adduct (SEQ ID NO: 46)

FIG. 54 The amino acid sequence of the NYA-2044 tag adduct (SEQ ID NO: 47); NYA-2044: amino acids 21 to 266

FIG. 55 The amino acid sequence of the NYA-2045 tag adduct (SEQ ID NO: 48); NYA-2045: amino acids 21 to 266

FIG. 56 The amino acid sequence of the NYA-0082 (SEQ ID NO: 49)

FIG. 57 The amino acid sequence of the NYA-2047 tag adduct (SEQ ID NO: 50); NYA-2047: amino acids 21 to 266

FIG. 58 The amino acid sequence of the NYA-2048 tag adduct (SEQ ID NO: 51); NYA-2048: amino acids 21 to 266

FIG. 59 The amino acid sequence of the NYA-2060 tag adduct (SEQ ID NO: 52); NYA-2060: amino acids 21 to 266

FIG. 60 The amino acid sequence of the NYA-2061 tag adduct (SEQ ID NO: 53); NYA-2061: amino acids 21 to 266

FIG. 61 The amino acid sequences of the CDRH1 to CDRH3 of the NYA-0001 heavy chain and CDRL1 to CDRL3 of the NYA-0001 light chain (SEQ ID NOs: 54 to 59)

FIG. 62 The amino acid sequence of CDRL1 of NYA-2023 (SEQ ID NO: 60)

FIG. 63 The amino acid sequence of CDRL3 of NYA-2027 (SEQ ID NO: 61)

FIG. 64 The amino acid sequences of CDRH3 and CDRL3 of NYA-1154 (SEQ ID NOs: 62 and 63)

FIG. 65 The amino acid sequence of CDRL1 of NYA-0035 (SEQ ID NO: 64)

FIG. 66 The nucleotide sequence of the NYC-0003 tag adduct (SEQ ID NO: 65)

FIG. 67 The nucleotide sequence of the NYC-0004 tag adduct (SEQ ID NO: 66)

FIG. 68 The amino acid sequence of the NYC-0003 tag adduct (SEQ ID NO: 67); NYC-0003: amino acids 21 to 263

FIG. 69 The amino acid sequence of the NYC-0004 tag adduct (SEQ ID NO: 68); NYC-0004: amino acids 21 to 263

FIG. 70 The nucleotide sequence of the NYA-0001 tag adduct (SEQ ID NO: 69)

FIG. 71 The amino acid sequence of the NYA-0001 tag adduct (SEQ ID NO: 70); NYA-0001: amino acids 21 to 266

FIG. 72 The nucleotide sequence of HC1 (SEQ ID NO: 71)

FIG. 73 The nucleotide sequence of NYF-0016-HC2 (SEQ ID NO: 72)

FIG. 74 The nucleotide sequence of NYF-0019-HC2 (SEQ ID NO: 73)

FIG. 75 The nucleotide sequence of NYF-0022-HC2 (SEQ ID NO: 74)

FIG. 76 The nucleotide sequence of NYF-0023-HC2 (SEQ ID NO: 75)

FIG. 77 The nucleotide sequence of NYF-0027-HC2 (SEQ ID NO: 76)

FIG. 78 The nucleotide sequence of NYF-0035-HC2 (SEQ ID NO: 77)

FIG. 79 The nucleotide sequence of NYF-0044-HC2 (SEQ ID NO: 78)

FIG. 80 The nucleotide sequence of NYF-0045-HC2 (SEQ ID NO: 79)

FIG. 81 The nucleotide sequence of NYF-0047-HC2 (SEQ ID NO: 80)

FIG. 82 The nucleotide sequence of NYF-0048-HC2 (SEQ ID NO: 81)

FIG. 83 The nucleotide sequence of NYF-0060-HC2 (SEQ ID NO: 82)

FIG. 84 The nucleotide sequence of NYF-0061-HC2 (SEQ ID NO: 83)

FIG. 85 The amino acid sequence of HC1 (SEQ ID NO: 84)

FIG. 86 The amino acid sequence of NYF-0016-HC2 (SEQ ID NO: 85); NYA-1143: amino acids 21 to 266; C3E-7085: amino acids 272 to 511

FIG. 87 The amino acid sequence of NYF-0019-HC2 (SEQ ID NO: 86); NYA-2143: amino acids 21 to 266; C3E-7085: amino acids 272 to 511

FIG. 88 The amino acid sequence of NYF-0022-HC2 (SEQ ID NO: 87); NYA-1163: amino acids 21 to 266; C3E-7085: amino acids 272 to 511

FIG. 89 The amino acid sequence of NYF-0023-HC2 (SEQ ID NO: 88); NYA-2023: amino acids 21 to 266; C3E-7085: amino acids 272 to 511

FIG. 90 The amino acid sequence of NYF-0027-HC2 (SEQ ID NO: 89); NYA-2027: amino acids 21 to 266; C3E-7085: amino acids 272 to 511

FIG. 91 The amino acid sequence of NYF-0035-HC2 (SEQ ID NO: 90); NYA-2035: amino acids 21 to 266; C3E-7085: amino acids 272 to 511

FIG. 92 The amino acid sequence of NYF-0044-HC2 (SEQ ID NO: 91); NYA-2044: amino acids 21 to 266; C3E-7085: amino acids 272 to 511

FIG. 93 The amino acid sequence of NYF-0045-HC2 (SEQ ID NO: 92); NYA-2045: amino acids 21 to 266; C3E-7085: amino acids 272 to 511

FIG. 94 The amino acid sequence of NYF-0047-HC2 (SEQ ID NO: 93); NYA-2047: amino acids 21 to 266; C3E-7085: amino acids 272 to 511

FIG. 95 The amino acid sequence of NYF-0048-HC2 (SEQ ID NO: 94); NYA-2048: amino acids 21 to 266; C3E-7085: amino acids 272 to 511

FIG. 96 The amino acid sequence of NYF-0060-HC2 (SEQ ID NO: 95); NYA-2060: amino acids 21 to 266; C3E-7085: amino acids 272 to 511

FIG. 97 The amino acid sequence of NYF-0061-HC2 (SEQ ID NO: 96); NYA-2061: amino acids 21 to 266; C3E-7085: amino acids 272 to 511

FIG. 98 The nucleotide sequence of NYA-0001-Fab-HC1-k delete (SEQ ID NO: 97)

FIG. 99 The nucleotide sequence of NYA-0001-LC (SEQ ID NO: 98)

FIG. 100 The amino acid sequence of NYA-0001-Fab-HC1-k delete (SEQ ID NO: 99); NYA-0001 heavy chain variable region: amino acids 20 to 139

FIG. 101 The amino acid sequence of NYA-0001-LC (SEQ ID NO: 100); NYA-0001 light chain variable region: amino acids 21 to 131

FIG. 102 The nucleotide sequence of NYA-1143-Fab-HC1-k delete (SEQ ID NO: 101)

FIG. 103 The nucleotide sequence of NYA-1143-LC (SEQ ID NO: 102)

Figure 3:
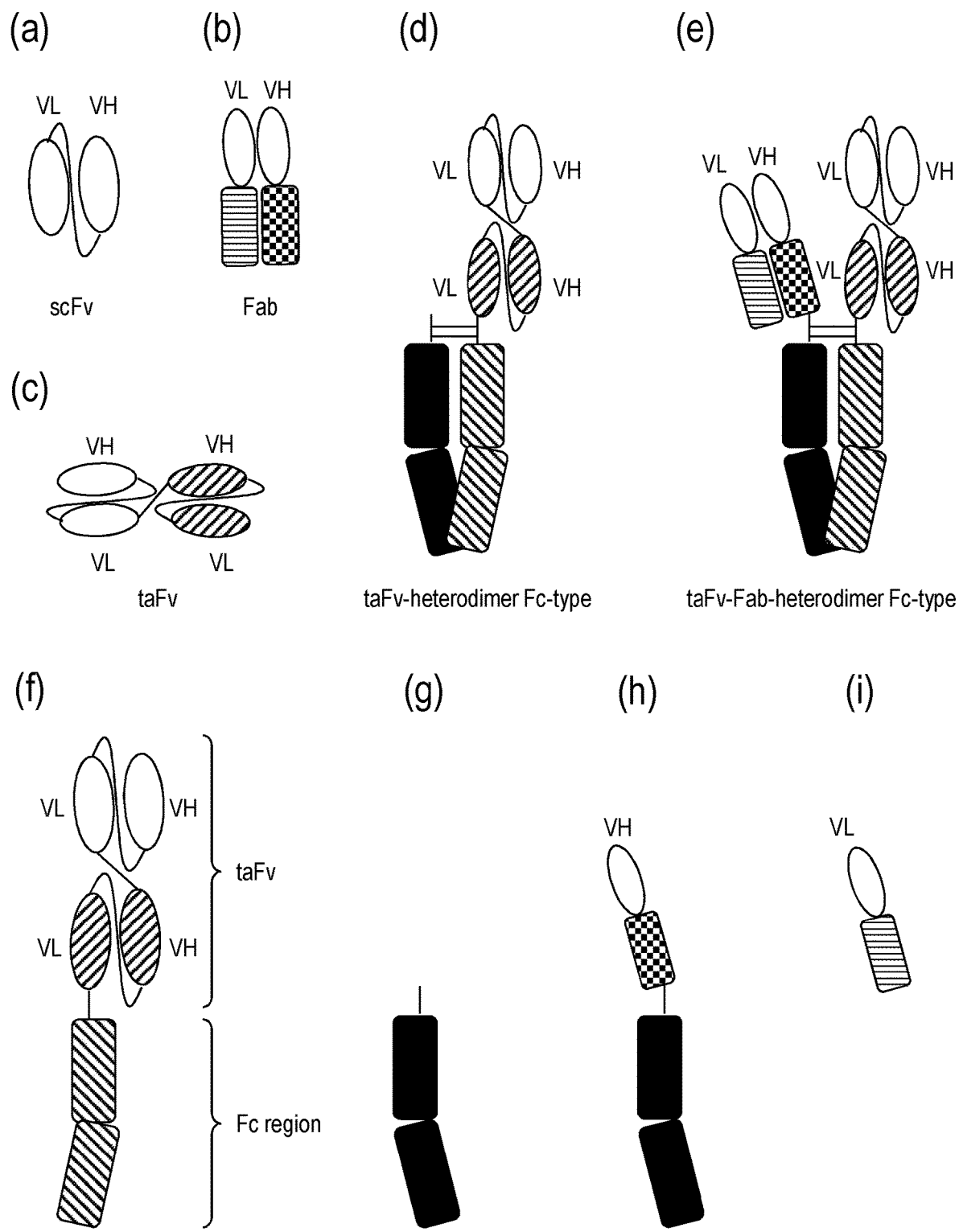
FIG. 3 shows antibody formats demonstrated in the examples. (a) shows an scFv format in which the antibody H chain variable region (VH, described below) is ligated to the antibody L chain variable region (VL, described below) (both blank) with a linker. In the Examples, an anti-HLA-A2/NY-ESO scFv and an anti-CD3 scFv were used for evaluation. (b) shows an Fab format that comprises VH (blank), the antibody H chain constant region (CH1: checkered pattern), VL (blank), and the antibody L chain constant region (border lines). In the Examples, anti-HLA-A2/NY-ESO Fab and the like were used for evaluation. (c) shows a taFv format in which two types of scFv constructs (blank and positive slopes) are ligated to each other with a linker. In the Examples, taFv including anti-HLA-A2/NY-ESO scFv and anti-CD3 scFv were used for evaluation. (d) shows a taFv-heterodimer Fc-type format in which Fc (negative slopes) comprising a heterodimer-forming mutation introduced into a C-terminal site of taFv (the first polypeptide) is heterologously associated with another Fc (solid: the second polypeptide). In the example, the taFv-heterodimer Fc comprising anti-HLA-A2/NY-ESO scFv and anti-CD3 scFv was used for evaluation. (e) shows a taFv-Fab-heterodimer Fc-type format in which Fab is added to the taFv-heterodimer Fc-type format. In the example, taFv including anti-HLA-A2/NY-ESO scFv and anti-CD3 scFv and taFv-Fab-heterodimer-Fc including HLA-A2/NY-ESO Fab were used for evaluation. (f) shows the first polypeptide that is common between the taFv-heterodimer Fc-type and the taFv-Fab-heterodimer Fc-type. The first polypeptide comprises scFv that binds specifically to human HLA/NY-ESO, scFv that binds specifically to CD3, and the Fc region (i) in that order from the N terminus toward the C terminus. (g) shows the second polypeptide of the taFv-heterodimer Fc-type. The second polypeptide comprises a hinge region and the Fc region (ii). (h) shows the second polypeptide of the taFv-Fab-heterodimer Fc-type. The second polypeptide comprises an immunoglobulin heavy chain comprising a hinge region and the Fc region (ii). (i) shows the third polypeptide of the taFv-Fab-heterodimer Fc-type. The third polypeptide comprises an immunoglobulin light chain.
Figure 4A:
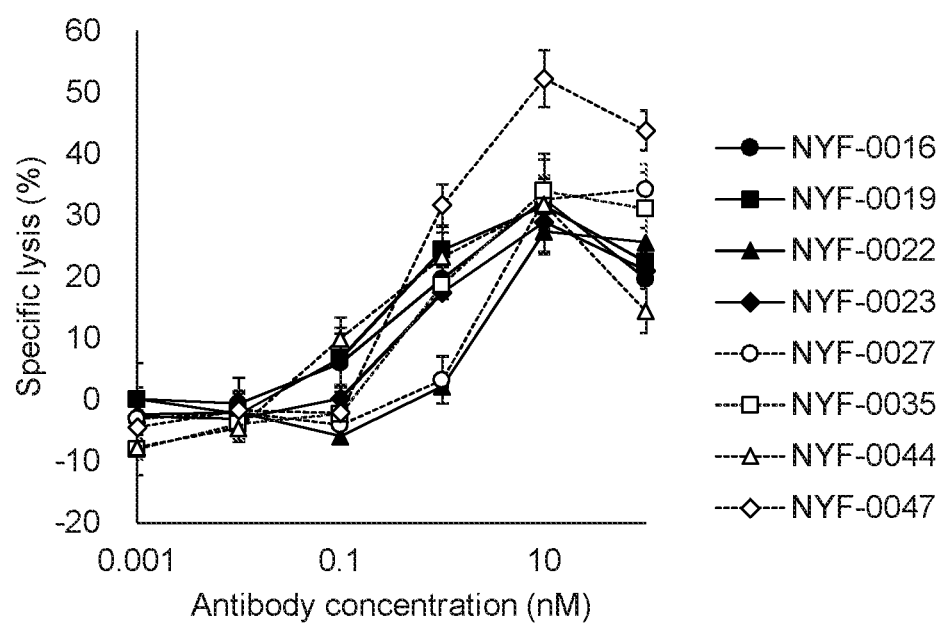
FIG. 4A demonstrates that the Fc-conjugated anti-HLA-A2/NY-ESO-anti-CD3 bispecific molecules; i.e., NYF-0016, NYF-0019, NYF-0022, NYF-0023, NYF-0027, NYF-0035, NYF-0044, and NYF-0047, exert cytotoxicity on human U266B1 cells endogenously expressing NY-ESO in the presence of human PBMC. An error bar in the figure indicates the standard deviation (n=3).
Figure 4B:
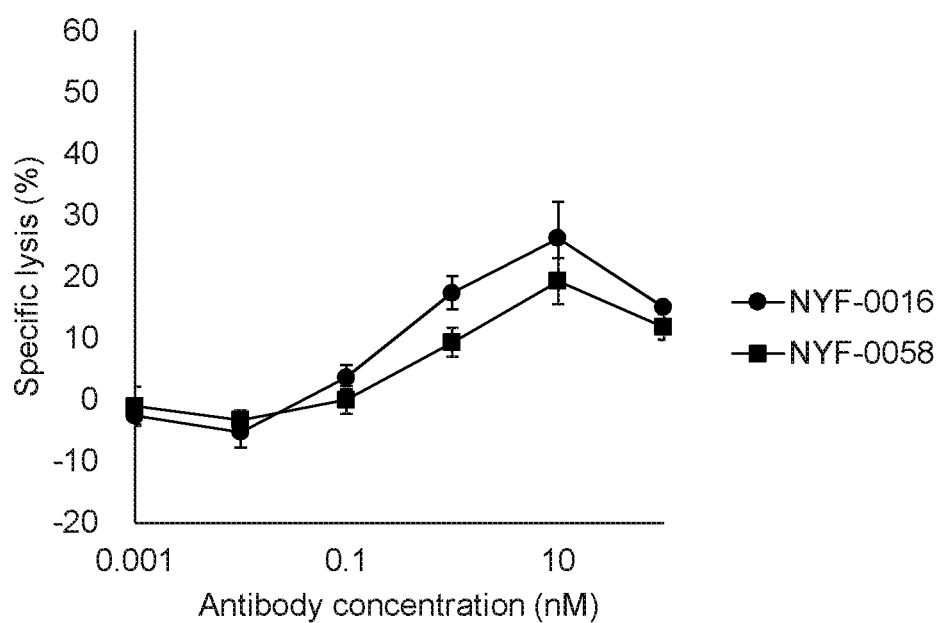
FIG. 4B demonstrates that the Fc-conjugated anti-HLA-A2/NY-ESO-anti-CD3 bispecific molecules; i.e., NYF-0016 and NYF-0058, exert cytotoxicity on human U266B1 cells endogenously expressing NY-ESO in the presence of human PBMC. An error bar in the figure indicates the standard deviation (n=3).
Figure 4C:
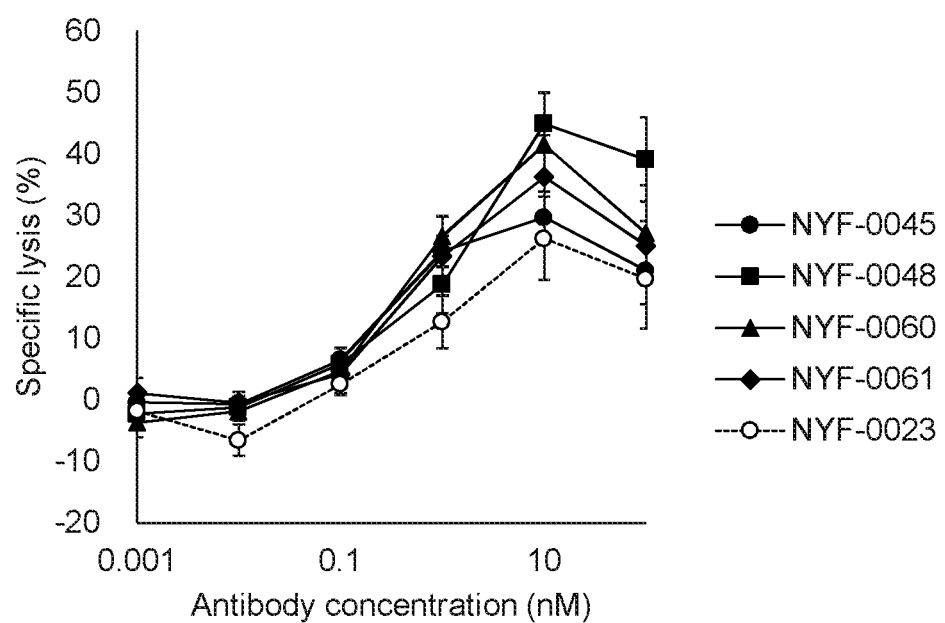
FIG. 4C demonstrates that the Fc-conjugated anti-HLA-A2/NY-ESO-anti-CD3 bispecific molecules; i.e., NYF-0023, NYF-0045, NYF-0048, NYF-0060, and NYF-0061, exert cytotoxicity on the endogenous human NY-ESO-expressing U266B1 cells endogenously expressing NY-ESO in the presence of human PBMC. An error bar in the figure indicates the standard deviation (n=3).
Figure 4D:
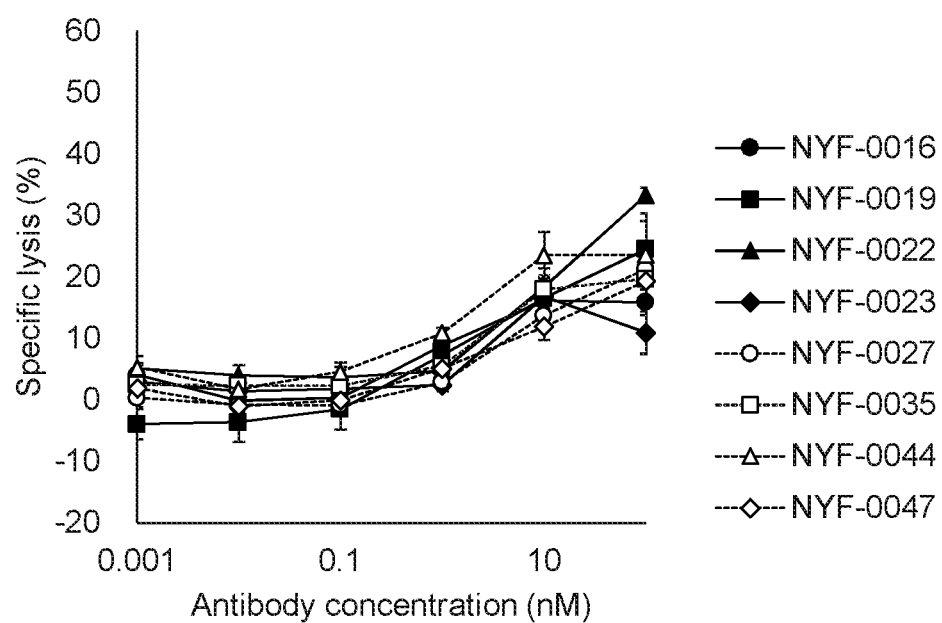
FIG. 4D demonstrates that the Fc-conjugated anti-HLA-A2/NY-ESO-anti-CD3 bispecific molecules; i.e., NYF-0016, NYF-0019, NYF-0022, NYF-0023, NYF-0027, NYF-0035, NYF-0044, and NYF-0047, exert cytotoxicity on human NCI-H1703 cells endogenously expressing NY-ESO in the presence of human PBMC. An error bar in the figure indicates the standard deviation (n=3).
Figure 4E:
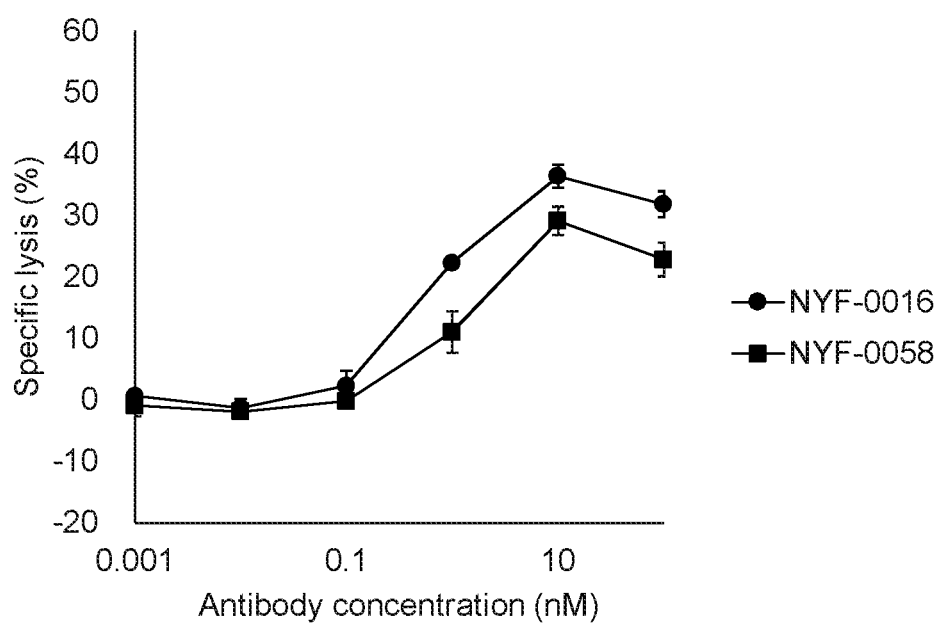
FIG. 4E demonstrates that the Fc-conjugated anti-HLA-A2/NY-ESO-anti-CD3 bispecific molecules; i.e., NYF-0016 and NYF-0058, exert cytotoxicity on human NCI-H1703 cells endogenously expressing NY-ESO in the presence of human PBMC. An error bar in the figure indicates the standard deviation (n=3).
Figure 4F:
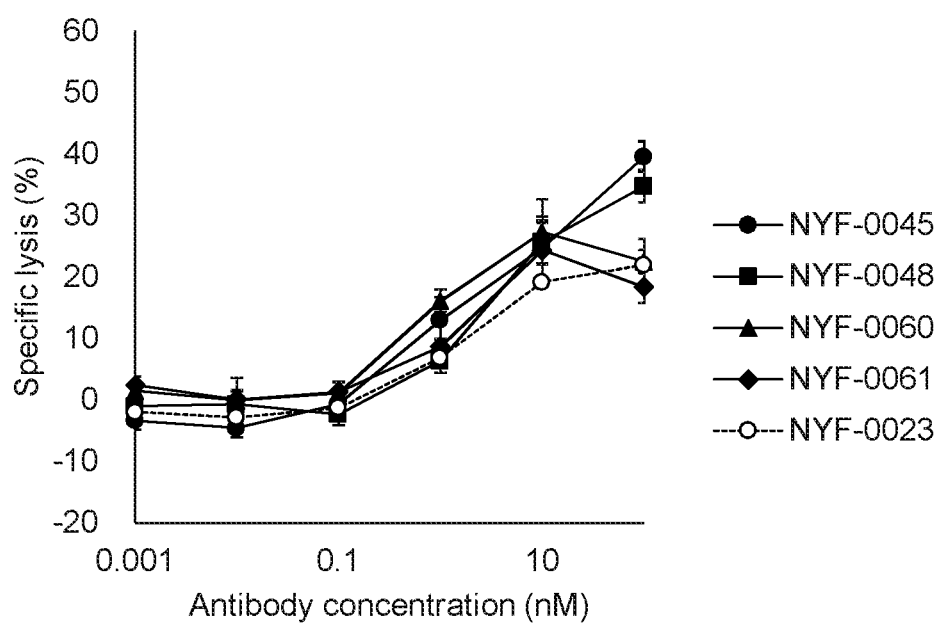
FIG. 4F demonstrates that the Fc-conjugated anti-HLA-A2/NY-ESO-anti-CD3 bispecific molecules; i.e., NYF-0023, NYF-0045, NYF-0048, NYF-0060, and NYF-0061, exert cytotoxicity on human NCI-H1703 cells endogenously expressing NY-ESO in the presence of human PBMC. An error bar in the figure indicates the standard deviation (n=3).
Figure 4G:
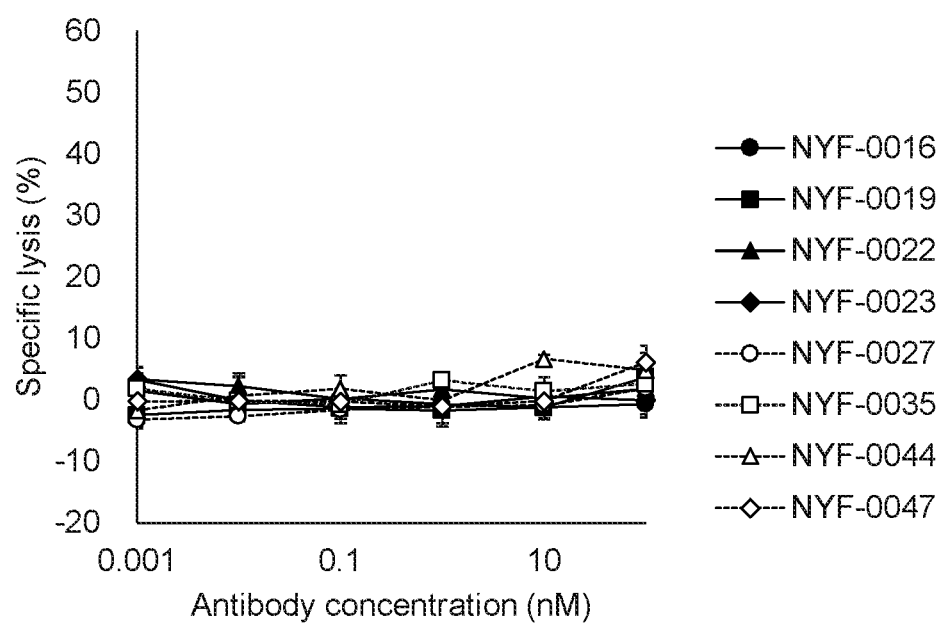
FIG. 4G demonstrates that the Fc-conjugated anti-HLA-A2/NY-ESO-anti-CD3 bispecific molecules; i.e., NYF-0016, NYF-0019, NYF-0022, NYF-0023, NYF-0027, NYF-0035, NYF-0044, and NYF-0047, do not exert cytotoxicity on human AGS cells endogenously non-expressing NY-ESO in the presence of human PBMC. An error bar in the figure indicates the standard deviation (n=3).
Figure 4H:
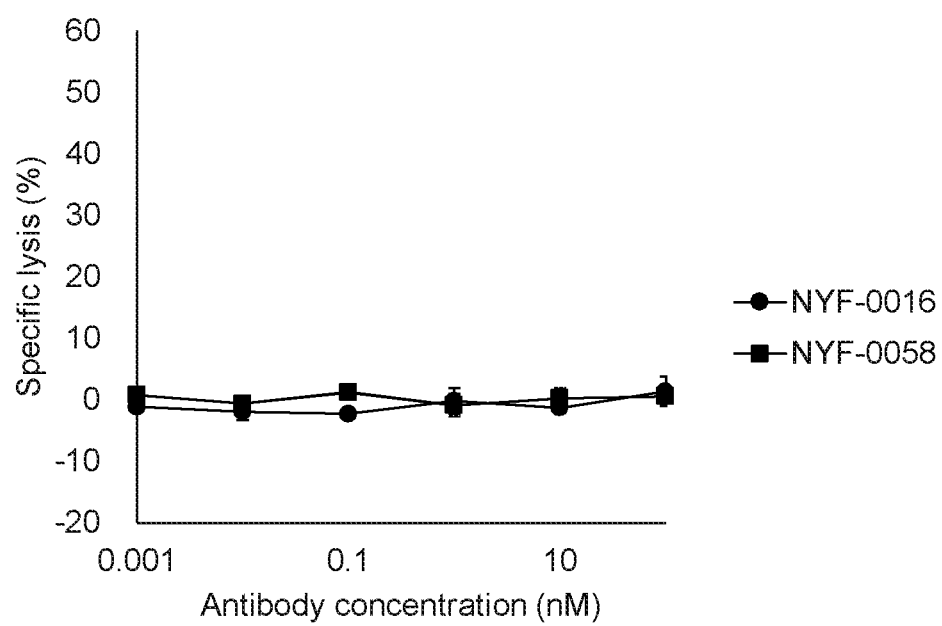
FIG. 4H demonstrates that the Fc-conjugated anti-HLA-A2/NY-ESO-anti-CD3 bispecific molecules; i.e., NYF-0016 and NYF-0058, do not exert cytotoxicity on human AGS cells endogenously non-expressing NY-ESO in the presence of human PBMC. An error bar in the figure indicates the standard deviation (n=3).
Figure 4I:
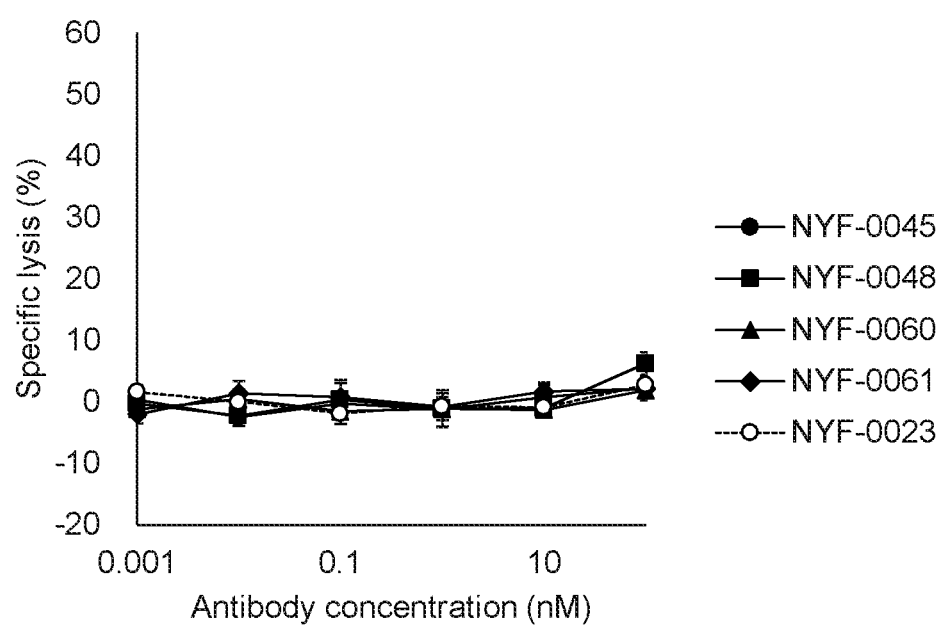
FIG. 4I demonstrates that the Fc-conjugated anti-HLA-A2/NY-ESO-anti-CD3 bispecific molecules; i.e., NYF-0023, NYF-0045, NYF-0048, NYF-0060, and NYF-0061, do not exert cytotoxicity on human AGS cells endogenously non-expressing NY-ESO in the presence of human PBMC. An error bar in the figure indicates the standard deviation (n=3).
Figure 4J:
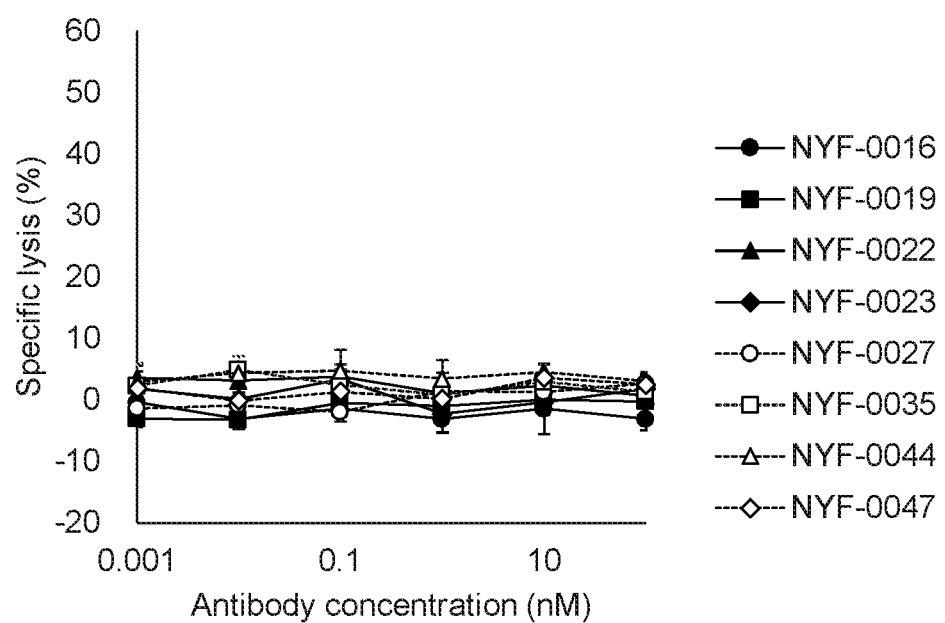
FIG. 4J demonstrates that the Fc-conjugated anti-HLA-A2/NY-ESO-anti-CD3 bispecific molecules; i.e., NYF-0016, NYF-0019, NYF-0022, NYF-0023, NYF-0027, NYF-0035, NYF-0044, and NYF-0047, do not exert cytotoxicity on human CFPAC-1 cells endogenously non-expressing NY-ESO in the presence of human PBMC. An error bar in the figure indicates the standard deviation (n=3).
Figure 4K:
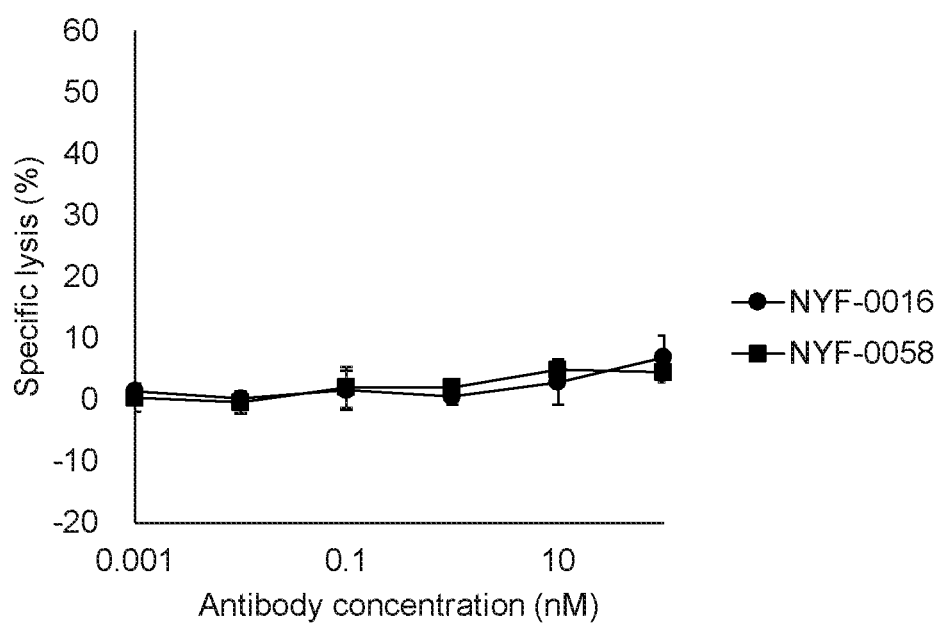
FIG. 4K demonstrates that the Fc-conjugated anti-HLA-A2/NY-ESO-anti-CD3 bispecific molecules; i.e., NYF-0016 and NYF-0058, do not exert cytotoxicity on human CFPAC-1 cells endogenously non-expressing NY-ESO in the presence of human PBMC. An error bar in the figure indicates the standard deviation (n=3).
Figure 4L:
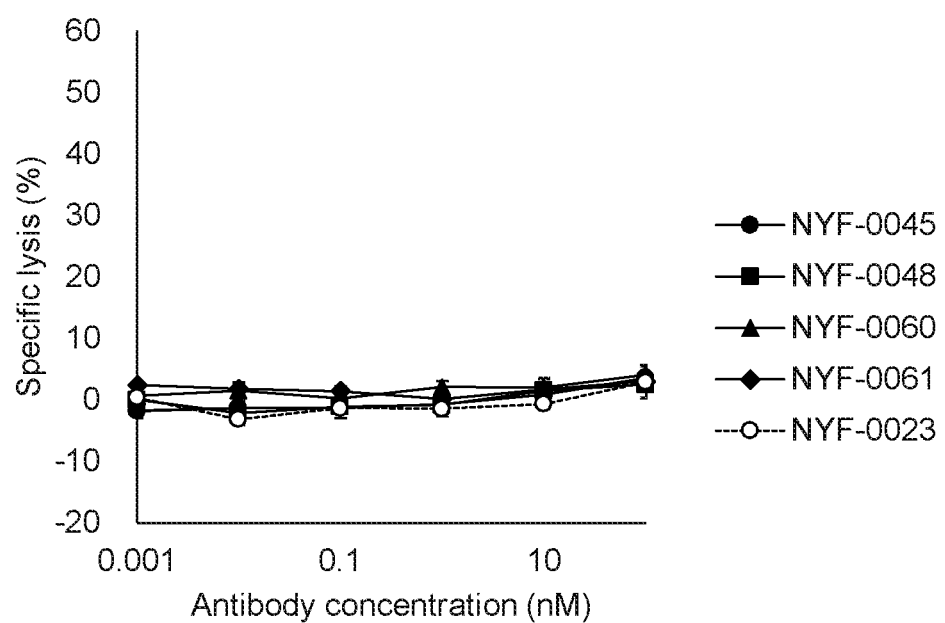
FIG. 4L demonstrates that the Fc-conjugated anti-HLA-A2/NY-ESO-anti-CD3 bispecific molecules; i.e., NYF-0023, NYF-0045, NYF-0048, NYF-0060, and NYF-0061, do not exert cytotoxicity on human CFPAC-1 cells endogenously non-expressing NY-ESO in the presence of human PBMC. An error bar in the figure indicates the standard deviation (n=3).

FIG. 104 The nucleotide sequence of C3E-7085-HC2-k deleteC (SEQ ID NO: 103)

FIG. 105 The amino acid sequence of NYA-1143-Fab-HC1-k delete (SEQ ID NO: 104); the NYA-1143 heavy chain variable region: amino acids 20 to 139

FIG. 106 The amino acid sequence of NYA-1143-LC (SEQ ID NO: 105); the NYA-1143 light chain variable region: amino acids 21 to 131

FIG. 107 The amino acid sequence of C3E-7085-HC2-k delete (SEQ ID NO: 106); C3E-7085: amino acids 21 to 260

FIG. 108 The nucleotide sequence of NYA-1143-HC1-k delete (SEQ ID NO: 107)

FIG. 109 The amino acid sequence of NYA-1143-HC1-k delete (SEQ ID NO: 108); NYA-1143: amino acids 21 to 266

FIG. 110 The nucleotide sequence of C3E-7085-NYA-1154-Fab-HC2-k delete (SEQ ID NO: 109)

FIG. 111 The nucleotide sequence of NYA-1154-LC (SEQ ID NO: 110)

FIG. 112 The nucleotide sequence of OAA-HC1-k delete (SEQ ID NO: 111)

FIG. 113 The amino acid sequence of C3E-7085-NYA-1154-Fab-HC2-k delete (SEQ ID NO: 112); C3E-7085: amino acids 21 to 260; the NYA-1154 heavy chain variable region: amino acids 266 to 285

FIG. 114 The amino acid sequence of NYA-1154-LC (SEQ ID NO: 113); the NYA-1154 light chain variable region: amino acids 21 to 131

FIG. 115 The amino acid sequence of OAA-HC1-k delete (SEQ ID NO: 114)

FIG. 116 The nucleotide sequence of NYF-0010-HC2-k delete (SEQ ID NO: 115)

FIG. 117 The nucleotide sequence of NYF-0004-HC2-k delete (SEQ ID NO: 116)

FIG. 118 The nucleotide sequence of NYF-0011-HC2-k delete (SEQ ID NO: 117)

FIG. 119 The amino acid sequence of NYF-0010-HC2-k delete (SEQ ID NO: 18); NYA-1154: amino acids 21 to 266; C3E-7085: amino acids 272 to 511

FIG. 120 The amino acid sequence of NYF-0004-HC2-k delete (SEQ ID NO: 119); C3E-7085: amino acids 21 to 260; NYA-1154: amino acids 272 to 511

FIG. 121 The amino acid sequence of NYF-0011-HC2-k delete (SEQ ID NO: 120); NYA-1143: amino acids 21 to 266; C3E-7085: amino acids 272 to 511

FIG. 122 The amino acid sequence of the point-mutant NY-ESO peptide 1F (SEQ ID NO: 121)

FIG. 123 The amino acid sequence of the point-mutant NY-ESO peptide 2M (SEQ ID NO: 122)

FIG. 124 The amino acid sequence of the point-mutant NY-ESO peptide 3A (SEQ ID NO: 123)

FIG. 125 The amino acid sequence of the point-mutant NY-ESO peptide 4A (SEQ ID NO: 124)

FIG. 126 The amino acid sequence of the point-mutant NY-ESO peptide 5A (SEQ ID NO: 125)

FIG. 127 The amino acid sequence of the point-mutant NY-ESO peptide 6L (SEQ ID NO: 126)

FIG. 128 The amino acid sequence of the point-mutant NY-ESO peptide 7F (SEQ ID NO: 127)

FIG. 129 The amino acid sequence of the point-mutant NY-ESO peptide 8A (SEQ ID NO: 128)

FIG. 130 The amino acid sequence of the point-mutant NY-ESO peptide 9A (SEQ ID NO: 129)

Figure 131:
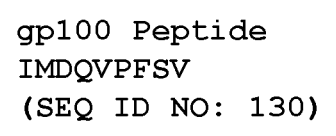

FIG. 131 The amino acid sequence of the gp100 peptide (SEQ ID NO: 130)

FIG. 132 The amino acid sequence of the homologous peptide DOLPP1 (SEQ ID NO: 131)

FIG. 133 The amino acid sequence of the homologous peptide IL20RB (SEQ ID NO: 132)

FIG. 134 The amino acid sequence of the homologous peptide PRKD2 (SEQ ID NO: 133)

FIG. 135 The amino acid sequence of the homologous peptide CD163 (SEQ ID NO: 134)

FIG. 136 The amino acid sequence of the homologous peptide P2RY8 (SEQ ID NO: 135)

FIG. 137 The amino acid sequence of C3E-7034 (SEQ ID NO: 136)

FIG. 138 The amino acid sequence of C3E-7036 (SEQ ID NO: 137)

FIG. 139 The amino acid sequence of C3E-7085 (SEQ ID NO: 138)

FIG. 140 The amino acid sequence of C3E-7088 (SEQ ID NO: 139)

FIG. 141 The amino acid sequence of C3E-7093 (SEQ ID NO: 140)

FIG. 142 The amino acid sequences of CDRH1 to CDRH3 of the C3E-7085 heavy chain and CDRL1 to CDRL3 of the C3E-7085 light chain (SEQ ID NOs: 141 to 146)

FIG. 143 The amino acid sequence of C3E-7078 (SEQ ID NO: 147)

FIG. 144 The nucleotide sequence of NYF-0014-HC2 (SEQ ID NO: 148)

FIG. 145 The amino acid sequence of NYF-0014-HC2 (SEQ ID NO: 149); NYA-0001: amino acids 21 to 266; C3E-7085: amino acids 272 to 511

FIG. 146 The amino acid sequence of NYF-0082-HC2 (SEQ ID NO: 150); NYA-0082: amino acids 21 to 266; C3E-7085: amino acids 272 to 511

FIG. 147 The amino acid sequence of human CD3 ε (SEQ ID NO: 151)

FIG. 148 The nucleotide sequence of the entire NYZ-0038-HC2 (SEQ ID NO: 152)

FIG. 149 The nucleotide sequence of the entire NYZ-0082-HC2 (SEQ ID NO: 153)

FIG. 150 The nucleotide sequence of the entire NYZ-0083-HC2 (SEQ ID NO: 154)

FIG. 151 The amino acid sequence of the entire NYZ-0038-HC2 (SEQ ID NO: 155); NYA-2061: amino acids 21 to 266; C3E-7096: amino acids 272 to 511

FIG. 152 The amino acid sequence of the entire NYZ-0082-HC2 (SEQ ID NO: 156); NYA-3061: amino acids 21 to 271; C3E-7096: amino acids 277 to 516.

FIG. 153 The amino acid sequence of the entire NYZ-0083-HC2 (SEQ ID NO: 157); NYA-3061: amino acids 21 to 271; C3E-7097: amino acids 277 to 516.

FIG. 154 The nucleotide sequence of the full-length NYZ-1010-HC2 (SEQ ID NO: 158)

FIG. 155 The nucleotide sequence of the full-length C3E-7085-LC (SEQ ID NO: 159)

FIG. 156 The amino acid sequence of the full-length NYZ-1010-HC2 (SEQ ID NO: 160); NYA-3061: amino acids 21 to 271; the C3E-7085 heavy chain variable region: amino acids 277 to 394

FIG. 157 The amino acid sequence of the full-length C3E-7085-LC (SEQ ID NO: 161) FIG. 158A shows a table demonstrating standardized gMFI of the Fc-conjugated anti-HLA-A2/NY-ESO-anti-CD3 bispecific molecules; NYZ-0038, NYZ-0082, NYZ-0083, and NYZ-1010, relative to CD3e knockout T2 cells supplemented with various point-mutant peptides. *Each underlined value indicates a half or lower than the standardized gMFI of each Fc-conjugated anti-HLA-A2/NY-ESO-anti-CD3 bispecific molecule, relative to CD3e knockout T2 cells supplemented with the NY-ESO peptide, and*each bold value indicates a quarter or lower of the standardized gMFI.

FIG. 158B shows a table demonstrating standardized gMFI of the Fc-conjugated anti-HLA-A2/NY-ESO-anti-CD3 bispecific molecules; NYZ-0038, NYZ-0082, NYZ-0083, and NYZ-1010, relative to CD3e knockout T2 cells supplemented with various homologous peptides. *Each underlined value indicates a value of each Fc-added anti-HLA-A2/NY-ESO-anti-CD3 bispecific molecule larger than the standardized gMFI of CD3e knockout T2 cells supplemented with DMSO.

Figure 159A:
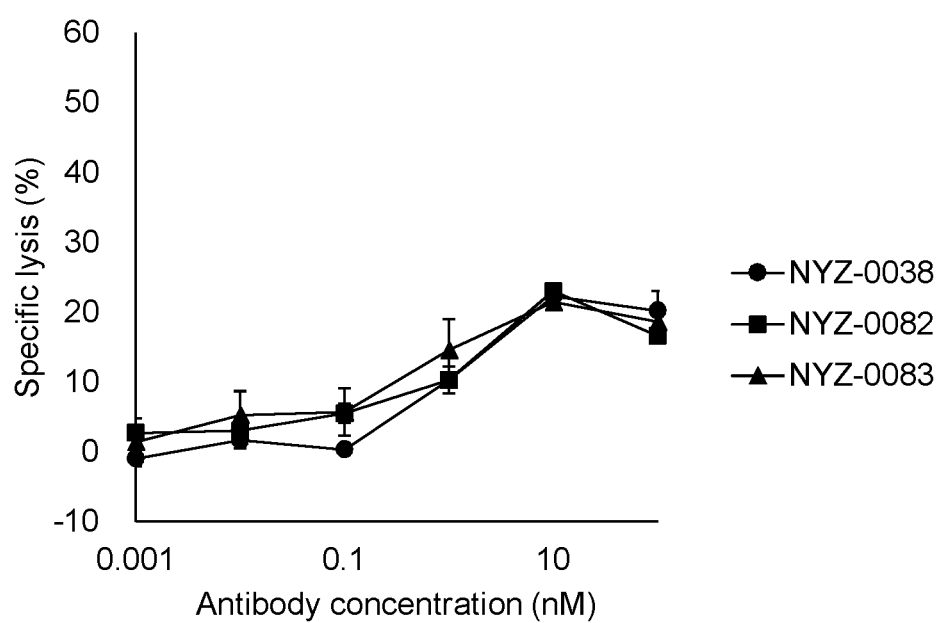

FIG. 159A demonstrates that the Fc-conjugated anti-HLA-A2/NY-ESO-anti-CD3 bispecific molecules; i.e., NYZ-0038, NYZ-0082, and NYZ-0083, exert cytotoxicity on human U266B1 cells endogenously expressing NY-ESO in the presence of human PBMC. An error bar in the figure indicates the standard deviation (n=3).

Figure 159B:
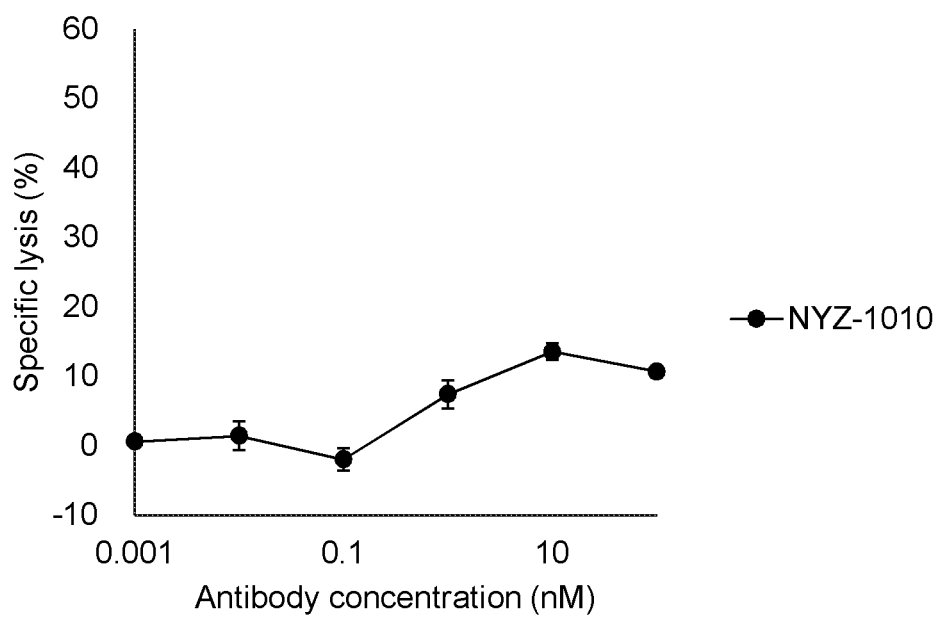

FIG. 159B demonstrates that the Fc-conjugated anti-HLA-A2/NY-ESO-anti-CD3 bispecific molecule; i.e., NYZ-1010, exerts cytotoxicity on human U266B1 cells endogenously expressing NY-ESO in the presence of human PBMC. An error bar in the figure indicates the standard deviation (n=3).

Figure 159C:
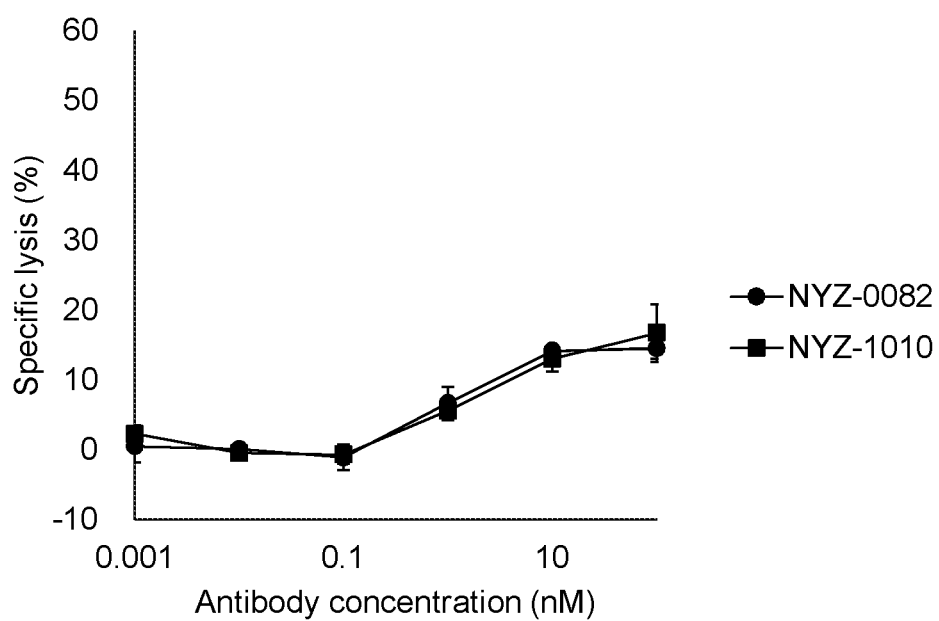

FIG. 159C demonstrates that the Fc-conjugated anti-HLA-A2/NY-ESO-anti-CD3 bispecific molecules; i.e., NYZ-0082 and NYZ-1010, exert cytotoxicity on human NCI-H1703 cells endogenously expressing NY-ESO in the presence of human PBMC. An error bar in the figure indicates the standard deviation (n=3).

Figure 159D:
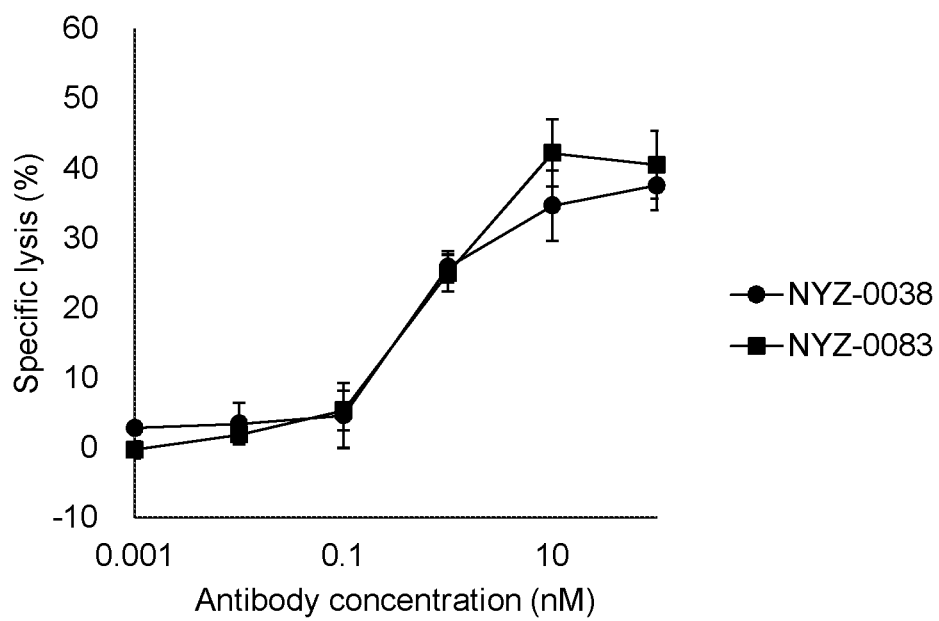

FIG. 159D demonstrates that the Fc-conjugated anti-HLA-A2/NY-ESO-anti-CD3 bispecific molecules; i.e., NYZ-0038 and NYZ-0083, exert cytotoxicity on human NCI-H1703 cells endogenously expressing NY-ESO in the presence of human PBMC. An error bar in the figure indicates the standard deviation (n=3).

Figure 159E:
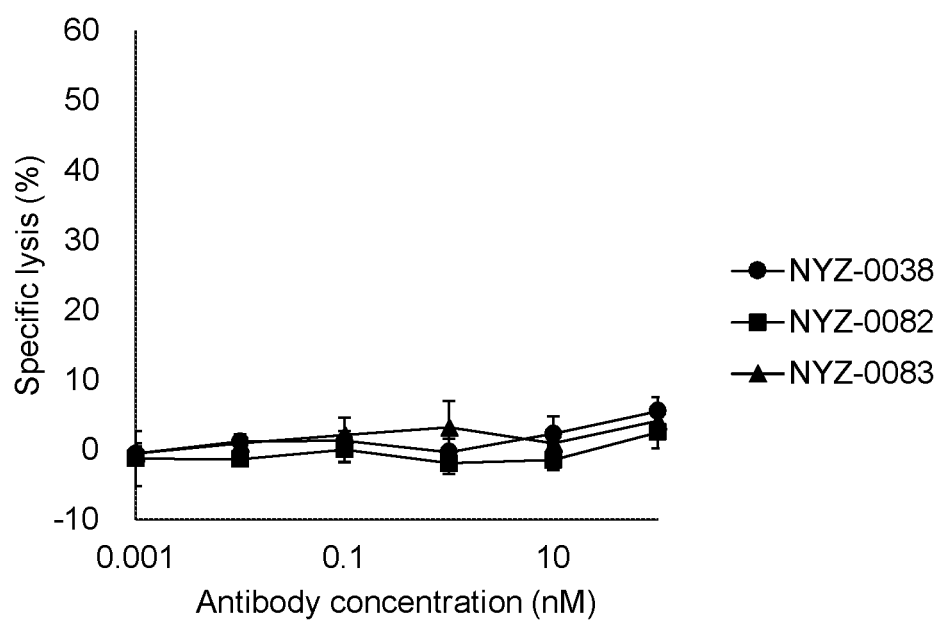

FIG. 159E demonstrates that the Fc-conjugated anti-HLA-A2/NY-ESO-anti-CD3 bispecific molecules; i.e., NYZ-0038, NYZ-0082, and NYZ-0083, do not exert cytotoxicity on human AGS cells endogenously expressing NY-ESO in the presence of human PBMC. An error bar in the figure indicates the standard deviation (n=3).

Figure 159F:
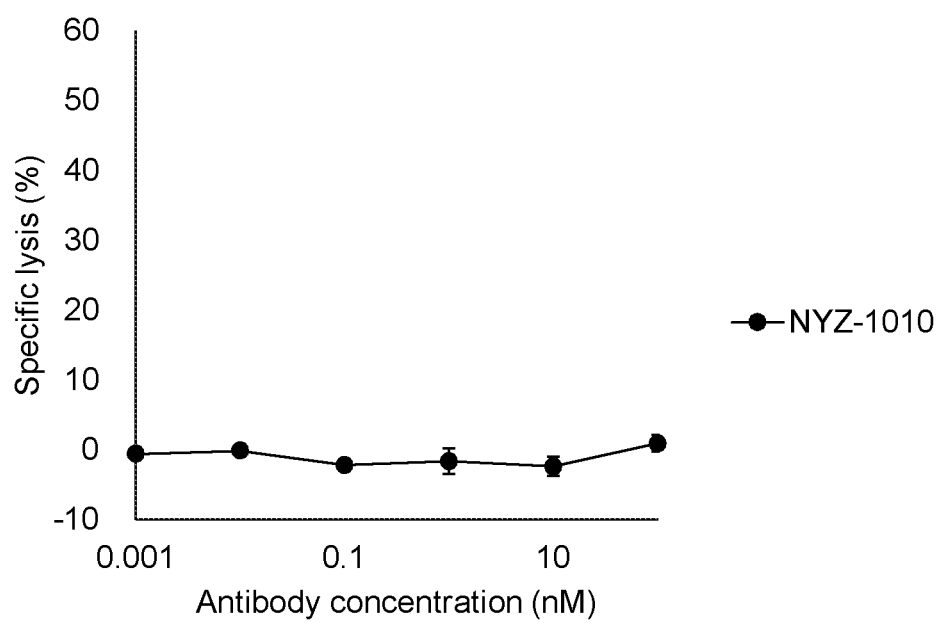

FIG. 159F demonstrates that the Fc-conjugated anti-HLA-A2/NY-ESO-anti-CD3 bispecific molecule; i.e., NYZ-1010, does not exert cytotoxicity on human AGS cells endogenously non-expressing NY-ESO in the presence of human PBMC. An error bar in the figure indicates the standard deviation (n=3).

Figure 159G:
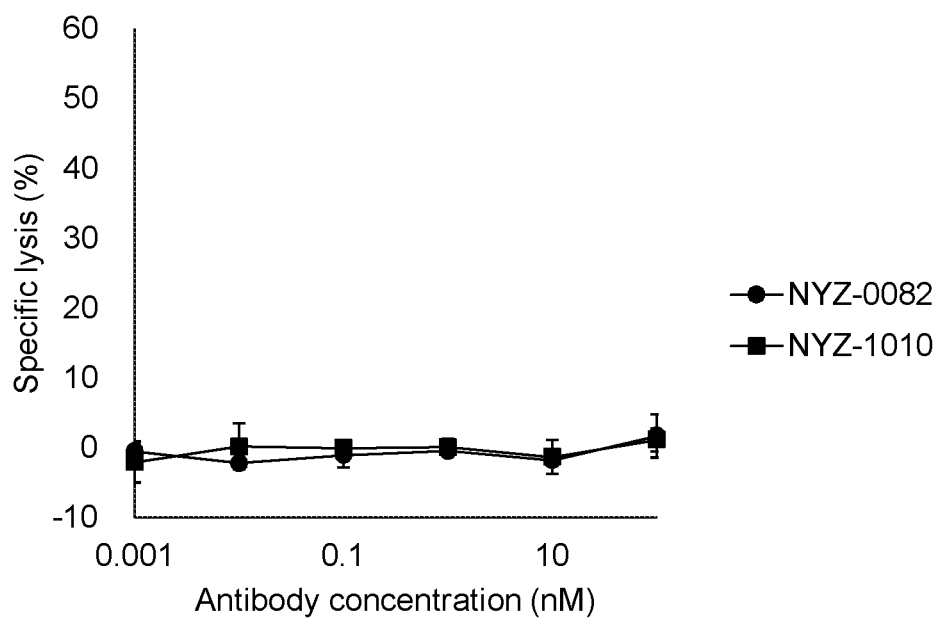

FIG. 159G demonstrates that the Fc-conjugated anti-HLA-A2/NY-ESO-anti-CD3 bispecific molecules; i.e., NYZ-0082 and NYZ-1010, do not exert cytotoxicity on human CFPAC-1 cells endogenously non-expressing NY-ESO in the presence of human PBMC. An error bar in the figure indicates the standard deviation (n=3).

Figure 159H:
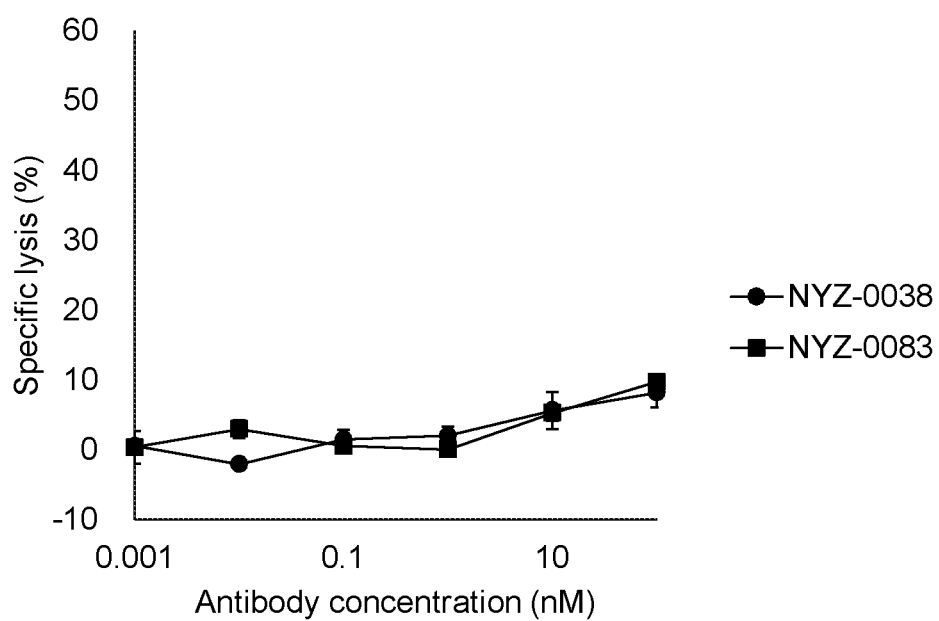

FIG. 159H demonstrates that the Fc-conjugated anti-HLA-A2/NY-ESO-anti-CD3 bispecific molecules; i.e., NYZ-0038 and NYZ-0083, do not exert cytotoxicity on human CFPAC-1 cells endogenously non-expressing NY-ESO in the presence of human PBMC. An error bar in the figure indicates the standard deviation (n=3).

Figure 160A:
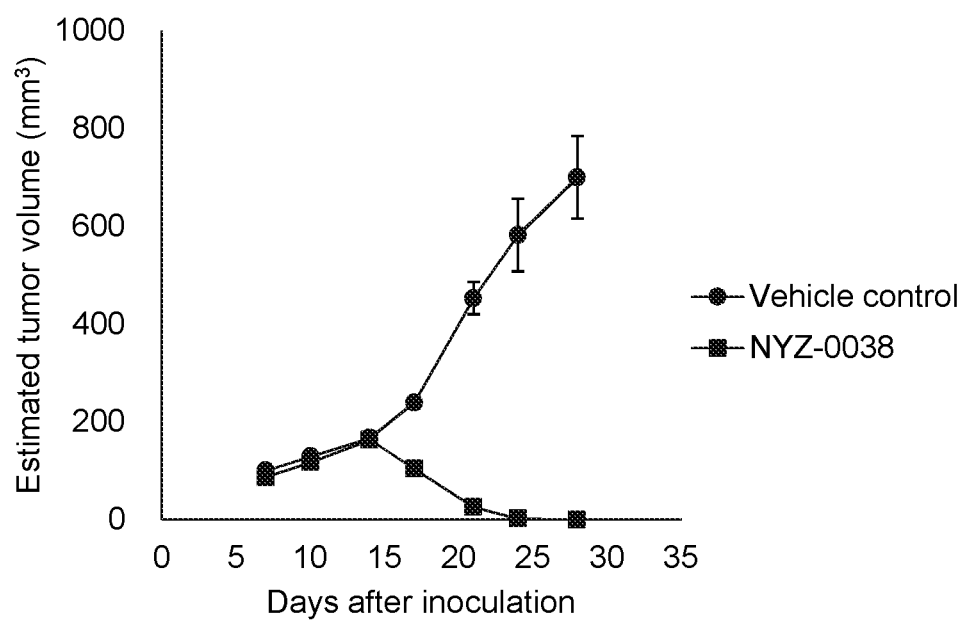

FIG. 160A demonstrates that the Fc-conjugated anti-HLA-A2/NY-ESO-anti-CD3 bispecific molecule; i.e., NYZ-0038, exerts antitumor activity on human PBMC-transfected models. An error bar in the figure indicates the standard deviation (n=5).

Figure 160B:
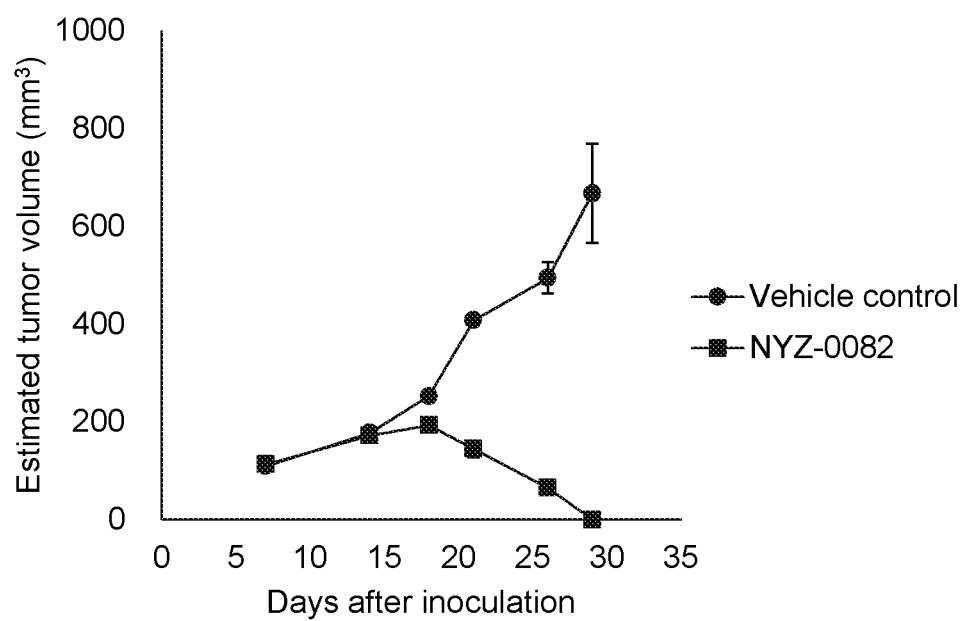

FIG. 160B demonstrates that the Fc-conjugated anti-HLA-A2/NY-ESO-anti-CD3 bispecific molecule; i.e., NYZ-0082, exerts antitumor activity on human PBMC-transfected models. An error bar in the figure indicates the standard deviation (n=5).

Figure 160C:
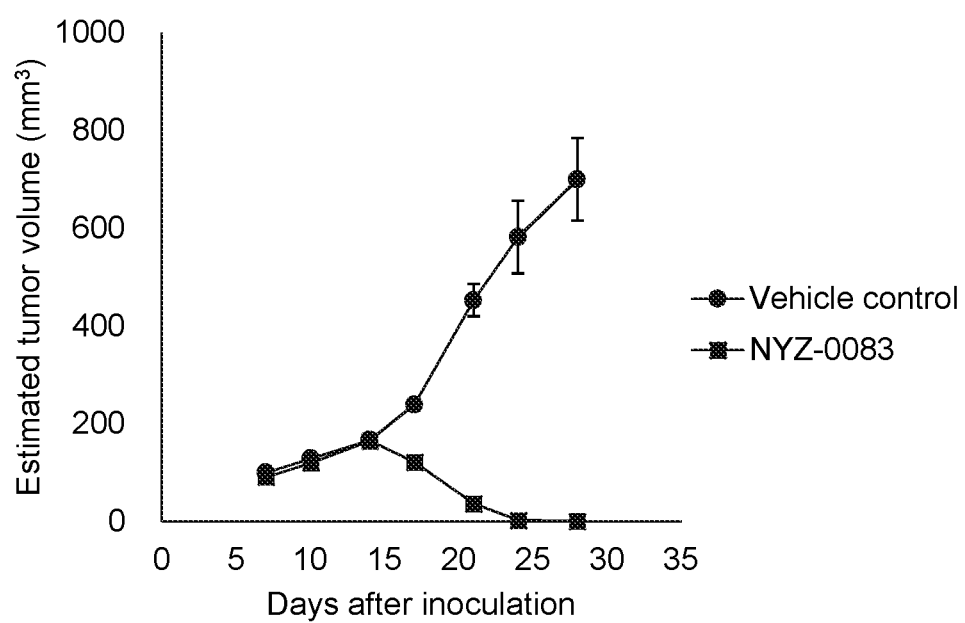

FIG. 160C demonstrates that the Fc-conjugated anti-HLA-A2/NY-ESO-anti-CD3 bispecific molecule; i.e., NYZ-0083, exerts antitumor activity on human PBMC-transfected models. An error bar in the figure indicates the standard deviation (n=5).

Figure 160D:
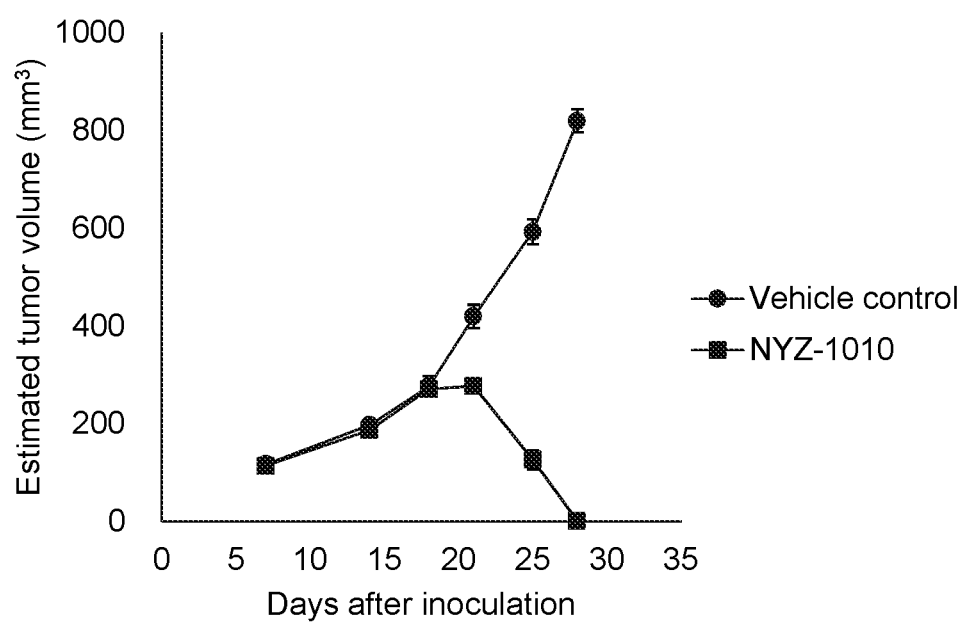

FIG. 160D demonstrates that the Fc-conjugated anti-HLA-A2/NY-ESO-anti-CD3 bispecific molecule; i.e., NYZ-1010, exerts antitumor activity on human PBMC-transfected models. An error bar in the figure indicates the standard deviation (n=5).

Figure 161:
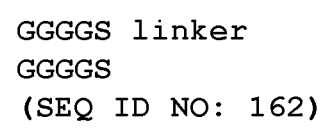

FIG. 161 The amino acid sequence of the peptide linker (SEQ ID NO: 162)

Figure 162:
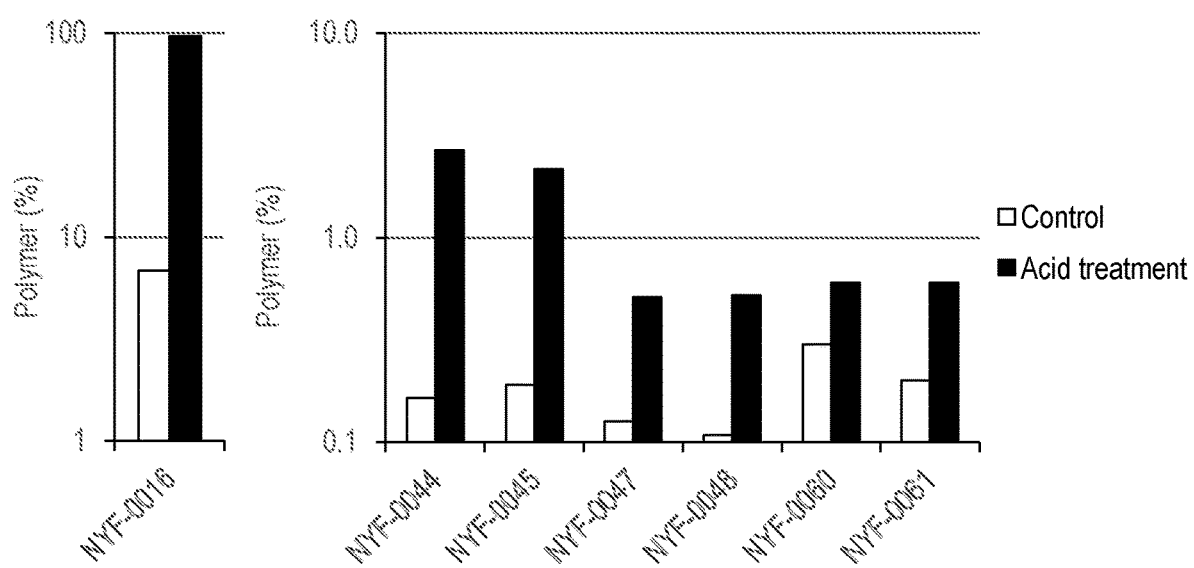

FIG. 162 shows the polymer content (%) upon acid treatment of various Fc-conjugated anti-HLA/NY-ESO-anti-CD3 bispecific molecules.

Figure 163:
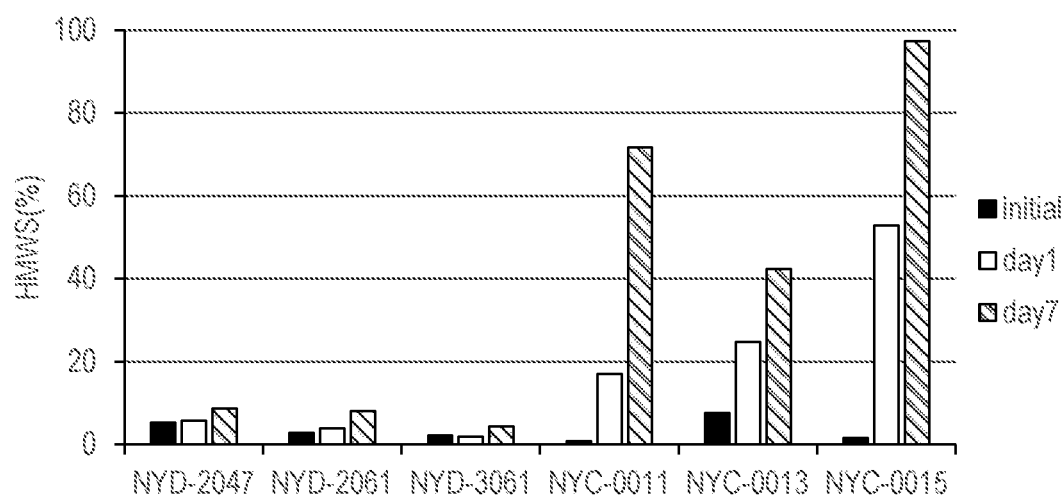

FIG. 163 shows the evaluation results of solution stability of anti-HLA/NY-ESO scFv-heterodimer Fc.

FIG. 164 The nucleotide sequence of the full-length NYA-3061 (SEQ ID NO: 163)

FIG. 165 The amino acid sequence of the full-length NYA-3061 (SEQ ID NO: 164)

FIG. 166 The nucleotide sequence of the full-length NYC-0005 (SEQ ID NO: 165)

FIG. 167 The amino acid sequence of the full-length NYC-0005 (SEQ ID NO: 166)

FIG. 168 The nucleotide sequence of the full-length NYC-0006 (SEQ ID NO: 167)

FIG. 169 The amino acid sequence of the full-length NYC-0006 (SEQ ID NO: 168)

FIG. 170 The nucleotide sequence of the full-length NYC-0007 (SEQ ID NO: 169)

FIG. 171 The amino acid sequence of the full-length NYC-0007 (SEQ ID NO: 170)

FIG. 172 The nucleotide sequence of the full-length NYC-0008 (SEQ ID NO: 171)

FIG. 173 The amino acid sequence of the full-length NYC-0008 (SEQ ID NO: 172)

FIG. 174 The nucleotide sequence of the full-length NYC-0009 (SEQ ID NO: 173)

FIG. 175 The amino acid sequence of the full-length NYC-0009 (SEQ ID NO: 174)

FIG. 176 The nucleotide sequence of the full-length NYC-0010 (SEQ ID NO: 175)

FIG. 177 The amino acid sequence of the full-length NYC-0010 (SEQ ID NO: 176)

FIG. 178 The nucleotide sequence of the full-length HC-h (SEQ ID NO: 177)

FIG. 179 The amino acid sequence of the full-length HC-h (SEQ ID NO: 178)

FIG. 180 The nucleotide sequence of the full-length NYD-2047-HC-k (SEQ ID NO: 179)

FIG. 181 The amino acid sequence of the full-length NYD-2047-HC-k (SEQ ID NO: 180)

FIG. 182 The nucleotide sequence of the full-length NYD-2061-HC-k (SEQ ID NO: 181)

FIG. 183 The amino acid sequence of the full-length NYD-2061-HC-k (SEQ ID NO: 182)

FIG. 184 The nucleotide sequence of the full-length NYD-3061-HC-k (SEQ ID NO: 183)

FIG. 185 The amino acid sequence of the full-length NYD-3061-HC-k (SEQ ID NO: 184)

FIG. 186 The nucleotide sequence of the full-length NYC-0011-HC-k (SEQ ID NO: 185)

FIG. 187 The amino acid sequence of the full-length NYC-0011-HC-k (SEQ ID NO: 186)

FIG. 188 The nucleotide sequence of the full-length NYC-0012-HC-k (SEQ ID NO: 187)

FIG. 189 The amino acid sequence of the full-length NYC-0012-HC-k (SEQ ID NO: 188)

FIG. 190 The nucleotide sequence of the full-length NYC-0013-HC-k (SEQ ID NO: 189)

FIG. 191 The amino acid sequence of the full-length NYC-0013-HC-k (SEQ ID NO: 190)

FIG. 192 The nucleotide sequence of the full-length NYC-0014-HC-k (SEQ ID NO: 191)

FIG. 193 The amino acid sequence of the full-length NYC-0014-HC-k (SEQ ID NO: 192)

FIG. 194 The nucleotide sequence of the full-length NYC-0015-HC-k (SEQ ID NO: 193)

FIG. 195 The amino acid sequence of the full-length NYC-0015-HC-k (SEQ ID NO: 194)

FIG. 196 The nucleotide sequence of the full-length NYC-0016-HC-k (SEQ ID NO: 195)

FIG. 197 The amino acid sequence of the full-length NYC-0016-HC-k (SEQ ID NO: 196)

FIG. 198 The amino acid sequence of the full-length NYZ-1007-HC2 (SEQ ID NO: 197); NYA-2061: amino acids 21 to 266; the C3E-7085 heavy chain variable region: amino acids 272 to 389

FIG. 199 The amino acid sequence of the full-length NYZ-1017-HC2 (SEQ ID NO: 198); NYA-2047: amino acids 21 to 266; the C3E-7085 heavy chain variable region: amino acids 277 to 389

DESCRIPTION OF EMBODIMENTS

Hereafter, the present invention is described in detail.

1. Definition

In the present invention, the term "gene" refers to a nucleotide chain including a nucleotide sequence encoding an amino acid of a protein or a complementary chain thereof. For example, a polynucleotide, oligonucleotide, DNA, mRNA, cDNA, cRNA, or the like, which is a nucleotide chain including a nucleotide sequence encoding an amino acid of a protein or a complementary chain thereof, is within the scope of the "gene," Such gene is a single-stranded, double-stranded, or triple or more-stranded nucleotide, and an association of a DNA chain and an RNA chain, a single nucleotide chain comprising both ribonucleotide (RNA) and deoxyribonucleotide (DNA), and a double-stranded or triple-stranded nucleotide comprising such a nucleotide chain are included within the scope of the "gene." In the present invention, the term "base sequence" is synonymous with the term "nucleotide sequence."

In the present invention, the terms "polynucleotide," "nucleotide chain," "nucleic acid," and "nucleic acid molecule" are synonymous. For example, DNA, RNA, probe, oligonucleotide, and primer are within the scope of "polynucleotide." Such a polynucleotide consists of 1, 2, 3, or more chains, and an association of a DNA chain and an RNA chain, a single polynucleotide chain comprising both ribonucleotide (RNA) and deoxyribonucleotide (DNA), and a double-stranded or triple-stranded nucleotide comprising such a polynucleotide chain are included within the scope of the "polynucleotide."

In the present invention, the terms "polypeptide," "peptide," and "protein" are synonymous.

In the present invention, the term "antigen" may refer to the term "immunogen," according to need.

In the present invention, the term "cell" encompasses various cells derived from animals, subculture cells, primary culture cells, cell lines, recombinant cells, and microorganisms.

In the present invention, the term "antibody" is synonymous with the term "immunoglobulin." However, the term "antibody" in the case of the anti-HLA/NY-ESO antibody according to the present invention refers to immunoglobulin comprising a constant region and a variable region. An antibody is not particularly limited, and it may be a naturally occurring or partially or completely synthesized immunoglobulin. The anti-HLA/NY-ESO antibody according to the present invention is included in the term "molecule" described below.

In the present invention, "NY-ESO peptide" indicates a peptide consisting of the 9 amino acids 157 to 165 of NY-ESO-1 and LAGE-1 (SLLMWITQC: SEQ ID NO: 1).

In the present invention, "HLA-A2/NY-ESO" indicates a complex of NY-ESO peptide and Histocompatibility Leukocyte Antigen-A2 (HLA-A2), and it is also denoted as "HLA/NY-ESO."

In the present invention, the term "anti-HLA-A2/NY-ESO antibody" refers to an antibody that binds to HLA-A2/NY-ESO. In other words, the term refers to an antibody that recognizes HLA-A2/NY-ESO. Also, the term "anti-HLA-A2/NY-ESO scFv" refers to scFv that binds to HLA/NY-ESO. In other words, the term refers to scFv that recognizes HLA-A2/NY-ESO. The terms "anti-HLA-A2/NY-ESO antibody" and "anti-HLA-A2/NY-ESO scFv" are also denoted as the "anti-HLA/NY-ESO antibody" and the "anti-HLA/NY-ESO scFv," respectively.

A basic four-chain antibody structure is composed of two identical light chains (L chains) and two identical heavy chains (H chains). A light chain binds to a heavy chain via a single covalent disulfide bond. Two heavy chains are bound to each other via one or more disulfide bonds in accordance with heavy chain isotypes. A light chain and a heavy chain each have an intra-chain disulfide bond at regular intervals. In a light chain and a heavy chain, there are a constant region exhibiting very high amino acid sequence similarity and a variable region exhibiting low amino acid sequence similarity. A light chain comprises, at its amino terminus, a variable region (VL) adjacent to a constant region (CL). A heavy chain comprises, at its amino terminus, a variable region (VH) adjacent to 3 constant regions (CH1/CH2/CH3). VL is paired with VH, and CL is aligned with a first constant region of a heavy chain (CH1). VL is paired with VH to form a single antigen-binding site.

A constant region of the antibody of the present invention is not particularly limited. The antibody of the present invention to be used for treatment or prevention of human diseases preferably comprises a constant region of a human antibody. Examples of heavy chain constant regions of a human antibody include Cγ1, Cγ2, Cγ3, Cγ4, Cμ, Cδ, Cα1, Cα2, and CF. Examples of light chain constant regions of a human antibody include Cκ and Cλ.

Fab comprises a heavy chain VH, CH1 adjacent thereto, a light chain VL, and CL adjacent thereto. VH and VL each comprise a complementarity determining region (CDR).

Fc (also referred to as an "Fc region") is a carboxyl terminal region of a heavy chain constant region, it comprises CH2 and CH3, and it is a dimer. Fc of the present invention may comprise a naturally occurring sequence or it may comprise a sequence derived from the naturally occurring sequence by mutation (referred to as "mutant Fc"). In the multispecific molecule and the bispecific molecule of the resent invention, a Fc region is preferably mutant Fc, and more preferably a combination of Fc regions capable of forming a heterodimer. An example of a combination of Fc regions is a combination of Fc (i) in the first polypeptide and Fc (ii) in the second polypeptide described below. A combination is not limited thereto, provided that such combination of Fc regions is capable of association (formation of a heterodimer).

Examples of mutant Fc include, but are not limited to, a modified Fc region included in a heteropolymer with improved stability (including a heterodimer Fc region) disclosed in WO 2013/063702, Fc including an immunoglobulin CD3 region induced from the IgG antibody with a "protrusion" and a "gap" included in a heteropolymer disclosed in WO 1996/27011, Fc including a CH3 domain included in a heterodimer that becomes electrostatically advantageous via substitution of one or more amino acids with charged amino acids disclosed in WO 2009/089004, a heterodimer Fc region included in a heterodimer involving steric mutation and/or pI (isoelectric point) mutation disclosed in WO 2014/110601, and a heterodimer Fc including a CH3 domain with a modification to eliminate or reduce the binding to protein A disclosed in WO 2010/151792.

A variable region is composed of a region with an extreme variability referred to as a hypervariable region (HVR) and relatively invariable regions referred to as framework regions (FRs) divided by the HVR. Naturally occurring heavy chain and light chain variable regions comprise 4 FRs connected by 3 hypervariable regions, a hypervariable region of each chain and a hypervariable region of other chains being maintained very close thereto, and such regions contribute to formation of an antigen-binding site of an antibody.

A heavy chain and a light chain of an antibody molecule are known to comprise 3 complementarity determining regions (CDRs). A complementarity determining region is also referred to as a hypervariable region, it is present within variable regions of a heavy chain and a light chain of the antibody where variability of a primary structure is particularly high, and, in general, it is separated in 3 positions in the primary structure of a polypeptide chain of a heavy chain and a light chain. In the present invention, complementarity determining regions of a heavy chain of an antibody are denoted as CDRH1, CDRH2, and CDRH3 from the amino terminus of the heavy chain amino acid sequence, and complementarity determining regions of a light chain are denoted as CDRL1, CDRL2, and CDRL3 from the amino terminus of the light chain amino acid sequence. These regions are adjacent to each other on a steric structure and determine specificity to the antigens to which they bind.

In the present invention, the position and the length of CDR were determined in accordance with the definition of IMGT (Developmental and Comparative Immunology 27, 2003, 55-77).

FR is a variable region other than CDR. In general, a variable region comprises 4 FRs; i.e., FR1, FR2, FR3, and FR4.

CDRs and FRs included in the heavy chain and in the light chain are provided in the orders of FRH1-CDRH1-FRH2-CDRH2-FRH3-CDRH3-FRH4 and FRL1-CDRL1-FRL2-CDRL2-FRL3-CDRL3-FRL4, respectively, from the amino terminus toward the carboxyl terminus.

CDR and FR positions can be determined in accordance with various definitions well known in the art, such as the definitions of Kabat, Chothia, AbM, contact, in addition to IMGT.

In the present invention, the term "an antigen-binding fragment of the antibody" refers to a partial fragment of an antibody having the activity of binding to an antigen, which is composed of a heavy chain variable region and a light chain variable region. Examples of "an antigen-binding fragment of the antibody" include, but are not limited to, antigen-binding fragments, such as Fab, F(ab')₂, scFv, Fab', Fv, and single-domain antibody (sdAb). Such antigen-binding fragment of the antibody may be obtained by treating a full-length molecule of an antibody protein with an enzyme such as papain or pepsin or it may be a recombinant protein produced in an adequate host cell with the use of a recombinant gene. In the present invention, the term "a binding fragment of the antibody" is synonymous with the term "an antigen-binding fragment of the antibody."

In the present invention, a "site" to which an antibody binds; i.e., a "site" that is recognized by an antibody, is a partial peptide or a partial higher-order structure of an antigen to which an antibody binds or which is recognized by the antibody.

In the present invention, such a site is referred to as an epitope or an antibody binding site. In the present invention, a "mutant antibody" refers to a polypeptide having an amino acid sequence derived from the amino acid sequence of the original antibody by substitution, deletion, or addition ("addition" encompasses "insertion") (hereafter, collectively referred to as "mutation") of amino acids and binding to HLA/NY-ESO of the present invention. The number of mutant amino acids in such a mutant antibody is 1, 2, 3, 4, 5, 6, 7, 8, 9, 10, 12, 15, 20, 25, 30, 40, or 50. Such a mutant antibody is within the scope of the "antibody" of the present invention.

In the present invention, the term "several" in "one or several" indicates 2 to 10.

The term "molecule" used herein indicates a molecule comprising the antibody or the antigen-binding fragment of the antibody described above. In addition, the term "molecule" encompasses a multispecific molecule formed of an antibody or a plurality of antigen-binding fragments derived therefrom.

The term "multispecific molecule" used herein is not particularly limited, provided that such a molecule is capable of binding to a plurality of different epitopes on a molecule and/or different epitopes on two or more molecules. A multispecific molecule encompasses an antibody comprising a heavy chain variable region (VH) and a light chain variable region (VL). Examples of such a multispecific molecule include, but are not limited to, a full-length antibody molecule comprising two or more different types of heavy chains and light chains; i.e., an IgG-type multispecific molecule, and a molecule comprising an antigen-binding fragment consisting of two or more types of VLs and VHs; i.e., a molecule derived from Fab, Fab', Fv, scFv, sdAb, or the like in combination, such as tandem scFv, a diabody, a single chain diabody, or a triabody. In addition, a molecule generated by genetically or chemically ligating a protein without an immunoglobulin skeleton and capable of binding to an antigen to an antigen-binding fragment is within the scope of the multispecific molecule. In the present invention, such a multispecific molecule may be referred to as a "multispecific antibody" except for the case in which the molecule does not comprise an antibody or an antigen-binding fragment thereof, according to need.

The anti-HLA/NY-ESO antibody according to the present invention, an antigen-binding fragment of such an antibody, or the molecule according to the present invention have, for example, biological activity and physicochemical properties (which may also be referred to as physical properties). Specific examples thereof include various biological activity, such as cytotoxicity, ADCC activity, or antitumor activity (described below), and physical properties, such as antigen- or epitope-binding activity, stability during production or storage, and heat stability.

In the present invention, "hybridization under stringent conditions" is performed in a solution containing 5×SSC at 65° C., in an aqueous solution containing 2×SSC and 0.1% SDS at 65° C. for 20 minutes, in an aqueous solution containing 0.5×SSC and 0.1% SDS at 65° C. for 20 minutes, or in an aqueous solution containing 0.2×SSC and 0.1% SDS at 65° C. for 20 minutes under washing conditions or conditions equivalent thereto. SSC is an aqueous solution of 150 mM NaCl and 15 mM sodium citrate, and n×SSC is SSC of n-fold concentration.

In the present invention, "cell damage" is any form of a pathological change that has occurred in a cell. In addition to an external injury, the term "cell damage" refers to any damage caused on a cell structure or functions, such as DNA cleavage, formation of nucleotide dimers, chromosome cleavage, mitotic apparatus damage, or lowering in various enzyme activity. In the present invention, "cytotoxicity" is induction of the cell damage.

In the present invention, the term "antibody-dependent cellular cytotoxicity (ADCC)" refers to activity of NK cells to damage target cells such as tumor cells mediated by an antibody.

In the present invention, the term "T-cell-redirecting cytotoxicity" refers to induction of cytotoxicity mediated by a multispecific molecule comprising an anti-tumor antigen antibody and the anti-HLA/NY-ESO antibody. Specifically, an anti-tumor antigen antibody binds to a target tumor cell, the anti-HLA/NY-ESO antibody binds to a T cell, the distance between the target tumor cell and the T cell is shortened, and cytotoxicity is induced by T cell activation. Such a molecule can be incorporated into a pharmaceutical composition.

2. Antigen 2-1. HLA/NY-ESO Antigen

In the present invention, "HLA/NY-ESO" is used in the same sense as "HLA/NY-ESO protein."

HLA/NY-ESO is a triple complex of HLA-A2, β2-microglobulin, and the NY-ESO peptide. HLA-A2 is an HLA allele, which is expressed at the highest frequency in Caucasians. HLA forms a triple complex with 02-microglobulin and a peptide fragment of an autologous protein in the cell endoplasmic reticulum; the complex is presented extracellularly, and it is recognized by the T cell receptor (TCR) of the T cell. The NY-ESO peptide (SLLMWITQC: SEQ ID NO: 1, FIG. 8) is reported to be a peptide consisting of 9 amino acids at positions 157 to 165 of NY-ESO-1 and LAGE-1, which is presented to HLA-A2.

2-2. CD3 Antigen

In the present invention, "CD3" is used in the same sense as the "CD3 protein."

CD3 is expressed on a T cell as a part of a multimolecular T cell receptor complex, and it is a complex of 5 types of polypeptide chains γ, δ, ε, ζ, and η (the molecular weights thereof are 25000-28000, 21000, 20000, 16000, and 22000, respectively).

Examples of CD3 complexes include γ, δ, ε, ζ, and η chains, which are also referred to as subunits. When the anti-CD3 antibody binds to a T cell, cell damage is induced by T cell activation. Many anti-CD3 antibodies bind to CD3 ε.

The nucleotide sequence of cDNA encoding human CD3 ε is registered under Accession Number: NM_000733 (NM 000733.3) at NCBI/GenBank, and the amino acid sequence of human CD3 ε is registered under Accession Number: NP_000724 (NM_000724.1) at NCBI/GenPept. The nucleotide sequence of cDNA encoding cynomolgus monkey CD3 is registered under Accession Number: NM_001283615.1 at GenBank. The amino acid sequence of human CD3 ε is shown in SEQ ID NO: 151 in the Sequence Listing (FIG. 147).

2-3. Preparation of Antigen

The antigen proteins used in the present invention described above; i.e., HLA/NY-ESO and CD3 (hereafter, HLA/NY-ESO and CD3 are collectively referred to as the antigen proteins) can be prepared from animal tissue (including body fluid), cells derived from the animal tissue, or a culture product of the cells via, for example, purification, isolation, gene recombination, in vitro translation, or chemical synthesis.

cDNA of the antigen protein can be obtained by a so-called PCR method in which a polymerase chain reaction (hereafter referred to as "PCR") using, as a template, the cDNA library of organs expressing mRNA of the antigen protein and primers specifically amplifying cDNA of the antigen protein (Saiki, R. K., et al., Science, 1988, 239, 487-49).

The cDNA of the antigen protein encompasses a polynucleotide hybridizing, under stringent conditions, to a polynucleotide consisting of a nucleotide sequence complementary to the nucleotide sequence encoding the antigen protein expressed in a human or rat and encoding a protein having biological activity equivalent to that of the antigen protein.

In addition, the cDNA of the antigen protein encompasses a splicing variant transcribed from the antigen protein locus expressed in a human or rat and a polynucleotide hybridizing, under stringent conditions, thereto, and encoding a protein having biological activity equivalent to that of the antigen protein.

A nucleotide sequence encoding a protein comprising the amino acid sequence of the human or rat antigen protein or an amino acid sequence derived from such amino acid sequence by substitution, deletion, or addition of one to several amino acids from which the signal sequence has been deleted and having biological activity equivalent to that of the antigen protein is included in the nucleotide sequence of the antigen protein gene.

A protein comprising an amino acid sequence encoded by the splicing variant transcribed from the human or rat antigen protein gene locus or an amino acid sequence derived from such an amino acid sequence by substitution, deletion, or addition of one or several amino acids and having biological activity equivalent to that of the antigen protein is included in the antigen protein.

2-4. Binding Specificity to Antigen Protein

The anti-HLA/NY-ESO antibody according to the present invention, an antigen-binding fragment thereof, and the like recognize HLA/NY-ESO. Specifically, they bind to the HLA/NY-ESO antigen. The presence of HLA/NY-ESO is not known in non-human animals, such as mice, rats, and cynomolgus monkeys.

The anti-CD3 antibody included in the multispecific molecule of the present invention, the binding fragments thereof, and the like recognize; i.e., bind to the CD3 antigen. Such anti-CD3 antibody and the like preferably bind to, for example, human CD3 and monkey CD3 and more preferably to human CD3 and cynomolgus monkey CD3. In contrast, such a preferable anti-CD3 antibody does not bind to rat and/or mouse CD3.

The anti-tumor activity of the multispecific molecule of the present invention can be evaluated by, for example, (i) transplanting human cancer cells or human cancer tissue into nonhuman animals into which human peripheral blood lymphocytes have been transplanted, preferably into rats or mice, and more preferably to rats or mice with deficient endogenous effector functions (e.g., immunodeficient rats or mice) or (ii) transplanting mouse cancer cells into which HLA and NY-ESO genes have been transduced into human CD3 gene knock-in nonhuman animals and preferably into rats or mice. By performing evaluation with the use of such immunodeficient animals or knock-in animals, various assays, immunohistochemical assays, and the like can be performed using mouse and/or rat bodies. This is preferable for medicines containing the multispecific molecule of the present invention, nonclinical development, and other purposes.

In the present invention, "recognition;" i.e., "binding" is binding that is not non-specific adsorption. Whether or not the antibody recognizes; i.e., binds, can be evaluated on the basis of, for example, the dissociation constant (KD). A preferable KD value of the antibody and the like according to the present invention to HLA/NY-ESO or CD3 is $1\times10^{-5}$ M or lower, $5\times10^{-6}$ M or lower, $2\times10^{-6}$ M or lower, or $1\times10^{-6}$ M or lower, a KD value thereof to HLA/NY-ESO is preferably $5\times10^{-7}$ M or lower, $2\times10^{-7}$ M or lower, $1\times10^{-7}$ M or lower, $5\times10^{-1}$ M or lower, $2\times10^{-1}$ M or lower, $1\times10^{-1}$ M or lower, $5\times10^{-9}$ M or lower, or $2\times10^{-9}$ M or lower and more preferably $1\times10^{-9}$ M or lower. Examples of the anti-HLA/NY-ESO scFv of the present invention having excellent antigen-binding activity include NYA-1143, NYA-2023, NYA-2143, NYA-2044, NYA-2045, NYA-2060, NYA-2061, and NYA-3061, and the KD value thereof to HLA/NY-ESO, such as NYA-1143, NYA-2044, NYA-2045, and NYA-2143, is $1\times10^{-9}$ M or lower (e.g., Example 4).

In the present invention, antigen-antibody binding can be assayed or evaluated by, for example, the system of biomolecular interaction analysis, such as SPR or BLI, ELISA, or RIA. Binding between an antigen and an antibody expressed on a cell surface can be assayed by, for example, flow cytometry.

The method of surface plasmon resonance (SPR) analysis performs reaction kinetic analysis to determine the association rate constant (Ka value) and the dissociation rate constant (Kd value) and determine the dissociation constant (KD value) serving as an affinity index. Examples of apparatuses used for SPR analysis include Biacore™ (GE Healthcare), ProteOn™ (BioRad), SPR-Navi™ (BioNavis), Spreeta™ (Texas Instruments), SPRi-PlexII™ (Horiba Ltd.), and Autolab SPR™ (Metrohm).

The method of BioLayer Interferometry (BLI) performs assaying the interaction between biomolecules using biolayer interference. An example of an apparatus used for interaction analysis by the BLI method is the Octet system (Pall ForteBio).

The method of enzyme-linked immunosorbent assay (ELISA) performs detection and quantification of the target antigen or antibody contained in a sample solution by capturing the target antigen or antibody using a specific antibody or antigen, respectively, with the utilization of an enzyme reaction. The enzyme-labeled antigen or antibody is integrated into the reaction system to detect enzymatic activity. Enzymatic activity is detected using a substrate exhibiting the absorption spectra varying depending on reactions and the enzymatic activity is quantified based on absorption assay.

Cell-ELISA performs detection and quantification of the target analyte on a cell surface by capturing the target analyte together with the cell with the utilization of an enzyme reaction.

The method of radio immunoassay (RIA) performs labeling an antibody with a radioactive substance and assaying the radioactivity of the antibody. Thus, the antibody can be quantified.

In the method of flow cytometry, cells are dispersed in fluid, the fluid is allowed to flow narrowly, and each cell is optically analyzed. The antibody labeled with a fluorescent dye is allowed to bind to a cell surface antigen by the antigen-antibody reaction, and the intensity of fluorescence emitted by the labeled antibody bound to the cell is assayed to quantify antigen-binding capability of the antibody.

Examples of the anti-HLA/NY-ESO antibodies according to the present invention exhibiting excellent antigen-binding specificity include anti-HLA/NY-ESO scFv, such as NYA-0001, NYA-1143, NYA-1163, NYA-2023, NYA-2027, NYA-2035, NYA-2044, NYA-2045, NYA-2047, NYA-2048, NYA-2060, NYA-2061, NYA-2143, and NYA-3061 (e.g., Example 6).

3. Antibody Binding Specifically to HLA/NY-ESO or the Binding Fragment Thereof 3-1. Anti-HLA/NY-ESO or the Binding Fragment Thereof The present invention provides an antibody that recognizes and binds to HLA/NY-ESO or a binding fragment thereof.

As described above, HLA/NY-ESO is a complex comprising HLA-A2 and a 9-mer NY-ESO peptide (SLL-MWITQC: SEQ ID NO: 1). The NY-ESO peptide is a peptide derived from NY-ESO-1 or LAGE-1, which is an intracellular protein and a cancer testis antigen. HLA/NY-ESO is expressed on a cancer cell surface.

The anti-HLA/NY-ESO antibody according to the present invention and an antigen-binding fragment of the antibody (which hereafter, may be referred to as "the antibody and the like of the present invention") may be monoclonal or polyclonal antibodies. In the present invention, an isotype of a monoclonal antibody isotype is not particularly limited, and examples include IgG such as IgG1, IgG2, IgG3 and IgG4, IgM, IgA such as IgA1 and IgA2, IgD, and Ig. An isotype and a subclass of a monoclonal antibody can be determined by, for example, the Ouchterlony method, ELISA, or RIA. Examples of the monoclonal antibodies of the present invention include an antibody derived from a non-human animal (a non-human animal antibody), a human antibody, a chimerized antibody (also referred to as a "chimeric antibody"), and a humanized antibody, with the human antibody being preferable. The antibody of the present invention encompasses a mutant of an antibody (the "mutant antibody" described below), and, for example, the human antibody encompasses a human mutant antibody.

Examples of non-human animal antibodies include antibodies derived from vertebrates, such as mammals and birds. Examples of mammalian-derived antibodies include antibodies derived from rodents, such as mouse antibody and rat antibody. An example of a bird-derived antibody is a chicken antibody.

Examples of chimerized antibodies include, but are not limited to, antibodies comprising a variable region derived from a non-human animal antibody bound to a constant region derived from a human antibody (human immunoglobulin).

Examples of humanized antibodies include, but are not limited to, a humanized antibody prepared by transplanting CDR in a variable region of a non-human animal antibody into a human antibody (a variable region of human immunoglobulin), a humanized antibody prepared by transplanting, in addition to CDR, a part of a sequence of a framework region of a non-human animal antibody into a human antibody, and a humanized antibody prepared by substitution of 1 or more amino acids derived from a non-human animal antibody with amino acids derived from a human antibody.

An antibody can be prepared by a variety of known techniques. For example, an antibody can be prepared by a method involving the use of a hybridoma, cell-mediated immunity, or genetic recombination. Also, a phage-display-derived human antibody selected from a human antibody library can be obtained. In a phage display method, for example, a human antibody variable region may be expressed as scFv on a phage surface, and an antigen-binding phage may then be selected. The gene of the phage selected upon its binding to the antigen may be analyzed, so that a DNA sequence encoding a human antigen variable region binding to the antigen can be determined. If a DNA sequence of the antigen-binding scFv is elucidated, an expression vector comprising such sequence may be prepared, introduced into an adequate host cell, and expressed therein. Thus, a human antibody can be obtained (WO 92/01047, WO 92/20791, WO 93/06213, WO 93/11236, WO 93/19172, WO 95/01438, WO 95/15388, Annu. Rev. Immunol., 1994, 12, 433-455).

The thus-obtained antibody with high activity may be used as a lead antibody, and a gene encoding such a lead antibody may be mutated, so that a mutant with higher activity can be prepared ("the mutant antibody" described below).

A preferable combination of CDRH1 to CDRH3 included in the heavy chain of the anti-HLA/NY-ESO antibody according to the present invention or an antigen-binding fragment thereof is CDRH1 consisting of the amino acid sequence as shown in SEQ ID NO: 54 (FIG. 61), CDRH2 consisting of the amino acid sequence as shown in SEQ ID NO: 55 (FIG. 61), and CDRH3 consisting of the amino acid sequence as shown in SEQ ID NO: 56 (FIG. 61) or an amino acid sequence derived from the amino acid sequence as shown in SEQ ID NO: 56 (FIG. 61) in which amino acid 6 is N (Asn). A more preferable combination of CDRH1 to CDRH3 is included in the NYA-0001 heavy chain variable region consisting of the amino acid sequence as shown in SEQ ID NO: 6 (FIG. 13), the NYA-0082 heavy chain variable region consisting of the amino acid sequence as shown in SEQ ID NO: 18 (FIG. 25), the NYA-2023 heavy chain variable region consisting of an amino acid sequence of amino acids 21 to 140 of the amino acid sequence as shown in SEQ ID NO: 27 (FIG. 34), the NYA-2027 heavy chain variable region consisting of an amino acid sequence of amino acids 21 to 140 of the amino acid sequence as shown in SEQ ID NO: 28 (FIG. 35), the NYA-1143 heavy chain variable region consisting of an amino acid sequence of amino acids 21 to 140 of the amino acid sequence as shown in SEQ ID NO: 29 (FIG. 36), the NYA-1163 heavy chain variable region consisting of an amino acid sequence of amino acids 21 to 140 of the amino acid sequence as shown in SEQ ID NO: 26 (FIG. 33), the NYA-2023 heavy chain variable region consisting of an amino acid sequence of amino acids 21 to 140 of the amino acid sequence as shown in SEQ ID NO: 27 (FIG. 34), the NYA-2027 heavy chain variable region consisting of an amino acid sequence of amino acids 21 to 140 of the amino acid sequence as shown in SEQ ID NO: 28 (FIG. 35), the NYA-2035 heavy chain variable region consisting of an amino acid sequence of amino acids 21 to 140 of the amino acid sequence as shown in SEQ ID NO: 36 (FIG. 43), the NYA-2044 heavy chain variable region consisting of an amino acid sequence of amino acids 21 to 140 of the amino acid sequence as shown in SEQ ID NO: 47 (FIG. 54), the NYA-2045 heavy chain variable region consisting of an amino acid sequence of amino acids 21 to 140 of the amino acid sequence as shown in SEQ ID NO: 48 (FIG. 55), the NYA-2047 heavy chain variable region consisting of an amino acid sequence of amino acids 21 to 140 of the amino acid sequence as shown in SEQ ID NO: 50 (FIG. 57), the NYA-2048 heavy chain variable region consisting of an amino acid sequence of amino acids 21 to 140 of the amino acid sequence as shown in SEQ ID NO: 51 (FIG. 58), the NYA-2060 heavy chain variable region consisting of an amino acid sequence of amino acids 21 to 140 of the amino acid sequence as shown in SEQ ID NO: 52 (FIG. 59), the NYA-2061 heavy chain variable region consisting of an amino acid sequence of amino acids 21 to 140 of the amino acid sequence as shown in SEQ ID NO: 53 (FIG. 60), or the NYA-2143 heavy chain variable region consisting of an amino acid sequence of amino acids 21 to 140 of the amino acid sequence as shown in SEQ ID NO: 30 (FIG. 37).

A further example of a combination of CDRH1 to CDRH3 is included in the NYA-3061 heavy chain variable region consisting of an amino acid sequence of amino acids 21 to 140 of the amino acid sequence as shown in SEQ ID NO: 156 (FIG. 152).

A preferable combination of CDRL1 to CDRL3 included in the light chain of the anti-HLA/NY-ESO antibody according to the present invention or an antigen-binding fragment thereof is CDRL1 consisting of the amino acid sequence as shown in SEQ ID NO: 57 (FIG. 61) or an amino acid sequence derived from the amino acid sequence as shown in SEQ ID NO: 57 (FIG. 61) in which amino acid 7 is W (Trp) or amino acid 8 is K (Lys), CDRL2 consisting of the amino acid sequence as shown in SEQ ID NO: 58 (FIG. 61), and CDRL3 consisting of the amino acid sequence as shown in SEQ ID NO: 59 (FIG. 61) or an amino acid sequence derived from the amino acid sequence as shown in SEQ ID NO: 59 (FIG. 61) in which amino acid 2 is A (Ala) or S (Ser).

A more preferable combination of CDRL1 to CDRL3 is included in the NYA-0001 light chain variable region consisting of the amino acid sequence as shown in SEQ ID NO: 8 (FIG. 15), the NYA-0082 light chain variable region consisting of the amino acid sequence as shown in SEQ ID NO: 20 (FIG. 27), the NYA-1143 light chain variable region consisting of amino acids 156 to 266 of the amino acid sequence as shown in SEQ ID NO: 29 (FIG. 36), the NYA-1163 light chain variable region consisting of amino acids 156 to 266 of the amino acid sequence as shown in SEQ ID NO: 26 (FIG. 33), the NYA-2023 light chain variable region consisting of amino acids 156 to 266 of the amino acid sequence as shown in SEQ ID NO: 27 (FIG. 34), the NYA-2027 light chain variable region consisting of amino acids 156 to 266 of the amino acid sequence as shown in SEQ ID NO: 28 (FIG. 35), the NYA-2035 light chain variable region consisting of amino acids 156 to 266 of the amino acid sequence as shown in SEQ ID NO: 36 (FIG. 43), the NYA-2044 light chain variable region consisting of amino acids 156 to 266 of the amino acid sequence as shown in SEQ ID NO: 47 (FIG. 54), the NYA-2045 light chain variable region consisting of amino acids 156 to 266 of the amino acid sequence as shown in SEQ ID NO: 48 (FIG. 55), the NYA-2047 light chain variable region consisting of amino acids 156 to 266 of the amino acid sequence as shown in SEQ ID NO: 50 (FIG. 57), the NYA-2048 light chain variable region consisting of amino acids 156 to 266 of the amino acid sequence as shown in SEQ ID NO: 51 (FIG. 58), the NYA-2060 light chain variable region consisting of amino acids 156 to 266 of the amino acid sequence as shown in SEQ ID NO: 52 (FIG. 59), the NYA-2061 light chain variable region consisting of amino acids 156 to 266 of the amino acid sequence as shown in SEQ ID NO: 53 (FIG. 60), or the NYA-2143 light chain variable region consisting of amino acids 156 to 266 of the amino acid sequence as shown in SEQ ID NO: 30 (FIG. 37).

A further example of a combination of CDRL1 to CDRL3 is included in the NYA-3061 light chain variable region consisting of amino acids 161 to 271 of the amino acid sequence as shown in SEQ ID NO: 156 (FIG. 152).

A preferable combination of CDRH1 to CDRH3 in the heavy chain and CDRL1 to CDRL3 in the light chain of the anti-HLA/NY-ESO antibody according to the present invention or an antigen-binding fragment thereof is a combination of CDRH1 consisting of the amino acid sequence as shown in SEQ ID NO: 54 (FIG. 61), CDRH2 consisting of the amino acid sequence as shown in SEQ ID NO: 55 (FIG. 61), and CDRH3 consisting of the amino acid sequence as shown in SEQ ID NO: 56 (FIG. 61) or an amino acid sequence derived from the amino acid sequence as shown in SEQ ID NO: 56 (FIG. 61) in which amino acid 6 is N (Asn) and a combination of CDRL1 consisting of the amino acid sequence as shown in SEQ ID NO: 57 (FIG. 61) or an amino acid sequence derived from the amino acid sequence as shown in SEQ ID NO: 57 (FIG. 61) in which amino acid 7 is N (Asn) and/or amino acid 8 is K (Lys), CDRL2 consisting of the amino acid sequence as shown in SEQ ID NO: 58 (FIG. 61), and CDRL3 consisting of the amino acid sequence as shown in SEQ ID NO: 59 (FIG. 61) or an amino acid sequence derived from the amino acid sequence as shown in SEQ ID NO: 59 in which amino acid 2 is A (Ala) or S (Ser). A more preferable combination of CDRH1 to CDRH3 and CDRL1 to CDRL3 is included in the NYA-0001 heavy chain variable region and light chain variable region consisting of the amino acid sequences as shown in SEQ ID NO: 6 and SEQ ID NO: 8, the NYA-1143 heavy chain variable region and light chain variable region consisting of amino acids 21 to 140 and amino acids 156 to 266 of the amino acid sequence as shown in SEQ ID NO: 29 (FIG. 36), the NYA-1163 heavy chain variable region and light chain variable region consisting of amino acids 21 to 140 and amino acids 156 to 266 of the amino acid sequence as shown in SEQ ID NO: 26 (FIG. 33), the NYA-2023 heavy chain variable region and light chain variable region consisting of amino acids 21 to 140 and amino acids 156 to 266 of the amino acid sequence as shown in SEQ ID NO: 27 (FIG. 34), the NYA-2027 heavy chain variable region and light chain variable region consisting of amino acids 21 to 140 and amino acids 156 to 266 of the amino acid sequence as shown in SEQ ID NO: 28 (FIG. 35), the NYA-2035 heavy chain variable region and light chain variable region consisting of amino acids 21 to 140 and amino acids 156 to 266 of the amino acid sequence as shown in SEQ ID NO: 36 (FIG. 43), the NYA-2044 heavy chain variable region and light chain variable region consisting of amino acids 21 to 140 and amino acids 156 to 266 of the amino acid sequence as shown in SEQ ID NO: 47 (FIG. 54), the NYA-2045 heavy chain variable region and light chain variable region consisting of amino acids 21 to 140 and amino acids 156 to 266 of the amino acid sequence as shown in SEQ ID NO: 48 (FIG. 55), the NYA-2047 heavy chain variable region and light chain variable region consisting of amino acids 21 to 140 and amino acids 156 to 266 of the amino acid sequence as shown in SEQ ID NO: 50 (FIG. 57), the NYA-2048 heavy chain variable region and light chain variable region consisting of amino acids 21 to 140 and amino acids 156 to 266 of the amino acid sequence as shown in SEQ ID NO: 51 (FIG. 58), the NYA-2060 heavy chain variable region and light chain variable region consisting of amino acids 21 to 140 and amino acids 156 to 266 of the amino acid sequence as shown in SEQ ID NO: 52 (FIG. 59), the NYA-2061 heavy chain variable region and light chain variable region consisting of amino acids 21 to 140 and amino acids 156 to 266 of the amino acid sequence as shown in SEQ ID NO: 53 (FIG. 60), or the NYA-2143 heavy chain variable region and light chain variable region consisting of amino acids 21 to 140 and amino acids 156 to 266 of the amino acid sequence as shown in SEQ ID NO: 30 (FIG. 37).

A further example of a combination of CDRH1 to CDRH3 and CDRL1 to CDRL3 is included in the NYA-3061 heavy chain variable region and light chain variable region consisting of amino acids 21 to 140 and amino acids 161 to 271 of the amino acid sequence as shown in SEQ ID NO: 156 (FIG. 152).

Preferable examples of a heavy chain variable region of the anti-HLA/NY-ESO antibody according to the present invention or an antigen-binding fragment thereof include the heavy chain CDRs described above and variable regions including such heavy chain CDRs in adequate combination. More preferable examples include the NYA-0001 heavy chain variable region, the NYA-0082 heavy chain variable region, the NYA-1143 heavy chain variable region, the NYA-1163 heavy chain variable region, the NYA-2023 heavy chain variable region, the NYA-2027 heavy chain variable region, the NYA-2035 heavy chain variable region, the NYA-2044 heavy chain variable region, the NYA-2045 heavy chain variable region, the NYA-2047 heavy chain variable region, the NYA-2048 heavy chain variable region, the NYA-2060 heavy chain variable region, the NYA-2061 heavy chain variable region, the NYA-2143 heavy chain variable region, and the NYA-3061 heavy chain variable region. The amino acid sequence of each heavy chain variable region is as described above.

Preferable examples of a light chain variable region of the anti-HLA/NY-ESO antibody according to the present invention or an antigen-binding fragment thereof include the light chain CDRs described above and variable regions including such light chain CDRs in adequate combination. More preferable examples include the NYA-0001 light chain variable region, the NYA-0082 light chain variable region, the NYA-1143 light chain variable region, the NYA-1163 light chain variable region, the NYA-2023 light chain variable region, the NYA-2027 light chain variable region, the NYA-2035 light chain variable region, the NYA-2044 light chain variable region, the NYA-2045 light chain variable region, the NYA-2047 light chain variable region, the NYA-2048 light chain variable region, the NYA-2060 light chain variable region, the NYA-2061 light chain variable region, the NYA-2143 light chain variable region, and the NYA-3061 light chain variable region. The amino acid sequence of each light chain variable region is as described above.

Preferable examples of a heavy chain variable region and a light chain variable region of the anti-HLA/NY-ESO antibody according to the present invention or an antigen-binding fragment thereof include the heavy chain and light chain CDRs described above or those including such CDRs in adequate combination. More preferable examples include the NYA-0001 heavy chain variable region and light chain variable region, the NYA-0082 heavy chain variable region and light chain variable region, the NYA-1143 heavy chain variable region and light chain variable region, the NYA-1163 heavy chain variable region and light chain variable region, the NYA-2023 heavy chain variable region and light chain variable region, the NYA-2027 heavy chain variable region and light chain variable region, the NYA-2035 heavy chain variable region and light chain variable region, the NYA-2044 heavy chain variable region and light chain variable region, the NYA-2045 heavy chain variable region and light chain variable region, the NYA-2047 heavy chain variable region and light chain variable region, the NYA-2048 heavy chain variable region and light chain variable region, the NYA-2060 heavy chain variable region and light chain variable region, the NYA-2061 heavy chain variable region and light chain variable region, the NYA-2143 heavy chain variable region and light chain variable region, and the NYA-3061 heavy chain variable region and light chain variable region.

Preferable examples of a heavy chain of the anti-HLA/NY-ESO antibody according to the present invention or an antigen-binding fragment thereof include heavy chains including the preferable or more preferable heavy chain variable regions described above. More preferable examples include the NYA-0001 heavy chain, the NYA-0082 heavy chain, the NYA-1143 heavy chain, the NYA-1163 heavy chain, the NYA-2023 heavy chain, the NYA-2027 heavy chain, the NYA-2035 heavy chain, the NYA-2044 heavy chain, the NYA-2045 heavy chain, the NYA-2047 heavy chain, the NYA-2048 heavy chain, the NYA-2060 heavy chain, the NYA-2061 heavy chain, the NYA-2143 heavy chain, and the NYA-3061 heavy chain.

Preferable examples of a light chain of the anti-HLA/NY-ESO antibody according to the present invention or an antigen-binding fragment thereof include light chains including the preferable or more preferable light chain variable regions described above. More preferable examples include the NYA-0001 light chain, the NYA-0082 light chain, the NYA-1143 light chain, the NYA-1163 light chain, the NYA-2023 light chain, the NYA-2027 light chain, the NYA-2035 light chain, the NYA-2044 light chain, the NYA-2045 light chain, the NYA-2047 light chain, the NYA-2048 light chain, the NYA-2060 light chain, the NYA-2061 light chain, the NYA-2143 light chain, and the NYA-3061 light chain.

Preferable examples of a heavy chain and a light chain of the anti-HLA/NY-ESO antibody according to the present invention or an antigen-binding fragment thereof include heavy chains and light chains including the preferable or more preferable heavy chain variable regions and light chain variable regions described above. More preferable examples include the NYA-0001 heavy chain and light chain, the NYA-1143 heavy chain and light chain, the NYA-1163 heavy chain and light chain, the NYA-2023 heavy chain and light chain, the NYA-2027 heavy chain and light chain, the NYA-2035 heavy chain and light chain, the NYA-2044 heavy chain and light chain, the NYA-2045 heavy chain and light chain, the NYA-2047 heavy chain and light chain, the NYA-2048 heavy chain and light chain, the NYA-2060 heavy chain and light chain, the NYA-2061 heavy chain and light chain, the NYA-2143 heavy chain and light chain, and the NYA-3061 heavy chain and light chain.

An antigen-binding fragment of the antibody is a fragment that retains at least the antigen-binding ability out of the functions of the original antibody or a modified product thereof. Examples of the functions of the antibody include, in general, antigen-binding activity, the activity of regulating antigen activity, antibody-dependent cellular cytotoxicity, and complement-dependent cytotoxicity. Examples of functions of the antibody and the like of the present invention and multispecific molecules comprising the antibody and the like of the present invention include T cell redirection, T cell activation, and cancer cytotoxicity caused by T cell activation.

An antigen-binding fragment of the antibody is not particularly limited, provided that such a fragment is derived from the antibody that retains at least antigen-binding ability out of the functions of the original antibody. Examples thereof include, but are not limited to, Fab, Fab', F(ab')$_2$, Fv, single chain Fv (scFv) comprising heavy chain Fv ligated to light chain Fv via an adequate linker, and the single domain antibody (sdAb). A molecule comprising a region other than the antigen-binding fragment of the antibody according to the present invention as in the case of scFv comprising a linker portion is within the scope of the antigen-binding fragment of the antibody of the present invention.

A molecule of the antibody protein lacking at least one or several amino acids from the amino terminus and/or carboxyl terminus and retaining some functions of the antibody is within the scope of the antigen-binding fragment of the antibody. A modified antigen-binding fragment of the antibody is within the scope of the antibody according to the present invention, an antigen-binding fragment thereof, or a modified antibody or fragment (described below).

An embodiment of the antibody of the present invention or an antigen-binding fragment thereof is scFv. scFv is obtained by ligating the heavy chain variable region of the antibody to the light chain variable region thereof with a polypeptide linker (Pluckthun A., The Pharmacology of Monoclonal Antibodies 113, Rosenburg and Moore (ed.), Springer Verlag, New York, 269-315, 1994, Nature Biotechnology, 2005, 23, 1126-1136). Also, tandem scFv prepared by connecting two scFv constructs with a polypeptide linker can be used as a bispecific molecule. In addition, a triabody or the like comprising 3 or more scFv constructs can be used as a multispecific molecule.

Preferable examples of HLA/NY-ESO-specific scFv (also referred to as "anti-HLA/NY-ESO scFv") include scFv comprising CDRH1 to CDRH3 and CDRL1 to CDRL3 described above, more preferable examples thereof include scFv comprising the heavy chain variable region and the light chain variable region, and further preferable examples thereof include NYA-0001 (amino acids 21 to 266 of the amino acid sequence as shown in SEQ ID NO: 70 (FIG. 71)), NYA-0082 (comprising the amino acid sequence as shown in SEQ ID NO: 18 (FIG. 25) and the amino acid sequence as shown in SEQ ID NO: 20 (FIG. 27)), NYA-1143 (amino acids 21 to 266 of the amino acid sequence as shown in SEQ ID NO: 29 (FIG. 36)), NYA-1163 (amino acids 21 to 266 of the amino acid sequence as shown in SEQ ID NO: 26 (FIG. 33)), NYA-2023 (amino acids 21 to 266 of the amino acid sequence as shown in SEQ ID NO: 27 (FIG. 34)), NYA-2027 (amino acids 21 to 266 of the amino acid sequence as shown in SEQ ID NO: 28 (FIG. 35)), NYA-2035 (amino acids 21 to 266 of the amino acid sequence as shown in SEQ ID NO: 36 (FIG. 43)), NYA-2044 (amino acids 21 to 266 of the amino acid sequence as shown in SEQ ID NO: 47 (FIG. 54)), NYA-2045 (amino acids 21 to 266 of the amino acid sequence as shown in SEQ ID NO: 48 (FIG. 55)), NYA-2047 (amino acids 21 to 266 of the amino acid sequence as shown in SEQ ID NO: 50 (FIG. 57)), NYA-2048 (amino acids 21 to 266 of the amino acid sequence as shown in SEQ ID NO: 51 (FIG. 58)), NYA-2060 (amino acids 21 to 266 of the amino acid sequence as shown in SEQ ID NO: 52 (FIG. 59)), NYA-2061 (amino acids 21 to 266 of the amino acid sequence as shown in SEQ ID NO: 53 (FIG. 60)), and NYA-2143 (amino acids 21 to 266 of the amino acid sequence as shown in SEQ ID NO: 30 (FIG. 37)). Another example is NYA-3061 (amino acids 21 to 271 of the amino acid sequence as shown in SEQ ID NO: 156 (FIG. 152)).

A preferable embodiment of anti-HLA/NY-ESO scFv is scFv comprising a FLAG-His tag fused to its carboxyl terminus (may be simply referred to as "tag adduct"). Examples of preferable tag adducts include NYA-0001 tag adduct (amino acids 20 to 292 of SEQ ID NO: 70 (FIG. 71)), NYA-1143 tag adduct (amino acids 20 to 292 of SEQ ID NO: 29 (FIG. 36)), NYA-1163 tag adduct (amino acids 20 to 292 of SEQ ID NO: 26 (FIG. 33)), NYA-2023 tag adduct (amino acids 20 to 292 of SEQ ID NO: 27 (FIG. 34)), NYA-2027 tag adduct (amino acids 20 to 292 of SEQ ID NO: 28 (FIG. 35)), NYA-2035 tag adduct (amino acids 20 to 292 of SEQ ID NO: 36 (FIG. 43)), NYA-2044 tag adduct (amino acids 20 to 292 of SEQ ID NO: 47 (FIG. 54)), NYA-2045 tag adduct (amino acids 20 to 292 of SEQ ID NO: 48 (FIG. 55)), NYA-2047 tag adduct (amino acids 20 to 292 of SEQ ID NO: 50 (FIG. 57)), NYA-2048 tag adduct (amino acids 20 to 292 of SEQ ID NO: 51 (FIG. 58)), NYA-2060 tag adduct (amino acids 20 to 292 of SEQ ID NO: 52 (FIG. 59)), NYA-2061 tag adduct (amino acids 20 to 292 of SEQ ID NO: 53 (FIG. 60)), and NYA-2143 tag adduct (amino acids 20 to 292 of SEQ ID NO: 30 (FIG. 37)).

Of these, NYA-2023 and its tag adduct, NYA-2047 and its tag adduct, NYA-2048 and its tag adduct, NYA-2060 and its tag adduct, and NYA-2061 and its tag adduct exert excellent biological activity, physical properties, and the like in Fc-added bispecific molecules and thus are more preferable.

When anti-HLA/NY-ESO scFv and its tag adduct are to be expressed in a host cell, a signal peptide can be added to its amino terminus. Examples of amino acid sequences of signal-peptide-added anti-HLA/NY-ESO scFv tag adducts include amino acid sequences as shown in SEQ ID NOs: 70, 29, 26 to 28, 36, 47, 48, 50 to 53, and 30 (FIGS. 71, 36, 33 to 35, 43, 54, 55, 57 to 60, and 37).

scFv can be obtained by the phage display method in which an antibody variable region is expressed as a single chain antibody (scFv) on a phage surface and an antigen-binding phage is then selected (Nature Biotechnology, 2005, 23, (9), pp. 1105-1116). The gene of the phage selected upon its binding to the antigen may be analyzed, so that a DNA sequence encoding a human antigen variable region binding to the antigen can be determined. If a DNA sequence of the antigen-binding scFv is elucidated, an expression vector comprising such sequence may be prepared, introduced into an adequate host cell, and expressed therein. Thus, a human antibody can be obtained (WO 92/01047, WO 92/20791, WO 93/06213, WO 93/11236, WO 93/19172, WO 95/01438, WO 95/15388, Annu. Rev. Immunol., 1994, 12, pp. 433-455, Nature Biotechnology, 2005, 23 (9), pp. 1105-1116).

The antibody of the present invention may comprise a single heavy chain variable region and may not comprise a light chain sequence. Such an antibody is referred to as a single domain antibody (sdAb) or nanobody and retains antigen-binding ability (Muyldemans S. et al., Protein Eng., 1994, 7 (9), 1129-35, Hamers-Casterman C. et al., Nature, 1993, 363 (6428), 446-448). Such antibodies are within the scope of the antigen-binding fragment of the antibody according to the present invention.

The present invention also includes a single chain immunoglobulin comprising the full-length sequence of the heavy chain ligated to that of the light chain of the antibody with an adequate linker (Lee, H-S, et al., Molecular Immunology, 1999, 36, 61-71; Shirrmann, T. et al., mAbs, 2010, 2 (1), 1-4). Such single chain immunoglobulin may be dimerized, so that it can retain the structure and activity similar to those of an antibody that is inherently a tetramer. The anti-HLA/NY-ESO antibody according to the present invention may be single chain immunoglobulin.

In scFv of the present invention, a heavy chain variable region may form a disulfide bond with a light chain variable region.

The anti-HLA/NY-ESO antibody according to the present invention may be composed of components derived from a plurality of different antibodies, provided that it binds to HLA/NY-ESO. Examples thereof include those resulting from replacement of heavy chains and/or light chains among a plurality of different antibodies, those resulting from replacement of full-length sequences of heavy chains and/or light chains, those resulting from selective replacement of either a variable region or a constant region, and those resulting from selective replacement of a part of or the entire CDR. In a chimerized antibody, a heavy chain variable region and a light chain variable region may be derived from a different anti-HLA/NY-ESO antibody according to the present invention. In the heavy chain and light chain variable regions of a humanized antibody, heavy chain CDR1 to heavy chain CDR3 and light chain CDR1 to light chain CDR3 may be derived from two or more types of the anti-HLA/NY-ESO antibodies according to the present invention. In the heavy chain and light chain variable regions of a human antibody, a combination of heavy chain CDR1 to heavy chain CDR3 and light chain CDR1 to light chain CDR3 may be derived from two or more types of the anti-HLA/NY-ESO antibodies according to the present invention.

The anti-HLA/NY-ESO antibody according to the present invention encompasses an antibody that comprises an amino acid sequence encoded by a nucleotide sequence included in a polynucleotide hybridizing, under stringent conditions, to a complementary strand of a polynucleotide comprising a nucleotide sequence encoding the amino acid sequence included in the anti-HLA/NY-ESO antibody according to the present invention and binding to HLA/NY-ESO.

It may be an antibody comprising an amino acid sequence exhibiting at least 90%, 91%, 92%, 93%, 94%, 95%, 96%, 97%, 98%, or 99% identity to the amino acid sequence included in the heavy chain variable region of the anti-HLA/NY-ESO antibody according to the present invention (preferably, an amino acid sequence of amino acids 21 to 140 of the amino acid sequence as shown in SEQ ID NO: 27, the amino acid sequence as shown in SEQ ID NO: 38, the amino acid sequence as shown in SEQ ID NO: 39, or an amino acid sequence of amino acids 21 to 140 of the amino acid sequence as shown in SEQ ID NO: 160, SEQ ID NO: 197, or SEQ ID NO: 198) and/or an amino acid sequence included in a light chain variable region thereof (preferably, an amino acid sequence of amino acids 156 to 266 of the amino acid sequence as shown in SEQ ID NO: 27, an amino acid sequence of amino acids 156 to 266 of the amino acid sequence as shown in SEQ ID NO: 52, the amino acid sequence as shown in SEQ ID NO: 40, an amino acid sequence of amino acids 161 to 271 of the amino acid sequence as shown in SEQ ID NO: 160, or an amino acid sequence of amino acids 156 to 266 of the amino acid sequence as shown in SEQ ID NO: 197 or SEQ ID NO: 198) or an antigen-binding fragment thereof.

When the position and the length of the light chain variable region are determined in accordance with a definition that is different from IMGT (e.g., Kabat, Chothia, AbM, contact), one or more amino acids, such as arginine or glycine, may further be included into the carboxyl terminus of the amino acid sequence of the light chain variable region defined in accordance with the definition of IMGT. Such antibody or the binding fragment thereof comprising such light chain variable region is within the scope of the antibody according to the present invention or the binding fragment thereof.

The antibody and the like of the present invention may be prepared by introducing a mutation into a binding fragment of the anti-HLA/NY-ESO antibody according to the present invention and optimizing the ability to bind to HLA/NY-ESO, and, in particular, to human and/or cynomolgus monkey HLA/NY-ESO. Specific examples of methods for introduction of a mutation include a random mutagenesis using error-prone PCR, site-directed amino acid introduction using NHK libraries, site-directed mutagenesis using structural information, and a combination of any thereof.

3-2. Mutant of the Anti-HLA/NY-ESO Antibody (Mutant Antibody)

A mutant antibody of the anti-HLA/NY-ESO antibody according to the present invention can be preferably provided with, for example, lowered susceptibility to protein degradation or oxidation, maintained or improved biological activity or functions, suppression of lowering or change in such activity or functions, improved or regulated antigen-binding ability, physicochemical properties, or functional properties. A protein is known to change its functions or activity upon alternation of a particular amino acid side chain on its surface, and examples include deamidation of an asparagine side chain and isomerization of an aspartic acid side chain. An antibody resulting from substitution of a particular amino acid with another amino acid so as to prevent the amino acid side chain from changing is within the scope of the mutant antibody of the present invention.

An example of the mutant antibody of the present invention is an antibody comprising an amino acid sequence derived from the amino acid sequence of the original antibody by conservative amino acid substitution. Conservative amino acid substitution occurs within an amino acid group associated with the amino acid side chain.

Preferable amino acid groups are as follows: the acidic group: aspartic acid and glutamic acid; the basic group: lysine, arginine, and histidine; the non-polar group: alanine, valine, leucine, isoleucine, proline, phenylalanine, methionine, and tryptophan; and the uncharged polar family: glycine, asparagine, glutamine, cysteine, serine, threonine, and tyrosine. Other preferable amino acid groups are as follows: the aliphatic hydroxy group: serine and threonine; the amide-containing group: asparagine and glutamine; the aliphatic group: alanine, valine, leucine, and isoleucine; and the aromatic group: phenylalanine, tryptophan, and tyrosine. In such mutant antibody, amino acid substitution is preferably carried out by refraining from lowering the antigen-binding activity of the original antibody.

The anti-HLA/NY-ESO antibody according to the present invention, an antigen-binding fragment thereof, a mutant thereof (a mutant antibody or an antigen-binding fragment thereof), or the molecule of the present invention encompasses: a mutant antibody comprising an amino acid sequence derived from the amino acid sequence of the antibody of the present invention, such as NYA-2023, by conservative amino acid substitution and/or other mutation and binding to HLA/NY-ESO, an antigen-binding fragment thereof, and molecules comprising the same; a chimerized antibody, a humanized antibody, or a human antibody comprising CDR of an amino acid sequence derived from the amino acid sequence of any of CDRH1 to CDRH3 and CDRL1 to CDRL3 derived from the antibody of the present invention, including NYA-2023, by conservative amino acid substitution and/or other mutation and binding to HLA/NY-ESO, an antigen-binding fragment thereof, or a molecule comprising the same.

3-3. Binding Fragment of the Anti-HLA/NY-ESO Antibody

An aspect of the present invention provides an antigen-binding fragment of the anti-HLA/NY-ESO antibody according to the present invention (hereafter, it is simply referred to as a "binding fragment"). Binding fragments of the anti-HLA/NY-ESO antibody according to the present invention include binging fragments of a chimerized antibody, a humanized antibody, and a human antibody. A binding fragment of an antibody is a fragment that retains at least antigen-binding ability of functions of the original antibody or a modified product thereof. In general, examples of such antibody functions include antigen-binding activity, the activity of regulating antigen activity (e.g., agonist activity), the activity of internalizing an antigen in a cell, and the activity of inhibiting or promoting interactions between an antigen and a substance interacting therewith.

A binding fragment of an antibody is not particularly limited, provided that it is a fragment of a fragment retaining at least antigen-binding ability of the activity of the original antibody. Examples of such binding fragment of an antibody include, but are not limited to, Fab, Fab', F(ab')$_2$, single chain Fab (scFab) in which the carboxyl terminus of the Fab light chain is ligated to the amino terminus of the Fab heavy chain via an adequate linker, Fv, single chain Fv (scFv) comprising heavy chain Fv ligated to light chain Fv via an adequate linker, and a single domain antibody (sdAb) with a single heavy chain variable region but without a light chain sequence, which is also referred to as a nanobody (Muyldemans S. et al., Protein Eng., 1994, 7 (9), 1129-35, Hamers-Casterman C. et al., Nature, 1993, 363 (6428), 446-448). A molecule comprising regions other than the binding fragment of the antibody of the present invention, such as scFab or scFv comprising a linker region, is within the scope of the binding fragment of the antibody of the present invention.

3-4. Modified Anti-HLA/NY-ESO Antibody, Modified Binding Fragment Thereof, or Complex Thereof The present invention provides a modified antibody or a modified binding fragment thereof. The modified antibody according to the present invention or the modified binding fragment thereof has been subjected to chemical or biological modification. Examples of chemical modification include a bond of a chemical portion to the amino acid skeleton and chemical modification of N-bound or O-bound carbohydrate chains. Examples of biological modification include post-translational modification (e.g., sugar chain addition to an N-bond or O-bond, processing of the amino terminal or carboxyl terminal region, deamidation, aspartic acid isomerization, and methionine oxidation), and methionine addition to the amino terminus via expression in a prokaryotic host cell. Also, labels that enable detection or isolation of the antibody or antigen according to the present invention, such as an enzyme label, a fluorescence label, and an affinity label, are within the scope of the modified antibody or antigen as described above. The modified antibody according to the present invention or the binding fragment thereof as described above is useful for improvement of stability and retentivity in blood of the original antibody according to the present invention or the binding fragment thereof, reduction of the antigenicity, detection or isolation of the antibody or antigen, and other purposes.

Examples of chemical portions included in the chemical modified antibody or fragment include water-soluble polymers, such as polyethylene glycol (PEG), ethylene glycol/propylene glycol polymer, carboxymethyl cellulose, dextran, and polyvinyl alcohol.

Examples of biological modification include enzyme treatment, cell treatment, addition of other peptides such as tags via genetic recombination, and use of host cells expressing endogenous or exogenous sugar chain modified enzymes.

Such modification may be provided at any desired position in the antibody or the binding fragment thereof, and the same or two or more different types of modification may be provided at one or more positions.

However, deletion of such a heavy chain sequence or modification of a heavy chain or light chain sequence would not significantly affect the antigen-binding ability and effector functions of the antibody (e.g., complement activation or antibody-dependent cytotoxicity).

Accordingly, the present invention encompasses the antibody subjected to such deletion or modification. Examples include a deletion mutant lacking 1 or 2 amino acids from the heavy chain carboxyl terminus (Journal of Chromatography A; 705; 129-134, 1995), a deletion mutant lacking 2 amino acids (glycine and lysine) from the heavy chain carboxyl terminus and subjected to amidation of proline at the carboxyl terminus (Analytical Biochemistry, 360: 75-83, 2007), and an antibody resulting from pyroglutamilation of an amino-terminal glutamine or glutamic acid of the heavy chain or the light chain (WO 2013/147153) (they are collectively referred to as "deletion mutants"). As long as the antigen-binding ability and effector functions are retained, the antibody of the present invention lacking the heavy chain terminus and the light chain carboxyl terminus is not limited to the deletion mutants described above. When the antibody of the present invention comprises 2 or more chains (e.g., heavy chains), either of or both of such 2 or more chains (e.g., heavy chains) may be the full-length heavy chain or a heavy chain selected from the group consisting of the deletion mutants described above. While the quantitative ratio or the number ratio of molecules of the deletion mutant would be influenced by the type and culture conditions of cultured cells of mammalian animals producing the antibody of the present invention, the main components of the antibody of the present invention can be both of the 2 heavy chains lacking an amino acid residue from the carboxyl terminus.

In addition, the antibody of the present invention or an antigen-binding fragment thereof (including those comprised in the molecule, the multispecific molecule, and the bispecific molecule of the present invention) comprising one to several amino acids derived from an expression vector and/or a signal sequence added to the amino terminus and/or carboxy terminus (and partially or entirely modified as described above) or the like are within the scope of the modified antibody of the present invention or the modified antigen-binding fragment thereof, as long as the antigen-binding activity of interest is maintained. A molecule comprising such modified antibody or modified antigen-binding fragment thereof is within the scope of the molecule of the present invention.

In the present invention, "the antibody or the binding fragment thereof" encompasses "the modified antibody or the modified antigen-binding fragment thereof." In addition, "the antibody or antigen-binding fragment thereof" included in the molecule, the multispecific molecule, and the bispecific molecule of the present invention encompasses "the modified antibody or the modified antigen-binding fragment thereof."

Antibody dependent cellular cytotoxicity can be potentiated by regulation (glycosylation, afucosylation, and the like) of sugar chain modification bound to the antibody of the present invention. Known techniques for regulation of antibody sugar chain modification are disclosed in, for example, WO 99/54342, WO 00/61739, and WO 02/31140, although the techniques are not limited thereto.

The present invention encompasses a complex of the antibody and other molecules ligated to each other with a linker (i.e., an immunoconjugate). An example of an antibody-drug complex comprising the antibody bound to a radioactive substance or a compound having pharmacological activity is an antibody-drug conjugate (ADC) (Methods Mol. Biol., 2013, 1045: 1-27; Nature Biotechnology, 2005, 23, pp. 1137-1146).

Further, the present invention encompasses a complex comprising such an antibody bound to another functional polypeptide. An example of such antibody-peptide complex is a complex of the antibody with an albumin-bound polypeptide (Protein Eng. Des. Sel., 2012, (2): 81-8).

The modified antibody, the antibody with regulated sugar chain modification, and the complex described above are within the scope of the antibody of the present invention, and the binding fragments of the modified antibody, the antibody with regulated sugar chain modification, and the complex are within the scope of the binding fragment of the antibody of the present invention.

4. Method for Producing Antibody

The antibody of the present invention can be produced in a cell as a recombinant antibody by, for example, inserting a DNA encoding a heavy chain variable region or a DNA encoding a light chain variable region into an expression vector, transforming a host cell for expression with the vector, and culturing the host cell.

Concerning DNAs encoding antibodies, a DNA encoding a heavy chain can be obtained by ligating a DNA encoding a heavy chain variable region to a DNA encoding a heavy chain constant region, and a DNA encoding a light chain can be obtained by ligating a DNA encoding a light chain variable region to a DNA encoding a light chain constant region.

The anti-HLA/NY-ESO antibody of the present invention can be produced by inserting the DNA encoding the heavy chain and the DNA encoding the light chain mentioned above into an expression vector, transforming a host cell with the vector, and culturing the host cell. In such a case, the DNA encoding the heavy chain and the DNA encoding the light chain mentioned above may be introduced into the same expression vector and the host cell may be transformed with the vector. Alternatively, the DNA encoding the heavy chain and the DNA encoding the light chain may be inserted into separate vectors and the host cell may be transformed with the two vectors. In this case, DNAs encoding the heavy chain variable region and the light chain variable region may be introduced into a vector into which the DNA encoding the heavy chain constant region and the DNA encoding a light chain constant region have been introduced in advance. Further, the vector may contain a DNA encoding a signal peptide, which promotes secretion of an antibody from a host cell. In this case, the DNA encoding the signal peptide and the DNA encoding the antibody are ligated in-frame in advance. An antibody can be obtained as a mature protein by removing the signal peptide after an antibody is produced.

In this case, the DNA encoding the heavy chain variable region, the DNA encoding the light chain variable region, the DNA comprising the DNA encoding the heavy chain variable region ligated to the DNA encoding the heavy chain constant region, or the DNA comprising the DNA encoding the light chain variable region ligated to the DNA encoding the light chain constant region may be operably ligated to an element, such as a promoter, an enhancer, or a polyadenylation signal. When DNA is "operably ligated" herein, DNA is ligated to an element, so that the element can exert their functions.

An expression vector is not particularly limited, as long as it can be replicated in an animal cell, a bacterial cell, a yeast cell, or other host, and examples thereof include known plasmids and phages. Examples of a vector used to construct an expression vector include pcDNA™ (Thermo Fisher Scientific), Flexi® vector (Promega), pUC19, pUEX2 (Amersham), pGEX-4T, pKK233-2 (Pharmacia), and pMAMneo (Clontech). As host cells, prokaryotic cells such as *Escherichia coli* and *Bacillus subtilis* and eukaryotic cells such as yeasts and animal cells can be used, with the use of eukaryotic cells being preferable. Examples of animal cells include the human embryonic kidney cell line HEK293 and the Chinese hamster ovary (CHO) cell. It is sufficient to introduce an expression vector into a host cell by a known method to transform the host cell. Examples of methods include an electroporation method, a calcium phosphate precipitation method, and a DEAE-dextran transfection method. The produced antibody can be purified by usual protein isolation or purification methods. For example, affinity chromatography or other chromatography techniques, filtration, ultrafiltration, salting out, dialysis, and the like can be suitably selected and combined.

5. Molecule that Binds to HLA/NY-ESO

The molecule of the present invention comprises the anti-HLA/NY-ESO antibody according to the present invention or an antigen-binding fragment thereof. The molecule of the present invention is preferably a multispecific molecule comprising 2 or more antigen-binding sites. Specifically, the molecule of the present invention can bind to 2 or more different epitopes on a molecule or different epitopes on 2 or more different molecules and such a molecule comprises a plurality of different antigen-binding fragments. Examples of such a multispecific molecule include, but are not limited to, an IgG-type multispecific molecule and a multispecific molecule comprising two or more types of variable regions, for example, antibody fragments, such as tandem scFv (taFv), single chain diabody, a diabody, and a triabody, and an antibody fragment resulting from covalent or noncovalent binding. A multispecific molecule may comprise Fc.

The multispecific molecule of the present invention may comprise, in addition to the anti-HLA/NY-ESO antibody according to the present invention or an antigen-binding fragment thereof, one type or two or more types of antibodies or antigen-binding fragments thereof. Examples of such antigen-binding fragments of the antibody include Fab, F(ab)', Fv, scFv, and sdAb.

A preferable multispecific molecule according to the present invention further comprises an anti-CD3 antibody or an antigen-binding fragment thereof, and it binds specifically to CD3 as well.

The anti-CD3 antibody or an antigen-binding fragment thereof included in the multispecific molecule according to the present invention is not particularly limited, provided that it is a human CD3-binding antibody or a binding fragment thereof, and it preferably binds to CD3 of a non-human primate, such as a cynomolgus monkey. A more preferable example of an anti-CD3 antibody or an antigen-binding fragment thereof is the antibody or antigen-binding fragment thereof comprising the heavy chain variable region CDRH1 consisting of the amino acid sequence as shown in SEQ ID NO: 141, the heavy chain variable region CDRH2 consisting of the amino acid sequence as shown in SEQ ID NO: 142, the heavy chain variable region CDRH3 consisting of the amino acid sequence as shown in SEQ ID NO: 143, the light chain variable region CDRL1 consisting of the amino acid sequence as shown in SEQ ID NO: 144, the light chain variable region CDRL2 consisting of the amino acid sequence as shown in SEQ ID NO: 145, and the light chain variable region CDRL3 consisting of the amino acid sequence as shown in SEQ ID NO: 146 (FIG. 142).

An example of the more preferable antibody or antigen-binding fragment thereof comprising CDRH1 to CDRH3 and CDRL1 to CDRL3 is the antibody or antigen-binding fragment thereof comprising the C3E-7034 heavy chain variable region consisting of an amino acid sequence of amino acids 2 to 119 of the amino acid sequence as shown in SEQ ID NO: 136 (FIG. 137), the C3E-7036 heavy chain variable region consisting of an amino acid sequence of amino acids 2 to 119 of the amino acid sequence as shown in SEQ ID NO: 137 (FIG. 138), the C3E-7085 heavy chain variable region consisting of an amino acid sequence of amino acids 2 to 119 of SEQ ID NO: 138 (FIG. 139), the C3E-7088 heavy chain variable region consisting of an amino acid sequence of amino acids 2 to 119 of the amino acid sequence as shown in SEQ ID NO: 139 (FIG. 140), the C3E-7093 heavy chain variable region consisting of an amino acid sequence of amino acids 2 to 119 of the amino acid sequence as shown in SEQ ID NO: 140 (FIG. 141), the C3E-7096 heavy chain variable region consisting of an amino acid sequence of amino acids 272 to 389 of the amino acid sequence as shown in SEQ ID NO: 155 (FIG. 151), the C3E-7096 heavy chain variable region consisting of an amino acid sequence of amino acids 277 to 394 of the amino acid sequence as shown in SEQ ID NO: 156 (FIG. 152), and the C3E-7097 heavy chain variable region consisting of an amino acid sequence of amino acids 277 to 394 of the amino acid sequence as shown in SEQ ID NO: 157 (FIG. 153).

An example of the more preferable antibody or antigen-binding fragment thereof comprising CDRH1 to CDRH3 and CDRL1 to CDRL3 is the antibody or antigen-binding fragment thereof comprising the C3E-7034 light chain variable region consisting of an amino acid sequence of amino acids 135 to 243 of the amino acid sequence as shown in SEQ ID NO: 136 (FIG. 137), the C3E-7036 light chain variable region consisting of an amino acid sequence of amino acids 135 to 241 of the amino acid sequence as shown in SEQ ID NO: 137 (FIG. 138), the C3E-7085 light chain variable region consisting of an amino acid sequence of amino acids 135 to 241 of the amino acid sequence as shown in SEQ ID NO: 138 (FIG. 139), the C3E-7088 light chain variable region consisting of an amino acid sequence of amino acids 135 to 243 of the amino acid sequence as shown in SEQ ID NO: 139 (FIG. 140), the C3E-7093 light chain variable region consisting of an amino acid sequence of amino acids 135 to 243 of the amino acid sequence as shown in SEQ ID NO: 140 (FIG. 141), the C3E-7096 light chain variable region consisting of an amino acid sequence of amino acids 405 to 511 of the amino acid sequence as shown in SEQ ID NO: 155 (FIG. 151), the C3E-7096 light chain variable region consisting of an amino acid sequence of amino acids 410 to 516 of the amino acid sequence as shown in SEQ ID NO: 156 (FIG. 152), and the C3E-7097 light chain variable region consisting of an amino acid sequence of amino acids 410 to 516 of the amino acid sequence as shown in SEQ ID NO: 157 (FIG. 153).

An example of the more preferable antibody or antigen-binding fragment thereof comprising CDRH1 to CDRH3 and CDRL1 to CDRL3 is the antibody or antigen-binding fragment thereof comprising a combination of the C3E-7034 heavy chain variable region and light chain variable region consisting of amino acids 2 to 119 and amino acids 135 to 243 of SEQ ID NO: 136 (FIG. 137), a combination of the C3E-7036 heavy chain variable region and light chain variable region consisting of amino acids 2 to 119 and amino acids 135 to 241 of SEQ ID NO: 137 (FIG. 138), a combination of the C3E-7078 heavy chain variable region and light chain variable region consisting of amino acids 2 to 119 and amino acids 135 to 243 of SEQ ID NO: 147 (FIG. 143), a combination of the C3E-7085 heavy chain variable region and light chain variable region consisting of amino acids 2 to 119 and amino acids 135 to 241 of SEQ ID NO: 138 (FIG. 139), a combination of the C3E-7088 heavy chain variable region and light chain variable region consisting of amino acids 2 to 119 and amino acids 135 to 243 of SEQ ID NO: 139 (FIG. 140), a combination of the C3E-7093 heavy chain variable region and light chain variable region consisting of amino acids 2 to 119 and amino acids 135 to 243 of SEQ ID NO: 140 (FIG. 141), a combination of the C3E-7096 heavy chain variable region and light chain variable region consisting of amino acids 272 to 389 and amino acids 405 to 511 of SEQ ID NO: 155 (FIG. 151), a combination of the C3E-7096 heavy chain variable region and light chain variable region consisting of amino acids 277 to 394 and amino acids 410 to 516 of SEQ ID NO: 156 (FIG. 152), and a combination of the C3E-7097 heavy chain variable region and light chain variable region consisting of amino acids 277 to 394 and amino acids 410 to 516 of SEQ ID NO: 157 (FIG. 153).

Further, examples of the more preferable antibody or antigen-binding fragment thereof comprising CDRH1 to CDRH3 and CDRL1 to CDRL3 include C3E-7034 scFv consisting of an amino acid sequence of amino acids 2 to 243 of the amino acid sequence as shown in SEQ ID NO: 136 (FIG. 137), C3E-7036 scFv consisting of an amino acid sequence of amino acids 2 to 241 of the amino acid sequence as shown in SEQ ID NO: 137 (FIG. 138), C3E-7078 scFv consisting of an amino acid sequence of amino acids 2 to 243 of the amino acid sequence as shown in SEQ ID NO: 147 (FIG. 143), C3E-7085 scFv consisting of an amino acid sequence of amino acids 2 to 241 of the amino acid sequence as shown in SEQ ID NO: 138 (FIG. 139), C3E-7088 scFv consisting of an amino acid sequence of amino acids 2 to 243 of the amino acid sequence as shown in SEQ ID NO: 139 (FIG. 140), C3E-7093 scFv consisting of an amino acid sequence of amino acids 2 to 243 of the amino acid sequence as shown in SEQ ID NO: 140 (FIG. 141), and an antibody or a binding fragment thereof comprising any one of such scFv constructs. A preferable embodiment of CD3-specific scFv (which may be referred to as "anti-CD3 scFv") includes scFv comprising a FLAG-His tag added to its carboxyl terminal side (may be simply referred to as "tag adduct"). Examples of preferable tag adducts include C3E-7034 (SEQ ID NO: 136; FIG. 137), C3E-7036 (SEQ ID NO: 137; FIG. 138), C3E-7085 (SEQ ID NO: 138; FIG. 139), C3E-7088 (SEQ ID NO: 139; FIG. 140), and C3E-7093 (SEQ ID NO: 140; FIG. 141), with C3E-7085 being more preferable.

A preferable example of the multispecific molecule of the present invention is a bispecific molecule. A "bispecific" molecule is capable of binding to two different epitopes on a single molecule or different epitopes on two molecules, and it includes an antibody or antigen-binding fragment having such bispecificity. The bispecific molecule of the present invention binds to HLA/NY-ESO and it further binds to CD3.

Examples of the bispecific molecule of the present invention include those having the structures (formats) described below.

In the dual scFv-type bispecific molecule, two types of scFv constructs binding to different epitopes are each allowed to bind to one Fc of a dimer with a linker or allowed to directly bind thereto without a linker. Alternatively, two types of scFv constructs binding to different epitopes are each allowed to bind to CH and CL with linkers and are further allowed to bind to one Fc of the dimer with linkers. In such a bispecific molecule, Fc comprising a heterodimer-forming mutation downstream of one scFv is heterologously associated with another Fc comprising a heterodimer-forming mutation downstream of another scFv. The dual scFv-type bispecific molecule is referred to as a dual-type bispecific molecule or simply as a dual-type (FIG. 6A (b)).

In the present invention, for example, a dual-type bispecific molecule consisting of anti-HLA-A2/NY-ESO scFv and anti-CD3 scFv may be used.

Alternatively, the bispecific molecule of the present invention may comprise Fab and scFv binding to different epitopes, Fab of the first antibody may be bound to one Fc of a dimer, and scFv of the second antibody may be bound to another Fc with linkers. In such bispecific molecule, Fc comprising a heterodimer-forming mutation downstream of Fab is heterologously associated with Fc comprising a heterodimer-forming mutation downstream of scFv. Such bispecific molecule is referred to as a "hybrid-type bispecific molecule" or a "hybrid-type" (FIG. 6A (a)). In the present invention, for example, a hybrid type consisting of anti-HLA-A2/NY-ESO Fab and anti-CD3 scFv can be used.

In addition, a bispecific molecule may allow Fab of the first antibody and scFv of the second antibody to attach to one Fc of a dimer with linkers. In such a case, Fab may be allowed to attach to Fc and scFv may be allowed to attach to such Fab. Alternatively, scFv may be allowed to attach to Fc and Fab may be allowed to attach to such scFv. Preferably, Fab may be allowed to attach to Fc and scFv may be allowed to attach to such Fab. scFv may be allowed to attach to a variable region of Fab with a linker. In such a bispecific molecule, Fc comprising a heterodimer-forming mutation is associated with a site downstream of where scFv is ligated to Fab. Such a bispecific molecule is referred to as an scFv-Fab-heterodimer Fc-type bispecific molecule or scFv-Fab-heterodimer Fc-type (FIG. 6A (c)).

In the present invention, for example, scFv-Fab-heterodimer Fc-type consisting of anti-CD3 scFv and anti-HLA-A2/NY-ESO Fab may be used.

In addition, taFv (FIG. 3 (c)) comprising two types of scFv constructs (of the first antibody and the second antibody) ligated to each other with a linker may be attached to one Fc of a dimer with a linker or directly without a linker. Such a bispecific molecule is referred to as a taFv-heterodimer Fc-type bispecific molecule or taFv-heterodimer Fc-type (FIG. 3 (d)). In such a bispecific molecule, Fc comprising a heterodimer-forming mutation is heterologously associated with another Fc comprising a heterodimer-forming mutation in a site downstream of taFv. The order for ligating the first antibody and the second antibody to taFv is not limited. The previously mentioned bispecific molecule is referred to as taFv-heterodimer Fc-type but when the order for ligating the first antibody and the second antibody to taFv is inverted, the bispecific molecule is referred to as taFv (inversed)-heterodimer Fc-type (taFv (inversed)-Fc type).

Figure 6A:
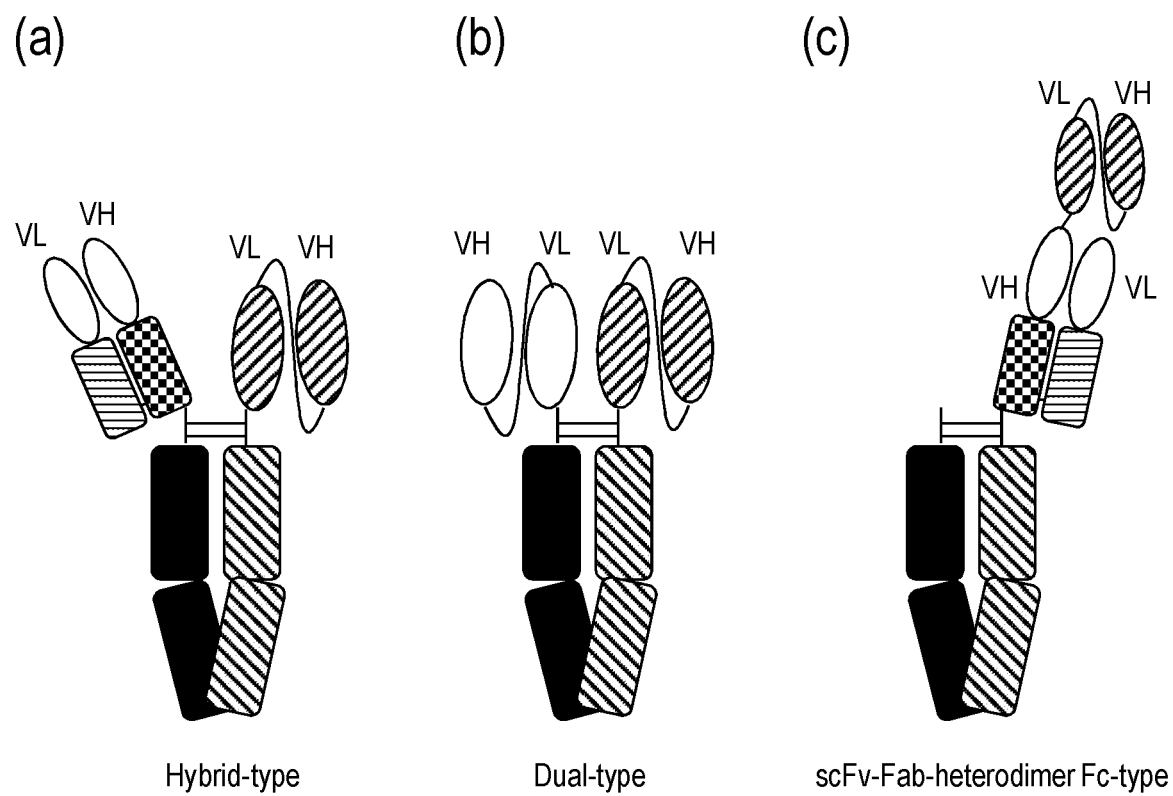
FIG. 6A shows antibody formats described in the examples. (a): Hybrid-type format: Fc (slopes) comprising a heterodimer-forming mutation and Fc (solid) comprising a heterodimer-forming mutation are added to the C terminal region of Fab and scFv, respectively, and the two Fc constructs are associated. In the example, a hybrid-type format comprising anti-HLA-A2/NY-ESO Fab and anti-CD3 scFv was used for evaluation. (b): Dual-type format: Fc (negative slopes) comprising a heterodimer-forming mutation and Fc (solid) comprising a heterodimer-forming mutation are added to the C terminal regions of two different types of scFv constructs and the two Fc constructs are heterologously associated. In the example, a dual-type format comprising anti-HLA-A2/NY-ESO scFv and anti-CD3 scFv was used for evaluation. (c): scFv-Fab-heterodimer Fc-type format: Fc (negative slopes) comprising a heterodimer-forming mutation is added to the C terminal region where scFv is ligated to Fab with a linker and associated with another Fc (solid). In the example, an scFv-Fab-heterodimer Fc-type format comprising anti-CD3 scFv (positive slopes) and anti-HLA-A2/NY-ESO Fab was used for evaluation. Also, the scFv-Fab-heterodimer Fc-type comprising anti-HLA-A2/NY-ESO scFv (positive slopes) and anti-CD3 Fab was used for evaluation.

FIG. 6A (a) shows a structure of a hybrid-type bispecific molecule, FIG. 6A (b) shows a structure of a dual-type bispecific molecule, and FIG. 6A (c) shows a structure of an scFv-Fab-heterodimer Fc-type bispecific molecule. FIG. 3 (a) shows a structure of scFv, FIG. 3 (b) shows a structure of Fab, FIG. 3 (c) shows a structure of taFv, FIG. 3 (d) shows a structure of taFv-heterodimer Fc-type bispecific molecule, and FIG. 3 (e) shows a structure of a taFv-Fab-heterodimer Fc-type bispecific molecule. FIG. 6. B (a) shows a structure of a taFv-heterodimer Fc-type bispecific molecule (the same as FIG. 3 (d)), FIG. 6. B (b) shows a structure of a taFv (inversed)-heterodimer Fc-type bispecific molecule, FIG. 6. B (c) shows a structure of the first polypeptide included in the taFv (inversed)-heterodimer Fc-type bispecific molecule, and FIG. 6 (d) shows a structure of the second polypeptide included in the taFv (inversed)-heterodimer Fc-type bispecific molecule.

In the bispecific molecule of the present invention, a plurality of polypeptides are associated.

In the present invention, a taFv, for example, one composed of an anti-HLA-A2/NY-ESO scFv and an anti-CD3 scFv may be used. The taFv-heterodimer Fc-type bispecific molecule preferably comprises (a) a first polypeptide comprising scFv that binds specifically to HLA/NY-ESO, scFv that binds specifically to CD3, and the immunoglobulin Fc region (i) in that order from the N terminus toward the C terminus and the second polypeptide comprising the hinge region and the Fc region (ii) of immunoglobulin. It more preferably comprises (b) the first polypeptide associated with a second polypeptide at the Fc region (i) and the Fc region (ii). Fc regions of the first polypeptide and of the second polypeptide may comprise a heterodimer-forming mutation. FIG. 3 (d) shows an example of the taFv-heterodimer Fc-type bispecific molecule. As shown in FIG. 3 (d), the Fc region (i) of the first polypeptide binds to the Fc region (ii) of the second polypeptide (solid), and the first polypeptide is thus associated with the second polypeptide. FIG. 3 (f) shows the first polypeptide and FIG. 3 (g) shows the second polypeptide. In FIG. 3 (d), for example, scFv shown as blank is anti-HLA-A2/NY-ESO scFv, and scFv indicated with positive slopes is anti-CD3 scFv.

The first polypeptide included in a more preferable taFv-heterodimer Fc-type bispecific molecule of the present invention comprises an amino acid sequence of amino acids 21 to 511 of the amino acid sequence as shown in SEQ ID NO: 85, an amino acid sequence of amino acids 21 to 511 of the amino acid sequence as shown in SEQ ID NO: 87, an amino acid sequence of amino acids 21 to 511 of the amino acid sequence as shown in SEQ ID NO: 88, an amino acid sequence of amino acids 21 to 511 of the amino acid sequence as shown in SEQ ID NO: 89, an amino acid sequence of amino acids 21 to 511 of the amino acid sequence as shown in SEQ ID NO: 90, an amino acid sequence of amino acids 21 to 511 of the amino acid sequence as shown in SEQ ID NO: 91, an amino acid sequence of amino acids 21 to 511 of the amino acid sequence as shown in SEQ ID NO: 92, an amino acid sequence of amino acids 21 to 511 of the amino acid sequence as shown in SEQ ID NO: 93, an amino acid sequence of amino acids 21 to 511 of the amino acid sequence as shown in SEQ ID NO: 94, an amino acid sequence of amino acids 21 to 511 of the amino acid sequence as shown in SEQ ID NO: 95, an amino acid sequence of amino acids 21 to 511 of the amino acid sequence as shown in SEQ ID NO: 96, an amino acid sequence of amino acids 21 to 511 of the amino acid sequence as shown in SEQ ID NO: 86, an amino acid sequence of amino acids 21 to 511 of the amino acid sequence as shown in SEQ ID NO: 149, an amino acid sequence of amino acids 21 to 511 of the amino acid sequence as shown in SEQ ID NO: 150, an amino acid sequence of amino acids 20 to 511 of the amino acid sequence as shown in SEQ ID NO: 155, an amino acid sequence of amino acids 20 to 516 of the amino acid sequence as shown in SEQ ID NO: 156, or an amino acid sequence of amino acids 20 to 516 of the amino acid sequence as shown in SEQ ID NO: 157. The first polypeptide included in a further preferable taFv-heterodimer Fc-type bispecific molecule comprises an amino acid sequence of amino acids 529 to 745 of the amino acid sequence as shown in SEQ ID NO: 85, 87, 88, 89, 90, 91, 92, 93, 94, 95, 96, 86, 149, 150, or 155 or an amino acid sequence of amino acids 534 to 750 of the amino acid sequence as shown in SEQ ID NO: 156 or 157. The first polypeptide included in a still further preferable taFv-heterodimer Fc-type bispecific molecule consists of an amino acid sequence of amino acids 21 to 745 of the amino acid sequence as shown in SEQ ID NO: 85, an amino acid sequence of amino acids 21 to 745 of the amino acid sequence as shown in SEQ ID NO: 87, an amino acid sequence of amino acids 21 to 745 of the amino acid sequence as shown in SEQ ID NO: 88, an amino acid sequence of amino acids 21 to 745 of the amino acid sequence as shown in SEQ ID NO: 89, an amino acid sequence of amino acids 21 to 745 of the amino acid sequence as shown in SEQ ID NO: 90, an amino acid sequence of amino acids 21 to 745 of the amino acid sequence as shown in SEQ ID NO: 91, an amino acid sequence of amino acids 21 to 745 of the amino acid sequence as shown in SEQ ID NO: 92, an amino acid sequence of amino acids 21 to 745 of the amino acid sequence as shown in SEQ ID NO: 93, an amino acid sequence of amino acids 21 to 745 of the amino acid sequence as shown in SEQ ID NO: 94, an amino acid sequence of amino acids 21 to 745 of the amino acid sequence as shown in SEQ ID NO: 95, an amino acid sequence of amino acids 21 to 745 of the amino acid sequence as shown in SEQ ID NO: 96, an amino acid sequence of amino acids 21 to 745 of the amino acid sequence as shown in SEQ ID NO: 86, an amino acid sequence of amino acids 21 to 745 of the amino acid sequence as shown in SEQ ID NO: 149, an amino acid sequence of amino acids 21 to 745 of the amino acid sequence as shown in SEQ ID NO: 150, or an amino acid sequence of amino acids 20 to 745 of the amino acid sequence as shown in SEQ ID NO: 155. Alternatively, the first polypeptide consists of an amino acid sequence of amino acids 20 to 750 of the amino acid sequence as shown in SEQ ID NO: 156 or an amino acid sequence of amino acids 20 to 750 of the amino acid sequence as shown in SEQ ID NO: 157.

The second polypeptide included in the preferable taFv-heterodimer Fc-type bispecific molecule of the present invention comprises a hinge region and mutant Fc derived from a human antibody. The second polypeptide included in the more preferable taFv-heterodimer Fc-type bispecific molecule comprises an amino acid sequence of amino acids 20 to 246 of the amino acid sequence as shown in SEQ ID NO: 84.

Of these, NYF-0016 in which the first polypeptide consisting of an amino acid sequence of amino acids 21 to 745 of the amino acid sequence as shown in SEQ ID NO: 85 is associated with the second polypeptide consisting of an amino acid sequence of amino acids 21 to 246 of the amino acid sequence as shown in SEQ ID NO: 84, NYF-0022 in which the first polypeptide consisting of an amino acid sequence of amino acids 21 to 745 of the amino acid sequence as shown in SEQ ID NO: 87 is associated with the second polypeptide consisting of an amino acid sequence of amino acids 21 to 246 of the amino acid sequence as shown in SEQ ID NO: 84, NYF-0023 in which the first polypeptide consisting of an amino acid sequence of amino acids 21 to 745 of the amino acid sequence as shown in SEQ ID NO: 88 is associated with the second polypeptide consisting of an amino acid sequence of amino acids 21 to 246 of the amino acid sequence as shown in SEQ ID NO: 84, NYF-0027 in which the first polypeptide consisting of an amino acid sequence of amino acids 21 to 745 of the amino acid sequence as shown in SEQ ID NO: 89 is associated with the second polypeptide consisting of an amino acid sequence of amino acids 21 to 246 of the amino acid sequence as shown in SEQ ID NO: 84, NYF-0035 in which the first polypeptide consisting of an amino acid sequence of amino acids 21 to 745 of the amino acid sequence as shown in SEQ ID NO: 90 is associated with the second polypeptide consisting of an amino acid sequence of amino acids 21 to 246 of the amino acid sequence as shown in SEQ ID NO: 84, NYF-0044 in which the first polypeptide consisting of an amino acid sequence of amino acids 21 to 745 of the amino acid sequence as shown in SEQ ID NO: 91 is associated with the second polypeptide consisting of an amino acid sequence of amino acids 21 to 246 of the amino acid sequence as shown in SEQ ID NO: 84, NYF-0045 in which the first polypeptide consisting of an amino acid sequence of amino acids 21 to 745 of the amino acid sequence as shown in SEQ ID NO: 92 is associated with the second polypeptide consisting of an amino acid sequence of amino acids 21 to 246 of the amino acid sequence as shown in SEQ ID NO: 84, NYF-0047 in which the first polypeptide consisting of an amino acid sequence of amino acids 21 to 745 of the amino acid sequence as shown in SEQ ID NO: 93 is associated with the second polypeptide consisting of an amino acid sequence of amino acids 21 to 246 of the amino acid sequence as shown in SEQ ID NO: 84, NYF-0048 in which the first polypeptide consisting of an amino acid sequence of amino acids 21 to 745 of the amino acid sequence as shown in SEQ ID NO: 94 is associated with the second polypeptide consisting of an amino acid sequence of amino acids 21 to 246 of the amino acid sequence as shown in SEQ ID NO: 84, NYF-0060 in which the first polypeptide consisting of an amino acid sequence of amino acids 21 to 745 of the amino acid sequence as shown in SEQ ID NO: 95 is associated with the second polypeptide consisting of an amino acid sequence of amino acids 21 to 246 of the amino acid sequence as shown in SEQ ID NO: 84, NYF-0061 in which the first polypeptide consisting of an amino acid sequence of amino acids 21 to 745 of the amino acid sequence as shown in SEQ ID NO: 96 is associated with the second polypeptide consisting of an amino acid sequence of amino acids 21 to 246 of the amino acid sequence as shown in SEQ ID NO: 84, NYF-0019 in which the first polypeptide consisting of an amino acid sequence of amino acids 21 to 745 of the amino acid sequence as shown in SEQ ID NO: 86 is associated with the second polypeptide consisting of an amino acid sequence of amino acids 21 to 246 of the amino acid sequence as shown in SEQ ID NO: 84, NYF-0014 in which the first polypeptide consisting of an amino acid sequence of amino acids 21 to 745 of the amino acid sequence as shown in SEQ ID NO: 149 is associated with the second polypeptide consisting of an amino acid sequence of amino acids 21 to 246 of the amino acid sequence as shown in SEQ ID NO: 84, and NYF-0082 in which the first polypeptide consisting of an amino acid sequence of amino acids 21 to 745 of the amino acid sequence as shown in SEQ ID NO: 150 is associated with the second polypeptide consisting of an amino acid sequence of amino acids 21 to 246 of the amino acid sequence as shown in SEQ ID NO: 84 can be exemplified as the preferable taFv-heterodimer Fc-type bispecific molecules of the present invention.

Further examples of the preferable taFv-heterodimer Fc-type bispecific molecules of the present invention include NYZ-0038 in which the first polypeptide consisting of an amino acid sequence of amino acids 20 to 745 of the amino acid sequence as shown in SEQ ID NO: 155 is associated with the second polypeptide consisting of an amino acid sequence of amino acids 20 to 246 of the amino acid sequence as shown in SEQ ID NO: 84, NYZ-0082 in which the first polypeptide consisting of an amino acid sequence of amino acids 20 to 750 of the amino acid sequence as shown in SEQ ID NO: 156 is associated with the second polypeptide consisting of an amino acid sequence of amino acids 20 to 246 of the amino acid sequence as shown in SEQ ID NO: 84, and NYZ-0083 in which the first polypeptide consisting of an amino acid sequence of amino acids 20 to 750 of the amino acid sequence as shown in SEQ ID NO: 157 is associated with the second polypeptide consisting of an amino acid sequence of amino acids 20 to 246 of the amino acid sequence as shown in SEQ ID NO: 84.

Of these, NYF-0023, NYF-0047, NYF-0048, NYF-0060, NYF-0061, NYZ-0038, NYZ-0082, and NYZ-0083 exert excellent biological activity, physical properties, and the like and thus are particularly preferable.

In addition, taFv of the first antibody may be allowed to attach to one Fc of a dimer with a linker or directly bound thereto without a linker, and Fab of the first antibody or the second antibody may be allowed to attach to another Fc with a linker or directly bound thereto without a linker. In such a bispecific molecule, Fab is added to a site upstream of the Fc region (ii) (solid) of the second polypeptide of the taFv-heterodimer Fc-type. Such a bispecific molecule is referred to as the taFv-Fab-heterodimer Fc-type bispecific molecule or taFv-Fab-heterodimer Fc-type (FIG. 3).

In the present invention, for example, taFv of anti-HLA-A2/NY-ESO scFv, taFv of anti-CD3 scFv, and Fab of HLA/NY-ESO may be used to be included in the taFv-Fab-heterodimer Fc-type bispecific molecule.

The taFv-Fab-heterodimer Fc-type bispecific molecule preferably comprises (a) a first polypeptide comprising scFv that binds specifically to human HLA/NY-ESO, scFv that binds specifically to CD3, and the immunoglobulin Fc region (i) in that order from the N terminus toward the C terminus, a second polypeptide consisting of an immunoglobulin heavy chain including the Fc region (ii), and a third polypeptide consisting of an immunoglobulin light chain. More preferably, (b) the second polypeptide is associated with the third polypeptide, and (c) the first polypeptide is associated with the second polypeptide at the Fc region (i) and the Fc region (ii). FIG. 3 (e) shows an example of the taFv-Fab-heterodimer Fc-type bispecific molecule, FIG. 3 (f) shows the first polypeptide, FIG. 3 (h) shows the second polypeptide, and FIG. 3 (i) shows the third polypeptide. As shown in FIG. 3 (e), the Fc region (ii) (solid) of the second polypeptide, consisting of an immunoglobulin heavy chain comprising the Fc region (ii), binds to the Fc region (i) of the first polypeptide, and an immunoglobulin light chain further attaches to the second polypeptide. Such preferable taFv-Fab-heterodimer Fc-type bispecific molecule can be composed of the taFv-heterodimer Fc-type bispecific molecule comprising taFv and the immunoglobulin Fc region and Fab bound thereto. Examples of amino acid sequences included in the first polypeptide of a preferable taFv-Fab-heterodimer Fc-type bispecific molecule include an amino acid sequence of amino acids 21 to 511 of the amino acid sequence as shown in SEQ ID NO: 85, an amino acid sequence of amino acids 21 to 511 of the amino acid sequence as shown in SEQ ID NO: 87, an amino acid sequence of amino acids 21 to 511 of the amino acid sequence as shown in SEQ ID NO: 88, an amino acid sequence of amino acids 21 to 511 of the amino acid sequence as shown in SEQ ID NO: 89, an amino acid sequence of amino acids 21 to 511 of the amino acid sequence as shown in SEQ ID NO: 90, an amino acid sequence of amino acids 21 to 511 of the amino acid sequence as shown in SEQ ID NO: 91, an amino acid sequence of amino acids 21 to 511 of the amino acid sequence as shown in SEQ ID NO: 92, an amino acid sequence of amino acids 21 to 511 of the amino acid sequence as shown in SEQ ID NO: 93, an amino acid sequence of amino acids 21 to 511 of the amino acid sequence as shown in SEQ ID NO: 94, an amino acid sequence of amino acids 21 to 511 of the amino acid sequence as shown in SEQ ID NO: 95, an amino acid sequence of amino acids 21 to 511 of the amino acid sequence as shown in SEQ ID NO: 96, an amino acid sequence of amino acids 21 to 511 of the amino acid sequence as shown in SEQ ID NO: 86, an amino acid sequence of amino acids 21 to 511 of the amino acid sequence as shown in SEQ ID NO: 149, and an amino acid sequence of amino acids 21 to 511 of the amino acid sequence as shown in SEQ ID NO: 150. The first polypeptide included in a more preferable taFv-Fab-heterodimer Fc-type bispecific molecule consists of an amino acid sequence of amino acids 21 to 745 of the amino acid sequence as shown in SEQ ID NO: 85, an amino acid sequence of amino acids 21 to 745 of the amino acid sequence as shown in SEQ ID NO: 87, an amino acid sequence of amino acids 21 to 745 of the amino acid sequence as shown in SEQ ID NO: 88, an amino acid sequence of amino acids 21 to 745 of the amino acid sequence as shown in SEQ ID NO: 89, an amino acid sequence of amino acids 21 to 745 of the amino acid sequence as shown in SEQ ID NO: 90, an amino acid sequence of amino acids 21 to 745 of the amino acid sequence as shown in SEQ ID NO: 91, an amino acid sequence of amino acids 21 to 745 of the amino acid sequence as shown in SEQ ID NO: 92, an amino acid sequence of amino acids 21 to 745 of the amino acid sequence as shown in SEQ ID NO: 93, an amino acid sequence of amino acids 21 to 745 of the amino acid sequence as shown in SEQ ID NO: 94, an amino acid sequence of amino acids 21 to 745 of the amino acid sequence as shown in SEQ ID NO: 95, an amino acid sequence of amino acids 21 to 745 of the amino acid sequence as shown in SEQ ID NO: 96, an amino acid sequence of amino acids 21 to 745 of the amino acid sequence as shown in SEQ ID NO: 86, an amino acid sequence of amino acids 21 to 745 of the amino acid sequence as shown in SEQ ID NO: 149, or an amino acid sequence of amino acids 21 to 745 of the amino acid sequence as shown in SEQ ID NO: 150.

The second polypeptide included in the preferable taFv-Fab-heterodimer Fc-type bispecific molecule of the present invention comprises the human antibody or humanized antibody heavy chain variable region, the CH1 region, a hinge region, and mutant Fc. The second polypeptide included in the more preferable taFv-Fab-heterodimer Fc-type bispecific molecule comprises an amino acid sequence of amino acids 20 to 242 of the amino acid sequence as shown in SEQ ID NO: 99.

The third polypeptide included in the preferable taFv-Fab-heterodimer Fc-type bispecific molecule of the present invention comprises the human antibody or humanized antibody light chain variable region and constant region. The third polypeptide included in the more preferable taFv-Fab-heterodimer Fc-type bispecific molecule comprises an amino acid sequence of amino acids 21 to 131 of the amino acid sequence as shown in SEQ ID NO: 100.

Of the second polypeptide included in such preferable taFv-Fab-heterodimer Fc-type bispecific molecule, the variable region, the CH1 region, and the third polypeptide constitute Fab, and Fab is preferably of the anti-HLA/NY-ESO antibody, such as Fab of NYA-0001.

In the present invention, for example, anti-HLA-A2/NY-ESO scFv, anti-CD3 scFv, HLA/NY-ESO Fab, or anti-CD3 Fab may be included in the scFv-Fab-heterodimer Fc-type bispecific molecule.

The scFv-Fab-heterodimer Fc-type bispecific molecule preferably comprises (a) a first polypeptide comprising scFv that binds specifically to human HLA/NY-ESO, the antibody heavy chain variable region and constant region CH1 binding specifically to CD3, and the immunoglobulin Fc region (i) in that order from the N terminus toward the C terminus, a second polypeptide comprising the immunoglobulin hinge region and Fc region (ii), and a third polypeptide consisting of an antibody light chain comprising a variable region and a constant region. More preferably, (b) the first polypeptide is associated with the second polypeptide via the Fc region (i) and the Fc region (ii), and the first polypeptide is associated with (the antibody light chain of) the third polypeptide via the antibody heavy chain variable region and constant region CH1 of the first polypeptide. The Fc regions of the first polypeptide and of the second polypeptide may be a wild-type or may contain a heterodimer-forming mutation. FIG. 6A (c) shows an example of the scFv-Fab-heterodimer Fc-type bispecific molecule. In FIG. 6A (c), the right half shows the first polypeptide and the third polypeptide and the left half shows the second polypeptide. As shown in FIG. 6A (c), the Fc region (i) of the first polypeptide is associated with the Fc region (ii) of the second polypeptide (solid), and the first polypeptide is associated with the third polypeptide. In FIG. 6A (c), scFv indicated with positive slopes is anti-HLA-A2/NY-ESO scFv, and Fab each indicated as blank, a checkered pattern, or horizontal lines is anti-CD3 Fab.

An example of an amino acid sequence included in the first polypeptide included in the preferable scFv-Fab-heterodimer Fc-type bispecific molecule is an amino acid sequence of amino acids 21 to 394 of the amino acid sequence as shown in SEQ ID NO: 160. A more preferable example thereof is an amino acid sequence of amino acids 20 to 724 of the amino acid sequence as shown in SEQ ID NO: 160.

An example of another amino acid sequence included in the first polypeptide included in the preferable scFv-Fab-heterodimer Fc-type bispecific molecule is an amino acid sequence of amino acids 21 to 389 of the amino acid sequence as shown in SEQ ID NO: 197. A more preferable example thereof is an amino acid sequence of amino acids 20 to 719 of the amino acid sequence as shown in SEQ ID NO: 197.

An example of another amino acid sequence included in the first polypeptide included in the preferable scFv-Fab-heterodimer Fc-type bispecific molecule is an amino acid sequence of amino acids 21 to 389 of the amino acid sequence as shown in SEQ ID NO: 198. A more preferable example thereof is an amino acid sequence of amino acids 20 to 719 of the amino acid sequence as shown in SEQ ID NO: 198.

The second polypeptide included in the preferable scFv-Fab-heterodimer Fc-type bispecific molecule of the present invention comprises a hinge region and mutant Fc derived from a human antibody. The second polypeptide included in the more preferable scFv-Fab-heterodimer Fc-type bispecific molecule comprises an amino acid sequence of amino acids 20 to 246 of the amino acid sequence as shown in SEQ ID NO: 84.

The third polypeptide included in the preferable scFv-Fab-heterodimer Fc-type bispecific molecule of the present invention comprises a human antibody-derived light chain. The third polypeptide included in the more preferable scFv-Fab-heterodimer Fc-type bispecific molecule comprises, for example, an amino acid sequence of amino acids 21 to 127 of the amino acid sequence as shown in SEQ ID NO: 161. A further preferable example thereof is an amino acid sequence of amino acids 21 to 233 of the amino acid sequence as shown in SEQ ID NO: 161.

Of these, NYZ-1010 in which the first polypeptide consisting of an amino acid sequence of amino acids 20 to 724 of the amino acid sequence as shown in SEQ ID NO: 160, the second polypeptide consisting of an amino acid sequence of amino acids 20 to 246 of the amino acid sequence as shown in SEQ ID NO: 84, and the third polypeptide consisting of an amino acid sequence of amino acids 21 to 233 of the amino acid sequence as shown in SEQ ID NO: 161 are associated with each other can be exemplified as the preferable scFv-Fab-heterodimer Fc-type bispecific molecule of the present invention.

In addition, NYZ-1007 in which the first polypeptide consisting of an amino acid sequence of amino acids 20 to 719 of the amino acid sequence as shown in SEQ ID NO: 197, the second polypeptide consisting of an amino acid sequence of amino acids 20 to 246 of the amino acid sequence as shown in SEQ ID NO: 84, and the third polypeptide consisting of an amino acid sequence of amino acids 21 to 233 of the amino acid sequence as shown in SEQ ID NO: 161 are associated with each other can be exemplified as the preferable scFv-Fab-heterodimer Fc-type bispecific molecule of the present invention.

Further, NYZ-1017 in which the first polypeptide consisting of an amino acid sequence of amino acids 20 to 719 of the amino acid sequence as shown in SEQ ID NO: 198, the second polypeptide consisting of an amino acid sequence of amino acids 20 to 246 of the amino acid sequence as shown in SEQ ID NO: 84, and the third polypeptide consisting of an amino acid sequence of amino acids 21 to 233 of the amino acid sequence as shown in SEQ ID NO: 161 are associated with each other can be exemplified as the preferable scFv-Fab-heterodimer Fc-type bispecific molecule of the present invention.

At least 1, 2, or 3 peptides included in the bispecific molecule of the present invention may be the "deletion mutant" described above. Specifically, 1 or 2 (or more) amino acids at its carboxyl terminus (at the carboxyl terminus derived from the antibody heavy chain, in particular) may be mutated (may also be deleted). For example, the carboxyl terminus of the amino acid sequence of the first polypeptide included in NYZ-1010, which is a preferable scFv-Fab-heterodimer Fc-type bispecific molecule of the present invention, may be any of Lys at position 724 of SEQ ID NO: 160, Gly at position 723 resulting from deletion of an amino acid, or a mixture of first polypeptides including Lys and Gly at the carboxyl terminus. Also, the carboxyl terminus of the amino acid sequence of the second polypeptide included in the preferable scFv-Fab-heterodimer Fc-type bispecific molecule of the present invention may be any of Lys at position 246 of SEQ ID NO: 84, Gly at position 245 resulting from deletion of an amino acid, or a mixture of second polypeptides including Lys and Gly at the carboxyl terminus.

scFv and Fab included in the bispecific molecule of the present invention are preferably derived from a humanized antibody or human antibody, and Fc is preferably derived from a human antibody.

In a variable region in the bispecific molecule of the present invention, a heavy chain variable region and a light chain variable region may be attached in that order from the amino terminus of the antibody. Alternatively, a light chain variable region and a heavy chain variable region may be attached in that order. A linker may optionally be present between two variable regions. A glycine residue may optionally be present at the amino terminus of the amino-terminal variable region. In a tandem scFv-type bispecific molecule, a linker, a FLAG tag, and/or a His tag may optionally be attached to the carboxyl terminus of the carboxyl-terminal variable region. In a preferable embodiment, for example, a heavy chain variable region, a first linker, a light chain variable region, a second linker, a FLAG tag, and, a His tag are attached in that order from the amino terminus.

Examples of linkers include a single chain polypeptide, a single chain oligopeptide, and synthetic products, such as PEG, nucleotide, sugar chain, and compounds. Other known linkers can also be used without particular limitation, as long as they can attach 2 polypeptides to each other.

A peptide linker can comprise, for example, 5 to 30 amino acids. When a bispecific molecule comprises a plurality linkers, all the peptide linkers may be of the same length, or peptide linkers of different lengths may be used.

An example of a peptide linker is a repetition of (Gly•Gly•Gly•Gly•Ser) (SEQ ID NO: 161). One to several amino acid residues other than Gly and Ser may be added thereto.

Among constructs (formats) of the multispecific antibody and, in particular, the bispecific antibody of the present invention as described above, taFv-heterodimer Fc-type, taFv-Fab-heterodimer Fc-type, and scFv-Fab-heterodimer Fc-type are preferable, and taFv-heterodimer Fc-type is more preferable. A format in which anti-HLA/NY-ESO scFv and anti-CD3 scFv are positioned in that order from the N terminus toward the C terminus (the taFv-heterodimer Fc-type) is more preferable than the format in which anti-CD3 scFv and anti-HLA/NY-ESO scFv are positioned in that order (the taFv (inversed)-heterodimer Fc-type) (e.g., Example 11). Another example of a more preferable format is the scFv-Fab-heterodimer Fc-type.

The present invention also encompasses a molecule that comprises an amino acid sequence encoded by a nucleotide sequence included in a polynucleotide which hybridizes, under stringent conditions, to a complementary strand of the polynucleotide comprising a nucleotide sequence encoding an amino acid sequence included in the molecule of the present invention, and that binds to HLA/NY-ESO, and further binds to CD3.

The present invention also encompasses a molecule that comprises an amino acid sequence exhibiting at least 90%, 91%, 92%, 93%, 94%, 95%, 96%, 97%, 98%, or 99% identity to the amino acid sequence included in the molecule of the present invention, and that binds to HLA/NY-ESO, and further binds to CD3.

The antibody of the present invention, the binding fragment thereof, and the multispecific antibody comprising the same have excellent biological activity, physicochemical properties (hereafter referred to as "physical properties"), safety, pharmacokinetics, and other properties. (a) Examples of biological activity or indicators thereof include antigen-binding activity, in vitro cytotoxicity, and in vivo antitumor activity. For example, the dissociation constant (KD value) to HLA/NY-ESO is 100 nM or lower or 50 nM or lower, preferably 20 nM or lower or 10 nM or lower, and more preferably 5 nM or lower. The $EC_{50}$ value of cytotoxicity exerted with the use of human peripheral blood mononuclear cells as effector cells to human U266B1 and/or NCI-H1703 cells endogenously expressing NY-ESO is 20 nM or lower, preferably 10 nM or lower, and more preferably 5 nM or lower (in vitro cytotoxicity can be assayed and determined in accordance with the method described in Example 8, although the method is not limited thereto). For example, 0.1 ml of a suspension of human squamous lung cancer cell lines NCI-H1703 ($6 \times 10^7$ cells/ml) is injected hypodermically to NOG mice, 0.2 ml of a suspension of human peripheral blood mononuclear cells ($3.75 \times 10^7$ cells/ml) is injected intravenously 4 days later, and antibody administration is initiated 14 days later and performed once a week in 3 instances. Thereafter, the tumor volume is measured. Tumor growth inhibitory activity relative to the control group to which a solvent has been administered is 50% or higher, preferably 75% or higher, and more preferably 90% or higher (in vivo antitumor activity can be assayed and determined in accordance with the method described in Example 9, although the method is not limited thereto). (b) Impurities contained in biopharmaceutical products are associated with drug safety. Thus, it is necessary to establish the adequate standard and to control the amount of impurities at the time of production and during storage. In particular, HMWS (aggregate) is a major impurity and is associated with an immunogenic risk or reduced drug efficacy. Thus, HMWS should be more strictly controlled. For the purpose of impurity control, evaluation should also be performed in respect of stability (whether or not the amount of impurities was increased) with the elapse of time during and after production, as well as at the time of production. Since the effective period of a pharmaceutical product is determined based on the results of the long-term stability test, a longer effective period can be determined for an antibody exhibiting stability over time. Thus, long-term stability can be used as an indicator to select a preferable antibody for a biopharmaceutical product. Examples of physicochemical properties in the present invention include acid resistance (for inhibition of HMWS production) and solution stability (for inhibition of HMWS production). An example of another indicator is a high yield of a culture product of recombinant cells obtained by introducing a gene encoding the amino acid sequence of the antibody of the present invention, the binding fragment thereof, or the molecule comprising the same into a host cell suitable for production thereof, such as the Expi293F cell. The preferable antibody of the present invention, the antigen-binding fragment thereof, and the multispecific antibody comprising the same with such physicochemical properties are advantageous for the following reasons. That is, a solution containing the antibody, the binding fragment thereof, or the multispecific antibody can be exposed to acidic conditions, and production processes thereof, such as protein A or ion-exchange chromatography and virus inactivation, can be thus performed or facilitated. Also, HMWS production can be controlled at low levels even in the form of a solution of the antibody, the binding fragment thereof, or the multispecific antibody, and, thus, production thereof, drug preparation, distribution or storage of pharmaceutical products comprising the same can be performed and facilitated. Further, pharmaceutical products containing the same can be efficiently produced. Concerning acid resistance, for example, the HMWS content determined by heating at pH 3.5 at room temperature for 1 hour and then measuring HMWS by size exclusion chromatography is 5% or lower, preferably 2% or lower, and more preferably 1% or lower (the HMWS content can be measured and determined for acid resistance evaluation in accordance with the method described in Example 19-1, although the method is not limited thereto). Concerning solution stability, for example, the analyte is dissolved to a concentration of 25 mg/ml in a solution comprising 25 mM histidine and 5% sorbitol at pH 6.0, the resultant is stored at 25° C. for 6 days, and HMWS is then measured by size exclusion chromatography. The HMWS content determined thereby is 20% or lower, and preferably 10% or lower (the HMWS content can be measured and determined for evaluation of solution stability in accordance with the method described in Example 19-2, although the method is not limited thereto). Production efficiency or yield can be measured and determined in accordance with the method described in Examples 20 and 21, although the method is not limited thereto. (c) Examples of safety and indicators thereof include antigen recognition properties and observations at the time of administration. For example, an antibody of interest that recognizes a plurality of amino acids on a wild-type NY-ESO peptide but does not bind to a homologous peptide comprising an amino acid sequence similar to but not identical to the wild-type NY-ESO peptide would produce a low risk of side effects caused by off-target effects. In addition, such an antibody can be predicted to exhibit low immunogenicity in ISPRI web-based immunogenicity screening (EpiVax, Inc) and exhibit a low risk of side effects such as cytokine production. Also, NYF-0023, NYF-0045, NYF-0047, NYF-0048, NYF-0060, NYF-0061, NYZ-0082, or NYZ-1010 included in the bispecific antibody of the present invention were administered to Balb/c mice. As a result, no significant problems were observed in the half-life in blood, and body weight loss or other apparent toxicity problems were not observed. As a result of single administration of NYZ-0082 or NYZ-1010 to cynomolgus monkeys, no significant problems were observed in the half-life in blood, and no changes resulting from administration were observed in terms of general conditions, body weight, the amount of feed intake, body temperature, and plasma cytokine levels. (d) Examples of kinetics or indicators thereof include the half-life in blood. In the present invention, no significant problems were observed in the half-life in blood as a result of administration of several bispecific antibodies to Balb/c mice or cynomolgus monkeys. The antibody of the present invention, the binding fragment thereof, and molecules provided with such excellent biological activity, physicochemical properties, safety, and kinetics can be preferably integrated into a pharmaceutical composition. Preferable examples of the antibody of the present invention or the antigen-binding fragment thereof having the antigen-binding activity described in (a) and various properties described in (b) include, but are not limited to, NYA-1143, NYA-1163, NYA-2023, NYA-2027, NYA-2035, NYA-2044, NYA-2045, NYA-2047, NYA-2048, NYA-2060, NYA-2031, NYA-2047, NYA-2061, NYA-2143, and NYA-3061. More preferable examples thereof include, but are not limited to, NYA-2047, NYA-2061, NYA-2143, and NYA-3061. Preferable examples of the multispecific antibody of the present invention having the properties (a) to (d) include, but are not limited to, NYF-0016, NYF-0019, NYF-0022, NYF-0023, NYF-0027, NYF-0035, NYF-0044, NYF-0045, NYF-0047, NYF-0048, NYF-00058, NYF-0060, NYF-0061, NYZ-0038, NYZ-0082, NYZ-0088, and NYZ-1010. More preferable examples thereof include, but are not limited to, NYF-0061, NYZ-0038, NYZ-0082, NYZ-0088, NYZ-1007, NYZ-1010, and NYZ-1017.

In the present invention, a "site" to which an antibody binds; i.e., a "site" that is recognized by an antibody, is a partial peptide or a partial higher-order structure of an antigen to which an antibody binds or which is recognized by the antibody. In the present invention, such a site is also referred to as an epitope or an antibody binding site. Examples of sites to which the anti-HLA/NY-ESO antibody according to the present invention binds or sites that are recognized thereby on HLA/NY-ESO include a plurality of amino acids and partial higher-order structures in the HLA/NY-ESO peptide.

The "antibody or the binding fragment thereof that binds to the same site" as the antibody according to the present invention or the binding fragment thereof is also within the scope of the present invention. The "antibody that binds to the same site" as a given antibody is another antibody that binds to a site on an antigen molecule recognized by such given antibody. If a second antibody binds to a partial peptide or partial conformation on an antigen molecule to which a first antibody binds, the first antibody and the second antibody can be evaluated to bind to the same site. When the first antibody of the present invention has the antigen-binding activity described in (a) above, the second antibody that binds to the same site on HLA/NY-ESO is highly likely to have similar activity, and such second antibody is thus within the scope of the present invention. An antibody that binds to HLA/NY-ESO competitively with the first antibody of the present invention having the antigen-binding activity described in (a) is within the scope of the present invention. An antibody that binds to a site on HLA/NY-ESO recognized by the monoclonal antibody of the present invention, an antibody that binds to HLA/NY-ESO competitively with the monoclonal antibody of the present invention, and binding fragments thereof preferably have at least one of in vitro cytotoxicity and in vivo antitumor activity described in (a) and properties described in (b) to (d), more preferably 3 or more thereof, and optimally all thereof.

A binding site of the antibody can be determined by a method well known to a person skilled in the art, such as an immunoassay technique. For example, a series of peptides are prepared by removing an antigen amino acid sequence from the C or N terminus as appropriate, reactivity of an antibody thereto is examined, a recognition site is roughly determined, a shorter peptide sequence is synthesized, and reactivity of an antibody thereto is examined. Thus, the binding site can be determined. Alternatively, a particular site or region of an amino acid sequence of an antigen or an antigen fragment peptide is deleted or substituted with another amino acid sequence, or a mutation is introduced into such site or region. By examining reactivity of an antibody to such peptide, the binding site can be determined. An antigen fragment peptide can be prepared by, for example, genetic recombination or peptide synthesis.

When an antibody binds to or recognizes a partial higher-order structure of an antigen, such antigen-binding site of the antibody can be determined by identifying an amino acid residue on an antigen adjacent to the antibody via x-ray structural analysis. For example, an antibody or a fragment thereof and an antigen or a fragment thereof are bound to each other, crystallized, and subjected to structural analysis. Thus, an amino acid residue on an antigen being at an interaction distance with the antibody can be identified. The interaction distance is 8 Å or less, preferably 6 Å or less, and more preferably 4 Å or less. One or more amino acid residues being at such an interaction distance with the antibody can constitute the antigen-binding site of the antibody (epitope). When there are two or more such amino acid residues, such amino acid residues may not be adjacent to each other on a one-dimensional sequence.

The anti-HLA/NY-ESO antibody according to the present invention or the binding fragment thereof specifically recognizes a plurality of amino acids in the HLA/NY-ESO amino acid sequence. An antibody or a binding fragment thereof that recognizes a plurality of amino acids, an antibody or a binding fragment thereof that binds to HLA/NY-ESO competitively with the antibody according to the present invention or the binding fragment thereof, and an antibody or a binding fragment thereof that has an interaction distance with such a plurality of amino acids are within the scope of the present invention. A multispecific antibody comprising such antibody or binding fragment thereof is also within the scope of the present invention.

6. Pharmaceutical Composition

The present invention encompasses an anti-cancer agent comprising, as an active ingredient, the anti-HLA/NY-ESO antibody according to the present invention or a multispecific molecule that binds to HLA/NY-ESO.

The anti-cancer agent of the present invention can be used for one type or two or more types of cancer species selected from carcinoma, sarcoma, lymphoma, leukemia, myeloma, germinoma, brain tumor, carcinoid, neuroblastoma, retinoblastoma, and nephroblastoma. Specific examples of carcinoma include kidney cancer, melanoma, squamous cell cancer, basal cell cancer, conjunctival cancer, oral cavity cancer, laryngeal cancer, pharyngeal cancer, thyroid gland cancer, lung cancer (non-small cell lung cancer (adenocarcinoma, epidermoid cancer, large cell cancer), and small cell lung cancer), breast cancer, esophageal cancer, gastric cancer, duodenal cancer, small bowel cancer, large bowel cancer, rectal cancer, appendiceal cancer, anal cancer, liver cancer, gallbladder cancer, bile duct cancer, pancreatic cancer, adrenal cancer, bladder cancer, prostate cancer, uterine cancer, and vaginal cancer. Specific examples of sarcoma include liposarcoma, angiosarcoma, chondrosarcoma, rhabdomyosarcoma, Ewing's sarcoma, osteosarcoma, undifferentiated pleomorphic sarcoma, myxofibrosarcoma, malignant peripheral neurilemmoma, retroperitoneal sarcoma, synoviosarcoma, uterine sarcoma, gastrointestinal stromal tumor, leiomyosarcoma, and epithelioid sarcoma. Specific examples of lymphoma include B-cell lymphoma, T/NK-cell lymphoma, and Hodgkin's lymphoma. Specific examples of leukemia include myelogenic leukemia, lymphatic leukemia, myeloproliferative disorder, and myelodysplastic syndrome. Specific examples of myeloma include multiple myeloma. Specific examples of germinoma include testicular cancer and ovarian cancer. Specific examples of brain tumor include neuroglioma and meningioma.

The anti-cancer agent of the present invention can contain the anti-HLA/NY-ESO antibody or a multispecific molecule that binds to HLA/NY-ESO in an amount effective for treatment, as well as pharmaceutically acceptable carriers, diluents, solubilizers, emulsifiers, preservatives, aids, and the like. The "pharmaceutically acceptable carriers" and the like can be suitably selected from a broad range according to the type of target disease and the dosage form of a drug. An administration method for the anti-cancer agent of the present invention can be suitably selected. For example, the anti-cancer agent can be injected, and local injection, intraperitoneal injection, selective intravenous infusion, intravenous injection, subcutaneous injection, organ perfusate infusion, and the like can be employed. Further, an injection solution can be formulated using a carrier comprising a salt solution, a glucose solution, or a mixture of salt water and a glucose solution, various types of buffer solutions, or the like. Further, a powder may be formulated and mixed with a liquid carrier to prepare an injection solution before use.

Other administration methods can be suitably selected along with development of a formulation. For example, oral solutions, powders, pills, capsules, tablets, and the like can be applied for oral administration. For oral solutions, oral liquid preparations such as suspensions and syrups can be produced using water, saccharides such as sucrose, sorbitol, and fructose, glycols such as PEG, oils such as sesame oil and soybean oil, preservatives such as alkyl parahydroxybenzoates, flavors such as strawberry flavor and peppermint, and the like. Powders, pills, capsules, and tablets can be formulated using excipients such as lactose, glucose, sucrose, and mannitol, disintegrating agents such as starch and alginate soda, lubricants such as magnesium stearate and talc, binders such as polyvinyl alcohol, hydroxypropyl cellulose, and gelatin, surfactants such as fatty acid esters, plasticizers such as glycerin, and the like. Tablets and capsules are preferred unit dosage forms for the composition of the present invention in that they are easily administered. Solid production carriers are used to produce tablets and capsules.

The effective dose of the anti-HLA/NY-ESO antibody or a multispecific molecule that binds to HLA/NY-ESO used for treatment can be changed according to the characteristics of the symptoms to be treated and the patient's age and condition and can be finally determined by a physician. For example, one dose is 0.0001 mg to 100 mg per kg of body weight. The predetermined dose may be administered once every one to 180 days, or the dose may be divided into two doses, three doses, four doses, or more doses per day at appropriate intervals.

The present invention also encompasses a polynucleotide encoding an amino acid sequence included in the anti-HLA/NY-ESO antibody according to the present invention or a multispecific molecule binding to HLA/NY-ESO, a vector comprising such a polynucleotide, a cell comprising such a polynucleotide or vector, and a pharmaceutical composition comprising, as an active ingredient, any of the polynucleotide, the vector and the cell. Such a pharmaceutical composition is preferably an anti-cancer agent.

In addition, the pharmaceutical composition of the present invention can be used in combination with other therapeutic agents or therapeutic techniques. Examples of other therapeutic agents or therapeutic techniques include, but are not particularly limited to, chemotherapeutic agents, radiation therapy, and biopharmaceutical products. The pharmaceutical composition of the present invention and other therapeutic agents can be administered simultaneously or according to a different schedule in the form of a single formulation or two or more different formulations containing the pharmaceutical composition of the present invention. Administration of the pharmaceutical composition can be performed in combination with other therapeutic techniques.

EXAMPLES

Hereafter, the present invention is described in greater detail with reference to the examples, although the present invention is not limited to these examples.

In the following examples, genetic engineering procedures were performed in accordance with the method described in Molecular Cloning (Sambrook, J., Fritsch, E. F. and Maniatis, T., Cold Spring Harbor Laboratory Press, 1989) and methods described in other experimental protocols employed by a person skilled in the art, unless otherwise specified. When a commercially available reagent or kit was to be used, the procedures in accordance with the instructions of such a commercial product were employed. Synthesis of primers required for gene synthesis or vector construction was outsourced, according to need (Fasmac Co., Ltd., Thermo Fisher Scientific, and Eurofins Genomics).

(Example 1) Acquisition of Human Antibody Phage Library-Derived Anti-HLA/NY-ESO Antibody 1)-1 Preparation of HLA/NY-ESO Antigen Protein Inclusion bodies prepared from *E. coli* cells (BL21 (DE3), Agilent Technologies) expressing the HLA-A*0201 (GenBank: ASA47534.1) truncate (biotin ligase recognition sequence added: SEQ ID NO: 33) and β2-microglobulin (UniProtKB-P61769: SEQ ID NO: 34) and the NY-ESO peptide: SLLMWITQC (SEQ ID NO: 1 of Sequence Listing) were subjected to refolding at a high dilution factor, and the HLA-A*0201/β2-microglobulin/NY-ESO peptide complex (hereafter, referred to as "HLA/NY-ESO") was then prepared using gel filtration columns (Superdex 200 10/300, GE Healthcare).

As a negative control antigen, the HLA-A*0201/β2-microglobulin/MAGEC-1 peptide complex (hereafter, referred to as "HLA/MC1") was prepared by refolding using the MAGEC-1 peptide: ILFGISLREV (SEQ ID NO: 2 of Sequence Listing). Further, the prepared HLA/NY-ESO and HLA/MC1 were biotinylated with *E. coli* biotin ligase and then fractionated using gel filtration columns (Superdex 200 10/300, GE Healthcare) to prepare biotinylated proteins.

1)-2 Isolation of scFv Capable of Binding to HLA/NY-ESO scFv binding to HLA/NY-ESO was isolated from the human antibody phage library. At the outset, phages were added to the biotinylated HLA/MC1-immobilized Dynabeads Streptavidin M-280 (Thermo Fisher Scientific), and unbound phages were collected. Subsequently, phages were added to the biotinylated HLA/NY-ESO-immobilized Dynabeads Streptavidin M-280Ag, and unbound phages were removed via washing using a magnet stand (DynaMag-2, Thermo Fisher Scientific).

Thereafter, *E. coli* (XL-1 Blue, Agilent Technologies) was infected with phages bound to HLA/NY-ESO, and the phages were collected and amplified. After a panning procedure was performed 3 times in total, the phages were transferred from the polyclonal phagemid to the *E. coli* expression vector comprising FLAG tag and a His tag added to the carboxyl terminus of scFv, the *E. coli* was transformed, scFv was expressed in the presence of IPTG (isopropyl-β-D-thiogalactopyranoside) (Sigma-Aldrich), and the expressed scFv was subjected to screening via ELISA.

1)-3 Screening of HLA/NY-ESO-Bound scFv Via ELISA

NeutrAvidin (Life Technologies) diluted to 1 µg/ml in PBS (0.01 M phosphate buffered saline containing 0.138 M sodium chloride and 0.0027 M potassium chloride (pH7.4), Sigma-Aldrich) was added in an amount of 50 µl each to a 384-well Maxi-sorp plate (Black, Nunc), and the place was allowed to stand at 4° C. overnight for immobilization. The plate was washed 3 times with PBS (ELISA buffer) containing 0.05% Tween-20 (BioRad), biotinylated HLA/NY-ESO, which was diluted to 1 µg/ml in PBS and used in Example 1)-2, was added, and the resultant was agitated at room temperature for 1 hour. The plate was washed 3 times with ELISA buffer, blocked with Blocker Casein (Thermo Fisher Scientific), and then washed 3 times with ELISA buffer. Thereafter, a culture solution of scFv-expressing *E. coli* was added, and the reaction was allowed to proceed at room temperature for 2 hours. After the resultant was washed 3 times with ELISA buffer, 50 µl of the horseradish peroxidase (HRP)-labeled anti-FLAG antibody (Sigma-Aldrich) diluted to 5,000-fold with ELISA buffer was added, and the reaction was allowed to proceed at room temperature for 1 hour. After the resultant was washed 5 times with ELISA buffer, the SuperSignal Pico ELISA Chemiluminescent substrate (Thermo Fisher Scientific) was added, chemiluminescence 10 minutes later was assayed using a plate reader (Envision 2104 Multilabel Reader, Perkin Elmer), and positive clones in HLA/NY-ESO-binding ELISA were then selected.

1)-4 Determination of Nucleotide Sequence and Amino Acid Sequence of ELISA-Positive Clone NY-R119

From among the ELISA-positive clones obtained in 1)-3, NY-R119 was selected as scFv exhibiting high binding affinity to HLA/NY-ESO and excellent recognition specificity. The nucleotide sequences of the heavy chain and light chain variable regions of NY-R119 were analyzed by the Dye Terminator method (BigDye®, Terminator v3.1, Thermo Fisher Scientific). Sequences of the primers used for sequence analysis are as demonstrated below.

```
Primer A:
    (SEQ ID NO: 3 of Sequence Listing (FIG. 10))
5'-CTCTTCGCTATTACGCCAGCTGGCGA-3'

Primer B:
    (SEQ ID NO: 4 of Sequence Listing (FIG. 11))
5'-ATAACAATTTCACACAGGAAACAGCTATGA-3'
```

SEQ ID NO: 5 (FIG. 12) shows the determined nucleotide sequence of cDNA encoding the heavy chain variable region of NY-R119 and SEQ ID NO: 6 (FIG. 13) shows the determined amino acid sequence thereof.

SEQ ID NO: 7 (FIG. 14) shows the determined nucleotide sequence of cDNA encoding the light chain variable region of NY-R119 and SEQ ID NO: 8 (FIG. 15) shows the determined amino acid sequence thereof.

The CDR sequences of NY-R119 in accordance with the definition of CDR provided by IMGT are represented as follows: CDRH1: SEQ ID NO: 54 (FIG. 61); CDRH2: SEQ ID NO: 55 (FIG. 61); CDRH3: SEQ ID NO: 56 (FIG. 61); CDRL1: SEQ ID NO: 57 (FIG. 61); CDRL2: SEQ ID NO: 58 (FIG. 61); and CDRL3: SEQ ID NO: 59 (FIG. 61).

1)-5 Preparation of NYA-0001

1)-5-1 Construction of NYA-0001 Expression Vector

In order to prepare various evaluation samples, an NY-R119 expression vector for mammalian cells was constructed. NY-R119 expressed in a cultured mammalian cell was designated as "NYA-0001." The amino acid sequences constituting the scFv region, the heavy chain and light chain variable regions, and CDRH1 to 3 and CDRL1 to 3 of NY-R119 are identical to those of NYA-0001. A DNA fragment encoding NYA-0001 was inserted into an expression vector for mammal cells comprising pcDNA3.3

(Thermo Fisher Scientific) as the backbone using the In-Fusion HD cloning kit (CLONTECH) to construct the NYA-0001 expression vector.

The nucleotide sequence of the constructed NYA-0001 expression vector was reanalyzed, and the nucleotide sequence of the full-length NYA-0001 was found to be the nucleotide sequence as shown in SEQ ID NO: 69 of Sequence Listing (FIG. 70). On the basis of the nucleotide sequence, in addition, the amino acid sequence of the entire NYA-0001 encoded thereby was found to be the amino acid sequence as shown in SEQ ID NO: 70 (FIG. 71). In such an amino acid sequence, amino acids 1 to 19 constitute a signal sequence, amino acids 21 to 266 constitute NYA-0001, and amino acids 267 to 292 constitute a Flag-His tag. Also, amino acids 46 to 53 constitute CDRH1, amino acids 71 to 78 constitute CDRH2, and amino acids 117 to 129 constitute CDRH3. Also, amino acids 181 to 188 constitute CDRL1, amino acids 206 to 208 constitute CDRL2, and amino acids 245 to 256 constitute CDRL3.

1)-5-2 Expression and Purification of NYA-0001

Expi293F cells (Thermo Fisher Scientific) were subcultured in accordance with the instructions. A culture solution of the Expi293F cells in a logarithmic growth phase was diluted to $2.5 \times 10^6$ cells/ml in the Expi293 Expression medium (Thermo Fisher Scientific) and used for NYA-0001 production. The NYA-0001 expression vector (0.3 mg) and 0.9 mg of polyethyleneimine (Polyscience #24765) were added to 20 ml of Opti-Pro SFM medium (Thermo Fisher Scientific). The mixture was stirred gently, allowed to stand for five minutes, and then added to the Expi293F cells. The culture supernatant obtained by agitation culture in an incubator at 37° C. in the presence of 8% $CO_2$ at 135 rpm for 6 days was filtered through a 0.2 μm-filter (Millipore). Thus, the culture supernatant of NYA-0001 was obtained. Purification was carried out by elution and concentration using Ni Sepharose excel (GE Healthcare) and then filtration through a gel filtration column (Superdex 200 Increase, GE Healthcare) equilibrated with 25 mM histidine, 300 mM NaCl, and 5% Sorbitol, pH6.0. Purified protein samples were subjected to analytical size exclusion chromatography (SEC), the degree of purification and the concentration were determined, and the samples were then subjected to various types of evaluation.

(Example 2) Preparation of NYA-0001 Mutant

2)-1 Acquisition of NYA-0001 Mutant

A phage library was constructed by a method in which the NYA-0001 gene was used as a template and a mutation was introduced via PCR (i.e., the error-prone-based library) or a method in which an oligomer was synthesized through random mutation of 20 types of amino acids for each of all CDR residues (i.e., the oligo-based library), clones with high binding affinity were screened for, NYA-0060, NYA-0068, and NYA-0082 were obtained as mutants with high binding affinity, and the nucleotide sequences thereof were then determined.

SEQ ID NO: 9 (FIG. 16) shows the nucleotide sequence of cDNA encoding the heavy chain variable region of NYA-0060 and SEQ ID NO: 10 (FIG. 17) shows the amino acid sequence thereof.

SEQ ID NO: 11 (FIG. 18) shows the nucleotide sequence of cDNA encoding the light chain variable region of NYA-0060 and SEQ ID NO: 12 (FIG. 19) shows the amino acid sequence thereof.

SEQ ID NO: 13 (FIG. 20) shows the nucleotide sequence of cDNA encoding the heavy chain variable region of NYA-0068 and SEQ ID NO: 14 (FIG. 21) shows the amino acid sequence thereof.

SEQ ID NO: 15 (FIG. 22) shows the nucleotide sequence of cDNA encoding the light chain variable region of NYA-0068 and SEQ ID NO: 16 (FIG. 23) shows the amino acid sequence thereof.

SEQ ID NO: 17 (FIG. 24) shows the nucleotide sequence of cDNA encoding the heavy chain variable region of NYA-0082 and SEQ ID NO: 18 (FIG. 25) shows the amino acid sequence thereof.

SEQ ID NO: 19 (FIG. 26) shows the nucleotide sequence of cDNA encoding the light chain variable region of NYA-0082 and SEQ ID NO: 20 (FIG. 27) shows the amino acid sequence thereof.

2)-2 Preparation of Mutants with High Binding Affinity Using the Sites of Mutation and Combination Identified in NYA-0060, NYA-0068, and NYA-0082

DNA fragments encoding NYA-1163 and NYA-2023 with sites of mutation of NYA-0060 and NYA-0068 were inserted into an expression vector for mammal cells comprising pcDNA3.3 (Thermo Fisher Scientific) as the backbone using the In-Fusion HD cloning kit (CLONTECH) to construct the scFv expression vectors for mammalian cell culture.

According to the sites of mutation and combination thereof identified in NYA-0060, NYA-0068, and NYA-0082, so NYA-2027, NYA-1143, and NYA-2143 were designed. DNA fragments encoding target scFv were inserted into the NYA-0001 expression vector constructed in 1)-5 via site-directed mutagenesis or an expression vector for mammal cells comprising pcDNA3.3 (Thermo Fisher Scientific) as the backbone using the In-Fusion HD cloning kit (CLONTECH) to construct the scFv expression vectors for mammal cell culture.

The nucleotide sequences of the constructed scFv expression vectors were reanalyzed, and the nucleotide sequence of the full-length NYA-1163 was found to be the nucleotide sequence as shown in SEQ ID NO: 21 of Sequence Listing (FIG. 28).

The nucleotide sequence of the full-length NYA-2023 was found to be the nucleotide sequence as shown in SEQ ID NO: 22 of Sequence Listing (FIG. 29).

The nucleotide sequence of the full-length NYA-2027 was found to be the nucleotide sequence as shown in SEQ ID NO: 23 of Sequence Listing (FIG. 30).

The nucleotide sequence of the full-length NYA-1143 was found to be the nucleotide sequence as shown in SEQ ID NO: 24 of Sequence Listing (FIG. 31).

The nucleotide sequence of the full-length NYA-2143 was found to be the nucleotide sequence as shown in SEQ ID NO: 25 of Sequence Listing (FIG. 32).

On the basis of the nucleotide sequences above, in addition, the amino acid sequences of the full-length NYA-1163, NYA-2023, NYA-2027, NYA-1143, and NYA-2143 encoded thereby were identified.

The amino acid sequence of the full-length NYA-1163 is the amino acid sequence as shown in SEQ ID NO: 26 of the Sequence Listing (FIG. 33). In such an amino acid sequence, amino acids 1 to 19 constitute a signal sequence, amino acids 21 to 266 constitute NYA-1163, and amino acids 267 to 292 constitute a Flag-His tag. Also, amino acids 46 to 53 constitute CDRH1, amino acids 71 to 78 constitute CDRH2, and amino acids 117 to 129 constitute CDRH3. Also, amino acids 181 to 188 constitute CDRL1, amino acids 206 to 208 constitute CDRL2, and amino acids 245 to 256 constitute CDRL3.

The amino acid sequence of the full-length NYA-2023 is the amino acid sequence as shown in SEQ ID NO: 27 of the Sequence Listing (FIG. 34). In such an amino acid sequence, amino acids 1 to 19 constitute a signal sequence, amino acids 21 to 266 constitute NYA-2023, and amino acids 267 to 292 constitute a Flag-His tag. Also, amino acids 46 to 53 constitute CDRH1, amino acids 71 to 78 constitute CDRH2, and amino acids 117 to 129 constitute CDRH3. Also, amino acids 181 to 188 constitute CDRL1, amino acids 206 to 208 constitute CDRL2, and amino acids 245 to 256 constitute CDRL3.

The amino acid sequence of the full-length NYA-2027 is the amino acid sequence as shown in SEQ ID NO: 28 of the Sequence Listing (FIG. 35). In such an amino acid sequence, amino acids 1 to 19 constitute a signal sequence, amino acids 21 to 266 constitute NYA-2027, and amino acids 267 to 292 constitute a Flag-His tag. Also, amino acids 46 to 53 constitute CDRH1, amino acids 71 to 78 constitute CDRH2, and amino acids 117 to 129 constitute CDRH3. Also, amino acids 181 to 188 constitute CDRL1, amino acids 206 to 208 constitute CDRL2, and amino acids 245 to 256 constitute CDRL3.

The amino acid sequence of the full-length NYA-1143 is the amino acid sequence as shown in SEQ ID NO: 26 of the Sequence Listing (FIG. 36). In such an amino acid sequence, amino acids 1 to 19 constitute a signal sequence, amino acids 21 to 266 constitute NYA-1143, and amino acids 267 to 292 constitute a Flag-His tag. Also, amino acids 46 to 53 constitute CDRH1, amino acids 71 to 78 constitute CDRH2, and amino acids 117 to 129 constitute CDRH3. Also, amino acids 181 to 188 constitute CDRL1, amino acids 206 to 208 constitute CDRL2, and amino acids 245 to 256 constitute CDRL3.

The amino acid sequence of the full-length NYA-2143 is the amino acid sequence as shown in SEQ ID NO: 30 of the Sequence Listing (FIG. 37). In such an amino acid sequence, amino acids 1 to 19 constitute a signal sequence, amino acids 21 to 266 constitute NYA-2143, and amino acids 267 to 292 constitute a Flag-His tag. Also, amino acids 46 to 53 constitute CDRH1, amino acids 71 to 78 constitute CDRH2, and amino acids 117 to 129 constitute CDRH3. Also, amino acids 181 to 188 constitute CDRL1, amino acids 206 to 208 constitute CDRL2, and amino acids 245 to 256 constitute CDRL3.

Figure 62:
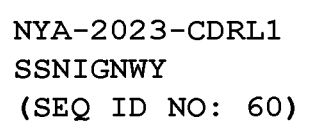
Figure 63:
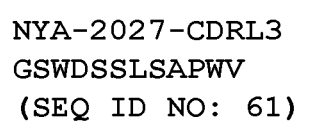

All the CDR sequences of NYA-1163 are identical to the CDR sequences of NYA-0001. The CDR sequences of NYA-1143, NYA-2143, and NYA-2023 are identical to each other, and these sequences are represented as follows: CDRH1: SEQ ID NO: 54 (FIG. 61); CDRH2: SEQ ID NO: 55 (FIG. 61); CDRH3: SEQ ID NO: 56 (FIG. 61); CDRL1: SEQ ID NO: 60 (FIG. 62); CDRL2: SEQ ID NO: 58 (FIG. 61); and CDRL3: SEQ ID NO: 59 (FIG. 61). The CDR sequences of NYA-2027 are represented as follows: CDRH1: SEQ ID NO: 54 (FIG. 61); CDRH2: SEQ ID NO: 55 (FIG. 61); CDRH3: SEQ ID NO: 56 (FIG. 61); CDRL1: SEQ ID NO: 57 (FIG. 61); CDRL2: SEQ ID NO: 58 (FIG. 61); and CDRL3: SEQ ID NO: 61 (FIG. 63).

Also, NYA-1154 comprising sites of binding and mutation observed at the time of screening of clones with high binding affinity in combination was designed and introduced into the NYA-0001 expression vector via site-directed mutagenesis to construct the NYA-1154 expression vector comprising pcDNA3.3 (Thermo Fisher Scientific) as the backbone. The nucleotide sequences of the constructed scFv expression vectors were reanalyzed and found to be the nucleotide sequence as shown in SEQ ID NO: 31 (FIG. 38). On the basis of the nucleotide sequences above, the amino acid sequence of the full-length NYA-1154 encoded thereby was identified (SEQ ID NO: 32 (FIG. 39)). In such an amino acid sequence, amino acids 1 to 19 constitute a signal sequence, amino acids 21 to 266 constitute NYA-1154, and amino acids 267 to 292 constitute a Flag-His tag. Also, amino acids 46 to 53 constitute CDRH1, amino acids 71 to 78 constitute CDRH2, and amino acids 117 to 129 constitute CDRH3. Also, amino acids 181 to 188 constitute CDRL1, amino acids 206 to 208 constitute CDRL2, and amino acids 245 to 256 constitute CDRL3.

The CDR sequences of NYA-1154 are represented as follows: CDRH1: SEQ ID NO: 54 (FIG. 61); CDRH2: SEQ ID NO: 55 (FIG. 61); CDRH3: SEQ ID NO: 62 (FIG. 64); CDRL1: SEQ ID NO: 57 (FIG. 61); CDRL2: SEQ ID NO: 58 (FIG. 61); and CDRL3: SEQ ID NO: 63 (FIG. 64).

NYA-1163, NYA-2023, NYA-2027, NYA-1143, NYA-2143, and NYA-1154 were expressed in the same manner as in 1)-5-2 to purify the target scFv constructs. Purified protein samples were subjected to analytical SEC, the degree of purification and the concentration were determined, and the samples were then subjected to various assays.

2)-3 Preparation of NYA-1143 Mutant

2)-3-1 Preparation of NYA-2035

Figure 65:
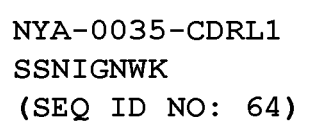

NYA-2035 was designed as an NYA-1143 mutant and introduced into the NYA-1143 expression vector for mammal cell culture via site-directed mutagenesis to construct an NYA-2035 expression vector. The nucleotide sequence of the constructed scFv expression vector was reanalyzed and found to be the nucleotide sequence as shown in SEQ ID NO: 35 (FIG. 42). On the basis of the nucleotide sequences above, the nucleotide sequence of the full-length NYA-2025 encoded thereby was determined (SEQ ID NO: 36 (FIG. 43)). In such an amino acid sequence, amino acids 1 to 19 constitute a signal sequence, amino acids 21 to 266 constitute NYA-2035, and amino acids 267 to 292 constitute a Flag-His tag. Also, amino acids 46 to 53 constitute CDRH1, amino acids 71 to 78 constitute CDRH2, and amino acids 117 to 129 constitute CDRH3. Also, amino acids 181 to 188 constitute CDRL1, amino acids 206 to 208 constitute CDRL2, and amino acids 245 to 256 constitute CDRL3. The CDR sequences of NYA-2035 in accordance with the definition of CDR provided by IMGT are represented as follows: CDRH1: SEQ ID NO: 54 (FIG. 61); CDRH2: SEQ ID NO: 55 (FIG. 61); CDRH3: SEQ ID NO: 56 (FIG. 61); CDRL1: SEQ ID NO: 64 (FIG. 65); CDRL2: SEQ ID NO: 58 (FIG. 61); and CDRL3: SEQ ID NO: 59 (FIG. 61).

2)-3-2 Preparation of NYA-1143 CDR Graft Mutant

In order to improve physical properties, the NYA-1143 CDR graft mutant was designed. The VH and VL framework sequences of NYA-1143 were compared with the framework sequences of the human subgroup consensus sequence or the germline sequence defined in KABAT et al. (Sequences of Proteins of Immunological Interest, 5th Ed., Public Health Service National Institutes of Health, Bethesda, MD., 1991). As a result, a consensus sequence between the human germline sequence IGHV3_30*15 and the human γ chain subgroup 3 was selected for VH and the human germline sequence IGLV1-44*01 was selected for VL as acceptors having a high identity in the framework regions. Subsequently, amino acid residues in the framework region of an acceptor were aligned with the amino acid residues of NYA-1143 to identify different amino acid residues.

Subsequently, a three-dimensional model of NYA-1143 was used to select framework residues to be transferred onto an acceptor with reference to the criteria provided by Queen et al. (Proc. Natl. Acad. Sci. U.S.A., 86, 10029-10033, 1989). In accordance with the technique described above, CDR graft mutant amino acid sequences of the VH regions of NYA-1143; i.e., NYA-1143-VH01, NYA-1143-VH02, and NYA-1143-VH03, were designed. Such amino acid sequences are as shown in SEQ ID NO: 37 (FIG. 44), SEQ ID NO:38 (FIG. 45), and SEQ ID NO:39 (FIG. 46). As a CDR graft mutant amino acid sequence of a VL region of NYA-1143, NYA-1143-VL01 was designed. Such an amino acid sequence is as shown in SEQ ID NO: 40 (FIG. 47).

Various scFv constructs were designed using the VH and VL sequences in combination. scFv resulting from substitution of the VH region of NYA-1143 with the amino acid sequence of NYA-1143-VH01 was designated as NYA-2044. scFv resulting from substitution of the VL region of NYA-2044 with the amino acid sequence of NYA-1143-VL01 was designated as NYA-2045.

scFv resulting from substitution of the VH region of NYA-1143 with the amino acid sequence of NYA-1143-VH02 was designated as NYA-2047. scFv resulting from substitution of the VL region of NYA-2047 with the amino acid sequence of NYA-1143-VL01 was designated as NYA-2048.

scFv resulting from substitution of the VH region of NYA-1143 with the amino acid sequence of NYA-1143-VH03 was designated as NYA-2060. scFv resulting from substitution of the VL region of NYA-2060 with the amino acid sequence of NYA-1143-VL01 was designated as NYA-2061.

The DNA fragments of the various designed NYA-1143 CDR graft mutants were fully synthesized (Fasmac Co., Ltd.) and bound to each other using the In-Fusion HD Cloning kit (CLONTECH) to construct the scFv expression vector for mammal cells comprising pcDNA3.3 (Thermo Fisher Scientific) as the backbone.

The nucleotide sequences of the constructed scFv expression vectors were reanalyzed, the nucleotide sequence of the full-length NYA-2044 was found to be the nucleotide sequence as shown in SEQ ID NO: 41 of the Sequence Listing (FIG. 48).

The nucleotide sequence of the full-length NYA-2045 was found to be the nucleotide sequence as shown in SEQ ID NO: 42 of the Sequence Listing (FIG. 49).

The nucleotide sequence of the full-length NYA-2047 was found to be the nucleotide sequence as shown in SEQ ID NO: 43 of the Sequence Listing (FIG. 50).

The nucleotide sequence of the full-length NYA-2048 was found to be the nucleotide sequence as shown in SEQ ID NO: 44 of the Sequence Listing (FIG. 51).

The nucleotide sequence of the full-length NYA-2060 was found to be the nucleotide sequence as shown in SEQ ID NO: 45 of the Sequence Listing (FIG. 52).

The nucleotide sequence of the full-length NYA-2061 was found to be the nucleotide sequence as shown in SEQ ID NO: 46 of the Sequence Listing (FIG. 53).

On the basis of the nucleotide sequences above, the amino acid sequences of the full-length NYA-2044, NYA-2045, NYA-2047, NYA-2048, NYA-2060, and NYA-2061 encoded thereby were identified. The CDR sequences of NYA-2044, NYA-2045, NYA-2047, NYA-2048, NYA-2060, and NYA-2061 are identical to those of NYA-1143.

The amino acid sequence of the full-length NYA-2044 is the amino acid sequence as shown in SEQ ID NO: 47 of the Sequence Listing (FIG. 54). In such an amino acid sequence, amino acids 1 to 19 constitute a signal sequence, amino acids 21 to 266 constitute NYA-2044, and amino acids 267 to 292 constitute a Flag-His tag. Also, amino acids 46 to 53 constitute CDRH1, amino acids 71 to 78 constitute CDRH2, and amino acids 117 to 129 constitute CDRH3. Also, amino acids 181 to 188 constitute CDRL1, amino acids 206 to 208 constitute CDRL2, and amino acids 245 to 256 constitute CDRL3.

The amino acid sequence of the full-length NYA-2045 is the amino acid sequence as shown in SEQ ID NO: 48 of the Sequence Listing (FIG. 55). In such an amino acid sequence, amino acids 1 to 19 constitute a signal sequence, amino acids 21 to 266 constitute NYA-2045, and amino acids 267 to 292 constitute a Flag-His tag. Also, amino acids 46 to 53 constitute CDRH1, amino acids 71 to 78 constitute CDRH2, and amino acids 117 to 129 constitute CDRH3. Also, amino acids 181 to 188 constitute CDRL1, amino acids 206 to 208 constitute CDRL2, and amino acids 245 to 256 constitute CDRL3.

The amino acid sequence of the full-length NYA-2047 is the amino acid sequence as shown in SEQ ID NO: 50 of the Sequence Listing (FIG. 57). In such an amino acid sequence, amino acids 1 to 19 constitute a signal sequence, amino acids 21 to 266 constitute NYA-2047, and amino acids 267 to 292 constitute a Flag-His tag. Also, amino acids 46 to 53 constitute CDRH1, amino acids 71 to 78 constitute CDRH2, and amino acids 117 to 129 constitute CDRH3. Also, amino acids 181 to 188 constitute CDRL1, amino acids 206 to 208 constitute CDRL2, and amino acids 245 to 256 constitute CDRL3.

The amino acid sequence of the full-length NYA-2048 is the amino acid sequence as shown in SEQ ID NO: 51 of the Sequence Listing (FIG. 58). In such an amino acid sequence, amino acids 1 to 19 constitute a signal sequence, amino acids 21 to 266 constitute NYA-2048, and amino acids 267 to 292 constitute a Flag-His tag. Also, amino acids 46 to 53 constitute CDRH1, amino acids 71 to 78 constitute CDRH2, and amino acids 117 to 129 constitute CDRH3. Also, amino acids 181 to 188 constitute CDRL1, amino acids 206 to 208 constitute CDRL2, and amino acids 245 to 256 constitute CDRL3.

The amino acid sequence of the full-length NYA-2060 is the amino acid sequence as shown in SEQ ID NO: 52 of the Sequence Listing (FIG. 59). In such an amino acid sequence, amino acids 1 to 19 constitute a signal sequence, amino acids 21 to 266 constitute NYA-2060, and amino acids 267 to 292 constitute a Flag-His tag. Also, amino acids 46 to 53 constitute CDRH1, amino acids 71 to 78 constitute CDRH2, and amino acids 117 to 129 constitute CDRH3. Also, amino acids 181 to 188 constitute CDRL1, amino acids 206 to 208 constitute CDRL2, and amino acids 245 to 256 constitute CDRL3.

The amino acid sequence of the full-length NYA-2061 is the amino acid sequence as shown in SEQ ID NO: 53 of the Sequence Listing (FIG. 60). In such an amino acid sequence, amino acids 1 to 19 constitute a signal sequence, amino acids 21 to 266 constitute NYA-2061, and amino acids 267 to 292 constitute a Flag-His tag. Also, amino acids 46 to 53 constitute CDRH1, amino acids 71 to 78 constitute CDRH2, and amino acids 117 to 129 constitute CDRH3. Also, amino acids 181 to 188 constitute CDRL1, amino acids 206 to 208 constitute CDRL2, and amino acids 245 to 256 constitute CDRL3.

2)-3-3 Expression and Purification of NYA-1143 Mutants

NYA-2035, NYA-2044, NYA-2045, NYA-2047, NYA-2048, NYA-2060, and NYA-2061 prepared in 2)-3-1 and 2)-3-2 were expressed in the same manner as in 1)-5-2 to purify the target scFv constructs. Purified protein samples were subjected to analytical SEC, the degree of purification and the concentration were determined, and the samples were then subjected to various assays.

(Example 3) Preparation of scFv of
Anti-HLA/NY-ESO Reference Antibody

The scFv constructs of the antibodies 3M4E5 and T1 with high binding affinity to HLA/NY-ESO (WO2010/106431) were designed; 3M4E5 scFv was designated as NYC-0003, and T1 scFv was designated as NYC-0004.

The DNA fragments of NYC-0003 and NYC-0004 were fully synthesized (Thermo Fisher Scientific), and the scFv expression vector for mammal cells comprising pcDNA3.3 (Thermo Fisher Scientific) as the backbone was constructed using the In-Fusion HD Cloning kit (CLONTECH).

The nucleotide sequences of the constructed scFv expression vectors were reanalyzed, and the nucleotide sequences of the full-length NYC-0003 and NYC-0004 were found to be the nucleotide sequences as shown in SEQ ID NO: 65 of the Sequence Listing (FIG. 66) and SEQ ID NO: 66 thereof (FIG. 67). On the basis of the nucleotide sequences, the amino acid sequence of the full-length NYC-0003 encoded thereby was found to be the amino acid sequence as shown in SEQ ID NO: 67 (FIG. 68), and the amino acid sequence of the full-length NYC-0004 was found to be the amino acid sequence as shown in SEQ ID NO: 68 (FIG. 69).

NYC-0003 and NYC-0004 were expressed in the same manner as in 1)-5-2 to purify the target scFv constructs. Purified protein samples were subjected to analytical SEC, the degree of purification and the concentration were determined, and the samples were then subjected to various assays.

(Example 4) Evaluation of Binding Affinity to
HLA/NY-ESO Using Biacore

With the use of Biacore T200, anti-HLA/NY-ESO scFv was captured as a ligand by the immobilized anti-His antibody, and the antigen was assayed as an analyte. As the antigen, HLA/NY-ESO prepared in 1)-1 was used. The anti-His antibody (His Capture kit, GE Healthcare) was immobilized on Sensor Chip CM5 (GE Healthcare) in accordance with the instructions of the kit. The anti-HLA/NY-ESO scFv constructs diluted to 0.5 µg/ml in HBS-EP+ (GE Healthcare) to be evaluated were brought into contact therewith at 10 µl/min for 60 seconds for immobilization. Thereafter, the samples were added to the HLA/NY-ESO analytes diluted to various levels with HBS-EP+ at a flow rate of 30 µl/min for 120 seconds and dissociation was assayed for 600 seconds. The results of the calculation obtained by such single cycle kinetics analysis, $K_D$, are shown in Table 1. In comparison with the parent antibody NYA-0001, all the mutants thereof were found to exhibit higher binding affinity to HLA/NY-ESO. In comparison with NYC-0004 NYA-1143, NYA-2023, NYA-2143, NYA-2044, NYA-2045, NYA-2060, and NYA-2061 were, in addition, found to exhibit higher binding affinity, and, in particular, NYA-1143, NYA-2044, NYA-2045, and NYA-2143 exhibited $K_D$ of 1 nM or lower.

TABLE 1

| Clone name | $K_D$ (nM) |
|---|---|
| NYA-0001 | 33.8 |
| NYA-1143 | 1.0 |
| NYA-1163 | 13.0 |

TABLE 1-continued

| Clone name | $K_D$ (nM) |
|---|---|
| NYA-2023 | 2.4 |
| NYA-2027 | 11.2 |
| NYA-2035 | 3.2 |
| NYA-2044 | 0.8 |
| NYA-2045 | 0.8 |
| NYA-2047 | 5.3 |
| NYA-2048 | 6.3 |
| NYA-2060 | 1.1 |
| NYA-2061 | 1.5 |
| NYA-2143 | 0.9 |
| NYC-0003 | 8.1 |
| NYC-0004 | 2.8 |

(Example 5) Analysis of Recognized Amino Acid
in NY-ESO Peptide of Anti-HLA/NY-ESO scFv The concentration of the T2 human lymphoblast fusion cells (ATCC) was adjusted to an adequate level in AIM-V medium (Thermo Fisher Scientific) containing 20% FBS, a solution of the NY-ESO peptide (SEQ ID NO: 1), the point-mutant NY-ESO peptides 1F, 2M, 3A, 4A, 5A, 6L, 7F, 8A, and 9A (SEQ ID NO: 121 (FIG. 122), SEQ ID NO: 122 (FIG. 123), SEQ ID NO: 123 (FIG. 124), SEQ ID NO: 124 (FIG. 125), SEQ ID NO: 125 (FIG. 126), SEQ ID NO: 126 (FIG. 127), SEQ ID NO: 127 (FIG. 128), SEQ ID NO: 128 (FIG. 129), and SEQ ID NO: 129 (FIG. 130)), or the gp100 peptide (SEQ ID NO: 130 (FIG. 131)) (Sigma Genosys) dissolved to 5 mM in DMSO was added to result in a final concentration of 50 µM, or DMSO was added in an amount of 1/100, and the resulting mixture was incubated at 37° C. for 4 hour. The resultant was washed two times in the AIM-V medium containing 20% FBS, the concentration thereof was adjusted to an adequate level with PBS containing 5% FBS, the LIVE/DEAD Fixable Dead Cell Stain Kit (Thermo Fisher Scientific) was added thereto, and the resultant was allowed to stand at 4° C. for 30 minutes. The cells were washed 2 times in PBS containing 5% FBS, the washed cells were divided into two groups, the cells in PBS containing 5% FBS were seeded on a 96-well U-bottom microplate at $10^5$ cells/well, and the plate was subjected to centrifugation, followed by removal of the supernatant. Anti-HLA/NY-ESO scFv diluted to 100 nM with PBS containing 5% FBS was added at 25 µl/well to one of the divided cells, and the resultant was allowed to stand at 4° C. for 30 minutes. The cells were washed 2 times in PBS containing 5% FBS, Penta-His Alexa Fluor488 (QIAGEN) diluted in PBS containing 5% FBS was added at 25 µl/well, and the resultant was allowed to stand at 4° C. for 30 minutes. The cells were washed 2 times in PBS containing 5% FBS, Anti-mouse-IgG Alexa Fluor488 (Thermo Fisher Scientific) diluted in PBS containing 5% FBS was added at 25 µl/well, and the resultant was allowed to stand at 4° C. for 30 minutes. The cells were washed 2 times in PBS containing 5% FBS, immobilized with Mildform 10 N (FUJIFILM Wako Pure Chemical Corporation) overnight, and resuspended in PBS containing 5% FBS. For standardization with the amount of the HLA/peptide complex, the HLA-A2 antibody BB7.2-Alexa Fluor 488 diluted to 10 µg/ml in PBS containing 5% FBS or mouse IgG2b-Alexa Fluor 488 was added at 25 µl/well to the other group of cells, and the resultant was allowed to stand at 4° C. for 30 minutes. The cells were washed 2 times in PBS containing 5% FBS, immobilized with Mildform 10 N (FUJIFILM Wako Pure Chemical Corporation) overnight, and resuspended in PBS containing 5% FBS. The cell suspensions were subjected to detection using a flow cytometer (CantoII, Becton Dickinson). Data analysis was performed using Flowjo (Treestar), and the geometric mean fluorescence intensity (gMFI) of Alexa Fluor 488 in a T2 cell fraction from which dead cells were removed was measured. The standardized gMFI indicating the binding affinity of each scFv standardized with the amount of the HLA/peptide complex on the T2 cells was determined in accordance with the following equation.

Standardized gMFI=$(A/B)/((C/D)/(E/F))$

A/B=Relative gMFI
A: gMFI of T2 cells supplemented with DMSO or peptide in the presence of antibody
B: gMFI of T2 cells supplemented with DMSO or peptide
(C/D)/(E/F)=Corrected amount of HLA/peptide complex of T2 cells supplemented with DMSO or peptide
C: gMFI of T2 cells supplemented with DMSO or peptide in the presence of HLA-A2 antibody
D: gMFI of T2 cells supplemented with DMSO or peptide in the presence of mouse IgG2b antibody or peptide
E: gMFI of T2 cells supplemented with DMSO containing HLA-A2 antibody
F: gMFI of T2 cells supplemented with DMSO containing mouse IgG2b antibody As shown in FIG. 1, anti-HLA/NY-ESO scFv: NYA-0001, 1143, 2044, 2045, 2047, 2048, 2060, and 2061, exhibited binding affinity to T2 cells supplemented with peptides comprising point mutations introduced into amino acids 1, 4, 5, and 7 decreased to a half or lower, compared with the wild-type NY-ESO peptide. This indicates that such scFv recognizes amino acids 1, 4, 5, and 7 of the NY-ESO peptide. This also indicates that NYA-1154 recognizes amino acids 1 and 5, NYA-1163 recognizes amino acids 1, 3, 4, 5, 6, and 7, NYA-2023, 2027, and 2035 recognize amino acids 1, 4, and 5, and NYA-2143 recognizes amino acids 1, 5, and 7. This further indicates that NYC-0003 and 0004 recognize amino acid 4 and 5.

(Example 6) Evaluation of Antigen-Binding Specificity of Anti-HLA/NY-ESO scFv

In order to search for a human peptide having an amino acid sequence similar but not identical to the amino acid sequence of the NY-ESO peptide: SLLMWITQC (SEQ ID NO: 1) to which the antibody may bind (hereafter such peptide is referred to as a "homologous peptide") from among human proteomes (Swiss-Prot), a 9-mer peptide comprising amino acids 1, 4, and 5 that are consistent with those of peptides recognized by the antibody was searched. The searched 9-mer peptide was analyzed using NetMHC-Pan2.8 concerning binding affinity to HLA-A0201, and IC50 thereof was predicted to be 500 nM or lower. The 9-mer peptide shown in FIG. 2A was selected as a homologous peptide for evaluation of binding specificity of anti-HLA/NY-ESO scFv. The concentration of the T2 cells was adjusted to an adequate level in AIM-V medium (Thermo Fisher Scientific) containing 20% FBS, a solution of the NY-ESO peptide (SEQ ID NO: 1), the homologous peptides DOLPP1, IL20RB, PRKD2, CD163, and P2RY8 (SEQ ID NO: 131 (FIG. 132), SEQ ID NO:132 (FIG. 133), SEQ ID NO:133 (FIG. 134), SEQ ID NO:134 (FIG. 135), and SEQ ID NO:135 (FIG. 136)), or the gp100 peptide (SEQ ID NO: 130 (FIG. 131)) (Sigma Genosys) dissolved to 5 mM in DMSO was added to result in a final concentration of 50 µM, or DMSO was added in an amount of 1/100, and binding affinity of the antibodies was evaluated in the same manner as in Example 5. The standardized gMFI indicating the binding affinity of each scFv standardized with the amount of the HLA/peptide complex on the T2 cells was determined in accordance with the following equation.

Standardized gMFI=$(A/B)/((C/D)/(E/F))$

A/B=Relative gMFI
A: gMFI of T2 cells supplemented with DMSO or peptide in the presence of antibody
B: gMFI of T2 cells supplemented with DMSO or peptide
(C/D)/(E/F)=Corrected amount of HLA/peptide complex of T2 cells supplemented with DMSO or peptide
C: gMFI of T2 cells supplemented with DMSO containing HLA-A2 antibody or peptide
D: gMFI of T2 cells supplemented with DMSO or peptide in the presence of mouse IgG2b antibody
E: gMFI of T2 cells supplemented with DMSO containing HLA-A2 antibody
F: gMFI of T2 cells supplemented with DMSO containing mouse IgG2b antibody As shown in FIG. 2B, anti-HLA/NY-ESO scFv: NYA-0001, 1143, 1163, 2023, 2027, 2035, 2044, 2045, 2047, 2048, 2060, 2061, and 2143, did not bind to T2 cells supplemented with any homologous peptides. This indicates that such scFv has high specificity. In contrast, NYA-1154, NYC-0003, and 0004 were observed to have bound to T2 cells supplemented with some homologous peptides.

(Example 7) Preparation of Fc-Conjugated Anti-HLA/NY-ESO-Anti-CD3 Bispecific Molecule 7)-1 Preparation of Fc-Conjugated Anti-HLA/NY-ESO-Anti-CD3 Bispecific Molecule Expression Vector
7)-1-1 Preparation of taFv-Heterodimer Fc-Type Bispecific Molecule Expression Vector In order to evaluate taFv-heterodimer Fc-type anti-HLA/NY-ESO-anti-CD3 bispecific molecules, expression vectors for various molecules were designed. The anti-HLA/NY-ESO antibodies used were NYA-1143, NYA-2143, NYA-1163, NYA-2023, NYA-2027, NYA-2035, NYA-2044, NYA-2045, NYA-2047, NYA-2048, NYA-2060, and NYA-2061. As the anti-CD3 antibody, humanized anti-CD3 scFv; i.e., C3E-7085 (WO 2018/117237), was used. As the heterodimer Fc sequence, the Fc sequence comprising a mutation introduced thereinto to lower effector functions and form a heteropolymer (WO 2014/190441) was used.

A DNA fragment encoding Fc (HC1 or HC2) comprising a mutation introduced thereinto to lower effector functions and form a heteropolymer was synthesized (Fasmac Co., Ltd.), an expression vector for mammal cells comprising pcDNA3.3 (Thermo Fisher Scientific) as the backbone was prepared using the In-Fusion HD cloning kit (CLONTECH), and the resulting vector was designated as "p_HC1."

An expression vector for mammal cells comprising a DNA fragment encoding HC2 integrated into the carboxyl terminus of taFv comprising NYA-1143 ligated to C3E-7085 with a GGGGS linker was prepared and designated as "p_NYF-0016-HC2."

An expression vector for mammal cells comprising a DNA fragment encoding HC2 integrated into the carboxyl terminus of taFv comprising NYA-2143 ligated to C3E-7085 with a GGGGS linker was prepared via site-directed mutagenesis into p_NYF-0016-HC2 and designated as "p_NYF-0019-HC2."

An expression vector for mammal cells comprising a DNA fragment encoding HC2 integrated into the carboxyl terminus of taFv comprising NYA-1163 ligated to C3E-7085 with a GGGGS linker was prepared via substitution of a nucleotide sequence encoding NYA-1143 of p_NYF-0016-HC2 with a DNA fragment encoding NYA-1163 using the In-Fusion HD cloning kit (CLONTECH) and designated as "p_NYF-0022-HC2."

An expression vector for mammal cells comprising a DNA fragment encoding HC2 integrated into the carboxyl terminus of taFv comprising NYA-2023 ligated to C3E-7085 with a GGGGS linker was prepared via site-directed mutagenesis into p_NYF-0016-HC2 and designated as "p_NYF-0023-HC2."

An expression vector for mammal cells comprising a DNA fragment encoding HC2 integrated into the carboxyl terminus of taFv comprising NYA-2027 ligated to C3E-7085 with a GGGGS linker was prepared via site-directed mutagenesis of an expression vector for mammal cells comprising a DNA fragment encoding HC2 integrated into the carboxyl terminus of taFv comprising NYA-0001 ligated to C3E-7085 with a GGGGS linker and designated as "p_NYF-0027-HC2."

An expression vector for mammal cells comprising a DNA fragment encoding HC2 integrated into the carboxyl terminus of taFv comprising NYA-2035 ligated to C3E-7085 with a GGGGS linker was prepared via site-directed mutagenesis into p_NYF-0016-HC2 and designated as "p_NYF-0035-HC2."

An expression vector for mammal cells comprising a DNA fragment encoding HC2 integrated into the carboxyl terminus of taFv comprising NYA-2044 ligated to C3E-7085 with a GGGGS linker was prepared via substitution of a nucleotide sequence encoding NYA-1143 of p_NYF-0016-HC2 with a DNA fragment encoding NYA-2044 using the In-Fusion HD cloning kit (CLONTECH) and designated as "p_NYF-0044-HC2."

An expression vector for mammal cells comprising a DNA fragment encoding HC2 integrated into the carboxyl terminus of taFv comprising NYA-2045 ligated to C3E-7085 with a GGGGS linker was prepared via substitution of a nucleotide sequence encoding NYA-1143 of p_NYF-0016-HC2 with a DNA fragment encoding NYA-2045 using the In-Fusion HD cloning kit (CLONTECH) and designated as "p_NYF-0045-HC2."

An expression vector for mammal cells comprising a DNA fragment encoding HC2 integrated into the carboxyl terminus of taFv comprising NYA-2047 ligated to C3E-7085 with a GGGGS linker was prepared via substitution of a nucleotide sequence encoding NYA-1143 of p_NYF-0016-HC2 with a DNA fragment encoding NYA-2047 using the In-Fusion HD cloning kit (CLONTECH) and designated as "p_NYF-0047-HC2."

An expression vector for mammal cells comprising a DNA fragment encoding HC2 integrated into the carboxyl terminus of taFv comprising NYA-2048 ligated to C3E-7085 with a GGGGS linker was prepared via substitution of a nucleotide sequence encoding NYA-1143 of p_NYF-0016-HC2 with a DNA fragment encoding NYA-2048 using the In-Fusion HD cloning kit (CLONTECH) and designated as "p_NYF-0048-HC2."

An expression vector for mammal cells comprising a DNA fragment encoding HC2 integrated into the carboxyl terminus of taFv comprising NYA-2060 ligated to C3E-7085 with a GGGGS linker was prepared via site-directed mutagenesis into p_NYF-0044-HC2 and designated as "p_NYF-0060-HC2."

An expression vector for mammal cells comprising a DNA fragment encoding HC2 integrated into the carboxyl terminus of taFv comprising NYA-2061 ligated to C3E-7085 with a GGGGS linker was prepared via site-directed mutagenesis into p_NYF-0045-HC2 and designated as "p_NYF-0061-HC2."

The nucleotide sequence of p_HC1 was reanalyzed, and the nucleotide sequence of the full-length HC1 was found to be the nucleotide sequence as shown in SEQ ID NO: 71 of the Sequence Listing (FIG. 72).

The nucleotide sequence of p_NYF-0016-HC2 was reanalyzed, and the nucleotide sequence of the full-length NYF-0016-HC2 was found to be the nucleotide sequence as shown in SEQ ID NO: 72 of the Sequence Listing (FIG. 73).

The nucleotide sequence of p_NYF-0019-HC2 was reanalyzed, and the nucleotide sequence of the full-length NYF-0019-HC2 was found to be the nucleotide sequence as shown in SEQ ID NO: 73 of the Sequence Listing (FIG. 74).

The nucleotide sequence of p_NYF-0022-HC2 was reanalyzed, and the nucleotide sequence of the full-length NYF-0022-HC2 was found to be the nucleotide sequence as shown in SEQ ID NO: 74 of the Sequence Listing (FIG. 75).

The nucleotide sequence of p_NYF-0023-HC2 was reanalyzed, and the nucleotide sequence of the full-length NYF-0023-HC2 was found to be the nucleotide sequence as shown in SEQ ID NO: 75 of the Sequence Listing (FIG. 76).

The nucleotide sequence of p_NYF-0027-HC2 was reanalyzed, and the nucleotide sequence of the full-length NYF-0027-HC2 was found to be the nucleotide sequence as shown in SEQ ID NO: 76 of the Sequence Listing (FIG. 77).

The nucleotide sequence of p_NYF-0035-HC2 was reanalyzed, and the nucleotide sequence of the full-length NYF-0035-HC2 was found to be the nucleotide sequence as shown in SEQ ID NO: 77 of the Sequence Listing (FIG. 78).

The nucleotide sequence of p_NYF-0044-HC2 was reanalyzed, and the nucleotide sequence of the full-length NYF-0044-HC2 was found to be the nucleotide sequence as shown in SEQ ID NO: 78 of the Sequence Listing (FIG. 79).

The nucleotide sequence of p_NYF-0045-HC2 was reanalyzed, and the nucleotide sequence of the full-length NYF-0045-HC2 was found to be the nucleotide sequence as shown in SEQ ID NO: 79 of the Sequence Listing (FIG. 80).

The nucleotide sequence of p_NYF-0047-HC2 was reanalyzed, and the nucleotide sequence of the full-length NYF-0047-HC2 was found to be the nucleotide sequence as shown in SEQ ID NO: 80 of the Sequence Listing (FIG. 81).

The nucleotide sequence of p_NYF-0048-HC2 was reanalyzed, and the nucleotide sequence of the full-length NYF-0048-HC2 was found to be the nucleotide sequence as shown in SEQ ID NO: 81 of the Sequence Listing (FIG. 82).

The nucleotide sequence of p_NYF-0060-HC2 was reanalyzed, and the nucleotide sequence of the full-length NYF-0060-HC2 was found to be the nucleotide sequence as shown in SEQ ID NO: 82 of the Sequence Listing (FIG. 83).

The nucleotide sequence of p_NYF-0061-HC2 was reanalyzed, and the nucleotide sequence of the full-length NYF-0061-HC2 was found to be the nucleotide sequence as shown in SEQ ID NO: 83 of the Sequence Listing (FIG. 84).

On the basis of the nucleotide sequences above, the amino acid sequences of the full-length HC1, NYF-0016-HC2, NYF-0019-HC2, NYF-0022-HC2, NYF-0023-HC2, NYF-0027-HC2, NYF-0035-HC2, NYF-0044-HC2, NYF-0045-HC2, NYF-0047-HC2, NYF-0048-HC2, NYF-0060-HC2, and NYF-0061-HC2 encoded thereby were identified.

The amino acid sequence of the full-length HC1 is the amino acid sequence as shown in SEQ ID NO: 84 of the Sequence Listing (FIG. 85). In such an amino acid sequence, amino acids 1 to 19 constitute a signal sequence, and amino acids 20 to 246 constitute HC.

The amino acid sequence of the full-length NYF-0016-HC2 is as shown in SEQ ID NO: 85 of the Sequence Listing (FIG. 86). In such an amino acid sequence, amino acids 1 to 19 constitute a signal sequence, amino acid 21 to 511 constitute NYA-1143-C3E-7085 taFv, amino acids 512 to 513 constitute a linker, and amino acids 514 to 745 constitute HC2.

The amino acid sequence of the full-length NYF-0019-HC2 is as shown in SEQ ID NO: 86 of the Sequence Listing (FIG. 87). In such an amino acid sequence, amino acids 1 to 19 constitute a signal sequence, amino acid 21 to 511 constitute NYA-2143-C3E-7085 taFv, amino acids 512 to 513 constitute a linker, and amino acids 514 to 745 constitute HC2.

The amino acid sequence of the full-length NYF-0022-HC2 is as shown in SEQ ID NO: 87 of the Sequence Listing (FIG. 88). In such an amino acid sequence, amino acids 1 to 19 constitute a signal sequence, amino acid 21 to 511 constitute NYA-1163-C3E-7085 taFv, amino acids 512 to 513 constitute a linker, and amino acids 514 to 745 constitute HC2.

The amino acid sequence of the full-length NYF-0023-HC2 is as shown in SEQ ID NO: 88 of the Sequence Listing (FIG. 89). In such an amino acid sequence, amino acids 1 to 19 constitute a signal sequence, amino acid 21 to 511 constitute NYA-2023-C3E-7085 taFv, amino acids 512 to 513 constitute a linker, and amino acids 514 to 745 constitute HC2.

The amino acid sequence of the full-length NYF-0027-HC2 is as shown in SEQ ID NO: 89 of the Sequence Listing (FIG. 90). In such an amino acid sequence, amino acids 1 to 19 constitute a signal sequence, amino acid 21 to 511 constitute NYA-2027-C3E-7085 taFv, amino acids 512 to 513 constitute a linker, and amino acids 514 to 745 constitute HC2.

The amino acid sequence of the full-length NYF-0035-HC2 is as shown in SEQ ID NO: 90 of the Sequence Listing (FIG. 91). In such an amino acid sequence, amino acids 1 to 19 constitute a signal sequence, amino acid 21 to 511 constitute NYA-2035-C3E-7085 taFv, amino acids 512 to 513 constitute a linker, and amino acids 514 to 745 constitute HC2.

The amino acid sequence of the full-length NYF-0044-HC2 is as shown in SEQ ID NO: 91 of the Sequence Listing (FIG. 92). In such an amino acid sequence, amino acids 1 to 19 constitute a signal sequence, amino acid 21 to 511 constitute NYA-2044-C3E-7085 taFv, amino acids 512 to 513 constitute a linker, and amino acids 514 to 745 constitute HC2.

The amino acid sequence of the full-length NYF-0045-HC2 is as shown in SEQ ID NO: 92 of the Sequence Listing (FIG. 93). In such an amino acid sequence, amino acids 1 to 19 constitute a signal sequence, amino acid 21 to 511 constitute NYA-2045-C3E-7085 taFv, amino acids 512 to 513 constitute a linker, and amino acids 514 to 745 constitute HC2.

The amino acid sequence of the full-length NYF-0047-HC2 is as shown in SEQ ID NO: 93 of the Sequence Listing (FIG. 94). In such an amino acid sequence, amino acids 1 to 19 constitute a signal sequence, amino acid 21 to 511 constitute NYA-2047-C3E-7085 taFv, amino acids 512 to 513 constitute a linker, and amino acids 514 to 745 constitute HC2.

The amino acid sequence of the full-length NYF-0048-HC2 is as shown in SEQ ID NO: 94 of the Sequence Listing (FIG. 95). In such an amino acid sequence, amino acids 1 to 19 constitute a signal sequence, amino acid 21 to 511 constitute NYA-2048-C3E-7085 taFv, amino acids 512 to 513 constitute a linker, and amino acids 514 to 745 constitute HC2.

The amino acid sequence of the full-length NYF-0060-HC2 is as shown in SEQ ID NO: 95 of Sequence Listing (FIG. 96). In such an amino acid sequence, amino acids 1 to 19 constitute a signal sequence, amino acid 21 to 511 constitute NYA-2060-C3E-7085 taFv, amino acids 512 to 513 constitute a linker, and amino acids 514 to 745 constitute HC2.

The amino acid sequence of the full-length NYF-0061-HC2 is as shown in SEQ ID NO: 96 of the Sequence Listing (FIG. 97). In such an amino acid sequence, amino acids 1 to 19 constitute a signal sequence, amino acid 21 to 511 constitute NYA-2061-C3E-7085 taFv, amino acids 512 to 513 constitute a linker, and amino acids 514 to 745 constitute HC2.

7)-1-2 Preparation of taFv-Fab-Heterodimer Fc-Type Bispecific Molecule Expression Vector A taFv-Fab-heterodimer Fc-type anti-HLA/NY-ESO-anti-CD3 bispecific molecule expression vector was designed. As the anti-HLA/NY-ESO antibody, NYA-0001 was used. As the anti-CD3 antibody, humanized anti-CD3 scFv; i.e., C3E-7085 (WO 2018/117237), was used. As the heterodimer Fc sequence, the Fc sequence comprising a mutation introduced thereinto to lower effector functions and form a heteropolymer (WO 2014/190441) was used.

An expression vector for mammal cells comprising DNA fragments encoding the heavy chain variable region of NYA-0001, the human IgG-derived CH1 region, and a region comprising a mutation that lowers effector functions and encodes HC1-k delete integrated thereinto was prepared and designated as "p_NYA-0001-Fab-HC1-k delete." Also, an expression vector for mammal cells comprising DNA fragments encoding the NYA-0001 light chain variable region and the human IgG-derived CL region integrated thereinto was prepared and designated as "p_NYA-0001-LC."

The nucleotide sequence of p_NYA-0001-Fab-HC1-k delete was reanalyzed, and the nucleotide sequence of the full-length NYA-0001-Fab-HC1-k delete was found to be the nucleotide sequence as shown in SEQ ID NO: 97 (FIG. 98) of the Sequence Listing.

The nucleotide sequence of p_NYA-0001-LC was reanalyzed, and the nucleotide sequence of the full-length NYA-0001-LC was found to be the nucleotide sequence as shown in SEQ ID NO: 98 (FIG. 99) of the Sequence Listing.

On the basis of the nucleotide sequences above, the amino acid sequences of the full-length NYA-0001-Fab-HC1-k delete and NYA-0001-LC encoded thereby were identified.

The amino acid sequence of the full-length NYA-0001-Fab-HC1-k delete is the amino acid sequence as shown in SEQ ID NO: 99 of the Sequence Listing (FIG. 100). In such an amino acid sequence, amino acids 1 to 19 constitute a signal sequence, amino acids 20 to 139 constitute a variable region, and amino acids 140 to 468 constitute a constant region. Also, amino acids 45 to 52 constitute CDRH1 (SEQ ID NO: 54 (FIG. 61)), amino acids 70 to 77 constitute CDRH2 (SEQ ID NO: 55 (FIG. 61)), and amino acids 116 to 128 constitute CDRH3 (SEQ ID NO: 56 (FIG. 61)).

The amino acid sequence of the full-length NYA-0001-LC is as shown in SEQ ID NO: 100 of the Sequence Listing (FIG. 101). In such an amino acid sequence, amino acids 1 to 20 constitute a signal sequence, amino acids 21 to 131 constitute a variable region, and amino acids 132 to 237 constitute a constant region. Also, amino acids 46 to 53 constitute CDRL1 (SEQ ID NO: 57 (FIG. 61)), amino acids 71 to 73 constitute CDRL2 (SEQ ID NO: 58 (FIG. 61)), and amino acids 110 to 121 constitute CDRL3 (SEQ ID NO: 59 (FIG. 61)).

7)-2 Expression of Fc-Conjugated Anti-HLA/NY-ESO-Anti-CD3 Bispecific Molecule

7)-2-1 Expression of taFv-Heterodimer Fc-Type Bispecific Molecule

Expi293F cells (Thermo Fisher Scientific) were subcultured in accordance with the instructions. A culture solution of the Expi293F cells in a logarithmic growth phase was diluted to $2.5\times10^6$ cells/ml in the Expi293 Expression medium (Thermo Fisher Scientific) and used for production of various bispecific molecules. A mixture (0.3 mg) comprising the p_NYF-0016-HC2 vector and p_HC1 at 1:1.5 and 0.9 mg of polyethyleneimine (Polyscience #24765) were added to 20 ml of Opti-Pro SFM medium (Thermo Fisher Scientific). The mixture was stirred gently, allowed to stand for five minutes, and then added to the Expi293F cells. The culture supernatant obtained by agitation culture in an incubator at 37° C. in the presence of 8% $CO_2$ at 135 rpm for 6 days was filtered through a 0.2 μm-filter (Millipore). Thus, the culture supernatant of the taFv-heterodimer Fc-type anti-HLA/NY-ESO-anti-CD3 bispecific molecule (NYF-0016) was obtained. The amino acid sequences obtained via expression of vectors constituting NYF-0016 are shown in SEQ ID NO: 85 of the Sequence Listing (FIG. 86) and SEQ ID NO: 84 of the Sequence Listing (FIG. 85).

In the same manner, the culture supernatant of the taFv-heterodimer Fc-type anti-HLA/NY-ESO-anti-CD3 bispecific molecule (NYF-0019) was prepared using p_NYF-0019-HC2 and p_HC1. The amino acid sequences obtained via expression of vectors constituting NYF-0019 are shown in SEQ ID NO: 86 of Sequence Listing (FIG. 87) and SEQ ID NO: 84 of the Sequence Listing (FIG. 85).

The culture supernatant of the taFv-heterodimer Fc-type anti-HLA/NY-ESO-anti-CD3 bispecific molecule (NYF-0022) was prepared using p_NYF-0022-HC2 and p_HC1. The amino acid sequences obtained via expression of vectors constituting NYF-0022 are shown in SEQ ID NO: 87 of the Sequence Listing (FIG. 88) and SEQ ID NO: 84 of the Sequence Listing (FIG. 85).

The culture supernatant of the taFv-heterodimer Fc-type anti-HLA/NY-ESO-anti-CD3 bispecific molecule (NYF-0023) was prepared using p_NYF-0023-HC2 and p_HC1. The amino acid sequences obtained via expression of vectors constituting NYF-0023 are shown in SEQ ID NO: 88 of the Sequence Listing (FIG. 89) and SEQ ID NO: 84 of the Sequence Listing (FIG. 85).

The culture supernatant of the taFv-heterodimer Fc-type anti-HLA/NY-ESO-anti-CD3 bispecific molecule (NYF-0027) was prepared using p_NYF-0027-HC2 and p_HC1. The amino acid sequences obtained via expression of vectors constituting NYF-0027 are shown in SEQ ID NO: 89 of the Sequence Listing (FIG. 90) and SEQ ID NO: 84 of the Sequence Listing (FIG. 85).

The culture supernatant of the taFv-heterodimer Fc-type anti-HLA/NY-ESO-anti-CD3 bispecific molecule (NYF-0035) was prepared using p_NYF-0035-HC2 and p_HC1. The amino acid sequences obtained via expression of vectors constituting NYF-0035 are shown in SEQ ID NO: 90 of the Sequence Listing (FIG. 91) and SEQ ID NO: 84 of the Sequence Listing (FIG. 85).

The culture supernatant of the taFv-heterodimer Fc-type anti-HLA/NY-ESO-anti-CD3 bispecific molecule (NYF-0044) was prepared using p_NYF-0044-HC2 and p_HC1. The amino acid sequences obtained via expression of vectors constituting NYF-0044 are shown in SEQ ID NO: 91 of the Sequence Listing (FIG. 92) and SEQ ID NO: 84 of the Sequence Listing (FIG. 85).

The culture supernatant of the taFv-heterodimer Fc-type anti-HLA/NY-ESO-anti-CD3 bispecific molecule (NYF-0045) was prepared using p_NYF-0045-HC2 and p_HC1. The amino acid sequences obtained via expression of vectors constituting NYF-0045 are shown in SEQ ID NO: 92 of the Sequence Listing (FIG. 93) and SEQ ID NO: 84 of the Sequence Listing (FIG. 85).

The culture supernatant of the taFv-heterodimer Fc-type anti-HLA/NY-ESO-anti-CD3 bispecific molecule (NYF-0047) was prepared using p_NYF-0047-HC2 and p_HC1. The amino acid sequences obtained via expression of vectors constituting NYF-0047 are shown in SEQ ID NO: 93 of the Sequence Listing (FIG. 94) and SEQ ID NO: 84 of the Sequence Listing (FIG. 85).

The culture supernatant of the taFv-heterodimer Fc-type anti-HLA/NY-ESO-anti-CD3 bispecific molecule (NYF-0048) was prepared using p_NYF-0048-HC2 and p_HC1. The amino acid sequences obtained via expression of vectors constituting NYF-0048 are shown in SEQ ID NO: 94 of the Sequence Listing (FIG. 95) and SEQ ID NO: 84 of the Sequence Listing (FIG. 85).

The culture supernatant of the taFv-heterodimer Fc-type anti-HLA/NY-ESO-anti-CD3 bispecific molecule (NYF-0060) was prepared using p_NYF-0060-HC2 and p_HC1. The amino acid sequences obtained via expression of vectors constituting NYF-0060 are shown in SEQ ID NO: 95 of the Sequence Listing (FIG. 96) and SEQ ID NO: 84 of the Sequence Listing (FIG. 85).

The culture supernatant of the taFv-heterodimer Fc-type anti-HLA/NY-ESO-anti-CD3 bispecific molecule (NYF-0061) was prepared using p_NYF-0061-HC2 and p_HC1. The amino acid sequences obtained via expression of vectors constituting NYF-0061 are shown in SEQ ID NO: 96 of the Sequence Listing (FIG. 97) and SEQ ID NO: 84 of the Sequence Listing (FIG. 85).

7)-2-2 Expression of taFv-Fab-heterodimer Fc-type bispecific molecules

In the same manner as in 7)-2-1, the culture supernatant of the taFv-Fab-heterodimer Fc-type bispecific molecule (NYF-0058) was prepared using a vector mixture comprising p_NYF-0023-HC2, p_NYA-0001-Fab-HC1-k delete, and p_NYA-0001-LC at 1:1:1.5. The amino acid sequences obtained via expression of vectors constituting NYF-0058 are shown in amino acids 20 to 745 of SEQ ID NO: 88 of the Sequence Listing (FIG. 89), amino acids 20 to 468 of SEQ ID NO: 99 of the Sequence Listing (FIG. 100), and amino acids 21 to 237 of SEQ ID NO: 100 of the Sequence Listing (FIG. 101).

7)-3 Purification of Fc-conjugated anti-HLA/NY-ESO-anti-CD3 bispecific molecule Various bispecific molecules were purified from the culture supernatants obtained in 7)-2 by 2 steps of protein A affinity chromatography and gel filtration chromatography.

The culture supernatant was applied to the MabSelect-SuRe column equilibrated with PBS at pH 7.4 (GE Healthcare Bioscience, also referred to simply as "GE Healthcare") to allow the target bispecific molecules to adsorb thereto. After the non-adsorbed components were removed by PBS, the adsorbed components were eluted using acetate buffer (pH 3.5). The elution fraction was neutralized with the aid of Tris buffer (pH 9.5), concentrated, and then applied to the gel filtration column Superdex 200 10/300 (GE Healthcare Bioscience) equilibrated with 25 mM histidine, 300 mM NaCl, 5% Sorbitol at pH 5.5 in advance. From the peak fraction obtained via gel filtration chromatography, fractions equivalent to the target heterodimer were collected, and generation of the target anti-HLA/NY-ESO-anti-CD3 bispecific molecule was confirmed via SDS-polyacrylamide electrophoresis (SDS-PAGE). Purified protein samples were subjected to analytical SEC, the degree of purification and the concentration were determined, and the samples were then subjected to various types of evaluation.

(Example 8) Evaluation of Cytotoxicity of Fc-Conjugated Anti-HLA-A2/NY-ESO-Anti-CD3 Bispecific Molecule 8)-1 Preparation of Target Cells The endogenous human NY-ESO-expressing cells (U266B1 and NCI-H1703) and the endogenous human NY-ESO-non-expressing cells (AGS and CFPAC-1) were adjusted to $1\times10^6$ cells/ml in RPMI 1640 medium containing 10% FBS (FUJIFILM Wako Pure Chemical Corporation), 100 μl of Chromium-51 Radionuclide (PerkinElmer) was added per 1 ml of each cell suspension, and the resultants were cultured at 37° C. in the presence of 5% $CO_2$ for 2 hours. The cells were washed 2 times in RPMI 1640 medium containing 10% FBS, resuspended to $1\times10^5$ cells/ml in RPMI 1640 medium containing 10% FBS, and then used as the target cells.

8)-2 Preparation of Effector Cells

Commercially available frozen human PBMCs (Cellular Technology Limited) were thawed at 37° C., transferred to a solution comprising RPMI 1640 medium containing 10% FBS supplemented with the Anti-aggregate Wash reagent (Cellular Technology Limited), washed 2 times, and adjusted to $1\times10^6$ cells/ml in RPMI 1640 medium containing 10% FBS to prepare effector cells.

8)-3 Cytotoxicity Assay

The target cells obtained in 8)-1 were seeded on a 96-well U-bottom microplate at 50 μl/well. Various Fc-conjugated anti-HLA-A2/NY-ESO-anti-CD3 bispecific molecules prepared in Example 7 adjusted to various concentrations were added thereto at 50 μl/well, the effector cells prepared in Example 8)-2 were added thereto at 100 μl/well, centrifugation was carried out at room temperature and 1,000 rpm for 1 minute, and then they were incubated at 37° C. in the presence of 5% $CO_2$ for 20 to 24 hours. The supernatant (50 μl) was collected on a LumaPlate (PerkinElmer), dried at 50° C. for approximately 2 hours, and then assayed using a plate reader (TopCount, PerkinElmer). The test was performed in triplicate, and the rate of cell lysis was determined in accordance with the following equation.

Rate of cell lysis (%)=$(A-B)/(C-B)\times100$

A: Sample well count
B: Mean of background (wells not supplemented with antibody) count (n=3).
When the antibody was added, 50 μl of an assay medium was added. Other procedures were the same as those for the sample wells.
C: Mean of maximal release (wells in which target cells were lysed with a surfactant) count (n=3).
When the antibody was added, 50 μl of an assay medium was added. A surfactant was added in an amount of 100 μl, a fraction of 50 μl was transferred to the LumaPlate as in the case of the sample wells, and assays were then performed.

As shown in FIG. 4A to FIG. 4F, various anti-HLA-A2/NY-ESO-anti-CD3 bispecific molecules exerted cytotoxicity on the endogenous human NY-ESO-expressing cells (U266B1 and NCI-H1703). The results of calculation of $EC_{50}$ obtained using the Four Parameter Logistic Curve equation of analytical software (Sigmaplot, version 12.0) concerning the U266B1 cells are shown in Table 2, and the results concerning the NCI-H1703 cells are shown in Table 3. "Not Applicable (NA)" indicates that it is impossible to perform curve fitting because the correlation coefficient (R) was not calculated. As shown in FIG. 4G to FIG. 4L, in contrast, no cytotoxicity was observed on the endogenous human NY-ESO-non-expressing cells (AGS and CFPAC-1).

TABLE 2

|    | Name     | $EC_{50}$ (nM) |
|----|----------|----------------|
| 1  | NYF-0016 | 0.30           |
| 2  | NYF-0019 | 0.20           |
| 3  | NYF-0022 | 1.30           |
| 4  | NYF-0023 | 0.90           |
| 5  | NYF-0027 | 2.68           |
| 6  | NYF-0035 | 0.97           |
| 7  | NYF-0044 | 0.10           |
| 8  | NYF-0045 | 0.18           |
| 9  | NYF-0047 | 0.93           |
| 10 | NYF-0048 | 1.10           |
| 11 | NYF-0058 | 0.95           |
| 12 | NYF-0060 | 0.39           |
| 13 | NYF-0061 | 0.40           |

TABLE 3

|    | Name     | $EC_{50}$ (nM) |
|----|----------|----------------|
| 1  | NYF-0016 | 0.90           |
| 2  | NYF-0019 | 4.28           |
| 3  | NYF-0022 | NA*            |
| 4  | NYF-0023 | 1.16           |
| 5  | NYF-0027 | 6.40           |
| 6  | NYF-0035 | 2.10           |
| 7  | NYF-0044 | 1.11           |
| 8  | NYF-0045 | 5.76           |
| 9  | NYF-0047 | 7.63           |
| 10 | NYF-0048 | 4.21           |
| 11 | NYF-0058 | 1.03           |
| 12 | NYF-0060 | 0.74           |
| 13 | NYF-0061 | 1.04           |

*NA = Not Applicable (Example 9) Evaluation of In Vivo Activity of Fc-Conjugated Anti-HLA-A2/NY-ESO-Anti-CD3 Bispecific Molecules in Human PBMC-Transfected Models The human squamous lung cancer cell lines NCI-H1703 (ATCC) were adjusted to $6\times10^7$ cells/ml in PBS containing 50% Matrigel (Corning) and 0.1 ml thereof was injected hypodermically into NOG mice (female, 6- to 7-week-old) (Day 0). On Day 4, human PBMCs were adjusted to $3.75\times10^7$ cells/ml in PBS, and 0.2 ml thereof was injected intravenously. Approximately 1 week thereafter (Day 6 to Day 7), measurement of the major diameter (mm) and the minor diameter (mm) of the tumor was initiated, measurement was performed using an electronic digital caliper with the elapse of time, and the estimated tumor volume was calculated in accordance with the equation below.

Estimated tumor volume ($mm^3$)=mean of estimated tumor volume among individuals Estimated tumor volume of an individual=major diameter×[minor diameter]$^2$/2

Figure 5A:
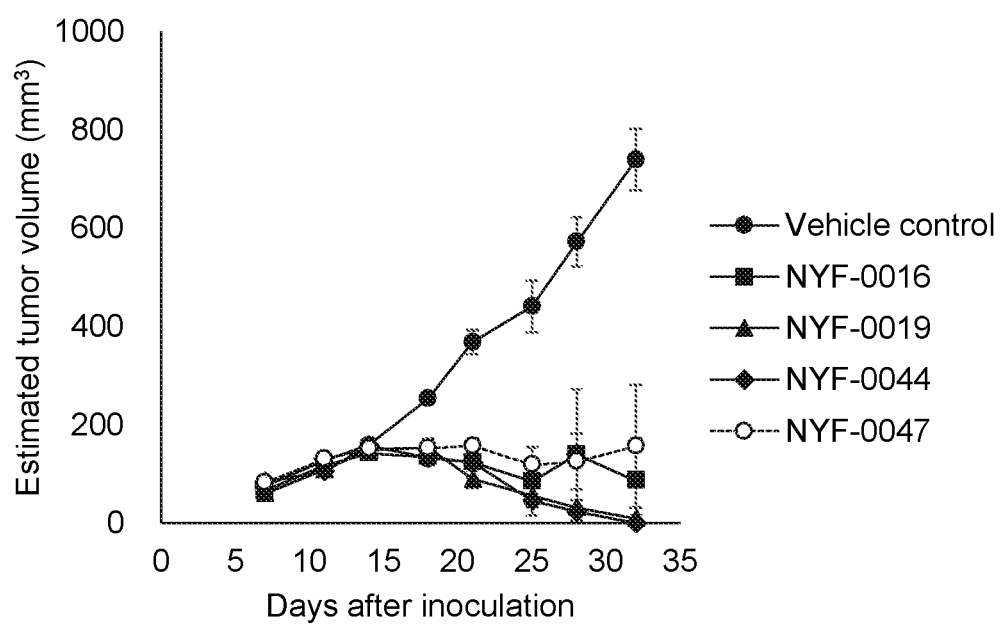
FIG. 5A demonstrates that the Fc-conjugated anti-HLA-A2/NY-ESO-anti-CD3 bispecific molecules; i.e., NYF-0016, NYF-0019, NYF-0044, and NYF-0047, exert antitumor activity on human PBMC-transfected models. An error bar in the figure indicates the standard deviation (n=5, but only n=4 on Day 32 in the NYF-0044 group).
Figure 5B:
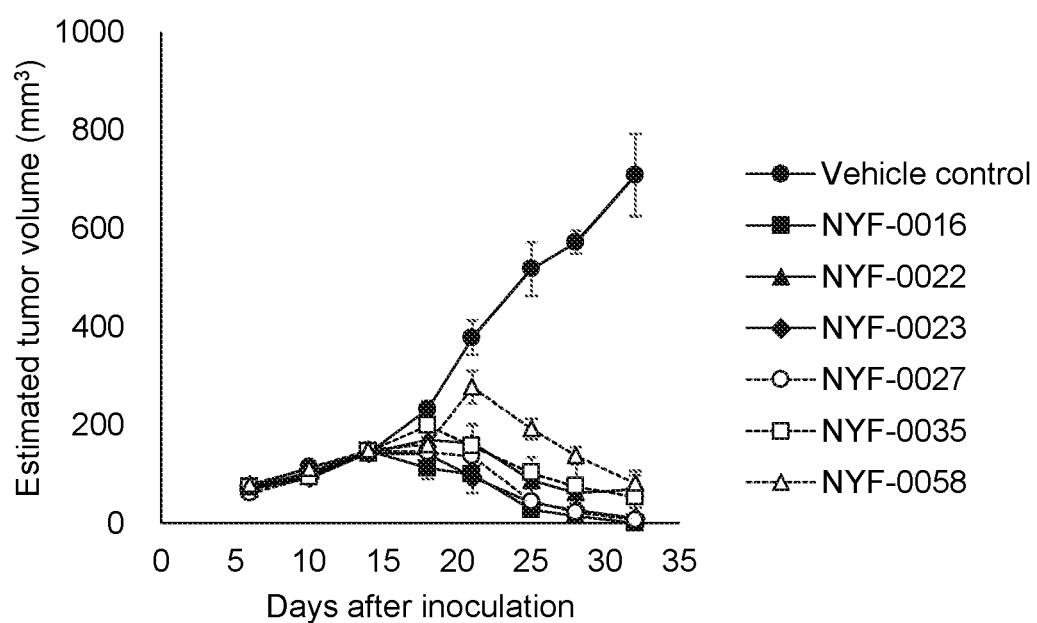
FIG. 5B demonstrates that the Fc-conjugated anti-HLA-A2/NY-ESO-anti-CD3 bispecific molecules; i.e., NYF-0016, NYF-0022, NYF-0023, NYF-0027, NYF-0035, and NYF-0058, exert antitumor activity on human PBMC-transfected models. An error bar in the figure indicates the standard deviation (n=5, n=6 only in the Vehicle control group).
Figure 5C:
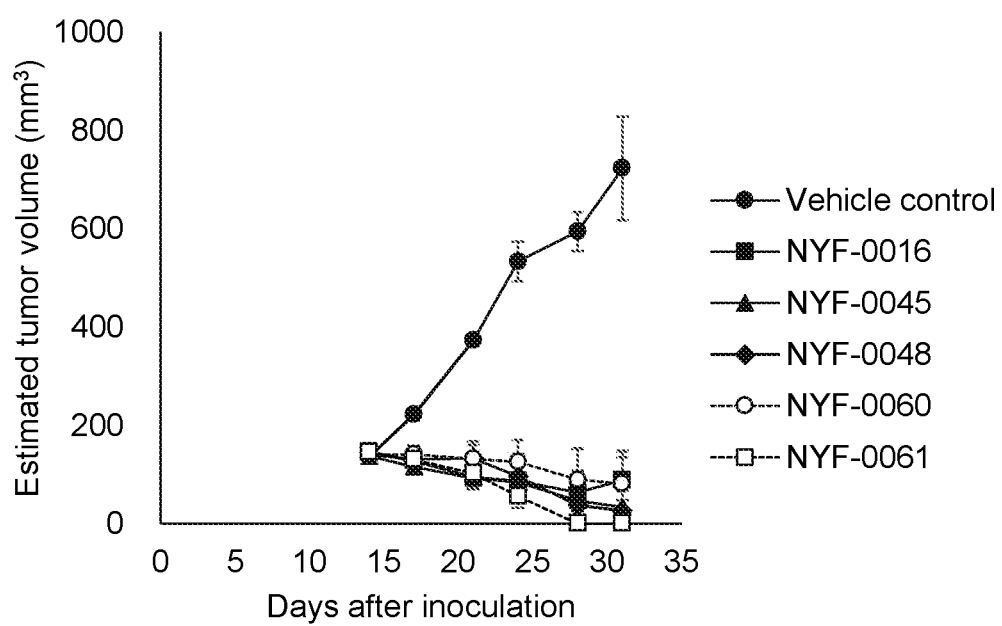
FIG. 5C demonstrates that the Fc-conjugated anti-HLA-A2/NY-ESO-anti-CD3 bispecific molecules; i.e., NYF-0016, NYF-0045, NYF-0048, NYF-0060, and NYF-0061, exert antitumor activity on human PBMC-transfected models. An error bar in the figure indicates the standard deviation (n=5).

On Day 14, mice were divided into groups each consisting of 5 or 6 mice on the basis of tumor volumes, and various anti-HLA-A2/NY-ESO-anti-CD3 bispecific molecules were administered intravenously (1 mg/kg, 1.5 mg/kg of NYF-0058 for comparison at the same molar weight). Administration was performed on Day 14, Day 21, and Day 28. Antitumor effects were observed in the treatment groups to which various anti-HLA-A2/NY-ESO-anti-CD3 bispecific molecules had been administered (FIG. 5A to FIG. 5C). The tumor growth inhibition (%) on Day 31 to Day 32 was calculated in accordance with the following equation and shown in Table 4.

Tumor growth inhibition (%)=100−(estimated tumor volume of treatment group/estimated tumor volume of vehicle control×100)

TABLE 4

| | Name | Tumor Growth Inhibition (%) |
|---|---|---|
| 1 | NYF-0016 | 100.0 |
| 2 | NYF-0019 | 98.8 |
| 3 | NYF-0022 | 90.3 |
| 4 | NYF-0023 | 98.6 |
| 5 | NYF-0027 | 99.1 |
| 6 | NYF-0035 | 92.5 |
| 7 | NYF-0044 | 100.0 |
| 8 | NYF-0045 | 95.4 |
| 9 | NYF-0047 | 78.9 |
| 10 | NYF-0048 | 96.3 |
| 11 | NYF-0058 | 88.5 |
| 12 | NYF-0060 | 88.8 |
| 13 | NYF-0061 | 100.0 |

(Example 10) Preparation of Various Fc-Conjugated Anti-HLA/NY-ESO-Anti-CD3 Bispecific Molecules 10)-1 Preparation of Various Fc-Conjugated Anti-HLA/NY-ESO-Anti-CD3 Bispecific Molecule Expression Vectors 10)-1-1 Preparation of Hybrid-Type Bispecific Molecule Expression Vector In order to evaluate hybrid-type anti-HLA/NY-ESO-anti-CD3 bispecific molecules, expression vectors for various molecules were designed. As the anti-HLA/NY-ESO antibody, NYA-1143 was used. As the anti-CD3 antibody, humanized anti-CD3 scFv; i.e., C3E-7085 (PCT/JP2017/046006), was used. As the heterodimer Fc sequence, the Fc sequence comprising a mutation introduced thereinto to lower effector functions and form a heteropolymer (WO 2014/190441) was used.

An expression vector for mammal cells comprising DNA fragments encoding the heavy chain variable region of NYA-1143, the human IgG-derived CH1 region, and the Fc region into which a mutation has been introduced therein to lower effector functions and form a heteropolymer was prepared and designated as "p_NYA-1143-Fab-HC1-k delete." Also, an expression vector for mammal cells comprising DNA fragments encoding the NYA-1143 light chain variable region and the human IgG-derived CL region was prepared and designated as "p_NYA-1143-LC." Further, an expression vector for mammal cells comprising a DNA fragment encoding the Fc region comprising a mutation to lower effector functions and form a heteropolymer introduced into the carboxyl terminus of humanized anti-CD3 scFv (C3E-7085) was prepared and designated as "p_C3E-7085-HC2-k delete."

The nucleotide sequence of p_NYA-1143-Fab-HC1-k delete was reanalyzed, and the nucleotide sequence of the full-length NYA-1143-Fab-HC1-k delete was found to be the nucleotide sequence as shown in SEQ ID NO: 101 of the Sequence Listing (FIG. 102).

The nucleotide sequence of p_NYA-1143-LC was reanalyzed, and the nucleotide sequence of the full-length NYA-1143-LC was found to be the nucleotide sequence as shown in SEQ ID NO: 102 of the Sequence Listing (FIG. 103).

The nucleotide sequence of p_C3E-7085-HC2-k delete was reanalyzed, and the nucleotide sequence of the full-length C3E-7085-HC2-k delete was found to be the nucleotide sequence as shown in SEQ ID NO: 103 of the Sequence Listing (FIG. 104).

On the basis of the nucleotide sequences above, the amino acid sequences of the full-length NYA-1143-Fab-HC1-k delete, NYA-1143-LC, and C3E-7085-HC2-k delete encoded thereby were identified.

The amino acid sequence of the full-length NYA-1143-Fab-HC1-k delete is the amino acid sequence as shown in SEQ ID NO: 104 of the Sequence Listing (FIG. 105). In such an amino acid sequence, amino acids 1 to 19 constitute a signal sequence, amino acids 21 to 139 constitute a variable region, and amino acids 140 to 468 constitute a constant region. Also, amino acids 45 to 52 constitute CDRH1 (SEQ ID NO: 54 (FIG. 61)), amino acids 70 to 77 constitute CDRH2 (SEQ ID NO: 55 (FIG. 61)), amino acids 116 to 128 constitute CDRH3 (SEQ ID NO: 56 (FIG. 61)).

The amino acid sequence of the full-length NYA-1143-LC is the amino acid sequence as shown in SEQ ID NO: 105 of the Sequence Listing (FIG. 106). In such an amino acid sequence, amino acids 1 to 20 constitute a signal sequence, amino acids 21 to 131 constitute a variable region, and amino acids 132 to 237 constitute a constant region. Also, amino acids 46 to 53 constitute CDRL1 (SEQ ID NO: 60 (FIG. 62)), amino acids 71 to 73 constitute CDRL2 (SEQ ID NO: 58 (FIG. 61)), and amino acids 110 to 121 constitute CDRL3 (SEQ ID NO: 59 (FIG. 61)).

The amino acid sequence of the full-length C3E-7085-HC2-k delete is the amino acid sequence as shown in SEQ ID NO: 106 of the Sequence Listing (FIG. 107). In such an amino acid sequence, amino acids 1 to 19 constitute a signal sequence, amino acids 21 to 260 constitute C3E-7085, amino acids 261 to 262 constitute a linker, and amino acids 263 to 493 constitute Fc comprising a mutation introduced thereinto to lower effector functions and form a heterodimer.

10)-1-2 Preparation of Dual-Type Bispecific Molecule Expression Vector

In order to evaluate the dual-type anti-HLA/NY-ESO-anti-CD3 bispecific molecules, the expression vector described below was designed. An expression vector for mammal cells comprising a DNA fragment encoding the Fc region comprising a mutation to lower effector functions and form a heteropolymer integrated into the carboxyl terminus of NYA-1143 was prepared and designated as "p_NYA-1143-HC1-k delete."

The nucleotide sequence of p_NYA-1143-HC1-k delete was reanalyzed, and the nucleotide sequence of the full-length NYA-1143-HC1-k delete was found to be the nucleotide sequence as shown in SEQ ID NO: 107 of the Sequence Listing (FIG. 108). On the basis of the nucleotide sequences above, the amino acid sequence of the full-length NYA-1143-HC1-k delete encoded was identified. The amino acid sequence of the full-length NYA-1143-HC1-k delete is the amino acid sequence as shown in SEQ ID NO: 108 (FIG. 109) of the Sequence Listing. In such an amino acid sequence, amino acids 1 to 19 constitute a signal sequence, amino acids 21 to 266 constitute NYA-1143, amino acids 267 to 268 constitute a linker, amino acids 269 to 499 constitute Fc comprising a mutation introduced thereinto to lower effector functions and form a heterodimer.

10)-1-3 Preparation of scFv-Fab-Heterodimer Fc-Type Bispecific Molecule Expression Vector In order to evaluate scFv-Fab-heterodimer Fc-type anti-HLA/NY-ESO-anti-CD3 bispecific molecules, expression vectors for various molecules were designed. As the anti-HLA/NY-ESO antibody, NYA-1154 was used, and, as the anti-CD3 antibody, C3E-7085 was used. As the heterodimer Fc sequence, the Fc sequence comprising a mutation introduced thereinto to lower effector functions and form a heteropolymer was used.

An expression vector for mammal cells comprising DNA fragments encoding the heavy chain variable region of NYA-1154, the human IgG-derived CH1 region, and the Fc region comprising a mutation to lower effector functions and form a heteropolymer integrated into the carboxyl terminus of C3E-7085 was prepared and designated as "p_C3E-7085-NYA-1154-Fab-HC2-k delete." Also, an expression vector for mammal cells comprising DNA fragments encoding the light chain variable region of NYA-1154 and the human IgG-derived CL region integrated therein was prepared and designated as "p_NYA-1154-LC." Further, an expression vector for mammal cells comprising a DNA fragment encoding HC1-k delete integrated therein was prepared and designated as "p_OAA-HC1-k delete."

The nucleotide sequence of p_C3E-7085-NYA-1154-Fab-HC2-k delete was reanalyzed, and the nucleotide sequence of the full-length C3E-7085-NYA-1154-Fab-HC2-k delete was found to be the nucleotide sequence as shown in SEQ ID NO: 109 of the Sequence Listing (FIG. 110).

The nucleotide sequence of p_NYA-1154-LC was reanalyzed, and the nucleotide sequence of the full-length NYA-1154-LC was found to be the nucleotide sequence as shown in SEQ ID NO: 110 (FIG. 111) of the Sequence Listing.

The nucleotide sequence of p_OAA-HC1-k delete was reanalyzed, and the nucleotide sequence of the full-length OAA-HC1-k delete was found to be the nucleotide sequence as shown in SEQ ID NO: 111 of the Sequence Listing (FIG. 112).

On the basis of the nucleotide sequences above, the amino acid sequences of the full-length C3E-7085-NYA-1154-Fab-HC2-k delete, NYA-1154-LC, and OAA-HC1-k delete encoded thereby were identified.

The amino acid sequence of the full-length C3E-7085-NYA-1154-Fab-HC2-k delete is the amino acid sequence as shown in SEQ ID NO: 112 of the Sequence Listing (FIG. 113). In such an amino acid sequence, amino acids 1 to 19 constitute a signal sequence, amino acids 21 to 260 constitute C3E-7085, amino acids 261 to 385 constitute a linker, and amino acids 266 to 385 constitute the heavy chain variable region of NYA-1154. Also, amino acids 386 to 714 constitute HC2-k delete.

The amino acid sequence of the full-length NYA-1154-LC is the amino acid sequence as shown in SEQ ID NO: 113 of the Sequence Listing (FIG. 114). In such an amino acid sequence, amino acids 1 to 20 constitute a signal sequence, amino acids 21 to 131 constitute a variable region, and amino acids 132 to 237 constitute a constant region. Also, amino acids 46 to 53 constitute CDRL1 (SEQ ID NO: 57 (FIG. 61)), amino acids 71 to 73 constitute CDRL2 (SEQ ID NO: 58 (FIG. 61)), and amino acids 110 to 121 constitute CDRL3 (SEQ ID NO: 63 (FIG. 64)).

The amino acid sequence of the full-length OAA-HC1-k delete is the amino acid sequence as shown in SEQ ID NO: 114 of the Sequence Listing (FIG. 115). In such an amino acid sequence, amino acids 1 to 19 constitute a signal sequence, and amino acids 20 to 245 constitute OAA-HC1-k delete.

10)-1-4 Preparation of taFv-Heterodimer Fc-Type Bispecific Molecule Expression Vectors for Evaluation of Various Formats In order to evaluate taFv-heterodimer Fc-type anti-HLA/NY-ESO-anti-CD3 bispecific molecules for evaluation of various formats, expression vectors for various molecules were designed. As the anti-HLA/NY-ESO antibodies, NYA-1143 and NYA-1154 were used. As the anti-CD3 antibody, humanized anti-CD3 scFv; i.e., C3E-7085, was used. As the heterodimer Fc sequence, the Fc sequence comprising a mutation introduced thereinto to lower effector functions and form a heteropolymer was used.

An expression vector for mammal cells comprising a DNA fragment encoding HC2-k delete integrated into the carboxyl terminus of taFv comprising NYA-1154 ligated to C3E-7085 with a GGGGS linker was prepared and designated as "p_NYF-0010-HC2-k delete."

An expression vector for mammal cells comprising a DNA fragment encoding HC2-k delete integrated into the carboxyl terminus of taFv comprising C3E-7085 ligated to NYA-1154 with a GGGGS linker was prepared and designated as "p_NYF-0004-HC2-k delete."

An expression vector for mammal cells comprising a DNA fragment encoding HC2-k delete integrated into the carboxyl terminus of taFv comprising NYA-1143 ligated to C3E-7085 with a GGGGS linker was prepared and designated as "p_NYF-0011-HC2-k delete."

The nucleotide sequence of p_NYF-0010-HC2-k delete was reanalyzed, and the nucleotide sequence of the full-length NYF-0010-HC2-k delete was found to be the nucleotide sequence as shown in SEQ ID NO: 115 of the Sequence Listing (FIG. 116).

The nucleotide sequence of p_NYF-0004-HC2-k delete was reanalyzed, and the nucleotide sequence of the full-length NYF-0004-HC2-k delete was found to be the nucleotide sequence as shown in SEQ ID NO: 116 of the Sequence Listing (FIG. 117).

The nucleotide sequence of p_NYF-0011-HC2-k delete was reanalyzed, and the nucleotide sequence of the full-length NYF-0011-HC2-k delete was found to be the nucleotide sequence as shown in SEQ ID NO: 117 of the Sequence Listing (FIG. 118).

On the basis of the nucleotide sequences above, the amino acid sequences of the full-length NYF-0010-HC2-k delete, NYF-0004-HC2-k delete, and NYF-0011-HC2-k delete encoded thereby were identified.

The amino acid sequence of the full-length NYF-0010-HC2-k delete is the amino acid sequence as shown in SEQ ID NO: 118 (FIG. 119) of the Sequence Listing. In such an amino acid sequence, amino acids 1 to 19 constitute a signal sequence, amino acid 21 to 511 constitute NYA-1154-C3E-7085 taFv, amino acids 512 to 513 constitute a linker, and amino acids 514 to 744 constitute HC2-k delete.

The amino acid sequence of the full-length NYF-0004-HC2-k delete is the amino acid sequence as shown in SEQ ID NO: 119 (FIG. 120) of the Sequence Listing. In such an amino acid sequence, amino acids 1 to 19 constitute a signal sequence, amino acid 21 to 511 constitute C3E-7085-NYA-1154 taFv, amino acids 512 to 513 constitute a linker, and amino acids 514 to 744 constitute HC2-k delete.

The amino acid sequence of the full-length NYF-0011-HC2-k delete is the amino acid sequence as shown in SEQ ID NO: 120 of the Sequence Listing (FIG. 121). In such an amino acid sequence, amino acids 1 to 19 constitute a signal sequence, amino acid 21 to 511 constitute NYA-1143-C3E-7085 taFv, amino acids 512 to 513 constitute a linker, and amino acids 514 to 745 constitute HC2-k delete.

10)-2 Expression of Fc-Conjugated Anti-HLA/NY-ESO-Anti-CD3 Bispecific Molecules of Various Formats 10)-2-1 Expression of Hybrid-Type Bispecific Molecules In the same manner as in 7)-2-1, the culture supernatant of the hybrid-type bispecific molecule (NYG-3143) was prepared using a vector mixture comprising p_NYA-1143-Fab-HC1-k delete, p_C3E-7085-HC2-k delete, and p_NYA-1143-LC at 1:1:1.5. The amino acid sequences obtained via expression of vectors constituting NYG-3143 are shown in SEQ ID NO: 104 of the Sequence Listing (FIG. 105), SEQ ID NO: 105 of the Sequence Listing (FIG. 106), and SEQ ID NO: 106 of the Sequence Listing (FIG. 107).

10)-2-2 Expression of Dual-Type Bispecific Molecules

In the same manner as in 7)-2-1, the culture supernatant of the dual-type bispecific molecule (NYG-2143) was prepared using a vector mixture comprising p_NYA-1143-HC1-k delete and p_C3E-7085-HC2-k delete at 2:1. The amino acid sequences obtained via expression of vectors constituting NYG-2143 are shown in SEQ ID NO: 108 of the Sequence Listing (FIG. 109) and SEQ ID NO: 106 of the Sequence Listing (FIG. 107).

10)-2-3 Expression of scFv-Fab-Heterodimer Fc-Type Bispecific Molecules

In the same manner as in 7)-2-1, the culture supernatant of the scFv-Fab-heterodimer Fc-type (scFv-Fab-Fc-type) bispecific molecule (NYF-0003) was prepared using a vector mixture comprising p_C3E-7085-NYA-1154-Fab-HC2-k delete, p_OAA-HC1-k delete, and p_NYA-1154-LC at 1:1:1.5. The amino acid sequences obtained via expression of vectors constituting NYF-0003 are shown in SEQ ID NO: 112 of the Sequence Listing (FIG. 113), SEQ ID NO: 113 of the Sequence Listing (FIG. 114), and SEQ ID NO: 114 of the Sequence Listing (FIG. 115).

10)-2-4 Expression of taFv-Heterodimer Fc-Type Bispecific Molecules for Evaluation of Various Formats In the same manner as in 7)-2-1, the culture supernatant of the taFv-heterodimer Fc-type (taFv-Fc-type) anti-HLA/NY-ESO-anti-CD3 bispecific molecule (NYF-0010) was prepared using p_NYF-0010-HC2-k delete and p_OAA-HC1-k delete. The amino acid sequences obtained via expression of vectors constituting NYF-0010 are shown in SEQ ID NO: 118 of the Sequence Listing (FIG. 119) and SEQ ID NO: 114 of the Sequence Listing (FIG. 115).

The culture supernatant of the taFv (inversed)-heterodimer Fc-type (taFv (inversed)-Fc-type) anti-HLA/NY-ESO-anti-CD3 bispecific molecule (NYF-0004) was prepared using p_NYF-0004-HC2-k delete and p_OAA-HC1-k delete. The amino acid sequences obtained via expression of vectors constituting NYF-0004 are shown in SEQ ID NO: 119 of the Sequence Listing (FIG. 120) and SEQ ID NO:114 of the Sequence Listing (FIG. 115).

The culture supernatant of the taFv-Fc-type anti-HLA/NY-ESO-anti-CD3 bispecific molecule (NYF-0011) was prepared using p_NYF-0011-HC2-k delete and p_OAA-HC1-k delete. The amino acid sequences obtained via expression of vectors constituting NYF-0011 are shown in SEQ ID NO: 120 of the Sequence Listing (FIG. 121) and SEQ ID NO: 114 of the Sequence Listing (FIG. 115).

10)-3 Purification of Fc-Conjugated Anti-HLA/NY-ESO-Anti-CD3 Bispecific Molecules of Various Formats Various bispecific molecules were purified from the culture supernatants obtained in 10)-2-1 and 10)-2-2 by 2 steps of protein A affinity chromatography and ceramic hydroxyapatite chromatography.

The culture supernatant was applied to the MabSelect-SuRe column equilibrated with PBS at pH 7.4 (GE Healthcare Bioscience) to allow the target bispecific molecules to adsorb thereto. After the non-adsorbed components were removed by PBS, the adsorbed components were eluted using acetate buffer (pH 3.6). The elution fraction was neutralized with the aid of Tris buffer (pH 9.5), and a buffer was exchanged with 25 mM histidine, 150 mM NaCl, 5% Sorbitol, at pH 5.5. The solution of the target fraction diluted to 5-fold with a buffer comprising 10 mM potassium phosphate and 50 mM MES (pH 6.5) was applied to the ceramic hydroxyapatite column (Bio-Scale CHT Type-1 Hydroxyapatite Column, BioRad Japan) equilibrated with 10 mM potassium phosphate and 50 mM MES (pH 6.5). Linear concentration gradient elution was performed using sodium chloride, and fractions equivalent to the target heterodimer were collected. The fractions were applied to the gel filtration column Superdex 200 10/300 (GE Healthcare Bioscience) equilibrated with 25 mM histidine, 300 mM NaCl, 5% Sorbitol at pH 6.0 in advance. From the peak fraction obtained via gel filtration chromatography, fractions equivalent to the target heterodimer were collected, and the buffer was exchanged with 25 mM histidine, 300 mM NaCl, 5% Sorbitol at pH 5.5. Generation of the target anti-HLA/NY-ESO-anti-CD3 bispecific molecule was confirmed via SDS-polyacrylamide electrophoresis (SDS-PAGE). Purified protein samples were subjected to analytical SEC, the degree of purification and the concentration were determined, and the samples were then subjected to various types of evaluation.

Various bispecific molecules were purified from the culture supernatants obtained in 10)-2-3 and 10)-2-4 by 2 steps of protein A affinity chromatography and gel filtration chromatography in the same manner as in 7)-3. Generation of the target anti-HLA/NY-ESO-anti-CD3 bispecific molecule was confirmed via SDS-polyacrylamide electrophoresis (SDS-PAGE). Purified protein samples were subjected to analytical SEC, the degree of purification and the concentration were determined, and the samples were then subjected to various types of evaluation.

(Example 11) Evaluation of In Vitro Activity of Fc-Conjugated Anti-HLA-A2/NY-ESO-Anti-CD3 Bispecific Molecules of Various Formats 11)-1 Evaluation of In Vitro Activity of Hybrid-Type, Dual-Type, and taFv-Fc-Type Anti-HLA-A2/NY-ESO-Anti-CD3 Bispecific Molecules 11)-1-1 Preparation of Target Cells U266B1 cells prepared in the same manner as in Example 8)-1 were used as the target cells.

11)-1-2 Preparation of Effector Cells

Commercially available frozen human PBMCs (Cellular Technology Limited) prepared in the same manner as in Example 8)-2 were used as the effector cells.

11)-1-3 Cytotoxicity Assay

The target cells obtained in Example 11)-1-1 were seeded on a 96-well U-bottom microplate at 50 µl/well. The anti-HLA-A2/NY-ESO-anti-CD3 bispecific molecules of various formats prepared in Example 10 and adjusted to various concentration levels were added thereto at 50 µl/well, the effector cells prepared in Example 11)-1-2 were added thereto at 100 µl/well, centrifugation was carried out at room temperature and 1,000 rpm for 1 minute, and then they were incubated at 37° C. in the presence of 5% $CO_2$ for 20 to 24 hours. The supernatant (50 µl) was collected on a LumaPlate (PerkinElmer), dried at 50° C. for approximately 2 hours, and then assayed using a plate reader (TopCount, PerkinElmer). The test was performed in triplicate, and the rate of cell lysis was determined in accordance with the following equation.

Rate of cell lysis (%)=$(A-B)/(C-B)\times 100$

A: Sample well count
B: Mean of background (wells not supplemented with antibody) count (n=3).

When the antibody was added, 50 µl of an assay medium was added. Other procedures were the same as those for the sample wells.

C: Mean of maximal release (wells in which target cells were lysed with a surfactant) count (n=3).

Figure 7A:
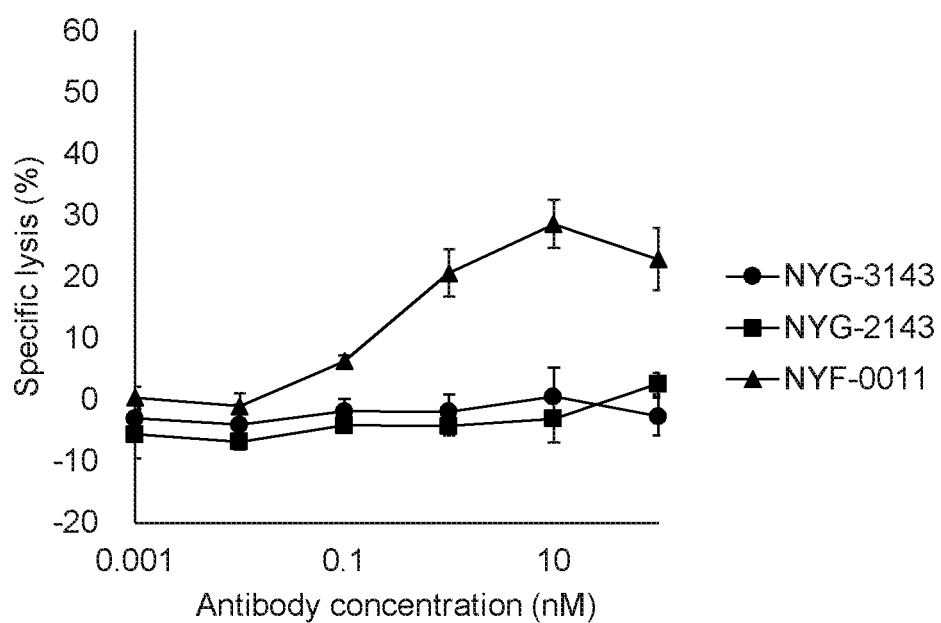
FIG. 7A demonstrates that various anti-HLA-A2/NY-ESO-anti-CD3 bispecific molecules; Hybrid-type (NYG-3143), Dual-type (NYG-2143), and taFv-heterodimer Fc-type (NYF-0011), exert cytotoxicity on human U266B1 cells endogenously expressing NY-ESO in the presence of human PBMC. An error bar in the figure indicates the standard deviation (n=3).

When the antibody was added, 50 µl of an assay medium was added. A surfactant was added in an amount of 100 µl, a fraction of 50 µl was transferred to the LumaPlate as in the case of the sample wells, and assays were then performed. As shown in FIG. 7A, the taFv-Fc type exerted cytotoxicity. The results of calculations of $EC_{50}$ obtained using the Four Parameter Logistic Curve equation of analytical software (Sigmaplot, version 12.0) are shown in Table 5. "Not Applicable (NA)" indicates that it is impossible to perform curve fitting because the correlation coefficient (R) was not calculated. Neither Hybrid-type nor Dual-type exerted cytotoxicity.

TABLE 5

| | Format | Name | $EC_{50}$ (nM) |
|---|---|---|---|
| 1 | Hybrid | NYG-3143 | NA* |
| 2 | Dual | NYG-2143 | NA* |
| 3 | taFv-Fc | NYF-0011 | 0.27 |

*NA = Not Applicable

11)-2 Evaluation of In Vitro Activity of scFv-Fab-Fc-Type, taFv-Fc-Type, and taFv (Inversed)-Fc-Type Anti-HLA-A2/NY-ESO-Anti-CD3 Bispecific Molecules
11)-2-1 Preparation of Target Cells
U266B1 cells prepared in the same manner as in Example 8)-1 were used as the target cells.
11)-2-2 Preparation of Effector Cells
Commercially available frozen human PBMCs (Cellular Technology Limited) prepared in the same manner as in Example 8)-2 were used as the effector cells.
11)-2-3 Cytotoxicity Assay
The target cells obtained in Example 11)-2-1 were seeded on a 96-well U-bottom microplate at 50 µl/well. The anti-HLA-A2/NY-ESO-anti-CD3 bispecific molecules of various formats prepared in Example 10 and adjusted to various concentration levels were added thereto at 50 µl/well, the effector cells prepared in Example 11)-1-2 were added thereto at 100 µl/well, centrifugation was carried out at room temperature and 1,000 rpm for 1 minute, and then they were incubated at 37° C. in the presence of 5% $CO_2$ for 20 to 24 hours. The supernatant (50 µl) was collected on a LumaPlate (PerkinElmer), dried at 50° C. for approximately 2 hours, and then assayed using a plate reader (TopCount, PerkinElmer). The test was performed in triplicate, and the rate of cell lysis was determined in accordance with the following equation.

Rate of cell lysis (%)=$(A-B)/(C-B)\times 100$

A: Sample well count
B: Mean of background (wells not supplemented with antibody) count (n=3).

When the antibody was added, 50 µl of an assay medium was added. Other procedures were the same as those for the sample wells.

C: Mean of maximal release (wells in which target cells were lysed with a surfactant) count (n=3).

Figure 7B:
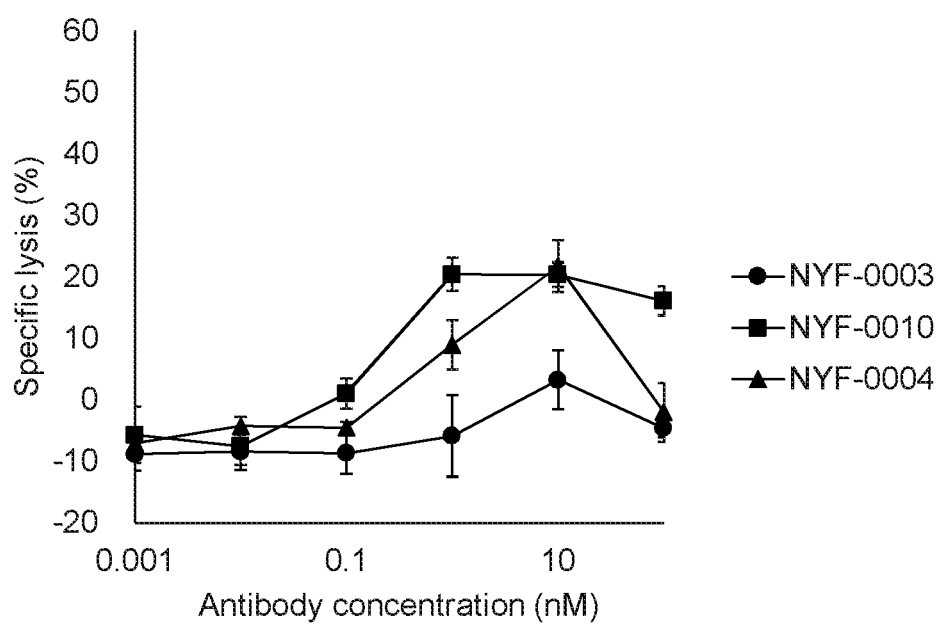
FIG. 7B demonstrates that various anti-HLA-A2/NY-ESO-anti-CD3 bispecific molecules; scFv-Fab-heterodimer Fc-type (NYF-0003), taFv-heterodimer Fc-type (NYF-0010), taFv (inversed)-heterodimer Fc-type (NYF-0004), exert cytotoxicity on human U266B1 cells endogenously expressing NY-ESO in the presence of human PBMC. An error bar in the figure indicates the standard deviation (n=3).

When the antibody was added, 50 µl of an assay medium was added. A surfactant was added in an amount of 100 µl, a fraction of 50 µl was transferred to the LumaPlate as in the case of the sample wells, and assays were then performed. As shown in FIG. 7B, the taFv-Fc type exerted cytotoxicity. The results of calculations of $EC_{50}$ obtained using the Four Parameter Logistic Curve equation of analytical software (Sigmaplot, version 12.0) are shown in Table 6. "Not Applicable (NA)" indicates that it is impossible to perform curve fitting because the correlation coefficient (R) was not calculated. In comparison with the taFv-heterodimer Fc-type, the scFv-Fab-heterodimer Fc-type and the taFv (inversed)-heterodimer Fc-type exhibited lower activity.

TABLE 6

| | Format | Name | $EC_{50}$ (nM) |
|---|---|---|---|
| 1 | scFv-Fab-heterodimer Fc | NYF-0003 | NA* |
| 2 | taFv-heterodimer Fc | NYF-0010 | 0.13 |
| 3 | taFv (inversed)-heterodimer Fc | NYF-0004 | 0.88 |

*NA = Not Applicable (Example 12) Preparation of Various Fc-Conjugated Anti-HLA/NY-ESO-Anti-CD3 Bispecific Molecules Via Mutagenesis and Format Modification of NYF-0061

12)-1 Preparation of Various Fc-Conjugated Anti-HLA/NY-ESO-Anti-CD3 Bispecific Molecule Expression Vectors Via Mutagenesis and Format Modification of NYF-0061

In order to improve physical properties, NYF-0061 mutants were designed and the vectors constituting the molecules described below were prepared.

A mutation was introduced into the C3E-7085 sequence of the p_NYF-0061-HC2 vector containing the nucleotide sequence encoding the amino acid sequence of NYF-0061 and the resultant was designated as "p_NYZ-0038-HC2."

A mutation was introduced into the NYA-2061 sequence and the C3E-7085 sequence of the p_NYF-0061-HC2 vector containing the nucleotide sequence encoding the amino acid sequence of NYF-0061 and the resultants were designated as "p_NYZ-0082-HC2" and "p_NYZ-0083-HC2," respectively.

The nucleotide sequence of p_NYZ-0038-HC2 was reanalyzed, and the nucleotide sequence of the full-length NYZ-0038-HC2 was found to be the nucleotide sequence as shown in SEQ ID NO: 152 of the Sequence Listing (FIG. 148).

The nucleotide sequence of p_NYZ-0082-HC2 was reanalyzed, and the nucleotide sequence of the full-length NYZ-0082-HC2 was found to be the nucleotide sequence as shown in SEQ ID NO: 153 of the Sequence Listing (FIG. 149).

The nucleotide sequence of p_NYZ-0083-HC2 was reanalyzed, and the nucleotide sequence of the full-length NYZ-0083-HC2 was found to be the nucleotide sequence as shown in SEQ ID NO: 154 of the Sequence Listing (FIG. 150).

On the basis of the nucleotide sequences above, the amino acid sequences of the full-length NYZ-0038-HC2, NYZ-0082-HC2, and NYZ-0083-HC2 encoded thereby were identified.

The amino acid sequence of the full-length NYZ-0038-HC2 is the amino acid sequence as shown in SEQ ID NO: 155 of the Sequence Listing (FIG. 151). In such an amino acid sequence, amino acids 1 to 19 constitute a signal sequence, amino acid 21 to 511 constitute NYA-2061-C3E-7096 taFv, amino acids 512 to 513 constitute a linker, and amino acids 514 to 745 constitute HC2.

The amino acid sequence of the full-length NYZ-0082-HC2 is the amino acid sequence as shown in SEQ ID NO: 156 of the Sequence Listing (FIG. 152). In such an amino acid sequence, amino acids 1 to 19 constitute a signal sequence, amino acids 21 to 516 constitute NYA-3061-C3E-7096 taFv, amino acids 517 to 518 constitute a linker, and amino acids 519 to 750 constitute HC2.

The amino acid sequence of the full-length NYZ-0083-HC2 is the amino acid sequence as shown in SEQ ID NO: 157 of the Sequence Listing (FIG. 153). In such an amino acid sequence, amino acids 1 to 19 constitute a signal sequence, amino acids 21 to 516 constitute NYA-3061-C3E-7097 taFv, amino acids 517 to 518 constitute a linker, and amino acids 519 to 750 constitute HC2.

In order to examine format modification of NYF-0061 into the scFv-Fab-heterodimer Fc-type, the vectors constituting the molecules described below were designed.

An expression vector for mammal cells comprising DNA fragments encoding an amino acid sequence included in a polypeptide comprising (i) the heavy chain variable region of C3E-7085, (ii) the human IgG-derived CH1 region, and (iii) the Fc region comprising a mutation to lower effector functions and form a heteropolymer integrated in that order into the carboxyl terminus of NYA-3061 was prepared and designated as "p_NYZ-1010-HC2." Also, an expression vector for mammal cells comprising a DNA fragment encoding an amino acid sequence included in a polypeptide comprising the human IgG-derived CL region added to the carboxyl terminus of the light chain variable region of C3E-7085 was prepared and designated as "p_C3E-7085-LC."

The nucleotide sequence of p_NYZ-1010-HC2 was reanalyzed, and the nucleotide sequence of the full-length NYZ-1010-HC2 was found to be the nucleotide sequence as shown in SEQ ID NO: 158 of the Sequence Listing (FIG. 154).

The nucleotide sequence of p_C3E-7085-LC was reanalyzed, and the nucleotide sequence of the full-length C3E-7085-LC was found to be the nucleotide sequence as shown in SEQ ID NO: 159 of the Sequence Listing (FIG. 155).

On the basis of the nucleotide sequences above, the amino acid sequences of the full-length NYZ-1010-HC2 and C3E-7085-LC encoded thereby were identified.

The amino acid sequence of the full-length NYZ-1010-HC2 is the amino acid sequence as shown in SEQ ID NO: 160 of the Sequence Listing (FIG. 156). In such an amino acid sequence, amino acids 1 to 19 constitute a signal sequence, amino acids 21 to 271 constitute NYA-3061, amino acids 272 to 276 constitute a linker, and amino acids 277 to 394 constitute the heavy chain variable region of C3E-7085. Also, amino acids 395 to 724 constitute a constant region.

The amino acid sequence of the full-length C3E-7085-LC is the amino acid sequence as shown in SEQ ID NO: 161 of the Sequence Listing (FIG. 157). In such an amino acid sequence, amino acids 1 to 20 constitute a signal sequence, amino acids 21 to 127 constitute a variable region, and amino acids 128 to 233 constitute a constant region. Also, amino acids 46 to 53 constitute CDRL1 (SEQ ID NO: 144 (FIG. 142)), amino acids 71 to 73 constitute CDRL2 (SEQ ID NO: 145 (FIG. 142)), and amino acids 110 to 117 constitute CDRL3 (SEQ ID NO: 146 (FIG. 142)).

12)-2 Expression and Purification of Various Fc-Conjugated Anti-HLA/NY-ESO-Anti-CD3 Bispecific Molecules Via Mutagenesis and Format Modification or NYF-0061

In the same manner as in 7)-2-1, the culture supernatant of the taFv-heterodimer Fc-type anti-HLA/NY-ESO-anti-CD3 bispecific molecule (NYZ-0038) was prepared using p_NYZ-0038-HC2 and p_HC1. The amino acid sequences obtained via expression of vectors constituting NYZ-0038 are shown in SEQ ID NO: 155 of the Sequence Listing (FIG. 151) and SEQ ID NO: 84 of the Sequence Listing (FIG. 85).

The culture supernatant of the taFv-heterodimer Fc-type anti-HLA/NY-ESO-anti-CD3 bispecific molecule (NYZ-0082) was prepared using p_NYZ-0082-HC2 and p_HC1. The amino acid sequences obtained via expression of vectors constituting NYZ-0082 are shown in SEQ ID NO: 156 of the Sequence Listing (FIG. 152) and SEQ ID NO: 84 of the Sequence Listing (FIG. 85).

The culture supernatant of the taFv-heterodimer Fc-type anti-HLA/NY-ESO-anti-CD3 bispecific molecule (NYZ-0083) was prepared using p_NYZ-0083-HC2 and p_HC1. The amino acid sequences obtained via expression of vectors constituting NYZ-0083 are shown in SEQ ID NO: 157 of the Sequence Listing (FIG. 153) and SEQ ID NO: 84 of the Sequence Listing (FIG. 85).

The culture supernatant of the scFv-Fab-heterodimer Fc-type anti-HLA/NY-ESO-anti-CD3 bispecific molecule (NYZ-1010) was prepared using p_NYZ-1010-HC2, p_C3E-7085-LC, and p_HC1. The amino acid sequences obtained via expression of vectors constituting NYZ-1010 are shown in SEQ ID NO: 160 of the Sequence Listing (FIG. 156), SEQ ID NO: 161 of the Sequence Listing (FIG. 157), and SEQ ID NO: 84 of the Sequence Listing (FIG. 85).

The culture supernatants prepared above were purified in the same manner as in 7)-3. Purified protein samples were subjected to analytical SEC, the degree of purification and the concentration were determined, and the samples were then subjected to various types of evaluation.

(Example 13) Evaluation of Binding Affinity to HLA/NY-ESO Using Biacore

With the use of Biacore T200, various Fc-conjugated anti-HLA/NY-ESO-anti-CD3 bispecific molecules were captured as ligands to the immobilized anti-human IgG (Fc) antibody, and the antigen was assayed as an analyte. As the antigen, HLA/NY-ESO prepared in 1)-1 was used. The anti-human IgG (Fc) antibody (Human antibody Capture kit, GE Healthcare) was immobilized on Sensor Chip CM5 (GE Healthcare) in accordance with the instructions of the kit. The Fc-conjugated anti-HLA/NY-ESO-anti-CD3 bispecific molecules diluted to 0.5 g/ml in HBS-EP+(GE Healthcare) to be evaluated were brought into contact therewith at 10 μl/min for 60 seconds for immobilization. Thereafter, the samples were added to the HLA/NY-ESO analytes diluted to various levels with HBS-EP+ at a flow rate of 30 μl/min for 120 seconds and dissociation was assayed for 600 seconds. The results of calculations obtained by such single cycle kinetics analysis, $K_D$, are shown in Table 7. NYZ-0038, NYZ-0082, NYZ-0083, and NYZ-1010 retained binding affinity equivalent to that of NYF-0061.

TABLE 7

| Clone name | $K_D$ (nM) |
| --- | --- |
| NYF-0061 | 1.5 |
| NYZ-0038 | 1.5 |
| NYZ-0082 | 1.8 |
| NYZ-0083 | 1.7 |
| NYZ-1010 | 1.9 |

(Example 14) Preparation of CD3e Knockout T2 Human Lymphoblast Fusion Cells

In order to knockout CD3e in the genome sequence of the T2 human lymphoblast fusion cells (ATCC) by the technique of CRISPR, the Cas9 expression plasmid (GE Healthcare) and the sgRNA expression plasmid were introduced via electroporation (LONZA). Thereafter, cell cloning was performed by limited dilution. The cells in which deletion of the target gene fragment from the introduced cells and CD3e gene expression were not observed as a result of genome analysis and RT-PCR analysis of total RNA, respectively, were subjected to the subsequent experiments.

(Example 15) Analysis of Recognition Amino Acid in NY-ESO Peptide of Fc-Conjugated Anti-HLA-A2/NY-ESO-Anti-CD3 Bispecific Molecule The concentration of the CD3e knockout T2 cells prepared in Example 14 was adjusted to an adequate level in AIM-V medium (Thermo Fisher Scientific) containing 20% FBS, the NY-ESO peptide (SEQ ID NO: 1), the point-mutant NY-ESO peptides 1F, 2M, 3A, 4A, 5A, 6L, 7F, 8A, and 9A (SEQ ID NO: 121 (FIG. 122), 122 (FIG. 123), 123 (FIG. 124), 124 (FIG. 125), 125 (FIG. 126), 126 (FIG. 127), 127 (FIG. 128), 128 (FIG. 129), and 129 (FIG. 130)), and the gp100 peptide (SEQ ID NO: 130 (FIG. 131)) (Sigma Genosys) were added in the same manner as in Example 5, cells stained with the use of the LIVE/DEAD Fixable Dead Cell Stain Kit (Thermo Fisher Scientific) were divided into two groups, the cells in PBS containing 5% FBS were seeded on a 96-well U-bottom microplate at $10^5$ cells/well, and the plate was subjected to centrifugation, followed by removal of the supernatant. The various Fc-conjugated anti-HLA-A2/NY-ESO-anti-CD3 bispecific molecules prepared in Example 12 and diluted to 100 nM with PBS containing 5% FBS were added at 25 µl/well to one of the two groups, and the resultant was allowed to stand at 4° C. for 30 minutes. The cells were washed 2 times in PBS containing 5% FBS, PE conjugated F(ab')2 Fragment Anti-Human IgG (Jackson Immuno Research Laboratories) diluted with PBS containing 5% FBS was added at 25 µl/well, and the resultant was allowed to stand at 4° C. for 30 minutes. The cells were washed 2 times in PBS containing 5% FBS, immobilized with Mildform 10 N (FUJIFILM Wako Pure Chemical Corporation) overnight, and resuspended in PBS containing 5% FBS. For standardization with the amount of the HLA/peptide complex, the HLA-A2 antibody BB7.2-Alexa Fluor 488 diluted to 10 µg/ml in PBS containing 5% FBS or mouse IgG2b-Alexa Fluor 488 (BioRAD) was added at 25 µl/well, and the resultant was allowed to stand at 4° C. for 30 minutes. The cells were washed 2 times in PBS containing 5% FBS, immobilized with Mildform 10 N (FUJIFILM Wako Pure Chemical Corporation) overnight, and resuspended in PBS containing 5% FBS. The cell suspensions were subjected to detection using a flow cytometer (CantoII, Becton Dickinson). Data analysis was performed using Flowjo (Treestar), and the geometric mean fluorescence intensity (gMFI) of PE or Alexa Fluor 488 in the CD3e knockout T2 cells from which dead cells were removed was measured. The standardized gMFI indicating the binding affinity of each Fc-conjugated anti-HLA-A2/NY-ESO-anti-CD3 bispecific molecule standardized with the amount of the HLA/peptide complex on the CD3e knockout T2 cells was determined in accordance with the following equation.

$$\text{Standardized gMFI} = (A/B)/((C/D)/(E/F))$$

A/B=Relative gMFI

A: gMFI of PE in CD3e knockout T2 cells supplemented with DMSO or peptide in the presence of antibody B: gMFI of PE in CD3e knockout T2 cells supplemented with DMSO or peptide (C/D)/(E/F)=Corrected amount of HLA/peptide complex in CD3e knockout T2 cells supplemented with DMSO or peptide C: gMFI of Alexa488 in CD3e knockout T2 cells supplemented with DMSO or peptide in the presence of HLA-A2 antibody D: gMFI of Alexa488 in CD3e knockout T2 cells supplemented with DMSO or peptide in the presence of mouse IgG2b antibody E: gMFI of Alexa488 in CD3e knockout T2 cells supplemented with DMSO containing HLA-A2 antibody F: gMFI of Alexa488 in CD3e knockout T2 cells supplemented with DMSO containing mouse IgG2b antibody As shown in FIG. 158A, the Fc-conjugated anti-HLA-A2/NY-ESO-anti-CD3 bispecific molecules; i.e., NYZ-0038, NYZ-0082, NYZ-0083, and NYZ-1010, exhibited binding affinity to the CD3e knockout T2 cells, supplemented with peptides comprising point mutations introduced into amino acids 1, 4, 5, and 7, that had been lowered to a quarter of the binding affinity for the wild-type NY-ESO peptide or lower. This indicates that such constructs strongly recognize amino acids 1, 4, 5, and 7 of the NY-ESO peptide.

(Example 16) Evaluation of Antigen-Binding Specificity of Fc-Conjugated Anti-HLA-A2/NY-ESO-Anti-CD3 Bispecific Molecules In the same manner as in Example 6), the 9-mer peptide shown in FIG. 2A exhibiting identity to the sequence of the NY-ESO peptide: SLLMWITQC (SEQ ID NO: 1) at amino acids 1, 4, and 5, which are indicated to be strongly recognized by the four types of antibodies, was selected as a homologous peptide, and binding specificity thereto was evaluated. The concentration of the CD3e knockout T2 cells was adjusted to an adequate level in AIM-V medium (Thermo Fisher Scientific) containing 20% FBS, a solution of the NY-ESO peptide (SEQ ID NO: 1), the homologous peptides DOLPP1, IL20RB, PRKD2, CD163, and P2RY8 (SEQ ID NO: 131 (FIG. 132), SEQ ID NO: 132 (FIG. 133), SEQ ID NO: 133 (FIG. 134), SEQ ID NO: 134 (FIG. 135), and SEQ ID NO: 135 (FIG. 136)), or the gp100 peptide (SEQ ID NO: 130 (FIG. 131)) (Sigma Genosys) dissolved to 5 mM in DMSO was added to result in a final concentration of 50 µM, or DMSO was added in an amount of 1/100, and binding affinity of the antibodies was evaluated in the same manner as in Example 15. The standardized gMFI indicating the binding affinity of each Fc-conjugated anti-HLA-A2/NY-ESO-anti-CD3 bispecific molecule standardized with the amount of the HLA/peptide complex on the CD3e knockout T2 cells was determined in accordance with the following equation.

Standardized gMFI=$(A/B)/((C/D)/(E/F))$

A: gMFI of PE in CD3e knockout T2 cells supplemented with DMSO or peptide in the presence of antibody
B: gMFI of PE in CD3e knockout T2 cells supplemented with DMSO or peptide
(C/D)/(E/F)=Corrected amount of HLA/peptide complex in CD3e knockout T2 cells supplemented with DMSO or peptide
C: gMFI of Alexa488 in CD3e knockout T2 cells supplemented with DMSO or peptide of the presence of HLA-A2 antibody
D: gMFI of Alexa488 in CD3e knockout T2 cells supplemented with DMSO or peptide containing mouse IgG2b antibody
E: gMFI of Alexa488 in CD3e knockout T2 cells supplemented with DMSO containing HLA-A2 antibody
F: gMFI of Alexa488 in CD3e knockout T2 cells supplemented with DMSO containing mouse IgG2b antibody As shown in FIG. 158B, none of the Fc-conjugated anti-HLA-A2/NY-ESO-anti-CD3 bispecific molecules; i.e., NYZ-0038, NYZ-0082, NYZ-0083, and NYZ-1010, had bound to cells supplemented with homologous peptides, and these molecules exhibited very high specificity.

(Example 17) Evaluation of Cytotoxicity of Fc-Conjugated Anti-HLA-A2/NY-ESO-Anti-CD3 Bispecific Molecules 17)-1 Preparation of Target Cells
In the same manner as in Example 8)-1, suspensions of the endogenous human NY-ESO-expressing cells (U266B1 and NCI-H1703) and the endogenous human NY-ESO-non-expressing cells (AGS and CFPAC-1) were prepared and used as the target cells.
17)-2 Preparation of Effector Cells
In the same manner as in Example 8)-2, a suspension of commercially available frozen human PBMCs (Cellular Technology Limited) was prepared and used as the effector cells.
17)-3 Cytotoxicity Assay
The target cells obtained in Example 17)-1 were seeded on a 96-well U-bottom microplate at 50 µl/well. The various Fc-conjugated anti-HLA-A2/NY-ESO-anti-CD3 bispecific molecules prepared in Example 12 and adjusted to various concentration levels were added thereto at 50 µl/well, the effector cells prepared in Example 17)-2 were added thereto at 100 µl/well, centrifugation was carried out at room temperature and 1,000 rpm for 1 minute, and then they were incubated at 37° C. in the presence of 5% $CO_2$ for 20 to 24 hours. The supernatant (50 µl) was collected on a LumaPlate (PerkinElmer), dried at 50° C. for approximately 2 hours, and then assayed using a plate reader (TopCount, PerkinElmer). The test was performed in triplicate, and the rate of cell lysis was determined in accordance with the following equation.

Rate of cell lysis (%)=$(A-B)/(C-B) \times 100$

A: Sample well count
B: Mean of background (wells not supplemented with antibody) count (n=3).
When the antibody was added, 50 µl of an assay medium was added. Other procedures were the same as those for the sample wells.

C: Mean of maximal release (wells in which target cells were lysed with a surfactant) count (n=3).
When the antibody was added, 50 µl of an assay medium was added. A surfactant was added in an amount of 100 µl, a fraction of 50 µl was transferred to the LumaPlate as in the case of the sample wells, and assays were then performed.

As shown in FIG. 159A to FIG. 159D, various anti-HLA-A2/NY-ESO-anti-CD3 bispecific molecules exerted cytotoxicity on the endogenous human NY-ESO-expressing cells (U266B1 and NCI-H1703). The results of calculations of $EC_{50}$ obtained using the Four Parameter Logistic Curve equation of analytical software (Sigmaplot, version 12.0) concerning the U266B1 cells are shown in Table 8, and the results concerning the NCI-H1703 cells are shown in Table 9. As shown in FIG. 159E to FIG. 159H, in contrast, no cytotoxicity was observed on the endogenous human NY-ESO-non-expressing cells (AGS and CFPAC-1).

TABLE 8

| | Name | $EC_{50}$ (nM) |
|---|---|---|
| 1 | NYZ-0038 | 1.01 |
| 2 | NYZ-0082 | 0.45 |
| 3 | NYZ-0083 | 0.25 |
| 4 | NYZ-1010 | 0.96 |

TABLE 9

| | Name | $EC_{50}$ (nM) |
|---|---|---|
| 1 | NYZ-0038 | 0.61 |
| 2 | NYZ-0082 | 1.00 |
| 3 | NYZ-0083 | 0.71 |
| 4 | NYZ-1010 | 2.56 |

(Example 18) Evaluation of In Vivo Activity of Fc-Conjugated Anti-HLA-A2/NY-ESO-Anti-CD3 Bispecific Molecules in Human PBMC-Transfected Models The human squamous lung cancer cell lines NCI-H1703 (ATCC) were adjusted to $6 \times 10^7$ cells/ml in PBS containing 50% Matrigel (Corning) and 0.1 ml thereof was injected hypodermically to NOG mice (female, 6- to 7-week-old) (Day 0). On Day 4, human PBMCs were adjusted to $3.75 \times 10^7$ to $5 \times 10^7$ cells/ml in PBS, and 0.2 ml thereof was injected intravenously. Approximately 1 week thereafter (Day 6 to Day 7), measurement of the major diameter (mm) and the minor diameter (mm) of the tumor was initiated, measurement was performed using an electronic digital caliper with the elapse of time, and the estimated tumor volume was calculated in accordance with the equation below.

Estimated tumor volume ($mm^3$)=mean of estimated tumor volume among individuals Estimated tumor volume of an individual=major diameter×[minor diameter]$^2$/2

On Day 14, mice were divided into groups each consisting of 5 or 6 mice on the basis of tumor volumes, and various anti-HLA-A2/NY-ESO-anti-CD3 bispecific molecules were administered intravenously (NYZ-1010 at 1 mg/kg, NYZ-1010 at 1.2 mg/kg for comparison at the same molar weight). Administration was performed on Day 14 and Day 21. Antitumor effects were observed in the treatment groups to which various anti-HLA-A2/NY-ESO-anti-CD3 bispecific molecules had been administered (FIG. 160A to FIG. 160D). The tumor growth inhibition (%) on Day 28 to Day 29 was calculated in accordance with the following equation and shown in Table 10.

Tumor growth inhibition (%)=100−(estimated tumor volume of treatment group/estimated tumor volume of vehicle control×100)

TABLE 10

| | Name | Tumor growth inhibition (%) |
|---|---|---|
| 1 | NYZ-0038 | 100.0 |
| 2 | NYZ-0082 | 100.0 |
| 3 | NYZ-0083 | 99.8 |
| 4 | NYZ-1010 | 99.9 |

(Example 19) Comparison of Physicochemical Properties of Various Fc-Conjugated Anti-HLA/NY-ESO-Anti-CD3 Bispecific Molecules 19)-1 Acid Treatment Evaluation NYF-0016 and various NYA-1143 CDR graft mutants (NYF-0044, NYF-0045, NYF-0047, NYF-0048, NYF-0060, and NYF-0061) prepared in 7)-2-1 were concentrated by centrifugation using Amicon (Millipore), the buffer was exchanged with 25 mM sodium acetate, 5% sorbitol (pH 5.5), and the concentration was adjusted to 15 mg/ml (NYF-0016 at 10 mg/ml). Subsequently, the samples were dialyzed using Xpress Micro Dialyzer (Scienova) against 100 mM sodium acetate (pH 3.5) or 25 mM sodium acetate, 5% sorbitol (pH 5.5) as a control, and the samples were collected and allowed to stand at room temperature for 1 hour. Subsequently, pH levels of the samples were adjusted to 5.0 using 500 mM Tris-HCl (pH 9.0). The samples were analyzed via size exclusion chromatography (SEC) using ACQUITY UPLC BEH200 SEC 1.7 m 4.6*150 mm (Waters). As the mobile phase, 0.2 M Ki/200 mM KCl/pH 7.0 was employed, and analysis was performed at a flow rate of 0.2 ml/min (detection wavelength: 280 nm). The peak contents (%) of polymers contained in the samples were analyzed and calculated by the area percentage method. The results are shown in FIG. 162. As a result of acid treatment, the polymer content in NYF-0016 was increased to 96%. In various NYA-1143 CDR graft mutants, in contrast, the amount of polymer formation upon acid treatment was decreased. In NYF-0047, NYF-0048, NYF-0060, and NYF-0061, in particular, the amount of polymer formation upon acid treatment was decreased to 1% or lower. This indicates that acid resistance was improved to a significant extent.

19)-2 Evaluation of Solution Stability

NYF-0061 prepared in 7)-2-1 and NYZ-0038, NYZ-0082, NYZ-0083, and NYZ-1010 prepared in 12)-2 were concentrated by centrifugation using Amicon Ultra-4 (Millipore), the buffer was exchanged with 25 mM histidine, 5% sorbitol (pH 6.0), 25 mM histidine and 5% sorbitol (pH 6.0) were added thereto, and the sample concentration was adjusted to 25 mg/ml to prepare evaluation samples. In the beginning, the high molecular weight species (HMWS) of each evaluation sample was determined by the area percentage method via size exclusion chromatography using AdvanceBio SEC 300A 2.7 m 4.6×300 mm (Agilent). As the mobile phase, 0.2 M Ki/200 mM KCl/pH 7.0 was employed, and analysis was performed at a flow rate of 0.2 ml/min (detection wavelength: 280 nm). The solution stability test of each sample was performed by storage at 25° C. for 6 days (NYF-0061: 7 days), size exclusion chromatography under the conditions as described above, and calculation of HMWS (%) of each sample by the area percentage method. The results are shown in Table 11. HMWS (%) of NYF-0061 was increased to approximately 10.6% with the elapse of storage time. In contrast, an increase in HMWS (%) of NYZ-0038, NYZ-0082, NYZ-0083, and NYZ-1010 was approximately 2% or lower. This demonstrates that solution stability of NYZ-0038, NYZ-0082, NYZ-0083, and NYZ-1010 is superior to that of NYF-0061.

TABLE 11

| Clone name | HMWS (%) |
|---|---|
| NYF-0061 | 10.6 |
| NYZ-0038 | 2.1 |
| NYZ-0082 | 1.7 |
| NYZ-0083 | 1.9 |
| NYZ-1010 | 0.8 |

(Example 20) Preparation of Anti-HLA/NY-ESO scFv

20)-1 Construction of Anti-HLA/NY-ESO scFv Expression Vector scFv constructs of antibodies that may have high binding affinity to HLA-A2/NY-ESO-1; i.e., mAb24955N, mAb24956N, mAb28075P, mAb28105P, mAb28113P, and mAb29822P2 (WO2021/003357), were designed, and scFv of mAb24955N was designated as NYC-0005, scFv of mAb24956N was designated as NYC-0006, scFv of mAb28075P was designated as NYC-0007, scFv of mAb28105P was designated as NYC-0008, scFv of mAb28113P was designated as NYC-0009, and scFv of mAb29822P2 was designated as NYC-0010.

Also, scFv expression vectors for NYC-0005, NYC-0006, NYC-0007, NYC-0008, NYC-0009, and NYC-0010 each comprising pcDNA3.4 (ThermoFisher Scientific) as the backbone in mammalian cells were designed. In order to compare expression levels of the same vector backbones and formats in mammalian cells, in addition, scFv expression vectors for NYA-2047, NYA-2061, and NYA-3061 in mammalian cells were designed.

The nucleotide sequences of the constructed scFv expression vectors were reanalyzed, and the nucleotide sequences of the full-length NYA-2047, NYA-2061, NYA-3061, NYC-0005, NYC-0006, NYC-0007, NYC-0008, NYC-0009, and NYC-0010 were found to be the nucleotide sequences as shown in SEQ ID NO: 43 (FIG. 50), SEQ ID NO: 46 (FIG. 53), SEQ ID NO: 163 (FIG. 164), SEQ ID NO: 165 (FIG. 166), SEQ ID NO: 167 (FIG. 168), SEQ ID NO: 169 (FIG. 170), SEQ ID NO: 171 (FIG. 172), SEQ ID NO: 173 (FIG. 174), and SEQ ID NO: 175 (FIG. 176) of Sequence Listing. On the basis of the nucleotide sequences indicated above, the amino acid sequences encoded thereby are as follows: the amino acid sequence of the full-length NYA-2047 is as shown in SEQ ID NO: 50 (FIG. 57); the amino acid sequence of the full-length NYA-2061 is as shown in SEQ ID NO: 53 (FIG. 60); the amino acid sequence of the full-length NYA-3061 is as shown in SEQ ID NO: 164 (FIG. 165); the amino acid sequence of the full-length NYC-0005 is as shown in SEQ ID NO: 166 (FIG. 167); the amino acid sequence of the full-length NYC-0006 is as shown in SEQ ID NO: 168 (FIG. 169); the amino acid sequence of the full-length NYC-0007 is as shown in SEQ ID NO: 170 (FIG.

171); the amino acid sequence of the full-length NYC-0008 is as shown in SEQ ID NO: 172 (FIG. 173); the amino acid sequence of the full-length NYC-0009 is as shown in SEQ ID NO: 174 (FIG. 175); and the amino acid sequence of the full-length NYC-0010 is as shown in SEQ ID NO: 176 (FIG. 177).

20)-2 Expression and Purification of Anti-HLA/NY-ESO scFv

Culture of and gene transfection into the Expi293F cells (ThermoFisher Scientific) were performed in the same manner as described in 1)-5-2. For evaluation of the amount of production, the cells were subjected to agitation culture in an incubator at 37° C. in the presence of 8% $CO_2$ at 135 rpm for 4 days after gene introduction, the culture supernatant was filtered through a 0.2-μm filter (ThermoFisher Scientific), and the culture supernatant of scFv of anti-HLA/NY-ESO was obtained. Purification was performed using Ni Sepharose excel (Cytiva), the eluate was subjected to analytical size exclusion chromatography (SEC), and the concentration was determined. Table 12 shows the amount of production. The amounts of production of NYA-2047, NYA-2061, and NYA-3061 determined with the use of Ni Sepharose excel relative to 1 liter of the culture supernatant in the purified eluate were higher than those of NYC-0005, NYC-0006, NYC-0007, NYC-0008, NYC-0009, and NYC-0010.

TABLE 12

| Clone name | Amount of production per 1 liter (mg) |
| --- | --- |
| NYA-2047 | 53.3 |
| NYA-2061 | 45.7 |
| NYA-3061 | 52.5 |
| NYC-0005 | 2.5 |
| NYC-0006 | 1.1 |
| NYC-0007 | 10.8 |
| NYC-0008 | 0.5 |
| NYC-0009 | 2.4 |
| NYC-0010 | 1.8 |

The eluate of each scFv obtained with the use of Ni Sepharose excel was concentrated and purified through a gel filtration column (Superdex 200 Increase, Cytiva) equilibrated with 25 mM histidine, 300 mM NaCl, 5% Sorbitol (pH 5.5). Purified protein samples were subjected to analytical SEC, the degree of purification and the concentration were determined, and the samples were then subjected to various types of evaluation.

(Example 21) Expression and Purification of scFv-Heterodimer-Fc of Anti-HLA/NY-ESO 21)-1 Construction of scFv-Heterodimer-Fc Expression Vector of Anti-HLA/NY-ESO For comparison of productivity resulting from different formats, an expression vector was constructed by format conversion of scFv of anti-HLA/NY-ESO into an Fc fusion type. As the heterodimer Fc sequences (hereafter, referred to as HC-h and HC-k), those reported in Nat. Biotechnol., Jul. 1998, 16 (7), 677-81 were used.

scFv-heterodimer-Fc constructs of antibodies that may have high binding affinity to HLA-A2/NY-ESO-1; i.e., mAb24955N, mAb24956N, mAb28075P, mAb28105P, mAb28113P, and mAb29822P2 (WO2021/003357), were designed, and scFv-heterodimer-Fc of mAb24955N was designated as NYC-0011, scFv-heterodimer-Fc of mAb24956N was designated as NYC-0012, scFv-heterodimer-Fc of mAb28075P was designated as NYC-0013, scFv-heterodimer-Fc of mAb28105P was designated as NYC-0014, scFv-heterodimer-Fc of mAb28113P was designated as NYC-0015, and scFv-heterodimer-Fc of mAb29822P2 was designated as NYC-0016. Also, scFv-heterodimer-Fc of NYA-2047 was designated as NYD-2047, scFv-heterodimer-Fc of NYA-2061 was designated as NYD-2061, and scFv-heterodimer-Fc of NYA-3061 was designated as NYD-3061.

Expression vectors for HC-h, NYC-0011-HC-k, NYC-0012-HC-k, NYC-0013-HC-k, NYC-0014-HC-k, NYC-0015-HC-k, and NYC-0016-HC-k each comprising pcDNA3.3 or pcDNA3.4 (ThermoFisher Scientific) as the backbone in mammalian cells were designed. Further, expression vectors for NYD-2047-HC-k, NYD-2061-HC-k, and NYD-3061-HC-k in mammalian cells were designed to compare expression levels in mammalian cells with the same vector backbones and formats.

The nucleotide sequences of the constructed scFv-heterodimer-Fc expression vectors were reanalyzed, and the nucleotide sequences of the full-length HC-h, NYD-2047-HC-k, NYD-2061-HC-k, NYD-3061-HC-k, NYC-0011-HC-k, NYC-0012-HC-k, NYC-0013-HC-k, NYC-0014-HC-k, NYC-0015-HC-k, and NYC-0016-HC-k were the nucleotide sequences as shown in SEQ ID NO: 177 (FIG. 178), SEQ ID NO: 179 (FIG. 180), SEQ ID NO: 181 (FIG. 182), SEQ ID NO: 183 (FIG. 184), SEQ ID NO: 185 (FIG. 186), SEQ ID NO: 187 (FIG. 188), SEQ ID NO: 189 (FIG. 190), SEQ ID NO: 191 (FIG. 192), SEQ ID NO: 193 (FIG. 194), and SEQ ID NO: 195 (FIG. 196) of Sequence Listing. On the basis of the nucleotide sequences indicated above, the full-length amino acid sequences encoded thereby are as follows: the amino acid sequence of the entire HC-h is as shown in SEQ ID NO: 178 (FIG. 179); the amino acid sequence of the full-length NYD-2047-HC-k is as shown in SEQ ID NO: 180 (FIG. 181); the amino acid sequence of the full-length NYD-2061-HC-k is as shown in SEQ ID NO: 182 (FIG. 183); the amino acid sequence of the full-length NYD-3061-HC-k is as shown in SEQ ID NO: 184 (FIG. 185); the amino acid sequence of the full-length NYC-0011-HC-k is as shown in SEQ ID NO: 186 (FIG. 187); the amino acid sequence of the full-length NYC-0012-HC-k is as shown in SEQ ID NO: 188 (FIG. 189); the amino acid sequence of the full-length NYC-0013-HC-k is as shown in SEQ ID NO: 190 (FIG. 191); the amino acid sequence of the full-length NYC-0014-HC-k is as shown in SEQ ID NO: 192 (FIG. 193); the amino acid sequence of the full-length NYC-0015-HC-k is as shown in SEQ ID NO: 194 (FIG. 195); and the amino acid sequence of the full-length NYC-0016-HC-k is as shown in SEQ ID NO: 196 (FIG. 197).

21)-2 Expression and Purification of scFv-Heterodimer-Fc of Anti-HLA/NY-ESO

Culture of and gene introduction into the Expi293F cells (ThermoFisher Scientific) were performed in the same manner as described in 1)-5-2. Plasmids used for preparation of clones are shown in Table 13 below.

TABLE 13

| Clone name | HC-k | HC-h |
| --- | --- | --- |
| NYD-2047 | NYD-2047-HC-k | HC-h |
| NYD-2061 | NYD-2061-HC-k | HC-h |
| NYD-3061 | NYD-3061-HC-k | HC-h |
| NYC-0011 | NYC-0011-HC-k | HC-h |
| NYC-0012 | NYC-0012-HC-k | HC-h |
| NYC-0013 | NYC-0013-HC-k | HC-h |
| NYC-0014 | NYC-0014-HC-k | HC-h |

TABLE 13-continued

| Clone name | HC-k | HC-h |
| --- | --- | --- |
| NYC-0015 | NYC-0015-HC-k | HC-h |
| NYC-0016 | NYC-0016-HC-k | HC-h |

For evaluation of the amount of production, the cells were subjected to agitation culture in an incubator at 37° C. in the presence of 8% $CO_2$ at 135 rpm for 4 days after gene introduction, the culture supernatant was filtered through a 0.2-μm filter (ThermoFisher Scientific), and the culture supernatant of scFv-heterodimer-Fc of anti-HLA/NY-ESO was obtained. For purification, the culture supernatant was applied to MabSelectSuRe resin (Cytiva) equilibrated with PBS (pH 7.4) to allow the target scFv-heterodimer-Fc of anti-HLA/NY-ESO to adsorb thereto. After the non-adsorbed components were removed by PBS, the adsorbed components were eluted using acetate buffer, the eluate was neutralized with the aid of Tris buffer, and the eluate was subjected to analytical size exclusion chromatography (SEC) to determine the purity and the concentration. Table 14 shows the amount of production relative to 1 liter of the culture supernatant. The amounts of production of NYA-2047, NYA-2061, and NYA-3061 determined with the use of MabSelectSuRe resin relative to 1 liter of the culture supernatant in the purified eluate were higher than those of NYC-0011, NYC-0012, NYC-0013, NYC-0014, NYC-0015, and NYC-0016.

TABLE 14

| Clone name | Amount of production per 1 liter (mg) |
| --- | --- |
| NYD-2047 | 93.3 |
| NYD-2061 | 112.2 |
| NYD-3061 | 127.5 |
| NYC-0011 | 17.2 |
| NYC-0012 | 4.2 |
| NYC-0013 | 54.1 |
| NYC-0014 | 1.8 |
| NYC-0015 | 12.2 |
| NYC-0016 | 16.6 |

The eluate of each scFv-heterodimer-Fc obtained with the use of MabSelectSuRe resin was concentrated and purified through a gel filtration column (Superdex 200 Increase, Cytiva) equilibrated with 25 mM histidine, 300 mM NaCl, 5% Sorbitol (pH 5.5). Purified protein samples were subjected to analytical size exclusion chromatography (SEC), and NYD-2047, NYD-2061, NYD-3061, NYC-0011, NYC-0013, and NYC-0015 with sufficient degrees of purity and amounts were used as samples for evaluation of solution stability. A target object was not detected in NYC-0016 within the elution time deduced by SEC. It was thus determined that a target object was not expressed in the culture supernatant.

(Example 22) Evaluation of Solution Stability of scFv-Heterodimer-Fc of Anti-HLA/NY-ESO NYD-2047, NYD-2061, NYD-3061, NYC-0011, NYC-0013, and NYC-0015 prepared in Example 21 were concentrated by centrifugation using Amicon Ultra-4 (Millipore), the buffer was exchanged with PBS, PBS was added thereto, and the sample concentration was adjusted to 5 mg/ml to prepare evaluation samples. In the beginning, HMWS (%) of each evaluation sample was determined by the area percentage method via size exclusion chromatography using AdvanceBio SEC 300A 2.7 m 4.6×150 mm (Agilent). As the mobile phase, 0.2 M Ki/200 mM KCl/pH 7.0 was employed, and analysis was performed at a flow rate of 0.2 ml/min (detection wavelength: 280 nm). The accelerated aging test of each sample was performed by storage at 40° C. for 1 day and 7 days, size exclusion chromatography under the conditions as described above, and calculation of HMWS (%) of each sample by the area percentage method. FIG. 163 shows the results demonstrating changes occurred in each sample upon storage at 40° C. with the elapse of time.

HMWS (%) of NYD-2047, NYD-2061, and NYD-3061 was increased to 8.7%, 8.1%, and 4.4%, respectively, with the elapse of storage time. In contrast, HMWS (%) of NYC-0011, NYC-0013, and NYC-0015 was increased to a significant extent; i.e., 71.8%, 42.4%, and 97.3%, respectively, with the elapse of storage time.

The results demonstrate that NYD-2047, NYD-2061 and NYD-3061 are superior to NYC-0011, NYC-0013, and NYC-0015 in terms of solution stability. In addition, HMWS (%) of NYD-3061 was the lowest among the evaluation samples. That is, NYD-3061 was excellent in terms of solution stability.

(Example 23) Evaluation of Binding Affinity to HLA/NY-ESO Using Biacore

NYC-0005, NYC-0007, and NYC-0008 equivalent to scFv constituting anti-HLA/NY-ESO of NYC-0011, NYC-0013, and NYC-0015 were used to evaluate binding affinity to HLA/NY-ESO With the use of Biacore T200, the anti-HLA/NY-ESO scFv was captured as a ligand to the immobilized anti-His antibody, and the antigen was assayed as an analyte. As the antigen, HLA/NY-ESO prepared in 1)-1 was used. The anti-His antibody (His Capture kit, Cytiva) was immobilized on Sensor Chip CM5 (Cytiva) in accordance with the instructions of the kit. The anti-HLA/NY-ESO scFv constructs diluted to 0.5 μg/ml in HBS-EP+(Cytiva) to be evaluated were brought into contact therewith at 10 μl/min for 60 seconds for immobilization. Thereafter, the samples were added to the HLA/NY-ESO analytes diluted to various levels with HBS-EP+ at a flow rate of 30 μl/min for 120 seconds and dissociation was assayed for 600 seconds. The results of calculations obtained by such single cycle kinetics analysis, $K_D$, are shown in Table 15. It was confirmed that NYC-0005, NYC-0007, and NYC-0008 would bind to HLA/NY-ESO under the conditions in which the binding affinity of NYA-2047 used as a positive control to HLA/NY-ESO was stably confirmed.

TABLE 15

| Clone name | $K_D$ |
| --- | --- |
| NYC-0005 | 9.3 nM |
| NYC-0007 | 1.0 μM |
| NYC-0008 | 7.9 nM |

INDUSTRIAL APPLICABILITY

The bispecific antibody of the present invention can be used as a therapeutic or preventive agent for cancer and the like.

All publications, patents, and patent applications cited herein are incorporated herein by reference in their entirety.

SEQUENCE LISTING FREE TEXT

Figure 8:
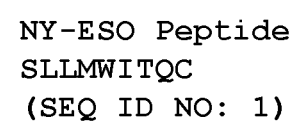

SEQ ID NO 1: The amino acid sequence of the peptide in NY-ESO (FIG. 8)

Figure 9:
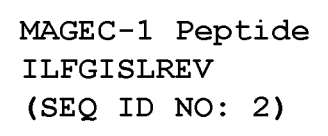

SEQ ID NO 2: The amino acid sequence of the peptide in MAGEC-1 (FIG. 9)

SEQ ID NO 3: The scFv sequence analysis primer 1 (FIG. 10)

SEQ ID NO 4: The scFv sequence analysis primer 2 (FIG. 11)

SEQ ID NO 5: The nucleotide sequence of the heavy chain variable region of NYA-0001 (FIG. 12)

SEQ ID NO 6: The amino acid sequence of the heavy chain variable region of NYA-0001 (FIG. 13)

SEQ ID NO 7: The nucleotide sequence of the light chain variable region of NYA-0001 (FIG. 14)

SEQ ID NO 8: The amino acid sequence of the light chain variable region of NYA-0001 (FIG. 15)

SEQ ID NO 9: The nucleotide sequence of the heavy chain variable region of NYA-0060 (FIG. 16)

SEQ ID NO 10: The amino acid sequence of the heavy chain variable region of NYA-0060 (FIG. 17)

SEQ ID NO 11: The nucleotide sequence of the light chain variable region of NYA-0060 (FIG. 18)

SEQ ID NO 12: The amino acid sequence of the light chain variable region of NYA-0060 (FIG. 19)

SEQ ID NO 13: The nucleotide sequence of the heavy chain variable region of NYA-0068 (FIG. 20)

SEQ ID NO 14: The amino acid sequence of the heavy chain variable region of NYA-0068 (FIG. 21)

SEQ ID NO 15: The nucleotide sequence of the light chain variable region of NYA-0068 (FIG. 22)

SEQ ID NO 16: The amino acid sequence of the light chain variable region of NYA-0068 (FIG. 23)

SEQ ID NO 17: The nucleotide sequence of the heavy chain variable region of NYA-0082 (FIG. 24)

SEQ ID NO 18: The amino acid sequence of the heavy chain variable region of NYA-0082 (FIG. 25)

SEQ ID NO 19: The nucleotide sequence of the light chain variable region of NYA-0082 (FIG. 26)

SEQ ID NO 20: The amino acid sequence of the light chain variable region of NYA-0082 (FIG. 27)

SEQ ID NO 21: The nucleotide sequence of the NYA-1163 tag adduct (FIG. 28)

SEQ ID NO 22: The nucleotide sequence of the NYA-2023 tag adduct (FIG. 29)

SEQ ID NO 23: The nucleotide sequence of the NYA-2027 tag adduct (FIG. 30)

SEQ ID NO 24: The nucleotide sequence of the NYA-1143 tag adduct (FIG. 31)

SEQ ID NO 25: The nucleotide sequence of the NYA-2143 tag adduct (FIG. 32)

SEQ ID NO 26: The amino acid sequence of the NYA-1163 tag adduct (FIG. 33); NYA-1163: amino acids 21 to 266

SEQ ID NO 27: The amino acid sequence of the NYA-2023 tag adduct (FIG. 34); NYA-2023: amino acids 21 to 266

SEQ ID NO 28: The amino acid sequence of the NYA-2027 tag adduct (FIG. 35); NYA-2027: amino acids 21 to 266

SEQ ID NO 29: The amino acid sequence of the NYA-1143 tag adduct (FIG. 36); NYA-1143: amino acids 21 to 266

SEQ ID NO 30: The amino acid sequence of the NYA-2143 tag adduct (FIG. 37); NYA-2143: amino acids 21 to 266

SEQ ID NO 31: The nucleotide sequence of the NYA-1154 tag adduct (FIG. 38)

SEQ ID NO 32: The amino acid sequence of the NYA-1154 tag adduct (FIG. 39); NYA-1154: amino acids 21 to 266

SEQ ID NO 33: The amino acid sequence of the HLA-A*0201 (GenBank: ASA47534.1) truncate (FIG. 40)

SEQ ID NO 34: The amino acid sequence of β2-microglobulin (FIG. 41)

SEQ ID NO 35: The nucleotide sequence of the NYA-2035 tag adduct (FIG. 42)

SEQ ID NO 36: The amino acid sequence of the NYA-2035 tag adduct (FIG. 43); NYA-2035: amino acids 21 to 266

SEQ ID NO 37: The amino acid sequence of NYA-1143-VH01 (FIG. 44)

SEQ ID NO 38: The amino acid sequence of NYA-1143-VH02 (FIG. 45)

SEQ ID NO 39: The amino acid sequence of NYA-1143-VH03 (FIG. 46)

SEQ ID NO 40: The amino acid sequence of NYA-1143-VL01 (FIG. 47)

SEQ ID NO 41: The nucleotide sequence of the NYA-2044 tag adduct (FIG. 48)

SEQ ID NO 42: The nucleotide sequence of the NYA-2045 tag adduct (FIG. 49)

SEQ ID NO 43: The nucleotide sequence of the NYA-2047 tag adduct (FIG. 50)

SEQ ID NO 44: The nucleotide sequence of the NYA-2048 tag adduct (FIG. 51)

SEQ ID NO 45: The nucleotide sequence of the NYA-2060 tag adduct (FIG. 52)

SEQ ID NO 46: The nucleotide sequence of the NYA-2061 tag adduct (FIG. 53)

SEQ ID NO 47: The amino acid sequence of the NYA-2044 tag adduct (FIG. 54); NYA-2044: amino acids 21 to 266

SEQ ID NO 48: The amino acid sequence of the NYA-2045 tag adduct (FIG. 55); NYA-2045: amino acids 21 to 266

SEQ ID NO 49: The amino acid sequence of NYA-0082 (FIG. 56)

SEQ ID NO 50: The amino acid sequence of the NYA-2047 tag adduct (FIG. 57); NYA-2047: amino acids 21 to 266

SEQ ID NO 51: The amino acid sequence of the NYA-2048 tag adduct (FIG. 58); NYA-2048: amino acids 21 to 266

SEQ ID NO 52: The amino acid sequence of the NYA-2060 tag adduct (FIG. 59); NYA-2060: amino acids 21 to 266

SEQ ID NO 53: The amino acid sequence of the NYA-2061 tag adduct (FIG. 60); NYA-2061: amino acids 21 to 266

SEQ ID NO 54: The heavy chain CDRH1 of NYA-0001 (FIG. 61)

SEQ ID NO 55: The heavy chain CDRH2 of NYA-0001 (FIG. 61)

SEQ ID NO 56: The heavy chain CDRH3 of NYA-0001 (FIG. 61)

SEQ ID NO 57: The light chain CDRL1 of NYA-0001 (FIG. 61)

SEQ ID NO 58: The light chain CDRL2 of NYA-0001 (FIG. 61)

SEQ ID NO 59: The light chain CDRL3 of NYA-0001 (FIG. 61)

SEQ ID NO 60: The amino acid sequence of CDRL1 of NYA-2023 (FIG. 62)

SEQ ID NO 61: The amino acid sequence of CDRL3 of NYA-2027 (FIG. 63)

SEQ ID NO 62: The heavy chain CDRH3 of NYA-1154 (FIG. 64)

SEQ ID NO 63: The light chain CDRL3 of NYA-1154 (FIG. 64)

SEQ ID NO 64: The amino acid sequence of CDRL1 of NYA-0035 (FIG. 65)

SEQ ID NO 65: The nucleotide sequence of the NYC-0003 tag adduct (FIG. 66)

SEQ ID NO 66: The nucleotide sequence of the NYC-0004 tag adduct (FIG. 67)

SEQ ID NO 67: The amino acid sequence of NYC-0003 tag adduct (FIG. 68); NYC-0003: amino acids 21 to 263

SEQ ID NO 68: The amino acid sequence of NYC-0004 tag adduct (FIG. 69); NYC-0004: amino acids 21 to 263

SEQ ID NO 69: The nucleotide sequence of the NYA-0001 tag adduct (FIG. 70)

SEQ ID NO 70: The amino acid sequence of the NYA-0001 tag adduct (FIG. 71); NYA-0001: amino acids 21 to 266

SEQ ID NO 71: The nucleotide sequence of HC1 (FIG. 72)

SEQ ID NO 72: The nucleotide sequence of NYF-0016-HC2 (FIG. 73)

SEQ ID NO 73: The nucleotide sequence of NYF-0019-HC2 (FIG. 74)

SEQ ID NO 74: The nucleotide sequence of NYF-0022-HC2 (FIG. 75)

SEQ ID NO 75: The nucleotide sequence of NYF-0023-HC2 (FIG. 76)

SEQ ID NO 76: The nucleotide sequence of NYF-0027-HC2 (FIG. 77)

SEQ ID NO 77: The nucleotide sequence of NYF-0035-HC2 (FIG. 78)

SEQ ID NO 78: The nucleotide sequence of NYF-0044-HC2 (FIG. 79)

SEQ ID NO 79: The nucleotide sequence of NYF-0045-HC2 (FIG. 80)

SEQ ID NO 80: The nucleotide sequence of NYF-0047-HC2 (FIG. 81)

SEQ ID NO 81: The nucleotide sequence of NYF-0048-HC2 (FIG. 82)

SEQ ID NO 82: The nucleotide sequence of NYF-0060-HC2 (FIG. 83)

SEQ ID NO 83: The nucleotide sequence of NYF-0061-HC2 (FIG. 84)

SEQ ID NO 84: The amino acid sequence of HC1 (FIG. 85)

SEQ ID NO 85: The amino acid sequence of NYF-0016-HC2 (FIG. 86); NYA-1143: amino acids 21 to 266; and C3E-7085: amino acids 272 to 511

SEQ ID NO 86: The amino acid sequence of NYF-0019-HC2 (FIG. 87); NYA-2143: amino acids 21 to 266; and C3E-7085: amino acids 272 to 511

SEQ ID NO 87: The amino acid sequence of NYF-0022-HC2 (FIG. 88); NYA-1163: amino acids 21 to 266; and C3E-7085: amino acids 272 to 511

SEQ ID NO 88: The amino acid sequence of NYF-0023-HC2 (FIG. 89); NYA-2023: amino acids 21 to 266; and C3E-7085: amino acids 272 to 511

SEQ ID NO 89: The amino acid sequence of NYF-0027-HC2 (FIG. 90); NYA-2027: amino acids 21 to 266; and C3E-7085: amino acids 272 to 511

SEQ ID NO 90: The amino acid sequence of NYF-0035-HC2 (FIG. 91); NYA-2035: amino acids 21 to 266; and C3E-7085: amino acids 272 to 511

SEQ ID NO 91: The amino acid sequence of NYF-0044-HC2 (FIG. 92); NYA-2044: amino acids 21 to 266; and C3E-7085: amino acids 272 to 511

SEQ ID NO 92: The amino acid sequence of NYF-0045-HC2 (FIG. 93); NYA-2045: amino acids 21 to 266; and C3E-7085: amino acids 272 to 511

SEQ ID NO 93: The amino acid sequence of NYF-0047-HC2 (FIG. 94); NYA-2047: amino acids 21 to 266; and C3E-7085: amino acids 272 to 511

SEQ ID NO 94: The amino acid sequence of NYF-0048-HC2 (FIG. 95); NYA-2048: amino acids 21 to 266; and C3E-7085: amino acids 272 to 511

SEQ ID NO 95: The amino acid sequence of NYF-0060-HC2 (FIG. 96); NYA-2060: amino acids 21 to 266; and C3E-7085: amino acids 272 to 511

SEQ ID NO 96: The amino acid sequence of NYF-0061-HC2 (FIG. 97); NYA-2061: amino acids 21 to 266; and C3E-7085: amino acids 272 to 511

SEQ ID NO 97: The nucleotide sequence of NYA-0001-Fab-HC1-k delete (FIG. 98)

SEQ ID NO 98: The nucleotide sequence of NYA-0001-LC (FIG. 99)

SEQ ID NO 99: The amino acid sequence of NYA-0001-Fab-HC1-k delete (FIG. 100); the NYA-0001 heavy chain variable region: amino acids 20 to 139

SEQ ID NO 100: The amino acid sequence of NYA-0001-LC (FIG. 101); the NYA-0001 light chain variable region: amino acids 21 to 131

SEQ ID NO 101: The nucleotide sequence of NYA-1143-Fab-HC1-k delete (FIG. 102)

SEQ ID NO 102: The nucleotide sequence of NYA-1143-LC (FIG. 103)

SEQ ID NO 103: The nucleotide sequence of C3E-7085-HC2-k deleteC (FIG. 104)

SEQ ID NO 104: The amino acid sequence of NYA-1143-Fab-HC1-k delete (FIG. 105); the NYA-1143 heavy chain variable region: amino acids 20 to 139

SEQ ID NO 105: The amino acid sequence of NYA-1143-LC (FIG. 106); the NYA-1143 light chain variable region: amino acids 21 to 131

SEQ ID NO 106: The amino acid sequence of C3E-7085-HC2-k delete (FIG. 107); C3E-7085: amino acids 21 to 260

SEQ ID NO 107: The nucleotide sequence of NYA-1143-HC1-k delete (FIG. 108)

SEQ ID NO 108: The amino acid sequence of NYA-1143-HC1-k delete (FIG. 109); NYA-1143: amino acids 21 to 266

SEQ ID NO 109: The nucleotide sequence of C3E-7085-NYA-1154-Fab-HC2-k delete (FIG. 110)

SEQ ID NO 110: The nucleotide sequence of NYA-1154-LC (FIG. 111)

SEQ ID NO 111: The nucleotide sequence of OAA-HC1-k delete (FIG. 112)

SEQ ID NO 112: The amino acid sequence of C3E-7085-NYA-1154-Fab-HC2-k delete (FIG. 113); C3E-7085: amino acids 21 to 260; the NYA-1154 heavy chain variable region: amino acids 266 to 285

SEQ ID NO 113: The amino acid sequence of NYA-1154-LC (FIG. 114); the NYA-1154 light chain variable region: amino acids 21 to 131

SEQ ID NO 114: The amino acid sequence of OAA-HC1-k delete (FIG. 115)

SEQ ID NO 115: The nucleotide sequence of NYF-0010-HC2-k delete (FIG. 116)
SEQ ID NO 116: The nucleotide sequence of NYF-0004-HC2-k delete (FIG. 117)
SEQ ID NO 117: The nucleotide sequence of NYF-0011-HC2-k delete (FIG. 118)
SEQ ID NO 118: The amino acid sequence of NYF-0010-HC2-k delete (FIG. 119); NYA-1154: amino acids 21 to 266; and C3E-7085: amino acids 272 to 511
SEQ ID NO 119: The amino acid sequence of NYF-0004-HC2-k delete (FIG. 120); C3E-7085: amino acids 21 to 260; and NYA-1154: amino acids 272 to 511
SEQ ID NO 120: The amino acid sequence of NYF-0011-HC2-k delete (FIG. 121); NYA-1143: amino acids 21 to 266; and C3E-7085: amino acids 272 to 511
SEQ ID NO 121: The amino acid sequence of the point-mutant NY-ESO peptide 1F (FIG. 122)
SEQ ID NO 122: The amino acid sequence of the point-mutant NY-ESO peptide 2M (FIG. 123)
SEQ ID NO 123: The amino acid sequence of the point-mutant NY-ESO peptide 3A (FIG. 124)
SEQ ID NO 124: The amino acid sequence of the point-mutant NY-ESO peptide 4A (FIG. 125)
SEQ ID NO 125: The amino acid sequence of the point-mutant NY-ESO peptide 5A (FIG. 126)
SEQ ID NO 126: The amino acid sequence of the point-mutant NY-ESO peptide 6L (FIG. 127)
SEQ ID NO 127: The amino acid sequence of the point-mutant NY-ESO peptide 7F (FIG. 128)
SEQ ID NO 128: The amino acid sequence of the point-mutant NY-ESO peptide 8A (FIG. 129)
SEQ ID NO 129: The amino acid sequence of the point-mutant NY-ESO peptide 9A (FIG. 130)
SEQ ID NO 130: The amino acid sequence of the gp100 peptide (FIG. 131)
SEQ ID NO 131: The amino acid sequence of the homologous peptide DOLPP1 (FIG. 132)
SEQ ID NO 132: The amino acid sequence of the homologous peptide IL20RB (FIG. 133)
SEQ ID NO 133: The amino acid sequence of the homologous peptide PRKD2 (FIG. 134)
SEQ ID NO 134: The amino acid sequence of the homologous peptide CD163 (FIG. 135)
SEQ ID NO 135: The amino acid sequence of the homologous peptide P2RY8 (FIG. 136)
SEQ ID NO 136: The amino acid sequence of C3E-7034 (FIG. 137)
SEQ ID NO 137: The amino acid sequence of C3E-7036 (FIG. 138)
SEQ ID NO 138: The amino acid sequence of C3E-7085 (FIG. 139)
SEQ ID NO 139: The amino acid sequence of C3E-7088 (FIG. 140)
SEQ ID NO 140: The amino acid sequence of C3E-7093 (FIG. 141)
SEQ ID NO 141: The heavy chain CDRH1 of C3E-7085 (FIG. 142)
SEQ ID NO 142: The heavy chain CDRH2 of C3E-7085 (FIG. 142)
SEQ ID NO 143: The heavy chain CDRH3 of C3E-7085 (FIG. 142)
SEQ ID NO 144: The light chain CDRL1 of C3E-7085 (FIG. 142)
SEQ ID NO 145: The light chain CDRL2 of C3E-7085 (FIG. 142)
SEQ ID NO 146: The light chain CDRL3 of C3E-7085 (FIG. 142)
SEQ ID NO 147: The amino acid sequence of C3E-7078 (FIG. 143)
SEQ ID NO 148: The nucleotide sequence of NYF-0014-HC2 (FIG. 144)
SEQ ID NO 149: The amino acid sequence of NYF-0014-HC2 (FIG. 145); NYA-0001: amino acids 21 to 266; and C3E-7085: amino acids 272 to 511
SEQ ID NO 150: The amino acid sequence of NYF-0082-HC2 (FIG. 146); NYA-0082: amino acids 21 to 266; and C3E-7085: amino acids 272 to 511
SEQ ID NO 151: The amino acid sequence of human CD3 ε (FIG. 147)
SEQ ID NO 152: The nucleotide sequence of the full-length NYZ-0038-HC2 (FIG. 148)
SEQ ID NO 153: The nucleotide sequence of the full-length NYZ-0082-HC2 (FIG. 149)
SEQ ID NO 154: The nucleotide sequence of the full-length NYZ-0083-HC2 (FIG. 150)
SEQ ID NO 155: The amino acid sequence of the full-length NYZ-0038-HC2 (FIG. 151)
SEQ ID NO 156: The amino acid sequence of the full-length NYZ-0082-HC2 (FIG. 152)
SEQ ID NO 157: The amino acid sequence of the full-length NYZ-0083-HC2 (FIG. 153)
SEQ ID NO 158: The nucleotide sequence of the full-length NYZ-1010-HC2 (FIG. 154)
SEQ ID NO 159: The nucleotide sequence of the full-length C3E-7085-LC (FIG. 155)
SEQ ID NO 160: The amino acid sequence of the full-length NYZ-1010-HC2 (FIG. 156)
SEQ ID NO 161: The amino acid sequence of the full-length C3E-7085-LC (FIG. 157)
SEQ ID NO 162: The amino acid sequence of the peptide linker (FIG. 161)
SEQ ID NO 163: The nucleotide sequence of the full-length NYA-3061 (FIG. 164)
SEQ ID NO 164: The amino acid sequence of the full-length NYA-3061 (FIG. 165)
SEQ ID NO 165: The nucleotide sequence of the full-length NYC-0005 (FIG. 166)
SEQ ID NO 166: The amino acid sequence of the full-length NYC-0005 (FIG. 167)
SEQ ID NO 167: The nucleotide sequence of the full-length NYC-0006 (FIG. 168)
SEQ ID NO 168: The amino acid sequence of the full-length NYC-0006 (FIG. 169)
SEQ ID NO 169: The nucleotide sequence of the full-length NYC-0007 (FIG. 170)
SEQ ID NO 170: The amino acid sequence of the full-length NYC-0007 (FIG. 171)
SEQ ID NO 171: The nucleotide sequence of the full-length NYC-0008 (FIG. 172)
SEQ ID NO 172: The amino acid sequence of the full-length NYC-0008 (FIG. 173)
SEQ ID NO 173: The nucleotide sequence of the full-length NYC-0009 (FIG. 174)
SEQ ID NO 174: The amino acid sequence of the full-length NYC-0009 (FIG. 175)
SEQ ID NO 175: The nucleotide sequence of the full-length NYC-0010 (FIG. 176)
SEQ ID NO 176: The amino acid sequence of the full-length NYC-0010 (FIG. 177)
SEQ ID NO 177: The nucleotide sequence of the full-length HC-h (FIG. 178)
SEQ ID NO 178: The amino acid sequence of the full-length HC-h (FIG. 179)

SEQ ID NO 179: The nucleotide sequence of the full-length NYD-2047-HC-k (FIG. 180)
SEQ ID NO 180: The amino acid sequence of the full-length NYD-2047-HC-k (FIG. 181)
SEQ ID NO 181: The nucleotide sequence of the full-length NYD-2061-HC-k (FIG. 182)
SEQ ID NO 182: The amino acid sequence of the full-length NYD-2061-HC-k (FIG. 183)
SEQ ID NO 183: The nucleotide sequence of the full-length NYD-3061-HC-k (FIG. 184)
SEQ ID NO 184: The amino acid sequence of the full-length NYD-3061-HC-k (FIG. 185)
SEQ ID NO 185: The nucleotide sequence of the full-length NYC-0011-HC-k (FIG. 186)
SEQ ID NO 186: The amino acid sequence of the full-length NYC-0011-HC-k (FIG. 187)
SEQ ID NO 187: The nucleotide sequence of the full-length NYC-0012-HC-k (FIG. 188)
SEQ ID NO 188: The amino acid sequence of the full-length NYC-0012-HC-k (FIG. 189)
SEQ ID NO 189: The nucleotide sequence of the full-length NYC-0013-HC-k (FIG. 190)
SEQ ID NO 190: The amino acid sequence of the full-length NYC-0013-HC-k (FIG. 191)
SEQ ID NO 191: The nucleotide sequence of the full-length NYC-0014-HC-k (FIG. 192)
SEQ ID NO 192: The amino acid sequence of the full-length NYC-0014-HC-k (FIG. 193)
SEQ ID NO 193: The nucleotide sequence of the full-length NYC-0015-HC-k (FIG. 194)
SEQ ID NO 194: The amino acid sequence of the full-length NYC-0015-HC-k (FIG. 195)
SEQ ID NO 195: The nucleotide sequence of the full-length NYC-0016-HC-k (FIG. 196)
SEQ ID NO 196: The amino acid sequence of the full-length NYC-0016-HC-k (FIG. 197)
SEQ ID NO 197: The amino acid sequence of the full-length NYZ-1007-HC (FIG. 198)
SEQ ID NO 198: The amino acid sequence of the full-length NYZ-1017-HC (FIG. 199)

---

The invention claimed is:

1. A bispecific antibody that comprises a site which binds specifically to human HLA/NY-ESO and a site which binds specifically to human CD3, wherein the site which binds specifically to human HLA/NY-ESO comprises:
   a heavy chain CDRH1 consisting of the amino acid sequence as shown in SEQ ID NO: 54,
   a heavy chain CDRH2 consisting of the amino acid sequence as shown in SEQ ID NO: 55,
   a heavy chain CDRH3 consisting of the amino acid sequence as shown in SEQ ID NO: 56,
   a light chain CDRL1 consisting of an amino acid sequence derived from the amino acid sequence as shown in SEQ ID NO: 57 in which amino acid 7 is W,
   a light chain CDRL2 consisting of the amino acid sequence represented by DNN, and
   a light chain CDRL3 consisting of the amino acid sequence as shown in SEQ ID NO: 59.

2. The bispecific antibody according to claim 1, wherein the site which binds specifically to human HLA/NY-ESO comprises:
   a heavy chain variable region consisting of an amino acid sequence having 95% or higher sequence identity to an amino acid sequence of amino acids 21 to 140 of the amino acid sequence as shown in SEQ ID NO: 53 and a light chain variable region consisting of an amino acid sequence having 95% or higher sequence identity to an amino acid sequence of amino acids 156 to 266 of the amino acid sequence as shown in SEQ ID NO: 53, or
   a heavy chain variable region consisting of an amino acid sequence having 95% or higher sequence identity to an amino acid sequence of amino acids 21 to 140 of the amino acid sequence as shown in SEQ ID NO: 156 and a light chain variable region consisting of an amino acid sequence having 95% or higher sequence identity to an amino acid sequence of amino acids 161 to 271 of the amino acid sequence as shown in SEQ ID NO: 156.

3. The bispecific antibody according to claim 1 which comprises:
   a heavy chain variable region consisting of an amino acid sequence derived from an amino acid sequence as shown in SEQ ID NO: 53 by substitution, deletion, addition or insertion of one or more amino acids and a light chain variable region consisting of an amino acid sequence derived from an amino acid sequence as shown in SEQ ID NO: 53 by substitution, deletion, addition or insertion of one or more amino acids, or
   a heavy chain variable region consisting of an amino acid sequence derived from an amino acid sequence of amino acids 21 to 140 of the amino acid sequence as shown in SEQ ID NO: 156 by substitution, deletion, addition or insertion of one or more amino acids and a light chain variable region consisting of an amino acid sequence derived from an amino acid sequence of amino acids 161 to 271 of the amino acid sequence as shown in SEQ ID NO: 156 by substitution, deletion, addition or insertion of one or more amino acids.

4. The bispecific antibody according to claim 1, wherein the site which binds specifically to human HLA/NY-ESO is scFv.

5. The bispecific antibody according to claim 1, wherein the site which binds specifically to human CD3 comprises:
   (CCH1) a heavy chain CDRH1 consisting of the amino acid sequence as shown in SEQ ID NO: 141;
   (CCH2) a heavy chain CDRH2 consisting of the amino acid sequence as shown in SEQ ID NO: 142 or a heavy chain CDRH2 consisting of an amino acid sequence derived from the amino acid sequence as shown in SEQ ID NO: 142 in which amino acid 3 is N or S;
   (CCH3) a heavy chain CDRH3 consisting of the amino acid sequence as shown in SEQ ID NO: 143;

(CCL1) a light chain CDRL1 consisting of the amino acid sequence as shown in SEQ ID NO: 144;
(CCL2) a light chain CDRL2 consisting of the amino acid sequence represented by RDD or a light chain CDRL2 consisting of an amino acid sequence derived from the amino acid sequence represented by RDD in which amino acid 2 is N; and
(CCL3) a light chain CDRL3 consisting of the amino acid sequence as shown in SEQ ID NO: 146.

6. The bispecific antibody according to claim 1, wherein the site which binds specifically to human CD3 comprises:
(CH1) a heavy chain variable region consisting of an amino acid sequence of amino acids 2 to 119 of the amino acid sequence as shown in SEQ ID NO: 136,
(CH2) a heavy chain variable region consisting of an amino acid sequence of amino acids 2 to 119 of the amino acid sequence as shown in SEQ ID NO: 137,
(CH3) a heavy chain variable region consisting of an amino acid sequence of amino acids 2 to 119 of the amino acid sequence as shown in SEQ ID NO: 147,
(CH4) a heavy chain variable region consisting of an amino acid sequence of amino acids 2 to 119 of the amino acid sequence as shown in SEQ ID NO: 138,
(CH5) a heavy chain variable region consisting of an amino acid sequence of amino acids 2 to 119 of the amino acid sequence as shown in SEQ ID NO: 139,
(CH6) a heavy chain variable region consisting of an amino acid sequence of amino acids 2 to 119 of the amino acid sequence as shown in SEQ ID NO: 140,
(CH7) a heavy chain variable region consisting of an amino acid sequence of amino acids 272 to 389 of the amino acid sequence as shown in SEQ ID NO: 155,
(CH8) a heavy chain variable region consisting of an amino acid sequence of amino acids 277 to 394 of the amino acid sequence as shown in SEQ ID NO: 156; or
(CH9) a heavy chain variable region consisting of an amino acid sequence of amino acids 277 to 394 of the amino acid sequence as shown in SEQ ID NO: 157; and
(CL1) a light chain variable region consisting of an amino acid sequence of amino acids 135 to 243 of the amino acid sequence as shown in SEQ ID NO: 136,
(CL2) a light chain variable region consisting of an amino acid sequence of amino acids 135 to 241 of the amino acid sequence as shown in SEQ ID NO: 137,
(CL3) a light chain variable region consisting of an amino acid sequence of amino acids 135 to 243 of the amino acid sequence as shown in SEQ ID NO: 147,
(CL4) a light chain variable region consisting of an amino acid sequence of amino acids 135 to 241 of the amino acid sequence as shown in SEQ ID NO: 138,
(CL5) a light chain variable region consisting of an amino acid sequence of amino acids 135 to 243 of the amino acid sequence as shown in SEQ ID NO: 139,
(CL6) a light chain variable region consisting of an amino acid sequence of amino acids 135 to 243 of the amino acid sequence as shown in SEQ ID NO: 140,
(CL7) a light chain variable region consisting of an amino acid sequence of amino acids 405 to 511 of the amino acid sequence as shown in SEQ ID NO: 155,
(CL8) a light chain variable region consisting of an amino acid sequence of amino acids 410 to 516 of the amino acid sequence as shown in SEQ ID NO: 156, or
(CL9) a light chain variable region consisting of an amino acid sequence of amino acids 410 to 516 of the amino acid sequence as shown in SEQ ID NO: 157.

7. The bispecific antibody according to claim 1, wherein the site which binds specifically to human CD3 comprises:
(CH1CL1) a heavy chain variable region consisting of an amino acid sequence of amino acids 2 to 119 of the amino acid sequence as shown in SEQ ID NO: 136 and a light chain variable region consisting of an amino acid sequence of amino acids 135 to 243 of the amino acid sequence as shown in SEQ ID NO: 136;
(CH2CL2) a heavy chain variable region consisting of an amino acid sequence of amino acids 2 to 119 of the amino acid sequence as shown in SEQ ID NO: 137 and a light chain variable region consisting of an amino acid sequence of amino acids 135 to 241 of the amino acid sequence as shown in SEQ ID NO: 137;
(CH3CL3) a heavy chain variable region consisting of an amino acid sequence of amino acids 2 to 119 of the amino acid sequence as shown in SEQ ID NO: 147 and a light chain variable region consisting of an amino acid sequence of amino acids 135 to 243 of the amino acid sequence as shown in SEQ ID NO: 147;
(CH4CL4) a heavy chain variable region consisting of an amino acid sequence of amino acids 2 to 119 of the amino acid sequence as shown in SEQ ID NO: 138 and a light chain variable region consisting of an amino acid sequence of amino acids 135 to 241 of the amino acid sequence as shown in SEQ ID NO: 138;
(CH5CL5) a heavy chain variable region consisting of an amino acid sequence of amino acids 2 to 119 of the amino acid sequence as shown in SEQ ID NO: 139 and a light chain variable region consisting of an amino acid sequence of amino acids 135 to 243 of the amino acid sequence as shown in SEQ ID NO: 139;
(CH6CL6) a heavy chain variable region consisting of an amino acid sequence of amino acids 2 to 119 of the amino acid sequence as shown in SEQ ID NO: 140 and a light chain variable region consisting of an amino acid sequence of amino acids 135 to 243 of the amino acid sequence as shown in SEQ ID NO: 140;
(CH7CL7) a heavy chain variable region consisting of an amino acid sequence of amino acids 272 to 389 of the amino acid sequence as shown in SEQ ID NO: 155 and a light chain variable region consisting of an amino acid sequence of amino acids 405 to 511 of the amino acid sequence as shown in SEQ ID NO: 155;
(CH8CL8) a heavy chain variable region consisting of an amino acid sequence of amino acids 277 to 394 of the amino acid sequence as shown in SEQ ID NO: 156 and a light chain variable region consisting of an amino acid sequence of amino acids 410 to 516 of the amino acid sequence as shown in SEQ ID NO: 156; or
(CH9CL9) a heavy chain variable region consisting of an amino acid sequence of amino acids 277 to 394 of the amino acid sequence as shown in SEQ ID NO: 157 and a light chain variable region consisting of an amino acid sequence of amino acids 410 to 516 of the amino acid sequence as shown in SEQ ID NO: 157.

8. The bispecific antibody according to claim 1, wherein the site which binds specifically to human CD3 is Fab.

9. The bispecific antibody according to claim 1, wherein the bispecific antibody comprises: a first polypeptide comprising scFv that binds specifically to human HLA/NY-ESO, a variable region of an antibody that binds specifically to human CD3, and an Fc region (i) in that order from the N terminus toward the C terminus, a second polypeptide comprising a hinge region and an Fc region (ii) of the immunoglobulin, and a third polypeptide comprising an antibody light chain consisting of a variable region and a constant region, wherein the first polypeptide is associated with the second polypeptide at the Fc region (i) and the Fc region (ii), and the first polypeptide is associated with the third polypeptide in the heavy chain variable region and the constant region CH1 of the antibody.

10. The bispecific antibody according to claim 9, wherein the first polypeptide comprises an amino acid sequence of amino acids 21 to 394 of the amino acid sequence as shown in SEQ ID NO: 160.

11. The bispecific antibody according to claim 10, wherein the first polypeptide comprises the amino acid sequence according to (i) or (ii) below:
   (i) an amino acid sequence of amino acids 20 to 724 of the amino acid sequence as shown in SEQ ID NO: 160; and
   (ii) an amino acid sequence of amino acids 20 to 719 of the amino acid sequence as shown in SEQ ID NO: 197.

12. The bispecific antibody according to claim 9, wherein the first polypeptide comprises the amino acid sequence according to (i) or (ii) below:
   (i) an amino acid sequence of amino acids 20 to 724 of the amino acid sequence as shown in SEQ ID NO: 160; and
   (ii) an amino acid sequence of amino acids 20 to 719 of the amino acid sequence as shown in SEQ ID NO: 197.

13. The bispecific antibody according to claim 9, wherein the second polypeptide comprises an amino acid sequence of amino acids 20 to 246 of the amino acid sequence as shown in SEQ ID NO: 84.

14. The bispecific antibody according to claim 9, wherein the third polypeptide comprises an amino acid sequence of amino acids 21 to 127 of the amino acid sequence as shown in SEQ ID NO: 161.

15. The bispecific antibody according to claim 9, wherein the third polypeptide comprises an amino acid sequence of amino acids 21 to 233 of the amino acid sequence as shown in SEQ ID NO: 161.

16. The bispecific antibody according to claim 1, wherein 1 or 2 amino acids are deleted from the carboxyl terminus of the amino acid sequence of at least one polypeptide included in the bispecific antibody.

17. A pharmaceutical composition comprising, as an active ingredient, the bispecific antibody according to claim 1.

18. The pharmaceutical composition according to claim 17, which comprises other therapeutic agents.

* * * * *

SEQUENCE LISTING

```
<160> NUMBER OF SEQ ID NOS: 198

<210> SEQ ID NO 1
<211> LENGTH: 9
<212> TYPE: PRT
<213> ORGANISM: Artificial
<220> FEATURE:
<223> OTHER INFORMATION: Peptide sequence of NY-ESO

<400> SEQUENCE: 1

Ser Leu Leu Met Trp Ile Thr Gln Cys
1               5

<210> SEQ ID NO 2
<211> LENGTH: 10
<212> TYPE: PRT
<213> ORGANISM: Artificial
<220> FEATURE:
<223> OTHER INFORMATION: Peptide sequence of MAGEC-1

<400> SEQUENCE: 2

Ile Leu Phe Gly Ile Ser Leu Arg Glu Val
1               5                   10

<210> SEQ ID NO 3
<211> LENGTH: 26
<212> TYPE: DNA
<213> ORGANISM: Artificial
<220> FEATURE:
<223> OTHER INFORMATION: Primer for analyzing scFv sequence

<400> SEQUENCE: 3
ctcttcgcta ttacgccagc tggcga                                          26

<210> SEQ ID NO 4
<211> LENGTH: 30
<212> TYPE: DNA
<213> ORGANISM: Artificial
<220> FEATURE:
<223> OTHER INFORMATION: Primer for analyzing scFv sequence

<400> SEQUENCE: 4
ataacaattt cacacaggaa acagctatga                                      30
```

```
<210> SEQ ID NO 5
<211> LENGTH: 360
<212> TYPE: DNA
<213> ORGANISM: Artificial
<220> FEATURE:
<223> OTHER INFORMATION: Nucleotide sequence of a heavy chain variable
      region of NYA-0001

<400> SEQUENCE: 5
gaggtgcagc tggtggagtc tgggggaggc gtggtccagc ctggggaggtc cctgacaccc      60 tcctgttcag cgtctggatt ctccatccgt agttatgata tacactgggt ccgccaggct     120
ccaggcaagg gctagagtg gtggccact atatcatatg atggaagtca gaagtacttc       180
gcagactccg tgaagggccg atttaccatc ttcagagacg aatcggagaa catggtgtat     240
ctgcaaatga gcggcctgag agttgaggac acggctgttt atcactgtgc gagagggagt     300
agtggtcatt atgaggcttt tgatatctgg ggccaaggga caatggtcac cgtctcttca     360

<210> SEQ ID NO 6
<211> LENGTH: 120
<212> TYPE: PRT
<213> ORGANISM: Artificial
<220> FEATURE:
<223> OTHER INFORMATION: Amino acid sequence of a heavy chain variable
      region of NYA-0001

<400> SEQUENCE: 6

Glu Val Gln Leu Val Glu Ser Gly Gly Gly Val Val Gln Pro Gly Arg
1               5                   10                  15

Ser Leu Thr Pro Ser Cys Ser Ala Ser Gly Phe Ser Ile Arg Ser Tyr
            20                  25                  30

Asp Ile His Trp Val Arg Gln Ala Pro Gly Lys Gly Leu Glu Trp Val
        35                  40                  45

Ala Thr Ile Ser Tyr Asp Gly Ser Gln Lys Tyr Phe Ala Asp Ser Val
    50                  55                  60

Lys Gly Arg Phe Thr Ile Phe Arg Asp Glu Ser Glu Asn Met Val Tyr
65                  70                  75                  80

Leu Gln Met Ser Gly Leu Arg Val Glu Asp Thr Ala Val Tyr His Cys
                85                  90                  95

Ala Arg Gly Ser Ser Gly His Tyr Glu Ala Phe Asp Ile Trp Gly Gln
            100                 105                 110

Gly Thr Met Val Thr Val Ser Ser
        115                 120

<210> SEQ ID NO 7
<211> LENGTH: 333
<212> TYPE: DNA
<213> ORGANISM: Artificial
<220> FEATURE:
<223> OTHER INFORMATION: Nucleotide sequence of a light chain variable
      region of NYA-0001

<400> SEQUENCE: 7
cagtctgtgt tgacgcagcc gccctcagtg tctgcggccc caggacagaa ggtcaccatc      60
tcctgctctg gaagcagctc caacattggg aataattatg tatcctggta ccagcagctc     120
ccaggaacag ccccccaaact cctcatttat gacaataata gcgaccctc agggattcct    180 gaccgattct ctggctccaa gtctggcacg tcagccaccc tgggcatcac cggactccag     240
actggggacg aggccgatta ttactgcgga acatgggata gcagcctgag tgccccttgg     300
gtgttcggcg gagggaccaa ggtcaccgtc cta                                   333
```

<210> SEQ ID NO 8
<211> LENGTH: 111
<212> TYPE: PRT
<213> ORGANISM: Artificial
<220> FEATURE:
<223> OTHER INFORMATION: Amino acid sequence of a light chain variable
      region of NYA-0001

<400> SEQUENCE: 8

Gln Ser Val Leu Thr Gln Pro Pro Ser Val Ser Ala Ala Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Pro Trp Val Phe Gly Gly Gly Thr Lys Val Thr Val Leu
            100                 105                 110

<210> SEQ ID NO 9
<211> LENGTH: 360
<212> TYPE: DNA
<213> ORGANISM: Artificial
<220> FEATURE:
<223> OTHER INFORMATION: Nucleotide sequence of a heavy chain variable
      region of NYA-0060

<400> SEQUENCE: 9
gaggtgcagc tggtggagtc tgggggaggc gtggtccagc ctggggaggtc cctgacaccc      60 tcctgttcag cgtctggatt ctccatccgt agctatgata tacactgggt ccgcctggct     120
ccaggcaagg ggctagagtg ggtggccact atatcatatg atggaagtca gaagtacttc     180
gcagactccg tgaagggccg atttaccatc ttcagagacg aatcggagaa catggtgtat     240
ctgcaaatga gcggcctgag agttgaggac acggctgttt atcactgtgc gagagggagt     300
agtggtcatt atgaggcttt tgatatctgg ggccaaggga caatggtcac cgtctcttca     360

<210> SEQ ID NO 10
<211> LENGTH: 120
<212> TYPE: PRT
<213> ORGANISM: Artificial
<220> FEATURE:
<223> OTHER INFORMATION: Amino acid sequence of a heavy chain variable
      region of NYA-0060

<400> SEQUENCE: 10

Glu Val Gln Leu Val Glu Ser Gly Gly Gly Val Val Gln Pro Gly Arg
1               5                   10                  15

Ser Leu Thr Pro Ser Cys Ser Ala Ser Gly Phe Ser Ile Arg Ser Tyr
            20                  25                  30

Asp Ile His Trp Val Arg Leu Ala Pro Gly Lys Gly Leu Glu Trp Val
        35                  40                  45

Ala Thr Ile Ser Tyr Asp Gly Ser Gln Lys Tyr Phe Ala Asp Ser Val
    50                  55                  60

```
Lys Gly Arg Phe Thr Ile Phe Arg Asp Glu Ser Glu Asn Met Val Tyr
 65                  70                  75                  80

Leu Gln Met Ser Gly Leu Arg Val Glu Asp Thr Ala Val Tyr His Cys
                 85                  90                  95

Ala Arg Gly Ser Ser Gly His Tyr Glu Ala Phe Asp Ile Trp Gly Gln
            100                 105                 110

Gly Thr Met Val Thr Val Ser Ser
        115                 120

<210> SEQ ID NO 11
<211> LENGTH: 333
<212> TYPE: DNA
<213> ORGANISM: Artificial
<220> FEATURE:
<223> OTHER INFORMATION: Nucleotide sequence of a light chain variable
      region of NYA-0060

<400> SEQUENCE: 11
cagtctgtgt tgacgcagcc gccctcagtg tctgcggccc caggacagaa ggtcaccatc    60
tcctgctctg gaagcagctc caacattggg aataattatg tatcctggta ccagcagctc   120
ccaggaacag cccccaaact cctcatttat gacaataata gcgaccctca gggattcct   180 gaccgattct ctggctccaa gtctggcacg tcagccaccc tgggcatcac cggactccag   240
actggggacg aggccgatta ttactgcgga acatgggata gcagcctgag tgccccttgg   300
gtgttcggcg gagggaccaa ggtcaccgtc cta                                333

<210> SEQ ID NO 12
<211> LENGTH: 111
<212> TYPE: PRT
<213> ORGANISM: Artificial
<220> FEATURE:
<223> OTHER INFORMATION: Amino acid sequence of a light chain variable
      region of NYA-0060

<400> SEQUENCE: 12

Gln Ser Val Leu Thr Gln Pro Pro Ser Val Ser Ala Ala Pro Gly Gln
 1               5                  10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Pro Trp Val Phe Gly Gly Gly Thr Lys Val Thr Val Leu
            100                 105                 110

<210> SEQ ID NO 13
<211> LENGTH: 360
<212> TYPE: DNA
<213> ORGANISM: Artificial
<220> FEATURE:
<223> OTHER INFORMATION: Nucleotide sequence of a heavy chain variable
      region of NYA-0068

<400> SEQUENCE: 13
gaggtgcagc tggtggagtc tgggggaggc gtggtccagc ctggggaggtc cctgacaccc    60
```

```
tcctgttcag cgtctggatt ctccatccgt agttatgata tacactgggt ccgccaggct    120
ccaggcaagg ggctagagtg ggtggccact atatcatatg atggaagtca gaagtacttc    180
gcagactccg tgaagggccg atttaccatc ttcagagacg aatcggagaa catggtgtat    240
ctgcaaatga gcggcctgag agttgaggac acggctgttt atcactgtgc gagagggagt    300
agtggtcatt atgaggcttt tgatatctgg ggccaaggga caatggtcac cgtctcttca    360
```

```
<210> SEQ ID NO 14
<211> LENGTH: 120
<212> TYPE: PRT
<213> ORGANISM: Artificial
<220> FEATURE:
<223> OTHER INFORMATION: Amino acid sequence of a heavy chain variable
      region of NYA-0068

<400> SEQUENCE: 14
```

Glu Val Gln Leu Val Glu Ser Gly Gly Gly Val Val Gln Pro Gly Arg
1               5                   10                  15

Ser Leu Thr Pro Ser Cys Ser Ala Ser Gly Phe Ser Ile Arg Ser Tyr
            20                  25                  30

Asp Ile His Trp Val Arg Gln Ala Pro Gly Lys Gly Leu Glu Trp Val
        35                  40                  45

Ala Thr Ile Ser Tyr Asp Gly Ser Gln Lys Tyr Phe Ala Asp Ser Val
    50                  55                  60

Lys Gly Arg Phe Thr Ile Phe Arg Asp Glu Ser Glu Asn Met Val Tyr
65                  70                  75                  80

Leu Gln Met Ser Gly Leu Arg Val Glu Asp Thr Ala Val Tyr His Cys
                85                  90                  95

Ala Arg Gly Ser Ser Gly His Tyr Glu Ala Phe Asp Ile Trp Gly Gln
            100                 105                 110

Gly Thr Met Val Thr Val Ser Ser
        115                 120

```
<210> SEQ ID NO 15
<211> LENGTH: 333
<212> TYPE: DNA
<213> ORGANISM: Artificial
<220> FEATURE:
<223> OTHER INFORMATION: Nucleotide sequence of a light chain variable
      region of NYA-0068

<400> SEQUENCE: 15
```

```
cagtctgtgt tgacgcagcc gccctcagtg tctgcggccc caggacagaa ggtcaccatc     60
tcctgctctg gaagcagctc caacattggg aattggtatg tatcctggta ccagcagctc    120
ccaggaacag cccccaaact cctcatttat gacaataata agcgaccctc agggattcct    180
gaccgattct ctggctccaa gtctggcacg tcagccaccc tgggcatcac cggactccag    240
actggggacg aggccgatta ttactgcgga acatgggata gcagcctgag tgccccttgg    300
gtgttcggcg gagggaccaa ggtcaccgtc cta                                  333
```

```
<210> SEQ ID NO 16
<211> LENGTH: 111
<212> TYPE: PRT
<213> ORGANISM: Artificial
<220> FEATURE:
<223> OTHER INFORMATION: Amino acid sequence of a light chain variable
      region of NYA-0068

<400> SEQUENCE: 16
```

Gln Ser Val Leu Thr Gln Pro Pro Ser Val Ala Ala Pro Gly Gln
1               5                   10                  15

Lys Val Thr Ile Ser Cys Ser Gly Ser Ser Asn Ile Gly Asn Trp
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
50                      55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Pro Trp Val Phe Gly Gly Gly Thr Lys Val Thr Val Leu
            100                 105                 110

<210> SEQ ID NO 17
<211> LENGTH: 360
<212> TYPE: DNA
<213> ORGANISM: Artificial
<220> FEATURE:
<223> OTHER INFORMATION: Nucleotide sequence of a heavy chain variable
      region of NYA-0082

<400> SEQUENCE: 17
gaggtgcagc tggtggagtc tgggggaggc gtggtccagc ctggggaggtc cctgacaccc      60 tcctgttcag cgtctggatt ctccatccgt agttatgata tacactgggt ccgccaggct     120
ccaggcaagg ggctagagtg ggtggccact atatcatatg atggaagtca gaagtacttc     180
gcagactccg tgaagggccg atttaccatc ttcagagacg aatcggagaa catggtgtat     240
ctgcaaatga gcggcctgag agttgaggac acggctgttt atcactgtgc gagagggagt     300
agtggtcatt atgaggcttt tgatatctgg ggccaaggga caatggtcac cgtctcttca     360

<210> SEQ ID NO 18
<211> LENGTH: 120
<212> TYPE: PRT
<213> ORGANISM: Artificial
<220> FEATURE:
<223> OTHER INFORMATION: Amino acid sequence of a heavy chain variable
      region of NYA-0082

<400> SEQUENCE: 18

Glu Val Gln Leu Val Glu Ser Gly Gly Gly Val Val Gln Pro Gly Arg
1               5                   10                  15

Ser Leu Thr Pro Ser Cys Ser Ala Ser Gly Phe Ser Ile Arg Ser Tyr
                20                  25                  30

Asp Ile His Trp Val Arg Gln Ala Pro Gly Lys Gly Leu Glu Trp Val
            35                  40                  45

Ala Thr Ile Ser Tyr Asp Gly Ser Gln Lys Tyr Phe Ala Asp Ser Val
50                      55                  60

Lys Gly Arg Phe Thr Ile Phe Arg Asp Glu Ser Glu Asn Met Val Tyr
65                  70                  75                  80

Leu Gln Met Ser Gly Leu Arg Val Glu Asp Thr Ala Val Tyr His Cys
                85                  90                  95

Ala Arg Gly Ser Ser Gly His Tyr Glu Ala Phe Asp Ile Trp Gly Gln
            100                 105                 110

Gly Thr Met Val Thr Val Ser Ser
            115                 120

<210> SEQ ID NO 19
<211> LENGTH: 333
<212> TYPE: DNA
<213> ORGANISM: Artificial
<220> FEATURE:
<223> OTHER INFORMATION: Nucleotide sequence of a light chain variable
      region of NYA-0082

<400> SEQUENCE: 19

```
cagtctgtgt tgacgcagcc gccctcagtg tctgcggccc caggacagaa ggtcaccatc      60
tcctgctctg gaagcagctc caacattggg aataattatg tatcctgta ccagcggctc     120 ccaggaacag cccccaaact cctcatttat gacaataata agcgaccctc agggattcct     180
gaccgattct ctggctccaa gtctggcacg tcagccaccc tgggcatcac cggactccag     240
actggggacg aggccgatta ttactgcgga tcatgggata gcagcctgag tgccccttgg     300
gtgttcggcg agggaccaa ggtcaccgtc cta                                   333
```

<210> SEQ ID NO 20
<211> LENGTH: 111
<212> TYPE: PRT
<213> ORGANISM: Artificial
<220> FEATURE:
<223> OTHER INFORMATION: Amino acid sequence of a light chain variable
      region of NYA-0082

<400> SEQUENCE: 20

```
Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Arg Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Ser Trp Asp Ser Ser Leu
                85                  90                  95

Ser Ala Pro Trp Val Phe Gly Gly Gly Thr Lys Val Thr Val Leu
            100                 105                 110
```

<210> SEQ ID NO 21
<211> LENGTH: 876
<212> TYPE: DNA
<213> ORGANISM: Artificial
<220> FEATURE:
<223> OTHER INFORMATION: Full-length nucleotide sequence of NYA-1163

<400> SEQUENCE: 21

```
atgaaacacc tgtggttctt cctcctgctg gtggcagctc ccagatgggt gctgagcgga      60
gaggtgcagc tggtggagtc tgggggaggc gtggtccagc ctgggaggtc cctgacaccc     120
tcctgttcag cgtctggatt ctccatccgt agctatgata tacactgggt ccgcctggct     180
ccaggcaagg ggctagagtg ggtggccact atatcatatg atggaagtca gaagtacttc     240
gcagactccg tgaagggccg atttaccatc tcagagacg aatcggagaa catggtgtat     300
ctgcaaatga gcggcctgag agttgaggac acggctgttt atcactgtgc gagagggagt     360
agtggtcatt atgaggcttt tgatatctgg ggccaaggga caatggtcac cgtctcttca     420
```

```
ggtggaggcg gttcaggcgg aggtggcagc ggcggtggcg ggagtcagtc tgtgttgacg    480
cagccgccct cagtgtctgc ggccccagga cagaaggtca ccatctcctg ctctggaagc    540
agctccaaca ttgggaataa ttatgtatcc tggtaccagc agctcccagg aacagccccc    600
aaactcctca tttatgacaa taataagcga ccctcaggga ttcctgaccg attctctggc    660
tccaagtctg gcacgtcagc caccctgggc atcaccggac tccagactgg ggacgaggcc    720
gattattact gcggaacatg ggatagcagc ctgagtgccc cttgggtgtt cggcggaggg    780
accaaggtca ccgtcctagg cgcggccgca ggtgcaggtg gtgattacaa agatgatgac    840
gataaaggtg cagcggcgca tcaccatcat caccac                              876
```

<210> SEQ ID NO 22
<211> LENGTH: 876
<212> TYPE: DNA
<213> ORGANISM: Artificial
<220> FEATURE:
<223> OTHER INFORMATION: Full-length nucleotide sequence of NYA-2023

<400> SEQUENCE: 22

```
atgaaacacc tgtggttctt cctcctgctg gtggcagctc ccagatgggt gctgagcgga     60
gaggtgcagc tggtggagtc tgggggaggc gtggtccagc ctgggaggtc cctgacaccc    120
tcctgttcag cgtctggatt ctccatccgt agttatgata cactgggt ccgccaggct     180 ccaggcaagg ggctagagtg ggtggccact atatcatatg atggaagtca gaagtacttc    240
gcagactccg tgaagggccg atttaccatc tccagacgc aatcggagaa catggtgtat    300
ctgcaaatga gcggcctgag agttgaggac acggctgttt atcactgtgc gagagggagt    360
agtggtcatt atgaggcttt tgatatctgg ggccaaggga caatggtcac cgtctcttca    420
ggtggaggcg gttcaggcgg aggtggcagc ggcggtggcg ggagtcagtc tgtgttgacg    480
cagccgccct cagtgtctgc ggccccagga cagaaggtca ccatctcctg ctctggaagc    540
agctccaaca ttgggaattg gtatgtatcc tggtaccagc agctcccagg aacagccccc    600
aaactcctca tttatgacaa taataagcga ccctcaggga ttcctgaccg attctctggc    660
tccaagtctg gcacgtcagc caccctgggc atcaccggac tccagactgg ggacgaggcc    720
gattattact gcggaacatg ggatagcagc ctgagtgccc cttgggtgtt cggcggaggg    780
accaaggtca ccgtcctagg cgcggccgca ggtgcaggtg gtgattacaa agatgatgac    840
gataaaggtg cagcggcgca tcaccatcat caccac                              876
```

<210> SEQ ID NO 23
<211> LENGTH: 876
<212> TYPE: DNA
<213> ORGANISM: Artificial
<220> FEATURE:
<223> OTHER INFORMATION: Full-length nucleotide sequence of NYA-2027

<400> SEQUENCE: 23

```
atgaaacacc tgtggttctt cctcctgctg gtggcagctc ccagatgggt gctgagcgga     60
gaggtgcagc tggtggagtc tgggggaggc gtggtccagc ctgggaggtc cctgacaccc    120
tcctgttcag cgtctggatt ctccatccgt agttatgata cactgggt ccgccaggct     180 ccaggcaagg ggctagagtg ggtggccact atatcatatg atggaagtca gaagtacttc    240
gcagactccg tgaagggccg atttaccatc tccagacgc aatcggagaa catggtgtat    300
ctgcaaatga gcggcctgag agttgaggac acggctgttt atcactgtgc gagagggagt    360
```

| | |
|---|---|
| agtggtcatt atgaggcttt tgatatctgg ggccaaggga caatggtcac cgtctcttca | 420 |
| ggtggaggcg gttcaggcgg aggtggcagc ggcggtggcg ggagtcagtc tgtgttgacg | 480 |
| cagccgccct cagtgtctgc ggccccagga cagaaggtca ccatctcctg ctctggaagc | 540 |
| agctccaaca ttgggaataa ttatgtatcc tggtaccagc agctcccagg aacagccccc | 600 |
| aaactcctca tttatgacaa taataagcga ccctcaggga ttcctgaccg attctctggc | 660 |
| tccaagtctg gcacgtcagc cacccctggg atcaccggac tccagactgg ggacgaggcc | 720 |
| gattattact gcggatcatg ggatagcagc ctgagtgccc cttgggtgtt cggcggaggg | 780 |
| accaaggtca ccgtcctagg cgcggccgca ggtgcaggtg gtgattacaa agatgatgac | 840 |
| gataaaggtg cagcggcgca tcaccatcat caccac | 876 |

<210> SEQ ID NO 24
<211> LENGTH: 876
<212> TYPE: DNA
<213> ORGANISM: Artificial
<220> FEATURE:
<223> OTHER INFORMATION: Full-length nucleotide sequence of NYA-1143

<400> SEQUENCE: 24

| | |
|---|---|
| atgaaacacc tgtggttctt cctcctgctg gtggcagctc ccagatgggt gctgagcgga | 60 |
| gaggtgcagc tggtggagtc tggggggaggc gtggtccagc ctgggaggtc cctgacaccc | 120 |
| tcctgttcag cgtctggatt ctccatccgt agctatgata tacactgggt ccgcctggct | 180 |
| ccaggcaagg ggctagagtg ggtggccact atatcatatg atggaagtca gaagtacttc | 240 |
| gcagactccg tgaagggccg atttaccatc ttcagagacg aatcggagaa catggtgtat | 300 |
| ctgcaaatga gcggcctgag agttgaggac acggctgttt atcactgtgc gagagggagt | 360 |
| agtggtcatt atgaggcttt tgatatctgg ggccaaggga caatggtcac cgtctcttca | 420 |
| ggtggaggcg gttcaggcgg aggtggcagc ggcggtggcg ggagtcagtc tgtgttgacg | 480 |
| cagccgccct cagtgtctgc ggccccagga cagaaggtca ccatctcctg ctctggaagc | 540 |
| agctccaaca ttgggaattg gtatgtatcc tggtaccagc agctcccagg aacagccccc | 600 |
| aaactcctca tttatgacaa taataagcga ccctcaggga ttcctgaccg attctctggc | 660 |
| tccaagtctg gcacgtcagc cacccctggg atcaccggac tccagactgg ggacgaggcc | 720 |
| gattattact gcggaacatg ggatagcagc ctgagtgccc cttgggtgtt cggcggaggg | 780 |
| accaaggtca ccgtcctagg cgcggccgca ggtgcaggtg gtgattacaa agatgatgac | 840 |
| gataaaggtg cagcggcgca tcaccatcat caccac | 876 |

<210> SEQ ID NO 25
<211> LENGTH: 876
<212> TYPE: DNA
<213> ORGANISM: Artificial
<220> FEATURE:
<223> OTHER INFORMATION: Full-length nucleotide sequence of NYA-2143

<400> SEQUENCE: 25

| | |
|---|---|
| atgaaacacc tgtggttctt cctcctgctg gtggcagctc ccagatgggt gctgagcgga | 60 |
| gaggtgcagc tggtggagtc tggggggaggc gtggtccagc ctgggaggtc cctgacaccc | 120 |
| tcctgttcag cgtctggatt ctccatccgt agctatgata tacactgggt ccgcctggct | 180 |
| ccaggcaagg ggctagagtg ggtggccact atatcatatg atggaagtca gaagtacttc | 240 |
| gcagactccg tgaagggccg atttaccatc ttcagagacg aatcggagaa catggtgtat | 300 |
| ctgcaaatga gcggcctgag agttgaggac acggctgttt atcactgtgc gagagggagt | 360 |

```
agtggtcatt atgaggcttt tgatatctgg ggccaaggga caatggtcac cgtctcttca      420
ggtggaggcg gttcaggcgg aggtggcagc ggcggtggcg ggagtcagtc tgtgttgacg      480
cagccgccct cagtgtctgc ggccccagga cagaaggtca ccatctcctg ctctggaagc      540
agctccaaca ttgggaattg gtatgtatcc tggtaccagc ggctcccagg aacagccccc      600
aaactcctca tttatgacaa taataagcga ccctcaggga ttcctgaccg attctctggc      660
tccaagtctg gcacgtcagc caccctgggc atcaccggac tccagactgg ggacgaggcc      720
gattattact gcggaacatg ggatagcagc ctgagtgccc cttgggtgtt cggcggaggg      780
accaaggtca ccgtcctagg cgcggccgca ggtgcaggtg gtgattacaa agatgatgac      840
gataaaggtg cagcggcgca tcaccatcat caccac                                876
```

<210> SEQ ID NO 26
<211> LENGTH: 292
<212> TYPE: PRT
<213> ORGANISM: Artificial
<220> FEATURE:
<223> OTHER INFORMATION: Full-length amino acid sequence of NYA-1163

<400> SEQUENCE: 26

```
Met Lys His Leu Trp Phe Phe Leu Leu Val Ala Ala Pro Arg Trp
1               5                  10                  15

Val Leu Ser Gly Glu Val Gln Leu Val Glu Ser Gly Gly Val Val
                20                  25                  30

Gln Pro Gly Arg Ser Leu Thr Pro Ser Cys Ser Ala Ser Gly Phe Ser
                35                  40                  45

Ile Arg Ser Tyr Asp Ile His Trp Val Arg Leu Ala Pro Gly Lys Gly
    50                  55                  60

Leu Glu Trp Val Ala Thr Ile Ser Tyr Asp Gly Ser Gln Lys Tyr Phe
65                  70                  75                  80

Ala Asp Ser Val Lys Gly Arg Phe Thr Ile Phe Arg Asp Glu Ser Glu
                85                  90                  95

Asn Met Val Tyr Leu Gln Met Ser Gly Leu Arg Val Glu Asp Thr Ala
                100                 105                 110

Val Tyr His Cys Ala Arg Gly Ser Ser Gly His Tyr Glu Ala Phe Asp
            115                 120                 125

Ile Trp Gly Gln Gly Thr Met Val Thr Val Ser Ser Gly Gly Gly
        130                 135                 140

Ser Gly Gly Gly Gly Ser Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Asn Tyr Val Ser Trp Tyr
            180                 185                 190

Gln Gln Leu Pro Gly Thr Ala Pro Lys Leu Leu Ile Tyr Asp Asn Asn
        195                 200                 205

Lys Arg Pro Ser Gly Ile Pro Asp Arg Phe Ser Gly Ser Lys Ser Gly
    210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Val Thr Val Leu Gly Ala Ala Gly Ala
                260                 265                 270
```

Gly Gly Asp Tyr Lys Asp Asp Asp Lys Gly Ala Ala Ala His His
            275                 280                 285

His His His His
        290

<210> SEQ ID NO 27
<211> LENGTH: 292
<212> TYPE: PRT
<213> ORGANISM: Artificial
<220> FEATURE:
<223> OTHER INFORMATION: Full-length amino acid sequence of NYA-2023

<400> SEQUENCE: 27

Met Lys His Leu Trp Phe Phe Leu Leu Val Ala Ala Pro Arg Trp
1               5                   10                  15

Val Leu Ser Gly Glu Val Gln Leu Val Glu Ser Gly Gly Val Val
                20                  25                  30

Gln Pro Gly Arg Ser Leu Thr Pro Ser Cys Ser Ala Ser Gly Phe Ser
            35                  40                  45

Ile Arg Ser Tyr Asp Ile His Trp Val Arg Gln Ala Pro Gly Lys Gly
    50                  55                  60

Leu Glu Trp Val Ala Thr Ile Ser Tyr Asp Gly Ser Gln Lys Tyr Phe
65                  70                  75                  80

Ala Asp Ser Val Lys Gly Arg Phe Thr Ile Phe Arg Asp Glu Ser Glu
                85                  90                  95

Asn Met Val Tyr Leu Gln Met Ser Gly Leu Arg Val Glu Asp Thr Ala
                100                 105                 110

Val Tyr His Cys Ala Arg Gly Ser Ser Gly His Tyr Glu Ala Phe Asp
            115                 120                 125

Ile Trp Gly Gln Gly Thr Met Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Trp Tyr Val Ser Trp Tyr
            180                 185                 190

Gln Gln Leu Pro Gly Thr Ala Pro Lys Leu Leu Ile Tyr Asp Asn Asn
    195                 200                 205

Lys Arg Pro Ser Gly Ile Pro Asp Arg Phe Ser Gly Ser Lys Ser Gly
210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Val Thr Val Leu Gly Ala Ala Ala Gly Ala
            260                 265                 270

Gly Gly Asp Tyr Lys Asp Asp Asp Lys Gly Ala Ala Ala His His
    275                 280                 285

His His His His
        290

<210> SEQ ID NO 28
<211> LENGTH: 292
<212> TYPE: PRT
<213> ORGANISM: Artificial

```
<220> FEATURE:
<223> OTHER INFORMATION: Full-length amino acid sequence of NYA-2027

<400> SEQUENCE: 28
```

| | | | | | | | | | | | | | | | |
|---|---|---|---|---|---|---|---|---|---|---|---|---|---|---|---|
| Met | Lys | His | Leu | Trp | Phe | Phe | Leu | Leu | Leu | Val | Ala | Ala | Pro | Arg | Trp |
| 1 | | | | 5 | | | | | 10 | | | | | 15 | |

Val Leu Ser Gly Glu Val Gln Leu Val Glu Ser Gly Gly Gly Val Val
                20                  25                  30

Gln Pro Gly Arg Ser Leu Thr Pro Ser Cys Ser Ala Ser Gly Phe Ser
            35                  40                  45

Ile Arg Ser Tyr Asp Ile His Trp Val Arg Gln Ala Pro Gly Lys Gly
 50                  55                  60

Leu Glu Trp Val Ala Thr Ile Ser Tyr Asp Gly Ser Gln Lys Tyr Phe
 65                  70                  75                  80

Ala Asp Ser Val Lys Gly Arg Phe Thr Ile Phe Arg Asp Glu Ser Glu
                85                  90                  95

Asn Met Val Tyr Leu Gln Met Ser Gly Leu Arg Val Glu Asp Thr Ala
            100                 105                 110

Val Tyr His Cys Ala Arg Gly Ser Gly His Tyr Glu Ala Phe Asp
        115                 120                 125

Ile Trp Gly Gln Gly Thr Met Val Thr Val Ser Ser Gly Gly Gly Gly
130                 135                 140

Ser Gly Gly Gly Ser Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Asn Ile Gly Asn Asn Tyr Val Ser Trp Tyr
            180                 185                 190

Gln Gln Leu Pro Gly Thr Ala Pro Lys Leu Leu Ile Tyr Asp Asn Asn
        195                 200                 205

Lys Arg Pro Ser Gly Ile Pro Asp Arg Phe Ser Gly Ser Lys Ser Gly
210                 215                 220

Thr Ser Ala Thr Leu Gly Ile Thr Gly Leu Gln Thr Gly Asp Glu Ala
225                 230                 235                 240

Asp Tyr Tyr Cys Gly Ser Trp Asp Ser Ser Leu Ser Ala Pro Trp Val
                245                 250                 255

Phe Gly Gly Gly Thr Lys Val Thr Val Leu Gly Ala Ala Ala Gly Ala
            260                 265                 270

Gly Gly Asp Tyr Lys Asp Asp Asp Lys Gly Ala Ala Ala His His
        275                 280                 285

His His His His
    290

```
<210> SEQ ID NO 29
<211> LENGTH: 292
<212> TYPE: PRT
<213> ORGANISM: Artificial
<220> FEATURE:
<223> OTHER INFORMATION: Full-length amino acid sequence of NYA-1143

<400> SEQUENCE: 29
```

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Val Val
                20                  25                  30

Gln Pro Gly Arg Ser Leu Thr Pro Ser Cys Ser Ala Ser Gly Phe Ser

```
                 35                  40                  45
Ile Arg Ser Tyr Asp Ile His Trp Val Arg Leu Ala Pro Gly Lys Gly
 50                  55                  60

Leu Glu Trp Val Ala Thr Ile Ser Tyr Asp Gly Ser Gln Lys Tyr Phe
 65                  70                  75                  80

Ala Asp Ser Val Lys Gly Arg Phe Thr Ile Phe Arg Asp Glu Ser Glu
                 85                  90                  95

Asn Met Val Tyr Leu Gln Met Ser Gly Leu Arg Val Glu Asp Thr Ala
                100                 105                 110

Val Tyr His Cys Ala Arg Gly Ser Gly His Tyr Glu Ala Phe Asp
                115                 120                 125

Ile Trp Gly Gln Gly Thr Met Val Thr Val Ser Ser Gly Gly Gly
130                 135                 140

Ser Gly Gly Gly Ser Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Trp Tyr Val Ser Trp Tyr
                180                 185                 190

Gln Gln Leu Pro Gly Thr Ala Pro Lys Leu Leu Ile Tyr Asp Asn Asn
                195                 200                 205

Lys Arg Pro Ser Gly Ile Pro Asp Arg Phe Ser Gly Ser Lys Ser Gly
210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Val Thr Val Leu Gly Ala Ala Ala Gly Ala
                260                 265                 270

Gly Gly Asp Tyr Lys Asp Asp Asp Lys Gly Ala Ala Ala His His
                275                 280                 285

His His His His
    290

<210> SEQ ID NO 30
<211> LENGTH: 292
<212> TYPE: PRT
<213> ORGANISM: Artificial
<220> FEATURE:
<223> OTHER INFORMATION: Full-length amino acid sequence of NYA-2143

<400> SEQUENCE: 30

Met Lys His Leu Trp Phe Phe Leu Leu Leu Val Ala Ala Pro Arg Trp
 1               5                  10                  15

Val Leu Ser Gly Glu Val Gln Leu Val Glu Ser Gly Gly Gly Val Val
                 20                  25                  30

Gln Pro Gly Arg Ser Leu Thr Pro Ser Cys Ser Ala Ser Gly Phe Ser
                 35                  40                  45

Ile Arg Ser Tyr Asp Ile His Trp Val Arg Leu Ala Pro Gly Lys Gly
 50                  55                  60

Leu Glu Trp Val Ala Thr Ile Ser Tyr Asp Gly Ser Gln Lys Tyr Phe
 65                  70                  75                  80

Ala Asp Ser Val Lys Gly Arg Phe Thr Ile Phe Arg Asp Glu Ser Glu
                 85                  90                  95

Asn Met Val Tyr Leu Gln Met Ser Gly Leu Arg Val Glu Asp Thr Ala
```

```
            100                 105                 110
Val Tyr His Cys Ala Arg Gly Ser Ser Gly His Tyr Glu Ala Phe Asp
        115                 120                 125

Ile Trp Gly Gln Gly Thr Met Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Asn Ile Gly Asn Trp Tyr Val Ser Trp Tyr
                180                 185                 190

Gln Arg Leu Pro Gly Thr Ala Pro Lys Leu Leu Ile Tyr Asp Asn Asn
        195                 200                 205

Lys Arg Pro Ser Gly Ile Pro Asp Arg Phe Ser Gly Ser Lys Ser Gly
    210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Val Thr Val Leu Gly Ala Ala Ala Gly Ala
                260                 265                 270

Gly Gly Asp Tyr Lys Asp Asp Asp Lys Gly Ala Ala Ala His His
        275                 280                 285

His His His His
        290

<210> SEQ ID NO 31
<211> LENGTH: 876
<212> TYPE: DNA
<213> ORGANISM: Artificial
<220> FEATURE:
<223> OTHER INFORMATION: Full-length nucleotide sequence of NYA-1154

<400> SEQUENCE: 31
atgaaacacc tgtggttctt cctcctgctg gtggcagctc ccagatgggt gctgagcgga      60
gaggtgcagc tggtggagtc tgggggaggc gtggtccagc ctgggaggtc cctgacaccc     120
tcctgttcag cgtctggatt ctccatccgt agttatgata tgcactgggt ccgccaggct     180
ccaggcaagg ggctagagtg ggtggccact atatcatatg atggaagtca gaagtacttc     240
gcagactccg tgaagggccg atttaccatc tcagacg aatcggagaa catggtgtat     300
ctgcaaatga gcggcctgag agttgaggac acggccgttt atcactgtgc gagagggagt     360
agtaatcatt atgaggcttt tgatatctgg ggccaaggga caatggtcac cgtctcttca     420
ggtggaggcg gttcaggcgg aggtggcagc ggcggtggcg ggagtcagtc tgtgttgacg     480
cagccgccct cagtgtctgc ggccccagga cagaaggtca ccatctcctg ctctggaagc     540
agctccaaca ttgggaataa ttatgtatcc tggtaccagc ggctcccagg aacagccccc     600
aaactcctca tttatgacaa taataagcga ccctcaggga ttcctgaccg attctctggc     660
tccaagtctg gcacgtcagc cacccctggc atcaccggac tccagactgg ggacgaggcc     720
gattactact gcggagcatg ggatagcagc ctgagtgccc cttgggtgtt cggcggaggg     780
accaaggtca ccgtcctagg cgcggccgca ggtgcaggtg gtgattacaa agatgatgac     840
gataaaggtg cagcggcgca tcaccatcat caccac                               876
```

```
<210> SEQ ID NO 32
<211> LENGTH: 292
<212> TYPE: PRT
<213> ORGANISM: Artificial
<220> FEATURE:
<223> OTHER INFORMATION: Full-length amino acid sequence of NYA-1154

<400> SEQUENCE: 32

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Val Val
            20                  25                  30

Gln Pro Gly Arg Ser Leu Thr Pro Ser Cys Ser Ala Ser Gly Phe Ser
        35                  40                  45

Ile Arg Ser Tyr Asp Met His Trp Val Arg Gln Ala Pro Gly Lys Gly
    50                  55                  60

Leu Glu Trp Val Ala Thr Ile Ser Tyr Asp Gly Ser Gln Lys Tyr Phe
65                  70                  75                  80

Ala Asp Ser Val Lys Gly Arg Phe Thr Ile Phe Arg Asp Glu Ser Glu
                85                  90                  95

Asn Met Val Tyr Leu Gln Met Ser Gly Leu Arg Val Glu Asp Thr Ala
            100                 105                 110

Val Tyr His Cys Ala Arg Gly Ser Ser Asn His Tyr Glu Ala Phe Asp
        115                 120                 125

Ile Trp Gly Gln Gly Thr Met Val Thr Val Ser Ser Gly Gly Gly Gly
    130                 135                 140

Ser Gly Gly Gly Ser Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Asn Tyr Val Ser Trp Tyr
            180                 185                 190

Gln Arg Leu Pro Gly Thr Ala Pro Lys Leu Leu Ile Tyr Asp Asn Asn
        195                 200                 205

Lys Arg Pro Ser Gly Ile Pro Asp Arg Phe Ser Gly Ser Lys Ser Gly
    210                 215                 220

Thr Ser Ala Thr Leu Gly Ile Thr Gly Leu Gln Thr Gly Asp Glu Ala
225                 230                 235                 240

Asp Tyr Tyr Cys Gly Ala Trp Asp Ser Ser Leu Ser Ala Pro Trp Val
                245                 250                 255

Phe Gly Gly Gly Thr Lys Val Thr Val Leu Gly Ala Ala Ala Gly Ala
            260                 265                 270

Gly Gly Asp Tyr Lys Asp Asp Asp Lys Gly Ala Ala Ala His His
        275                 280                 285

His His His His
    290

<210> SEQ ID NO 33
<211> LENGTH: 290
<212> TYPE: PRT
<213> ORGANISM: Artificial
<220> FEATURE:
<223> OTHER INFORMATION: Amino acid sequence of truncated form of
      HLA-A*0201(UniProtKB-P01892)

<400> SEQUENCE: 33

Met Ser His Ser Met Arg Tyr Phe Phe Thr Ser Val Ser Arg Pro Gly
1               5                   10                  15
```

```
Arg Gly Glu Pro Arg Phe Ile Ala Val Gly Tyr Val Asp Asp Thr Gln
                20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Gly Glu Thr
 50                  55                  60

Arg Lys Val Lys Ala His Ser Gln Thr His Arg Val Asp Leu Gly Thr
 65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
                115                 120                 125

Asp Leu Arg Ser Trp Thr Ala Ala Asp Met Ala Ala Gln Thr Thr Lys
130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Gly Leu Asn Asp Ile Phe Glu Ala Gln Lys Ile Glu Trp
        275                 280                 285

His Glu
    290

<210> SEQ ID NO 34
<211> LENGTH: 100
<212> TYPE: PRT
<213> ORGANISM: Artificial
<220> FEATURE:
<223> OTHER INFORMATION: Amino acid sequence of beta 2-microglobulin

<400> SEQUENCE: 34

Met Ile Gln Arg Thr Pro Lys Ile Gln Val Tyr Ser Arg His Pro Ala
1               5                   10                  15

Glu Asn Gly Lys Ser Asn Phe Leu Asn Cys Tyr Val Ser Gly Phe His
                20                  25                  30

Pro Ser Asp Ile Glu Val Asp Leu Leu Lys Asn Gly Glu Arg Ile Glu
            35                  40                  45

Lys Val Glu His Ser Asp Leu Ser Phe Ser Lys Asp Trp Ser Phe Tyr
 50                  55                  60

Leu Leu Tyr Tyr Thr Glu Phe Thr Pro Thr Glu Lys Asp Glu Tyr Ala
65                  70                  75                  80
```

Cys Arg Val Asn His Val Thr Leu Ser Gln Pro Lys Ile Val Lys Trp
            85                  90                  95

Asp Arg Asp Met
            100

<210> SEQ ID NO 35
<211> LENGTH: 876
<212> TYPE: DNA
<213> ORGANISM: Artificial
<220> FEATURE:
<223> OTHER INFORMATION: Full-length nucleotide sequence of NYA-2035

<400> SEQUENCE: 35

| | |
|---|---|
| atgaaacacc tgtggttctt cctcctgctg gtggcagctc ccagatgggt gctgagcgga | 60 |
| gaggtgcagc tggtggagtc tgggggaggc gtggtccagc ctgggaggtc cctgacaccc | 120 |
| tcctgttcag cgtctggatt ctccatccgt agctatgata tacactgggt ccgcctggct | 180 |
| ccaggcaagg ggctagagtg gtggccact atatcatatg atggaagtca gaagtacttc | 240 |
| gcagactccg tgaagggccg atttaccatc ttcagagacg aatcggagaa catggtgtat | 300 |
| ctgcaaatga gcggcctgag agttgaggac acggctgttt atcactgtgc gagagggagt | 360 |
| agtggtcatt atgaggcttt tgatatctgg ggccaaggga caatggtcac cgtctcttca | 420 |
| ggtgaggcg gttcaggcgg aggtggcagc ggcggtggcg ggagtcagtc tgtgttgacg | 480 |
| cagccgccct cagtgtctgc ggccccagga cagaaggtca ccatctcctg ctctggaagc | 540 |
| agctccaaca ttgggaattg aaggtatcc tggtaccagc agctcccagg aacagccccc | 600 |
| aaactcctca tttatgacaa taataagcga ccctcaggga ttcctgaccg attctctggc | 660 |
| tccaagtctg gcacgtcagc cacccctggggc atcaccggac tccagactgg ggacgaggcc | 720 |
| gattattact gcggaacatg ggatagcagc ctgagtgccc cttgggtgtt cggcggaggg | 780 |
| accaaggtca ccgtcctagg cgcggccgca ggtgcaggtg gtgattacaa agatgatgac | 840 |
| gataaaggtg cagcggcgca tcaccatcat caccac | 876 |

<210> SEQ ID NO 36
<211> LENGTH: 292
<212> TYPE: PRT
<213> ORGANISM: Artificial
<220> FEATURE:
<223> OTHER INFORMATION: Full-length amino acid sequence of NYA-2035

<400> SEQUENCE: 36

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Val Val
            20                  25                  30

Gln Pro Gly Arg Ser Leu Thr Pro Ser Cys Ser Ala Ser Gly Phe Ser
        35                  40                  45

Ile Arg Ser Tyr Asp Ile His Trp Val Arg Leu Ala Pro Gly Lys Gly
    50                  55                  60

Leu Glu Trp Val Ala Thr Ile Ser Tyr Asp Gly Ser Gln Lys Tyr Phe
65                  70                  75                  80

Ala Asp Ser Val Lys Gly Arg Phe Thr Ile Phe Arg Asp Glu Ser Glu
                85                  90                  95

Asn Met Val Tyr Leu Gln Met Ser Gly Leu Arg Val Glu Asp Thr Ala
            100                 105                 110

Val Tyr His Cys Ala Arg Gly Ser Ser Gly His Tyr Glu Ala Phe Asp

```
            115                 120                 125
Ile Trp Gly Gln Gly Thr Met Val Thr Val Ser Ser Gly Gly Gly
    130                 135                 140

Ser Gly Gly Gly Ser Gly Gly Gly Ser Gln Ser Val Leu Thr
145                 150                 155                 160

Gln Pro Pro Ser Val Ser Ala Ala Pro Gly Gln Lys Val Thr Ile Ser
                    165                 170                 175

Cys Ser Gly Ser Ser Ser Asn Ile Gly Asn Trp Lys Val Ser Trp Tyr
                180                 185                 190

Gln Gln Leu Pro Gly Thr Ala Pro Lys Leu Leu Ile Tyr Asp Asn Asn
            195                 200                 205

Lys Arg Pro Ser Gly Ile Pro Asp Arg Phe Ser Gly Ser Lys Ser Gly
    210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Val Thr Val Leu Gly Ala Ala Ala Gly Ala
                260                 265                 270

Gly Gly Asp Tyr Lys Asp Asp Asp Lys Gly Ala Ala Ala His His
                275                 280                 285

His His His His
        290

<210> SEQ ID NO 37
<211> LENGTH: 120
<212> TYPE: PRT
<213> ORGANISM: Artificial
<220> FEATURE:
<223> OTHER INFORMATION: Amino acid sequence of NYA-1143-VH01

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ile Arg Ser Tyr
            20                  25                  30

Asp Ile His Trp Val Arg Leu Ala Pro Gly Lys Gly Leu Glu Trp Val
        35                  40                  45

Ala Thr Ile Ser Tyr Asp Gly Ser Gln Lys Tyr Tyr Ala Asp Ser Val
    50                  55                  60

Lys Gly Arg Phe Thr Ile Ser Arg Asp Glu Ser Lys Asn Thr Leu Tyr
65                  70                  75                  80

Leu Gln Met Asn Ser Leu Arg Ala Glu Asp Thr Ala Val Tyr His Cys
                85                  90                  95

Ala Arg Gly Ser Ser Gly His Tyr Glu Ala Phe Asp Ile Trp Gly Gln
            100                 105                 110

Gly Thr Leu Val Thr Val Ser Ser
        115                 120

<210> SEQ ID NO 38
<211> LENGTH: 120
<212> TYPE: PRT
<213> ORGANISM: Artificial
<220> FEATURE:
<223> OTHER INFORMATION: Amino acid sequence of NYA-1143-VH02

<400> SEQUENCE: 38
```

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Ile Arg Ser Tyr
            20                  25                  30

Asp Met His Trp Val Arg Gln Ala Pro Gly Lys Gly Leu Glu Trp Val
        35                  40                  45

Ala Thr Ile Ser Tyr Asp Gly Ser Gln Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr His Cys
            85                  90                  95

Ala Arg Gly Ser Ser Gly His Tyr Glu Ala Phe Asp Ile Trp Gly Gln
                100                 105                 110

Gly Thr Leu Val Thr Val Ser Ser
            115                 120

<210> SEQ ID NO 39
<211> LENGTH: 120
<212> TYPE: PRT
<213> ORGANISM: Artificial
<220> FEATURE:
<223> OTHER INFORMATION: Amino acid sequence of NYA-1143-VH03

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ile Arg Ser Tyr
            20                  25                  30

Asp Ile His Trp Val Arg Gln Ala Pro Gly Lys Gly Leu Glu Trp Val
        35                  40                  45

Ala Thr Ile Ser Tyr Asp Gly Ser Gln Lys Tyr Tyr Ala Asp Ser Val
    50                  55                  60

Lys Gly Arg Phe Thr Ile Ser Arg Asp Glu Ser Lys Asn Thr Leu Tyr
65                  70                  75                  80

Leu Gln Met Asn Ser Leu Arg Ala Glu Asp Thr Ala Val Tyr His Cys
            85                  90                  95

Ala Arg Gly Ser Ser Gly His Tyr Glu Ala Phe Asp Ile Trp Gly Gln
                100                 105                 110

Gly Thr Leu Val Thr Val Ser Ser
            115                 120

<210> SEQ ID NO 40
<211> LENGTH: 111
<212> TYPE: PRT
<213> ORGANISM: Artificial
<220> FEATURE:
<223> OTHER INFORMATION: Amino acid sequence of NYA-1143-VL01

<400> SEQUENCE: 40

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Trp
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Val Pro Asp Arg Phe Ser
    50                  55                  60

```
Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Gly Thr Trp Asp Ser Ser Leu
                85                  90                  95

Ser Ala Pro Trp Val Phe Gly Gly Gly Thr Lys Leu Thr Val Leu
            100                 105                 110
```

<210> SEQ ID NO 41
<211> LENGTH: 876
<212> TYPE: DNA
<213> ORGANISM: Artificial
<220> FEATURE:
<223> OTHER INFORMATION: Full-length nucleotide sequence of NYA-2044

<400> SEQUENCE: 41

| | | |
|---|---|---|
| atgaaacacc tgtggttctt cctcctgctg gtggcagctc ccagatgggt gctgagcggt | 60 |
| gaggtacagc tggtggaatc cggtggaggc cttgtgcaac cgggaggctc cctgcgactc | 120 |
| tcttgcgccg catctggctt ttccatacga tcctacgata ttcattgggt ccgactcgcc | 180 |
| cctggcaaag gtcttgaatg ggttgccact atctcctacg acgggtctca gaaatattat | 240 |
| gcggattcag tgaaggggcg gttcacaatt tcacgagacg agtcaaagaa tacactgtac | 300 |
| ctccaaatga attcactgag agccgaggat actgcagtct atcattgtgc aagagggtcc | 360 |
| tcaggccact acgaggcctt tgatatatgg ggccaaggca ccttggtaac cgttagtagc | 420 |
| ggaggtggag aagcggagg cggcggttcc ggaggaggtg aagtcaatc cgttctgact | 480 |
| cagccaccct ccgtgagtgc agcgcctgga cagaaggtca caatatcatg ttctggctct | 540 |
| tcaagcaaca tcggaaactg gtacgtgagc tggtaccagc agctccccgg cacggcgccc | 600 |
| aagcttctga tatatgacaa caacaaacg cccagtggaa tccctgacag attcagtggg | 660 |
| tctaaaagtg gtacaagcgc taccctgggt atcaccggat gcagaccgg agatgaggcg | 720 |
| gactattatt gcggaacctg ggactccagc ctgagcgctc cctgggtttt cggcggaggt | 780 |
| actaaggtta ccgtcttggg cgcggccgca ggtgcaggtg gtgattacaa agatgatgac | 840 |
| gataaaggtg cagcggcgca tcaccatcat caccac | 876 |

<210> SEQ ID NO 42
<211> LENGTH: 876
<212> TYPE: DNA
<213> ORGANISM: Artificial
<220> FEATURE:
<223> OTHER INFORMATION: Full-length nucleotide sequence of NYA-2045

<400> SEQUENCE: 42

| | | |
|---|---|---|
| atgaaacacc tgtggttctt cctcctgctg gtggcagctc ccagatgggt gctgagcggt | 60 |
| gaggtacagc tggtggaatc cggtggaggc cttgtgcaac cgggaggctc cctgcgactc | 120 |
| tcttgcgccg catctggctt ttccatacga tcctacgata ttcattgggt ccgactcgcc | 180 |
| cctggcaaag gtcttgaatg ggttgccact atctcctacg acgggtctca gaaatattat | 240 |
| gcggattcag tgaaggggcg gttcacaatt tcacgagacg agtcaaagaa tacactgtac | 300 |
| ctccaaatga attcactgag agccgaggat actgcagtct atcattgtgc aagagggtcc | 360 |
| tcaggccact acgaggcctt tgatatatgg ggccaaggca ccttggtaac cgttagtagc | 420 |
| ggaggtggag aagcggagg cggcggttcc ggaggaggtg aagtcaatc cgttctgact | 480 |
| cagccaccct ccgcctctgg caccccgggc aacgggtca atatcatg ttctggctct | 540 |
| tcaagcaaca tcggaaactg gtacgtgagc tggtaccagc agctccccgg cacggcgccc | 600 |

```
aagcttctga tatatgacaa caacaaacgg cccagtggag ttcctgacag attcagtggg    660
tctaaaagtg gtacaagcgc tagcctggcc ataagtggtc tgcagagtga agatgaggcg    720
gactattatt gcggaacctg ggactccagc ctgagcgctc cctgggtttt cggcggaggt    780
actaagctga ccgtcttggg cgcggccgca ggtgcaggtg gtgattacaa agatgatgac    840
gataaaggtg cagcggcgca tcaccatcat caccac                              876
```

<210> SEQ ID NO 43
<211> LENGTH: 876
<212> TYPE: DNA
<213> ORGANISM: Artificial
<220> FEATURE:
<223> OTHER INFORMATION: Full-length nucleotide sequence of NYA-2047

<400> SEQUENCE: 43

```
atgaaacacc tgtggttctt cctcctgctg gtggcagctc ccagatgggt gctgagcggt     60
caagtacagc tggtggaatc cggtggaggc gtggtccagc cgggacgcag cttgagactg    120
tcctgcgctg catctggctt ttccatacga tcctacgata tgcactgggt tcgccaagcc    180
cctggcaaag gtcttgaatg ggttgccact atctcctacg acgggtctca gaaatattac    240
gcggattcag tgaaggggcg gttcacaatt tcacgggaca attcaaagaa taccttgtat    300
ctccagatgt cttcactgag agccgaggat actgcagtct atcattgtgc aagagggtcc    360
tcaggccact acgaggcctt tgatatatgg ggccaaggca ccttggtaac cgttagtagc    420
ggaggtggag gaagcggagg cggcggttcc ggaggaggtg gaagtcaatc cgttctgact    480
cagccaccct ccgtgagtgc agcgcctgga cagaaggtca caatatcatg ttctggctct    540
tcaagcaaca tcggaaactg gtacgtgagc tggtaccagc agctccccgg cacggcgccc    600
aagcttctga tatatgacaa caacaaacgg cccagtggaa tccctgacag attcagtggg    660
tctaaaagtg gtacaagcgc taccctgggt atcaccggat tgcagaccgg agatgaggcg    720
gactattatt gcggaacctg ggactccagc ctgagcgctc cctgggtttt cggcggaggt    780
actaaggtta ccgtcttggg cgcggccgca ggtgcaggtg gtgattacaa agatgatgac    840
gataaaggtg cagcggcgca tcaccatcat caccac                              876
```

<210> SEQ ID NO 44
<211> LENGTH: 876
<212> TYPE: DNA
<213> ORGANISM: Artificial
<220> FEATURE:
<223> OTHER INFORMATION: Full-length nucleotide sequence of NYA-2048

<400> SEQUENCE: 44

```
atgaaacacc tgtggttctt cctcctgctg gtggcagctc ccagatgggt gctgagcgga     60
caagttcaac tcgtggaatc tggtggaggg gtggtacaac caggccggtc acttagactg    120
tcctgcgctg cgagtggatt ttccatcaga tcttacgaca tgcactgggt tcgccaagca    180
cccggaaagg gtttggaatg ggtggctacg atctcctacg atggatccca gaagtattac    240
gccgacagcg tcaagggccg atttacaata tcacgggaca attcaaagaa taccttgtat    300
ctccagatgt cttcactgag agccgaggat actgcagtct atcattgtgc aagagggtcc    360
tcaggccact acgaggcctt tgatatatgg ggccaaggca ccttggtaac cgttagtagc    420
ggaggtggag gaagcggagg cggcggttcc ggaggaggtg gaagtcaatc cgttctgact    480
cagccaccct ccgcctctgg caccccgggc caacgggtca caatatcatg ttctggctct    540
```

```
tcaagcaaca tcggaaactg gtacgtgagc tggtaccagc agctccccgg cacggcgccc    600
aagcttctga tatatgacaa caacaaacgg cccagtggag ttcctgacag attcagtggg    660
tctaaaagtg gtacaagcgc tagcctggcc ataagtggtc tgcagagtga agatgaggcg    720
gactattatt gcggaacctg ggactccagc ctgagcgctc cctgggtttt cggcggaggt    780
actaagctga ccgtcttggg cgcggccgca ggtgcaggtg gtgattacaa agatgatgac    840
gataaaggtg cagcggcgca tcaccatcat caccac                             876

<210> SEQ ID NO 45
<211> LENGTH: 876
<212> TYPE: DNA
<213> ORGANISM: Artificial
<220> FEATURE:
<223> OTHER INFORMATION: Full-length nucleotide sequence of NYA-2060

<400> SEQUENCE: 45
atgaaacacc tgtggttctt cctcctgctg gtggcagctc ccagatgggt gctgagcggt     60
gaggtacagc tggtggaatc cggtggaggc cttgtgcaac cggaggctc cctgcgactc     120 tcttgcgccg catctggctt ttccatacga tcctacgata ttcattgggt ccgacaagcc    180
cctggcaaag gtcttgaatg ggttgccact atctcctacg acgggtctca gaaatattat    240
gcggattcag tgaaggggcg gttcacaatt tcacgagacg agtcaaagaa tacactgtac    300
ctccaaatga attcactgag agccgaggat actgcagtct atcattgtgc aagagggtcc    360
tcaggccact acgaggcctt tgatatatgg ggccaaggca ccttggtaac cgttagtagc    420
ggaggtggag gaagcggagg cggcggttcc ggaggaggtg gaagtcaatc cgttctgact    480
cagccaccct ccgtgagtgc agcgcctgga cagaaggtca atatcatg ttctggctct     540 tcaagcaaca tcggaaactg gtacgtgagc tggtaccagc agctccccgg cacggcgccc    600
aagcttctga tatatgacaa caacaaacgg cccagtggaa tccctgacag attcagtggg    660
tctaaaagtg gtacaagcgc tacgctgggt atcaccggat tgcagaccgg agatgaggcg    720
gactattatt gcggaacctg ggactccagc ctgagcgctc cctgggtttt cggcggaggt    780
actaaggtta ccgtcttggg cgcggccgca ggtgcaggtg gtgattacaa agatgatgac    840
gataaaggtg cagcggcgca tcaccatcat caccac                             876

<210> SEQ ID NO 46
<211> LENGTH: 876
<212> TYPE: DNA
<213> ORGANISM: Artificial
<220> FEATURE:
<223> OTHER INFORMATION: Full-length nucleotide sequence of NYA-2061

<400> SEQUENCE: 46
atgaaacacc tgtggttctt cctcctgctg gtggcagctc ccagatgggt gctgagcggt     60
gaggtacagc tggtggaatc cggtggaggc cttgtgcaac cggaggctc cctgcgactc     120 tcttgcgccg catctggctt ttccatacga tcctacgata ttcattgggt ccgacaagcc    180
cctggcaaag gtcttgaatg ggttgccact atctcctacg acgggtctca gaaatattat    240
gcggattcag tgaaggggcg gttcacaatt tcacgagacg agtcaaagaa tacactgtac    300
ctccaaatga attcactgag agccgaggat actgcagtct atcattgtgc aagagggtcc    360
tcaggccact acgaggcctt tgatatatgg ggccaaggca ccttggtaac cgttagtagc    420
ggaggtggag gaagcggagg cggcggttcc ggaggaggtg gaagtcaatc cgttctgact    480
cagccaccct ccgcctctgg caccccgggc caacgggtca atatcatg ttctggctct     540
```

```
tcaagcaaca tcggaaactg gtacgtgagc tggtaccagc agctccccgg cacggcgccc    600
aagcttctga tatatgacaa caacaaacgg cccagtggag ttcctgacag attcagtggg    660
tctaaaagtg gtacaagcgc tagcctggcc ataagtggtc tgcagagtga agatgaggcg    720
gactattatt gcggaacctg ggactccagc ctgagcgctc cctgggtttt cggcggaggt    780
actaagctga ccgtcttggg cgcggccgca ggtgcaggtg gtgattacaa agatgatgac    840
gataaaggtg cagcggcgca tcaccatcat caccac                              876

<210> SEQ ID NO 47
<211> LENGTH: 292
<212> TYPE: PRT
<213> ORGANISM: Artificial
<220> FEATURE:
<223> OTHER INFORMATION: Full-length amino acid sequence of NYA-2044

<400> SEQUENCE: 47

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Ser
        35                  40                  45

Ile Arg Ser Tyr Asp Ile His Trp Val Arg Leu Ala Pro Gly Lys Gly
    50                  55                  60

Leu Glu Trp Val Ala Thr Ile Ser Tyr Asp Gly Ser Gln Lys Tyr Tyr
65                  70                  75                  80

Ala Asp Ser Val Lys Gly Arg Phe Thr Ile Ser Arg Asp Glu Ser Lys
                85                  90                  95

Asn Thr Leu Tyr Leu Gln Met Asn Ser Leu Arg Ala Glu Asp Thr Ala
            100                 105                 110

Val Tyr His Cys Ala Arg Gly Ser Ser His Tyr Glu Ala Phe Asp
        115                 120                 125

Ile Trp Gly Gln Gly Thr Leu Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Trp Tyr Val Ser Trp Tyr
            180                 185                 190

Gln Gln Leu Pro Gly Thr Ala Pro Lys Leu Leu Ile Tyr Asp Asn Asn
        195                 200                 205

Lys Arg Pro Ser Gly Ile Pro Asp Arg Phe Ser Gly Ser Lys Ser Gly
    210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Val Thr Val Leu Gly Ala Ala Ala Gly Ala
            260                 265                 270

Gly Gly Asp Tyr Lys Asp Asp Asp Lys Gly Ala Ala Ala His His
        275                 280                 285

His His His His
    290
```

<210> SEQ ID NO 48
<211> LENGTH: 292
<212> TYPE: PRT
<213> ORGANISM: Artificial
<220> FEATURE:
<223> OTHER INFORMATION: Full-length amino acid sequence of NYA-2045

<400> SEQUENCE: 48

```
Met Lys His Leu Trp Phe Phe Leu Leu Leu Val Ala Ala Pro Arg Trp
 1               5                  10                  15

Val Leu Ser Gly Glu Val Gln Leu Val Glu Ser Gly Gly Gly Leu Val
             20                  25                  30

Gln Pro Gly Gly Ser Leu Arg Leu Ser Cys Ala Ala Ser Gly Phe Ser
         35                  40                  45

Ile Arg Ser Tyr Asp Ile His Trp Val Arg Leu Ala Pro Gly Lys Gly
     50                  55                  60

Leu Glu Trp Val Ala Thr Ile Ser Tyr Asp Gly Ser Gln Lys Tyr Tyr
 65                  70                  75                  80

Ala Asp Ser Val Lys Gly Arg Phe Thr Ile Ser Arg Asp Glu Ser Lys
                 85                  90                  95

Asn Thr Leu Tyr Leu Gln Met Asn Ser Leu Arg Ala Glu Asp Thr Ala
            100                 105                 110

Val Tyr His Cys Ala Arg Gly Ser Ser Gly His Tyr Glu Ala Phe Asp
        115                 120                 125

Ile Trp Gly Gln Gly Thr Leu Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Ala Ser Gly Thr Pro Gly Gln Arg Val Thr Ile Ser
                165                 170                 175

Cys Ser Gly Ser Ser Ser Asn Ile Gly Asn Trp Tyr Val Ser Trp Tyr
            180                 185                 190

Gln Gln Leu Pro Gly Thr Ala Pro Lys Leu Leu Ile Tyr Asp Asn Asn
        195                 200                 205

Lys Arg Pro Ser Gly Val Pro Asp Arg Phe Ser Gly Ser Lys Ser Gly
    210                 215                 220

Thr Ser Ala Ser Leu Ala Ile Ser Gly Leu Gln Ser Glu Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Leu Thr Val Leu Gly Ala Ala Ala Gly Ala
            260                 265                 270

Gly Gly Asp Tyr Lys Asp Asp Asp Lys Gly Ala Ala Ala His His
        275                 280                 285

His His His His
        290
```

<210> SEQ ID NO 49
<211> LENGTH: 246
<212> TYPE: PRT
<213> ORGANISM: Artificial
<220> FEATURE:
<223> OTHER INFORMATION: Full-length amino acid sequence of NYA-0082

<400> SEQUENCE: 49

```
Glu Val Gln Leu Val Glu Ser Gly Gly Gly Val Val Gln Pro Gly Arg
```

```
               1               5                  10                 15
            Ser Leu Thr Pro Ser Cys Ser Ala Ser Gly Phe Ser Ile Arg Ser Tyr
                            20                 25                 30

Asp Ile His Trp Val Arg Gln Ala Pro Gly Lys Gly Leu Glu Trp Val
                            35                 40                 45

Ala Thr Ile Ser Tyr Asp Gly Ser Gln Lys Tyr Phe Ala Asp Ser Val
                    50                 55                 60

Lys Gly Arg Phe Thr Ile Phe Arg Asp Glu Ser Glu Asn Met Val Tyr
             65                 70                 75                 80

Leu Gln Met Ser Gly Leu Arg Val Glu Asp Thr Ala Val Tyr His Cys
                            85                 90                 95

Ala Arg Gly Ser Ser Gly His Tyr Glu Ala Phe Asp Ile Trp Gly Gln
                           100                105                110

Gly Thr Met Val Thr Val Ser Ser Gly Gly Gly Ser Gly Gly Gly
                           115                120                125

Gly Ser Gly Gly Gly Ser Gln Ser Val Leu Thr Gln Pro Pro Ser
                    130                135                140

Val Ser Ala Ala Pro Gly Gln Lys Val Thr Ile Ser Cys Ser Gly Ser
            145                150                155                160

Ser Ser Asn Ile Gly Asn Asn Tyr Val Ser Trp Tyr Gln Arg Leu Pro
                           165                170                175

Gly Thr Ala Pro Lys Leu Leu Ile Tyr Asp Asn Asn Lys Arg Pro Ser
                           180                185                190

Gly Ile Pro Asp Arg Phe Ser Gly Ser Lys Ser Gly Thr Ser Ala Thr
                           195                200                205

Leu Gly Ile Thr Gly Leu Gln Thr Gly Asp Glu Ala Asp Tyr Tyr Cys
                    210                215                220

Gly Ser Trp Asp Ser Ser Leu Ser Ala Pro Trp Val Phe Gly Gly Gly
            225                230                235                240

Thr Lys Val Thr Val Leu
                           245

<210> SEQ ID NO 50
<211> LENGTH: 292
<212> TYPE: PRT
<213> ORGANISM: Artificial
<220> FEATURE:
<223> OTHER INFORMATION: Full-length amino acid sequence of NYA-2047

<400> SEQUENCE: 50

Met Lys His Leu Trp Phe Phe Leu Leu Leu Val Ala Ala Pro Arg Trp
 1               5                  10                 15

Val Leu Ser Gly Gln Val Gln Leu Val Glu Ser Gly Gly Gly Val Val
                20                 25                 30

Gln Pro Gly Arg Ser Leu Arg Leu Ser Cys Ala Ala Ser Gly Phe Ser
                35                 40                 45

Ile Arg Ser Tyr Asp Met His Trp Val Arg Gln Ala Pro Gly Lys Gly
         50                 55                 60

Leu Glu Trp Val Ala Thr Ile Ser Tyr Asp Gly Ser Gln Lys Tyr Tyr
 65                 70                 75                 80

Ala Asp Ser Val Lys Gly Arg Phe Thr Ile Ser Arg Asp Asn Ser Lys
                85                 90                 95

Asn Thr Leu Tyr Leu Gln Met Ser Ser Leu Arg Ala Glu Asp Thr Ala
               100                105                110

Val Tyr His Cys Ala Arg Gly Ser Ser Gly His Tyr Glu Ala Phe Asp
```

Ile Trp Gly Gln Gly Thr Leu Val Thr Val Ser Ser Gly Gly Gly
    130                 135                 140

Ser Gly Gly Gly Ser Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Trp Tyr Val Ser Trp Tyr
            180                 185                 190

Gln Gln Leu Pro Gly Thr Ala Pro Lys Leu Leu Ile Tyr Asp Asn Asn
            195                 200                 205

Lys Arg Pro Ser Gly Ile Pro Asp Arg Phe Ser Gly Ser Lys Ser Gly
            210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Val Thr Val Leu Gly Ala Ala Ala Gly Ala
            260                 265                 270

Gly Gly Asp Tyr Lys Asp Asp Asp Lys Gly Ala Ala Ala His His
            275                 280                 285

His His His His
        290

<210> SEQ ID NO 51
<211> LENGTH: 292
<212> TYPE: PRT
<213> ORGANISM: Artificial
<220> FEATURE:
<223> OTHER INFORMATION: Full-length amino acid sequence of NYA-2048

<400> SEQUENCE: 51

Met Lys His Leu Trp Phe Phe Leu Leu Leu Val Ala Ala Pro Arg Trp
1               5                   10                  15

Val Leu Ser Gly Gln Val Gln Leu Val Glu Ser Gly Gly Gly Val Val
                20                  25                  30

Gln Pro Gly Arg Ser Leu Arg Leu Ser Cys Ala Ala Ser Gly Phe Ser
            35                  40                  45

Ile Arg Ser Tyr Asp Met His Trp Val Arg Gln Ala Pro Gly Lys Gly
    50                  55                  60

Leu Glu Trp Val Ala Thr Ile Ser Tyr Asp Gly Ser Gln Lys Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Ser Ser Leu Arg Ala Glu Asp Thr Ala
            100                 105                 110

Val Tyr His Cys Ala Arg Gly Ser Gly His Tyr Glu Ala Phe Asp
            115                 120                 125

Ile Trp Gly Gln Gly Thr Leu Val Thr Val Ser Ser Gly Gly Gly
    130                 135                 140

Ser Gly Gly Gly Gly Ser Gly Gly Gly Ser Gln Ser Val Leu Thr
145                 150                 155                 160

Gln Pro Pro Ser Ala Ser Gly Thr Pro Gly Gln Arg Val Thr Ile Ser
                165                 170                 175

Cys Ser Gly Ser Ser Ser Asn Ile Gly Asn Trp Tyr Val Ser Trp Tyr

```
            180                 185                 190
Gln Gln Leu Pro Gly Thr Ala Pro Lys Leu Leu Ile Tyr Asp Asn Asn
            195                 200                 205

Lys Arg Pro Ser Gly Val Pro Asp Arg Phe Ser Gly Ser Lys Ser Gly
        210                 215                 220

Thr Ser Ala Ser Leu Ala Ile Ser Gly Leu Gln Ser Glu Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Leu Thr Val Leu Gly Ala Ala Ala Gly Ala
            260                 265                 270

Gly Gly Asp Tyr Lys Asp Asp Asp Lys Gly Ala Ala Ala His His
        275                 280                 285

His His His His
        290

<210> SEQ ID NO 52
<211> LENGTH: 292
<212> TYPE: PRT
<213> ORGANISM: Artificial
<220> FEATURE:
<223> OTHER INFORMATION: Full-length amino acid sequence of NYA-2060

<400> SEQUENCE: 52

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Ser
        35                  40                  45

Ile Arg Ser Tyr Asp Ile His Trp Val Arg Gln Ala Pro Gly Lys Gly
    50                  55                  60

Leu Glu Trp Val Ala Thr Ile Ser Tyr Asp Gly Ser Gln Lys Tyr Tyr
65                  70                  75                  80

Ala Asp Ser Val Lys Gly Arg Phe Thr Ile Ser Arg Asp Glu Ser Lys
                85                  90                  95

Asn Thr Leu Tyr Leu Gln Met Asn Ser Leu Arg Ala Glu Asp Thr Ala
            100                 105                 110

Val Tyr His Cys Ala Arg Gly Ser Ser Gly His Tyr Glu Ala Phe Asp
        115                 120                 125

Ile Trp Gly Gln Gly Thr Leu Val Thr Val Ser Gly Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Trp Tyr Val Ser Trp Tyr
            180                 185                 190

Gln Gln Leu Pro Gly Thr Ala Pro Lys Leu Leu Ile Tyr Asp Asn Asn
        195                 200                 205

Lys Arg Pro Ser Gly Ile Pro Asp Arg Phe Ser Gly Ser Lys Ser Gly
    210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
```

```
                    245                 250                 255
Phe Gly Gly Gly Thr Lys Val Thr Val Leu Gly Ala Ala Ala Gly Ala
                260                 265                 270

Gly Gly Asp Tyr Lys Asp Asp Asp Lys Gly Ala Ala Ala His His
            275                 280                 285

His His His His
        290

<210> SEQ ID NO 53
<211> LENGTH: 292
<212> TYPE: PRT
<213> ORGANISM: Artificial
<220> FEATURE:
<223> OTHER INFORMATION: Full-length amino acid sequence of NYA-2061

<400> SEQUENCE: 53

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Ser
        35                  40                  45

Ile Arg Ser Tyr Asp Ile His Trp Val Arg Gln Ala Pro Gly Lys Gly
    50                  55                  60

Leu Glu Trp Val Ala Thr Ile Ser Tyr Asp Gly Ser Gln Lys Tyr Tyr
65                  70                  75                  80

Ala Asp Ser Val Lys Gly Arg Phe Thr Ile Ser Arg Asp Glu Ser Lys
                85                  90                  95

Asn Thr Leu Tyr Leu Gln Met Asn Ser Leu Arg Ala Glu Asp Thr Ala
            100                 105                 110

Val Tyr His Cys Ala Arg Gly Ser Ser Gly His Tyr Glu Ala Phe Asp
        115                 120                 125

Ile Trp Gly Gln Gly Thr Leu Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Ala Ser Gly Thr Pro Gly Gln Arg Val Thr Ile Ser
                165                 170                 175

Cys Ser Gly Ser Ser Ser Asn Ile Gly Asn Trp Tyr Val Ser Trp Tyr
            180                 185                 190

Gln Gln Leu Pro Gly Thr Ala Pro Lys Leu Leu Ile Tyr Asp Asn Asn
        195                 200                 205

Lys Arg Pro Ser Gly Val Pro Asp Arg Phe Ser Gly Ser Lys Ser Gly
    210                 215                 220

Thr Ser Ala Ser Leu Ala Ile Ser Gly Leu Gln Ser Glu Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Leu Thr Val Leu Gly Ala Ala Ala Gly Ala
            260                 265                 270

Gly Gly Asp Tyr Lys Asp Asp Asp Lys Gly Ala Ala Ala His His
        275                 280                 285

His His His His
    290
```

```
<210> SEQ ID NO 54
<211> LENGTH: 8
<212> TYPE: PRT
<213> ORGANISM: Artificial
<220> FEATURE:
<223> OTHER INFORMATION: Amino acid sequence of NYA-0001-CDRH1

<400> SEQUENCE: 54

Gly Phe Ser Ile Arg Ser Tyr Asp
1               5

<210> SEQ ID NO 55
<211> LENGTH: 8
<212> TYPE: PRT
<213> ORGANISM: Artificial
<220> FEATURE:
<223> OTHER INFORMATION: Amino acid sequence of NYA-0001-CDRH2

<400> SEQUENCE: 55

Ile Ser Tyr Asp Gly Ser Gln Lys
1               5

<210> SEQ ID NO 56
<211> LENGTH: 13
<212> TYPE: PRT
<213> ORGANISM: Artificial
<220> FEATURE:
<223> OTHER INFORMATION: Amino acid sequence of NYA-0001-CDRH3

<400> SEQUENCE: 56

Ala Arg Gly Ser Ser Gly His Tyr Glu Ala Phe Asp Ile
1               5                   10

<210> SEQ ID NO 57
<211> LENGTH: 8
<212> TYPE: PRT
<213> ORGANISM: Artificial
<220> FEATURE:
<223> OTHER INFORMATION: Amino acid sequence of NYA-0001-CDRL1

<400> SEQUENCE: 57

Ser Ser Asn Ile Gly Asn Asn Tyr
1               5

<210> SEQ ID NO 58

<400> SEQUENCE: 58

000

<210> SEQ ID NO 59
<211> LENGTH: 12
<212> TYPE: PRT
<213> ORGANISM: Artificial
<220> FEATURE:
<223> OTHER INFORMATION: Amino acid sequence of NYA-0001-CDRL3

<400> SEQUENCE: 59

Gly Thr Trp Asp Ser Ser Leu Ser Ala Pro Trp Val
1               5                   10

<210> SEQ ID NO 60
<211> LENGTH: 8
<212> TYPE: PRT
<213> ORGANISM: Artificial
<220> FEATURE:
<223> OTHER INFORMATION: Amino acid sequence of NYA-2023-CDRL1
```

```
<400> SEQUENCE: 60

Ser Ser Asn Ile Gly Asn Trp Tyr
1               5

<210> SEQ ID NO 61
<211> LENGTH: 12
<212> TYPE: PRT
<213> ORGANISM: Artificial
<220> FEATURE:
<223> OTHER INFORMATION: Amino acid sequence of NYA-2027-CDRL3

<400> SEQUENCE: 61

Gly Ser Trp Asp Ser Ser Leu Ser Ala Pro Trp Val
1               5                   10

<210> SEQ ID NO 62
<211> LENGTH: 13
<212> TYPE: PRT
<213> ORGANISM: Artificial
<220> FEATURE:
<223> OTHER INFORMATION: Amino acid sequence of NYA-1154-CDRH3

<400> SEQUENCE: 62

Ala Arg Gly Ser Ser Asn His Tyr Glu Ala Phe Asp Ile
1               5                   10

<210> SEQ ID NO 63
<211> LENGTH: 12
<212> TYPE: PRT
<213> ORGANISM: Artificial
<220> FEATURE:
<223> OTHER INFORMATION: Amino acid sequence of NYA-1154-CDRL3

<400> SEQUENCE: 63

Gly Ala Trp Asp Ser Ser Leu Ser Ala Pro Trp Val
1               5                   10

<210> SEQ ID NO 64
<211> LENGTH: 8
<212> TYPE: PRT
<213> ORGANISM: Artificial
<220> FEATURE:
<223> OTHER INFORMATION: Amino acid sequence of NYA-0035-CDRL1

<400> SEQUENCE: 64

Ser Ser Asn Ile Gly Asn Trp Lys
1               5

<210> SEQ ID NO 65
<211> LENGTH: 867
<212> TYPE: DNA
<213> ORGANISM: Artificial
<220> FEATURE:
<223> OTHER INFORMATION: Full-length nucleotide sequence of NYC-0003

<400> SEQUENCE: 65
atgaaacacc tgtggttctt cctcctgctg gtggcagctc ccagatgggt gctgagcggc    60
gaagtccagc tgttggagtc aggtggcgga ttggtgcaac ctggcgggtc actgaggctg   120
agttgtgcag ctagcggctt cacattctct acgtatcaga tgagctgggt gagacaggct   180
ccaggaaagg gtctggaatg ggtcagcggg attgtgtcta gcggtggctc cactgcctat   240
gccgatagcg taaaaggccg ctttacgatc tctcgggaca actctaagaa cacactctat   300
ctgcagatga attcccttag agccgaagat accgccgtgt actactgtgc tggggaactg   360
```

```
ctcccgtatt acggtatgga cgtttggggc caaggcacca ctgtcacagt gagttccggt    420
ggaggcgggt caggcggagg cggtagtgga ggtggaggat cacaaagcga gctgacacag    480
cctaggtccg tatccggaag tccagggcag agcgtcacca tcagctgcac tggcacctct    540
cgagatgtcg gcggatacaa ctacgtgtct tggtatcagc agcatcccgg caaagcgccc    600
aaactcatca tacacgacgt gattgagcgg tccagtgggg ttcccgatcg tttcagcggg    660
tcaaagtccg gaaataccgc aagcctgacc atttctgggc ttcaggcaga ggatgaggct    720
gactactact gctggtcctt tgccgggagc tattacgtgt ttgggacagg gactgacgtg    780
actgttctgg gcgcggccgc aggtgcaggt ggtgattaca agatgatga cgataaaggt    840 gcagcggcgc atcaccatca tcaccac                                        867
```

<210> SEQ ID NO 66
<211> LENGTH: 867
<212> TYPE: DNA
<213> ORGANISM: Artificial
<220> FEATURE:
<223> OTHER INFORMATION: Full-length nucleotide sequence of NYC-0004

<400> SEQUENCE: 66

```
atgaaacacc tgtggttctt cctcctgctg gtggcagctc ccagatgggt gctgagcggc     60
gaagtccagc tgttggagtc aggtggcgga ttggtgcaac ctggcgggtc actgaggctg    120
agttgtgcag ctagcggctt cacattctct acgtatcaga tgagctgggt gagacaggct    180
ccaggaaagg gtctggaatg ggtcagcggg attgtgtcta gcggtggctc cactgcctat    240
gccgatagcg taaaaggccg ctttacgatc tctcgggaca actctaagaa cacactctat    300
ctgcagatga attcccttag agccgaagat accgccgtgt actactgtgc tggggaactg    360
ctcccgtatt acggtatgga cgtttggggc caaggcacca ctgtcacagt gagttccggt    420
ggaggcgggt caggcggagg cggtagtgga ggtggaggat cacaaagcga gctgacacag    480
cctaggtccg tatccggaag tccagggcag agcgtcacca tcagctgcac tggcacccgag    540 cgagatgtcg gcggatacaa ctacgtgtct tggtatcagc agcatcccgg caaagcgccc    600
aaactcatca tacacgacgt gattgagcgg tccagtgggg ttcccgatcg tttcagcggg    660
tcaaagtccg gaaataccgc aagcctgacc atttctgggc ttcaggcaga ggatgaggct    720
gactactact gctggtcctt tgccgggggc tattacgtgt ttgggacagg gactgacgtg    780
actgttctgg gcgcggccgc aggtgcaggt ggtgattaca agatgatga cgataaaggt    840 gcagcggcgc atcaccatca tcaccac                                        867
```

<210> SEQ ID NO 67
<211> LENGTH: 289
<212> TYPE: PRT
<213> ORGANISM: Artificial
<220> FEATURE:
<223> OTHER INFORMATION: Full-length amino acid sequence of NYC-0003

<400> SEQUENCE: 67

```
Met Lys His Leu Trp Phe Phe Leu Leu Leu Val Ala Ala Pro Arg Trp
1               5                   10                  15

Val Leu Ser Gly Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Thr Tyr Gln Met Ser Trp Val Arg Gln Ala Pro Gly Lys Gly
    50                  55                  60
```

Leu Glu Trp Val Ser Gly Ile Val Ser Ser Gly Ser Thr Ala Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Gly Glu Leu Leu Pro Tyr Tyr Gly Met Asp Val
        115                 120                 125

Trp Gly Gln Gly Thr Thr Val Thr Val Ser Ser Gly Gly Gly Gly Ser
    130                 135                 140

Gly Gly Gly Gly Ser Gly Gly Gly Ser Gln Ser Glu Leu Thr Gln
145                 150                 155                 160

Pro Arg Ser Val Ser Gly Ser Pro Gly Gln Ser Val Thr Ile Ser Cys
                165                 170                 175

Thr Gly Thr Ser Arg Asp Val Gly Gly Tyr Asn Tyr Val Ser Trp Tyr
            180                 185                 190

Gln Gln His Pro Gly Lys Ala Pro Lys Leu Ile Ile His Asp Val Ile
        195                 200                 205

Glu Arg Ser Ser Gly Val Pro Asp Arg Phe Ser Gly Ser Lys Ser Gly
    210                 215                 220

Asn Thr Ala Ser Leu Thr Ile Ser Gly Leu Gln Ala Glu Asp Glu Ala
225                 230                 235                 240

Asp Tyr Tyr Cys Trp Ser Phe Ala Gly Ser Tyr Tyr Val Phe Gly Thr
                245                 250                 255

Gly Thr Asp Val Thr Val Leu Gly Ala Ala Ala Gly Ala Gly Gly Asp
            260                 265                 270

Tyr Lys Asp Asp Asp Asp Lys Gly Ala Ala Ala His His His His His
        275                 280                 285

His

<210> SEQ ID NO 68
<211> LENGTH: 289
<212> TYPE: PRT
<213> ORGANISM: Artificial
<220> FEATURE:
<223> OTHER INFORMATION: Full-length amino acid sequence of NYC-0004

<400> SEQUENCE: 68

Met Lys His Leu Trp Phe Phe Leu Leu Leu Val Ala Ala Pro Arg Trp
1               5                   10                  15

Val Leu Ser Gly Glu Val Gln Leu Leu Glu Ser Gly Gly Gly Leu Val
                20                  25                  30

Gln Pro Gly Gly Ser Leu Arg Leu Ser Cys Ala Ala Ser Gly Phe Thr
            35                  40                  45

Phe Ser Thr Tyr Gln Met Ser Trp Val Arg Gln Ala Pro Gly Lys Gly
        50                  55                  60

Leu Glu Trp Val Ser Gly Ile Val Ser Ser Gly Ser Thr Ala Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Gly Glu Leu Leu Pro Tyr Tyr Gly Met Asp Val
        115                 120                 125

Trp Gly Gln Gly Thr Thr Val Thr Val Ser Ser Gly Gly Gly Ser
            130                 135                 140
Gly Gly Gly Gly Ser Gly Gly Gly Ser Gln Ser Glu Leu Thr Gln
145                 150                 155                 160
Pro Arg Ser Val Ser Gly Ser Pro Gly Gln Ser Val Thr Ile Ser Cys
                165                 170                 175
Thr Gly Thr Glu Arg Asp Val Gly Gly Tyr Asn Tyr Val Ser Trp Tyr
                180                 185                 190
Gln Gln His Pro Gly Lys Ala Pro Lys Leu Ile Ile His Asp Val Ile
                195                 200                 205
Glu Arg Ser Ser Gly Val Pro Asp Arg Phe Ser Gly Ser Lys Ser Gly
    210                 215                 220
Asn Thr Ala Ser Leu Thr Ile Ser Gly Leu Gln Ala Glu Asp Glu Ala
225                 230                 235                 240
Asp Tyr Tyr Cys Trp Ser Phe Ala Gly Tyr Tyr Val Phe Gly Thr
                245                 250                 255
Gly Thr Asp Val Thr Val Leu Gly Ala Ala Ala Gly Ala Gly Gly Asp
                260                 265                 270
Tyr Lys Asp Asp Asp Asp Lys Gly Ala Ala Ala His His His His His
                275                 280                 285
His

<210> SEQ ID NO 69
<211> LENGTH: 876
<212> TYPE: DNA
<213> ORGANISM: Artificial
<220> FEATURE:
<223> OTHER INFORMATION: Full-length nucleotide sequence of NYA-0001

<400> SEQUENCE: 69
atgaaacacc tgtggttctt cctcctgctg gtggcagctc ccagatgggt gctgagcgga      60
gaggtgcagc tggtggagtc tgggggaggc gtggtccagc ctgggaggtc cctgacaccc     120
tcctgttcag cgtctggatt ctccatccgt agttatgata cactgggt ccgccaggct       180 ccaggcaagg ggctagagtg ggtggccact atatcatatg atggaagtca gaagtacttc     240
gcagactccg tgaagggccg atttaccatc tcagagacg aatcggagaa catggtgtat      300
ctgcaaatga cggcctgag agttgaggac acggctgttt atcactgtgc gagagggagt      360
agtggtcatt atgaggcttt tgatatctgg ggccaaggga caatggtcac cgtctcttca    420 ggtgaggcg gttcaggcgg aggtggcagc ggcggtggcg ggagtcagtc tgtgttgacg     480
cagccgccct cagtgtctgc ggccccagga cagaaggtca ccatctcctg ctctggaagc   540
agctccaaca ttgggaataa ttatgtatcc tggtaccagc agctcccagg aacagccccc   600
aaactcctca tttatgacaa taataagcga ccctcaggga ttcctgaccg attctctggc   660
tccaagtctg gcacgtcagc caccctgggc atcaccggac tccagactgg ggacgaggcc   720
gattattact gcggaacatg ggatagcagc ctgagtgccc cttgggtgtt cggcggaggg   780
accaaggtca ccgtcctagg cgcggccgca ggtgcaggtg tgattacaa agatgatgac    840 gataaaggtg cagcggcgca tcaccatcat caccac                              876

<210> SEQ ID NO 70
<211> LENGTH: 292
<212> TYPE: PRT
<213> ORGANISM: Artificial
<220> FEATURE:
<223> OTHER INFORMATION: Full-length amino acid sequence of NYA-0001

-continued

<400> SEQUENCE: 70

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Val Val
            20                  25                  30

Gln Pro Gly Arg Ser Leu Thr Pro Ser Cys Ser Ala Ser Gly Phe Ser
        35                  40                  45

Ile Arg Ser Tyr Asp Ile His Trp Val Arg Gln Ala Pro Gly Lys Gly
    50                  55                  60

Leu Glu Trp Val Ala Thr Ile Ser Tyr Asp Gly Ser Gln Lys Tyr Phe
65                  70                  75                  80

Ala Asp Ser Val Lys Gly Arg Phe Thr Ile Phe Arg Asp Glu Ser Glu
                85                  90                  95

Asn Met Val Tyr Leu Gln Met Ser Gly Leu Arg Val Glu Asp Thr Ala
            100                 105                 110

Val Tyr His Cys Ala Arg Gly Ser Ser Gly His Tyr Glu Ala Phe Asp
        115                 120                 125

Ile Trp Gly Gln Gly Thr Met Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Asn Tyr Val Ser Trp Tyr
            180                 185                 190

Gln Gln Leu Pro Gly Thr Ala Pro Lys Leu Leu Ile Tyr Asp Asn Asn
        195                 200                 205

Lys Arg Pro Ser Gly Ile Pro Asp Arg Phe Ser Gly Ser Lys Ser Gly
    210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Val Thr Val Leu Gly Ala Ala Gly Ala
            260                 265                 270

Gly Gly Asp Tyr Lys Asp Asp Asp Lys Gly Ala Ala Ala His His
        275                 280                 285

His His His His
    290

<210> SEQ ID NO 71
<211> LENGTH: 738
<212> TYPE: DNA
<213> ORGANISM: Artificial
<220> FEATURE:
<223> OTHER INFORMATION: Full-length nucleotide sequence of HC1

<400> SEQUENCE: 71
atgaaacacc tgtggttctt cctcctgctg gtggcagctc ccagatgggt gctgagcgac     60
aaaactcaca catgcccacc ctgcccagca cctgaagccg caggggggacc ctcagtcttc    120 ctcttccccc caaaacccaa ggacaccctc atgatctccc ggacccctga ggtcacatgc    180
gtggtggtgt cagtgagcca cgaagaccct gaggtcaagt tcaactggta cgtggacggc    240
gtggaggtgc ataatgccaa gacaaagccc cggaggagc agtacaacag cacgtaccgg    300

| | |
|---|---|
| gtggtcagcg tcctcaccgt cctgcaccag gactggctga atggcaagga gtacaagtgc | 360 |
| aaggtctcca acaaagccct cccagccccc atcgagaaaa ccatctccaa agccaaaggc | 420 |
| cagccccggg aaccacaggt gtacgtgctg cccccatccc gggacgagct gaccaagaac | 480 |
| caggtcagcc tgctgtgcct ggtcaaaggc ttctatccca gcgacatcgc cgtggagtgg | 540 |
| gagagcaatg ccagcccga gaacaactac ctgacctggc ctcccgtgct ggactccgac | 600 |
| ggctccttct cctctacag caagctcacc gtggacaaga gcaggtggca gcagggcaac | 660 |
| gtcttctcat gctccgtgat gcatgaggct ctgcacaacc actacaccca gaagagcctc | 720 |
| tccctgtctc ccggcaag | 738 |

<210> SEQ ID NO 72
<211> LENGTH: 2235
<212> TYPE: DNA
<213> ORGANISM: Artificial
<220> FEATURE:
<223> OTHER INFORMATION: Full-length nucleotide sequence of NYF-0016-HC2

<400> SEQUENCE: 72

| | |
|---|---|
| atgaaacacc tgtggttctt cctcctgctg gtggcagctc ccagatgggt gctgagcgga | 60 |
| gaggtgcagc tggtggagtc tggggggaggc gtggtccagc ctggggaggtc cctgacaccc | 120 |
| tcctgttcag cgtctggatt ctccatccgt agctatgata tacactgggt ccgcctggct | 180 |
| ccaggcaagg ggctagagtg ggtggccact atatcatatg atggaagtca gaagtacttc | 240 |
| gcagactccg tgaagggccg atttaccatc tccagagacg aatcggagaa catggtgtat | 300 |
| ctgcaaatga gcggcctgag agttgaggac acggctgttt atcactgtgc gagagggagt | 360 |
| agtggtcatt atgaggcttt tgatatctgg ggccaaggga caatggtcac cgtctcttca | 420 |
| ggtggaggcg gttcaggcgg aggtggcagc ggcggtggcg ggagtcagtc tgtgttgacg | 480 |
| cagccgccct cagtgtctgc ggccccagga cagaaggtca ccatctcctg ctctggaagc | 540 |
| agctccaaca ttgggaattg gtatgtatcc tggtaccagc agctcccagg aacagccccc | 600 |
| aaactcctca tttatgacaa taataagcga ccctcaggga ttcctgaccg attctctggc | 660 |
| tccaagtctg gcacgtcagc caccctgggc atcaccggac tccagactgg ggacgaggcc | 720 |
| gattattact gcggaacatg ggatagcagc ctgagtgccc cttgggtgtt cggcggaggg | 780 |
| accaaggtca ccgtcctagg gggaggcggt tcagaagtgc agctggtgga atccggggggg | 840 |
| ggcctggtgc agcctggggg gagcctgaga ctgagttgtg ccgcctctgg ggtgacattt | 900 |
| aactactatg gcatgtcttg gatccgccag gcacctggaa agggcctgga gtgggtggcc | 960 |
| agcatcacta ggtccggcgg gcgaatctac tatcccgaca gcgtcaaggg caggttcaca | 1020 |
| atttcccgcg agaacacaca gaaaactctg tacctgcaga tgaatagcct gagagccgaa | 1080 |
| gatacagctg tgtactattg cactctggac ggcagggatg ggtgggtcgc ctattggggg | 1140 |
| caggaacccc tggtgacagt cagctccgga ggaggaggat ctggcggagg aggcagtggg | 1200 |
| ggaggcgggt caaactttat gctcactcag ccgtcctctg tttctggcgt acctggccaa | 1260 |
| cgggtgacca ttagctgtac gggtaatacc gggaatatcg gtctaacta cgtgaactgg | 1320 |
| tatcagcagc ttcagggac agctcccaag ttgctgatct atcgcgacga caaaagaccc | 1380 |
| tcagggtcc ctgaccgatt tagtggcagc aaaagcggta cttccgcttc cctggcgata | 1440 |
| accggctttc aggccgaaga tgaggcagac tactattgcc agtcatattc cagcggcttc | 1500 |
| atcttcggag gcggaactaa gctgacagtg ttggcagccg agcccaaatc ttctgacaaa | 1560 |

| | |
|---|---|
| actcacacat gcccaccctg cccagcacct gaagccgcag ggggaccctc agtcttcctc | 1620 |
| ttccccccaa aacccaagga caccctcatg atctcccgga cccctgaggt cacatgcgtg | 1680 |
| gtggtgtcag tgagccacga agaccctgag gtcaagttca actggtacgt ggacggcgtg | 1740 |
| gaggtgcata atgccaagac aaagccccgg gaggagcagt acaacagcac gtaccgggtg | 1800 |
| gtcagcgtcc tcaccgtcct gcaccaggac tggctgaatg gcaaggagta caagtgcaag | 1860 |
| gtctccaaca aagccctccc agcccccatc gagaaaacca tctccaaagc caaaggccag | 1920 |
| ccccgggaac cacaggtgta cgtgtacccc ccatcccggg acgagctgac caagaaccag | 1980 |
| gtcagcctga cctgcctggt caaaggcttc tatcccagcg acatcgccgt ggagtgggag | 2040 |
| agcaatgggc agcccgagaa caactacaag accacccctc ccgtgctgga ctccgacggc | 2100 |
| tccttcgccc tcgtgagcaa gctcaccgtg gacaagagca ggtggcagca gggcaacgtc | 2160 |
| ttctcatgct ccgtgatgca tgaggctctg cacaaccact acacccagaa gagcctctcc | 2220 |
| ctgtctcccg gcaag | 2235 |

<210> SEQ ID NO 73
<211> LENGTH: 2235
<212> TYPE: DNA
<213> ORGANISM: Artificial
<220> FEATURE:
<223> OTHER INFORMATION: Full-length nucleotide sequence of NYF-0019-HC2

<400> SEQUENCE: 73

| | |
|---|---|
| atgaaacacc tgtggttctt cctcctgctg gtggcagctc ccagatgggt gctgagcgga | 60 |
| gaggtgcagc tggtggagtc tgggggaggc gtggtccagc ctgggaggtc cctgacaccc | 120 |
| tcctgttcag cgtctggatt ctccatccgt agctatgata tacactgggt ccgcctggct | 180 |
| ccaggcaagg ggctagagtg ggtggccact atatcatatg atggaagtca gaagtacttc | 240 |
| gcagactccg tgaagggccg atttaccatc tcagagacg aatcggagaa catggtgtat | 300 |
| ctgcaaatga cggcctgag agttgaggac acggctgttt atcactgtgc gagagggagt | 360 |
| agtggtcatt atgaggcttt tgatatctgg ggccaaggga caatggtcac cgtctcttca | 420 |
| ggtggaggcg gttcaggcgg aggtggcagc ggcggtggcg ggagtcagtc tgtgttgacg | 480 |
| cagccgccct cagtgtctgc ggccccagga cagaaggtca ccatctcctg ctctggaagc | 540 |
| agctccaaca ttgggaattg gtatgtatcc tggtaccagc ggctcccagg aacagccccc | 600 |
| aaactcctca tttatgacaa taataagcga ccctcaggga ttcctgaccg attctctggc | 660 |
| tccaagtctg gcacgtcagc caccctgggc atcaccggac tccagactgg ggacgaggcc | 720 |
| gattattact gcggaacatg ggatagcagc ctgagtgccc cttgggtgtt cggcggaggg | 780 |
| accaaggtca ccgtcctagg gggaggcggt tcagaagtgc agctggtgga atccgggggg | 840 |
| ggcctggtgc agcctggggg gagcctgaga ctgagttgtg ccgcctctgg ggtgacattt | 900 |
| aactactatg gcatgtcttg gatccgccag gcacctggaa agggcctgga gtgggtggcc | 960 |
| agcatcacta ggtccggcgg gcgaatctac tatcccgaca cgtcaaggg caggttcaca | 1020 |
| atttcccgcg agaacacaca gaaaactctg tacctgcaga tgaatagcct gagagccgaa | 1080 |
| gatacagctg tgtactattg cactctggac ggcaggatg gtgggtcgc ctattggggg | 1140 |
| cagggaaccc tggtgacagt cagctccgga ggaggaggat ctggcggagg aggcagtggg | 1200 |
| ggaggcgggt caaactttat gctcactcag ccgtcctctg tttctggcgt acctggccaa | 1260 |
| cggggtgacca ttagctgtac gggtaatacc gggaatatcg gtctaactac gtgaactgg | 1320 |
| tatcagcagc ttccagggac agctcccaag ttgctgatct atcgcgacga caaaagaccc | 1380 |

```
tcaggggtcc ctgaccgatt tagtggcagc aaaagcggta cttccgcttc cctggcgata    1440
accggctttc aggccgaaga tgaggcagac tactattgcc agtcatattc cagcggcttc    1500
atcttcggag gcggaactaa gctgacagtg ttggcagccg agcccaaatc ttctgacaaa    1560
actcacacat gcccaccctg cccagcacct gaagccgcag ggggaccctc agtcttcctc    1620
ttccccccaa aacccaagga caccctcatg atctcccgga cccctgaggt cacatgcgtg    1680
gtggtgtcag tgagccacga agaccctgag gtcaagttca actggtacgt ggacggcgtg    1740
gaggtgcata atgccaagac aaagccccgg gaggagcagt acaacagcac gtaccgggtg    1800
gtcagcgtcc tcaccgtcct gcaccaggac tggctgaatg gcaaggagta caagtgcaag    1860
gtctccaaca aagccctccc agcccccatc gagaaaacca tctccaaagc caaaggccag    1920
ccccgggaac cacaggtgta cgtgtacccc ccatcccggg acgagctgac caagaaccag    1980
gtcagcctga cctgcctggt caaaggcttc tatcccagcg acatcgccgt ggagtgggag    2040
agcaatgggc agcccgagaa caactacaag accacccctc ccgtgctgga ctccgacggc    2100
tccttcgccc tcgtgagcaa gctcaccgtg gacaagagca ggtggcagca gggcaacgtc    2160
ttctcatgct ccgtgatgca tgaggctctg cacaaccact acacccagaa gagcctctcc    2220
ctgtctcccg gcaag                                                     2235

<210> SEQ ID NO 74
<211> LENGTH: 2235
<212> TYPE: DNA
<213> ORGANISM: Artificial
<220> FEATURE:
<223> OTHER INFORMATION: Full-length nucleotide sequence of NYF-0022-HC2

<400> SEQUENCE: 74
atgaaacacc tgtggttctt cctcctgctg gtggcagctc ccagatgggt gctgagcgga      60
gaggtgcagc tggtggagtc tgggggaggc gtggtccagc ctgggaggtc cctgacaccc     120
tcctgttcag cgtctggatt ctccatccgt agctatgata tacactgggt ccgcctggct     180
ccaggcaagg ggctagagtg ggtggccact atatcatatg atggaagtca gaagtacttc     240
gcagactccg tgaagggccg atttaccatc ttcagagaca atcgagaa catggtgtat     300 ctgcaaatga gcggcctgag agttgaggac acggctgttt atcactgtgc gagagggagt     360
agtggtcatt atgaggcttt tgatatctgg ggccaaggga caatggtcac cgtctcttca     420
ggtggaggcg gttcaggcgg aggtggcagc ggcggtggcg ggagtcagtc tgtgttgacg     480 cagccgcccct cagtgtctgc ggccccagga cagaaggtca ccatctcctg ctctggaagc     540
agctccaaca ttgggaataa ttatgtatcc tggtaccagc agctcccagg aacagcccc     600 aaactcctca tttatgacaa taataagcga ccctcaggga ttcctgaccg attctctggc     660
tccaagtctg gcacgtcagc caccctgggc atcaccggac tccagactgg ggacgaggcc     720
gattattact gcgaacatg gatagcagc ctgagtgccc cttgggtgtt cggcggaggg     780
accaaggtca ccgtcctagg gggaggcggt tcagaagtgc agctggtgga atccggggg     840 ggcctggtgc agcctggggg gagcctgaga ctgagttgtg ccgcctctgg ggtgacattt     900
aactactatg gcatgtcttg gatccgccag gcacctggaa agggcctgga gtgggtggcc     960
agcatcacta ggtccggcgg gcgaatctac tatcccgaca cgtcaaggg caggttcaca    1020 atttcccgcg agaacacaca gaaaactctg tacctgcaga tgaatagcct gagagccgaa    1080
gatacagctg tgtactattg cactctggac ggcagggatg ggtgggtcgc ctattggggg    1140
```

```
cagggaaccc tggtgacagt cagctccgga ggaggaggat ctggcggagg aggcagtggg    1200
ggaggcgggt caaactttat gctcactcag ccgtcctctg tttctggcgt acctggccaa    1260
cgggtgacca ttagctgtac gggtaatacc gggaatatcg ggtctaacta cgtgaactgg    1320
tatcagcagc ttccagggac agctcccaag ttgctgatct atcgcgacga caaaagaccc    1380
tcaggggtcc ctgaccgatt tagtggcagc aaaagcggta cttccgcttc cctggcgata    1440
accggctttc aggccgaaga tgaggcagac tactattgcc agtcatattc cagcggcttc    1500
atcttcggag gcggaactaa gctgacagtg ttggcagccg agcccaaatc ttctgacaaa    1560
actcacacat gcccaccctg cccagcacct gaagccgcag ggggaccctc agtcttcctc    1620
ttccccccaa aacccaagga caccctcatg atctcccgga cccctgaggt cacatgcgtg    1680
gtggtgtcag tgagccacga agaccctgag gtcaagttca actggtacgt ggacggcgtg    1740
gaggtgcata atgccaagac aaagccccgg gaggagcagt acaacagcac gtaccgggtg    1800
gtcagcgtcc tcaccgtcct gcaccaggac tggctgaatg gcaaggagta caagtgcaag    1860
gtctccaaca aagccctccc agcccccatc gagaaaacca tctccaaagc caaaggccag    1920
ccccgggaac cacaggtgta cgtgtacccc ccatcccggg acgagctgac caagaaccag    1980
gtcagcctga cctgcctggt caaaggcttc tatcccagcg acatcgccgt ggagtgggag    2040
agcaatggcc agcccgagaa caactacaag accaccccctc ccgtgctgga ctccgacggc    2100
tccttcgccc tcgtgagcaa gctcaccgtg gacaagagca ggtggcagca gggcaacgtc    2160
ttctcatgct ccgtgatgca tgaggctctg cacaaccact acacccagaa gagcctctcc    2220
ctgtctcccg gcaag                                                      2235

<210> SEQ ID NO 75
<211> LENGTH: 2235
<212> TYPE: DNA
<213> ORGANISM: Artificial
<220> FEATURE:
<223> OTHER INFORMATION: Full-length nucleotide sequence of NYF-0023-HC2

<400> SEQUENCE: 75
atgaaacacc tgtggttctt cctcctgctg gtggcagctc ccagatgggt gctgagcgga      60
gaggtgcagc tggtggagtc tggggggaggc gtggtccagc ctgggaggtc cctgacaccc    120
tcctgttcag cgtctggatt ctccatccgt agttatgata cactgggt ccgccaggct      180 ccaggcaagg ggctagagtg ggtggccact atatcatatg atggaagtca gaagtacttc     240
gcagactccg tgaagggccg atttaccatc tccagacgg aatcggagaa catggtgtat      300
ctgcaaatga gcggcctgag agttgaggac acggctgttt atcactgtgc gagagggagt     360
agtggtcatt atgaggcttt tgatatctgg ggccaaggga caatggtcac cgtctcttca    420
ggtggaggcg gttcaggcgg aggtggcagc ggcggtggcg ggagtcagtc tgtgttgacg    480
cagccgccct cagtgtctgc ggccccagga cagaaggtca ccatctcctg ctctggaagc    540
agctccaaca ttgggaattg gtatgtatcc tggtaccagc agctcccagg aacagccccc    600
aaactcctca tttatgacaa taataagcga ccctcaggga ttcctgaccg attctctggc    660
tccaagtctg gcacgtcagc caccctgggc atcaccggac tccagactgg ggacgaggcc    720
gattattact gcggaacatg ggatagcagc ctgagtgccc ttgggtgttc ggcggaggg     780 accaaggtca ccgtcctagg ggaggcggt tcagaagtgc agctggtgga atccggggggg    840 ggcctggtgc agcctggggg gagcctgaga ctgagttgtg ccgcctctgg ggtgacattt    900
aactactatg gcatgtcttg gatccgccag gcaccctgga aagggcctgga gtgggtggcc     960
```

```
agcatcacta ggtccggcgg gcgaatctac tatcccgaca gcgtcaaggg caggttcaca    1020
atttcccgcg agaacacaca gaaaactctg tacctgcaga tgaatagcct gagagccgaa    1080
gatacagctg tgtactattg cactctggac ggcagggatg ggtgggtcgc ctattggggg    1140
cagggaaccc tggtgacagt cagctccgga ggaggaggat ctggcggagg aggcagtggg    1200
ggaggcgggt caaactttat gctcactcag ccgtcctctg tttctggcgt acctggccaa    1260
cgggtgacca ttagctgtac gggtaatacc gggaatatcg ggtctaacta cgtgaactgg    1320
tatcagcagc ttccagggac agctcccaag ttgctgatct atcgcgacga caaaagaccc    1380
tcaggggtcc ctgaccgatt tagtggcagc aaaagcggta cttccgcttc cctggcgata    1440
accggctttc aggccgaaga tgaggcagac tactattgcc agtcatattc cagcggcttc    1500
atcttcggag gcggaactaa gctgacagtg ttggcagccg agcccaaatc ttctgacaaa    1560
actcacacat gcccaccctg cccagcacct gaagccgcag gggacccctc agtcttcctc    1620
ttccccccaa aacccaagga caccctcatg atctcccgga cccctgaggt cacatgcgtg    1680
gtggtgtcag tgagccacga agaccctgag gtcaagttca actggtacgt ggacggcgtg    1740
gaggtgcata atgccaagac aaagcccggg aggagcagt acaacagcac gtaccgggtg     1800
gtcagcgtcc tcaccgtcct gcaccaggac tggctgaatg gcaaggagta caagtgcaag    1860
gtctccaaca aagccctccc agcccccatc gagaaaacca tctccaaagc caaaggccag    1920
ccccgggaac cacaggtgta cgtgtacccc ccatcccggg acgagctgac caagaaccag    1980
gtcagcctga cctgcctggt caaaggcttc tatcccagcg acatcgccgt ggagtgggag    2040
agcaatggcc agcccgagaa caactacaag accacccctc ccgtgctgga ctccgacggc    2100
tccttcgccc tcgtgagcaa gctcaccgtg gacaagagca ggtggcagca gggcaacgtc    2160
ttctcatgct ccgtgatgca tgaggctctg cacaaccact acacccagaa gagcctctcc    2220
ctgtctcccg gcaag                                                     2235
```

<210> SEQ ID NO 76
<211> LENGTH: 2235
<212> TYPE: DNA
<213> ORGANISM: Artificial
<220> FEATURE:
<223> OTHER INFORMATION: Full-length nucleotide sequence of NYF-0027-HC2

<400> SEQUENCE: 76

```
atgaaacacc tgtggttctt cctcctgctg gtggcagctc ccagatgggt gctgagcgga     60
gaggtgcagc tggtggagtc tgggggaggc gtggtccagc ctgggaggtc cctgacaccc    120
tcctgttcag cgtctggatt ctccatccgt agttatgata cactgggt ccgccaggct      180 ccaggcaagg ggctagagtg ggtggccact atatcatatg atggaagtca gaagtacttc    240
gcagactccg tgaagggccg atttaccatc tcagagacg aatcggagaa catggtgtat     300
ctgcaaatga gcgcctgag agttgaggac acggctgttt atcactgtgc gagagggagt    360
agtggtcatt atgaggcttt tgatatctgg ggccaaggga caatggtcac cgtctcttca    420
ggtggaggcg gttcaggcgg aggtggcagc ggcggtggcg ggagtcagtc tgtgttgacg    480
cagccgccct cagtgtctgc ggccccagga cagaaggtca ccatctcctg ctctggaagc    540
agctccaaca ttgggaataa ttatgtatcc tggtaccagc agctcccagg aacagccccc    600
aaactcctca tttatgacaa taataagcga ccctcaggga ttcctgaccg attctctggc    660
tccaagtctg gcacgtcagc caccctgggc atcaccggac tccagactgg ggacgaggcc    720
```

```
gattattact gcggatcatg ggatagcagc ctgagtgccc cttgggtgtt cggcggaggg    780
accaaggtca ccgtcctagg gggaggcggt tcagaagtgc agctggtgga atccgggggg    840
ggcctggtgc agcctggggg gagcctgaga ctgagttgtg ccgcctctgg ggtgacattt    900
aactactatg gcatgtcttg gatccgccag gcacctggaa agggcctgga gtgggtggcc    960
agcatcacta ggtccggcgg gcgaatctac tatcccgaca cgtcaaggg caggttcaca    1020 atttcccgcg agaacacaca gaaaactctg tacctgcaga tgaatagcct gagagccgaa    1080
gatacagctg tgtactattg cactctggac ggcagggatg ggtgggtcgc ctattggggg    1140
cagggaaccc tggtgacagt cagctccgga ggaggaggat ctggcggagg aggcagtggg    1200
ggaggcgggt caaactttat gctcactcag ccgtcctctg tttctggcgt acctggccaa    1260
cgggtgacca ttagctgtac gggtaatacc gggaatatcg ggtctaacta cgtgaactgg    1320
tatcagcagc ttccagggac agctcccaag ttgctgatct atcgcgacga caaaagaccc    1380
tcaggggtcc ctgaccgatt tagtggcagc aaaagcggta cttccgcttc cctggcgata    1440
accggctttc aggccgaaga tgaggcagac tactattgcc agtcatattc cagcggcttc    1500
atcttcggag gcggaactaa gctgacagtg ttggcagccg agcccaaatc ttctgacaaa    1560
actcacacat gcccacctg cccagcacct gaagccgcag gggaccctc agtcttcctc    1620 ttcccccaa acccaagga caccctcatg atctcccgga cccctgaggt cacatgcgtg    1680
gtggtgtcag tgagccacga agaccctgag gtcaagttca actggtacgt ggacggcgtg    1740
gaggtgcata atgccaagac aaagcccgg gaggagcagt acaacagcac gtaccgggtg    1800
gtcagcgtcc tcaccgtcct gcaccaggac tggctgaatg gcaaggagta caagtgcaag    1860
gtctccaaca aagccctccc agccccatc gagaaaacca tctccaaagc caaaggccag    1920
ccccgggaac cacaggtgta cgtgtacccc ccatcccggg acgagctgac caagaaccag    1980
gtcagcctga cctgcctggt caaaggcttc tatcccagcg acatcgccgt ggagtgggag    2040
agcaatgggc agcccgagaa caactacaag accacccctc ccgtgctgga ctccgacggc    2100
tccttcgccc tcgtgagcaa gctcaccgtg gacaagagca ggtggcagca gggcaacgtc    2160
ttctcatgct ccgtgatgca tgaggctctg cacaaccact acacccagaa gagcctctcc    2220
ctgtctcccg gcaag    2235

<210> SEQ ID NO 77
<211> LENGTH: 2235
<212> TYPE: DNA
<213> ORGANISM: Artificial
<220> FEATURE:
<223> OTHER INFORMATION: Full-length nucleotide sequence of NYF-0035-HC2

<400> SEQUENCE: 77
atgaaacacc tgtggttctt cctcctgctg gtggcagctc ccagatgggt gctgagcgga    60
gaggtgcagc tggtggagtc tgggggaggc gtggtccagc ctgggaggtc cctgacaccc    120
tcctgttcag cgtctggatt ctccatccgt agctatgata tacactgggt ccgcctggct    180
ccaggcaagg ggctagagtg ggtggccact atatcatatg atggaagtca gaagtacttc    240
gcagactccg tgaagggccg atttaccatc ttcagacg aatcgagaa catggtgtat    300 ctgcaaatga gcggcctgag agttgaggac acggctgttt atcactgtgc gagagggagt    360
agtggtcatt atgaggcttt tgatatctgg ggccaaggga caatggtcac cgtctcttca    420 ggtgaggcg ttcagcggg aggtggcagc ggcggtggcg ggagtcagtc tgtgttgacg    480
cagccgccct cagtgtctgc ggccccagga cagaaggtca ccatctcctg ctctggaagc    540
```

```
agctccaaca ttgggaattg aaggtatcc tggtaccagc agctcccagg aacagccccc      600
aaactcctca tttatgacaa taataagcga ccctcaggga ttcctgaccg attctctggc      660
tccaagtctg gcacgtcagc caccctgggc atcaccggac tccagactgg ggacgaggcc      720
gattattact gcggaacatg ggatagcagc ctgagtgccc cttgggtgtt cggcggaggg      780
accaaggtca ccgtcctagg gggaggcggt tcagaagtgc agctggtgga atccgggggg      840
ggcctggtgc agcctggggg gagcctgaga ctgagttgtg ccgcctctgg ggtgacattt      900
aactactatg gcatgtcttg gatccgccag gcacctggaa agggcctgga gtgggtggcc      960
agcatcacta ggtccggcgg gcgaatctac tatcccgaca cgtcaaggg caggttcaca     1020 atttcccgcg agaacacaca gaaaactctg tacctgcaga tgaatagcct gagagccgaa     1080
gatacagctg tgtactattg cactctggac ggcaggatg ggtgggtcgc ctattggggg     1140
cagggaaccc tggtgacagt cagctccgga ggaggaggat ctggcggagg aggcagtggg     1200
ggaggcgggt caaactttat gctcactcag ccgtcctctg tttctggcgt acctggccaa     1260
cgggtgacca ttagctgtac gggtaatacc gggaatatcg gtctaacta cgtgaactgg     1320 tatcagcagc ttccagggac agctcccaag ttgctgatct atcgcgacga caaaagaccc     1380
tcaggggtcc ctgaccgatt tagtggcagc aaaagcggta cttccgcttc cctggcgata     1440
accggctttc aggccgaaga tgaggcagac tactattgcc agtcatattc cagcggcttc     1500
atcttcggag gcggaactaa gctgacagtg ttggcagccg agcccaaatc ttctgacaaa     1560
actcacacat gcccaccctg cccagcacct gaagccgcag ggggaccctc agtcttcctc     1620
ttccccccaa acccaagga caccctcatg atctcccgga cccctgaggt cacatgcgtg     1680
gtggtgtcag tgagccacga agaccctgag gtcaagttca actggtacgt ggacggcgtg     1740
gaggtgcata atgccaagac aaagccccgg gaggagcagt acaacagcac gtaccgggtg     1800
gtcagcgtcc tcaccgtcct gcaccaggac tggctgaatg gcaaggagta caagtgcaag     1860
gtctccaaca aagcccctccc agcccccatc gagaaaacca tctccaaagc caaaggccag     1920
ccccgggaac cacaggtgta cgtgtacccc ccatcccggg acgagctgac caagaaccag     1980
gtcagcctga cctgcctggt caaaggcttc tatcccagcg acatcgccgt ggagtgggag     2040
agcaatggcc agcccgagaa caactacaag accaccccctc ccgtgctgga ctccgacggc     2100
tccttcgccc tcgtgagcaa gctcaccgtg gacaagagca ggtggcagca gggcaacgtc     2160
ttctcatgct ccgtgatgca tgaggctctg cacaaccact acacccagaa gagcctctcc     2220
ctgtctcccg gcaag                                                      2235

<210> SEQ ID NO 78
<211> LENGTH: 2235
<212> TYPE: DNA
<213> ORGANISM: Artificial
<220> FEATURE:
<223> OTHER INFORMATION: Full-length nucleotide sequence of NYF-0044-HC2

<400> SEQUENCE: 78
atgaaacacc tgtggttctt cctcctgctg gtggcagctc ccagatgggt gctgagcggt       60
gaggtacagc tggtggaatc cggtggaggc cttgtgcaac cggaggctc cctgcgactc      120 tcttgcgccg catctggctt ttccatacga tcctacgata ttcattgggt ccgactcgcc      180
cctggcaaag tcttgaatg ggttgccact atctcctacg acgggtctca gaaatattat      240
gcggattcag tgaaggggcg gttcacaatt tcacgagacg agtcaaagaa tacactgtac      300
```

```
ctccaaatga attcactgag agccgaggat actgcagtct atcattgtgc aagagggtcc      360
tcaggccact acgaggcctt tgatatatgg ggccaaggca ccttggtaac cgttagtagc      420
ggaggtggag gaagcggagg cggcggttcc ggaggaggtg gaagtcaatc cgttctgact      480
cagccaccct ccgtgagtgc agcgcctgga cagaaggtca caatatcatg ttctggctct      540
tcaagcaaca tcggaaactg gtacgtgagc tggtaccagc agctccccgg cacggcgccc      600
aagcttctga tatatgacaa caacaaacgc cccagtggaa tccctgacag attcagtggg      660
tctaaaagtg gtacaagcgc taccctgggt atcaccggat gcagaccgg agatgaggcg       720 gactattatt gcggaacctg ggactccagc ctgagcgctc cctgggtttt cggcggaggt      780
actaaggtta ccgtcttggg aggaggcggt tcagaagtgc agctggtgga atccgggggg      840
ggcctggtgc agcctggggg gagcctgaga ctgagttgtg ccgcctctgg ggtgacattt      900
aactactatg gcatgtcttg gatccgccag gcacctggaa agggcctgga gtgggtggcc      960
agcatcacta gtccggcgg gcgaatctac tatcccgaca gcgtcaaggg caggttcaca      1020
atttcccgcg agaacacaca gaaaactctg tacctgcaga tgaatagcct gagagccgaa      1080
gatacagctg tgtactattg cactctggac ggcagggatg ggtgggtcgc ctattggggg      1140
cagggaaccc tggtgacagt cagctccgga ggaggaggat ctggcggagg aggcagtggg      1200
ggaggcgggt caaactttat gctcactcag ccgtcctctg tttctggcgt acctggccaa      1260
cgggtgacca ttagctgtac gggtaatacc gggaatatcg gtctaacta cgtgaactgg       1320 tatcagcagc ttccagggac agctcccaag ttgctgatct atcgcgacga caaaagaccc      1380
tcaggggtcc ctgaccgatt tagtggcagc aaaagcggta cttccgcttc cctggcgata      1440
accggctttc aggccgaaga tgaggcagac tactattgcc agtcatattc cagcggcttc      1500
atcttcggag gcgaactaa gctgacagtg ttggcagccg agcccaaatc ttctgacaaa      1560
actcacacat gcccaccctg cccagcacct gaagccgcag ggggaccctc agtcttcctc      1620
ttccccccaa aacccaagga cacccctcatg atctcccgga cccctgaggt cacatgcgtg      1680
gtggtgtcag tgagccacga agaccctgag gtcaagttca actggtacgt ggacggcgtg      1740
gaggtgcata atgccaagac aaagccccgg gaggagcagt acaacagcac gtaccgggtg      1800
gtcagcgtcc tcaccgtcct gcaccaggac tggctgaatg gcaaggagta caagtgcaag      1860
gtctccaaca aagccctccc agcccccatc gagaaaacca tctccaaagc caaaggccag      1920
ccccgggaac cacaggtgta cgtgtacccc ccatcccggg acgagctgac caagaaccag      1980
gtcagcctga cctgcctggt caaaggcttc tatcccagcg acatcgccgt ggagtgggag      2040
agcaatggcc agcccgagaa caactacaag accaccccctc ccgtgctgga ctccgacggc      2100
tccttcgccc tcgtgagcaa gctcaccgtg gacaagagca ggtggcagca gggcaacgtc      2160
ttctcatgct ccgtgatgca tgaggctctg cacaaccact acacccagaa gagcctctcc      2220
ctgtctcccg gcaag                                                      2235
```

<210> SEQ ID NO 79
<211> LENGTH: 2235
<212> TYPE: DNA
<213> ORGANISM: Artificial
<220> FEATURE:
<223> OTHER INFORMATION: Full-length nucleotide sequence of NYF-0045-HC2

<400> SEQUENCE: 79

```
atgaaacacc tgtggttctt cctcctgctg gtggcagctc ccagatgggt gctgagcggt       60
gaggtacagc tggtggaatc cggtggaggc cttgtgcaac cgggaggctc cctgcgactc      120
```

```
tcttgcgccg catctggctt ttccatacga tcctacgata ttcattgggt ccgactcgcc      180
cctggcaaag gtcttgaatg ggttgccact atctcctacg acgggtctca gaaatattat      240
gcggattcag tgaaggggcg gttcacaatt tcacgagacg agtcaaagaa tacactgtac      300
ctccaaatga attcactgag agccgaggat actgcagtct atcattgtgc aagagggtcc      360
tcaggccact acgaggcctt tgatatatgg ggccaaggca ccttggtaac cgttagtagc      420
ggaggtggag gaagcggagg cggcggttcc ggaggaggtg gaagtcaatc cgttctgact      480
cagccaccct ccgcctctgg caccccgggc aacgggtca caatatcatg ttctggctct       540
tcaagcaaca tcgaaactg gtacgtgagc tggtaccagc agctccccgg cacggcgccc       600
aagcttctga tatatgacaa caacaaacgg cccagtggag ttcctgacag attcagtggg      660
tctaaaagtg gtacaagcgc tagcctggcc ataagtggtc tgcagagtga agatgaggcg      720
gactattatt gcggaaccctg ggactccagc ctgagcgctc cctgggtttt cggcggaggt     780
actaagctga ccgtcttggg aggaggcggt tcagaagtgc agctggtgga atccggggg       840
ggcctggtgc agcctggggg gagcctgaga ctgagttgtg ccgcctctgg ggtgacattt      900
aactactatg gcatgtcttg gatccgccag gcacctggaa agggcctgga gtgggtggcc     960
agcatcacta ggtccggcgg gcgaatctac tatcccgaca gcgtcaaggg caggttcaca     1020
atttcccgcg agaacacaca gaaaactctg tacctgcaga tgaatagcct gagagccgaa     1080
gatacagctg tgtactattg cactctggac ggcagggatg ggtgggtcgc ctattggggg     1140
cagggaaccc tggtgacagt cagctccgga ggaggaggat ctggcggagg aggcagtggg     1200
ggaggcgggt caaactttat gctcactcag ccgtcctctg tttctggcgt acctggccaa     1260
cgggtgacca ttagctgtac gggtaatacc gggaatatcg gtctaactta cgtgaactgg     1320
tatcagcagc ttccagggac agctcccaag ttgctgatct atcgcgacga caaaagaccc     1380
tcaggggtcc ctgaccgatt tagtggcagc aaaagcggta cttccgcttc cctggcgata     1440
accggctttc aggccgaaga tgaggcagac tactattgcc agtcatattc cagcggcttc     1500
atcttcggag gcggaactaa gctgacagtg ttggcagccg agcccaaatc ttctgacaaa     1560
actcacacat gcccaccctg cccagcacct gaagccgcag ggggaccctc agtcttcctc     1620
ttccccccaa aacccaagga caccctcatg atctcccgga cccctgaggt cacatgcgtg     1680
gtggtgtcag tgagccacga agaccctgag gtcaagttca actggtacgt ggacggcgtg     1740
gaggtgcata atgccaagac aaagccccgg gaggagcagt acaacagcac gtaccgggtg     1800
gtcagcgtcc tcaccgtcct gcaccaggac tggctgaatg gcaaggagta caagtgcaag     1860
gtctccaaca aagccctccc agcccccatc gagaaaacca tctccaaagc caaaggccag     1920
ccccgggaac acaggtgta cgtgtacccc ccatcccggg acgagctgac caagaaccag     1980
gtcagcctga cctgcctggt caaaggcttc tatcccagcg acatcgccgt ggagtgggag     2040
agcaatgggc agcccgagaa caactacaag accacccctc ccgtgctgga ctccgacggc     2100
tccttcgccc tcgtgagcaa gctcaccgtg gacaagagca ggtggcagca gggcaacgtc     2160
ttctcatgct ccgtgatgca tgaggctctg cacaaccact acacccagaa gagcctctcc     2220
ctgtctcccg gcaag                                                       2235
```

<210> SEQ ID NO 80
<211> LENGTH: 2235
<212> TYPE: DNA
<213> ORGANISM: Artificial
<220> FEATURE:

<223> OTHER INFORMATION: Full-length nucleotide sequence of NYF-0047-HC2

<400> SEQUENCE: 80

| | | | | | |
|---|---|---|---|---|---|
| atgaaacacc | tgtggttctt | cctcctgctg | gtggcagctc | ccagatgggt | gctgagcggt | 60 |
| caagtacagc | tggtggaatc | cggtggaggc | gtggtccagc | cgggacgcag | cttgagactg | 120 |
| tcctgcgctg | catctggctt | ttccatacga | tcctacgata | tgcactgggt | tcgccaagcc | 180 |
| cctggcaaag | tcttgaatg | ggttgccact | atctcctacg | acgggtctca | gaaatattac | 240 |
| gcggattcag | tgaaggggcg | gttcacaatt | tcacgggaca | attcaaagaa | taccttgtat | 300 |
| ctccagatgt | cttcactgag | agccgaggat | actgcagtct | atcattgtgc | aagagggtcc | 360 |
| tcaggccact | acgaggcctt | tgatatatgg | ggccaaggca | ccttggtaac | cgttagtagc | 420 |
| ggaggtggag | gaagcggagg | cggcggttcc | ggaggaggtg | gaagtcaatc | cgttctgact | 480 |
| cagccaccct | ccgtgagtgc | agcgcctgga | cagaaggtca | caatatcatg | ttctggctct | 540 |
| tcaagcaaca | tcggaaactg | gtacgtgagc | tggtaccagc | agctcccgg | cacggcgccc | 600 |
| aagcttctga | tatatgacaa | caacaaacg | cccagtggaa | tccctgacag | attcagtggg | 660 |
| tctaaaagtg | gtacaagcgc | taccctgggt | atcaccggat | tgcagaccgg | agatgaggcg | 720 |
| gactattatt | gcggaacctg | ggactccagc | ctgagcgctc | cctgggtttt | cggcggaggt | 780 |
| actaaggtta | ccgtcttggg | aggaggcggt | tcagaagtgc | agctggtgga | atccggggg | 840 |
| ggcctggtgc | agcctggggg | gagcctgaga | ctgagttgtg | ccgcctctgg | ggtgacattt | 900 |
| aactactatg | gcatgtcttg | gatccgccag | gcacctggaa | agggcctgga | gtgggtggcc | 960 |
| agcatcacta | ggtccggcgg | gcgaatctac | tatcccgaca | gcgtcaaggg | caggttcaca | 1020 |
| atttcccgcg | agaacacaca | gaaaactctg | tacctgcaga | tgaatagcct | gagagccgaa | 1080 |
| gatacagctg | tgtactattg | cactctggac | ggcagggatg | ggtgggtcgc | ctattgggg | 1140 |
| cagggaaccc | tggtgacagt | cagctccgga | ggaggaggat | ctggcggagg | aggcagtggg | 1200 |
| ggaggcgggt | caaactttat | gctcactcag | ccgtcctctg | tttctggcgt | acctggccaa | 1260 |
| cgggtgacca | ttagctgtac | gggtaatacc | gggaatatcg | ggtctaacta | cgtgaactgg | 1320 |
| tatcagcagc | ttccagggac | agctcccaag | ttgctgatct | atcgcgacga | caaaagaccc | 1380 |
| tcaggggtcc | ctgaccgatt | tagtggcagc | aaaagcggta | cttccgcttc | cctggcgata | 1440 |
| accggctttc | aggccgaaga | tgaggcagac | tactattgcc | agtcatattc | cagcggcttc | 1500 |
| atcttcggag | gcggaactaa | gctgacagtg | ttggcagccg | agcccaaatc | ttctgacaaa | 1560 |
| actcacacat | gcccaccctg | cccagcacct | gaagccgcag | ggggaccctc | agtcttcctc | 1620 |
| ttccccccaa | aacccaagga | caccctcatg | atctcccgga | cccctgaggt | cacatgcgtg | 1680 |
| gtggtgtcag | tgagccacga | agaccctgag | gtcaagttca | actggtacgt | ggacggcgtg | 1740 |
| gaggtgcata | atgccaagac | aaagccccgg | gaggagcagt | acaacagcac | gtaccgggtg | 1800 |
| gtcagcgtcc | tcaccgtcct | gcaccaggac | tggctgaatg | gcaaggagta | caagtgcaag | 1860 |
| gtctccaaca | aagccctccc | agcccccatc | gagaaaacca | tctccaaagc | caaaggccag | 1920 |
| ccccgggaac | cacaggtgta | cgtgtacccc | ccatcccggg | acgagctgac | caagaaccag | 1980 |
| gtcagcctga | cctgcctggt | caaaggcttc | tatcccagcg | acatcgccgt | ggagtgggag | 2040 |
| agcaatggcc | agcccgagaa | caactacaag | accaccccctc | ccgtgctgga | ctccgacggc | 2100 |
| tccttcgccc | tcgtgagcaa | gctcaccgtg | gacaagagca | ggtggcagca | gggcaacgtc | 2160 |
| ttctcatgct | ccgtgatgca | tgaggctctg | cacaaccact | acacccagaa | gagcctctcc | 2220 |
| ctgtctcccg | gcaag | | | | | 2235 |

<210> SEQ ID NO 81
<211> LENGTH: 2235
<212> TYPE: DNA
<213> ORGANISM: Artificial
<220> FEATURE:
<223> OTHER INFORMATION: Full-length nucleotide sequence of NYF-0048-HC2

<400> SEQUENCE: 81

| | | | | | |
|---|---|---|---|---|---|
| atgaaacacc | tgtggttctt | cctcctgctg | gtggcagctc | ccagatgggt | gctgagcgga | 60 |
| caagttcaac | tcgtggaatc | tggtggaggg | gtggtacaac | caggccggtc | acttagactg | 120 |
| tcctgcgctg | cgagtggatt | ttccatcaga | tcttacgaca | tgcactgggt | tcgccaagca | 180 |
| cccggaaagg | gtttggaatg | ggtggctacg | atctcctacg | atggatccca | gaagtattac | 240 |
| gccgacagcg | tcaagggccg | atttacaata | tcacgggaca | attcaaagaa | taccttgtat | 300 |
| ctccagatgt | cttcactgag | agccgaggat | actgcagtct | atcattgtgc | aagagggtcc | 360 |
| tcaggccact | acgaggcctt | tgatatatgg | ggccaaggca | ccttggtaac | cgttagtagc | 420 |
| ggaggtggag | gaagcggagg | cggcggttcc | ggaggaggtg | gaagtcaatc | cgttctgact | 480 |
| cagccaccct | ccgcctctgg | caccccgggc | caacgggtca | caatatcatg | ttctggctct | 540 |
| tcaagcaaca | tcggaaactg | gtacgtgagc | tggtaccagc | agctccccgg | cacggcgccc | 600 |
| aagcttctga | tatatgacaa | caacaaacgc | cccagtggag | ttcctgacag | attcagtggg | 660 |
| tctaaaagtg | gtacaagcgc | tagcctggcc | ataagtggtc | tgcagagtga | agatgaggcg | 720 |
| gactattatt | gcggaacctg | ggactccagc | ctgagcgctc | cctgggtttt | cggcggaggt | 780 |
| actaagctga | ccgtcttggg | aggaggcggt | tcagaagtgc | agctggtgga | atccgggggg | 840 |
| ggcctggtgc | agcctggggg | gagcctgaga | ctgagttgtg | ccgcctctgg | ggtgacattt | 900 |
| aactactatg | gcatgtcttg | gatccgccag | gcacctggaa | agggcctgga | gtgggtggcc | 960 |
| agcatcacta | ggtccggcgg | gcgaatctac | tatcccgaca | gcgtcaaggg | caggttcaca | 1020 |
| atttcccgcg | agaacacaca | gaaaactctg | tacctgcaga | tgaatagcct | gagagccgaa | 1080 |
| gatacagctg | tgtactattg | cactctggac | ggcagggatg | ggtgggtcgc | ctattggggg | 1140 |
| cagggaaccc | tggtgacagt | cagctccgga | ggaggaggat | ctggcggagg | aggcagtggg | 1200 |
| ggaggcgggt | caaactttat | gctcactcag | ccgtcctctg | tttctggcgt | acctggccaa | 1260 |
| cgggtgacca | ttagctgtac | gggtaatacc | gggaatatcg | gtctaactac | cgtgaactgg | 1320 |
| tatcagcagc | ttccagggac | agctcccaag | ttgctgatct | atcgcgacga | caaaagaccc | 1380 |
| tcaggggtcc | ctgaccgatt | tagtggcagc | aaaagcggta | cttccgcttc | cctggcgata | 1440 |
| accggctttc | aggccgaaga | tgaggcagac | tactattgcc | agtcatattc | cagcggcttc | 1500 |
| atcttcggag | gcggaactaa | gctgacagtg | ttggcagccg | agcccaaatc | ttctgacaaa | 1560 |
| actcacacat | gcccaccctg | cccagcacct | gaagccgcag | gggaccctc | agtcttcctc | 1620 |
| ttccccccaa | aacccaagga | caccctcatg | atctcccgga | cccctgaggt | cacatgcgtg | 1680 |
| gtggtgtcag | tgagccacga | agaccctgag | gtcaagttca | actggtacgt | ggacggcgtg | 1740 |
| gaggtgcata | atgccaagac | aaagccccgg | gaggagcagt | acaacagcac | gtaccgggtg | 1800 |
| gtcagcgtcc | tcaccgtcct | gcaccaggac | tggctgaatg | gcaaggagta | caagtgcaag | 1860 |
| gtctccaaca | aagccctccc | agcccccatc | gagaaaacca | tctccaaagc | caaaggccag | 1920 |
| ccccgggaac | cacaggtgta | cgtgtacccc | ccatcccggg | acgagctgac | caagaaccag | 1980 |
| gtcagcctga | cctgcctggt | caaaggcttc | tatcccagcg | acatcgccgt | ggagtgggag | 2040 |

| | |
|---|---:|
| agcaatggcc agcccgagaa caactacaag accacccctc ccgtgctgga ctccgacggc | 2100 |
| tccttcgccc tcgtgagcaa gctcaccgtg gacaagagca ggtggcagca gggcaacgtc | 2160 |
| ttctcatgct ccgtgatgca tgaggctctg cacaaccact acacccagaa gagcctctcc | 2220 |
| ctgtctcccg gcaag | 2235 |

<210> SEQ ID NO 82
<211> LENGTH: 2235
<212> TYPE: DNA
<213> ORGANISM: Artificial
<220> FEATURE:
<223> OTHER INFORMATION: Full-length nucleotide sequence of NYF-0060-HC2

<400> SEQUENCE: 82

| | |
|---|---:|
| atgaaacacc tgtggttctt cctcctgctg gtggcagctc ccagatgggt gctgagcggt | 60 |
| gaggtacagc tggtggaatc cggtggaggc cttgtgcaac cgggaggctc cctgcgactc | 120 |
| tcttgcgccg catctggctt ttccatacga tcctacgata ttcattgggt ccgacaagcc | 180 |
| cctggcaaag gtcttgaatg ggttgccact atctcctacg acgggtctca gaaatattat | 240 |
| gcggattcag tgaaggggcg gttcacaatt tcacgagacg agtcaaagaa tacactgtac | 300 |
| ctccaaatga attcactgag agccgaggat actgcagtct atcattgtgc aagagggtcc | 360 |
| tcaggccact acgaggcctt tgatatatgg ggccaaggca ccttggtaac cgttagtagc | 420 |
| ggaggtggag gaagcggagg cggcggttcc ggaggaggtg gaagtcaatc cgttctgact | 480 |
| cagccaccct ccgtgagtgc agcgcctgga cagaaggtca caatatcatg ttctggctct | 540 |
| tcaagcaaca tcgaaactg gtacgtgagc tggtaccagc agctccccgg cacggcgccc | 600 |
| aagcttctga tatatgacaa caacaaacgg cccagtggaa tccctgacag attcagtggg | 660 |
| tctaaaagtg gtacaagcgc tacccctggg atcaccggat gcagaccggg agatgaggcg | 720 |
| gactattatt gcggaaacctg ggactccagc ctgagcgctc cctgggtttt cggcggaggt | 780 |
| actaaggtta ccgtcttggg aggaggcggt tcagaagtgc agctggtgga atccgggggg | 840 |
| ggcctggtgc agcctggggg gagcctgaga ctgagttgtg ccgcctctgg ggtgacattt | 900 |
| aactactatg gcatgtcttg gatccgccag gcacctggaa agggcctgga gtgggtggcc | 960 |
| agcatcacta ggtccggcgg gcgaatctac tatcccgaca gcgtcaaggg caggttcaca | 1020 |
| atttcccgcg agaacacaca gaaaactctg tacctgcaga tgaatagcct gagagccgaa | 1080 |
| gatacagctg tgtactattg cactctggac ggcagggatg ggtgggtcgc ctattgggg | 1140 |
| cagggaaccc tggtgacagt cagctccgga ggaggaggat ctggcggagg aggcagtggg | 1200 |
| ggaggcgggt caaactttat gctcactcag ccgtcctctg tttctggcgt acctggccaa | 1260 |
| cgggtgacca ttagctgtac gggtaatacc gggaatatcg gtctaactac cgtgaactgg | 1320 |
| tatcagcagc ttccagggac agctcccaag ttgctgatct atcgcgacga caaaagaccc | 1380 |
| tcaggggtcc ctgaccgatt tagtggcagc aaaagcggta cttccgcttc cctggcgata | 1440 |
| accggcttc aggccgaaga tgaggcagac tactattgcc agtcatattc cagcggcttc | 1500 |
| atcttcggag gcggaactaa gctgacagtg ttggcagccg agcccaaatc ttctgacaaa | 1560 |
| actcacacat gcccacctg cccagcacct gaagccgcag gggaccctc agtcttcctc | 1620 |
| ttccccccaa aacccaagga caccctcatg atctcccgga cccctgaggt cacatgcgtg | 1680 |
| gtggtgtcag tgagccacga agaccctgag gtcaagttca actggtacgt ggacggcgtg | 1740 |
| gaggtgcata atgccaagac aaagcccgg gaggagcagt acaacagcac gtaccgggtg | 1800 |
| gtcagcgtcc tcaccgtcct gcaccaggac tggctgaatg gcaaggagta caagtgcaag | 1860 |

```
gtctccaaca aagccctccc agccccatc gagaaaacca tctccaaagc caaaggccag   1920 cccgggaac cacaggtgta cgtgtacccc ccatcccggg acgagctgac caagaaccag   1980
gtcagcctga cctgcctggt caaaggcttc tatcccagcg acatcgccgt ggagtgggag   2040
agcaatggcc agcccgagaa caactacaag accacccctc ccgtgctgga ctccgacggc   2100
tccttcgccc tcgtgagcaa gctcaccgtg gacaagagca ggtggcagca gggcaacgtc   2160
ttctcatgct ccgtgatgca tgaggctctg cacaaccact acacccagaa gagcctctcc   2220
ctgtctcccg gcaag                                                   2235
```

<210> SEQ ID NO 83
<211> LENGTH: 2235
<212> TYPE: DNA
<213> ORGANISM: Artificial
<220> FEATURE:
<223> OTHER INFORMATION: Full-length nucleotide sequence of NYF-0061-HC2

<400> SEQUENCE: 83

```
atgaaacacc tgtggttctt cctcctgctg gtggcagctc ccagatgggt gctgagcggt     60
gaggtacagc tggtggaatc cggtggaggc cttgtgcaac cgggaggctc cctgcgactc    120
tcttgcgccg catctggctt ttccatacga tcctacgata ttcattgggt ccgacaagcc    180
cctggcaaag gtcttgaatg ggttgccact atctcctacg acgggtctca gaaatattat    240
gcggattcag tgaaggggcg gttcacaatt tcacgagacg agtcaaagaa tacactgtac    300
ctccaaatga attcactgag agccgaggat actgcagtct atcattgtgc aagagggtcc    360
tcaggccact acgaggcctt tgatatatgg ggccaaggca ccttggtaac cgttagtagc    420
ggaggtggag gaagcggagg cggcggttcc ggaggaggtg aagtcaatc cgttctgact    480 cagccaccct ccgcctctgg caccccgggc aacgggtca aatatcatg ttctggctct    540 tcaagcaaca tcggaaactg gtacgtgagc tggtaccagc agctccccgg cacggcgccc    600
aagcttctga tatatgacaa caacaaacgg cccagtggag ttcctgacag attcagtggg    660
tctaaaagtg gtacaagcgc tagcctggcc ataagtggtc tgcagagtga agatgaggcg    720
gactattatt gcggaacctg ggactccagc ctgagcgctc cctgggtttt cggcggaggt    780
actaagctga ccgtcttggg aggaggcggt tcagaagtgc agctggtgga atccggggggg   840 ggcctggtgc agcctggggg gagcctgaga ctgagttgtg ccgcctctgg ggtgacattt   900
aactactatg gcatgtcttg gatccgccag gcacctggaa agggcctgga gtgggtggcc   960
agcatcacta ggtccggcgg gcgaatctac tatcccgaca cgtcaaggg caggttcaca  1020 atttccgcg agaacacaca gaaaactctg tacctgcaga tgaatagcct gagagccgaa  1080
gatacagctg tgtactattg cactctggac ggcaggatg ggtgggtcgc ctattggggg   1140
cagggaaccc tggtgacagt cagctccgga ggaggaggat ctggcggagg aggcagtggg   1200
ggaggcgggt caaactttat gctcactcag ccgtcctctg tttctggcgt acctggccaa  1260
cgggtgacca ttagctgtac gggtaatacc gggaatatcg gtctaacta cgtgaactgg  1320 tatcagcagc ttccagggac agctcccaag ttgctgatct atcgcgacga caaaagaccc  1380
tcaggggtcc ctgaccgatt tagtggcagc aaaagcggta cttccgcttc cctggcgata  1440
accggctttc aggccgaaga tgaggcagac tactattgcc agtcatattc cagcggcttc  1500
atcttcggag gcgaactaa gctgacagtg ttggcagccg agcccaaatc ttctgacaaa  1560
actcacacat gcccaccctg cccagcacct gaagccgcag ggggaccctc agtcttcctc  1620
```

-continued

```
ttcccccccaa aacccaagga caccctcatg atctcccgga ccccctgaggt cacatgcgtg    1680 gtggtgtcag tgagccacga agaccctgag gtcaagttca actggtacgt ggacggcgtg    1740
gaggtgcata atgccaagac aaagccccgg gaggagcagt acaacagcac gtaccgggtg    1800
gtcagcgtcc tcaccgtcct gcaccaggac tggctgaatg gcaaggagta caagtgcaag    1860
gtctccaaca aagccctccc agcccccatc gagaaaacca tctccaaagc caaaggccag    1920
ccccgggaac cacaggtgta cgtgtacccc ccatcccggg acgagctgac caagaaccag    1980
gtcagcctga cctgcctggt caaaggcttc tatcccagcg acatcgccgt ggagtgggag    2040
agcaatggcc agcccgagaa caactacaag accacccctc ccgtgctgga ctccgacggc    2100
tccttcgccc tcgtgagcaa gctcaccgtg gacaagagca ggtggcagca gggcaacgtc    2160
ttctcatgct ccgtgatgca tgaggctctg cacaaccact acacccagaa gagcctctcc    2220
ctgtctcccg gcaag                                                     2235
```

<210> SEQ ID NO 84
<211> LENGTH: 246
<212> TYPE: PRT
<213> ORGANISM: Artificial
<220> FEATURE:
<223> OTHER INFORMATION: Full-length amino acid sequence of HC1

<400> SEQUENCE: 84

```
Met Lys His Leu Trp Phe Phe Leu Leu Leu Val Ala Ala Pro Arg Trp
 1               5                  10                  15

Val Leu Ser Asp Lys Thr His Thr Cys Pro Pro Cys Pro Ala Pro Glu
            20                  25                  30

Ala Ala Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Ser
    50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Tyr Val Leu Pro Pro Ser Arg Asp Glu Leu Thr Lys Asn
145                 150                 155                 160

Gln Val Ser Leu Leu Cys Leu Val Lys Gly Phe Tyr Pro Ser Asp Ile
                165                 170                 175

Ala Val Glu Trp Glu Ser Asn Gly Gln Pro Glu Asn Asn Tyr Leu Thr
            180                 185                 190

Trp Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245
```

<210> SEQ ID NO 85
<211> LENGTH: 745
<212> TYPE: PRT
<213> ORGANISM: Artificial
<220> FEATURE:
<223> OTHER INFORMATION: Full-length amino acid sequence of NYF-0016-HC

<400> SEQUENCE: 85

Met Lys His Leu Trp Phe Phe Leu Leu Val Ala Ala Pro Arg Trp
1               5                   10                  15

Val Leu Ser Gly Glu Val Gln Leu Val Glu Ser Gly Gly Val Val
                20                  25                  30

Gln Pro Gly Arg Ser Leu Thr Pro Ser Cys Ser Ala Ser Gly Phe Ser
            35                  40                  45

Ile Arg Ser Tyr Asp Ile His Trp Val Arg Leu Ala Pro Gly Lys Gly
        50                  55                  60

Leu Glu Trp Val Ala Thr Ile Ser Tyr Asp Gly Ser Gln Lys Tyr Phe
65                  70                  75                  80

Ala Asp Ser Val Lys Gly Arg Phe Thr Ile Phe Arg Asp Glu Ser Glu
                85                  90                  95

Asn Met Val Tyr Leu Gln Met Ser Gly Leu Arg Val Glu Asp Thr Ala
            100                 105                 110

Val Tyr His Cys Ala Arg Gly Ser Ser His Tyr Glu Ala Phe Asp
        115                 120                 125

Ile Trp Gly Gln Gly Thr Met Val Thr Val Ser Ser Gly Gly Gly Gly
130                 135                 140

Ser Gly Gly Gly Gly Ser Gly Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Trp Tyr Val Ser Trp Tyr
            180                 185                 190

Gln Gln Leu Pro Gly Thr Ala Pro Lys Leu Leu Ile Tyr Asp Asn Asn
        195                 200                 205

Lys Arg Pro Ser Gly Ile Pro Asp Arg Phe Ser Gly Ser Lys Ser Gly
    210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Val Thr Val Leu Gly Gly Gly Gly Ser Glu
            260                 265                 270

Val Gln Leu Val Glu Ser Gly Gly Gly Leu Val Gln Pro Gly Gly Ser
        275                 280                 285

Leu Arg Leu Ser Cys Ala Ala Ser Gly Val Thr Phe Asn Tyr Tyr Gly
    290                 295                 300

Met Ser Trp Ile Arg Gln Ala Pro Gly Lys Gly Leu Glu Trp Val Ala
305                 310                 315                 320

Ser Ile Thr Arg Ser Gly Gly Arg Ile Tyr Tyr Pro Asp Ser Val Lys
                325                 330                 335

Gly Arg Phe Thr Ile Ser Arg Glu Asn Thr Gln Lys Thr Leu Tyr Leu
            340                 345                 350

Gln Met Asn Ser Leu Arg Ala Glu Asp Thr Ala Val Tyr Tyr Cys Thr
        355                 360                 365

Leu Asp Gly Arg Asp Gly Trp Val Ala Tyr Trp Gln Gly Thr Leu
    370                 375                 380

Val Thr Val Ser Ser Gly Gly Gly Ser Gly Gly Gly Ser Gly
385                 390                 395                 400

Gly Gly Gly Ser Asn Phe Met Leu Thr Gln Pro Ser Ser Val Ser Gly
                405                 410                 415

Val Pro Gly Gln Arg Val Thr Ile Ser Cys Thr Gly Asn Thr Gly Asn
            420                 425                 430

Ile Gly Ser Asn Tyr Val Asn Trp Tyr Gln Gln Leu Pro Gly Thr Ala
        435                 440                 445

Pro Lys Leu Leu Ile Tyr Arg Asp Asp Lys Arg Pro Ser Gly Val Pro
    450                 455                 460

Asp Arg Phe Ser Gly Ser Lys Ser Gly Thr Ser Ala Ser Leu Ala Ile
465                 470                 475                 480

Thr Gly Phe Gln Ala Glu Asp Glu Ala Asp Tyr Tyr Cys Gln Ser Tyr
                485                 490                 495

Ser Ser Gly Phe Ile Phe Gly Gly Gly Thr Lys Leu Thr Val Leu Ala
            500                 505                 510

Ala Glu Pro Lys Ser Ser Asp Lys Thr His Thr Cys Pro Pro Cys Pro
        515                 520                 525

Ala Pro Glu Ala Ala Gly Gly Pro Ser Val Phe Leu Phe Pro Pro Lys
    530                 535                 540

Pro Lys Asp Thr Leu Met Ile Ser Arg Thr Pro Glu Val Thr Cys Val
545                 550                 555                 560

Val Val Ser Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
    610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Val Tyr Pro Pro Ser Arg Asp Glu Leu
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Ala Leu
    690                 695                 700

Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 86
<211> LENGTH: 745
<212> TYPE: PRT
<213> ORGANISM: Artificial
<220> FEATURE:

<223> OTHER INFORMATION: Full-length amino acid sequence of NYF-0019-HC2

<400> SEQUENCE: 86

```
Met Lys His Leu Trp Phe Phe Leu Leu Val Ala Ala Pro Arg Trp
1               5                   10                  15

Val Leu Ser Gly Glu Val Gln Leu Val Glu Ser Gly Gly Gly Val
            20                  25                  30

Gln Pro Gly Arg Ser Leu Thr Pro Ser Cys Ser Ala Ser Gly Phe Ser
        35                  40                  45

Ile Arg Ser Tyr Asp Ile His Trp Val Arg Leu Ala Pro Gly Lys Gly
    50                  55                  60

Leu Glu Trp Val Ala Thr Ile Ser Tyr Asp Gly Ser Gln Lys Tyr Phe
65                  70                  75                  80

Ala Asp Ser Val Lys Gly Arg Phe Thr Ile Phe Arg Asp Glu Ser Glu
                85                  90                  95

Asn Met Val Tyr Leu Gln Met Ser Gly Leu Arg Val Glu Asp Thr Ala
            100                 105                 110

Val Tyr His Cys Ala Arg Gly Ser Ser Gly His Tyr Glu Ala Phe Asp
        115                 120                 125

Ile Trp Gly Gln Gly Thr Met Val Thr Val Ser Ser Gly Gly Gly
    130                 135                 140

Ser Gly Gly Gly Ser Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Asn Ile Gly Asn Trp Tyr Val Ser Trp Tyr
            180                 185                 190

Gln Arg Leu Pro Gly Thr Ala Pro Lys Leu Leu Ile Tyr Asp Asn Asn
        195                 200                 205

Lys Arg Pro Ser Gly Ile Pro Asp Arg Phe Ser Gly Ser Lys Ser Gly
    210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Val Thr Val Leu Gly Gly Gly Ser Glu
            260                 265                 270

Val Gln Leu Val Glu Ser Gly Gly Gly Leu Val Gln Pro Gly Gly Ser
        275                 280                 285

Leu Arg Leu Ser Cys Ala Ala Ser Gly Val Thr Phe Asn Tyr Tyr Gly
    290                 295                 300

Met Ser Trp Ile Arg Gln Ala Pro Gly Lys Gly Leu Glu Trp Val Ala
305                 310                 315                 320

Ser Ile Thr Arg Ser Gly Gly Arg Ile Tyr Tyr Pro Asp Ser Val Lys
                325                 330                 335

Gly Arg Phe Thr Ile Ser Arg Glu Asn Thr Gln Lys Thr Leu Tyr Leu
            340                 345                 350

Gln Met Asn Ser Leu Arg Ala Glu Asp Thr Ala Val Tyr Tyr Cys Thr
        355                 360                 365

Leu Asp Gly Arg Asp Gly Trp Val Ala Tyr Trp Gly Gln Gly Thr Leu
    370                 375                 380

Val Thr Val Ser Ser Gly Gly Gly Gly Ser Gly Gly Gly Gly Ser Gly
385                 390                 395                 400
```

```
Gly Gly Gly Ser Asn Phe Met Leu Thr Gln Pro Ser Val Ser Gly
            405                 410                 415

Val Pro Gly Gln Arg Val Thr Ile Ser Cys Thr Gly Asn Thr Gly Asn
        420                 425                 430

Ile Gly Ser Asn Tyr Val Asn Trp Tyr Gln Gln Leu Pro Gly Thr Ala
        435                 440                 445

Pro Lys Leu Leu Ile Tyr Arg Asp Asp Lys Arg Pro Ser Gly Val Pro
    450                 455                 460

Asp Arg Phe Ser Gly Ser Lys Ser Gly Thr Ser Ala Ser Leu Ala Ile
465                 470                 475                 480

Thr Gly Phe Gln Ala Glu Asp Glu Ala Asp Tyr Tyr Cys Gln Ser Tyr
            485                 490                 495

Ser Ser Gly Phe Ile Phe Gly Gly Thr Lys Leu Thr Val Leu Ala
            500                 505                 510

Ala Glu Pro Lys Ser Ser Asp Lys Thr His Thr Cys Pro Pro Cys Pro
            515                 520                 525

Ala Pro Glu Ala Ala Gly Gly Pro Ser Val Phe Leu Phe Pro Pro Lys
    530                 535                 540

Pro Lys Asp Thr Leu Met Ile Ser Arg Thr Pro Glu Val Thr Cys Val
545                 550                 555                 560

Val Val Ser Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
            595                 600                 605

Gln Asp Trp Leu Asn Gly Lys Glu Tyr Lys Cys Lys Val Ser Asn Lys
    610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Val Tyr Pro Pro Ser Arg Asp Glu Leu
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
            675                 680                 685

Tyr Lys Thr Thr Pro Pro Val Leu Asp Ser Asp Gly Ser Phe Ala Leu
    690                 695                 700

Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 87
<211> LENGTH: 745
<212> TYPE: PRT
<213> ORGANISM: Artificial
<220> FEATURE:
<223> OTHER INFORMATION: Full-length amino acid sequence of NYF-0022-HC2

<400> SEQUENCE: 87

Met Lys His Leu Trp Phe Phe Leu Leu Leu Val Ala Ala Pro Arg Trp
1               5                   10                  15
```

```
Val Leu Ser Gly Glu Val Gln Leu Val Glu Ser Gly Gly Val Val
             20                  25                  30

Gln Pro Gly Arg Ser Leu Thr Pro Ser Cys Ser Ala Ser Gly Phe Ser
         35                  40                  45

Ile Arg Ser Tyr Asp Ile His Trp Val Arg Leu Ala Pro Gly Lys Gly
     50                  55                  60

Leu Glu Trp Val Ala Thr Ile Ser Tyr Asp Gly Ser Gln Lys Tyr Phe
65                  70                  75                  80

Ala Asp Ser Val Lys Gly Arg Phe Thr Ile Phe Arg Asp Glu Ser Glu
                 85                  90                  95

Asn Met Val Tyr Leu Gln Met Ser Gly Leu Arg Val Glu Asp Thr Ala
             100                 105                 110

Val Tyr His Cys Ala Arg Gly Ser Ser Gly His Tyr Glu Ala Phe Asp
         115                 120                 125

Ile Trp Gly Gln Gly Thr Met Val Thr Val Ser Ser Gly Gly Gly Gly
     130                 135                 140

Ser Gly Gly Gly Gly Ser Gly Gly Gly Gly Ser Gln Ser Val Leu Thr
145                 150                 155                 160

Gln Pro Pro Ser Val Ser Ala Ala Pro Gly Gln Lys Val Thr Ile Ser
                 165                 170                 175

Cys Ser Gly Ser Ser Ser Asn Ile Gly Asn Asn Tyr Val Ser Trp Tyr
             180                 185                 190

Gln Gln Leu Pro Gly Thr Ala Pro Lys Leu Leu Ile Tyr Asp Asn Asn
         195                 200                 205

Lys Arg Pro Ser Gly Ile Pro Asp Arg Phe Ser Gly Ser Lys Ser Gly
     210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
                 245                 250                 255

Phe Gly Gly Gly Thr Lys Val Thr Val Leu Gly Gly Gly Gly Ser Glu
             260                 265                 270

Val Gln Leu Val Glu Ser Gly Gly Leu Val Gln Pro Gly Gly Ser
         275                 280                 285

Leu Arg Leu Ser Cys Ala Ala Ser Gly Val Thr Phe Asn Tyr Tyr Gly
     290                 295                 300

Met Ser Trp Ile Arg Gln Ala Pro Gly Lys Gly Leu Glu Trp Val Ala
305                 310                 315                 320

Ser Ile Thr Arg Ser Gly Gly Arg Ile Tyr Tyr Pro Asp Ser Val Lys
                 325                 330                 335

Gly Arg Phe Thr Ile Ser Arg Glu Asn Thr Gln Lys Thr Leu Tyr Leu
             340                 345                 350

Gln Met Asn Ser Leu Arg Ala Glu Asp Thr Ala Val Tyr Tyr Cys Thr
         355                 360                 365

Leu Asp Gly Arg Asp Gly Trp Val Ala Tyr Trp Gly Gln Gly Thr Leu
     370                 375                 380

Val Thr Val Ser Ser Gly Gly Gly Gly Ser Gly Gly Gly Gly Ser Gly
385                 390                 395                 400

Gly Gly Gly Ser Asn Phe Met Leu Thr Gln Pro Ser Ser Val Ser Gly
                 405                 410                 415

Val Pro Gly Gln Arg Val Thr Ile Ser Cys Thr Gly Asn Thr Gly Asn
             420                 425                 430

Ile Gly Ser Asn Tyr Val Asn Trp Tyr Gln Gln Leu Pro Gly Thr Ala
```

```
                    435                 440                 445
Pro Lys Leu Leu Ile Tyr Arg Asp Asp Lys Arg Pro Ser Gly Val Pro
    450                 455                 460

Asp Arg Phe Ser Gly Ser Lys Ser Gly Thr Ser Ala Ser Leu Ala Ile
465                 470                 475                 480

Thr Gly Phe Gln Ala Glu Asp Glu Ala Asp Tyr Tyr Cys Gln Ser Tyr
                    485                 490                 495

Ser Ser Gly Phe Ile Phe Gly Gly Thr Lys Leu Thr Val Leu Ala
                500                 505                 510

Ala Glu Pro Lys Ser Ser Asp Lys Thr His Thr Cys Pro Pro Cys Pro
        515                 520                 525

Ala Pro Glu Ala Ala Gly Gly Pro Ser Val Phe Leu Phe Pro Pro Lys
    530                 535                 540

Pro Lys Asp Thr Leu Met Ile Ser Arg Thr Pro Glu Val Thr Cys Val
545                 550                 555                 560

Val Val Ser Val Ser His Glu Asp Pro Glu Val Lys Phe Asn Trp Tyr
                    565                 570                 575

Val Asp Gly Val Glu Val His Asn Ala Lys Thr Lys Pro Arg Glu Glu
                580                 585                 590

Gln Tyr Asn Ser Thr Tyr Arg Val Val Ser Val Leu Thr Val Leu His
            595                 600                 605

Gln Asp Trp Leu Asn Gly Lys Glu Tyr Lys Cys Lys Val Ser Asn Lys
        610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Val Tyr Pro Pro Ser Arg Asp Glu Leu
                    645                 650                 655

Thr Lys Asn Gln Val Ser Leu Thr Cys Leu Val Lys Gly Phe Tyr Pro
                660                 665                 670

Ser Asp Ile Ala Val Glu Trp Glu Ser Asn Gly Gln Pro Glu Asn Asn
            675                 680                 685

Tyr Lys Thr Thr Pro Pro Val Leu Asp Ser Asp Gly Ser Phe Ala Leu
        690                 695                 700

Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                    725                 730                 735

Lys Ser Leu Ser Leu Ser Pro Gly Lys
                740                 745

<210> SEQ ID NO 88
<211> LENGTH: 745
<212> TYPE: PRT
<213> ORGANISM: Artificial
<220> FEATURE:
<223> OTHER INFORMATION: Full-length amino acid sequence of NYF-0023-HC2

<400> SEQUENCE: 88

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Val Val
                20                  25                  30

Gln Pro Gly Arg Ser Leu Thr Pro Ser Cys Ser Ala Ser Gly Phe Ser
            35                  40                  45

Ile Arg Ser Tyr Asp Ile His Trp Val Arg Gln Ala Pro Gly Lys Gly
```

```
              50                  55                  60
Leu Glu Trp Val Ala Thr Ile Ser Tyr Asp Gly Ser Gln Lys Tyr Phe
 65                  70                  75                  80

Ala Asp Ser Val Lys Gly Arg Phe Thr Ile Phe Arg Asp Glu Ser Glu
                 85                  90                  95

Asn Met Val Tyr Leu Gln Met Ser Gly Leu Arg Val Glu Asp Thr Ala
            100                 105                 110

Val Tyr His Cys Ala Arg Gly Ser Ser His Tyr Glu Ala Phe Asp
            115                 120                 125

Ile Trp Gly Gln Gly Thr Met Val Thr Val Ser Ser Gly Gly Gly
        130                 135                 140

Ser Gly Gly Gly Gly Ser Gly Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Trp Tyr Val Ser Trp Tyr
                180                 185                 190

Gln Gln Leu Pro Gly Thr Ala Pro Lys Leu Leu Ile Tyr Asp Asn Asn
            195                 200                 205

Lys Arg Pro Ser Gly Ile Pro Asp Arg Phe Ser Gly Ser Lys Ser Gly
210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Val Thr Val Leu Gly Gly Gly Gly Ser Glu
                260                 265                 270

Val Gln Leu Val Glu Ser Gly Gly Gly Leu Val Gln Pro Gly Gly Ser
            275                 280                 285

Leu Arg Leu Ser Cys Ala Ala Ser Gly Val Thr Phe Asn Tyr Tyr Gly
            290                 295                 300

Met Ser Trp Ile Arg Gln Ala Pro Gly Lys Gly Leu Glu Trp Val Ala
305                 310                 315                 320

Ser Ile Thr Arg Ser Gly Gly Arg Ile Tyr Tyr Pro Asp Ser Val Lys
                325                 330                 335

Gly Arg Phe Thr Ile Ser Arg Glu Asn Thr Gln Lys Thr Leu Tyr Leu
            340                 345                 350

Gln Met Asn Ser Leu Arg Ala Glu Asp Thr Ala Val Tyr Tyr Cys Thr
            355                 360                 365

Leu Asp Gly Arg Asp Gly Trp Val Ala Tyr Trp Gly Gln Gly Thr Leu
370                 375                 380

Val Thr Val Ser Ser Gly Gly Gly Ser Gly Gly Gly Gly Ser Gly
385                 390                 395                 400

Gly Gly Gly Ser Asn Phe Met Leu Thr Gln Pro Ser Ser Val Ser Gly
                405                 410                 415

Val Pro Gly Gln Arg Val Thr Ile Ser Cys Thr Gly Asn Thr Gly Asn
                420                 425                 430

Ile Gly Ser Asn Tyr Val Asn Trp Tyr Gln Gln Leu Pro Gly Thr Ala
            435                 440                 445

Pro Lys Leu Leu Ile Tyr Arg Asp Asp Lys Arg Pro Ser Gly Val Pro
            450                 455                 460

Asp Arg Phe Ser Gly Ser Lys Ser Gly Thr Ser Ala Ser Leu Ala Ile
465                 470                 475                 480
```

Thr Gly Phe Gln Ala Glu Asp Glu Ala Asp Tyr Tyr Cys Gln Ser Tyr
            485                 490                 495

Ser Ser Gly Phe Ile Phe Gly Gly Gly Thr Lys Leu Thr Val Leu Ala
            500                 505                 510

Ala Glu Pro Lys Ser Ser Asp Lys Thr His Thr Cys Pro Pro Cys Pro
            515                 520                 525

Ala Pro Glu Ala Ala Gly Gly Pro Ser Val Phe Leu Phe Pro Pro Lys
            530                 535                 540

Pro Lys Asp Thr Leu Met Ile Ser Arg Thr Pro Glu Val Thr Cys Val
545                 550                 555                 560

Val Val Ser Val Ser His Glu Asp Pro Glu Val Lys Phe Asn Trp Tyr
            565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
            595                 600                 605

Gln Asp Trp Leu Asn Gly Lys Glu Tyr Lys Cys Lys Val Ser Asn Lys
            610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Val Tyr Pro Pro Ser Arg Asp Glu Leu
            645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
            675                 680                 685

Tyr Lys Thr Thr Pro Pro Val Leu Asp Ser Asp Gly Ser Phe Ala Leu
            690                 695                 700

Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
            725                 730                 735

Lys Ser Leu Ser Leu Ser Pro Gly Lys
            740                 745

<210> SEQ ID NO 89
<211> LENGTH: 745
<212> TYPE: PRT
<213> ORGANISM: Artificial
<220> FEATURE:
<223> OTHER INFORMATION: Full-length amino acid sequence of NYF-0027-HC2

<400> SEQUENCE: 89

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Val Val
            20                  25                  30

Gln Pro Gly Arg Ser Leu Thr Pro Ser Cys Ser Ala Ser Gly Phe Ser
            35                  40                  45

Ile Arg Ser Tyr Asp Ile His Trp Val Arg Gln Ala Pro Gly Lys Gly
            50                  55                  60

Leu Glu Trp Val Ala Thr Ile Ser Tyr Asp Gly Ser Gln Lys Tyr Phe
65                  70                  75                  80

Ala Asp Ser Val Lys Gly Arg Phe Thr Ile Phe Arg Asp Glu Ser Glu
            85                  90                  95

```
Asn Met Val Tyr Leu Gln Met Ser Gly Leu Arg Val Glu Asp Thr Ala
            100                 105                 110
Val Tyr His Cys Ala Arg Gly Ser Ser Gly His Tyr Glu Ala Phe Asp
        115                 120                 125
Ile Trp Gly Gln Gly Thr Met Val Thr Val Ser Ser Gly Gly Gly Gly
130                 135                 140
Ser Gly Gly Gly Gly Ser Gly Gly Gly Ser Gln Ser Val Leu Thr
145                 150                 155                 160
Gln Pro Pro Ser Val Ser Ala Ala Pro Gly Gln Lys Val Thr Ile Ser
                165                 170                 175
Cys Ser Gly Ser Ser Ser Asn Ile Gly Asn Asn Tyr Val Ser Trp Tyr
                180                 185                 190
Gln Gln Leu Pro Gly Thr Ala Pro Lys Leu Leu Ile Tyr Asp Asn Asn
            195                 200                 205
Lys Arg Pro Ser Gly Ile Pro Asp Arg Phe Ser Gly Ser Lys Ser Gly
        210                 215                 220
Thr Ser Ala Thr Leu Gly Ile Thr Gly Leu Gln Thr Gly Asp Glu Ala
225                 230                 235                 240
Asp Tyr Tyr Cys Gly Ser Trp Asp Ser Ser Leu Ser Ala Pro Trp Val
                245                 250                 255
Phe Gly Gly Gly Thr Lys Val Thr Val Leu Gly Gly Gly Ser Glu
                260                 265                 270
Val Gln Leu Val Glu Ser Gly Gly Gly Leu Val Gln Pro Gly Gly Ser
            275                 280                 285
Leu Arg Leu Ser Cys Ala Ala Ser Gly Val Thr Phe Asn Tyr Tyr Gly
        290                 295                 300
Met Ser Trp Ile Arg Gln Ala Pro Gly Lys Gly Leu Glu Trp Val Ala
305                 310                 315                 320
Ser Ile Thr Arg Ser Gly Gly Arg Ile Tyr Tyr Pro Asp Ser Val Lys
                325                 330                 335
Gly Arg Phe Thr Ile Ser Arg Glu Asn Thr Gln Lys Thr Leu Tyr Leu
            340                 345                 350
Gln Met Asn Ser Leu Arg Ala Glu Asp Thr Ala Val Tyr Tyr Cys Thr
        355                 360                 365
Leu Asp Gly Arg Asp Gly Trp Val Ala Tyr Trp Gly Gln Gly Thr Leu
370                 375                 380
Val Thr Val Ser Ser Gly Gly Gly Gly Ser Gly Gly Gly Gly Ser Gly
385                 390                 395                 400
Gly Gly Gly Ser Asn Phe Met Leu Thr Gln Pro Ser Ser Val Ser Gly
                405                 410                 415
Val Pro Gly Gln Arg Val Thr Ile Ser Cys Thr Gly Asn Thr Gly Asn
            420                 425                 430
Ile Gly Ser Asn Tyr Val Asn Trp Tyr Gln Gln Leu Pro Gly Thr Ala
        435                 440                 445
Pro Lys Leu Leu Ile Tyr Arg Asp Asp Lys Arg Pro Ser Gly Val Pro
    450                 455                 460
Asp Arg Phe Ser Gly Ser Lys Ser Gly Thr Ser Ala Ser Leu Ala Ile
465                 470                 475                 480
Thr Gly Phe Gln Ala Glu Asp Glu Ala Asp Tyr Tyr Cys Gln Ser Tyr
                485                 490                 495
Ser Ser Gly Phe Ile Phe Gly Gly Thr Lys Leu Thr Val Leu Ala
            500                 505                 510
```

Ala Glu Pro Lys Ser Ser Asp Lys Thr His Thr Cys Pro Cys Pro
            515                 520                 525

Ala Pro Glu Ala Ala Gly Gly Pro Ser Val Phe Leu Phe Pro Pro Lys
530                 535                 540

Pro Lys Asp Thr Leu Met Ile Ser Arg Thr Pro Glu Val Thr Cys Val
545                 550                 555                 560

Val Val Ser Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
    610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Val Tyr Pro Pro Ser Arg Asp Glu Leu
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Ala Leu
    690                 695                 700

Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 90
<211> LENGTH: 745
<212> TYPE: PRT
<213> ORGANISM: Artificial
<220> FEATURE:
<223> OTHER INFORMATION: Full-length amino acid sequence of NYF-0035-HC2

<400> SEQUENCE: 90

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Val Val
            20                  25                  30

Gln Pro Gly Arg Ser Leu Thr Pro Ser Cys Ser Ala Ser Gly Phe Ser
        35                  40                  45

Ile Arg Ser Tyr Asp Ile His Trp Val Arg Leu Ala Pro Gly Lys Gly
    50                  55                  60

Leu Glu Trp Val Ala Thr Ile Ser Tyr Asp Gly Ser Gln Lys Tyr Phe
65                  70                  75                  80

Ala Asp Ser Val Lys Gly Arg Phe Thr Ile Phe Arg Asp Glu Ser Glu
                85                  90                  95

Asn Met Val Tyr Leu Gln Met Ser Gly Leu Arg Val Glu Asp Thr Ala
            100                 105                 110

Val Tyr His Cys Ala Arg Gly Ser Ser Gly His Tyr Glu Ala Phe Asp
        115                 120                 125

-continued

```
Ile Trp Gly Gln Gly Thr Met Val Thr Val Ser Ser Gly Gly Gly
    130                 135                 140
Ser Gly Gly Gly Ser Gly Gly Gly Ser Gln Ser Val Leu Thr
145                 150                 155                 160
Gln Pro Pro Ser Val Ser Ala Ala Pro Gly Gln Lys Val Thr Ile Ser
                165                 170                 175
Cys Ser Gly Ser Ser Ser Asn Ile Gly Asn Trp Lys Val Ser Trp Tyr
                180                 185                 190
Gln Gln Leu Pro Gly Thr Ala Pro Lys Leu Leu Ile Tyr Asp Asn Asn
            195                 200                 205
Lys Arg Pro Ser Gly Ile Pro Asp Arg Phe Ser Gly Ser Lys Ser Gly
210                 215                 220
Thr Ser Ala Thr Leu Gly Ile Thr Gly Leu Gln Thr Gly Asp Glu Ala
225                 230                 235                 240
Asp Tyr Tyr Cys Gly Thr Trp Asp Ser Ser Leu Ser Ala Pro Trp Val
                245                 250                 255
Phe Gly Gly Gly Thr Lys Val Thr Val Leu Gly Gly Gly Ser Glu
                260                 265                 270
Val Gln Leu Val Glu Ser Gly Gly Gly Leu Val Gln Pro Gly Gly Ser
            275                 280                 285
Leu Arg Leu Ser Cys Ala Ala Ser Gly Val Thr Phe Asn Tyr Tyr Gly
    290                 295                 300
Met Ser Trp Ile Arg Gln Ala Pro Gly Lys Gly Leu Glu Trp Val Ala
305                 310                 315                 320
Ser Ile Thr Arg Ser Gly Gly Arg Ile Tyr Tyr Pro Asp Ser Val Lys
                325                 330                 335
Gly Arg Phe Thr Ile Ser Arg Glu Asn Thr Gln Lys Thr Leu Tyr Leu
            340                 345                 350
Gln Met Asn Ser Leu Arg Ala Glu Asp Thr Ala Val Tyr Tyr Cys Thr
        355                 360                 365
Leu Asp Gly Arg Asp Gly Trp Val Ala Tyr Trp Gly Gln Gly Thr Leu
    370                 375                 380
Val Thr Val Ser Ser Gly Gly Gly Gly Ser Gly Gly Gly Gly Ser Gly
385                 390                 395                 400
Gly Gly Gly Ser Asn Phe Met Leu Thr Gln Pro Ser Ser Val Ser Gly
                405                 410                 415
Val Pro Gly Gln Arg Val Thr Ile Ser Cys Thr Gly Asn Thr Gly Asn
            420                 425                 430
Ile Gly Ser Asn Tyr Val Asn Trp Tyr Gln Gln Leu Pro Gly Thr Ala
        435                 440                 445
Pro Lys Leu Leu Ile Tyr Arg Asp Asp Lys Arg Pro Ser Gly Val Pro
    450                 455                 460
Asp Arg Phe Ser Gly Ser Lys Ser Gly Thr Ser Ala Ser Leu Ala Ile
465                 470                 475                 480
Thr Gly Phe Gln Ala Glu Asp Glu Ala Asp Tyr Tyr Cys Gln Ser Tyr
                485                 490                 495
Ser Ser Gly Phe Ile Phe Gly Gly Thr Lys Leu Thr Val Leu Ala
            500                 505                 510
Ala Glu Pro Lys Ser Ser Asp Lys Thr His Thr Cys Pro Pro Cys Pro
        515                 520                 525
Ala Pro Glu Ala Ala Gly Gly Pro Ser Val Phe Leu Phe Pro Pro Lys
    530                 535                 540
Pro Lys Asp Thr Leu Met Ile Ser Arg Thr Pro Glu Val Thr Cys Val
```

```
545                 550                 555                 560
Val Val Ser Val Ser His Glu Asp Pro Glu Val Lys Phe Asn Trp Tyr
                565                 570                 575
Val Asp Gly Val Glu Val His Asn Ala Lys Thr Lys Pro Arg Glu Glu
                580                 585                 590
Gln Tyr Asn Ser Thr Tyr Arg Val Val Ser Val Leu Thr Val Leu His
                595                 600                 605
Gln Asp Trp Leu Asn Gly Lys Glu Tyr Lys Cys Lys Val Ser Asn Lys
                610                 615                 620
Ala Leu Pro Ala Pro Ile Glu Lys Thr Ile Ser Lys Ala Lys Gly Gln
625                 630                 635                 640
Pro Arg Glu Pro Gln Val Tyr Val Tyr Pro Pro Ser Arg Asp Glu Leu
                645                 650                 655
Thr Lys Asn Gln Val Ser Leu Thr Cys Leu Val Lys Gly Phe Tyr Pro
                660                 665                 670
Ser Asp Ile Ala Val Glu Trp Glu Ser Asn Gly Gln Pro Glu Asn Asn
                675                 680                 685
Tyr Lys Thr Thr Pro Pro Val Leu Asp Ser Asp Gly Ser Phe Ala Leu
                690                 695                 700
Val Ser Lys Leu Thr Val Asp Lys Ser Arg Trp Gln Gln Gly Asn Val
705                 710                 715                 720
Phe Ser Cys Ser Val Met His Glu Ala Leu His Asn His Tyr Thr Gln
                725                 730                 735
Lys Ser Leu Ser Leu Ser Pro Gly Lys
                740                 745

<210> SEQ ID NO 91
<211> LENGTH: 745
<212> TYPE: PRT
<213> ORGANISM: Artificial
<220> FEATURE:
<223> OTHER INFORMATION: Full-length amino acid sequence of NYF-0044-HC2

<400> SEQUENCE: 91

Met Lys His Leu Trp Phe Phe Leu Leu Leu Val Ala Ala Pro Arg Trp
1               5                   10                  15
Val Leu Ser Gly Glu Val Gln Leu Val Glu Ser Gly Gly Gly Leu Val
                20                  25                  30
Gln Pro Gly Gly Ser Leu Arg Leu Ser Cys Ala Ala Ser Gly Phe Ser
                35                  40                  45
Ile Arg Ser Tyr Asp Ile His Trp Val Arg Leu Ala Pro Gly Lys Gly
                50                  55                  60
Leu Glu Trp Val Ala Thr Ile Ser Tyr Asp Gly Ser Gln Lys Tyr Tyr
65                  70                  75                  80
Ala Asp Ser Val Lys Gly Arg Phe Thr Ile Ser Arg Asp Glu Ser Lys
                85                  90                  95
Asn Thr Leu Tyr Leu Gln Met Asn Ser Leu Arg Ala Glu Asp Thr Ala
                100                 105                 110
Val Tyr His Cys Ala Arg Gly Ser Ser Gly His Tyr Glu Ala Phe Asp
                115                 120                 125
Ile Trp Gly Gln Gly Thr Leu Val Thr Val Ser Ser Gly Gly Gly Gly
                130                 135                 140
Ser Gly Gly Gly Gly Ser Gly Gly Gly Gly Ser Gln Ser Val Leu Thr
145                 150                 155                 160
Gln Pro Pro Ser Val Ser Ala Ala Pro Gly Gln Lys Val Thr Ile Ser
```

```
            165                 170                 175
Cys Ser Gly Ser Ser Asn Ile Gly Asn Trp Tyr Val Ser Trp Tyr
            180                 185                 190
Gln Gln Leu Pro Gly Thr Ala Pro Lys Leu Leu Ile Tyr Asp Asn Asn
            195                 200                 205
Lys Arg Pro Ser Gly Ile Pro Asp Arg Phe Ser Gly Ser Lys Ser Gly
    210                 215                 220
Thr Ser Ala Thr Leu Gly Ile Thr Gly Leu Gln Thr Gly Asp Glu Ala
225                 230                  235                 240
Asp Tyr Tyr Cys Gly Thr Trp Asp Ser Ser Leu Ser Ala Pro Trp Val
                245                 250                 255
Phe Gly Gly Gly Thr Lys Val Thr Val Leu Gly Gly Gly Ser Glu
                260                 265                 270
Val Gln Leu Val Glu Ser Gly Gly Leu Val Gln Pro Gly Gly Ser
            275                 280                 285
Leu Arg Leu Ser Cys Ala Ala Ser Gly Val Thr Phe Asn Tyr Tyr Gly
    290                 295                 300
Met Ser Trp Ile Arg Gln Ala Pro Gly Lys Gly Leu Glu Trp Val Ala
305                 310                 315                 320
Ser Ile Thr Arg Ser Gly Gly Arg Ile Tyr Tyr Pro Asp Ser Val Lys
                325                 330                 335
Gly Arg Phe Thr Ile Ser Arg Glu Asn Thr Gln Lys Thr Leu Tyr Leu
                340                 345                 350
Gln Met Asn Ser Leu Arg Ala Glu Asp Thr Ala Val Tyr Tyr Cys Thr
                355                 360                 365
Leu Asp Gly Arg Asp Gly Trp Val Ala Tyr Trp Gly Gln Gly Thr Leu
    370                 375                 380
Val Thr Val Ser Ser Gly Gly Gly Gly Ser Gly Gly Gly Gly Ser Gly
385                 390                 395                 400
Gly Gly Gly Ser Asn Phe Met Leu Thr Gln Pro Ser Ser Val Ser Gly
                405                 410                 415
Val Pro Gly Gln Arg Val Thr Ile Ser Cys Thr Gly Asn Thr Gly Asn
                420                 425                 430
Ile Gly Ser Asn Tyr Val Asn Trp Tyr Gln Gln Leu Pro Gly Thr Ala
            435                 440                 445
Pro Lys Leu Leu Ile Tyr Arg Asp Asp Lys Arg Pro Ser Gly Val Pro
    450                 455                 460
Asp Arg Phe Ser Gly Ser Lys Ser Gly Thr Ser Ala Ser Leu Ala Ile
465                 470                 475                 480
Thr Gly Phe Gln Ala Glu Asp Glu Ala Asp Tyr Tyr Cys Gln Ser Tyr
                485                 490                 495
Ser Ser Gly Phe Ile Phe Gly Gly Gly Thr Lys Leu Thr Val Leu Ala
            500                 505                 510
Ala Glu Pro Lys Ser Ser Asp Lys Thr His Thr Cys Pro Pro Cys Pro
            515                 520                 525
Ala Pro Glu Ala Ala Gly Gly Pro Ser Val Phe Leu Phe Pro Pro Lys
            530                 535                 540
Pro Lys Asp Thr Leu Met Ile Ser Arg Thr Pro Glu Val Thr Cys Val
545                 550                 555                 560
Val Val Ser Val Ser His Glu Asp Pro Glu Val Lys Phe Asn Trp Tyr
                565                 570                 575
Val Asp Gly Val Glu Val His Asn Ala Lys Thr Lys Pro Arg Glu Glu
            580                 585                 590
```

```
Gln Tyr Asn Ser Thr Tyr Arg Val Val Ser Val Leu Thr Val Leu His
            595                 600                 605

Gln Asp Trp Leu Asn Gly Lys Glu Tyr Lys Cys Lys Val Ser Asn Lys
        610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Val Tyr Pro Pro Ser Arg Asp Glu Leu
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Ala Leu
690                 695                 700

Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 92
<211> LENGTH: 745
<212> TYPE: PRT
<213> ORGANISM: Artificial
<220> FEATURE:
<223> OTHER INFORMATION: Full-length amino acid sequence of NYF-0045-HC2

<400> SEQUENCE: 92

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Ser
        35                  40                  45

Ile Arg Ser Tyr Asp Ile His Trp Val Arg Leu Ala Pro Gly Lys Gly
    50                  55                  60

Leu Glu Trp Val Ala Thr Ile Ser Tyr Asp Gly Ser Gln Lys Tyr Tyr
65                  70                  75                  80

Ala Asp Ser Val Lys Gly Arg Phe Thr Ile Ser Arg Asp Glu Ser Lys
                85                  90                  95

Asn Thr Leu Tyr Leu Gln Met Asn Ser Leu Arg Ala Glu Asp Thr Ala
            100                 105                 110

Val Tyr His Cys Ala Arg Gly Ser Ser Gly His Tyr Glu Ala Phe Asp
        115                 120                 125

Ile Trp Gly Gln Gly Thr Leu Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Ala Ser Gly Thr Pro Gly Gln Arg Val Thr Ile Ser
                165                 170                 175

Cys Ser Gly Ser Ser Ser Asn Ile Gly Asn Trp Tyr Val Ser Trp Tyr
            180                 185                 190

Gln Gln Leu Pro Gly Thr Ala Pro Lys Leu Leu Ile Tyr Asp Asn Asn
        195                 200                 205
```

```
Lys Arg Pro Ser Gly Val Pro Asp Arg Phe Ser Gly Ser Lys Ser Gly
    210                 215                 220

Thr Ser Ala Ser Leu Ala Ile Ser Gly Leu Gln Ser Glu Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Leu Thr Val Leu Gly Gly Gly Ser Glu
            260                 265                 270

Val Gln Leu Val Glu Ser Gly Gly Gly Leu Val Gln Pro Gly Gly Ser
        275                 280                 285

Leu Arg Leu Ser Cys Ala Ala Ser Gly Val Thr Phe Asn Tyr Tyr Gly
    290                 295                 300

Met Ser Trp Ile Arg Gln Ala Pro Gly Lys Gly Leu Glu Trp Val Ala
305                 310                 315                 320

Ser Ile Thr Arg Ser Gly Gly Arg Ile Tyr Tyr Pro Asp Ser Val Lys
                325                 330                 335

Gly Arg Phe Thr Ile Ser Arg Glu Asn Thr Gln Lys Thr Leu Tyr Leu
            340                 345                 350

Gln Met Asn Ser Leu Arg Ala Glu Asp Thr Ala Val Tyr Tyr Cys Thr
    355                 360                 365

Leu Asp Gly Arg Asp Gly Trp Val Ala Tyr Trp Gly Gln Gly Thr Leu
370                 375                 380

Val Thr Val Ser Ser Gly Gly Gly Ser Gly Gly Gly Ser Gly
385                 390                 395                 400

Gly Gly Gly Ser Asn Phe Met Leu Thr Gln Pro Ser Ser Val Ser Gly
                405                 410                 415

Val Pro Gly Gln Arg Val Thr Ile Ser Cys Thr Gly Asn Thr Gly Asn
            420                 425                 430

Ile Gly Ser Asn Tyr Val Asn Trp Tyr Gln Gln Leu Pro Gly Thr Ala
        435                 440                 445

Pro Lys Leu Leu Ile Tyr Arg Asp Lys Arg Pro Ser Gly Val Pro
    450                 455                 460

Asp Arg Phe Ser Gly Ser Lys Ser Gly Thr Ser Ala Ser Leu Ala Ile
465                 470                 475                 480

Thr Gly Phe Gln Ala Glu Asp Glu Ala Asp Tyr Tyr Cys Gln Ser Tyr
                485                 490                 495

Ser Ser Gly Phe Ile Phe Gly Gly Gly Thr Lys Leu Thr Val Leu Ala
            500                 505                 510

Ala Glu Pro Lys Ser Ser Asp Lys Thr His Thr Cys Pro Pro Cys Pro
    515                 520                 525

Ala Pro Glu Ala Ala Gly Gly Pro Ser Val Phe Leu Phe Pro Pro Lys
530                 535                 540

Pro Lys Asp Thr Leu Met Ile Ser Arg Thr Pro Glu Val Thr Cys Val
545                 550                 555                 560

Val Val Ser Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
    610                 615                 620
```

```
Ala Leu Pro Ala Pro Ile Glu Lys Thr Ile Ser Lys Ala Lys Gly Gln
625                 630                 635                 640

Pro Arg Glu Pro Gln Val Tyr Val Tyr Pro Pro Ser Arg Asp Glu Leu
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Ala Leu
    690                 695                 700

Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
                740                 745

<210> SEQ ID NO 93
<211> LENGTH: 745
<212> TYPE: PRT
<213> ORGANISM: Artificial
<220> FEATURE:
<223> OTHER INFORMATION: Full-length amino acid sequence of NYF-0047-HC2

<400> SEQUENCE: 93

Met Lys His Leu Trp Phe Phe Leu Leu Leu Val Ala Ala Pro Arg Trp
1               5                   10                  15

Val Leu Ser Gly Gln Val Gln Leu Val Glu Ser Gly Gly Gly Val Val
                20                  25                  30

Gln Pro Gly Arg Ser Leu Arg Leu Ser Cys Ala Ala Ser Gly Phe Ser
            35                  40                  45

Ile Arg Ser Tyr Asp Met His Trp Val Arg Gln Ala Pro Gly Lys Gly
        50                  55                  60

Leu Glu Trp Val Ala Thr Ile Ser Tyr Asp Gly Ser Gln Lys Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Ser Ser Leu Arg Ala Glu Asp Thr Ala
            100                 105                 110

Val Tyr His Cys Ala Arg Gly Ser Gly His Tyr Glu Ala Phe Asp
        115                 120                 125

Ile Trp Gly Gln Gly Thr Leu Val Thr Val Ser Ser Gly Gly Gly Gly
130                 135                 140

Ser Gly Gly Gly Gly Ser Gly Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Trp Tyr Val Ser Trp Tyr
            180                 185                 190

Gln Gln Leu Pro Gly Thr Ala Pro Lys Leu Leu Ile Tyr Asp Asn Asn
        195                 200                 205

Lys Arg Pro Ser Gly Ile Pro Asp Arg Phe Ser Gly Ser Lys Ser Gly
    210                 215                 220

Thr Ser Ala Thr Leu Gly Ile Thr Gly Leu Gln Thr Gly Asp Glu Ala
225                 230                 235                 240
```

```
Asp Tyr Tyr Cys Gly Thr Trp Asp Ser Ser Leu Ser Ala Pro Trp Val
                245                 250                 255

Phe Gly Gly Gly Thr Lys Val Thr Val Leu Gly Gly Gly Gly Ser Glu
            260                 265                 270

Val Gln Leu Val Glu Ser Gly Gly Leu Val Gln Pro Gly Gly Ser
        275                 280                 285

Leu Arg Leu Ser Cys Ala Ala Ser Gly Val Thr Phe Asn Tyr Tyr Gly
        290                 295                 300

Met Ser Trp Ile Arg Gln Ala Pro Gly Lys Gly Leu Glu Trp Val Ala
305                 310                 315                 320

Ser Ile Thr Arg Ser Gly Gly Arg Ile Tyr Tyr Pro Asp Ser Val Lys
                325                 330                 335

Gly Arg Phe Thr Ile Ser Arg Glu Asn Thr Gln Lys Thr Leu Tyr Leu
                340                 345                 350

Gln Met Asn Ser Leu Arg Ala Glu Asp Thr Ala Val Tyr Tyr Cys Thr
            355                 360                 365

Leu Asp Gly Arg Asp Gly Trp Val Ala Tyr Trp Gly Gln Gly Thr Leu
        370                 375                 380

Val Thr Val Ser Ser Gly Gly Gly Gly Ser Gly Gly Gly Gly Ser Gly
385                 390                 395                 400

Gly Gly Gly Ser Asn Phe Met Leu Thr Gln Pro Ser Ser Val Ser Gly
                405                 410                 415

Val Pro Gly Gln Arg Val Thr Ile Ser Cys Thr Gly Asn Thr Gly Asn
                420                 425                 430

Ile Gly Ser Asn Tyr Val Asn Trp Tyr Gln Gln Leu Pro Gly Thr Ala
            435                 440                 445

Pro Lys Leu Leu Ile Tyr Arg Asp Asp Lys Arg Pro Ser Gly Val Pro
        450                 455                 460

Asp Arg Phe Ser Gly Ser Lys Ser Gly Thr Ser Ala Ser Leu Ala Ile
465                 470                 475                 480

Thr Gly Phe Gln Ala Glu Asp Glu Ala Asp Tyr Tyr Cys Gln Ser Tyr
                485                 490                 495

Ser Ser Gly Phe Ile Phe Gly Gly Gly Thr Lys Leu Thr Val Leu Ala
            500                 505                 510

Ala Glu Pro Lys Ser Ser Asp Lys Thr His Thr Cys Pro Pro Cys Pro
        515                 520                 525

Ala Pro Glu Ala Ala Gly Gly Pro Ser Val Phe Leu Phe Pro Pro Lys
        530                 535                 540

Pro Lys Asp Thr Leu Met Ile Ser Arg Thr Pro Glu Val Thr Cys Val
545                 550                 555                 560

Val Val Ser Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
        610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Val Tyr Pro Pro Ser Arg Asp Glu Leu
                645                 650                 655

Thr Lys Asn Gln Val Ser Leu Thr Cys Leu Val Lys Gly Phe Tyr Pro
```

```
              660                 665                 670
Ser Asp Ile Ala Val Glu Trp Glu Ser Asn Gly Gln Pro Glu Asn Asn
            675                 680                 685

Tyr Lys Thr Thr Pro Val Leu Asp Ser Asp Gly Ser Phe Ala Leu
            690                 695                 700

Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 94
<211> LENGTH: 745
<212> TYPE: PRT
<213> ORGANISM: Artificial
<220> FEATURE:
<223> OTHER INFORMATION: Full-length amino acid sequence of NYF-0048-HC2

<400> SEQUENCE: 94

Met Lys His Leu Trp Phe Phe Leu Leu Leu Val Ala Ala Pro Arg Trp
1               5                   10                  15

Val Leu Ser Gly Gln Val Gln Leu Val Glu Ser Gly Gly Gly Val Val
            20                  25                  30

Gln Pro Gly Arg Ser Leu Arg Leu Ser Cys Ala Ala Ser Gly Phe Ser
        35                  40                  45

Ile Arg Ser Tyr Asp Met His Trp Val Arg Gln Ala Pro Gly Lys Gly
    50                  55                  60

Leu Glu Trp Val Ala Thr Ile Ser Tyr Asp Gly Ser Gln Lys Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Ser Ser Leu Arg Ala Glu Asp Thr Ala
            100                 105                 110

Val Tyr His Cys Ala Arg Gly Ser Ser Gly His Tyr Glu Ala Phe Asp
        115                 120                 125

Ile Trp Gly Gln Gly Thr Leu Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Ala Ser Gly Thr Pro Gly Gln Arg Val Thr Ile Ser
                165                 170                 175

Cys Ser Gly Ser Ser Ser Asn Ile Gly Asn Trp Tyr Val Ser Trp Tyr
            180                 185                 190

Gln Gln Leu Pro Gly Thr Ala Pro Lys Leu Leu Ile Tyr Asp Asn Asn
        195                 200                 205

Lys Arg Pro Ser Gly Val Pro Asp Arg Phe Ser Gly Ser Lys Ser Gly
    210                 215                 220

Thr Ser Ala Ser Leu Ala Ile Ser Gly Leu Gln Ser Glu Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Leu Thr Val Leu Gly Gly Gly Gly Ser Glu
            260                 265                 270

Val Gln Leu Val Glu Ser Gly Gly Gly Leu Val Gln Pro Gly Gly Ser
```

-continued

```
                275                 280                 285
Leu Arg Leu Ser Cys Ala Ala Ser Gly Val Thr Phe Asn Tyr Tyr Gly
290                 295                 300
Met Ser Trp Ile Arg Gln Ala Pro Gly Lys Gly Leu Glu Trp Val Ala
305                 310                 315                 320
Ser Ile Thr Arg Ser Gly Gly Arg Ile Tyr Tyr Pro Asp Ser Val Lys
                325                 330                 335
Gly Arg Phe Thr Ile Ser Arg Glu Asn Thr Gln Lys Thr Leu Tyr Leu
                340                 345                 350
Gln Met Asn Ser Leu Arg Ala Glu Asp Thr Ala Val Tyr Tyr Cys Thr
                355                 360                 365
Leu Asp Gly Arg Asp Gly Trp Val Ala Tyr Trp Gly Gln Gly Thr Leu
370                 375                 380
Val Thr Val Ser Ser Gly Gly Gly Gly Ser Gly Gly Gly Gly Ser Gly
385                 390                 395                 400
Gly Gly Gly Ser Asn Phe Met Leu Thr Gln Pro Ser Ser Val Ser Gly
                405                 410                 415
Val Pro Gly Gln Arg Val Thr Ile Ser Cys Thr Gly Asn Thr Gly Asn
                420                 425                 430
Ile Gly Ser Asn Tyr Val Asn Trp Tyr Gln Gln Leu Pro Gly Thr Ala
                435                 440                 445
Pro Lys Leu Leu Ile Tyr Arg Asp Asp Lys Arg Pro Ser Gly Val Pro
450                 455                 460
Asp Arg Phe Ser Gly Ser Lys Ser Gly Thr Ser Ala Ser Leu Ala Ile
465                 470                 475                 480
Thr Gly Phe Gln Ala Glu Asp Glu Ala Asp Tyr Tyr Cys Gln Ser Tyr
                485                 490                 495
Ser Ser Gly Phe Ile Phe Gly Gly Gly Thr Lys Leu Thr Val Leu Ala
                500                 505                 510
Ala Glu Pro Lys Ser Ser Asp Lys Thr His Thr Cys Pro Pro Cys Pro
                515                 520                 525
Ala Pro Glu Ala Ala Gly Gly Pro Ser Val Phe Leu Phe Pro Pro Lys
530                 535                 540
Pro Lys Asp Thr Leu Met Ile Ser Arg Thr Pro Glu Val Thr Cys Val
545                 550                 555                 560
Val Val Ser Val Ser His Glu Asp Pro Glu Val Lys Phe Asn Trp Tyr
                565                 570                 575
Val Asp Gly Val Glu Val His Asn Ala Lys Thr Lys Pro Arg Glu Glu
                580                 585                 590
Gln Tyr Asn Ser Thr Tyr Arg Val Val Ser Val Leu Thr Val Leu His
                595                 600                 605
Gln Asp Trp Leu Asn Gly Lys Glu Tyr Lys Cys Lys Val Ser Asn Lys
                610                 615                 620
Ala Leu Pro Ala Pro Ile Glu Lys Thr Ile Ser Lys Ala Lys Gly Gln
625                 630                 635                 640
Pro Arg Glu Pro Gln Val Tyr Val Tyr Pro Pro Ser Arg Asp Glu Leu
                645                 650                 655
Thr Lys Asn Gln Val Ser Leu Thr Cys Leu Val Lys Gly Phe Tyr Pro
                660                 665                 670
Ser Asp Ile Ala Val Glu Trp Glu Ser Asn Gly Gln Pro Glu Asn Asn
                675                 680                 685
Tyr Lys Thr Thr Pro Pro Val Leu Asp Ser Asp Gly Ser Phe Ala Leu
                690                 695                 700
```

-continued

```
Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
            740                 745

<210> SEQ ID NO 95
<211> LENGTH: 745
<212> TYPE: PRT
<213> ORGANISM: Artificial
<220> FEATURE:
<223> OTHER INFORMATION: Full-length amino acid sequence of NYF-0060-HC2

<400> SEQUENCE: 95

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Ser
        35                  40                  45

Ile Arg Ser Tyr Asp Ile His Trp Val Arg Gln Ala Pro Gly Lys Gly
    50                  55                  60

Leu Glu Trp Val Ala Thr Ile Ser Tyr Asp Gly Ser Gln Lys Tyr Tyr
65                  70                  75                  80

Ala Asp Ser Val Lys Gly Arg Phe Thr Ile Ser Arg Asp Glu Ser Lys
                85                  90                  95

Asn Thr Leu Tyr Leu Gln Met Asn Ser Leu Arg Ala Glu Asp Thr Ala
            100                 105                 110

Val Tyr His Cys Ala Arg Gly Ser Ser Gly His Tyr Glu Ala Phe Asp
        115                 120                 125

Ile Trp Gly Gln Gly Thr Leu Val Thr Val Ser Ser Gly Gly Gly Gly
    130                 135                 140

Ser Gly Gly Gly Gly Ser Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Trp Tyr Val Ser Trp Tyr
            180                 185                 190

Gln Gln Leu Pro Gly Thr Ala Pro Lys Leu Leu Ile Tyr Asp Asn Asn
        195                 200                 205

Lys Arg Pro Ser Gly Ile Pro Asp Arg Phe Ser Gly Ser Lys Ser Gly
    210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Val Thr Val Leu Gly Gly Gly Ser Glu
            260                 265                 270

Val Gln Leu Val Glu Ser Gly Gly Leu Val Gln Pro Gly Gly Ser
        275                 280                 285

Leu Arg Leu Ser Cys Ala Ala Ser Gly Val Thr Phe Asn Tyr Tyr Gly
    290                 295                 300

Met Ser Trp Ile Arg Gln Ala Pro Gly Lys Gly Leu Glu Trp Val Ala
305                 310                 315                 320
```

-continued

Ser Ile Thr Arg Ser Gly Gly Arg Ile Tyr Tyr Pro Asp Ser Val Lys
                325                 330                 335

Gly Arg Phe Thr Ile Ser Arg Glu Asn Thr Gln Lys Thr Leu Tyr Leu
            340                 345                 350

Gln Met Asn Ser Leu Arg Ala Glu Asp Thr Ala Val Tyr Tyr Cys Thr
        355                 360                 365

Leu Asp Gly Arg Asp Gly Trp Val Ala Tyr Trp Gly Gln Gly Thr Leu
    370                 375                 380

Val Thr Val Ser Ser Gly Gly Gly Ser Gly Gly Gly Ser Gly
385                 390                 395                 400

Gly Gly Ser Asn Phe Met Leu Thr Gln Pro Ser Ser Val Ser Gly
                405                 410                 415

Val Pro Gly Gln Arg Val Thr Ile Ser Cys Thr Gly Asn Thr Gly Asn
            420                 425                 430

Ile Gly Ser Asn Tyr Val Asn Trp Tyr Gln Gln Leu Pro Gly Thr Ala
        435                 440                 445

Pro Lys Leu Leu Ile Tyr Arg Asp Asp Lys Arg Pro Ser Gly Val Pro
    450                 455                 460

Asp Arg Phe Ser Gly Ser Lys Ser Gly Thr Ser Ala Ser Leu Ala Ile
465                 470                 475                 480

Thr Gly Phe Gln Ala Glu Asp Glu Ala Asp Tyr Tyr Cys Gln Ser Tyr
                485                 490                 495

Ser Ser Gly Phe Ile Phe Gly Gly Thr Lys Leu Thr Val Leu Ala
            500                 505                 510

Ala Glu Pro Lys Ser Ser Asp Lys Thr His Thr Cys Pro Pro Cys Pro
        515                 520                 525

Ala Pro Glu Ala Ala Gly Gly Pro Ser Val Phe Leu Phe Pro Pro Lys
    530                 535                 540

Pro Lys Asp Thr Leu Met Ile Ser Arg Thr Pro Glu Val Thr Cys Val
545                 550                 555                 560

Val Val Ser Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
    610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Val Tyr Pro Pro Ser Arg Asp Glu Leu
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Ala Leu
    690                 695                 700

Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

```
Lys Ser Leu Ser Leu Ser Pro Gly Lys
            740                 745

<210> SEQ ID NO 96
<211> LENGTH: 745
<212> TYPE: PRT
<213> ORGANISM: Artificial
<220> FEATURE:
<223> OTHER INFORMATION: Full-length amino acid sequence of NYF-0061-HC2

<400> SEQUENCE: 96

Met Lys His Leu Trp Phe Phe Leu Leu Val Ala Ala Pro Arg Trp
1               5                   10                  15

Val Leu Ser Gly Glu Val Gln Leu Val Glu Ser Gly Gly Gly Leu Val
                20                  25                  30

Gln Pro Gly Gly Ser Leu Arg Leu Ser Cys Ala Ala Ser Gly Phe Ser
            35                  40                  45

Ile Arg Ser Tyr Asp Ile His Trp Val Arg Gln Ala Pro Gly Lys Gly
        50                  55                  60

Leu Glu Trp Val Ala Thr Ile Ser Tyr Asp Gly Ser Gln Lys Tyr Tyr
65              70                  75                  80

Ala Asp Ser Val Lys Gly Arg Phe Thr Ile Ser Arg Asp Glu Ser Lys
                85                  90                  95

Asn Thr Leu Tyr Leu Gln Met Asn Ser Leu Arg Ala Glu Asp Thr Ala
            100                 105                 110

Val Tyr His Cys Ala Arg Gly Ser Gly His Tyr Glu Ala Phe Asp
        115                 120                 125

Ile Trp Gly Gln Gly Thr Leu Val Thr Val Ser Ser Gly Gly Gly Gly
130                 135                 140

Ser Gly Gly Gly Gly Ser Gly Gly Gly Gly Ser Gln Ser Val Leu Thr
145                 150                 155                 160

Gln Pro Pro Ser Ala Ser Gly Thr Pro Gly Gln Arg Val Thr Ile Ser
                165                 170                 175

Cys Ser Gly Ser Ser Ser Asn Ile Gly Asn Trp Tyr Val Ser Trp Tyr
            180                 185                 190

Gln Gln Leu Pro Gly Thr Ala Pro Lys Leu Leu Ile Tyr Asp Asn Asn
        195                 200                 205

Lys Arg Pro Ser Gly Val Pro Asp Arg Phe Ser Gly Ser Lys Ser Gly
210                 215                 220

Thr Ser Ala Ser Leu Ala Ile Ser Gly Leu Gln Ser Glu Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Leu Thr Val Leu Gly Gly Gly Gly Ser Glu
            260                 265                 270

Val Gln Leu Val Glu Ser Gly Gly Gly Leu Val Gln Pro Gly Gly Ser
        275                 280                 285

Leu Arg Leu Ser Cys Ala Ala Ser Gly Val Thr Phe Asn Tyr Tyr Gly
290                 295                 300

Met Ser Trp Ile Arg Gln Ala Pro Gly Lys Gly Leu Glu Trp Val Ala
305                 310                 315                 320

Ser Ile Thr Arg Ser Gly Gly Arg Ile Tyr Tyr Pro Asp Ser Val Lys
                325                 330                 335

Gly Arg Phe Thr Ile Ser Arg Glu Asn Thr Gln Lys Thr Leu Tyr Leu
            340                 345                 350
```

```
Gln Met Asn Ser Leu Arg Ala Glu Asp Thr Ala Val Tyr Tyr Cys Thr
        355                 360                 365

Leu Asp Gly Arg Asp Gly Trp Val Ala Tyr Trp Gly Gln Gly Thr Leu
370                 375                 380

Val Thr Val Ser Ser Gly Gly Gly Ser Gly Gly Gly Ser Gly
385                 390                 395                 400

Gly Gly Gly Ser Asn Phe Met Leu Thr Gln Pro Ser Val Ser Gly
                405                 410                 415

Val Pro Gly Gln Arg Val Thr Ile Ser Cys Thr Gly Asn Thr Gly Asn
                420                 425                 430

Ile Gly Ser Asn Tyr Val Asn Trp Tyr Gln Gln Leu Pro Gly Thr Ala
        435                 440                 445

Pro Lys Leu Leu Ile Tyr Arg Asp Asp Lys Arg Pro Ser Gly Val Pro
    450                 455                 460

Asp Arg Phe Ser Gly Ser Lys Ser Gly Thr Ser Ala Ser Leu Ala Ile
465                 470                 475                 480

Thr Gly Phe Gln Ala Glu Asp Glu Ala Asp Tyr Tyr Cys Gln Ser Tyr
                485                 490                 495

Ser Ser Gly Phe Ile Phe Gly Gly Thr Lys Leu Thr Val Leu Ala
            500                 505                 510

Ala Glu Pro Lys Ser Ser Asp Lys Thr His Thr Cys Pro Pro Cys Pro
    515                 520                 525

Ala Pro Glu Ala Ala Gly Gly Pro Ser Val Phe Leu Phe Pro Pro Lys
    530                 535                 540

Pro Lys Asp Thr Leu Met Ile Ser Arg Thr Pro Glu Val Thr Cys Val
545                 550                 555                 560

Val Val Ser Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
                580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
    610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Val Tyr Pro Pro Ser Arg Asp Glu Leu
                645                 650                 655

Thr Lys Asn Gln Val Ser Leu Thr Cys Leu Val Lys Gly Phe Tyr Pro
                660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Ala Leu
    690                 695                 700

Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
        740                 745

<210> SEQ ID NO 97
<211> LENGTH: 1404
<212> TYPE: DNA
```

<213> ORGANISM: Artificial
<220> FEATURE:
<223> OTHER INFORMATION: Full-length nucleotide sequence of NYA-0001-Fab-HC1-k delete

<400> SEQUENCE: 97

| | | | | | |
|---|---|---|---|---|---|
| atgaaacacc | tgtggttctt | cctcctgctg | gtggcagctc | ccagatgggt | gctgagcgag | 60 |
| gtgcagctgg | tggagtctgg | gggaggcgtg | gtccagcctg | gaggtccct | gacaccctcc | 120 |
| tgttcagcgt | ctggattctc | catccgtagt | tatgatatac | actgggtccg | ccaggctcca | 180 |
| ggcaaggggc | tagagtgggt | ggccactata | tcatatgatg | gaagtcagaa | gtacttcgca | 240 |
| gactccgtga | agggccgatt | taccatcttc | agagacgaat | cggagaacat | ggtgtatctg | 300 |
| caaatgagcg | gcctgagagt | tgaggacacg | gctgtttatc | actgtgcgag | agggagtagt | 360 |
| ggtcattatg | aggcttttga | tatctggggc | caagggacaa | tggtcaccgt | ctcttcagcc | 420 |
| tccaccaagg | gcccaagcgt | cttccccctg | gcaccctcct | ccaagagcac | ctctggcggc | 480 |
| acagccgccc | tgggctgcct | ggtcaaggac | tacttccccg | aacccgtgac | cgtgagctgg | 540 |
| aactcaggcg | ccctgaccag | cggcgtgcac | accttccccg | ctgtcctgca | gtcctcagga | 600 |
| ctctactccc | tcagcagcgt | ggtgaccgtg | ccctccagca | gcttgggcac | ccagacctac | 660 |
| atctgcaacg | tgaatcacaa | gcccagcaac | accaaggtgg | acaagagagt | tgagcccaaa | 720 |
| tcttgtgaca | aaactcacac | atgcccaccc | tgcccagcac | ctgaagccgc | aggggaccc | 780 |
| tcagtcttcc | tcttcccccc | aaaacccaag | gacaccctca | tgatctcccg | gacccctgag | 840 |
| gtcacatgcg | tggtggtgtc | agtgagccac | gaagaccctg | aggtcaagtt | caactggtac | 900 |
| gtggacggcg | tggaggtgca | taatgccaag | acaaagcccc | gggaggagca | gtacaacagc | 960 |
| acgtaccggg | tggtcagcgt | cctcaccgtc | ctgcaccagg | actggctgaa | tggcaaggag | 1020 |
| tacaagtgca | aggtctccaa | caaagccctc | ccagccccca | tcgagaaaac | catctccaaa | 1080 |
| gccaaaggcc | agccccggga | accacaggtg | tacgtgctgc | ccccatcccg | ggacgagctg | 1140 |
| accaagaacc | aggtcagcct | gctgtgcctg | gtcaaaggct | tctatcccag | cgacatcgcc | 1200 |
| gtggagtggg | agagcaatgg | ccagcccgag | aacaactacc | tgacctggcc | tcccgtgctg | 1260 |
| gactccgacg | gctccttctt | cctctacagc | aagctcaccg | tggacaagag | caggtggcag | 1320 |
| cagggcaacg | tcttctcatg | ctccgtgatg | catgaggctc | tgcacaacca | ctacacccag | 1380 |
| aagagcctct | ccctgtctcc | cggc | | | | 1404 |

<210> SEQ ID NO 98
<211> LENGTH: 711
<212> TYPE: DNA
<213> ORGANISM: Artificial
<220> FEATURE:
<223> OTHER INFORMATION: Full-length nucleotide sequence of NYA-0001-LC

<400> SEQUENCE: 98

| | | | | | |
|---|---|---|---|---|---|
| atggtgctgc | agacccaggt | gttcatctcc | ctgctgctgt | ggatctccgg | cgcgtacggc | 60 |
| cagtctgtgt | tgacgcagcc | gccctcagtg | tctgcggccc | caggacagaa | ggtcaccatc | 120 |
| tcctgctctg | gaagcagctc | caacattggg | aataattatg | tatcctggta | ccagcagctc | 180 |
| ccaggaacag | cccccaaact | cctcatttat | gacaataata | agcgaccctc | agggattcct | 240 |
| gaccgattct | ctggctccaa | gtctggcacg | tcagccaccc | tgggcatcac | cggactccag | 300 |
| actggggacg | aggccgatta | ttactgcgga | acatgggata | gcagcctgag | tgccccttgg | 360 |
| gtgttcggcg | gagggaccaa | ggtcaccgtc | ctaggccagc | ctaaggctgc | ccctagcgtg | 420 |

```
accctgttcc ctccttccag cgaggagctt caagctaaca aggccaccct ggtgtgtctt    480
atctctgact tctaccctgg cgctgtgacc gtggcctgga aggctgacag ctcccctgtg    540
aaggccggag tggagaccac cacacctagc aagcagtcta acaacaagta cgctgccagc    600
tcctacctga gccttacccc tgagcagtgg aagtctcaca gaagctactc ctgtcaagtg    660
acccacgagg gcagcaccgt ggagaagacc gtggctccta ccgagtgttc c             711
```

<210> SEQ ID NO 99
<211> LENGTH: 468
<212> TYPE: PRT
<213> ORGANISM: Artificial
<220> FEATURE:
<223> OTHER INFORMATION: Full-length amino acid sequence of NYA-0001-
      Fab-HC1-k delete

<400> SEQUENCE: 99

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Val Val Gln
            20                  25                  30

Pro Gly Arg Ser Leu Thr Pro Ser Cys Ser Ala Ser Gly Phe Ser Ile
        35                  40                  45

Arg Ser Tyr Asp Ile His Trp Val Arg Gln Ala Pro Gly Lys Gly Leu
    50                  55                  60

Glu Trp Val Ala Thr Ile Ser Tyr Asp Gly Ser Gln Lys Tyr Phe Ala
65                  70                  75                  80

Asp Ser Val Lys Gly Arg Phe Thr Ile Phe Arg Asp Glu Ser Glu Asn
                85                  90                  95

Met Val Tyr Leu Gln Met Ser Gly Leu Arg Val Glu Asp Thr Ala Val
            100                 105                 110

Tyr His Cys Ala Arg Gly Ser Ser Gly His Tyr Glu Ala Phe Asp Ile
        115                 120                 125

Trp Gly Gln Gly Thr Met Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Ala
                245                 250                 255

Ala Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Ser Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
```

```
            305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
                340                 345                 350
Pro Ile Glu Lys Thr Ile Ser Lys Ala Lys Gly Gln Pro Arg Glu Pro
                355                 360                 365
Gln Val Tyr Val Leu Pro Pro Ser Arg Asp Glu Leu Thr Lys Asn Gln
                370                 375                 380
Val Ser Leu Leu Cys Leu Val Lys Gly Phe Tyr Pro Ser Asp Ile Ala
385                 390                 395                 400
Val Glu Trp Glu Ser Asn Gly Gln Pro Glu Asn Asn Tyr Leu Thr Trp
                405                 410                 415
Pro Pro Val Leu Asp Ser Asp Gly Ser Phe Phe Leu Tyr Ser Lys Leu
                420                 425                 430
Thr Val Asp Lys Ser Arg Trp Gln Gln Gly Asn Val Phe Ser Cys Ser
                435                 440                 445
Val Met His Glu Ala Leu His Asn His Tyr Thr Gln Lys Ser Leu Ser
        450                 455                 460
Leu Ser Pro Gly
465

<210> SEQ ID NO 100
<211> LENGTH: 237
<212> TYPE: PRT
<213> ORGANISM: Artificial
<220> FEATURE:
<223> OTHER INFORMATION: Full-length amino acid sequence of NYA-0001-LC

<400> SEQUENCE: 100

Met Val Leu Gln Thr Gln Val Phe Ile Ser Leu Leu Leu Trp Ile Ser
1               5                   10                  15
Gly Ala Tyr Gly Gln Ser Val Leu Thr Gln Pro Pro Ser Val Ser Ala
                20                  25                  30
Ala Pro Gly Gln Lys Val Thr Ile Ser Cys Ser Gly Ser Ser Ser Asn
            35                  40                  45
Ile Gly Asn Asn Tyr Val Ser Trp Tyr Gln Gln Leu Pro Gly Thr Ala
        50                  55                  60
Pro Lys Leu Leu Ile Tyr Asp Asn Asn Lys Arg Pro Ser Gly Ile Pro
65                  70                  75                  80
Asp Arg Phe Ser Gly Ser Lys Ser Gly Thr Ser Ala Thr Leu Gly Ile
                85                  90                  95
Thr Gly Leu Gln Thr Gly Asp Glu Ala Asp Tyr Tyr Cys Gly Thr Trp
                100                 105                 110
Asp Ser Ser Leu Ser Ala Pro Trp Val Phe Gly Gly Gly Thr Lys Val
            115                 120                 125
Thr Val Leu Gly Gln Pro Lys Ala Ala Pro Ser Val Thr Leu Phe Pro
        130                 135                 140
Pro Ser Ser Glu Glu Leu Gln Ala Asn Lys Ala Thr Leu Val Cys Leu
145                 150                 155                 160
Ile Ser Asp Phe Tyr Pro Gly Ala Val Thr Val Ala Trp Lys Ala Asp
                165                 170                 175
Ser Ser Pro Val Lys Ala Gly Val Glu Thr Thr Thr Pro Ser Lys Gln
            180                 185                 190
Ser Asn Asn Lys Tyr Ala Ala Ser Ser Tyr Leu Ser Leu Thr Pro Glu
```

```
                195                 200                 205
Gln Trp Lys Ser His Arg Ser Tyr Ser Cys Gln Val Thr His Glu Gly
        210                 215                 220
Ser Thr Val Glu Lys Thr Val Ala Pro Thr Glu Cys Ser
225                 230                 235
```

<210> SEQ ID NO 101
<211> LENGTH: 1404
<212> TYPE: DNA
<213> ORGANISM: Artificial
<220> FEATURE:
<223> OTHER INFORMATION: Full-length nucleotide sequence of NYA-1143-Fab-HC1-k delete

<400> SEQUENCE: 101

| | | | | | |
|---|---|---|---|---|---|
| atgaaacacc | tgtggttctt | cctcctgctg | gtggcagctc | ccagatgggt | gctgagcgag | 60 |
| gtgcagctgg | tggagtctgg | gggaggcgtg | gtccagcctg | gaggtccct | gacaccctcc | 120 |
| tgttcagcgt | ctggattctc | catccgtagc | tatgatatac | actgggtccg | cctggctcca | 180 |
| ggcaaggggc | tagagtgggt | ggccactata | tcatatgatg | gaagtcagaa | gtacttcgca | 240 |
| gactccgtga | agggccgatt | taccatcttc | agagacgaat | cggagaacat | ggtgtatctg | 300 |
| caaatgagcg | gcctgagagt | tgaggacacg | gctgtttatc | actgtgcgag | agggagtagt | 360 |
| ggtcattatg | aggcttttga | tatctggggc | caagggacaa | tggtcaccgt | ctcttcagcc | 420 |
| tccaccaagg | gcccaagcgt | cttccccctg | gcaccctcct | ccaagagcac | ctctggcggc | 480 |
| acagccgccc | tgggctgcct | ggtcaaggac | tacttcccg | aacccgtgac | cgtgagctgg | 540 |
| aactcaggcg | ccctgaccag | cggcgtgcac | accttcccg | ctgtcctgca | gtcctcagga | 600 |
| ctctactccc | tcagcagcgt | ggtgaccgtg | ccctccagca | gcttgggcac | ccagacctac | 660 |
| atctgcaacg | tgaatcacaa | gcccagcaac | accaaggtgg | acaagagagt | tgagcccaaa | 720 |
| tcttgtgaca | aaactcacac | atgcccaccc | tgcccagcac | ctgaagccgc | aggggggaccc | 780 |
| tcagtcttcc | tcttcccccc | aaaacccaag | gacaccctca | tgatctcccg | gacccctgag | 840 |
| gtcacatgcg | tggtggtgtc | agtgagccac | gaagaccctg | aggtcaagtt | caactggtac | 900 |
| gtggacggcg | tggaggtgca | taatgccaag | acaaagcccc | gggaggagca | gtacaacagc | 960 |
| acgtaccggg | tggtcagcgt | cctcaccgtc | ctgcaccagg | actggctgaa | tggcaaggag | 1020 |
| tacaagtgca | aggtctccaa | caaagccctc | ccagccccca | tcgagaaaac | catctccaaa | 1080 |
| gccaaaggcc | agccccggga | accacaggtg | tacgtgctgc | ccccatcccg | ggacgagctg | 1140 |
| accaagaacc | aggtcagcct | gctgtgcctg | gtcaaaggct | tctatcccag | cgacatcgcc | 1200 |
| gtggagtggg | agagcaatgg | ccagcccgag | aacaactacc | tgacctggcc | tcccgtgctg | 1260 |
| gactccgacg | gctccttctt | cctctacagc | aagctcaccg | tggacaagag | caggtggcag | 1320 |
| cagggcaacg | tcttctcatg | ctccgtgatg | catgaggctc | tgcacaacca | ctacacccag | 1380 |
| aagagcctct | ccctgtctcc | cggc | | | | 1404 |

<210> SEQ ID NO 102
<211> LENGTH: 711
<212> TYPE: DNA
<213> ORGANISM: Artificial
<220> FEATURE:
<223> OTHER INFORMATION: Full-length nucleotide sequence of NYA-1143-LC

<400> SEQUENCE: 102

| | | | | | |
|---|---|---|---|---|---|
| atggtgctgc | agacccaggt | gttcatctcc | ctgctgctgt | ggatctccgg | cgcgtacggc | 60 |

| | |
|---|---|
| cagtctgtgt tgacgcagcc gccctcagtg tctgcggccc caggacagaa ggtcaccatc | 120 |
| tcctgctctg gaagcagctc caacattggg aattggtatg tatcctggta ccagcagctc | 180 |
| ccaggaacag cccccaaact cctcatttat gacaataata agcgaccctc agggattcct | 240 |
| gaccgattct ctggctccaa gtctggcacg tcagccaccc tgggcatcac cggactccag | 300 |
| actggggacg aggccgatta ttactgcgga acatgggata gcagcctgag tgccccttgg | 360 |
| gtgttcggcg agggaccaa ggtcaccgtc ctaggccagc ctaaggctgc ccctagcgtg | 420 |
| accctgttcc ctccttccag cgaggagctt caagctaaca aggccaccct ggtgtgtctt | 480 |
| atctctgact tctaccctgg cgctgtgacc gtggcctgga aggctgacag ctcccctgtg | 540 |
| aaggccggag tggagaccac cacacctagc aagcagtcta acaacaagta cgctgccagc | 600 |
| tcctacctga gccttacccc tgagcagtgg aagtctcaca gaagctactc ctgtcaagtg | 660 |
| acccacgagg gcagcaccgt ggagaagacc gtggctccta ccgagtgttc c | 711 |

<210> SEQ ID NO 103
<211> LENGTH: 1476
<212> TYPE: DNA
<213> ORGANISM: Artificial
<220> FEATURE:
<223> OTHER INFORMATION: Full-length nucleotide sequence of C3E-7085-
     HC2-k delete

<400> SEQUENCE: 103

| | |
|---|---|
| atgaaacacc tgtggttctt cctcctgctg gtggcagctc ccagatgggt gctgagcgga | 60 |
| gaagtgcagc tggtggaatc cggggggggc ctggtgcagc tgggggggag cctgagactg | 120 |
| agttgtgccg cctctggggt gacatttaac tactatggca tgtcttggat ccgccaggca | 180 |
| cctggaaagg gcctggagtg ggtggccagc atcactaggt ccggcgggcg aatctactat | 240 |
| cccgacagcg tcaagggcag gttcacaatt tcccgcgaga cacacagaa aactctgtac | 300 |
| ctgcagatga atagcctgag agccgaagat acagctgtgt actattgcac tctggacggc | 360 |
| agggatgggt gggtcgccta ttgggggcag ggaaccctgg tgacagtcag ctccggagga | 420 |
| ggaggatctg gcggaggagg cagtggggga ggcgggtcaa actttatgct cactcagccg | 480 |
| tcctctgttt ctggcgtacc tggccaacgg gtgaccatta gctgtacggg taataccggg | 540 |
| aatatcgggt ctaactacgt gaactggtat cagcagcttc agggacagc tcccaagttg | 600 |
| ctgatctatc gcgacgacaa aagaccctca ggggtccctg accgatttag tggcagcaaa | 660 |
| agcggtactt ccgcttccct ggcgataacc ggctttcagg ccgaagatga ggcagactac | 720 |
| tattgccagt catattccag cggcttcatc ttcggaggcg gaactaagct gacagtgttg | 780 |
| gcagccgagc ccaaatcttc tgacaaaact cacacatgcc caccctgccc agcacctgaa | 840 |
| gccgcagggg gaccctcagt cttcctcttc ccccccaaaac ccaaggacac cctcatgatc | 900 |
| tcccggaccc ctgaggtcac atgcgtggtg gtgtcagtga gccacgaaga ccctgaggtc | 960 |
| aagttcaact ggtacgtgga cggcgtggag gtgcataatg ccaagacaaa gccccgggag | 1020 |
| gagcagtaca acagcacgta ccgggtggtc agcgtcctca ccgtcctgca ccaggactgg | 1080 |
| ctgaatggca aggagtacaa gtgcaaggtc tccaacaaag ccctcccagc ccccatcgag | 1140 |
| aaaaccatct ccaaagccaa aggccagccc cgggaaccac aggtgtacgt gtaccccccca | 1200 |
| tcccgggacg agctgaccaa gaaccaggtc agcctgacct gcctggtcaa aggcttctat | 1260 |
| cccagcgaca tcgccgtgga gtgggagagc aatggccagc cgagaacaa ctacaagacc | 1320 |
| accctcccg tgctggactc cgacggctcc ttcgccctcg tgagcaagct caccgtggac | 1380 |

-continued

```
aagagcaggt ggcagcaggg caacgtcttc tcatgctccg tgatgcatga ggctctgcac    1440
aaccactaca cccagaagag cctctccctg tctccc                              1476
```

<210> SEQ ID NO 104
<211> LENGTH: 468
<212> TYPE: PRT
<213> ORGANISM: Artificial
<220> FEATURE:
<223> OTHER INFORMATION: Full-length amino acid sequence of NYA-1143-
    Fab-HC1-k delete

<400> SEQUENCE: 104

Met Lys His Leu Trp Phe Phe Leu Leu Val Ala Ala Pro Arg Trp
1               5                   10                  15

Val Leu Ser Glu Val Gln Leu Val Glu Ser Gly Gly Gly Val Gln
                20                  25                  30

Pro Gly Arg Ser Leu Thr Pro Ser Cys Ser Ala Ser Gly Phe Ser Ile
                35                  40                  45

Arg Ser Tyr Asp Ile His Trp Val Arg Leu Ala Pro Gly Lys Gly Leu
        50                  55                  60

Glu Trp Val Ala Thr Ile Ser Tyr Asp Gly Ser Gln Lys Tyr Phe Ala
65                  70                  75                  80

Asp Ser Val Lys Gly Arg Phe Thr Ile Phe Arg Asp Glu Ser Glu Asn
                85                  90                  95

Met Val Tyr Leu Gln Met Ser Gly Leu Arg Val Glu Asp Thr Ala Val
                100                 105                 110

Tyr His Cys Ala Arg Gly Ser Ser Gly His Tyr Glu Ala Phe Asp Ile
            115                 120                 125

Trp Gly Gln Gly Thr Met Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Ala
                245                 250                 255

Ala Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Ser Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala

```
              340                 345                 350
Pro Ile Glu Lys Thr Ile Ser Lys Ala Lys Gly Gln Pro Arg Glu Pro
            355                 360                 365

Gln Val Tyr Val Leu Pro Pro Ser Arg Asp Glu Leu Thr Lys Asn Gln
        370                 375                 380

Val Ser Leu Leu Cys Leu Val Lys Gly Phe Tyr Pro Ser Asp Ile Ala
385                 390                 395                 400

Val Glu Trp Glu Ser Asn Gly Gln Pro Glu Asn Asn Tyr Leu Thr Trp
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465

<210> SEQ ID NO 105
<211> LENGTH: 237
<212> TYPE: PRT
<213> ORGANISM: Artificial
<220> FEATURE:
<223> OTHER INFORMATION: Full-length amino acid sequence of NYA-1143-LC

<400> SEQUENCE: 105

Met Val Leu Gln Thr Gln Val Phe Ile Ser Leu Leu Trp Ile Ser
1               5                   10                  15

Gly Ala Tyr Gly Gln Ser Val Leu Thr Gln Pro Pro Ser Val Ser Ala
            20                  25                  30

Ala Pro Gly Gln Lys Val Thr Ile Ser Cys Ser Gly Ser Ser Ser Asn
        35                  40                  45

Ile Gly Asn Trp Tyr Val Ser Trp Tyr Gln Gln Leu Pro Gly Thr Ala
    50                  55                  60

Pro Lys Leu Leu Ile Tyr Asp Asn Asn Lys Arg Pro Ser Gly Ile Pro
65                  70                  75                  80

Asp Arg Phe Ser Gly Ser Lys Ser Gly Thr Ser Ala Thr Leu Gly Ile
                85                  90                  95

Thr Gly Leu Gln Thr Gly Asp Glu Ala Asp Tyr Tyr Cys Gly Thr Trp
            100                 105                 110

Asp Ser Ser Leu Ser Ala Pro Trp Val Phe Gly Gly Thr Lys Val
        115                 120                 125

Thr Val Leu Gly Gln Pro Lys Ala Ala Pro Ser Val Thr Leu Phe Pro
    130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
```

<210> SEQ ID NO 106
<211> LENGTH: 493
<212> TYPE: PRT
<213> ORGANISM: Artificial
<220> FEATURE:
<223> OTHER INFORMATION: Full-length amino acid sequence of C3E-7085-HC2-k delete

<400> SEQUENCE: 106

| | | | | | | | | | | | | | | |
|---|---|---|---|---|---|---|---|---|---|---|---|---|---|---|
| Met | Lys | His | Leu | Trp | Phe | Phe | Leu | Leu | Leu | Val | Ala | Ala | Pro | Arg | Trp |
| 1 | | | | 5 | | | | | 10 | | | | | 15 | |

Val Leu Ser Gly Glu Val Gln Leu Val Glu Ser Gly Gly Gly Leu Val
            20                  25                  30

Gln Pro Gly Gly Ser Leu Arg Leu Ser Cys Ala Ala Ser Gly Val Thr
        35                  40                  45

Phe Asn Tyr Tyr Gly Met Ser Trp Ile Arg Gln Ala Pro Gly Lys Gly
50                  55                  60

Leu Glu Trp Val Ala Ser Ile Thr Arg Ser Gly Gly Arg Ile Tyr Tyr
65                  70                  75                  80

Pro Asp Ser Val Lys Gly Arg Phe Thr Ile Ser Arg Glu Asn Thr Gln
                85                  90                  95

Lys Thr Leu Tyr Leu Gln Met Asn Ser Leu Arg Ala Glu Asp Thr Ala
            100                 105                 110

Val Tyr Tyr Cys Thr Leu Asp Gly Arg Asp Gly Trp Val Ala Tyr Trp
        115                 120                 125

Gly Gln Gly Thr Leu Val Thr Val Ser Ser Gly Gly Gly Ser Gly
130                 135                 140

Gly Gly Gly Ser Gly Gly Gly Ser Asn Phe Met Leu Thr Gln Pro
145                 150                 155                 160

Ser Ser Val Ser Gly Val Pro Gly Gln Arg Val Thr Ile Ser Cys Thr
                165                 170                 175

Gly Asn Thr Gly Asn Ile Gly Ser Asn Tyr Val Asn Trp Tyr Gln Gln
            180                 185                 190

Leu Pro Gly Thr Ala Pro Lys Leu Leu Ile Tyr Arg Asp Asp Lys Arg
        195                 200                 205

Pro Ser Gly Val Pro Asp Arg Phe Ser Gly Ser Lys Ser Gly Thr Ser
210                 215                 220

Ala Ser Leu Ala Ile Thr Gly Phe Gln Ala Glu Asp Glu Ala Asp Tyr
225                 230                 235                 240

Tyr Cys Gln Ser Tyr Ser Ser Gly Phe Ile Phe Gly Gly Gly Thr Lys
                245                 250                 255

Leu Thr Val Leu Ala Ala Glu Pro Lys Ser Ser Asp Lys Thr His Thr
            260                 265                 270

Cys Pro Pro Cys Pro Ala Pro Glu Ala Ala Gly Gly Pro Ser Val Phe
        275                 280                 285

Leu Phe Pro Pro Lys Pro Lys Asp Thr Leu Met Ile Ser Arg Thr Pro
290                 295                 300

Glu Val Thr Cys Val Val Val Ser Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

| | | | | | | | | | | | |
|---|---|---|---|---|---|---|---|---|---|---|---|
|Leu|Thr|Val|Leu|His|Gln|Asp|Trp|Leu|Asn|Gly|Lys|Glu|Tyr|Lys|Cys|
| | |355| | | |360| | | |365| |

Lys Val Ser Asn Lys Ala Leu Pro Ala Pro Ile Glu Lys Thr Ile Ser
    370                375                380

Lys Ala Lys Gly Gln Pro Arg Glu Pro Gln Val Tyr Val Tyr Pro Pro
385                390                395              400

Ser Arg Asp Glu Leu Thr Lys Asn Gln Val Ser Leu Thr Cys Leu Val
            405                410              415

Lys Gly Phe Tyr Pro Ser Asp Ile Ala Val Glu Trp Glu Ser Asn Gly
        420              425              430

Gln Pro Glu Asn Asn Tyr Lys Thr Thr Pro Pro Val Leu Asp Ser Asp
            435              440              445

Gly Ser Phe Ala Leu Val Ser Lys Leu Thr Val Asp Lys Ser Arg Trp
450                455              460

Gln Gln Gly Asn Val Phe Ser Cys Ser Val Met His Glu Ala Leu His
465                470              475              480

Asn His Tyr Thr Gln Lys Ser Leu Ser Leu Ser Pro Gly
            485                490

<210> SEQ ID NO 107
<211> LENGTH: 1497
<212> TYPE: DNA
<213> ORGANISM: Artificial
<220> FEATURE:
<223> OTHER INFORMATION: Full-length nucleotide sequence of NYA-1143-
     HC1-k delete

<400> SEQUENCE: 107

```
atgaaacacc tgtggttctt cctcctgctg gtggcagctc ccagatgggt gctgagcgga      60
gaggtgcagc tggtggagtc tgggggaggc gtggtccagc ctgggaggtc cctgacaccc     120
tcctgttcag cgtctggatt ctccatccgt agctatgata tacactgggt ccgcctggct     180
ccaggcaagg gctagagtg gtggccact atatcatatg atggaagtca gaagtacttc       240
gcagactccg tgaagggccg atttaccatc ttcagagacg aatcggagaa catggtgtat     300
ctgcaaatga gcggcctgag agttgaggac acggctgttt atcactgtgc gagagggagt     360
agtggtcatt atgaggcttt tgatatctgg ggccaaggga caatggtcac cgtctcttca     420 ggtgaggcg ttcaggcgg aggtggcagc ggcggtggcg ggagtcagtc tgtgttgacg       480
cagccgccct cagtgtctgc ggccccagga cagaaggtca ccatctcctg ctctggaagc     540
agctccaaca ttgggaattg gtatgtatcc tggtaccagc agctcccagg aacagccccc     600
aaactcctca tttatgacaa taataagcga ccctcaggga ttcctgaccg attctctggc     660
tccaagtctg gcacgtcagc caccctgggc atcaccggac tccagactgg ggacgaggcc     720
gattattact gcggaacatg ggatagcagc ctgagtgccc ttgggtgtt cggcggaggg     780 accaaggtca ccgtcctagc agccgagccc aaatcttctg acaaaactca cacatgccca     840
ccctgcccag cacctgaagc cgcagggga ccctcagtct tcctcttccc cccaaaaccc      900
aaggacaccc tcatgatctc ccggacccct gaggtcacat gcgtggtggt gtcagtgagc     960
cacgaagacc ctgaggtcaa gttcaactgg tacgtgacg gcgtggaggt gcataatgcc     1020
aagacaaagc cccgggagga gcagtacaac agcacgtacc gggtggtcag cgtcctcacc    1080
gtcctgcacc aggactggct gaatggcaag gagtacaagt gcaaggtctc caacaaagcc    1140
ctcccagccc ccatcgagaa aaccatctcc aaagccaaag gccagccccg ggaaccacag    1200
gtgtacgtgc tgccccatc ccgggacgag ctgaccaaga accaggtcag cctgctgtgc    1260
```

```
ctggtcaaag gcttctatcc cagcgacatc gccgtggagt gggagagcaa tggccagccc    1320
gagaacaact acctgacctg gcctcccgtg ctggactccg acggctcctt cttcctctac    1380
agcaagctca ccgtggacaa gagcaggtgg cagcagggca acgtcttctc atgctccgtg    1440
atgcatgagg ctctgcacaa ccactacacc cagaagagcc tctccctgtc tcccggc       1497

<210> SEQ ID NO 108
<211> LENGTH: 499
<212> TYPE: PRT
<213> ORGANISM: Artificial
<220> FEATURE:
<223> OTHER INFORMATION: Full-length amino acid sequence of NYA-1143-
      HC1-k delete

<400> SEQUENCE: 108

Met Lys His Leu Trp Phe Phe Leu Leu Val Ala Ala Pro Arg Trp
1               5                   10                  15

Val Leu Ser Gly Glu Val Gln Leu Val Glu Ser Gly Gly Val Val
                20                  25                  30

Gln Pro Gly Arg Ser Leu Thr Pro Ser Cys Ser Ala Ser Gly Phe Ser
                35                  40                  45

Ile Arg Ser Tyr Asp Ile His Trp Val Arg Leu Ala Pro Gly Lys Gly
        50                  55                  60

Leu Glu Trp Val Ala Thr Ile Ser Tyr Asp Gly Ser Gln Lys Tyr Phe
65                  70                  75                  80

Ala Asp Ser Val Lys Gly Arg Phe Thr Ile Phe Arg Asp Glu Ser Glu
                85                  90                  95

Asn Met Val Tyr Leu Gln Met Ser Gly Leu Arg Val Glu Asp Thr Ala
                100                 105                 110

Val Tyr His Cys Ala Arg Gly Ser Ser Gly His Tyr Glu Ala Phe Asp
            115                 120                 125

Ile Trp Gly Gln Gly Thr Met Val Thr Val Ser Ser Gly Gly Gly Gly
        130                 135                 140

Ser Gly Gly Gly Gly Ser Gly Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Trp Tyr Val Ser Trp Tyr
            180                 185                 190

Gln Gln Leu Pro Gly Thr Ala Pro Lys Leu Leu Ile Tyr Asp Asn Asn
        195                 200                 205

Lys Arg Pro Ser Gly Ile Pro Asp Arg Phe Ser Gly Ser Lys Ser Gly
    210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Val Thr Val Leu Ala Ala Glu Pro Lys Ser
            260                 265                 270

Ser Asp Lys Thr His Thr Cys Pro Pro Cys Pro Ala Pro Glu Ala Ala
        275                 280                 285

Gly Gly Pro Ser Val Phe Leu Phe Pro Pro Lys Pro Lys Asp Thr Leu
    290                 295                 300

Met Ile Ser Arg Thr Pro Glu Val Thr Cys Val Val Val Ser Val Ser
305                 310                 315                 320
```

```
His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Val Leu Pro Pro Ser Arg Asp Glu Leu Thr Lys Asn Gln Val
                405                 410                 415

Ser Leu Leu Cys Leu Val Lys Gly Phe Tyr Pro Ser Asp Ile Ala Val
            420                 425                 430

Glu Trp Glu Ser Asn Gly Gln Pro Glu Asn Asn Tyr Leu Thr Trp Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly

<210> SEQ ID NO 109
<211> LENGTH: 2142
<212> TYPE: DNA
<213> ORGANISM: Artificial
<220> FEATURE:
<223> OTHER INFORMATION: Full-length nucleotide sequence of C3E-7085-
      NYA-1154-Fab-HC2-k delete

<400> SEQUENCE: 109
atgaaacacc tgtggttctt cctcctgctg gtggcagctc ccagatgggt gctgagcgga     60
gaagtgcagc tggtggaatc cggggggggc ctggtgcagc tgggggggag cctgagactg    120
agttgtgccg cctctggggt gacatttaac tactatggca tgtcttggat ccgccaggca    180
cctggaaagg gcctggagtg ggtggccagc atcactaggt ccggcgggcg aatctactat    240
cccgacagcg tcaagggcag gttcacaatt cccgcgaga acacacagaa aactctgtac    300
ctgcagatga atagcctgag agccgaagat acagctgtgt actattgcac tctggacggc    360
agggatgggt gggtcgccta ttgggggcag ggaaccctgg tgacagtcag ctccggagga    420
ggaggatctg gcgaggagg cagtggggga ggcgggtcaa actttatgct cactcagccg    480
tcctctgttt ctggcgtacc tggccaacgg gtgaccatta gctgtacggg taataccggg    540
aatatcgggt ctaactacgt gaactggtat cagcagcttc agggacagc tcccaagttg    600 ctgatctatc gcgacgacaa aagaccctca ggggtccctg accgatttag tggcagcaaa    660
agcggtactt ccgcttccct ggcgataacc ggctttcagg ccgaagatga ggcagactac    720
tattgccagt catattccag cggcttcatc ttcggaggcg aactaagct gacagtgttg    780 gggggaggcg gttcagaggt gcagctggtg gagtctgggg gaggcgtggt ccagcctggg    840
aggtccctga caccctcctg ttcagcgtct ggattctcca tccgtagtta tgatatgcac    900
tgggtccgcc aggctccagg caaggggcta gagtgggtgg ccactatatc atatgatgga    960
```

| | |
|---|---|
| agtcagaagt acttcgcaga ctccgtgaag gccgattta ccatcttcag agacgaatcg | 1020 |
| gagaacatgg tgtatctgca aatgagcggc ctgagagttg aggacacggc cgtttatcac | 1080 |
| tgtgcgagag ggagtagtaa tcattatgag cttttgata tctggggcca agggacaatg | 1140 |
| gtcaccgtct cttcagcctc caccaagggc ccaagcgtct tcccctggc accctcctcc | 1200 |
| aagagcacct ctggcggcac agccgccctg gctgcctgg tcaaggacta cttccccgaa | 1260 |
| cccgtgaccg tgagctggaa ctcaggcgcc ctgaccagcg gcgtgcacac cttcccgct | 1320 |
| gtcctgcagt cctcaggact ctactccctc agcagcgtgg tgaccgtgcc ctccagcagc | 1380 |
| ttgggcaccc agacctacat ctgcaacgtg aatcacaagc ccagcaacac caaggtggac | 1440 |
| aagagagttg agcccaaatc ttgtgacaaa actcacacat gcccaccctg cccagcacct | 1500 |
| gaagccgcag ggggaccctc agtcttcctc ttcccccca aacccaagga cccctcatg | 1560 |
| atctcccgga ccctgaggt cacatgcgtg gtggtgtcag tgagccacga agaccctgag | 1620 |
| gtcaagttca actggtacgt ggacggcgtg gaggtgcata atgccaagac aaagccccgg | 1680 |
| gaggagcagt acaacagcac gtaccgggtg gtcagcgtcc tcaccgtcct gcaccaggac | 1740 |
| tggctgaatg gcaaggagta caagtgcaag gtctccaaca agccctccc agccccatc | 1800 |
| gagaaaacca tctccaaagc caaaggccag ccccgggaac acaggtgta cgtgtaccc | 1860 |
| ccatcccggg acgagctgac caagaaccag gtcagcctga cctgcctggt caaaggcttc | 1920 |
| tatcccagcg acatcgccgt ggagtgggag agcaatggcc agcccgagaa caactacaag | 1980 |
| accacccctc ccgtgctgga ctccgacggc tccttcgccc tcgtgagcaa gctcaccgtg | 2040 |
| gacaagagca ggtggcagca gggcaacgtc ttctcatgct ccgtgatgca tgaggctctg | 2100 |
| cacaaccact acacccagaa gagcctctcc ctgtctcccg gc | 2142 |

<210> SEQ ID NO 110
<211> LENGTH: 711
<212> TYPE: DNA
<213> ORGANISM: Artificial
<220> FEATURE:
<223> OTHER INFORMATION: Full-length nucleotide sequence of NYA-1154-LC

<400> SEQUENCE: 110

| | |
|---|---|
| atggtgctgc agacccaggt gttcatctcc ctgctgctgt ggatctccgg cgcgtacggc | 60 |
| cagtctgtgt tgacgcagcc gccctcagtg tctgcggccc caggacagaa ggtcaccatc | 120 |
| tcctgctctg gaagcagctc caacattggg aataattatg tatcctggta ccagcggctc | 180 |
| ccaggaacag ccccccaaact cctcatttat gacaataata gcgaccctc agggattcct | 240 |
| gaccgattct ctggctccaa gtctggcacg tcagccaccc tgggcatcac cggactccag | 300 |
| actggggacg aggccgatta ctactgcgga gcatgggata gcagcctgag tgcccccttgg | 360 |
| gtgttcggcg agggaccaa ggtcaccgtc ctaggccagc ctaaggctgc ccctagcgtg | 420 |
| accctgttcc ctccttccag cgaggagctt caagctaaca aggccaccct ggtgtgtctt | 480 |
| atctctgact ctaccctgg cgctgtgacc gtggcctgga agctgacag ctcccctgtg | 540 |
| aaggccggag tggagaccac cacacctagc aagcagtcta acaacaagta cgctgccagc | 600 |
| tcctacctga gccttacccc tgagcagtgg aagtctcaca gaagctactc ctgtcaagtg | 660 |
| acccacgagg gcagcaccgt ggagaagacc gtggctccta ccgagtgttc c | 711 |

<210> SEQ ID NO 111
<211> LENGTH: 735
<212> TYPE: DNA
<213> ORGANISM: Artificial

```
<220> FEATURE:
<223> OTHER INFORMATION: Full-length nucleotide sequence of OAA-HC1-k
      delete

<400> SEQUENCE: 111
atgaaacacc tgtggttctt cctcctgctg gtggcagctc ccagatgggt gctgagcgac      60
aaaactcaca catgcccacc ctgcccagca cctgaagccg caggggggacc ctcagtcttc    120 ctcttccccc caaaacccaa ggacaccctc atgatctccc ggacccctga ggtcacatgc    180
gtggtggtgt cagtgagcca cgaagaccct gaggtcaagt tcaactggta cgtggacggc    240
gtggaggtgc ataatgccaa gacaaagccc cgggaggagc agtacaacag cacgtaccgg    300
gtggtcagcg tcctcaccgt cctgcaccag gactggctga atggcaagga gtacaagtgc    360
aaggtctcca acaaagccct cccagccccc atcgagaaaa ccatctccaa agccaaaggc    420
cagccccggg aaccacaggt gtacgtgctg cccccatccc gggacgagct gaccaagaac    480
caggtcagcc tgctgtgcct ggtcaaaggc ttctatccca gcgacatcgc cgtggagtgg    540
gagagcaatg gccagcccga gaacaactac ctgacctggc tcccgtgct ggactccgac     600 ggctccttct cctctacag caagctcacc gtggacaaga gcaggtggca gcagggcaac     660
gtcttctcat gctccgtgat gcatgaggct ctgcacaacc actacaccca gaagagcctc    720
tccctgtctc ccggc                                                     735

<210> SEQ ID NO 112
<211> LENGTH: 714
<212> TYPE: PRT
<213> ORGANISM: Artificial
<220> FEATURE:
<223> OTHER INFORMATION: Full-length amino acid sequence of C3E-7085-
      NYA-1154-Fab-HC2-k delete

<400> SEQUENCE: 112

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Leu Val
                20                  25                  30

Gln Pro Gly Gly Ser Leu Arg Leu Ser Cys Ala Ala Ser Gly Val Thr
            35                  40                  45

Phe Asn Tyr Tyr Gly Met Ser Trp Ile Arg Gln Ala Pro Gly Lys Gly
        50                  55                  60

Leu Glu Trp Val Ala Ser Ile Thr Arg Ser Gly Gly Arg Ile Tyr Tyr
65                  70                  75                  80

Pro Asp Ser Val Lys Gly Arg Phe Thr Ile Ser Arg Glu Asn Thr Gln
                85                  90                  95

Lys Thr Leu Tyr Leu Gln Met Asn Ser Leu Arg Ala Glu Asp Thr Ala
            100                 105                 110

Val Tyr Tyr Cys Thr Leu Asp Gly Arg Asp Gly Trp Val Ala Tyr Trp
        115                 120                 125

Gly Gln Gly Thr Leu Val Thr Val Ser Ser Gly Gly Gly Gly Ser Gly
    130                 135                 140

Gly Gly Ser Gly Gly Gly Gly Ser Asn Phe Met Leu Thr Gln Pro
145                 150                 155                 160

Ser Ser Val Ser Gly Val Pro Gly Gln Arg Val Thr Ile Ser Cys Thr
                165                 170                 175

Gly Asn Thr Gly Asn Ile Gly Ser Asn Tyr Val Asn Trp Tyr Gln Gln
            180                 185                 190
```

Leu Pro Gly Thr Ala Pro Lys Leu Ile Tyr Arg Asp Asp Lys Arg
            195                 200                 205

Pro Ser Gly Val Pro Asp Arg Phe Ser Gly Ser Lys Ser Gly Thr Ser
210                 215                 220

Ala Ser Leu Ala Ile Thr Gly Phe Gln Ala Glu Asp Glu Ala Asp Tyr
225                 230                 235                 240

Tyr Cys Gln Ser Tyr Ser Ser Gly Phe Ile Phe Gly Gly Gly Thr Lys
                245                 250                 255

Leu Thr Val Leu Gly Gly Gly Ser Glu Val Gln Leu Val Glu Ser
            260                 265                 270

Gly Gly Gly Val Val Gln Pro Gly Arg Ser Leu Thr Pro Ser Cys Ser
            275                 280                 285

Ala Ser Gly Phe Ser Ile Arg Ser Tyr Asp Met His Trp Val Arg Gln
290                 295                 300

Ala Pro Gly Lys Gly Leu Glu Trp Val Ala Thr Ile Ser Tyr Asp Gly
305                 310                 315                 320

Ser Gln Lys Tyr Phe Ala Asp Ser Val Lys Gly Arg Phe Thr Ile Phe
                325                 330                 335

Arg Asp Glu Ser Glu Asn Met Val Tyr Leu Gln Met Ser Gly Leu Arg
            340                 345                 350

Val Glu Asp Thr Ala Val Tyr His Cys Ala Arg Gly Ser Ser Asn His
            355                 360                 365

Tyr Glu Ala Phe Asp Ile Trp Gly Gln Gly Thr Met Val Thr Val Ser
370                 375                 380

Ser Ala Ser Thr Lys Gly Pro Ser Val Phe Pro Leu Ala Pro Ser Ser
385                 390                 395                 400

Lys Ser Thr Ser Gly Gly Thr Ala Ala Leu Gly Cys Leu Val Lys Asp
                405                 410                 415

Tyr Phe Pro Glu Pro Val Thr Val Ser Trp Asn Ser Gly Ala Leu Thr
            420                 425                 430

Ser Gly Val His Thr Phe Pro Ala Val Leu Gln Ser Ser Gly Leu Tyr
            435                 440                 445

Ser Leu Ser Ser Val Val Thr Val Pro Ser Ser Ser Leu Gly Thr Gln
450                 455                 460

Thr Tyr Ile Cys Asn Val Asn His Lys Pro Ser Asn Thr Lys Val Asp
465                 470                 475                 480

Lys Arg Val Glu Pro Lys Ser Cys Asp Lys Thr His Thr Cys Pro Pro
                485                 490                 495

Cys Pro Ala Pro Glu Ala Ala Gly Gly Pro Ser Val Phe Leu Phe Pro
            500                 505                 510

Pro Lys Pro Lys Asp Thr Leu Met Ile Ser Arg Thr Pro Glu Val Thr
            515                 520                 525

Cys Val Val Val Ser Val Ser His Glu Asp Pro Glu Val Lys Phe Asn
530                 535                 540

Trp Tyr Val Asp Gly Val Glu Val His Asn Ala Lys Thr Lys Pro Arg
545                 550                 555                 560

Glu Glu Gln Tyr Asn Ser Thr Tyr Arg Val Val Ser Val Leu Thr Val
                565                 570                 575

Leu His Gln Asp Trp Leu Asn Gly Lys Glu Tyr Lys Cys Lys Val Ser
            580                 585                 590

Asn Lys Ala Leu Pro Ala Pro Ile Glu Lys Thr Ile Ser Lys Ala Lys
            595                 600                 605

Gly Gln Pro Arg Glu Pro Gln Val Tyr Val Tyr Pro Pro Ser Arg Asp

```
                610                 615                 620
Glu Leu Thr Lys Asn Gln Val Ser Leu Thr Cys Leu Val Lys Gly Phe
625                 630                 635                 640

Tyr Pro Ser Asp Ile Ala Val Glu Trp Glu Ser Asn Gly Gln Pro Glu
                645                 650                 655

Asn Asn Tyr Lys Thr Thr Pro Pro Val Leu Asp Ser Asp Gly Ser Phe
                660                 665                 670

Ala Leu Val Ser Lys Leu Thr Val Asp Lys Ser Arg Trp Gln Gln Gly
                675                 680                 685

Asn Val Phe Ser Cys Ser Val Met His Glu Ala Leu His Asn His Tyr
                690                 695                 700

Thr Gln Lys Ser Leu Ser Leu Ser Pro Gly
705                 710

<210> SEQ ID NO 113
<211> LENGTH: 237
<212> TYPE: PRT
<213> ORGANISM: Artificial
<220> FEATURE:
<223> OTHER INFORMATION: Full-length amino acid sequence of NYA-1154-LC

<400> SEQUENCE: 113

Met Val Leu Gln Thr Gln Val Phe Ile Ser Leu Leu Leu Trp Ile Ser
1               5                   10                  15

Gly Ala Tyr Gly Gln Ser Val Leu Thr Gln Pro Pro Ser Val Ser Ala
                20                  25                  30

Ala Pro Gly Gln Lys Val Thr Ile Ser Cys Ser Gly Ser Ser Ser Asn
            35                  40                  45

Ile Gly Asn Asn Tyr Val Ser Trp Tyr Gln Arg Leu Pro Gly Thr Ala
        50                  55                  60

Pro Lys Leu Leu Ile Tyr Asp Asn Asn Lys Arg Pro Ser Gly Ile Pro
65                  70                  75                  80

Asp Arg Phe Ser Gly Ser Lys Ser Gly Thr Ser Ala Thr Leu Gly Ile
                85                  90                  95

Thr Gly Leu Gln Thr Gly Asp Glu Ala Asp Tyr Tyr Cys Gly Ala Trp
            100                 105                 110

Asp Ser Ser Leu Ser Ala Pro Trp Val Phe Gly Gly Gly Thr Lys Val
        115                 120                 125

Thr Val Leu Gly Gln Pro Lys Ala Ala Pro Ser Val Thr Leu Phe Pro
130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235

<210> SEQ ID NO 114
<211> LENGTH: 245
<212> TYPE: PRT
```

<210> ORGANISM: Artificial
<220> FEATURE:
<223> OTHER INFORMATION: Full-length amino acid sequence of OAA-HC1-k delete

<400> SEQUENCE: 114

```
Met Lys His Leu Trp Phe Phe Leu Leu Val Ala Ala Pro Arg Trp
1               5                   10                  15
Val Leu Ser Asp Lys Thr His Thr Cys Pro Pro Cys Pro Ala Pro Glu
            20                  25                  30
Ala Ala Gly Gly Pro Ser Val Phe Leu Phe Pro Pro Lys Pro Lys Asp
                35                  40                  45
Thr Leu Met Ile Ser Arg Thr Pro Glu Val Thr Cys Val Val Val Ser
        50                  55                  60
Val Ser His Glu Asp Pro Glu Val Lys Phe Asn Trp Tyr Val Asp Gly
65                  70                  75                  80
Val Glu Val His Asn Ala Lys Thr Lys Pro Arg Glu Glu Gln Tyr Asn
                85                  90                  95
Ser Thr Tyr Arg Val Val Ser Val Leu Thr Val Leu His Gln Asp Trp
            100                 105                 110
Leu Asn Gly Lys Glu Tyr Lys Cys Lys Val Ser Asn Lys Ala Leu Pro
        115                 120                 125
Ala Pro Ile Glu Lys Thr Ile Ser Lys Ala Lys Gly Gln Pro Arg Glu
    130                 135                 140
Pro Gln Val Tyr Val Leu Pro Pro Ser Arg Asp Glu Leu Thr Lys Asn
145                 150                 155                 160
Gln Val Ser Leu Leu Cys Leu Val Lys Gly Phe Tyr Pro Ser Asp Ile
                165                 170                 175
Ala Val Glu Trp Glu Ser Asn Gly Gln Pro Glu Asn Asn Tyr Leu Thr
            180                 185                 190
Trp Pro Pro Val Leu Asp Ser Asp Gly Ser Phe Phe Leu Tyr Ser Lys
        195                 200                 205
Leu Thr Val Asp Lys Ser Arg Trp Gln Gln Gly Asn Val Phe Ser Cys
    210                 215                 220
Ser Val Met His Glu Ala Leu His Asn His Tyr Thr Gln Lys Ser Leu
225                 230                 235                 240
Ser Leu Ser Pro Gly
            245
```

<210> SEQ ID NO 115
<211> LENGTH: 2232
<212> TYPE: DNA
<213> ORGANISM: Artificial
<220> FEATURE:
<223> OTHER INFORMATION: Full-length nucleotide sequence of NYF-0010-HC2-k delete

<400> SEQUENCE: 115

```
atgaaacacc tgtggttctt cctcctgctg gtggcagctc ccagatgggt gctgagcgga    60
gaggtgcagc tggtggagtc tggggggaggc gtggtccagc ctgggaggtc cctgacaccc    120
tcctgttcag cgtctggatt ctccatccgt agttatgata tgcactgggt ccgccaggct    180
ccaggcaagg ggctagagtg ggtggccact atatcatatg atggaagtca gaagtacttc    240
gcagactccg tgaagggccg atttaccatc tcagagacg aatcggagaa catggtgtat    300
ctgcaaatga gcggcctgag agttgaggac acgccgtttt atcactgtgc gagagggagt    360
agtaatcatt atgaggcttt tgatatctgg ggccaaggga caatggtcac cgtctcttca    420
```

```
ggtggaggcg gttcaggcgg aggtggcagc ggcggtggcg ggagtcagtc tgtgttgacg      480
cagccgccct cagtgtctgc ggccccagga cagaaggtca ccatctcctg ctctggaagc      540
agctccaaca ttgggaataa ttatgtatcc tggtaccagc ggctcccagg aacagccccc      600
aaactcctca tttatgacaa taataagcga ccctcaggga ttcctgaccg attctctggc      660
tccaagtctg gcacgtcagc caccctgggc atcaccggac tccagactgg ggacgaggcc      720
gattactact gcgagcatg ggatagcagc ctgagtgccc cttgggtgtt cggcggaggg       780
accaaggtca ccgtcctagg gggaggcggt tcagaagtgc agctggtgga atccgggggg      840
ggcctggtgc agcctggggg gagcctgaga ctgagttgtg ccgcctctgg ggtgacattt      900
aactactatg gcatgtcttg gatccgccag gcacctggaa agggcctgga gtgggtggcc      960
agcatcacta ggtccggcgg gcgaatctac tatcccgaca cgtcaaggg caggttcaca      1020 atttcccgcg agaacacaca gaaaactctg tacctgcaga tgaatagcct gagagccgaa     1080
gatacagctg tgtactattg cactctggac ggcaggatg ggtgggtcgc ctattggggg       1140
cagggaaccc tggtgacagt cagctccgga ggaggaggat ctggcggagg aggcagtggg     1200
ggaggcgggt caaactttat gctcactcag ccgtcctctg tttctggcgt acctggccaa     1260
cgggtgacca ttagctgtac gggtaatacc gggaatatcg gtctaacta cgtgaactgg      1320 tatcagcagc ttccagggac agctcccaag ttgctgatct atcgcgacga caaaagaccc     1380
tcaggggtcc ctgaccgatt tagtggcagc aaaagcggta cttccgcttc cctggcgata     1440
accggctttc aggccgaaga tgaggcagac tactattgcc agtcatattc cagcggcttc     1500
atcttcggag gcggaactaa gctgacagtg ttggcagccg agcccaaatc ttctgacaaa     1560
actcacacat gcccaccctg cccagcacct gaagccgcag ggggaccctc agtcttcctc     1620
ttccccccaa aacccaagga caccctcatg atctcccgga cccctgaggt cacatgcgtg     1680
gtggtgtcag tgagccacga agaccctgag gtcaagttca actggtacgt ggacggcgtg     1740
gaggtgcata atgccaagac aaagccccgg gaggagcagt acaacagcac gtaccgggtg     1800
gtcagcgtcc tcaccgtcct gcaccaggac tggctgaatg gcaaggagta caagtgcaag     1860
gtctccaaca aagccctccc agcccccatc gagaaaacca tctccaaagc caaaggccag     1920
ccccgggaac cacaggtgta cgtgtacccc ccatcccggg acgagctgac caagaaccag     1980
gtcagcctga cctgcctggt caaaggcttc tatcccagcg acatcgccgt ggagtgggag     2040
agcaatggcc agcccgagaa caactacaag accacccctc ccgtgctgga ctccgacggc     2100
tccttcgccc tcgtgagcaa gctcaccgtg gacaagagca ggtggcagca gggcaacgtc     2160
ttctcatgct ccgtgatgca tgaggctctg cacaaccact acacccagaa gagcctctcc     2220
ctgtctcccg gc                                                         2232
```

<210> SEQ ID NO 116
<211> LENGTH: 2232
<212> TYPE: DNA
<213> ORGANISM: Artificial
<220> FEATURE:
<223> OTHER INFORMATION: Full-length nucleotide sequence of NYF-0004-
     HC2-k delete

<400> SEQUENCE: 116

```
atgaaacacc tgtggttctt cctcctgctg gtggcagctc ccagatgggt gctgagcgga       60
gaagtgcagc tggtggaatc cggggggggc tggtgcagc tgggggggag cctgagactg       120
agttgtgccg cctctggggt gacatttaac tactatggca tgtcttggat ccgccaggca     180
```

```
cctggaaagg gcctggagtg ggtggccagc atcactaggt ccggcgggcg aatctactat      240
cccgacagcg tcaagggcag gttcacaatt tcccgcgaga acacacagaa aactctgtac      300
ctgcagatga atagcctgag agccgaagat acagctgtgt actattgcac tctggacggc      360
agggatgggt gggtcgccta ttgggggcag ggaaccctgg tgacagtcag ctccggagga      420
ggaggatctg gcggaggagg cagtggggga ggcgggtcaa actttatgct cactcagccg      480
tcctctgttt ctggcgtacc tggccaacgg gtgaccatta gctgtacggg taataccggg      540
aatatcgggt ctaactacgt gaactggtat cagcagcttc agggacagc tcccaagttg       600 ctgatctatc gcgacgacaa aagaccctca ggggtccctg accgatttag tggcagcaaa      660
agcggtactt ccgcttccct ggcgataacc ggctttcagg ccgaagatga ggcagactac      720
tattgccagt catattccag cggcttcatc ttcggaggcg aactaagct gacagtgttg       780 gggggaggcg gttcagaggt gcagctggtg gagtctgggg gaggcgtggt ccagcctggg      840
aggtccctga caccctcctg ttcagcgtct ggattctcca tccgtagtta tgatatgcac      900
tgggtccgcc aggctccagg caaggggcta gagtgggtgg ccactatatc atatgatgga      960
agtcagaagt acttcgcaga ctccgtgaag ggccgattta ccatcttcag agacgaatcg     1020
gagaacatgg tgtatctgca aatgagcggc ctgagagttg aggacacggc cgtttatcac     1080
tgtgcgagag ggagtagtaa tcattatgag gctttttgata tctggggcca agggacaatg   1140
gtcaccgtct cttcaggtgg aggcggttca ggcggaggtg gcagcggcgg tggcgggagt    1200
cagtctgtgt tgacgcagcc gccctcagtg tctgcggccc caggacagaa ggtcaccatc    1260
tcctgctctg gaagcagctc caacattggg aataattatg tatcctggta ccagcggctc    1320
ccaggaacag ccccc aaact cctcatttat gacaataata agcgaccctc agggattcct   1380
gaccgattct ctggctccaa gtctggcacg tcagccaccc tgggcatcac cggactccag    1440
actggggacg aggccgatta ctactgcgga gcatgggata gcagcctgag tgcccccttgg  1500 gtgttcggcg gagggaccaa ggtcaccgtc ctagcagccg agcccaaatc ttctgacaaa    1560
actcacacat gcccaccctg cccagcacct gaagccgcag ggggaccctc agtcttcctc    1620
ttccccccaa aacccaagga caccctcatg atctcccgga cccctgaggt cacatgcgtg    1680
gtggtgtcag tgagccacga agaccctgag gtcaagttca actggtacgt ggacggcgtg    1740
gaggtgcata atgccaagac aaagcccgg gaggagcagt acaacagcac gtaccgggtg     1800
gtcagcgtcc tcaccgtcct gcaccaggac tggctgaatg caaggagta caagtgcaag     1860 gtctccaaca aagcccctccc agcccccatc gagaaaacca tctccaaagc caaggccag    1920 ccccgggaac acaggtgta cgtgtacccc ccatcccggg acgagctgac caagaaccag    1980
gtcagcctga cctgcctggt caaaggcttc tatcccagcg acatcgccgt ggagtgggag    2040
agcaatggcc agcccgagaa caactacaag accaccccctc ccgtgctgga ctccgacggc   2100
tccttcgccc tcgtgagcaa gctcaccgtg gacaagagca ggtggcagca gggcaacgtc    2160
ttctcatgct ccgtgatgca tgaggctctg cacaaccact acacccagaa gagcctctcc    2220
ctgtctcccg gc                                                         2232
```

<210> SEQ ID NO 117
<211> LENGTH: 2232
<212> TYPE: DNA
<213> ORGANISM: Artificial
<220> FEATURE:
<223> OTHER INFORMATION: Full-length nucleotide sequence of NYF-0011-
      HC2-k delete

<400> SEQUENCE: 117

```
atgaaacacc tgtggttctt cctcctgctg gtggcagctc ccagatgggt gctgagcgga      60
gaggtgcagc tggtggagtc tgggggaggc gtggtccagc ctggaggtc cctgacaccc     120
tcctgttcag cgtctggatt ctccatccgt agctatgata tacactgggt ccgcctggct     180
ccaggcaagg ggctagagtg ggtggccact atatcatatg atggaagtca gaagtacttc     240
gcagactccg tgaagggccg atttaccatc ttcagagacg aatcggagaa catggtgtat     300
ctgcaaatga gcggcctgag agttgaggac acggctgttt atcactgtgc gagagggagt     360
agtggtcatt atgaggcttt tgatatctgg ggccaaggga caatggtcac cgtctcttca     420
ggtggaggcg gttcaggcgg aggtggcagc ggcggtggcg ggagtcagtc tgtgttgacg     480
cagccgccct cagtgtctgc ggccccagga cagaaggtca ccatctcctg ctctggaagc     540
agctccaaca ttgggaattg gtatgtatcc tggtaccagc agctcccagg aacagccccc     600
aaactcctca tttatgacaa taataagcga ccctcaggga ttcctgaccg attctctggc     660
tccaagtctg gcacgtcagc caccctgggc atcaccggac tccagactgg ggacgaggcc     720
gattattact gcggaacatg ggatagcagc ctgagtgccc cttgggtgtt cggcggaggg     780
accaaggtca ccgtcctagg ggggaggcggt tcagaagtgc agctggtgga atccgggggg     840
ggcctggtgc agcctggggg gagcctgaga ctgagttgtg ccgcctctgg ggtgacattt     900
aactactatg gcatgtcttg gatccgccag gcacctggaa agggcctgga gtgggtggcc     960
agcatcacta ggtccggcgg gcgaatctac tatcccgaca cgtcaagggc aggttcaca    1020
atttcccgcg agaacacaca gaaaactctg tacctgcaga tgaatagcct gagagccgaa    1080
gatacagctg tgtactattg cactctggac ggcaggatg ggtgggtcgc ctattggggg     1140
cagggaaccc tggtgacagt cagctccgga ggaggaggat ctggcggagg aggcagtggg    1200
ggaggcgggt caaactttat gctcactcag ccgtcctctg tttctggcgt acctggccaa    1260
cgggtgacca ttagctgtac gggtaatacc gggaatatcg gtctaactat cgtgaactgg    1320
tatcagcagc ttccagggac agctcccaag ttgctgatct atcgcgacga caaaagaccc    1380
tcagggtcc ctgaccgatt tagtggcagc aaaagcggta cttccgcttc cctggcgata    1440
accggctttc aggccgaaga tgaggcagac tactattgcc agtcatattc cagcggcttc    1500
atcttcggag cgaactaa gctgacagtg ttggcagccg agcccaaatc ttctgacaaa    1560
actcacacat gcccaccctg cccagcacct gaagccgcag ggggaccctc agtcttcctc    1620
ttccccccaa aacccaagga caccctcatg atctcccgga cccctgaggt cacatgcgtg    1680
gtggtgtcag tgagccacga agaccctgag gtcaagttca actggtacgt ggacggcgtg    1740
gaggtgcata atgccaagac aaagccccgg gaggagcagt acaacagcac gtaccgggtg    1800
gtcagcgtcc tcaccgtcct gcaccaggac tggctgaatg gcaaggagta caagtgcaag    1860
gtctccaaca agccctccc agcccccatc gagaaaacca tctccaaagc caaaggccag    1920
ccccgggaac cacaggtgta cgtgtacccc ccatcccggg acgagctgac caagaaccag    1980
gtcagcctga cctgcctggt caaaggcttc tatcccagcg acatcgccgt ggagtgggag    2040
agcaatggcc agcccgagaa caactacaag accaccctc ccgtgctgga ctccgacggc    2100
tccttcgccc tcgtgagcaa gctcaccgtg gacaagagca ggtggcagca gggcaacgtc    2160
ttctcatgct ccgtgatgca tgaggctctg cacaaccact acacccagaa gagcctctcc    2220
ctgtctcccg gc                                                        2232
```

<210> SEQ ID NO 118
<211> LENGTH: 744
<212> TYPE: PRT
<213> ORGANISM: Artificial
<220> FEATURE:
<223> OTHER INFORMATION: Full-length amino acid sequence of NYF-0010-HC2-k delete

<400> SEQUENCE: 118

```
Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Val Val
            20                  25                  30

Gln Pro Gly Arg Ser Leu Thr Pro Ser Cys Ser Ala Ser Gly Phe Ser
        35                  40                  45

Ile Arg Ser Tyr Asp Met His Trp Val Arg Gln Ala Pro Gly Lys Gly
    50                  55                  60

Leu Glu Trp Val Ala Thr Ile Ser Tyr Asp Gly Ser Gln Lys Tyr Phe
65                  70                  75                  80

Ala Asp Ser Val Lys Gly Arg Phe Thr Ile Phe Arg Asp Glu Ser Glu
                85                  90                  95

Asn Met Val Tyr Leu Gln Met Ser Gly Leu Arg Val Glu Asp Thr Ala
            100                 105                 110

Val Tyr His Cys Ala Arg Gly Ser Ser Asn His Tyr Glu Ala Phe Asp
        115                 120                 125

Ile Trp Gly Gln Gly Thr Met Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Asn Tyr Val Ser Trp Tyr
            180                 185                 190

Gln Arg Leu Pro Gly Thr Ala Pro Lys Leu Leu Ile Tyr Asp Asn Asn
        195                 200                 205

Lys Arg Pro Ser Gly Ile Pro Asp Arg Phe Ser Gly Ser Lys Ser Gly
    210                 215                 220

Thr Ser Ala Thr Leu Gly Ile Thr Gly Leu Gln Thr Gly Asp Glu Ala
225                 230                 235                 240

Asp Tyr Tyr Cys Gly Ala Trp Asp Ser Ser Leu Ser Ala Pro Trp Val
                245                 250                 255

Phe Gly Gly Gly Thr Lys Val Thr Val Leu Gly Gly Gly Gly Ser Glu
            260                 265                 270

Val Gln Leu Val Glu Ser Gly Gly Gly Leu Val Gln Pro Gly Gly Ser
        275                 280                 285

Leu Arg Leu Ser Cys Ala Ala Ser Gly Val Thr Phe Asn Tyr Tyr Gly
    290                 295                 300

Met Ser Trp Ile Arg Gln Ala Pro Gly Lys Gly Leu Glu Trp Val Ala
305                 310                 315                 320

Ser Ile Thr Arg Ser Gly Gly Arg Ile Tyr Tyr Pro Asp Ser Val Lys
                325                 330                 335

Gly Arg Phe Thr Ile Ser Arg Glu Asn Thr Gln Lys Thr Leu Tyr Leu
            340                 345                 350

Gln Met Asn Ser Leu Arg Ala Glu Asp Thr Ala Val Tyr Tyr Cys Thr
        355                 360                 365
```

Leu Asp Gly Arg Asp Gly Trp Val Ala Tyr Trp Gln Gly Thr Leu
        370                 375                 380

Val Thr Val Ser Ser Gly Gly Gly Ser Gly Gly Gly Ser Gly
385                 390                 395                 400

Gly Gly Gly Ser Asn Phe Met Leu Thr Gln Pro Ser Ser Val Ser Gly
                405                 410                 415

Val Pro Gly Gln Arg Val Thr Ile Ser Cys Thr Gly Asn Thr Gly Asn
            420                 425                 430

Ile Gly Ser Asn Tyr Val Asn Trp Tyr Gln Gln Leu Pro Gly Thr Ala
        435                 440                 445

Pro Lys Leu Leu Ile Tyr Arg Asp Asp Lys Arg Pro Ser Gly Val Pro
450                 455                 460

Asp Arg Phe Ser Gly Ser Lys Ser Gly Thr Ser Ala Ser Leu Ala Ile
465                 470                 475                 480

Thr Gly Phe Gln Ala Glu Asp Glu Ala Asp Tyr Tyr Cys Gln Ser Tyr
                485                 490                 495

Ser Ser Gly Phe Ile Phe Gly Gly Gly Thr Lys Leu Thr Val Leu Ala
            500                 505                 510

Ala Glu Pro Lys Ser Ser Asp Lys Thr His Thr Cys Pro Pro Cys Pro
        515                 520                 525

Ala Pro Glu Ala Ala Gly Gly Pro Ser Val Phe Leu Phe Pro Pro Lys
530                 535                 540

Pro Lys Asp Thr Leu Met Ile Ser Arg Thr Pro Glu Val Thr Cys Val
545                 550                 555                 560

Val Val Ser Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Val Tyr Pro Pro Ser Arg Asp Glu Leu
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Ala Leu
690                 695                 700

Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly
            740

<210> SEQ ID NO 119
<211> LENGTH: 744
<212> TYPE: PRT
<213> ORGANISM: Artificial
<220> FEATURE:

<223> OTHER INFORMATION: Full-length amino acid sequence of NYF-0004-HC2-k delete

<400> SEQUENCE: 119

```
Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Leu Val
            20                  25                  30

Gln Pro Gly Gly Ser Leu Arg Leu Ser Cys Ala Ala Ser Gly Val Thr
        35                  40                  45

Phe Asn Tyr Tyr Gly Met Ser Trp Ile Arg Gln Ala Pro Gly Lys Gly
50                  55                  60

Leu Glu Trp Val Ala Ser Ile Thr Arg Ser Gly Gly Arg Ile Tyr Tyr
65                  70                  75                  80

Pro Asp Ser Val Lys Gly Arg Phe Thr Ile Ser Arg Glu Asn Thr Gln
                85                  90                  95

Lys Thr Leu Tyr Leu Gln Met Asn Ser Leu Arg Ala Glu Asp Thr Ala
            100                 105                 110

Val Tyr Tyr Cys Thr Leu Asp Gly Arg Asp Gly Trp Val Ala Tyr Trp
        115                 120                 125

Gly Gln Gly Thr Leu Val Thr Val Ser Ser Gly Gly Gly Ser Gly
130                 135                 140

Gly Gly Gly Ser Gly Gly Gly Ser Asn Phe Met Leu Thr Gln Pro
145                 150                 155                 160

Ser Ser Val Ser Gly Val Pro Gly Gln Arg Val Thr Ile Ser Cys Thr
                165                 170                 175

Gly Asn Thr Gly Asn Ile Gly Ser Asn Tyr Val Asn Trp Tyr Gln Gln
            180                 185                 190

Leu Pro Gly Thr Ala Pro Lys Leu Leu Ile Tyr Arg Asp Asp Lys Arg
        195                 200                 205

Pro Ser Gly Val Pro Asp Arg Phe Ser Gly Ser Lys Ser Gly Thr Ser
210                 215                 220

Ala Ser Leu Ala Ile Thr Gly Phe Gln Ala Glu Asp Glu Ala Asp Tyr
225                 230                 235                 240

Tyr Cys Gln Ser Tyr Ser Ser Gly Phe Ile Phe Gly Gly Gly Thr Lys
                245                 250                 255

Leu Thr Val Leu Gly Gly Gly Ser Glu Val Gln Leu Val Glu Ser
            260                 265                 270

Gly Gly Gly Val Val Gln Pro Gly Arg Ser Leu Thr Pro Ser Cys Ser
        275                 280                 285

Ala Ser Gly Phe Ser Ile Arg Ser Tyr Asp Met His Trp Val Arg Gln
290                 295                 300

Ala Pro Gly Lys Gly Leu Glu Trp Val Ala Thr Ile Ser Tyr Asp Gly
305                 310                 315                 320

Ser Gln Lys Tyr Phe Ala Asp Ser Val Lys Gly Arg Phe Thr Ile Phe
                325                 330                 335

Arg Asp Glu Ser Glu Asn Met Val Tyr Leu Gln Met Ser Gly Leu Arg
            340                 345                 350

Val Glu Asp Thr Ala Val Tyr His Cys Ala Arg Gly Ser Ser Asn His
        355                 360                 365

Tyr Glu Ala Phe Asp Ile Trp Gly Gln Gly Thr Met Val Thr Val Ser
370                 375                 380

Ser Gly Gly Gly Gly Ser Gly Gly Gly Gly Ser Gly Gly Gly Gly Ser
385                 390                 395                 400
```

```
Gln Ser Val Leu Thr Gln Pro Pro Ser Val Ala Ala Pro Gly Gln
            405                 410                 415

Lys Val Thr Ile Ser Cys Ser Gly Ser Ser Asn Ile Gly Asn Asn
        420                 425                 430

Tyr Val Ser Trp Tyr Gln Arg Leu Pro Gly Thr Ala Pro Lys Leu Leu
            435                 440                 445

Ile Tyr Asp Asn Asn Lys Arg Pro Ser Gly Ile Pro Asp Arg Phe Ser
450                 455                 460

Gly Ser Lys Ser Gly Thr Ser Ala Thr Leu Gly Ile Thr Gly Leu Gln
465                 470                 475                 480

Thr Gly Asp Glu Ala Asp Tyr Tyr Cys Gly Ala Trp Asp Ser Ser Leu
                485                 490                 495

Ser Ala Pro Trp Val Phe Gly Gly Thr Lys Val Thr Val Leu Ala
            500                 505                 510

Ala Glu Pro Lys Ser Ser Asp Lys Thr His Thr Cys Pro Pro Cys Pro
        515                 520                 525

Ala Pro Glu Ala Ala Gly Gly Pro Ser Val Phe Leu Phe Pro Pro Lys
        530                 535                 540

Pro Lys Asp Thr Leu Met Ile Ser Arg Thr Pro Glu Val Thr Cys Val
545                 550                 555                 560

Val Val Ser Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
            595                 600                 605

Gln Asp Trp Leu Asn Gly Lys Glu Tyr Lys Cys Lys Val Ser Asn Lys
        610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Val Tyr Pro Pro Ser Arg Asp Glu Leu
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Ala Leu
        690                 695                 700

Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly
            740

<210> SEQ ID NO 120
<211> LENGTH: 744
<212> TYPE: PRT
<213> ORGANISM: Artificial
<220> FEATURE:
<223> OTHER INFORMATION: Full-length amino acid sequence of NYF-0011-
      HC2-k delete

<400> SEQUENCE: 120

Met Lys His Leu Trp Phe Phe Leu Leu Leu Val Ala Ala Pro Arg Trp
```

-continued

```
1               5                   10                  15
Val Leu Ser Gly Glu Val Gln Leu Val Glu Ser Gly Gly Val Val
            20                  25                  30
Gln Pro Gly Arg Ser Leu Thr Pro Ser Cys Ser Ala Ser Gly Phe Ser
            35                  40                  45
Ile Arg Ser Tyr Asp Ile His Trp Val Arg Leu Ala Pro Gly Lys Gly
            50                  55                  60
Leu Glu Trp Val Ala Thr Ile Ser Tyr Asp Gly Ser Gln Lys Tyr Phe
65                  70                  75                  80
Ala Asp Ser Val Lys Gly Arg Phe Thr Ile Phe Arg Asp Glu Ser Glu
            85                  90                  95
Asn Met Val Tyr Leu Gln Met Ser Gly Leu Arg Val Glu Asp Thr Ala
            100                 105                 110
Val Tyr His Cys Ala Arg Gly Ser Ser His Tyr Glu Ala Phe Asp
            115                 120                 125
Ile Trp Gly Gln Gly Thr Met Val Thr Val Ser Ser Gly Gly Gly Gly
            130                 135                 140
Ser Gly Gly Gly Gly Ser Gly Gly Gly Ser Gln Ser Val Leu Thr
145                 150                 155                 160
Gln Pro Pro Ser Val Ser Ala Ala Pro Gly Gln Lys Val Thr Ile Ser
            165                 170                 175
Cys Ser Gly Ser Ser Ser Asn Ile Gly Asn Trp Tyr Val Ser Trp Tyr
            180                 185                 190
Gln Gln Leu Pro Gly Thr Ala Pro Lys Leu Leu Ile Tyr Asp Asn Asn
            195                 200                 205
Lys Arg Pro Ser Gly Ile Pro Asp Arg Phe Ser Gly Ser Lys Ser Gly
210                 215                 220
Thr Ser Ala Thr Leu Gly Ile Thr Gly Leu Gln Thr Gly Asp Glu Ala
225                 230                 235                 240
Asp Tyr Tyr Cys Gly Thr Trp Asp Ser Ser Leu Ser Ala Pro Trp Val
            245                 250                 255
Phe Gly Gly Gly Thr Lys Val Thr Val Leu Gly Gly Gly Ser Glu
            260                 265                 270
Val Gln Leu Val Glu Ser Gly Gly Gly Leu Val Gln Pro Gly Gly Ser
            275                 280                 285
Leu Arg Leu Ser Cys Ala Ala Ser Gly Val Thr Phe Asn Tyr Gly
            290                 295                 300
Met Ser Trp Ile Arg Gln Ala Pro Gly Lys Gly Leu Glu Trp Val Ala
305                 310                 315                 320
Ser Ile Thr Arg Ser Gly Gly Arg Ile Tyr Tyr Pro Asp Ser Val Lys
            325                 330                 335
Gly Arg Phe Thr Ile Ser Arg Glu Asn Thr Gln Lys Thr Leu Tyr Leu
            340                 345                 350
Gln Met Asn Ser Leu Arg Ala Glu Asp Thr Ala Val Tyr Tyr Cys Thr
            355                 360                 365
Leu Asp Gly Arg Asp Gly Trp Val Ala Tyr Trp Gly Gln Gly Thr Leu
            370                 375                 380
Val Thr Val Ser Ser Gly Gly Gly Gly Ser Gly Gly Gly Gly Ser Gly
385                 390                 395                 400
Gly Gly Gly Ser Asn Phe Met Leu Thr Gln Pro Ser Ser Val Ser Gly
            405                 410                 415
Val Pro Gly Gln Arg Val Thr Ile Ser Cys Thr Gly Asn Thr Gly Asn
            420                 425                 430
```

-continued

```
Ile Gly Ser Asn Tyr Val Asn Trp Tyr Gln Gln Leu Pro Gly Thr Ala
            435                 440                 445

Pro Lys Leu Leu Ile Tyr Arg Asp Asp Lys Arg Pro Ser Gly Val Pro
    450                 455                 460

Asp Arg Phe Ser Gly Ser Lys Ser Gly Thr Ser Ala Ser Leu Ala Ile
465                 470                 475                 480

Thr Gly Phe Gln Ala Glu Asp Glu Ala Asp Tyr Tyr Cys Gln Ser Tyr
                485                 490                 495

Ser Ser Gly Phe Ile Phe Gly Gly Thr Lys Leu Thr Val Leu Ala
            500                 505                 510

Ala Glu Pro Lys Ser Ser Asp Lys Thr His Thr Cys Pro Pro Cys Pro
        515                 520                 525

Ala Pro Glu Ala Ala Gly Gly Pro Ser Val Phe Leu Phe Pro Pro Lys
    530                 535                 540

Pro Lys Asp Thr Leu Met Ile Ser Arg Thr Pro Glu Val Thr Cys Val
545                 550                 555                 560

Val Val Ser Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
        595                 600                 605

Gln Asp Trp Leu Asn Gly Lys Glu Tyr Lys Cys Lys Val Ser Asn Lys
    610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Val Tyr Pro Pro Ser Arg Asp Glu Leu
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
        675                 680                 685

Tyr Lys Thr Thr Pro Pro Val Leu Asp Ser Asp Gly Ser Phe Ala Leu
    690                 695                 700

Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly
            740
```

```
<210> SEQ ID NO 121
<211> LENGTH: 9
<212> TYPE: PRT
<213> ORGANISM: Artificial
<220> FEATURE:
<223> OTHER INFORMATION: Amino acid sequence of point mutated NY-ESO
      peptide 1F

<400> SEQUENCE: 121

Phe Leu Leu Met Trp Ile Thr Gln Cys
1               5

<210> SEQ ID NO 122
<211> LENGTH: 9
<212> TYPE: PRT
```

<213> ORGANISM: Artificial
<220> FEATURE:
<223> OTHER INFORMATION: Amino acid sequence of point mutated NY-ESO
      peptide 2M

<400> SEQUENCE: 122

Ser Met Leu Met Trp Ile Thr Gln Cys
1               5

<210> SEQ ID NO 123
<211> LENGTH: 9
<212> TYPE: PRT
<213> ORGANISM: Artificial
<220> FEATURE:
<223> OTHER INFORMATION: Amino acid sequence of point mutated NY-ESO
      peptide 3A

<400> SEQUENCE: 123

Ser Leu Ala Met Trp Ile Thr Gln Cys
1               5

<210> SEQ ID NO 124
<211> LENGTH: 9
<212> TYPE: PRT
<213> ORGANISM: Artificial
<220> FEATURE:
<223> OTHER INFORMATION: Amino acid sequence of point mutated NY-ESO
      peptide 4A

<400> SEQUENCE: 124

Ser Leu Leu Ala Trp Ile Thr Gln Cys
1               5

<210> SEQ ID NO 125
<211> LENGTH: 9
<212> TYPE: PRT
<213> ORGANISM: Artificial
<220> FEATURE:
<223> OTHER INFORMATION: Amino acid sequence of point mutated NY-ESO
      peptide 5A

<400> SEQUENCE: 125

Ser Leu Leu Met Ala Ile Thr Gln Cys
1               5

<210> SEQ ID NO 126
<211> LENGTH: 9
<212> TYPE: PRT
<213> ORGANISM: Artificial
<220> FEATURE:
<223> OTHER INFORMATION: Amino acid sequence of point mutated NY-ESO
      peptide 6L

<400> SEQUENCE: 126

Ser Leu Leu Met Trp Leu Thr Gln Cys
1               5

<210> SEQ ID NO 127
<211> LENGTH: 9
<212> TYPE: PRT
<213> ORGANISM: Artificial
<220> FEATURE:
<223> OTHER INFORMATION: Amino acid sequence of point mutated NY-ESO
      peptide 7F

<400> SEQUENCE: 127

Ser Leu Leu Met Trp Ile Phe Gln Cys
1               5

```
<210> SEQ ID NO 128
<211> LENGTH: 9
<212> TYPE: PRT
<213> ORGANISM: Artificial
<220> FEATURE:
<223> OTHER INFORMATION: Amino acid sequence of point mutated NY-ESO
      peptide 8A

<400> SEQUENCE: 128

Ser Leu Leu Met Trp Ile Thr Ala Cys
1               5

<210> SEQ ID NO 129
<211> LENGTH: 9
<212> TYPE: PRT
<213> ORGANISM: Artificial
<220> FEATURE:
<223> OTHER INFORMATION: Amino acid sequence of point mutated NY-ESO
      peptide 9A

<400> SEQUENCE: 129

Ser Leu Leu Met Trp Ile Thr Gln Ala
1               5

<210> SEQ ID NO 130
<211> LENGTH: 9
<212> TYPE: PRT
<213> ORGANISM: Artificial
<220> FEATURE:
<223> OTHER INFORMATION: Amino acid sequence of gp100 peptide

<400> SEQUENCE: 130

Ile Met Asp Gln Val Pro Phe Ser Val
1               5

<210> SEQ ID NO 131
<211> LENGTH: 9
<212> TYPE: PRT
<213> ORGANISM: Artificial
<220> FEATURE:
<223> OTHER INFORMATION: Amino acid sequence of homologous peptide
      DOLPP1

<400> SEQUENCE: 131

Ser Gln Phe Met Trp Phe Phe Ser Val
1               5

<210> SEQ ID NO 132
<211> LENGTH: 9
<212> TYPE: PRT
<213> ORGANISM: Artificial
<220> FEATURE:
<223> OTHER INFORMATION: Amino acid sequence of homologous peptide
      IL20RB

<400> SEQUENCE: 132

Ser Leu Phe Met Trp Phe Phe Tyr Ala
1               5

<210> SEQ ID NO 133
<211> LENGTH: 9
<212> TYPE: PRT
<213> ORGANISM: Artificial
<220> FEATURE:
<223> OTHER INFORMATION: Amino acid sequence of homologous peptide PRKD2

<400> SEQUENCE: 133
```

```
Ser Leu Asp Met Trp Ser Val Gly Val
1               5
```

<210> SEQ ID NO 134
<211> LENGTH: 9
<212> TYPE: PRT
<213> ORGANISM: Artificial
<220> FEATURE:
<223> OTHER INFORMATION: Amino acid sequence of homologous peptide CD163

<400> SEQUENCE: 134

```
Ser Ile Pro Met Trp Val Asp Asn Val
1               5
```

<210> SEQ ID NO 135
<211> LENGTH: 9
<212> TYPE: PRT
<213> ORGANISM: Artificial
<220> FEATURE:
<223> OTHER INFORMATION: Amino acid sequence of homologous peptide P2RY8

<400> SEQUENCE: 135

```
Ser Val Ala Met Trp Ala Val Phe Leu
1               5
```

<210> SEQ ID NO 136
<211> LENGTH: 269
<212> TYPE: PRT
<213> ORGANISM: Artificial
<220> FEATURE:
<223> OTHER INFORMATION: Amino acid sequence of C3E-7034

<400> SEQUENCE: 136

```
Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Asn Ser Gly Gly Arg Ile Tyr Tyr Pro Asp Ser
    50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Asn Phe Met Leu Thr Gln Pro His Ser Val
    130                 135                 140

Ser Glu Ser Pro Gly Lys Thr Val Thr Ile Ser Cys Lys Arg Asn Thr
145                 150                 155                 160

Gly Asn Ile Gly Ser Asn Tyr Val Asn Trp Tyr Gln Gln His Glu Gly
                165                 170                 175

Ser Ser Pro Thr Thr Ile Ile Tyr Arg Asp Asp Lys Arg Pro Asp Gly
            180                 185                 190

Val Ser Asp Arg Phe Ser Gly Ser Ile Asp Arg Ser Ser Lys Ser Ala
        195                 200                 205
```

-continued

```
Ser Leu Thr Ile Ser Asn Leu Lys Thr Glu Asp Glu Ala Asp Tyr Phe
    210                 215                 220

Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
                245                 250                 255

Asp Asp Lys Gly Ala Ala Ala His His His His His His
            260                 265

<210> SEQ ID NO 137
<211> LENGTH: 267
<212> TYPE: PRT
<213> ORGANISM: Artificial
<220> FEATURE:
<223> OTHER INFORMATION: Amino acid sequence of C3E-7036

<400> SEQUENCE: 137

Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Asn Ser Gly Gly Arg Ile Tyr Tyr Pro Asp Ser
50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Asn Phe Met Leu Thr Gln Pro Ser Ser Val
    130                 135                 140

Ser Gly Val Pro Gly Gln Arg Val Thr Ile Ser Cys Thr Gly Asn Thr
145                 150                 155                 160

Gly Asn Ile Gly Ser Asn Tyr Val Asn Trp Tyr Gln Gln Leu Pro Gly
                165                 170                 175

Thr Ala Pro Lys Leu Leu Ile Tyr Arg Asp Asp Lys Arg Pro Ser Gly
            180                 185                 190

Val Pro Asp Arg Phe Ser Gly Ser Lys Ser Gly Thr Ser Ala Ser Leu
        195                 200                 205

Ala Ile Thr Gly Phe Gln Ala Glu Asp Glu Ala Asp Tyr Tyr Cys Gln
    210                 215                 220

Ser Tyr Ser Ser Gly Phe Ile Phe Gly Gly Gly Thr Lys Leu Thr Val
225                 230                 235                 240

Leu Gly Ala Ala Ala Gly Ala Gly Gly Asp Tyr Lys Asp Asp Asp Asp
                245                 250                 255

Lys Gly Ala Ala Ala His His His His His His
            260                 265

<210> SEQ ID NO 138
<211> LENGTH: 267
<212> TYPE: PRT
<213> ORGANISM: Artificial
<220> FEATURE:
```

<223> OTHER INFORMATION: Amino acid sequence of C3E-7085

<400> SEQUENCE: 138

```
Gly Glu Val Gln Leu Val Glu Ser Gly Gly Gly Leu Val Gln Pro Gly
1               5                   10                  15
Gly Ser Leu Arg Leu Ser Cys Ala Ala Ser Gly Val Thr Phe Asn Tyr
            20                  25                  30
Tyr Gly Met Ser Trp Ile Arg Gln Ala Pro Gly Lys Gly Leu Glu Trp
        35                  40                  45
Val Ala Ser Ile Thr Arg Ser Gly Gly Arg Ile Tyr Tyr Pro Asp Ser
    50                  55                  60
Val Lys Gly Arg Phe Thr Ile Ser Arg Glu Asn Thr Gln Lys Thr Leu
65                  70                  75                  80
Tyr Leu Gln Met Asn Ser Leu Arg Ala Glu Asp Thr Ala Val Tyr Tyr
                85                  90                  95
Cys Thr Leu Asp Gly Arg Asp Gly Trp Val Ala Tyr Trp Gly Gln Gly
            100                 105                 110
Thr Leu Val Thr Val Ser Ser Gly Gly Gly Ser Gly Gly Gly
        115                 120                 125
Ser Gly Gly Gly Ser Asn Phe Met Leu Thr Gln Pro Ser Ser Val
130                 135                 140
Ser Gly Val Pro Gly Gln Arg Val Thr Ile Ser Cys Thr Gly Asn Thr
145                 150                 155                 160
Gly Asn Ile Gly Ser Asn Tyr Val Asn Trp Tyr Gln Gln Leu Pro Gly
                165                 170                 175
Thr Ala Pro Lys Leu Leu Ile Tyr Arg Asp Asp Lys Arg Pro Ser Gly
            180                 185                 190
Val Pro Asp Arg Phe Ser Gly Ser Lys Ser Gly Thr Ser Ala Ser Leu
        195                 200                 205
Ala Ile Thr Gly Phe Gln Ala Glu Asp Glu Ala Asp Tyr Tyr Cys Gln
    210                 215                 220
Ser Tyr Ser Ser Gly Phe Ile Phe Gly Gly Gly Thr Lys Leu Thr Val
225                 230                 235                 240
Leu Gly Ala Ala Ala Gly Ala Gly Gly Asp Tyr Lys Asp Asp Asp Asp
                245                 250                 255
Lys Gly Ala Ala Ala His His His His His His
            260                 265
```

<210> SEQ ID NO 139
<211> LENGTH: 269
<212> TYPE: PRT
<213> ORGANISM: Artificial
<220> FEATURE:
<223> OTHER INFORMATION: Amino acid sequence of C3E-7088

<400> SEQUENCE: 139

```
Gly Glu Val Gln Leu Val Glu Ser Gly Gly Gly Leu Val Gln Pro Gly
1               5                   10                  15
Gly Ser Leu Arg Leu Ser Cys Ala Ala Ser Gly Val Thr Phe Asn Tyr
            20                  25                  30
Tyr Gly Met Ser Trp Ile Arg Gln Ala Pro Gly Lys Gly Leu Glu Trp
        35                  40                  45
Val Ala Ser Ile Thr Arg Ser Gly Gly Arg Ile Tyr Tyr Pro Asp Ser
    50                  55                  60
Val Lys Gly Arg Phe Thr Ile Ser Arg Glu Asn Thr Gln Lys Thr Leu
65                  70                  75                  80
```

```
Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Asn Phe Met Leu Thr Gln Pro His Ser Val
130                 135                 140

Ser Glu Ser Pro Gly Lys Thr Val Thr Ile Ser Cys Lys Arg Asn Thr
145                 150                 155                 160

Gly Asn Ile Gly Ser Asn Tyr Val Asn Trp Tyr Gln Gln His Glu Gly
                165                 170                 175

Ser Ser Pro Thr Thr Ile Ile Tyr Arg Asn Asp Lys Arg Pro Asp Gly
            180                 185                 190

Val Ser Asp Arg Phe Ser Gly Ser Ile Asp Arg Ser Ser Lys Ser Ala
        195                 200                 205

Ser Leu Thr Ile Ser Asn Leu Lys Thr Glu Asp Glu Ala Asp Tyr Phe
210                 215                 220

Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
            245                 250                 255

Asp Asp Lys Gly Ala Ala Ala His His His His His His
            260                 265

<210> SEQ ID NO 140
<211> LENGTH: 269
<212> TYPE: PRT
<213> ORGANISM: Artificial
<220> FEATURE:
<223> OTHER INFORMATION: Amino acid sequence of C3E-7093

<400> SEQUENCE: 140

Gly Glu Val Gln Leu Val Glu Ser Gly Gly Gly Leu Val Gln Pro Gly
1               5                   10                  15

Gly Ser Leu Arg Leu Ser Cys Ala Ala Ser Gly Val Thr Phe Asn Tyr
            20                  25                  30

Tyr Gly Met Ser Trp Ile Arg Gln Ala Pro Gly Lys Gly Leu Glu Trp
        35                  40                  45

Val Ala Ser Ile Thr Ser Ser Gly Gly Arg Ile Tyr Tyr Pro Asp Ser
50                  55                  60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asn Phe Met Leu Thr Gln Pro His Ser Val
130                 135                 140

Ser Glu Ser Pro Gly Lys Thr Val Thr Ile Ser Cys Lys Arg Asn Thr
145                 150                 155                 160

Gly Asn Ile Gly Ser Asn Tyr Val Asn Trp Tyr Gln Gln His Glu Gly
                165                 170                 175
```

```
Ser Ser Pro Thr Thr Ile Ile Tyr Arg Asn Asp Lys Arg Pro Asp Gly
            180                 185                 190

Val Ser Asp Arg Phe Ser Gly Ser Ile Asp Arg Ser Ser Lys Ser Ala
        195                 200                 205

Ser Leu Thr Ile Ser Asn Leu Lys Thr Glu Glu Ala Asp Tyr Phe
    210                 215                 220

Cys Gln Ser Tyr Ser Ser Gly Phe Ile Phe Gly Gly Thr Lys Leu
225                 230                 235                 240

Thr Val Leu Gly Ala Ala Gly Ala Gly Gly Asp Tyr Lys Asp Asp
                245                 250                 255

Asp Asp Lys Gly Ala Ala Ala His His His His His His
            260                 265
```

<210> SEQ ID NO 141
<211> LENGTH: 8
<212> TYPE: PRT
<213> ORGANISM: Artificial
<220> FEATURE:
<223> OTHER INFORMATION: Amino acid sequence of heavy chain CDR1 of
      C3E-7085

<400> SEQUENCE: 141

```
Gly Val Thr Phe Asn Tyr Tyr Gly
1               5
```

<210> SEQ ID NO 142
<211> LENGTH: 8
<212> TYPE: PRT
<213> ORGANISM: Artificial
<220> FEATURE:
<223> OTHER INFORMATION: Amino acid sequence of heavy chain CDR2 of
      C3E-7085

<400> SEQUENCE: 142

```
Ile Thr Arg Ser Gly Gly Arg Ile
1               5
```

<210> SEQ ID NO 143
<211> LENGTH: 11
<212> TYPE: PRT
<213> ORGANISM: Artificial
<220> FEATURE:
<223> OTHER INFORMATION: Amino acid sequence of heavy chain CDR3 of
      C3E-7085

<400> SEQUENCE: 143

```
Thr Leu Asp Gly Arg Asp Gly Trp Val Ala Tyr
1               5                   10
```

<210> SEQ ID NO 144
<211> LENGTH: 8
<212> TYPE: PRT
<213> ORGANISM: Artificial
<220> FEATURE:
<223> OTHER INFORMATION: Amino acid sequence of light chain CDR1 of
      C3E-7085

<400> SEQUENCE: 144

```
Thr Gly Asn Ile Gly Ser Asn Tyr
1               5
```

<210> SEQ ID NO 145

<400> SEQUENCE: 145

```
000

<210> SEQ ID NO 146
<211> LENGTH: 8
<212> TYPE: PRT
<213> ORGANISM: Artificial
<220> FEATURE:
<223> OTHER INFORMATION: Amino acid sequence of light chain CDR3 of
      C3E-7085

<400> SEQUENCE: 146

Gln Ser Tyr Ser Ser Gly Phe Ile
1               5

<210> SEQ ID NO 147
<211> LENGTH: 269
<212> TYPE: PRT
<213> ORGANISM: Artificial
<220> FEATURE:
<223> OTHER INFORMATION: Amino acid sequence of C3E-7078

<400> SEQUENCE: 147

Gly Glu Val Gln Leu Val Glu Ser Gly Gly Leu Val Gln Pro Gly
1               5                   10                  15

Gly Ser Leu Arg Leu Ser Cys Ala Ala Ser Gly Val Thr Phe Asn Tyr
                20                  25                  30

Tyr Gly Met Ser Trp Ile Arg Gln Ala Pro Gly Lys Gly Leu Glu Trp
            35                  40                  45

Val Ala Ser Ile Thr Arg Ser Gly Gly Arg Ile Tyr Tyr Pro Asp Ser
50                  55                      60

Val Lys Gly Arg Phe Thr Ile Ser Arg Glu Asn Thr Gln Lys Thr Leu
65                  70                  75                  80

Tyr Leu Gln Met Asn Ser Leu Arg Ala Glu Asp Thr Ala Val Tyr Tyr
                85                  90                  95

Cys Thr Leu Asp Gly Arg Asp Gly Trp Val Ala Tyr Trp Gly Gln Gly
                100                 105                 110

Thr Leu Val Thr Val Ser Ser Gly Gly Gly Ser Gly Gly Gly Gly
            115                 120                 125

Ser Gly Gly Gly Gly Ser Asn Phe Met Leu Thr Gln Pro His Ser Val
    130                 135                 140

Ser Glu Ser Pro Gly Lys Thr Val Thr Ile Ser Cys Lys Arg Asn Thr
145                 150                 155                 160

Gly Asn Ile Gly Ser Asn Tyr Val Asn Trp Tyr Gln Gln His Glu Gly
                165                 170                 175

Ser Ser Pro Thr Thr Ile Ile Tyr Arg Asp Asp Lys Arg Pro Asp Gly
            180                 185                 190

Val Ser Asp Arg Phe Ser Gly Ser Ile Asp Arg Ser Ser Lys Ser Ala
        195                 200                 205

Ser Leu Thr Ile Ser Asn Leu Lys Thr Glu Asp Glu Ala Asp Tyr Phe
    210                 215                 220

Cys Gln Ser Tyr Ser Ser Gly Phe Ile Phe Gly Gly Gly Thr Lys Leu
225                 230                 235                 240

Thr Val Leu Gly Ala Ala Ala Gly Ala Gly Gly Asp Tyr Lys Asp Asp
                245                 250                 255

Asp Asp Lys Gly Ala Ala Ala His His His His His His
                260                 265
```

<210> SEQ ID NO 148
<211> LENGTH: 2235
<212> TYPE: DNA
<213> ORGANISM: Artificial
<220> FEATURE:
<223> OTHER INFORMATION: Full-length nucleotide sequence of NYF-0014-HC2

<400> SEQUENCE: 148

| | | | | | |
|---|---|---|---|---|---|
| atgaaacacc | tgtggttctt | cctcctgctg | gtggcagctc | ccagatgggt gctgagcgga | 60 |
| gaggtgcagc | tggtggagtc | tgggggaggc | gtggtccagc | ctgggaggtc cctgacaccc | 120 |
| tcctgttcag | cgtctggatt | ctccatccgt | agttatgata | cactgggt ccgccaggct | 180 |
| ccaggcaagg | ggctagagtg | ggtggccact | atatcatatg | atggaagtca gaagtacttc | 240 |
| gcagactccg | tgaagggccg | atttaccatc | tcagagacg | aatcggagaa catggtgtat | 300 |
| ctgcaaatga | gcggcctgag | agttgaggac | acggctgttt | atcactgtgc gagagggagt | 360 |
| agtggtcatt | atgaggcttt | tgatatctgg | ggccaaggga | caatggtcac cgtctcttca | 420 |
| ggtgaggcg | gttcaggcgg | aggtggcagc | ggcgtggcg | ggagtcagtc tgtgttgacg | 480 |
| cagccgccct | cagtgtctgc | ggccccagga | cagaaggtca | ccatctcctg ctctggaagc | 540 |
| agctccaaca | ttgggaataa | ttatgtatcc | tggtaccagc | agctcccagg aacagccccc | 600 |
| aaactcctca | tttatgacaa | taataagcga | ccctcaggga | ttcctgaccg attctctggc | 660 |
| tccaagtctg | gcacgtcagc | cacccctggggg | atcaccggac | tccagactgg ggacgaggcc | 720 |
| gattattact | gcggaacatg | ggatagcagc | ctgagtgccc | cttgggtgtt cggcggaggg | 780 |
| accaaggtca | ccgtcctagg | gggaggcggt | tcagaagtgc | agctggtgga atccgggggg | 840 |
| ggcctggtgc | agcctggggg | gagcctgaga | ctgagttgtg | ccgcctctgg ggtgacattt | 900 |
| aactactatg | catgtcttg | gatccgccag | gcacctggaa | agggcctgga gtgggtggcc | 960 |
| agcatcacta | ggtccggcgg | gcgaatctac | tatcccgaca | gcgtcaaggg caggttcaca | 1020 |
| atttcccgcg | agaacacaca | gaaaaactctg | tacctgcaga | tgaatagcct gagagccgaa | 1080 |
| gatacagctg | tgtactattg | cactctggac | ggcagggatg | ggtgggtcgc ctattggggg | 1140 |
| cagggaaccc | tggtgacagt | cagctccgga | ggaggaggat | ctggcggagg aggcagtggg | 1200 |
| ggaggcgggt | caaactttat | gctcactcag | ccgtcctctg | tttctggcgt acctggccaa | 1260 |
| cgggtgacca | ttagctgtac | gggtaatacc | gggaatatcg | gtctaacta cgtgaactgg | 1320 |
| tatcagcagc | ttccagggac | agctcccaag | ttgctgatct | atcgcgacga caaaagaccc | 1380 |
| tcaggggtcc | ctgaccgatt | tagtggcagc | aaaagcggta | cttccgcttc cctggcgata | 1440 |
| accggctttc | aggccgaaga | tgaggcagac | tactattgcc | agtcatattc cagcggcttc | 1500 |
| atcttcggag | gcggaactaa | gctgacagtg | ttggcagccg | agcccaaatc ttctgacaaa | 1560 |
| actcacacat | gcccaccctg | cccagcacct | gaagccgcag | gggacccctc agtcttcctc | 1620 |
| ttccccccaa | aacccaagga | caccctcatg | atctcccgga | cccctgaggt cacatgcgtg | 1680 |
| gtggtgtcag | tgagccacga | agaccctgag | gtcaagttca | actggtacgt ggacggcgtg | 1740 |
| gaggtgcata | atgccaagac | aaagccccgg | gaggagcagt | acaacagcac gtaccgggtg | 1800 |
| gtcagcgtcc | tcaccgtcct | gcaccaggac | tggctgaatg | gcaaggagta caagtgcaag | 1860 |
| gtctccaaca | aagccctccc | agcccccatc | gagaaaacca | tctccaaagc caaaggccag | 1920 |
| ccccgggaac | cacaggtgta | cgtgtacccc | ccatcccggg | acgagctgac caagaaccag | 1980 |
| gtcagcctga | cctgcctggt | caaaggcttc | tatcccagcg | acatcgccgt ggagtgggag | 2040 |
| agcaatggcc | agcccgagaa | caactacaag | accacccctc | ccgtgctgga ctccgacggc | 2100 |

```
tccttcgccc tcgtgagcaa gctcaccgtg acaagagca ggtggcagca gggcaacgtc      2160
ttctcatgct ccgtgatgca tgaggctctg cacaaccact acacccagaa gagcctctcc      2220
ctgtctcccg gcaag                                                       2235
```

<210> SEQ ID NO 149
<211> LENGTH: 745
<212> TYPE: PRT
<213> ORGANISM: Artificial
<220> FEATURE:
<223> OTHER INFORMATION: Full-length amino acid sequence of NYF-0014-HC2

<400> SEQUENCE: 149

```
Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Val Val
            20                  25                  30

Gln Pro Gly Arg Ser Leu Thr Pro Ser Cys Ser Ala Ser Gly Phe Ser
        35                  40                  45

Ile Arg Ser Tyr Asp Ile His Trp Val Arg Gln Ala Pro Gly Lys Gly
    50                  55                  60

Leu Glu Trp Val Ala Thr Ile Ser Tyr Asp Gly Ser Gln Lys Tyr Phe
65                  70                  75                  80

Ala Asp Ser Val Lys Gly Arg Phe Thr Ile Phe Arg Asp Glu Ser Glu
                85                  90                  95

Asn Met Val Tyr Leu Gln Met Ser Gly Leu Arg Val Glu Asp Thr Ala
            100                 105                 110

Val Tyr His Cys Ala Arg Gly Ser Gly His Tyr Glu Ala Phe Asp
        115                 120                 125

Ile Trp Gly Gln Gly Thr Met Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Asn Tyr Val Ser Trp Tyr
            180                 185                 190

Gln Gln Leu Pro Gly Thr Ala Pro Lys Leu Leu Ile Tyr Asp Asn Asn
        195                 200                 205

Lys Arg Pro Ser Gly Ile Pro Asp Arg Phe Ser Gly Ser Lys Ser Gly
    210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Val Thr Val Leu Gly Gly Gly Gly Ser Glu
            260                 265                 270

Val Gln Leu Val Glu Ser Gly Gly Gly Leu Val Gln Pro Gly Gly Ser
        275                 280                 285

Leu Arg Leu Ser Cys Ala Ala Ser Gly Val Thr Phe Asn Tyr Tyr Gly
    290                 295                 300

Met Ser Trp Ile Arg Gln Ala Pro Gly Lys Gly Leu Glu Trp Val Ala
305                 310                 315                 320

Ser Ile Thr Arg Ser Gly Gly Arg Ile Tyr Tyr Pro Asp Ser Val Lys
                325                 330                 335
```

```
Gly Arg Phe Thr Ile Ser Arg Glu Asn Thr Gln Lys Thr Leu Tyr Leu
                340                 345                 350

Gln Met Asn Ser Leu Arg Ala Glu Asp Thr Ala Val Tyr Tyr Cys Thr
            355                 360                 365

Leu Asp Gly Arg Asp Gly Trp Val Ala Tyr Trp Gly Gln Gly Thr Leu
        370                 375                 380

Val Thr Val Ser Ser Gly Gly Gly Gly Ser Gly Gly Gly Gly Ser Gly
385                 390                 395                 400

Gly Gly Ser Asn Phe Met Leu Thr Gln Pro Ser Ser Val Ser Gly
                405                 410                 415

Val Pro Gly Gln Arg Val Thr Ile Ser Cys Thr Gly Asn Thr Gly Asn
            420                 425                 430

Ile Gly Ser Asn Tyr Val Asn Trp Tyr Gln Gln Leu Pro Gly Thr Ala
        435                 440                 445

Pro Lys Leu Leu Ile Tyr Arg Asp Asp Lys Arg Pro Ser Gly Val Pro
    450                 455                 460

Asp Arg Phe Ser Gly Ser Lys Ser Gly Thr Ser Ala Ser Leu Ala Ile
465                 470                 475                 480

Thr Gly Phe Gln Ala Glu Asp Glu Ala Asp Tyr Tyr Cys Gln Ser Tyr
            485                 490                 495

Ser Ser Gly Phe Ile Phe Gly Gly Thr Lys Leu Thr Val Leu Ala
        500                 505                 510

Ala Glu Pro Lys Ser Ser Asp Lys Thr His Thr Cys Pro Pro Cys Pro
    515                 520                 525

Ala Pro Glu Ala Ala Gly Gly Pro Ser Val Phe Leu Phe Pro Pro Lys
    530                 535                 540

Pro Lys Asp Thr Leu Met Ile Ser Arg Thr Pro Glu Val Thr Cys Val
545                 550                 555                 560

Val Val Ser Val Ser His Glu Asp Pro Glu Val Lys Phe Asn Trp Tyr
            565                 570                 575

Val Asp Gly Val Glu Val His Asn Ala Lys Thr Lys Pro Arg Glu Glu
        580                 585                 590

Gln Tyr Asn Ser Thr Tyr Arg Val Val Ser Val Leu Thr Val Leu His
    595                 600                 605

Gln Asp Trp Leu Asn Gly Lys Glu Tyr Lys Cys Lys Val Ser Asn Lys
    610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Val Tyr Pro Pro Ser Arg Asp Glu Leu
            645                 650                 655

Thr Lys Asn Gln Val Ser Leu Thr Cys Leu Val Lys Gly Phe Tyr Pro
        660                 665                 670

Ser Asp Ile Ala Val Glu Trp Glu Ser Asn Gly Gln Pro Glu Asn Asn
    675                 680                 685

Tyr Lys Thr Thr Pro Pro Val Leu Asp Ser Asp Gly Ser Phe Ala Leu
    690                 695                 700

Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
            725                 730                 735

Lys Ser Leu Ser Leu Ser Pro Gly Lys
            740                 745
```

```
<210> SEQ ID NO 150
<211> LENGTH: 745
<212> TYPE: PRT
<213> ORGANISM: Artificial
<220> FEATURE:
<223> OTHER INFORMATION: Full-length amino acid sequence of NYF-0082-HC2

<400> SEQUENCE: 150

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Val Val
            20                  25                  30

Gln Pro Gly Arg Ser Leu Thr Pro Ser Cys Ser Ala Ser Gly Phe Ser
        35                  40                  45

Ile Arg Ser Tyr Asp Ile His Trp Val Arg Gln Ala Pro Gly Lys Gly
    50                  55                  60

Leu Glu Trp Val Ala Thr Ile Ser Tyr Asp Gly Ser Gln Lys Tyr Phe
65                  70                  75                  80

Ala Asp Ser Val Lys Gly Arg Phe Thr Ile Phe Arg Asp Glu Ser Glu
                85                  90                  95

Asn Met Val Tyr Leu Gln Met Ser Gly Leu Arg Val Glu Asp Thr Ala
            100                 105                 110

Val Tyr His Cys Ala Arg Gly Ser Gly His Tyr Glu Ala Phe Asp
        115                 120                 125

Ile Trp Gly Gln Gly Thr Met Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Asn Tyr Val Ser Trp Tyr
            180                 185                 190

Gln Arg Leu Pro Gly Thr Ala Pro Lys Leu Leu Ile Tyr Asp Asn Asn
        195                 200                 205

Lys Arg Pro Ser Gly Ile Pro Asp Arg Phe Ser Gly Ser Lys Ser Gly
    210                 215                 220

Thr Ser Ala Thr Leu Gly Ile Thr Gly Leu Gln Thr Gly Asp Glu Ala
225                 230                 235                 240

Asp Tyr Tyr Cys Gly Ser Trp Asp Ser Ser Leu Ser Ala Pro Trp Val
                245                 250                 255

Phe Gly Gly Gly Thr Lys Val Thr Val Leu Gly Gly Gly Gly Ser Glu
            260                 265                 270

Val Gln Leu Val Glu Ser Gly Gly Gly Leu Val Gln Pro Gly Gly Ser
        275                 280                 285

Leu Arg Leu Ser Cys Ala Ala Ser Gly Val Thr Phe Asn Tyr Tyr Gly
    290                 295                 300

Met Ser Trp Ile Arg Gln Ala Pro Gly Lys Gly Leu Glu Trp Val Ala
305                 310                 315                 320

Ser Ile Thr Arg Ser Gly Gly Arg Ile Tyr Tyr Pro Asp Ser Val Lys
                325                 330                 335

Gly Arg Phe Thr Ile Ser Arg Glu Asn Thr Gln Lys Thr Leu Tyr Leu
            340                 345                 350

Gln Met Asn Ser Leu Arg Ala Glu Asp Thr Ala Val Tyr Tyr Cys Thr
        355                 360                 365

Leu Asp Gly Arg Asp Gly Trp Val Ala Tyr Trp Gly Gln Gly Thr Leu
```

```
                370                 375                 380
Val Thr Val Ser Ser Gly Gly Gly Ser Gly Gly Gly Ser Gly
385                 390                 395                 400

Gly Gly Gly Ser Asn Phe Met Leu Thr Gln Pro Ser Val Ser Gly
                405                 410                 415

Val Pro Gly Gln Arg Val Thr Ile Ser Cys Thr Gly Asn Thr Gly Asn
                420                 425                 430

Ile Gly Ser Asn Tyr Val Asn Trp Tyr Gln Gln Leu Pro Gly Thr Ala
            435                 440                 445

Pro Lys Leu Leu Ile Tyr Arg Asp Asp Lys Arg Pro Ser Gly Val Pro
450                 455                 460

Asp Arg Phe Ser Gly Ser Lys Ser Gly Thr Ser Ala Ser Leu Ala Ile
465                 470                 475                 480

Thr Gly Phe Gln Ala Glu Asp Glu Ala Asp Tyr Tyr Cys Gln Ser Tyr
                485                 490                 495

Ser Ser Gly Phe Ile Phe Gly Gly Thr Lys Leu Thr Val Leu Ala
                500                 505                 510

Ala Glu Pro Lys Ser Ser Asp Lys Thr His Thr Cys Pro Pro Cys Pro
            515                 520                 525

Ala Pro Glu Ala Ala Gly Gly Pro Ser Val Phe Leu Phe Pro Pro Lys
530                 535                 540

Pro Lys Asp Thr Leu Met Ile Ser Arg Thr Pro Glu Val Thr Cys Val
545                 550                 555                 560

Val Val Ser Val Ser His Glu Asp Pro Glu Val Lys Phe Asn Trp Tyr
                565                 570                 575

Val Asp Gly Val Glu Val His Asn Ala Lys Thr Lys Pro Arg Glu Glu
            580                 585                 590

Gln Tyr Asn Ser Thr Tyr Arg Val Val Ser Val Leu Thr Val Leu His
            595                 600                 605

Gln Asp Trp Leu Asn Gly Lys Glu Tyr Lys Cys Lys Val Ser Asn Lys
610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Val Tyr Pro Pro Ser Arg Asp Glu Leu
                645                 650                 655

Thr Lys Asn Gln Val Ser Leu Thr Cys Leu Val Lys Gly Phe Tyr Pro
            660                 665                 670

Ser Asp Ile Ala Val Glu Trp Glu Ser Asn Gly Gln Pro Glu Asn Asn
            675                 680                 685

Tyr Lys Thr Thr Pro Pro Val Leu Asp Ser Asp Gly Ser Phe Ala Leu
690                 695                 700

Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                725                 730                 735

Lys Ser Leu Ser Leu Ser Pro Gly Lys
                740                 745

<210> SEQ ID NO 151
<211> LENGTH: 207
<212> TYPE: PRT
<213> ORGANISM: Homo sapiens

<400> SEQUENCE: 151
```

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
            115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
            195                 200                 205

<210> SEQ ID NO 152
<211> LENGTH: 2235
<212> TYPE: DNA
<213> ORGANISM: Artificial
<220> FEATURE:
<223> OTHER INFORMATION: Full-length nucleotide sequence of NYZ-0038-HC2

<400> SEQUENCE: 152
atgaaacacc tgtggttctt cctcctgctg gtggcagctc ccagatgggt gctgagcggt      60
gaggtacagc tggtggaatc cggtggaggc cttgtgcaac cgggaggctc cctgcgactc     120
tcttgcgccg catctggctt ttccatacga tcctacgata ttcattgggt ccgacaagcc     180
cctggcaaag gtcttgaatg ggttgccact atctcctacg acgggtctca gaaatattat     240
gcggattcag tgaaggggcg gttcacaatt tcacgacacg agtcaaagaa tacactgtac     300
ctccaaatga attcactgag agccgaggat actgcagtct atcattgtgc aagagggtcc     360
tcaggccact acgaggcctt tgatatatgg ggccaaggca ccttggtaac cgttagtagc     420
ggaggtggag gaagcggagg cggcggttcc ggaggaggtg aagtcaatc cgttctgact      480 cagccaccct ccgcctctgg caccccgggc aacgggtca caatatcatg ttctggctct     540
tcaagcaaca tcggaaactg gtacgtgagc tggtaccagc agctccccgg cacggcgccc     600
aagcttctga tatatgacaa caacaaacgg cccagtggag ttcctgacag attcagtggg     660
tctaaaagtg gtacaagcgc tagcctggcc ataagtggtc tgcagagtga agatgaggcg     720
gactattatt gcggaacctg ggactccagc ctgagcgctc cctgggtttt cggcggaggt     780
actaagctga ccgtcttggg aggaggcggt tcagaagtgc agctggtgga atccgggggg     840
ggcctggtgc agcctggggg gagcctgaga ctgagttgtg ccgcctctgg ggtgacattt     900

| | |
|---|---|
| aactactatg gcatgtcttg gatccgccag gcacctggaa agggcctgga gtgggtggcc | 960 |
| agcatcacta ggtccggcgg gcgaatctac tatcccgaca gcgtcaaggg caggttcaca | 1020 |
| atttcccgcg agaacacaca gaaaactctg tacctgcaga tgaatagcct gagagccgaa | 1080 |
| gatacagctg tgtactattg cactctggac ggcaggatg ggtgggtcgc ctattggggg | 1140 |
| tgtggaaccc tggtgacagt cagctccgga ggaggaggat ctggcggagg aggcagtggg | 1200 |
| ggaggcgggt caaactttat gctcactcag ccgtcctctg tttctggcgt acctggccaa | 1260 |
| cgggtgacca ttagctgtac gggtaatacc gggaatatcg ggtctaacta cgtgaactgg | 1320 |
| tatcagcagc ttccagggac atgtcccaag ttgctgatct atcgcgacga caaaagaccc | 1380 |
| tcaggggtcc ctgaccgatt tagtggcagc aaaagcggta cttccgcttc cctggcgata | 1440 |
| accggctttc aggccgaaga tgaggcagac tactattgcc agtcatattc cagcggcttc | 1500 |
| atcttcggag gcggaactaa gctgacagtg ttggcagccg agcccaaatc ttctgacaaa | 1560 |
| actcacacat gcccaccctg cccagcacct gaagccgcag ggggacccct cagtcttcctc | 1620 |
| ttcccccccaa aacccaagga caccctcatg atctcccgga cccctgaggt cacatgcgtg | 1680 |
| gtggtgtcag tgagccacga agaccctgag gtcaagttca actggtacgt ggacggcgtg | 1740 |
| gaggtgcata atgccaagac aaagcccccgg gaggagcagt acaacagcac gtaccgggtg | 1800 |
| gtcagcgtcc tcaccgtcct gcaccaggac tggctgaatg gcaaggagta caagtgcaag | 1860 |
| gtctccaaca aagcccctccc agcccccatc gagaaaacca tctccaaagc caaaggccag | 1920 |
| ccccgggaac cacaggtgta cgtgtacccc ccatcccggg acgagctgac caagaaccag | 1980 |
| gtcagcctga cctgcctggt caaaggcttc tatcccagcg acatcgccgt ggagtgggag | 2040 |
| agcaatggcc agcccgagaa caactacaag accacccctc ccgtgctgga ctccgacggc | 2100 |
| tccttcgccc tcgtgagcaa gctcaccgtg gacaagagca ggtggcagca gggcaacgtc | 2160 |
| ttctcatgct ccgtgatgca tgaggctctg cacaaccact acacccagaa gagcctctcc | 2220 |
| ctgtctcccg gcaag | 2235 |

<210> SEQ ID NO 153
<211> LENGTH: 2250
<212> TYPE: DNA
<213> ORGANISM: Artificial
<220> FEATURE:
<223> OTHER INFORMATION: Full-length nucleotide sequence of NYZ-0082-HC2

<400> SEQUENCE: 153

| | |
|---|---|
| atgaaacacc tgtggttctt cctcctgctg gtggcagctc ccagatgggt gctgagcggt | 60 |
| gaggtacagc tggtggaatc cggtggaggc cttgtgcaac cgggaggctc cctgcgactc | 120 |
| tcttgcgccg catctggctt ttccatacga tcctacgata ttcattgggt ccgacaagcc | 180 |
| cctggcaaag gtcttgaatg ggttgccact atctcctacg acgggtctca gaaatattat | 240 |
| gcggattcag tgaaggggcg gttcacaatt tcacgagacg agtcaaagaa tacactgtac | 300 |
| ctccaaatga attcactgag agccgaggat actgcagtct atcattgtgc aagagggtcc | 360 |
| tcaggccact acgaggcctt tgatatatgg ggccaaggca ccttggtaac cgttagtagc | 420 |
| ggaggtggag gaagcggagg cggcggttcc ggaggaggtg gaagtggagg aggtggatct | 480 |
| caatccgttc tgactcagcc accctccgcc tctggcaccc cgggccaacg ggtcacaata | 540 |
| tcatgttctg gctcttcaag caacatcgga aactggtacg tgagctggta ccagcagctc | 600 |
| cccgcacgg cgcccaagct tctgatatat gacaacaaca acggcccag tggagttcct | 660 |
| gacagattca gtgggtctaa aagtggtaca agcgctagcc tggccataag tggtctgcag | 720 |

| | |
|---|---:|
| agtgaagatg aggcggacta ttattgcgga acctgggact ccagcctgag cgctccctgg | 780 |
| gttttcggcg gaggtactaa gctgaccgtc ttgggaggag gcggttcaga agtgcagctg | 840 |
| gtggaatccg ggggggggcct ggtgcagcct ggggggagcc tgagactgag ttgtgccgcc | 900 |
| tctggggtga catttaacta ctatggcatg tcttggatcc gccaggcacc tggaaagggc | 960 |
| ctggagtggg tggccagcat cactaggtcc ggcgggcgaa tctactatcc cgacagcgtc | 1020 |
| aagggcaggt tcacaatttc ccgcgagaac acacagaaaa ctctgtacct gcagatgaat | 1080 |
| agcctgagag ccgaagatac agctgtgtac tattgcactc tggacggcag ggatgggtgg | 1140 |
| gtcgcctatt gggggtgtgg aaccctggtg acagtcagct ccggaggagg aggatctggc | 1200 |
| ggaggaggca gtgggggagg cgggtcaaac tttatgctca ctcagccgtc ctctgtttct | 1260 |
| ggcgtacctg gccaacgggt gaccattagc tgtacgggta ataccgggaa tatcgggtct | 1320 |
| aactacgtga actggtatca gcagcttcca gggacatgtc ccaagttgct gatctatcgc | 1380 |
| gacgacaaaa gaccctcagg ggtccctgac cgatttagtg gcagcaaaag cggtacttcc | 1440 |
| gcttccctgg cgataaccgg ctttcaggcc gaagatgagg cagactacta ttgccagtca | 1500 |
| tattccagcg gcttcatctt cggaggcgga actaagctga cagtgttggc agccgagccc | 1560 |
| aaatcttctg acaaaactca cacatgccca ccctgcccag cacctgaagc cgcaggggga | 1620 |
| ccctcagtct tcctcttccc cccaaaaccc aaggacaccc tcatgatctc ccggacccct | 1680 |
| gaggtcacat gcgtggtggt gtcagtgagc cacgaagacc ctgaggtcaa gttcaactgg | 1740 |
| tacgtggacg gcgtggaggt gcataatgcc aagacaaagc cccgggagga gcagtacaac | 1800 |
| agcacgtacc gggtggtcag cgtcctcacc gtcctgcacc aggactggct gaatggcaag | 1860 |
| gagtacaagt gcaaggtctc caacaaagcc ctcccagccc ccatcgagaa aaccatctcc | 1920 |
| aaagccaaag gccagccccg ggaaccacag gtgtacgtgt accccccatc ccgggacgag | 1980 |
| ctgaccaaga accaggtcag cctgacctgc ctggtcaaag gcttctatcc cagcgacatc | 2040 |
| gccgtggagt gggagagcaa tggccagccc gagaacaact acaagaccac ccctcccgtg | 2100 |
| ctggactccg acggctcctt cgccctcgtg agcaagctca ccgtggacaa gagcaggtgg | 2160 |
| cagcagggca acgtcttctc atgctccgtg atgcatgagg ctctgcacaa ccactacacc | 2220 |
| cagaagagcc tctccctgtc tcccggcaag | 2250 |

<210> SEQ ID NO 154
<211> LENGTH: 2250
<212> TYPE: DNA
<213> ORGANISM: Artificial
<220> FEATURE:
<223> OTHER INFORMATION: Full-length nucleotide sequence of NYZ-0083-HC2

<400> SEQUENCE: 154

| | |
|---|---:|
| atgaaacacc tgtggttctt cctcctgctg gtggcagctc ccagatgggt gctgagcggt | 60 |
| gaggtacagc tggtggaatc cgtggaggc cttgtgcaac cggagggctc cctgcgactc | 120 |
| tcttgcgccg catctggctt ttccatacga tcctacgata ttcattgggt ccgacaagcc | 180 |
| cctggcaaag tcttgaatg ggttgccact atctcctacg acgggtctca gaaatattat | 240 |
| gcggattcag tgaaggggcg gttcacaatt tcacgagaca gtcaaagaa tacactgtac | 300 |
| ctccaaatga attcactgag agccgaggat actgcagtct atcattgtgc aagagggtcc | 360 |
| tcaggccact acgaggcctt tgatatatgg ggccaaggca ccttggtaac cgttagtagc | 420 |
| ggaggtggag gaagcggagg cggcggttcc ggaggaggtg aagtggagg aggtggatct | 480 |

```
caatccgttc tgactcagcc accctccgcc tctggcaccc cgggccaacg ggtcacaata    540
tcatgttctg gctcttcaag caacatcgga aactggtacg tgagctggta ccagcagctc    600
cccggcacgg cgcccaagct tctgatatat gacaacaaca aacggcccag tggagttcct    660
gacagattca gtgggtctaa aagtggtaca agcgctagcc tggccataag tggtctgcag    720
agtgaagatg aggcggacta ttattgcgga acctgggact ccagcctgag cgctccctgg    780
gttttcggcg gaggtactaa gctgaccgtc ttgggaggag gcggttcaga agtgcagctg    840
gtggaatccg gggggggcct ggtgcagcct ggggggagcc tgagactgag ttgtgccgcc    900
tctggggtga catttaacta ctatggcatg tcttggatcc gccaggcacc tggaaagtgt    960
ctggagtggg tggccagcat cactaggtcc ggcgggcgaa tctactatcc cgacagcgtc   1020
aagggcaggt tcacaatttc ccgcgagaac acacagaaaa ctctgtacct gcagatgaat   1080
agcctgagag ccgaagatac agctgtgtac tattgcactc tggacggcag ggatgggtgg   1140
gtcgcctatt gggggcaggg aaccctggtc acagtcagct ccggaggagg aggatctggc   1200
ggaggaggca gtgggggagg cgggtcaaac tttatgctca ctcagccgtc ctctgtttct   1260
ggcgtacctg gccaacgggt gaccattagc tgtacgggta ataccgggaa tatcgggtct   1320
aactacgtga actggtatca gcagcttcca gggacagctc ccaagttgct gatctatcgc   1380
gacgacaaaa gaccctcagg ggtccctgac cgatttagtg gcagcaaaag cggtacttcc   1440
gcttccctgg cgataaccgg ctttcaggcc gaagatgagg cagactacta ttgccagtca   1500
tattccagcg gcttcatctt cggatgtgga actaagctga cagtgttggc agccgagccc   1560
aaaatcttctg acaaaactca cacatgccca ccctgcccag cacctgaagc cgcaggggga   1620
ccctcagtct tcctcttccc cccaaaaccc aaggacaccc tcatgatctc ccggacccct   1680
gaggtcacat gcgtggtggt gtcagtgagc cacgaagacc ctgaggtcaa gttcaactgg   1740
tacgtggacg gcgtggaggt gcataatgcc aagacaaagc cccgggagga gcagtacaac   1800
agcacgtacc gggtggtcag cgtcctcacc gtcctgcacc aggactggct gaatggcaag   1860
gagtacaagt gcaaggtctc caacaaagcc ctcccagccc ccatcgagaa aaccatctcc   1920
aaagccaaag gccagccccg ggaaccacag gtgtacgtgt accccccatc ccgggacgag   1980
ctgaccaaga accaggtcag cctgacctgc ctggtcaaag gcttctatcc cagcgacatc   2040
gccgtggagt gggagagcaa tggccagccc gagaacaact acaagaccac ccctcccgtg   2100
ctggactccg acggctcctt cgccctcgtg agcaagctca ccgtggacaa gagcaggtgg   2160
cagcagggca acgtcttctc atgctccgtg atgcatgagg ctctgcacaa ccactacacc   2220
cagaagagcc tctccctgtc tcccggcaag                                     2250
```

<210> SEQ ID NO 155
<211> LENGTH: 745
<212> TYPE: PRT
<213> ORGANISM: Artificial
<220> FEATURE:
<223> OTHER INFORMATION: Full-length amino acid sequence of NYZ-0038-HC2

<400> SEQUENCE: 155

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Ser
        35                  40                  45

```
Ile Arg Ser Tyr Asp Ile His Trp Val Arg Gln Ala Pro Gly Lys Gly
 50                  55                  60
Leu Glu Trp Val Ala Thr Ile Ser Tyr Asp Gly Ser Gln Lys Tyr Tyr
 65                  70                  75                  80
Ala Asp Ser Val Lys Gly Arg Phe Thr Ile Ser Arg Asp Glu Ser Lys
                 85                  90                  95
Asn Thr Leu Tyr Leu Gln Met Asn Ser Leu Arg Ala Glu Asp Thr Ala
                100                 105                 110
Val Tyr His Cys Ala Arg Gly Ser Gly His Tyr Glu Ala Phe Asp
            115                 120                 125
Ile Trp Gly Gln Gly Thr Leu Val Thr Val Ser Ser Gly Gly Gly Gly
130                 135                 140
Ser Gly Gly Gly Gly Ser Gly Gly Gly Ser Gln Ser Val Leu Thr
145                 150                 155                 160
Gln Pro Pro Ser Ala Ser Gly Thr Pro Gly Gln Arg Val Thr Ile Ser
                165                 170                 175
Cys Ser Gly Ser Ser Asn Ile Gly Asn Trp Tyr Val Ser Trp Tyr
            180                 185                 190
Gln Gln Leu Pro Gly Thr Ala Pro Lys Leu Leu Ile Tyr Asp Asn Asn
                195                 200                 205
Lys Arg Pro Ser Gly Val Pro Asp Arg Phe Ser Gly Ser Lys Ser Gly
210                 215                 220
Thr Ser Ala Ser Leu Ala Ile Ser Gly Leu Gln Ser Glu Asp Glu Ala
225                 230                 235                 240
Asp Tyr Tyr Cys Gly Thr Trp Asp Ser Ser Leu Ser Ala Pro Trp Val
                245                 250                 255
Phe Gly Gly Gly Thr Lys Leu Thr Val Leu Gly Gly Gly Gly Ser Glu
                260                 265                 270
Val Gln Leu Val Glu Ser Gly Gly Gly Leu Val Gln Pro Gly Gly Ser
            275                 280                 285
Leu Arg Leu Ser Cys Ala Ala Ser Gly Val Thr Phe Asn Tyr Tyr Gly
            290                 295                 300
Met Ser Trp Ile Arg Gln Ala Pro Gly Lys Gly Leu Glu Trp Val Ala
305                 310                 315                 320
Ser Ile Thr Arg Ser Gly Gly Arg Ile Tyr Tyr Pro Asp Ser Val Lys
                325                 330                 335
Gly Arg Phe Thr Ile Ser Arg Glu Asn Thr Gln Lys Thr Leu Tyr Leu
                340                 345                 350
Gln Met Asn Ser Leu Arg Ala Glu Asp Thr Ala Val Tyr Tyr Cys Thr
            355                 360                 365
Leu Asp Gly Arg Asp Gly Trp Val Ala Tyr Trp Gly Cys Gly Thr Leu
            370                 375                 380
Val Thr Val Ser Ser Gly Gly Gly Gly Ser Gly Gly Gly Gly Ser Gly
385                 390                 395                 400
Gly Gly Gly Ser Asn Phe Met Leu Thr Gln Pro Ser Ser Val Ser Gly
                405                 410                 415
Val Pro Gly Gln Arg Val Thr Ile Ser Cys Thr Gly Asn Thr Gly Asn
                420                 425                 430
Ile Gly Ser Asn Tyr Val Asn Trp Tyr Gln Gln Leu Pro Gly Thr Cys
            435                 440                 445
Pro Lys Leu Leu Ile Tyr Arg Asp Asp Lys Arg Pro Ser Gly Val Pro
450                 455                 460
Asp Arg Phe Ser Gly Ser Lys Ser Gly Thr Ser Ala Ser Leu Ala Ile
```

```
                465                 470                 475                 480
Thr Gly Phe Gln Ala Glu Asp Glu Ala Asp Tyr Tyr Cys Gln Ser Tyr
                    485                 490                 495

Ser Ser Gly Phe Ile Phe Gly Gly Thr Lys Leu Thr Val Leu Ala
                500                 505                 510

Ala Glu Pro Lys Ser Ser Asp Lys Thr His Thr Cys Pro Cys Pro
                515                 520                 525

Ala Pro Glu Ala Ala Gly Gly Pro Ser Val Phe Leu Phe Pro Lys
                530                 535                 540

Pro Lys Asp Thr Leu Met Ile Ser Arg Thr Pro Glu Val Thr Cys Val
545                 550                 555                 560

Val Val Ser Val Ser His Glu Asp Pro Glu Val Lys Phe Asn Trp Tyr
                    565                 570                 575

Val Asp Gly Val Glu Val His Asn Ala Lys Thr Lys Pro Arg Glu Glu
                580                 585                 590

Gln Tyr Asn Ser Thr Tyr Arg Val Val Ser Val Leu Thr Val Leu His
                595                 600                 605

Gln Asp Trp Leu Asn Gly Lys Glu Tyr Lys Cys Lys Val Ser Asn Lys
            610                 615                 620

Ala Leu Pro Ala Pro Ile Glu Lys Thr Ile Ser Lys Ala Lys Gly Gln
625                 630                 635                 640

Pro Arg Glu Pro Gln Val Tyr Val Tyr Pro Pro Ser Arg Asp Glu Leu
                    645                 650                 655

Thr Lys Asn Gln Val Ser Leu Thr Cys Leu Val Lys Gly Phe Tyr Pro
                660                 665                 670

Ser Asp Ile Ala Val Glu Trp Glu Ser Asn Gly Gln Pro Glu Asn Asn
                675                 680                 685

Tyr Lys Thr Thr Pro Pro Val Leu Asp Ser Asp Gly Ser Phe Ala Leu
            690                 695                 700

Val Ser Lys Leu Thr Val Asp Lys Ser Arg Trp Gln Gln Gly Asn Val
705                 710                 715                 720

Phe Ser Cys Ser Val Met His Glu Ala Leu His Asn His Tyr Thr Gln
                    725                 730                 735

Lys Ser Leu Ser Leu Ser Pro Gly Lys
                740                 745

<210> SEQ ID NO 156
<211> LENGTH: 750
<212> TYPE: PRT
<213> ORGANISM: Artificial
<220> FEATURE:
<223> OTHER INFORMATION: Full-length amino acid sequence of NYZ-0082-HC2

<400> SEQUENCE: 156

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Leu Val
                20                  25                  30

Gln Pro Gly Gly Ser Leu Arg Leu Ser Cys Ala Ala Ser Gly Phe Ser
            35                  40                  45

Ile Arg Ser Tyr Asp Ile His Trp Val Arg Gln Ala Pro Gly Lys Gly
        50                  55                  60

Leu Glu Trp Val Ala Thr Ile Ser Tyr Asp Gly Ser Gln Lys Tyr Tyr
65                  70                  75                  80

Ala Asp Ser Val Lys Gly Arg Phe Thr Ile Ser Arg Asp Glu Ser Lys
```

-continued

```
                 85                  90                  95
Asn Thr Leu Tyr Leu Gln Met Asn Ser Leu Arg Ala Glu Asp Thr Ala
                100                 105                 110
Val Tyr His Cys Ala Arg Gly Ser Ser Gly His Tyr Glu Ala Phe Asp
            115                 120                 125
Ile Trp Gly Gln Gly Thr Leu Val Thr Val Ser Ser Gly Gly Gly Gly
        130                 135                 140
Ser Gly Gly Gly Gly Ser Gly Gly Gly Gly Ser Gly Gly Gly Gly Ser
145                 150                 155                 160
Gln Ser Val Leu Thr Gln Pro Pro Ser Ala Ser Gly Thr Pro Gly Gln
                165                 170                 175
Arg Val Thr Ile Ser Cys Ser Gly Ser Ser Ser Asn Ile Gly Asn Trp
            180                 185                 190
Tyr Val Ser Trp Tyr Gln Gln Leu Pro Gly Thr Ala Pro Lys Leu Leu
        195                 200                 205
Ile Tyr Asp Asn Asn Lys Arg Pro Ser Gly Val Pro Asp Arg Phe Ser
    210                 215                 220
Gly Ser Lys Ser Gly Thr Ser Ala Ser Leu Ala Ile Ser Gly Leu Gln
225                 230                 235                 240
Ser Glu Asp Glu Ala Asp Tyr Tyr Cys Gly Thr Trp Asp Ser Ser Leu
                245                 250                 255
Ser Ala Pro Trp Val Phe Gly Gly Gly Thr Lys Leu Thr Val Leu Gly
            260                 265                 270
Gly Gly Gly Ser Glu Val Gln Leu Val Glu Ser Gly Gly Gly Leu Val
        275                 280                 285
Gln Pro Gly Gly Ser Leu Arg Leu Ser Cys Ala Ala Ser Gly Val Thr
    290                 295                 300
Phe Asn Tyr Tyr Gly Met Ser Trp Ile Arg Gln Ala Pro Gly Lys Gly
305                 310                 315                 320
Leu Glu Trp Val Ala Ser Ile Thr Arg Ser Gly Gly Arg Ile Tyr Tyr
                325                 330                 335
Pro Asp Ser Val Lys Gly Arg Phe Thr Ile Ser Arg Glu Asn Thr Gln
            340                 345                 350
Lys Thr Leu Tyr Leu Gln Met Asn Ser Leu Arg Ala Glu Asp Thr Ala
        355                 360                 365
Val Tyr Tyr Cys Thr Leu Asp Gly Arg Asp Gly Trp Val Ala Tyr Trp
    370                 375                 380
Gly Cys Gly Thr Leu Val Thr Val Ser Ser Gly Gly Gly Gly Ser Gly
385                 390                 395                 400
Gly Gly Gly Ser Gly Gly Gly Ser Asn Phe Met Leu Thr Gln Pro
                405                 410                 415
Ser Ser Val Ser Gly Val Pro Gly Gln Arg Val Thr Ile Ser Cys Thr
            420                 425                 430
Gly Asn Thr Gly Asn Ile Gly Ser Asn Tyr Val Asn Trp Tyr Gln Gln
        435                 440                 445
Leu Pro Gly Thr Cys Pro Lys Leu Leu Ile Tyr Arg Asp Asp Lys Arg
    450                 455                 460
Pro Ser Gly Val Pro Asp Arg Phe Ser Gly Ser Lys Ser Gly Thr Ser
465                 470                 475                 480
Ala Ser Leu Ala Ile Thr Gly Phe Gln Ala Glu Asp Glu Ala Asp Tyr
                485                 490                 495
Tyr Cys Gln Ser Tyr Ser Ser Gly Phe Ile Phe Gly Gly Gly Thr Lys
            500                 505                 510
```

```
Leu Thr Val Leu Ala Ala Glu Pro Lys Ser Ser Asp Lys Thr His Thr
            515                 520                 525

Cys Pro Pro Cys Pro Ala Pro Glu Ala Ala Gly Gly Pro Ser Val Phe
        530                 535                 540

Leu Phe Pro Pro Lys Pro Lys Asp Thr Leu Met Ile Ser Arg Thr Pro
545                 550                 555                 560

Glu Val Thr Cys Val Val Val Ser Val Ser His Glu Asp Pro Glu Val
                565                 570                 575

Lys Phe Asn Trp Tyr Val Asp Gly Val Glu Val His Asn Ala Lys Thr
            580                 585                 590

Lys Pro Arg Glu Glu Gln Tyr Asn Ser Thr Tyr Arg Val Val Ser Val
        595                 600                 605

Leu Thr Val Leu His Gln Asp Trp Leu Asn Gly Lys Glu Tyr Lys Cys
    610                 615                 620

Lys Val Ser Asn Lys Ala Leu Pro Ala Pro Ile Glu Lys Thr Ile Ser
625                 630                 635                 640

Lys Ala Lys Gly Gln Pro Arg Glu Pro Gln Val Tyr Val Tyr Pro Pro
                645                 650                 655

Ser Arg Asp Glu Leu Thr Lys Asn Gln Val Ser Leu Thr Cys Leu Val
            660                 665                 670

Lys Gly Phe Tyr Pro Ser Asp Ile Ala Val Glu Trp Glu Ser Asn Gly
        675                 680                 685

Gln Pro Glu Asn Asn Tyr Lys Thr Thr Pro Pro Val Leu Asp Ser Asp
    690                 695                 700

Gly Ser Phe Ala Leu Val Ser Lys Leu Thr Val Asp Lys Ser Arg Trp
705                 710                 715                 720

Gln Gln Gly Asn Val Phe Ser Cys Ser Val Met His Glu Ala Leu His
                725                 730                 735

Asn His Tyr Thr Gln Lys Ser Leu Ser Leu Ser Pro Gly Lys
            740                 745                 750

<210> SEQ ID NO 157
<211> LENGTH: 750
<212> TYPE: PRT
<213> ORGANISM: Artificial
<220> FEATURE:
<223> OTHER INFORMATION: Full-length amino acid sequence of NYZ-0083-HC2

<400> SEQUENCE: 157

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Ser
        35                  40                  45

Ile Arg Ser Tyr Asp Ile His Trp Val Arg Gln Ala Pro Gly Lys Gly
    50                  55                  60

Leu Glu Trp Val Ala Thr Ile Ser Tyr Asp Gly Ser Gln Lys Tyr Tyr
65                  70                  75                  80

Ala Asp Ser Val Lys Gly Arg Phe Thr Ile Ser Arg Asp Glu Ser Lys
                85                  90                  95

Asn Thr Leu Tyr Leu Gln Met Asn Ser Leu Arg Ala Glu Asp Thr Ala
            100                 105                 110

Val Tyr His Cys Ala Arg Gly Ser Ser Gly His Tyr Glu Ala Phe Asp
        115                 120                 125
```

```
Ile Trp Gly Gln Gly Thr Leu Val Thr Val Ser Ser Gly Gly Gly
130                 135                 140
Ser Gly Gly Gly Gly Ser Gly Gly Gly Gly Ser Gly Gly Gly Ser
145                 150                 155                 160
Gln Ser Val Leu Thr Gln Pro Pro Ser Ala Ser Gly Thr Pro Gly
                165                 170                 175
Arg Val Thr Ile Ser Cys Ser Gly Ser Ser Asn Ile Gly Asn Trp
                180                 185                 190
Tyr Val Ser Trp Tyr Gln Gln Leu Pro Gly Thr Ala Pro Lys Leu Leu
                195                 200                 205
Ile Tyr Asp Asn Asn Lys Arg Pro Ser Gly Val Pro Asp Arg Phe Ser
210                 215                 220
Gly Ser Lys Ser Gly Thr Ser Ala Ser Leu Ala Ile Ser Gly Leu Gln
225                 230                 235                 240
Ser Glu Asp Glu Ala Asp Tyr Tyr Cys Gly Thr Trp Asp Ser Ser Leu
                245                 250                 255
Ser Ala Pro Trp Val Phe Gly Gly Thr Lys Leu Thr Val Leu Gly
                260                 265                 270
Gly Gly Gly Ser Glu Val Gln Leu Val Glu Ser Gly Gly Leu Val
                275                 280                 285
Gln Pro Gly Gly Ser Leu Arg Leu Ser Cys Ala Ala Ser Gly Val Thr
290                 295                 300
Phe Asn Tyr Tyr Gly Met Ser Trp Ile Arg Gln Ala Pro Gly Lys Cys
305                 310                 315                 320
Leu Glu Trp Val Ala Ser Ile Thr Arg Ser Gly Arg Ile Tyr Tyr
                325                 330                 335
Pro Asp Ser Val Lys Gly Arg Phe Thr Ile Ser Arg Glu Asn Thr Gln
                340                 345                 350
Lys Thr Leu Tyr Leu Gln Met Asn Ser Leu Arg Ala Glu Asp Thr Ala
                355                 360                 365
Val Tyr Tyr Cys Thr Leu Asp Gly Arg Asp Gly Trp Val Ala Tyr Trp
370                 375                 380
Gly Gln Gly Thr Leu Val Thr Val Ser Ser Gly Gly Gly Gly Ser Gly
385                 390                 395                 400
Gly Gly Gly Ser Gly Gly Gly Gly Ser Asn Phe Met Leu Thr Gln Pro
                405                 410                 415
Ser Ser Val Ser Gly Val Pro Gly Gln Arg Val Thr Ile Ser Cys Thr
                420                 425                 430
Gly Asn Thr Gly Asn Ile Gly Ser Asn Tyr Val Asn Trp Tyr Gln Gln
                435                 440                 445
Leu Pro Gly Thr Ala Pro Lys Leu Leu Ile Tyr Arg Asp Asp Lys Arg
450                 455                 460
Pro Ser Gly Val Pro Asp Arg Phe Ser Gly Ser Lys Ser Gly Thr Ser
465                 470                 475                 480
Ala Ser Leu Ala Ile Thr Gly Phe Gln Ala Glu Asp Glu Ala Asp Tyr
                485                 490                 495
Tyr Cys Gln Ser Tyr Ser Ser Gly Phe Ile Phe Gly Cys Gly Thr Lys
                500                 505                 510
Leu Thr Val Leu Ala Ala Glu Pro Lys Ser Ser Asp Lys Thr His Thr
                515                 520                 525
Cys Pro Pro Cys Pro Ala Pro Glu Ala Ala Gly Gly Pro Ser Val Phe
530                 535                 540
```

Leu Phe Pro Pro Lys Pro Lys Asp Thr Leu Met Ile Ser Arg Thr Pro
545                 550                 555                 560

Glu Val Thr Cys Val Val Val Ser Val Ser His Glu Asp Pro Glu Val
            565                 570                 575

Lys Phe Asn Trp Tyr Val Asp Gly Val Glu Val His Asn Ala Lys Thr
                580                 585                 590

Lys Pro Arg Glu Glu Gln Tyr Asn Ser Thr Tyr Arg Val Val Ser Val
            595                 600                 605

Leu Thr Val Leu His Gln Asp Trp Leu Asn Gly Lys Glu Tyr Lys Cys
610                 615                 620

Lys Val Ser Asn Lys Ala Leu Pro Ala Pro Ile Glu Lys Thr Ile Ser
625                 630                 635                 640

Lys Ala Lys Gly Gln Pro Arg Glu Pro Gln Val Tyr Val Tyr Pro Pro
            645                 650                 655

Ser Arg Asp Glu Leu Thr Lys Asn Gln Val Ser Leu Thr Cys Leu Val
            660                 665                 670

Lys Gly Phe Tyr Pro Ser Asp Ile Ala Val Glu Trp Glu Ser Asn Gly
                675                 680                 685

Gln Pro Glu Asn Asn Tyr Lys Thr Thr Pro Pro Val Leu Asp Ser Asp
690                 695                 700

Gly Ser Phe Ala Leu Val Ser Lys Leu Thr Val Asp Lys Ser Arg Trp
705                 710                 715                 720

Gln Gln Gly Asn Val Phe Ser Cys Ser Val Met His Glu Ala Leu His
                725                 730                 735

Asn His Tyr Thr Gln Lys Ser Leu Ser Leu Ser Pro Gly Lys
            740                 745                 750

<210> SEQ ID NO 158
<211> LENGTH: 2172
<212> TYPE: DNA
<213> ORGANISM: Artificial
<220> FEATURE:
<223> OTHER INFORMATION: Full-length nucleotide sequence of NYZ-1010-HC2

<400> SEQUENCE: 158
atgaaacacc tgtggttctt cctcctgctg gtggcagctc ccagatgggt gctgagcggt      60
gaggtacagc tggtggaatc cggtggaggc cttgtgcaac cgggaggctc cctgcgactc     120
tcttgcgccg catctggctt ttccatacga tcctacgata tcattgggt ccgacaagcc      180 cctggcaaag gtcttgaatg ggttgccact atctcctacg acgggtctca gaaatattat     240
gcggattcag tgaaggggcg gttcacaatt tcacgacg agtcaaagaa tacactgtac       300
ctccaaatga attcactgag agccgaggat actgcagtct atcattgtgc aagagggtcc     360
tcaggccact acgaggcctt tgatatatgg ggccaaggca ccttggtaac cgttagtagc     420
ggaggtggag gaagcggagg cggcggttcc ggaggaggtg aagtggagg aggtggatct     480 caatccgttc tgactcagcc accctccgcc tctggcaccc cgggccaacg ggtcacaata     540
tcatgttctg gctcttcaag caacatcgga aactggtacg tgagctggta ccagcagctc     600
cccggcacgg cgcccaagct tctgatatat gacaacaaca acggcccag tggagttcct     660 gacagattca gtgggtctaa aagtggtaca agcgctagcc tggccataag tggtctgcag     720
agtgaagatg aggcggacta ttattgcgga acctgggact ccagcctgag cgctccctgg     780
gttttcggcg gaggtactaa gctgaccgtc ttgggaggag gcggttcaga agtgcagctg     840
gtggaatccg ggggggcct ggtgcagcct ggggggagcc tgagactgag ttgtgccgcc     900

```
tctggggtga catttaacta ctatggcatg tcttggatcc gccaggcacc tggaaagggc    960
ctggagtggg tggccagcat cactaggtcc ggcgggcgaa tctactatcc cgacagcgtc   1020
aagggcaggt tcacaatttc ccgcgagaac acacagaaaa ctctgtacct gcagatgaat   1080
agcctgagag ccgaagatac agctgtgtac tattgcactc tggacggcag ggatgggtgg   1140
gtcgcctatt ggggtcaggg aaccctggtg acagtcagct ccgcctccac caagggccca   1200
agcgtcttcc ccctggcacc ctcctccaag agcacctctg gcggcacagc cgccctgggc   1260
tgcctggtca aggactactt ccccgaaccc gtgaccgtga gctggaactc aggcgccctg   1320
accagcggcg tgcacacctt ccccgctgtc ctgcagtcct caggactcta ctccctcagc   1380
agcgtggtga ccgtgccctc cagcagcttg ggcacccaga cctacatctg caacgtgaat   1440
cacaagccca gcaacaccaa ggtggacaag agagttgagc ccaagtcttg cgacaaaact   1500
cacacatgcc caccctgccc agcacctgaa gccgcagggg gaccctcagt cttcctcttc   1560
cccccaaaac ccaaggacac cctcatgatc tcccggaccc ctgaggtcac atgcgtggtg   1620
gtgtcagtga gccacgaaga ccctgaggtc aagttcaact ggtacgtgga cggcgtggag   1680
gtgcataatg ccaagacaaa gccccgggag gagcagtaca acagcacgta ccgggtggtc   1740
agcgtcctca ctgtcctgca ccaggactgg ctgaatggca aggagtacaa gtgcaaggtc   1800
tccaacaaag ccctcccagc ccccatcgag aaaaccatct ccaaagccaa aggccagccc   1860
cgggaaccac aggtgtacgt gtaccccccca tcccgggacg agctgaccaa gaaccaggtc   1920
agcctgacct gcctggtcaa aggcttctat cccagcgaca tcgccgtgga gtgggagagc   1980
aatggccagc ccgagaacaa ctacaagacc acccctcccg tgctggactc cgacggctcc   2040
ttcgccctcg tgagcaagct caccgtggac aagagcaggt ggcagcaggg caacgtcttc   2100
tcatgctccg tgatgcatga ggctctgcac aaccactaca cccagaagag cctctccctg   2160
tctccccggca ag                                                     2172
```

<210> SEQ ID NO 159
<211> LENGTH: 699
<212> TYPE: DNA
<213> ORGANISM: Artificial
<220> FEATURE:
<223> OTHER INFORMATION: Full-length nucleotide sequence of C3E-7085-LC

<400> SEQUENCE: 159

```
atggtgctgc agacccaggt gttcatctcc ctgctgctgt ggatctccgg cgcgtacggc     60
aactttatgc tcactcagcc gtcctctgtt tctggcgtac ctggccaacg ggtgaccatt    120
agctgtacgg gtaataccgg gaatatcggg tctaactacg tgaactggta tcagcagctt    180
ccagggacag ctcccaagtt gctgatctat cgcgacgaca aaagaccctc aggggtccct    240
gaccgattta gtggcagcaa aagcggtact tccgcttccc tggcgataac cggctttcag    300
gccgaagatg aggcagacta ctattgccag tcatattcca gcggcttcat cttcggaggc    360
ggaactaagc tgacagtgct gggccagcct aaggctgccc ctagcgtgac cctgttccct    420
ccttccagcg aggagcttca agctaacaag gccaccctgg tgtgtcttat ctctgacttc    480
taccctggcg ctgtgaccgt ggcctggaag gctgacagct cccctgtgaa ggccggagtg    540
gagaccacca cacctagcaa gcagtctaac aacaagtacg ctgccagctc ctacctgagc    600
cttacccctg agcagtggaa gtctcacaga agctactcct gtcaagtgac ccacgagggc    660
agcaccgtgg agaagaccgt ggctcctacc gagtgttcc                            699
```

<210> SEQ ID NO 160
<211> LENGTH: 724
<212> TYPE: PRT
<213> ORGANISM: Artificial
<220> FEATURE:
<223> OTHER INFORMATION: Full-length amino acid sequence of NYZ-1010-HC2

<400> SEQUENCE: 160

```
Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Ser
        35                  40                  45

Ile Arg Ser Tyr Asp Ile His Trp Val Arg Gln Ala Pro Gly Lys Gly
    50                  55                  60

Leu Glu Trp Val Ala Thr Ile Ser Tyr Asp Gly Ser Gln Lys Tyr Tyr
65                  70                  75                  80

Ala Asp Ser Val Lys Gly Arg Phe Thr Ile Ser Arg Asp Glu Ser Lys
                85                  90                  95

Asn Thr Leu Tyr Leu Gln Met Asn Ser Leu Arg Ala Glu Asp Thr Ala
            100                 105                 110

Val Tyr His Cys Ala Arg Gly Ser Ser Gly His Tyr Glu Ala Phe Asp
        115                 120                 125

Ile Trp Gly Gln Gly Thr Leu Val Thr Val Ser Ser Gly Gly Gly Gly
    130                 135                 140

Ser Gly Gly Gly Gly Ser Gly Gly Gly Gly Ser Gly Gly Gly Gly Ser
145                 150                 155                 160

Gln Ser Val Leu Thr Gln Pro Pro Ser Ala Ser Gly Thr Pro Gly Gln
                165                 170                 175

Arg Val Thr Ile Ser Cys Ser Gly Ser Ser Ser Asn Ile Gly Asn Trp
            180                 185                 190

Tyr Val Ser Trp Tyr Gln Gln Leu Pro Gly Thr Ala Pro Lys Leu Leu
        195                 200                 205

Ile Tyr Asp Asn Asn Lys Arg Pro Ser Gly Val Pro Asp Arg Phe Ser
    210                 215                 220

Gly Ser Lys Ser Gly Thr Ser Ala Ser Leu Ala Ile Ser Gly Leu Gln
225                 230                 235                 240

Ser Glu Asp Glu Ala Asp Tyr Tyr Cys Gly Thr Trp Asp Ser Ser Leu
                245                 250                 255

Ser Ala Pro Trp Val Phe Gly Gly Gly Thr Lys Leu Thr Val Leu Gly
            260                 265                 270

Gly Gly Gly Ser Glu Val Gln Leu Val Glu Ser Gly Gly Gly Leu Val
        275                 280                 285

Gln Pro Gly Gly Ser Leu Arg Leu Ser Cys Ala Ala Ser Gly Val Thr
    290                 295                 300

Phe Asn Tyr Tyr Gly Met Ser Trp Ile Arg Gln Ala Pro Gly Lys Gly
305                 310                 315                 320

Leu Glu Trp Val Ala Ser Ile Thr Arg Ser Gly Gly Arg Ile Tyr Tyr
                325                 330                 335

Pro Asp Ser Val Lys Gly Arg Phe Thr Ile Ser Arg Glu Asn Thr Gln
            340                 345                 350

Lys Thr Leu Tyr Leu Gln Met Asn Ser Leu Arg Ala Glu Asp Thr Ala
        355                 360                 365

Val Tyr Tyr Cys Thr Leu Asp Gly Arg Asp Gly Trp Val Ala Tyr Trp
```

```
            370                 375                 380
Gly Gln Gly Thr Leu Val Thr Val Ser Ser Ala Ser Thr Lys Gly Pro
385                 390                 395                 400

Ser Val Phe Pro Leu Ala Pro Ser Ser Lys Ser Thr Ser Gly Gly Thr
                405                 410                 415

Ala Ala Leu Gly Cys Leu Val Lys Asp Tyr Phe Pro Glu Pro Val Thr
            420                 425                 430

Val Ser Trp Asn Ser Gly Ala Leu Thr Ser Gly Val His Thr Phe Pro
        435                 440                 445

Ala Val Leu Gln Ser Ser Gly Leu Tyr Ser Leu Ser Ser Val Val Thr
450                 455                 460

Val Pro Ser Ser Ser Leu Gly Thr Gln Thr Tyr Ile Cys Asn Val Asn
465                 470                 475                 480

His Lys Pro Ser Asn Thr Lys Val Asp Lys Arg Val Glu Pro Lys Ser
                485                 490                 495

Cys Asp Lys Thr His Thr Cys Pro Pro Cys Pro Ala Pro Glu Ala Ala
            500                 505                 510

Gly Gly Pro Ser Val Phe Leu Phe Pro Pro Lys Pro Lys Asp Thr Leu
        515                 520                 525

Met Ile Ser Arg Thr Pro Glu Val Thr Cys Val Val Val Ser Val Ser
530                 535                 540

His Glu Asp Pro Glu Val Lys Phe Asn Trp Tyr Val Asp Gly Val Glu
545                 550                 555                 560

Val His Asn Ala Lys Thr Lys Pro Arg Glu Glu Gln Tyr Asn Ser Thr
                565                 570                 575

Tyr Arg Val Val Ser Val Leu Thr Val Leu His Gln Asp Trp Leu Asn
            580                 585                 590

Gly Lys Glu Tyr Lys Cys Lys Val Ser Asn Lys Ala Leu Pro Ala Pro
        595                 600                 605

Ile Glu Lys Thr Ile Ser Lys Ala Lys Gly Gln Pro Arg Glu Pro Gln
610                 615                 620

Val Tyr Val Tyr Pro Pro Ser Arg Asp Glu Leu Thr Lys Asn Gln Val
625                 630                 635                 640

Ser Leu Thr Cys Leu Val Lys Gly Phe Tyr Pro Ser Asp Ile Ala Val
                645                 650                 655

Glu Trp Glu Ser Asn Gly Gln Pro Glu Asn Asn Tyr Lys Thr Thr Pro
            660                 665                 670

Pro Val Leu Asp Ser Asp Gly Ser Phe Ala Leu Val Ser Lys Leu Thr
        675                 680                 685

Val Asp Lys Ser Arg Trp Gln Gln Gly Asn Val Phe Ser Cys Ser Val
690                 695                 700

Met His Glu Ala Leu His Asn His Tyr Thr Gln Lys Ser Leu Ser Leu
705                 710                 715                 720

Ser Pro Gly Lys

<210> SEQ ID NO 161
<211> LENGTH: 233
<212> TYPE: PRT
<213> ORGANISM: Artificial
<220> FEATURE:
<223> OTHER INFORMATION: Full-length amino acid sequence of C3E-7085-LC

<400> SEQUENCE: 161

Met Val Leu Gln Thr Gln Val Phe Ile Ser Leu Leu Leu Trp Ile Ser
1               5                   10                  15
```

Gly Ala Tyr Gly Asn Phe Met Leu Thr Gln Pro Ser Ser Val Ser Gly
            20                  25                  30

Val Pro Gly Gln Arg Val Thr Ile Ser Cys Thr Gly Asn Thr Gly Asn
        35                  40                  45

Ile Gly Ser Asn Tyr Val Asn Trp Tyr Gln Gln Leu Pro Gly Thr Ala
    50                  55                  60

Pro Lys Leu Leu Ile Tyr Arg Asp Asp Lys Arg Pro Ser Gly Val Pro
65                  70                  75                  80

Asp Arg Phe Ser Gly Ser Lys Ser Gly Thr Ser Ala Ser Leu Ala Ile
                85                  90                  95

Thr Gly Phe Gln Ala Glu Asp Glu Ala Asp Tyr Tyr Cys Gln Ser Tyr
            100                 105                 110

Ser Ser Gly Phe Ile Phe Gly Gly Thr Lys Leu Thr Val Leu Gly
        115                 120                 125

Gln Pro Lys Ala Ala Pro Ser Val Thr Leu Phe Pro Pro Ser Ser Glu
130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Arg Ser Tyr Ser Cys Gln Val Thr His Glu Gly Ser Thr Val Glu
210                 215                 220

Lys Thr Val Ala Pro Thr Glu Cys Ser
225                 230

<210> SEQ ID NO 162
<211> LENGTH: 5
<212> TYPE: PRT
<213> ORGANISM: Artificial
<220> FEATURE:
<223> OTHER INFORMATION: Peptide linker

<400> SEQUENCE: 162

Gly Gly Gly Gly Ser
1               5

<210> SEQ ID NO 163
<211> LENGTH: 891
<212> TYPE: DNA
<213> ORGANISM: Artificial
<220> FEATURE:
<223> OTHER INFORMATION: Full-length nucleotide sequence of NYA-3061

<400> SEQUENCE: 163
atgaaacacc tgtggttctt cctcctgctg gtggcagctc ccagatgggt gctgagcggt      60
gaggtacagc tggtggaatc cggtggaggc cttgtgcaac cgggaggctc cctgcgactc     120
tcttgcgccg catctggctt ttccatacga tcctacgata ttcattgggt ccgacaagcc     180
cctggcaaag gtcttgaatg ggttgccact atctcctacg acgggtctca gaaatattat     240
gcggattcag tgaagggggcg gttcacaatt tcacgagacg agtcaaagaa tacactgtac     300
ctccaaatga attcactgag agccgaggat actgcagtct atcattgtgc aagagggtcc     360
tcaggccact acgaggcctt tgatatatgg ggccaaggca ccttggtaac cgttagtagc     420

```
ggaggtggag gaagcggagg cggcggttcc ggaggaggtg gaagtggagg aggtggatct    480
caatccgttc tgactcagcc accctccgcc tctggcaccc cgggccaacg ggtcacaata    540
tcatgttctg gctcttcaag caacatcgga aactggtacg tgagctggta ccagcagctc    600
cccggcacgg cgcccaagct tctgatatat gacaacaaca acggcccag tggagttcct     660 gacagattca gtgggtctaa aagtggtaca agcgctagcc tggccataag tggtctgcag    720
agtgaagatg aggcggacta ttattgcgga acctgggact ccagcctgag cgctccctgg    780
gttttcggcg gaggtactaa gctgaccgtc ttgggcgcgg ccgcaggtgc aggtggtgat    840
tacaaagatg atgacgataa aggtgcagcg gcgcatcacc atcatcacca c             891
```

<210> SEQ ID NO 164
<211> LENGTH: 297
<212> TYPE: PRT
<213> ORGANISM: Artificial
<220> FEATURE:
<223> OTHER INFORMATION: Full-length amino acid sequence of NYA-3061

<400> SEQUENCE: 164

```
Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Ser
        35                  40                  45

Ile Arg Ser Tyr Asp Ile His Trp Val Arg Gln Ala Pro Gly Lys Gly
    50                  55                  60

Leu Glu Trp Val Ala Thr Ile Ser Tyr Asp Gly Ser Gln Lys Tyr Tyr
65                  70                  75                  80

Ala Asp Ser Val Lys Gly Arg Phe Thr Ile Ser Arg Asp Glu Ser Lys
                85                  90                  95

Asn Thr Leu Tyr Leu Gln Met Asn Ser Leu Arg Ala Glu Asp Thr Ala
            100                 105                 110

Val Tyr His Cys Ala Arg Gly Ser Ser Gly His Tyr Glu Ala Phe Asp
        115                 120                 125

Ile Trp Gly Gln Gly Thr Leu Val Thr Val Ser Ser Gly Gly Gly Gly
    130                 135                 140

Ser Gly Gly Gly Gly Ser Gly Gly Gly Gly Ser Gly Gly Gly Gly Ser
145                 150                 155                 160

Gln Ser Val Leu Thr Gln Pro Pro Ser Ala Ser Gly Thr Pro Gly Gln
                165                 170                 175

Arg Val Thr Ile Ser Cys Ser Gly Ser Ser Ser Asn Ile Gly Asn Trp
            180                 185                 190

Tyr Val Ser Trp Tyr Gln Gln Leu Pro Gly Thr Ala Pro Lys Leu Leu
        195                 200                 205

Ile Tyr Asp Asn Asn Lys Arg Pro Ser Gly Val Pro Asp Arg Phe Ser
    210                 215                 220

Gly Ser Lys Ser Gly Thr Ser Ala Ser Leu Ala Ile Ser Gly Leu Gln
225                 230                 235                 240

Ser Glu Asp Glu Ala Asp Tyr Tyr Cys Gly Thr Trp Asp Ser Ser Leu
                245                 250                 255

Ser Ala Pro Trp Val Phe Gly Gly Gly Thr Lys Leu Thr Val Leu Gly
            260                 265                 270

Ala Ala Ala Gly Ala Gly Gly Asp Tyr Lys Asp Asp Asp Asp Lys Gly
```

-continued

```
                275                 280                 285
Ala Ala Ala His His His His His
        290                 295
```

<210> SEQ ID NO 165
<211> LENGTH: 903
<212> TYPE: DNA
<213> ORGANISM: Artificial
<220> FEATURE:
<223> OTHER INFORMATION: Full-length nucleotide sequence of NYC-0005

<400> SEQUENCE: 165

| | | | | | |
|---|---|---|---|---|---|
| atgaagcacc | tgtggttctt | tctgctgctg | gtggccgctc | ctagatgggt | gttgtctggc | 60 |
| gaagtgcagc | tggtggaatc | tggtggcgga | gttgttcagc | ctggcggctc | tctgagactg | 120 |
| agctgtgtgg | ccagcggctt | caccttcgac | gactacgcca | tgtactgggt | ccgacaggtg | 180 |
| ccaggcaagg | acctggaatg | gtgtccctg | atttctggcg | acggcgacat | cacctactac | 240 |
| gtggactctg | tgaagggcag | attcaccgtg | tccagagaca | acaacaagaa | cagcctgtac | 300 |
| ctgcagatga | agtccctgcg | cgtggaagat | acagccctgt | actactgcgc | caaggacatg | 360 |
| atctactacg | cctcttggag | cggctacggc | agcagcgatt | actactacta | tgtgatggac | 420 |
| gtgtggggcc | agggcaccac | cgttacagtt | tctagcggag | gcggaggaag | tggcggcgga | 480 |
| ggatctggcg | gtggtggttc | tgatatccag | atgacacaga | gcccagcag | cctgtctgcc | 540 |
| tctgtgggag | acagagtgac | catcacctgt | agagccagcc | agagcatcag | cagctacctg | 600 |
| aactggtatc | agcagaagcc | cggcaaggcc | cctaaactgc | tgatctatgc | cgcctccagt | 660 |
| ctgcagagcg | gagtgcctag | cagatttct | ggcagcggct | ccggcaccga | tttcaccctg | 720 |
| accatatcta | gcctgcagcc | tgaggacttc | gccacctact | attgccagca | gagctacagc | 780 |
| accctcctct | caccttggg | ccaggaacc | agactggaaa | tcaaaggcgc | tgctgcaggc | 840 |
| gctggcggcg | actacaaaga | cgatgatgat | aagggcgctg | ccgctcacca | ccaccatcac | 900 |
| cat | | | | | | 903 |

<210> SEQ ID NO 166
<211> LENGTH: 301
<212> TYPE: PRT
<213> ORGANISM: Artificial
<220> FEATURE:
<223> OTHER INFORMATION: Full-length amino acid sequence of NYC-0005

<400> SEQUENCE: 166

```
Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Val Val
            20                  25                  30

Gln Pro Gly Gly Ser Leu Arg Leu Ser Cys Val Ala Ser Gly Phe Thr
        35                  40                  45

Phe Asp Asp Tyr Ala Met Tyr Trp Val Arg Gln Val Pro Gly Lys Asp
    50                  55                  60

Leu Glu Trp Val Ser Leu Ile Ser Gly Asp Gly Asp Ile Thr Tyr Tyr
65                  70                  75                  80

Val Asp Ser Val Lys Gly Arg Phe Thr Val Ser Arg Asp Asn Asn Lys
                85                  90                  95

Asn Ser Leu Tyr Leu Gln Met Lys Ser Leu Arg Val Glu Asp Thr Ala
            100                 105                 110

Leu Tyr Tyr Cys Ala Lys Asp Met Ile Tyr Tyr Ala Ser Trp Ser Gly
```

```
            115                 120                 125
Tyr Gly Ser Ser Asp Tyr Tyr Tyr Val Met Asp Val Trp Gly Gln
    130                 135                 140
Gly Thr Thr Val Thr Val Ser Gly Gly Gly Ser Gly Gly Gly
145                 150                 155                 160
Gly Ser Gly Gly Gly Ser Asp Ile Gln Met Thr Gln Ser Pro Ser
                165                 170                 175
Ser Leu Ser Ala Ser Val Gly Asp Arg Val Thr Ile Thr Cys Arg Ala
            180                 185                 190
Ser Gln Ser Ile Ser Ser Tyr Leu Asn Trp Tyr Gln Gln Lys Pro Gly
        195                 200                 205
Lys Ala Pro Lys Leu Leu Ile Tyr Ala Ala Ser Ser Leu Gln Ser Gly
    210                 215                 220
Val Pro Ser Arg Phe Ser Gly Ser Gly Ser Gly Thr Asp Phe Thr Leu
225                 230                 235                 240
Thr Ile Ser Ser Leu Gln Pro Glu Asp Phe Ala Thr Tyr Tyr Cys Gln
                245                 250                 255
Gln Ser Tyr Ser Thr Pro Pro Ile Thr Phe Gly Gln Gly Thr Arg Leu
            260                 265                 270
Glu Ile Lys Gly Ala Ala Ala Gly Ala Gly Gly Asp Tyr Lys Asp Asp
        275                 280                 285
Asp Asp Lys Gly Ala Ala Ala His His His His His His
    290                 295                 300
```

<210> SEQ ID NO 167
<211> LENGTH: 903
<212> TYPE: DNA
<213> ORGANISM: Artificial
<220> FEATURE:
<223> OTHER INFORMATION: Full-length nucleotide sequence of NYC-0006

<400> SEQUENCE: 167

```
atgaagcacc tgtggttctt tctgctgctg gtggccgctc ctagatgggt gttgtctggc      60
gaagtgcagc tggtggaatc tggtggcgga gttgttcagc ctggcggctc tctgagactg     120
tcttgtgccg ccagcggctt caccttcgac gactacgcca tgtactgggt ccgacaggcc     180
cctggcaaag gccttgaatg ggtgtccctg atcagcggag atggcggcag catgtactac     240
gccgatagcg tgaagggcag attcaccatc agccgggaca cagcaagaa cagcctgtac     300
ctgcagatga actccctgcg gaccgaggac acagccctgt actactgcgc caaggatatg     360
atcttctacg cctttggag cggctacggc agcagcgatt actactacta cgtgatggac     420
gtgtggggcc agggcaccac agtgacagtt tattctggcg gcggaggatc tggcggaggt     480
ggaagcggag gcgtggatc tgatatccag atgacacaga gccccagcag cctgtctgcc     540
tctgtgggag acagagtgac catcacctgt cgggccagcc agagaatcag cacctacctg     600
aactggtatc agcagaagcc cggcaaggcc cctaagctgc tgatctatgc tgcctccagt     660
ctgcagagcg gcgtgccaag cagatttct ggcagcggct ctggcaccga cttcaccctg     720
accatatcta gcctgcagcc tgaggacttc gccacctact actgccagca gagctacagc     780
acccctccta tcacctttgg ccagggaacc agactggaaa tcaaaggcgc tgctgcaggc     840
gcaggcggcg actacaaaga cgatgatgat aagggcgctg ccgctcacca ccaccatcac     900
cat                                                                   903
```

<210> SEQ ID NO 168

<211> LENGTH: 301
<212> TYPE: PRT
<213> ORGANISM: Artificial
<220> FEATURE:
<223> OTHER INFORMATION: Full-length amino acid sequence of NYC-0006

<400> SEQUENCE: 168

Met Lys His Leu Trp Phe Phe Leu Leu Val Ala Ala Pro Arg Trp
1               5                   10                  15

Val Leu Ser Gly Glu Val Gln Leu Val Glu Ser Gly Gly Val Val
            20                  25                  30

Gln Pro Gly Gly Ser Leu Arg Leu Ser Cys Ala Ala Ser Gly Phe Thr
        35                  40                  45

Phe Asp Asp Tyr Ala Met Tyr Trp Val Arg Gln Ala Pro Gly Lys Gly
50                  55                  60

Leu Glu Trp Val Ser Leu Ile Ser Gly Asp Gly Ser Met Tyr Tyr
65                  70                  75                  80

Ala Asp Ser Val Lys Gly Arg Phe Thr Ile Ser Arg Asp Asn Ser Lys
                85                  90                  95

Asn Ser Leu Tyr Leu Gln Met Asn Ser Leu Arg Thr Glu Asp Thr Ala
            100                 105                 110

Leu Tyr Tyr Cys Ala Lys Asp Met Ile Phe Tyr Ala Phe Trp Ser Gly
        115                 120                 125

Tyr Gly Ser Ser Asp Tyr Tyr Tyr Val Met Asp Val Trp Gly Gln
130                 135                 140

Gly Thr Thr Val Thr Val Tyr Ser Gly Gly Gly Ser Gly Gly Gly
145                 150                 155                 160

Gly Ser Gly Gly Gly Ser Asp Ile Gln Met Thr Gln Ser Pro Ser
                165                 170                 175

Ser Leu Ser Ala Ser Val Gly Asp Arg Val Thr Ile Thr Cys Arg Ala
            180                 185                 190

Ser Gln Arg Ile Ser Thr Tyr Leu Asn Trp Tyr Gln Gln Lys Pro Gly
        195                 200                 205

Lys Ala Pro Lys Leu Leu Ile Tyr Ala Ala Ser Ser Leu Gln Ser Gly
210                 215                 220

Val Pro Ser Arg Phe Ser Gly Ser Gly Ser Gly Thr Asp Phe Thr Leu
225                 230                 235                 240

Thr Ile Ser Ser Leu Gln Pro Glu Asp Phe Ala Thr Tyr Tyr Cys Gln
                245                 250                 255

Gln Ser Tyr Ser Thr Pro Pro Ile Thr Phe Gly Gln Gly Thr Arg Leu
            260                 265                 270

Glu Ile Lys Gly Ala Ala Ala Gly Ala Gly Gly Asp Tyr Lys Asp Asp
        275                 280                 285

Asp Asp Lys Gly Ala Ala Ala His His His His His
290                 295                 300

<210> SEQ ID NO 169
<211> LENGTH: 888
<212> TYPE: DNA
<213> ORGANISM: Artificial
<220> FEATURE:
<223> OTHER INFORMATION: Full-length nucleotide sequence of NYC-0007

<400> SEQUENCE: 169
atgaagcacc tgtggttctt tctgctgctg gtggccgctc ctagatgggt gttgtctggc     60
gaagtgcagc tggtggaatc tggtggcgga gttgttcagc ctggcggctc tctgagactg    120

```
tcttgtgccg ccagcggctt caccttcgac gattatgcca tgcactgggt ccgacaggcc    180
cctggcaaag gacttgaatg ggtgtccctg atcagcggcg acggcgacaa tacctactac    240
gccgatagcg tgaagggcag attcaccatc agccgggaca caacaagaa cagcctgtac     300 ctgcagatga actccctgcg gaccgaggac accgccttct actactgtgc caaagagctg    360
atcttcggca aggtgctgca cgactttta tactacgtga tggacgtgtg gggccagggc     420
accacagtga cagtttctag cggaggcgga ggaagtggcg gcggaggatc tggcggtggt    480
ggttctgata tccagatgac acagagcccc agcagcctgt ctgcctctgt gggagacaga    540
gtgaccatca cctgtagagc cagccagagc atcagcagct acctgaactg gtatcagcag    600
aagcccggca aggcccctaa actgctgatc tatgccgcct ccagtctgca gagcggagtg    660
cctagcagat ttctggcag cggctccggc accgatttca ccctgaccat atctagcctg     720
cagcctgagg acttcgccac ctactactgc cagcagagct acagcacccc tcctatcacc    780
tttggccagg gaaccagact ggaaatcaaa ggcgctgctg caggcgcagg cggcgactac    840
aaagacgatg atgataaggg cgctgccgct caccaccacc atcaccat                 888
```

<210> SEQ ID NO 170
<211> LENGTH: 296
<212> TYPE: PRT
<213> ORGANISM: Artificial
<220> FEATURE:
<223> OTHER INFORMATION: Full-length amino acid sequence of NYC-0007

<400> SEQUENCE: 170

| | | | | | | | | | | | | | | |
|---|---|---|---|---|---|---|---|---|---|---|---|---|---|---|
| Met | Lys | His | Leu | Trp | Phe | Phe | Leu | Leu | Leu | Val | Ala | Ala | Pro | Arg | Trp |
| 1 | | | | 5 | | | | | 10 | | | | | 15 | |
| Val | Leu | Ser | Gly | Glu | Val | Gln | Leu | Val | Glu | Ser | Gly | Gly | Gly | Val | Val |
| | | | 20 | | | | | 25 | | | | | 30 | | |
| Gln | Pro | Gly | Gly | Ser | Leu | Arg | Leu | Ser | Cys | Ala | Ala | Ser | Gly | Phe | Thr |
| | | | | 35 | | | | | 40 | | | | | 45 | |
| Phe | Asp | Asp | Tyr | Ala | Met | His | Trp | Val | Arg | Gln | Ala | Pro | Gly | Lys | Gly |
| | 50 | | | | | 55 | | | | | 60 | | | | |
| Leu | Glu | Trp | Val | Ser | Leu | Ile | Ser | Gly | Asp | Gly | Asp | Asn | Thr | Tyr | Tyr |
| 65 | | | | | 70 | | | | | 75 | | | | | 80 |
| Ala | Asp | Ser | Val | Lys | Gly | Arg | Phe | Thr | Ile | Ser | Arg | Asp | Asn | Asn | Lys |
| | | | | 85 | | | | | 90 | | | | | 95 | |
| Asn | Ser | Leu | Tyr | Leu | Gln | Met | Asn | Ser | Leu | Arg | Thr | Glu | Asp | Thr | Ala |
| | | | 100 | | | | | 105 | | | | | 110 | | |
| Phe | Tyr | Tyr | Cys | Ala | Lys | Glu | Leu | Ile | Phe | Gly | Lys | Val | Leu | His | Asp |
| | | | | 115 | | | | | 120 | | | | | 125 | |
| Phe | Tyr | Tyr | Tyr | Val | Met | Asp | Val | Trp | Gly | Gln | Gly | Thr | Thr | Val | Thr |
| | 130 | | | | | 135 | | | | | 140 | | | | |
| Val | Ser | Ser | Gly | Gly | Gly | Gly | Ser | Gly | Gly | Gly | Gly | Ser | Gly | Gly | Gly |
| 145 | | | | | 150 | | | | | 155 | | | | | 160 |
| Gly | Ser | Asp | Ile | Gln | Met | Thr | Gln | Ser | Pro | Ser | Ser | Leu | Ser | Ala | Ser |
| | | | | 165 | | | | | 170 | | | | | 175 | |
| Val | Gly | Asp | Arg | Val | Thr | Ile | Thr | Cys | Arg | Ala | Ser | Gln | Ser | Ile | Ser |
| | | | 180 | | | | | 185 | | | | | 190 | | |
| Ser | Tyr | Leu | Asn | Trp | Tyr | Gln | Gln | Lys | Pro | Gly | Lys | Ala | Pro | Lys | Leu |
| | | | | 195 | | | | | 200 | | | | | 205 | |
| Leu | Ile | Tyr | Ala | Ala | Ser | Ser | Leu | Gln | Ser | Gly | Val | Pro | Ser | Arg | Phe |
| | 210 | | | | | 215 | | | | | 220 | | | | |
| Ser | Gly | Ser | Gly | Ser | Gly | Thr | Asp | Phe | Thr | Leu | Thr | Ile | Ser | Ser | Leu |

```
                225                 230                 235                 240

Gln Pro Glu Asp Phe Ala Thr Tyr Tyr Cys Gln Gln Ser Tyr Ser Thr
                245                 250                 255

Pro Pro Ile Thr Phe Gly Gln Gly Thr Arg Leu Glu Ile Lys Gly Ala
            260                 265                 270

Ala Ala Gly Ala Gly Gly Asp Tyr Lys Asp Asp Asp Lys Gly Ala
        275                 280                 285

Ala Ala His His His His His His
        290                 295

<210> SEQ ID NO 171
<211> LENGTH: 888
<212> TYPE: DNA
<213> ORGANISM: Artificial
<220> FEATURE:
<223> OTHER INFORMATION: Full-length nucleotide sequence of NYC-0008

<400> SEQUENCE: 171
atgaagcacc tgtggttctt tctgctgctg gtggccgctc ctagatgggt gttgtctggc      60
gaagtgcagc tggtggaatc tggtggcgga gttgttcagc ctggcggctc tctgagactg     120
agctgtgaag cctccggctt catcttcgac gactacgcca tgcactgggt ccgacaggca     180
cctggcaaag gccttgaatg ggtgtccctg atctctggcg acggcgacat catctactac     240
gccgactctg tgaagggcag attcaccatc agccgggaca cagcaagaa cagcctgtac      300 ctgcagatga actccctgat catcgaggac acagccctgt actactgcgc caaggattgg     360
gtgttcggcg tcgtgatgac ccactactgg tacttcggcc tggatgtgtg gggccaggga     420
accacagtga cagtttctag cggaggcgga ggaagtggcg gcggaggatc tgcggtggt     480 ggttctgata tccagatgac acagagcccc agcagcctgt ctgcctctga aggcgacaga     540
gtgaccatca cctgtagagc cagccagagc atcagcacct acctgaactg gtatcagcag     600
aagcccggca aggccctaa gctgctgatc tatggtgcct ccagtctgca gagcggcgtg     660
ccaagcagat ttctggcag cggctctggc accgacttca ccctgaccat atctagcctg     720
cagcctgagg acttcgccac ctactactgc cagcagtcct acagcacccc tcctatcaca     780
tttggccagg gcaccaaggt ggaaatcaaa ggcgctgctg caggcgctgg cggcgactac     840
aaagacgatg atgataaggg cgctgccgct caccaccacc atcaccat                  888

<210> SEQ ID NO 172
<211> LENGTH: 296
<212> TYPE: PRT
<213> ORGANISM: Artificial
<220> FEATURE:
<223> OTHER INFORMATION: Full-length amino acid sequence of NYC-0008

<400> SEQUENCE: 172

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Val Val
            20                  25                  30

Gln Pro Gly Gly Ser Leu Arg Leu Ser Cys Glu Ala Ser Gly Phe Ile
        35                  40                  45

Phe Asp Asp Tyr Ala Met His Trp Val Arg Gln Ala Pro Gly Lys Gly
    50                  55                  60

Leu Glu Trp Val Ser Leu Ile Ser Gly Asp Gly Asp Ile Ile Tyr Tyr
65                  70                  75                  80
```

Ala Asp Ser Val Lys Gly Arg Phe Thr Ile Ser Arg Asp Asn Ser Lys
                    85                  90                  95

Asn Ser Leu Tyr Leu Gln Met Asn Ser Leu Ile Ile Glu Asp Thr Ala
            100                 105                 110

Leu Tyr Tyr Cys Ala Lys Asp Trp Val Phe Gly Val Val Met Thr His
            115                 120                 125

Tyr Trp Tyr Phe Gly Leu Asp Val Trp Gly Gln Gly Thr Thr Val Thr
            130                 135                 140

Val Ser Ser Gly Gly Gly Gly Ser Gly Gly Gly Gly Ser Gly Gly Gly
145                 150                 155                 160

Gly Ser Asp Ile Gln Met Thr Gln Ser Pro Ser Ser Leu Ser Ala Ser
            165                 170                 175

Glu Gly Asp Arg Val Thr Ile Thr Cys Arg Ala Ser Gln Ser Ile Ser
            180                 185                 190

Thr Tyr Leu Asn Trp Tyr Gln Gln Lys Pro Gly Lys Ala Pro Lys Leu
            195                 200                 205

Leu Ile Tyr Gly Ala Ser Ser Leu Gln Ser Gly Val Pro Ser Arg Phe
            210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Ser Tyr Ser Thr
            245                 250                 255

Pro Pro Ile Thr Phe Gly Gln Gly Thr Lys Val Glu Ile Lys Gly Ala
            260                 265                 270

Ala Ala Gly Ala Gly Gly Asp Tyr Lys Asp Asp Asp Asp Lys Gly Ala
            275                 280                 285

Ala Ala His His His His His His
            290                 295

<210> SEQ ID NO 173
<211> LENGTH: 885
<212> TYPE: DNA
<213> ORGANISM: Artificial
<220> FEATURE:
<223> OTHER INFORMATION: Full-length nucleotide sequence of NYC-0009

<400> SEQUENCE: 173
atgaagcacc tgtggttctt tctgctgctg gtggccgctc ctagatgggt gttgtctggc      60
gaagtgcagc tggtggaatc tggtggcgga gttgttcagc ctggcggctc tctgagactg     120
tcttgtgccg ccagcggctt caccttcgac gattatgcca tgcactgggt ccgacaggcc     180
cctggcaaag acttgaatg gggtgtccctg atctctggcg aggcggcgg aacctactac      240 agcgattctg tgaagggcag attcaccatc agccgggaca ccagcaagga cagcctgtac     300
ctgcagatga acagcctgcg gaccgaggac acagccctgt actactgcgc caaggacatg     360
gtgttcggcg tggtcacccc ttactactac ttcgccctgg atgtgtgggg ccagggcaca     420
acagtgacag tctcttctgg cggcggagga agcggaggcg gaggatccgg tggtggtgga     480
tctgacatcc agatgacaca gagccccagc agcctgtctg cctctgtggg agacagagtg     540
accatcacct gtagagccag ccagagcatc aacagctacc tgaactggta tcagcagaag     600
cccggcaagg cccctaagct gctgatctat ggtgcctcca gtctgcagag cggcgtgcca     660
agcagatttt ctggcagcgg ctctggcacc gacttcaccc tgaccatatc tagcctgcag     720
cctgaggact tcgccaccta ctactgccag cagagctaca gcgcccctcc tatcacattt     780
ggccagggaa ccagactgga aatcaaaggc gctgctgcag gcgcaggcgg cgactacaaa     840
gacgatgatg ataagggcgc tgccgctcac caccatcacc atcat 885

<210> SEQ ID NO 174
<211> LENGTH: 295
<212> TYPE: PRT
<213> ORGANISM: Artificial
<220> FEATURE:
<223> OTHER INFORMATION: Full-length amino acid sequence of NYC-0009

<400> SEQUENCE: 174

| | | | | | | | | | | | | | | |
|---|---|---|---|---|---|---|---|---|---|---|---|---|---|---|
| Met | Lys | His | Leu | Trp | Phe | Phe | Leu | Leu | Val | Ala | Ala | Pro | Arg | Trp |
| 1 | | | | 5 | | | | | 10 | | | | | 15 |
| Val | Leu | Ser | Gly | Glu | Val | Gln | Leu | Val | Glu | Ser | Gly | Gly | Gly | Val |
| | | | 20 | | | | | 25 | | | | | 30 | |
| Gln | Pro | Gly | Gly | Ser | Leu | Arg | Leu | Ser | Cys | Ala | Ala | Ser | Gly | Phe | Thr |
| | | 35 | | | | | 40 | | | | | 45 | | |
| Phe | Asp | Asp | Tyr | Ala | Met | His | Trp | Val | Arg | Gln | Ala | Pro | Gly | Lys | Gly |
| | 50 | | | | | 55 | | | | | 60 | | | | |
| Leu | Glu | Trp | Val | Ser | Leu | Ile | Ser | Gly | Gly | Gly | Gly | Thr | Tyr | Tyr |
| 65 | | | | | 70 | | | | | 75 | | | | | 80 |
| Ser | Asp | Ser | Val | Lys | Gly | Arg | Phe | Thr | Ile | Ser | Arg | Asp | Thr | Ser | Lys |
| | | | | 85 | | | | | 90 | | | | | 95 | |
| Asp | Ser | Leu | Tyr | Leu | Gln | Met | Asn | Ser | Leu | Arg | Thr | Glu | Asp | Thr | Ala |
| | | | 100 | | | | | 105 | | | | | 110 | | |
| Leu | Tyr | Tyr | Cys | Ala | Lys | Asp | Met | Val | Phe | Gly | Val | Val | Thr | Pro | Tyr |
| | | 115 | | | | | 120 | | | | | 125 | | | |
| Tyr | Tyr | Phe | Ala | Leu | Asp | Val | Trp | Gly | Gln | Gly | Thr | Thr | Val | Thr | Val |
| | 130 | | | | | 135 | | | | | 140 | | | | |
| Ser | Ser | Gly | Gly | Gly | Gly | Ser | Gly | Gly | Gly | Gly | Ser | Gly | Gly | Gly | Gly |
| 145 | | | | | 150 | | | | | 155 | | | | | 160 |
| Ser | Asp | Ile | Gln | Met | Thr | Gln | Ser | Pro | Ser | Ser | Leu | Ser | Ala | Ser | Val |
| | | | | 165 | | | | | 170 | | | | | 175 | |
| Gly | Asp | Arg | Val | Thr | Ile | Thr | Cys | Arg | Ala | Ser | Gln | Ser | Ile | Asn | Ser |
| | | | 180 | | | | | 185 | | | | | 190 | | |
| Tyr | Leu | Asn | Trp | Tyr | Gln | Gln | Lys | Pro | Gly | Lys | Ala | Pro | Lys | Leu | Leu |
| | | 195 | | | | | 200 | | | | | 205 | | | |
| Ile | Tyr | Ala | Ala | Ser | Ser | Leu | Gln | Ser | Gly | Val | Pro | Ser | Arg | Phe | Ser |
| | 210 | | | | | 215 | | | | | 220 | | | | |
| Gly | Ser | Gly | Ser | Gly | Thr | Asp | Phe | Thr | Leu | Thr | Ile | Ser | Ser | Leu | Gln |
| 225 | | | | | 230 | | | | | 235 | | | | | 240 |
| Pro | Glu | Asp | Phe | Ala | Thr | Tyr | Tyr | Cys | Gln | Gln | Ser | Tyr | Ser | Ala | Pro |
| | | | | 245 | | | | | 250 | | | | | 255 | |
| Pro | Ile | Thr | Phe | Gly | Gln | Gly | Thr | Arg | Leu | Glu | Ile | Lys | Gly | Ala | Ala |
| | | | 260 | | | | | 265 | | | | | 270 | | |
| Ala | Gly | Ala | Gly | Gly | Asp | Tyr | Lys | Asp | Asp | Asp | Asp | Lys | Gly | Ala | Ala |
| | | 275 | | | | | 280 | | | | | 285 | | | |
| Ala | His | His | His | His | His | | | | | | | | | | |
| | 290 | | | | | 295 | | | | | | | | | |

<210> SEQ ID NO 175
<211> LENGTH: 888
<212> TYPE: DNA
<213> ORGANISM: Artificial
<220> FEATURE:
<223> OTHER INFORMATION: Full-length nucleotide sequence of NYC-0010

<400> SEQUENCE: 175

```
atgaagcacc tgtggttctt tctgctgctg gtggccgctc ctagatgggt gttgtctggc    60
gaagtgcagc tggtggaatc tggtggcgga gttgttcagc ctggcggctc tctgagactg   120
agctgtgctg tgtccggctt caccttcgac gactacgcca tgcactgggt ccgacaggca   180
cctggcaaag gccttgaatg ggtgtccctg atcagcggag atggcggcag acacactac   240
gccgattctg tgaagggcag attcaccatc agccgggaca acagcaagaa cagcctgtac   300
ctgcagatga actccctgcg gacaggcgac acagccctgt actactgcgc caaggacatg   360
atcttcgccg tggtcatcac cgactaccac tactacggca tggacgtgtg gggccaggga   420
accacagtga cagtttctag cggaggcgga ggaagtggcg gcggaggatc tggcggtggt   480
ggttctgata tccagatgac acagagcccc agcagcctgt ctgcctctgt gggagacaga   540
gtgaccatca cctgtagagc cagccagagc atcagcagct acctgaactg gtatcagcag   600
aagcccggca aggcccctaa actgctgatc tatgccgcct ccagtctgca gagcggagtg   660
cctagcagat ttctggcag cggctccggc accgatttca ccctgaccat atctagcctg   720
cagcctgagg acttcgccac ctactactgc cagcagagct acagcacccc tcctatcacc   780
tttggccagg gcaccagact ggaaatcaaa ggcgctgctg caggcgctgg cggcgactac   840
aaagacgatg atgataaggg cgctgccgct caccaccacc atcaccat                888
```

<210> SEQ ID NO 176
<211> LENGTH: 296
<212> TYPE: PRT
<213> ORGANISM: Artificial
<220> FEATURE:
<223> OTHER INFORMATION: Full-length amino acid sequence of NYC-0010

<400> SEQUENCE: 176

```
Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Val Val
            20                  25                  30

Gln Pro Gly Gly Ser Leu Arg Leu Ser Cys Ala Val Ser Gly Phe Thr
        35                  40                  45

Phe Asp Asp Tyr Ala Met His Trp Val Arg Gln Ala Pro Gly Lys Gly
    50                  55                  60

Leu Glu Trp Val Ser Leu Ile Ser Gly Asp Gly Gly Ser Thr His Tyr
65                  70                  75                  80

Ala Asp Ser Val Lys Gly Arg Phe Thr Ile Ser Arg Asp Asn Ser Lys
                85                  90                  95

Asn Ser Leu Tyr Leu Gln Met Asn Ser Leu Arg Thr Gly Asp Thr Ala
            100                 105                 110

Leu Tyr Tyr Cys Ala Lys Asp Met Ile Phe Ala Val Val Ile Thr Asp
        115                 120                 125

Tyr His Tyr Tyr Gly Met Asp Val Trp Gly Gln Gly Thr Thr Val Thr
    130                 135                 140

Val Ser Ser Gly Gly Gly Gly Ser Gly Gly Gly Gly Ser Gly Gly Gly
145                 150                 155                 160

Gly Ser Asp Ile Gln Met Thr Gln Ser Pro Ser Ser Leu Ser Ala Ser
                165                 170                 175

Val Gly Asp Arg Val Thr Ile Thr Cys Arg Ala Ser Gln Ser Ile Ser
            180                 185                 190

Ser Tyr Leu Asn Trp Tyr Gln Gln Lys Pro Gly Lys Ala Pro Lys Leu
        195                 200                 205
```

Leu Ile Tyr Ala Ala Ser Ser Leu Gln Ser Gly Val Pro Ser Arg Phe
    210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Ser Tyr Ser Thr
            245                 250                 255

Pro Pro Ile Thr Phe Gly Gln Gly Thr Arg Leu Glu Ile Lys Gly Ala
            260                 265                 270

Ala Ala Gly Ala Gly Gly Asp Tyr Lys Asp Asp Asp Lys Gly Ala
        275                 280                 285

Ala Ala His His His His His His
        290                 295

<210> SEQ ID NO 177
<211> LENGTH: 738
<212> TYPE: DNA
<213> ORGANISM: Artificial
<220> FEATURE:
<223> OTHER INFORMATION: Full-length nucleotide sequence of HC-h

<400> SEQUENCE: 177
atgaaacacc tgtggttctt cctcctgctg gtggcagctc ccagatgggt gctgagcgac      60
aaaactcaca catgcccacc ctgcccagca cctgaagccg ccggcggacc ctcagtcttc     120
ctcttccccc caaaacccaa ggacaccctc atgatctccc ggacccctga ggtcacatgc     180
gtggtggtgg acgtgagcca cgaagaccct gaggtcaagt tcaactggta cgtggacggc     240
gtggaggtgc ataatgccaa gaccaagcct agagaggaac agtacaacag cacctaccgg     300
gtggtgtccg tgctgacagt gctgcaccag gactggctga acggcaaaga gtacaagtgc     360
aaggtgtcca acaaggccct gcctgccccc atcgagaaaa ccatcagcaa ggccaagggc     420
cagccccgcg aacctcaagt gtgcaccctg ccaccctccc gggatgagct gaccaagaac     480
caggtgtccc tgagctgtgc cgtgaagggc ttctacccct ccgatatcgc cgtggaatgg     540
gagagcaacg gccagcccga gaacaactac aagaccaccc ccctgtgct ggacagcgac     600 ggctcattct tcctggtgtc caagctgacc gtggacaagt ccagatggca gcagggcaac     660
gtcttctcat gctccgtgat gcatgaggct ctgcacaacc actacaccca gaagagcctc     720
tccctgtctc ccggcaaa                                                   738

<210> SEQ ID NO 178
<211> LENGTH: 246
<212> TYPE: PRT
<213> ORGANISM: Artificial
<220> FEATURE:
<223> OTHER INFORMATION: Full-length amino acid sequence of HC-h

<400> SEQUENCE: 178

Met Lys His Leu Trp Phe Phe Leu Leu Leu Val Ala Ala Pro Arg Trp
1               5                   10                  15

Val Leu Ser Asp Lys Thr His Thr Cys Pro Pro Cys Pro Ala Pro Glu
            20                  25                  30

Ala Ala Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
    50                  55                  60

Val Ser His Glu Asp Pro Glu Val Lys Phe Asn Trp Tyr Val Asp Gly
65                  70                  75                  80

```
Val Glu Val His Asn Ala Lys Thr Lys Pro Arg Glu Glu Gln Tyr Asn
                 85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Pro
        115                 120                 125

Ala Pro Ile Glu Lys Thr Ile Ser Lys Ala Lys Gly Gln Pro Arg Glu
    130                 135                 140

Pro Gln Val Cys Thr Leu Pro Pro Ser Arg Asp Glu Leu Thr Lys Asn
145                 150                 155                 160

Gln Val Ser Leu Ser Cys Ala Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Val Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 179
<211> LENGTH: 1500
<212> TYPE: DNA
<213> ORGANISM: Artificial
<220> FEATURE:
<223> OTHER INFORMATION: Full-length nucleotide sequence of NYD-2047-
      HC-k

<400> SEQUENCE: 179
atgaagcacc tgtggttctt tctgctgctg gtggccgctc ctagatgggt gctgtctggt    60
caagtacagc tggtggaatc cggtggaggc gtggtccagc cgggacgcag cttgagactg   120
tcctgcgctg catctggctt ttccatacga tcctacgata tgcactgggt tcgccaagcc   180
cctggcaaag gtcttgaatg ggttgccact atctcctacg acgggtctca gaaatattac   240
gcggattcag tgaaggggcg gttcacaatt tcacgggaca ttcaaagaa taccttgtat   300 ctccagatgt cttcactgag agccgaggat actgcagtct atcattgtgc aagagggtcc   360
tcaggccact acgaggcctt tgatatatgg ggccaaggca ccttggtaac cgttagtagc   420
ggaggtggag gaagcggagg cggcggttcc ggaggaggtg aagtcaatc cgttctgact   480 cagccaccct ccgtgagtgc agcgcctgga cagaaggtca caatatcatg ttctggctct   540
tcaagcaaca tcggaaactg gtacgtgagc tggtaccagc agctccccgg cacggcgccc   600
aagcttctga tatatgacaa caacaaacg cccgtggaa tccctgacag attcagtggg   660
tctaaaagtg gtacaagcgc tacctggt atcaccggat gcagaccgg agatgaggcg   720 gactattatt gcggaaccct ggactccagc ctgagcgctc cctgggtttt cggcggaggt   780
actaaggtta ccgtcttggg cggagaaccc aagagcgcag acaagaccca cacctgtcct   840
ccatgtcctg ctccagaagc tgcaggcggc ccttccgtgt ttctgttccc tccaaagcct   900
aaggacaccc tgatgatcag ccggacacct gaagtgacct gcgtggtggt ggatgtgtcc   960
cacgaggatc ccgaagtgaa gttcaattgg tacgtggacg gcgtggaagt gcacaacgcc  1020
```

-continued

```
aagaccaagc ctagagagga acagtacaac agcacctaca gagtggtgtc tgtgctgaca    1080
gtgctgcacc aggactggct gaacggcaaa gagtacaagt gcaaggtgtc caacaaggcc    1140
ctgcctgctc ctatcgagaa aaccatcagc aaggccaagg ccagcctag  ggaaccccag    1200 gtttacaccc tgcctccatg cagggatgag ctgaccaaga accaggtgtc cctgtggtgc    1260
ctggttaagg gcttctaccc ctccgatatc gccgtggaat gggagagcaa tggccagcca    1320
gagaacaact acaagacaac ccctcctgtg ctggactccg acggctcatt cttcctgtac    1380
agcaagctga ccgtggacaa gagcagatgg cagcagggca cgtgttcag  ctgcagcgtg    1440 atgcacgagg ccctgcacaa ccactacaca cagaagtccc tgtctctgag ccccggcaaa    1500
```

<210> SEQ ID NO 180
<211> LENGTH: 500
<212> TYPE: PRT
<213> ORGANISM: Artificial
<220> FEATURE:
<223> OTHER INFORMATION: Full-length amino acid sequence of NYD-2047-HC-k

<400> SEQUENCE: 180

```
Met Lys His Leu Trp Phe Phe Leu Leu Leu Val Ala Ala Pro Arg Trp
1               5                   10                  15

Val Leu Ser Gly Gln Val Gln Leu Val Glu Ser Gly Gly Gly Val Val
            20                  25                  30

Gln Pro Gly Arg Ser Leu Arg Leu Ser Cys Ala Ala Ser Gly Phe Ser
        35                  40                  45

Ile Arg Ser Tyr Asp Met His Trp Val Arg Gln Ala Pro Gly Lys Gly
    50                  55                  60

Leu Glu Trp Val Ala Thr Ile Ser Tyr Asp Gly Ser Gln Lys Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Ser Ser Leu Arg Ala Glu Asp Thr Ala
            100                 105                 110

Val Tyr His Cys Ala Arg Gly Ser Ser Gly His Tyr Glu Ala Phe Asp
        115                 120                 125

Ile Trp Gly Gln Gly Thr Leu Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Val Ser Ala Ala Pro Gly Gln Lys Val Thr Ile Ser
                165                 170                 175

Cys Ser Gly Ser Ser Ser Asn Ile Gly Asn Trp Tyr Val Ser Trp Tyr
            180                 185                 190

Gln Gln Leu Pro Gly Thr Ala Pro Lys Leu Leu Ile Tyr Asp Asn Asn
        195                 200                 205

Lys Arg Pro Ser Gly Ile Pro Asp Arg Phe Ser Gly Ser Lys Ser Gly
    210                 215                 220

Thr Ser Ala Thr Leu Gly Ile Thr Gly Leu Gln Thr Gly Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Val Thr Val Leu Gly Gly Glu Pro Lys Ser
            260                 265                 270

Ala Asp Lys Thr His Thr Cys Pro Pro Cys Pro Ala Pro Glu Ala Ala
```

```
                        275                 280                 285
Gly Gly Pro Ser Val Phe Leu Phe Pro Pro Lys Pro Lys Asp Thr Leu
        290                 295                 300

Met Ile Ser Arg Thr Pro Glu Val Thr Cys Val Val Asp Val Ser
305                 310                 315                 320

His Glu Asp Pro Glu Val Lys Phe Asn Trp Tyr Val Asp Gly Val Glu
                325                 330                 335

Val His Asn Ala Lys Thr Lys Pro Arg Glu Glu Gln Tyr Asn Ser Thr
            340                 345                 350

Tyr Arg Val Val Ser Val Leu Thr Val Leu His Gln Asp Trp Leu Asn
        355                 360                 365

Gly Lys Glu Tyr Lys Cys Lys Val Ser Asn Lys Ala Leu Pro Ala Pro
    370                 375                 380

Ile Glu Lys Thr Ile Ser Lys Ala Lys Gly Gln Pro Arg Glu Pro Gln
385                 390                 395                 400

Val Tyr Thr Leu Pro Pro Cys Arg Asp Glu Leu Thr Lys Asn Gln Val
                405                 410                 415

Ser Leu Trp Cys Leu Val Lys Gly Phe Tyr Pro Ser Asp Ile Ala Val
            420                 425                 430

Glu Trp Glu Ser Asn Gly Gln Pro Glu Asn Asn Tyr Lys Thr Thr Pro
        435                 440                 445

Pro Val Leu Asp Ser Asp Gly Ser Phe Phe Leu Tyr Ser Lys Leu Thr
    450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
                485                 490                 495

Ser Pro Gly Lys
        500

<210> SEQ ID NO 181
<211> LENGTH: 1500
<212> TYPE: DNA
<213> ORGANISM: Artificial
<220> FEATURE:
<223> OTHER INFORMATION: Full-length nucleotide sequence of NYD-2061-
      HC-k

<400> SEQUENCE: 181
atgaagcacc tgtggttctt tctgctgctg gtggccgctc ctagatgggt gctgtctggt      60
gaggtacagc tggtggaatc cggtggaggc cttgtgcaac ggggaggctc cctgcgactc     120
tcttgcgccg catctggctt ttccatacga tcctacgata ttcattgggt ccgacaagcc     180
cctggcaaag tcttgaatg ggttgccact atctcctacg acgggtctca gaaatattat     240
gcggattcag tgaaggggcg gttcacaatt tcacgagacg agtcaaagaa tacactgtac     300
ctccaaatga attcactgag agccgaggat actgcagtct atcattgtgc aagagggtcc     360
tcaggccact acgaggcctt tgatatatgg ggccaaggca ccttggtaac cgttagtagc     420
ggaggtggag gaagcggagg cggcggttcc ggaggaggtg gaagtcaatc cgttctgact     480
cagccaccct ccgcctctgg caccccgggc aacgggtca caatatcatg ttctggctct     540
tcaagcaaca tcggaaactg gtacgtgagc tggtaccagc agctccccgg cacggcgccc     600
aagcttctga tatatgacaa caacaaacgg cccgtggag ttcctgacag attcagtggg     660
tctaaaagtg gtacaagcgc tagcctggcc ataagtggtc tgcagagtga agatgaggcg     720
```

```
gactattatt gcggaacctg ggactccagc ctgagcgctc cctgggtttt cggcggaggt    780
actaagctga ccgtcttggg cggagaaccc aagagcgcag acaagaccca cacctgtcct    840
ccatgtcctg ctccagaagc tgcaggcggc ccttccgtgt ttctgttccc tccaaagcct    900
aaggacaccc tgatgatcag ccggacacct gaagtgacct gcgtggtggt ggatgtgtcc    960
cacgaggatc ccgaagtgaa gttcaattgg tacgtggacg gcgtggaagt gcacaacgcc   1020
aagaccaagc ctagagagga acagtacaac agcacctaca gagtggtgtc tgtgctgaca   1080
gtgctgcacc aggactggct gaacggcaaa gagtacaagt gcaaggtgtc caacaaggcc   1140
ctgcctgctc ctatcgagaa aaccatcagc aaggccaagg ccagcctag gaacccccag    1200 gtttacaccc tgcctccatg cagggatgag ctgaccaaga accaggtgtc cctgtggtgc   1260
ctggttaagg gcttctaccc ctccgatatc gccgtggaat gggagagcaa tggccagcca   1320
gagaacaact acaagacaac ccctcctgtg ctggactccg acggctcatt cttcctgtac   1380
agcaagctga ccgtggacaa gagcagatgg cagcagggca cgtgttcag ctgcagcgtg    1440 atgcacgagg ccctgcacaa ccactacaca cagaagtccc tgtctctgag ccccggcaaa   1500
```

<210> SEQ ID NO 182
<211> LENGTH: 500
<212> TYPE: PRT
<213> ORGANISM: Artificial
<220> FEATURE:
<223> OTHER INFORMATION: Full-length amino acid sequence of NYD-2061-HC-k

<400> SEQUENCE: 182

```
Met Lys His Leu Trp Phe Phe Leu Leu Leu Val Ala Ala Pro Arg Trp
  1               5                  10                  15

Val Leu Ser Gly Glu Val Gln Leu Val Glu Ser Gly Gly Gly Leu Val
                 20                  25                  30

Gln Pro Gly Gly Ser Leu Arg Leu Ser Cys Ala Ala Ser Gly Phe Ser
             35                  40                  45

Ile Arg Ser Tyr Asp Ile His Trp Val Arg Gln Ala Pro Gly Lys Gly
         50                  55                  60

Leu Glu Trp Val Ala Thr Ile Ser Tyr Asp Gly Ser Gln Lys Tyr Tyr
 65                  70                  75                  80

Ala Asp Ser Val Lys Gly Arg Phe Thr Ile Ser Arg Asp Glu Ser Lys
                 85                  90                  95

Asn Thr Leu Tyr Leu Gln Met Asn Ser Leu Arg Ala Glu Asp Thr Ala
            100                 105                 110

Val Tyr His Cys Ala Arg Gly Ser Ser Gly His Tyr Glu Ala Phe Asp
        115                 120                 125

Ile Trp Gly Gln Gly Thr Leu Val Thr Val Ser Ser Gly Gly Gly Gly
    130                 135                 140

Ser Gly Gly Gly Gly Ser Gly Gly Gly Gly Ser Gln Ser Val Leu Thr
145                 150                 155                 160

Gln Pro Pro Ser Ala Ser Gly Thr Pro Gly Gln Arg Val Thr Ile Ser
                165                 170                 175

Cys Ser Gly Ser Ser Ser Asn Ile Gly Asn Trp Tyr Val Ser Trp Tyr
            180                 185                 190

Gln Gln Leu Pro Gly Thr Ala Pro Lys Leu Leu Ile Tyr Asp Asn Asn
        195                 200                 205

Lys Arg Pro Ser Gly Val Pro Asp Arg Phe Ser Gly Ser Lys Ser Gly
    210                 215                 220
```

-continued

```
Thr Ser Ala Ser Leu Ala Ile Ser Gly Leu Gln Ser Glu Asp Glu Ala
225                 230                 235                 240

Asp Tyr Tyr Cys Gly Thr Trp Asp Ser Ser Leu Ser Ala Pro Trp Val
            245                 250                 255

Phe Gly Gly Gly Thr Lys Leu Thr Val Leu Gly Gly Glu Pro Lys Ser
        260                 265                 270

Ala Asp Lys Thr His Thr Cys Pro Pro Cys Pro Ala Pro Glu Ala Ala
    275                 280                 285

Gly Gly Pro Ser Val Phe Leu Phe Pro Pro Lys Pro Lys Asp Thr Leu
290                 295                 300

Met Ile Ser Arg Thr Pro Glu Val Thr Cys Val Val Val Asp Val Ser
305                 310                 315                 320

His Glu Asp Pro Glu Val Lys Phe Asn Trp Tyr Val Asp Gly Val Glu
            325                 330                 335

Val His Asn Ala Lys Thr Lys Pro Arg Glu Glu Gln Tyr Asn Ser Thr
        340                 345                 350

Tyr Arg Val Val Ser Val Leu Thr Val Leu His Gln Asp Trp Leu Asn
    355                 360                 365

Gly Lys Glu Tyr Lys Cys Lys Val Ser Asn Lys Ala Leu Pro Ala Pro
370                 375                 380

Ile Glu Lys Thr Ile Ser Lys Ala Lys Gly Gln Pro Arg Glu Pro Gln
385                 390                 395                 400

Val Tyr Thr Leu Pro Pro Cys Arg Asp Glu Leu Thr Lys Asn Gln Val
            405                 410                 415

Ser Leu Trp Cys Leu Val Lys Gly Phe Tyr Pro Ser Asp Ile Ala Val
        420                 425                 430

Glu Trp Glu Ser Asn Gly Gln Pro Glu Asn Asn Tyr Lys Thr Thr Pro
    435                 440                 445

Pro Val Leu Asp Ser Asp Gly Ser Phe Phe Leu Tyr Ser Lys Leu Thr
450                 455                 460

Val Asp Lys Ser Arg Trp Gln Gln Gly Asn Val Phe Ser Cys Ser Val
465                 470                 475                 480

Met His Glu Ala Leu His Asn His Tyr Thr Gln Lys Ser Leu Ser Leu
            485                 490                 495

Ser Pro Gly Lys
            500
```

<210> SEQ ID NO 183
<211> LENGTH: 1515
<212> TYPE: DNA
<213> ORGANISM: Artificial
<220> FEATURE:
<223> OTHER INFORMATION: Full-length nucleotide sequence of NYD-3061-HC-k

<400> SEQUENCE: 183

```
atgaagcacc tgtggttctt tctgctgctg gtggccgctc ctagatgggt gctgtctggt      60
gaggtacagc tggtggaatc cggtggaggc cttgtgcaac cgggaggctc cctgcgactc     120
tcttgcgccg catctggctt ttccatacga tcctacgata ttcattgggt ccgacaagcc     180
cctggcaaag gtcttgaatg ggttgccact atctcctacg acgggtctca gaaatattat     240
gcggattcag tgaaggggcg gttcacaatt tcacgagacg agtcaaagaa tacactgtac     300
ctccaaatga attcactgag agccgaggat actgcagtct atcattgtgc aagagggtcc     360
tcaggccact acgaggcctt tgatatatgg ggccaaggca ccttggtaac cgttagtagc     420
```

```
ggaggtggag gaagcggagg cggcggttcc ggaggaggtg gaagtggagg aggtggatct    480
caatccgttc tgactcagcc accctccgcc tctggcaccc cgggccaacg ggtcacaata    540
tcatgttctg gctcttcaag caacatcgga aactggtacg tgagctggta ccagcagctc    600
cccggcacgg cgcccaagct tctgatatat gacaacaaca aacggcccag tggagttcct    660
gacagattca gtgggtctaa agtggtaca agcgctagcc tggccataag tggtctgcag    720
agtgaagatg aggcggacta ttattgcgga acctgggact ccagcctgag cgctccctgg    780
gttttcggcg gaggtactaa gctgaccgtc ttgggcggag aacccaagag cgcagacaag    840
acccacacct gtcctccatg tcctgctcca gaagctgcag gcggcccttc cgtgtttctg    900
ttccctccaa agcctaagga caccctgatg atcagccgga cacctgaagt gacctgcgtg    960
gtggtggatg tgtcccacga ggatcccgaa gtgaagttca attggtacgt ggacggcgtg   1020
gaagtgcaca acgccaagac caagcctaga gaggaacagt acaacagcac ctacagagtg   1080
gtgtctgtgc tgacagtgct gcaccaggac tggctgaacg gcaaagagta caagtgcaag   1140
gtgtccaaca aggccctgcc tgctcctatc gagaaaacca tcagcaaggc caagggccag   1200
cctagggaac cccaggttta caccctgcct ccatgcaggg atgagctgac caagaaccag   1260
gtgtccctgt ggtgcctggt taagggcttc taccctcccg atatcgccgt ggaatgggag   1320
agcaatggcc agccagagaa caactacaag acaaccctc ctgtgctgga ctccgacggc   1380
tcattcttcc tgtacagcaa gctgaccgtg gacaagagca gatggcagca gggcaacgtg   1440
ttcagctgca gcgtgatgca cgaggccctg cacaaccact acacacagaa gtccctgtct   1500
ctgagccccg gcaaa                                                    1515
```

<210> SEQ ID NO 184
<211> LENGTH: 505
<212> TYPE: PRT
<213> ORGANISM: Artificial
<220> FEATURE:
<223> OTHER INFORMATION: Full-length amino acid sequence of NYD-3061-HC-k

<400> SEQUENCE: 184

```
Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Leu Val
                20                  25                  30

Gln Pro Gly Gly Ser Leu Arg Leu Ser Cys Ala Ala Ser Gly Phe Ser
            35                  40                  45

Ile Arg Ser Tyr Asp Ile His Trp Val Arg Gln Ala Pro Gly Lys Gly
        50                  55                  60

Leu Glu Trp Val Ala Thr Ile Ser Tyr Asp Gly Ser Gln Lys Tyr Tyr
65                  70                  75                  80

Ala Asp Ser Val Lys Gly Arg Phe Thr Ile Ser Arg Asp Glu Ser Lys
                85                  90                  95

Asn Thr Leu Tyr Leu Gln Met Asn Ser Leu Arg Ala Glu Asp Thr Ala
            100                 105                 110

Val Tyr His Cys Ala Arg Gly Ser Ser Gly His Tyr Glu Ala Phe Asp
        115                 120                 125

Ile Trp Gly Gln Gly Thr Leu Val Thr Val Ser Ser Gly Gly Gly Gly
    130                 135                 140

Ser Gly Gly Gly Gly Ser Gly Gly Gly Gly Ser Gly Gly Gly Gly Ser
145                 150                 155                 160
```

```
Gln Ser Val Leu Thr Gln Pro Pro Ser Ala Ser Gly Thr Pro Gly Gln
                165                 170                 175

Arg Val Thr Ile Ser Cys Ser Gly Ser Ser Asn Ile Gly Asn Trp
            180                 185                 190

Tyr Val Ser Trp Tyr Gln Gln Leu Pro Gly Thr Ala Pro Lys Leu Leu
            195                 200                 205

Ile Tyr Asp Asn Asn Lys Arg Pro Ser Gly Val Pro Asp Arg Phe Ser
        210                 215                 220

Gly Ser Lys Ser Gly Thr Ser Ala Ser Leu Ala Ile Ser Gly Leu Gln
225                 230                 235                 240

Ser Glu Asp Glu Ala Asp Tyr Tyr Cys Gly Thr Trp Asp Ser Ser Leu
                245                 250                 255

Ser Ala Pro Trp Val Phe Gly Gly Gly Thr Lys Leu Thr Val Leu Gly
                260                 265                 270

Gly Glu Pro Lys Ser Ala Asp Lys Thr His Thr Cys Pro Pro Cys Pro
            275                 280                 285

Ala Pro Glu Ala Ala Gly Gly Pro Ser Val Phe Leu Phe Pro Pro Lys
        290                 295                 300

Pro Lys Asp Thr Leu Met Ile Ser Arg Thr Pro Glu Val Thr Cys Val
305                 310                 315                 320

Val Val Asp Val Ser His Glu Asp Pro Glu Val Lys Phe Asn Trp Tyr
                325                 330                 335

Val Asp Gly Val Glu Val His Asn Ala Lys Thr Lys Pro Arg Glu Glu
            340                 345                 350

Gln Tyr Asn Ser Thr Tyr Arg Val Val Ser Val Leu Thr Val Leu His
        355                 360                 365

Gln Asp Trp Leu Asn Gly Lys Glu Tyr Lys Cys Lys Val Ser Asn Lys
370                 375                 380

Ala Leu Pro Ala Pro Ile Glu Lys Thr Ile Ser Lys Ala Lys Gly Gln
385                 390                 395                 400

Pro Arg Glu Pro Gln Val Tyr Thr Leu Pro Pro Cys Arg Asp Glu Leu
                405                 410                 415

Thr Lys Asn Gln Val Ser Leu Trp Cys Leu Val Lys Gly Phe Tyr Pro
            420                 425                 430

Ser Asp Ile Ala Val Glu Trp Glu Ser Asn Gly Gln Pro Glu Asn Asn
        435                 440                 445

Tyr Lys Thr Thr Pro Pro Val Leu Asp Ser Asp Gly Ser Phe Phe Leu
    450                 455                 460

Tyr Ser Lys Leu Thr Val Asp Lys Ser Arg Trp Gln Gln Gly Asn Val
465                 470                 475                 480

Phe Ser Cys Ser Val Met His Glu Ala Leu His Asn His Tyr Thr Gln
                485                 490                 495

Lys Ser Leu Ser Leu Ser Pro Gly Lys
                500                 505

<210> SEQ ID NO 185
<211> LENGTH: 1527
<212> TYPE: DNA
<213> ORGANISM: Artificial
<220> FEATURE:
<223> OTHER INFORMATION: Full-length nucleotide sequence of NYC-0011-
      HC-k

<400> SEQUENCE: 185
atgaagcacc tgtggttctt tctgctgctg gtggccgctc ctagatgggt gctgtctggc        60
```

```
gaagtgcagc tggtggaatc tggtggcgga gttgttcagc ctggcggctc tctgagactg      120
agctgtgtgg ccagcggctt caccttcgac gactacgcca tgtactgggt ccgacaggtg      180
ccaggcaagg acctggaatg ggtgtccctg atttctggcg acggcgacat cacctactac      240
gtggactctg tgaagggcag attcaccgtg tccagagaca caacaagaa cagcctgtac       300 ctgcagatga agtccctgcg cgtggaagat acagccctgt actactgcgc caaggacatg      360
atctactacg cctcttggag cggctacggc agcagcgatt actactacta tgtgatggac      420
gtgtggggcc agggcaccac cgttacagtt tctagcggag gcggaggaag tggcggcgga      480
ggatctggcg gtggtggttc tgatatccag atgacacaga gccccagcag cctgtctgcc      540
tctgtgggag acagagtgac catcacctgt agagccagcc agagcatcag cagctacctg      600
aactggtatc agcagaagcc cggcaaggcc cctaaactgc tgatctatgc cgcctccagt      660
ctgcagagcg gagtgcctag cagattttct ggcagcggcc ccggcaccga tttcaccctg      720
accatatcta gcctgcagcc tgaggacttc gccacctact attgccagca gagctacagc      780
acccctccta tcacctttgg ccagggaacc agactggaaa tcaaaggcgg agaacccaag      840
agcgcagaca gacccacac ctgtcctcca tgtcctgctc cagaagctgc aggcggccct       900
tccgtgtttc tgttccctcc aaagcctaag gacaccctga tgatcagccg gacacctgaa      960
gtgacctgcg tggtggtgga tgtgtcccac gaggatcccg aagtgaagtt caattggtac     1020
gtggacggcg tggaagtgca caacgccaag accaagccta gagaggaaca gtacaacagc     1080
acctacagag tggtgtctgt gctgacagtg ctgcaccagg actggctgaa cggcaaagag     1140
tacaagtgca aggtgtccaa caaggccctg cctgctccta tcgagaaaac catcagcaag     1200
gccaagggcc agcctaggga accccaggtt tacaccctgc ctccatgcag ggatgagctg     1260
accaagaacc aggtgtccct gtggtgcctg gttaagggct tctacccctc cgatatcgcc     1320
gtggaatggg agagcaatgg ccagccagag aacaactaca agacaacccc tcctgtgctg     1380
gactccgacg gctcattctt cctgtacagc aagctgaccg tggacaagag cagatggcag     1440
cagggcaacg tgttcagctg cagcgtgatg cacgaggccc tgcacaacca ctacacacag     1500
aagtccctgt ctctgagccc cggcaaa                                         1527
```

<210> SEQ ID NO 186
<211> LENGTH: 509
<212> TYPE: PRT
<213> ORGANISM: Artificial
<220> FEATURE:
<223> OTHER INFORMATION: Full-length amino acid sequence of NYC-0011-
      HC-k

<400> SEQUENCE: 186

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Val Val
                20                  25                  30

Gln Pro Gly Gly Ser Leu Arg Leu Ser Cys Val Ala Ser Gly Phe Thr
            35                  40                  45

Phe Asp Asp Tyr Ala Met Tyr Trp Val Arg Gln Val Pro Gly Lys Asp
        50                  55                  60

Leu Glu Trp Val Ser Leu Ile Ser Gly Asp Gly Asp Ile Thr Tyr Tyr
65                  70                  75                  80

Val Asp Ser Val Lys Gly Arg Phe Thr Val Ser Arg Asp Asn Asn Lys
                85                  90                  95

-continued

```
Asn Ser Leu Tyr Leu Gln Met Lys Ser Leu Arg Val Glu Asp Thr Ala
            100                 105                 110

Leu Tyr Tyr Cys Ala Lys Asp Met Ile Tyr Tyr Ala Ser Trp Ser Gly
        115                 120                 125

Tyr Gly Ser Ser Asp Tyr Tyr Tyr Val Met Asp Val Trp Gly Gln
    130                 135                 140

Gly Thr Thr Val Thr Val Ser Ser Gly Gly Gly Gly Ser Gly Gly Gly
145                 150                 155                 160

Gly Ser Gly Gly Gly Gly Ser Asp Ile Gln Met Thr Gln Ser Pro Ser
                165                 170                 175

Ser Leu Ser Ala Ser Val Gly Asp Arg Val Thr Ile Thr Cys Arg Ala
            180                 185                 190

Ser Gln Ser Ile Ser Ser Tyr Leu Asn Trp Tyr Gln Gln Lys Pro Gly
        195                 200                 205

Lys Ala Pro Lys Leu Leu Ile Tyr Ala Ala Ser Ser Leu Gln Ser Gly
    210                 215                 220

Val Pro Ser Arg Phe Ser Gly Ser Gly Ser Gly Thr Asp Phe Thr Leu
225                 230                 235                 240

Thr Ile Ser Ser Leu Gln Pro Glu Asp Phe Ala Thr Tyr Tyr Cys Gln
                245                 250                 255

Gln Ser Tyr Ser Thr Pro Pro Ile Thr Phe Gly Gln Gly Thr Arg Leu
            260                 265                 270

Glu Ile Lys Gly Gly Glu Pro Lys Ser Ala Asp Lys Thr His Thr Cys
        275                 280                 285

Pro Pro Cys Pro Ala Pro Glu Ala Ala Gly Gly Pro Ser Val Phe Leu
    290                 295                 300

Phe Pro Pro Lys Pro Lys Asp Thr Leu Met Ile Ser Arg Thr Pro Glu
305                 310                 315                 320

Val Thr Cys Val Val Val Asp Val Ser His Glu Asp Pro Glu Val Lys
                325                 330                 335

Phe Asn Trp Tyr Val Asp Gly Val Glu Val His Asn Ala Lys Thr Lys
            340                 345                 350

Pro Arg Glu Glu Gln Tyr Asn Ser Thr Tyr Arg Val Val Ser Val Leu
        355                 360                 365

Thr Val Leu His Gln Asp Trp Leu Asn Gly Lys Glu Tyr Lys Cys Lys
    370                 375                 380

Val Ser Asn Lys Ala Leu Pro Ala Pro Ile Glu Lys Thr Ile Ser Lys
385                 390                 395                 400

Ala Lys Gly Gln Pro Arg Glu Pro Gln Val Tyr Thr Leu Pro Pro Cys
                405                 410                 415

Arg Asp Glu Leu Thr Lys Asn Gln Val Ser Leu Trp Cys Leu Val Lys
            420                 425                 430

Gly Phe Tyr Pro Ser Asp Ile Ala Val Glu Trp Glu Ser Asn Gly Gln
        435                 440                 445

Pro Glu Asn Asn Tyr Lys Thr Thr Pro Pro Val Leu Asp Ser Asp Gly
    450                 455                 460

Ser Phe Phe Leu Tyr Ser Lys Leu Thr Val Asp Lys Ser Arg Trp Gln
465                 470                 475                 480

Gln Gly Asn Val Phe Ser Cys Ser Val Met His Glu Ala Leu His Asn
                485                 490                 495

His Tyr Thr Gln Lys Ser Leu Ser Leu Ser Pro Gly Lys
            500                 505
```

<210> SEQ ID NO 187
<211> LENGTH: 1527
<212> TYPE: DNA
<213> ORGANISM: Artificial
<220> FEATURE:
<223> OTHER INFORMATION: Full-length nucleotide sequence of NYC-0012-HC-k

<400> SEQUENCE: 187

```
atgaagcacc tgtggttctt tctgctgctg gtggccgctc ctagatgggt gctgtctggc      60
gaagtgcagc tggtggaatc tggtggcgga gttgttcagc ctggcggctc tctgagactg     120
tcttgtgccg ccagcggctt caccttcgac gactacgcca tgtactgggt ccgacaggcc     180
cctggcaaag gccttgaatg ggtgtccctg atcagcggag atggcggcag catgtactac     240
gccgatagcg tgaagggcag attcaccatc agccgggaca acagcaagaa cagcctgtac     300
ctgcagatga actccctgcg gaccgaggac acagccctgt actactgcgc aaggatatg      360
atcttctacg ccttttggag cggctacggc agcagcgatt actactacta cgtgatggac     420
gtgtggggcc agggcaccac agtgacagtt tattctggcg gcggaggatc tggcggaggt     480
ggaagcggag gcggtggatc tgatatccag atgacacaga gccccagcag cctgtctgcc     540
tctgtgggag acagagtgac catcacctgt cgggccagcc agagaatcag cacctacctg     600
aactggtatc agcagaagcc cggcaaggcc cctaagctgc tgatctatgc tgcctccagt     660
ctgcagagcg gcgtgccaag cagatttttct ggcagcggct ctggcaccga cttcaccctg     720
accatatcta gcctgcagcc tgaggacttc gccacctact actgccagca gagctacagc     780
accccctcta tcacctttgg ccagggaacc agactggaaa tcaaaggcgg agaacccaag     840
agcgcagaca gacccacac ctgtcctcca tgtcctgctc agaagctgc aggcggccct      900
tccgtgtttc tgttccctcc aaagcctaag gacaccctga tgatcagccg gacacctgaa     960
gtgacctgcg tggtggtgga tgtgtcccac gaggatcccg aagtgaagtt caattggtac    1020
gtggacggcg tggaagtgca caacgccaag accaagccta gagaggaaca gtacaacagc    1080
acctacagag tggtgtctgt gctgacagtg ctgcaccagg actggctgaa cggcaaagag    1140
tacaagtgca aggtgtccaa caaggccctg cctgctccta tcgagaaaac catcagcaag    1200
gccaagggcc agcctaggga acccagggtt tacaccctgc ctccatgcag ggatgagctg    1260
accaagaacc aggtgtccct gtggtgcctg gttaagggct tctacccctc cgatatcgcc    1320
gtggaatggg agagcaatgg ccagccagag aacaactaca agacaacccc tcctgtgctg    1380
gactccgacg gctcattctt cctgtacagc aagctgaccg tggacaagag cagatggcag    1440
cagggcaacg tgttcagctg cagcgtgatg cacgaggccc tgcacaacca ctacacacag    1500
aagtccctgt ctctgagccc cggcaaa                                        1527
```

<210> SEQ ID NO 188
<211> LENGTH: 509
<212> TYPE: PRT
<213> ORGANISM: Artificial
<220> FEATURE:
<223> OTHER INFORMATION: Full-length amino acid sequence of NYC-0012-HC-k

<400> SEQUENCE: 188

```
Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Val Val
            20                  25                  30
```

-continued

Gln Pro Gly Gly Ser Leu Arg Leu Ser Cys Ala Ala Ser Gly Phe Thr
      35                  40                  45

Phe Asp Asp Tyr Ala Met Tyr Trp Val Arg Gln Ala Pro Gly Lys Gly
 50                  55                  60

Leu Glu Trp Val Ser Leu Ile Ser Gly Asp Gly Gly Ser Met Tyr Tyr
 65                  70                  75                  80

Ala Asp Ser Val Lys Gly Arg Phe Thr Ile Ser Arg Asp Asn Ser Lys
                  85                  90                  95

Asn Ser Leu Tyr Leu Gln Met Asn Ser Leu Arg Thr Glu Asp Thr Ala
              100                 105                 110

Leu Tyr Tyr Cys Ala Lys Asp Met Ile Phe Tyr Ala Phe Trp Ser Gly
          115                 120                 125

Tyr Gly Ser Ser Asp Tyr Tyr Tyr Val Met Asp Val Trp Gly Gln
      130                 135                 140

Gly Thr Thr Val Thr Val Tyr Ser Gly Gly Gly Ser Gly Gly Gly
145                 150                 155                 160

Gly Ser Gly Gly Gly Ser Asp Ile Gln Met Thr Gln Ser Pro Ser
                  165                 170                 175

Ser Leu Ser Ala Ser Val Gly Asp Arg Val Thr Ile Thr Cys Arg Ala
              180                 185                 190

Ser Gln Arg Ile Ser Thr Tyr Leu Asn Trp Tyr Gln Gln Lys Pro Gly
          195                 200                 205

Lys Ala Pro Lys Leu Leu Ile Tyr Ala Ala Ser Ser Leu Gln Ser Gly
      210                 215                 220

Val Pro Ser Arg Phe Ser Gly Ser Gly Ser Gly Thr Asp Phe Thr Leu
225                 230                 235                 240

Thr Ile Ser Ser Leu Gln Pro Glu Asp Phe Ala Thr Tyr Tyr Cys Gln
                  245                 250                 255

Gln Ser Tyr Ser Thr Pro Pro Ile Thr Phe Gly Gln Gly Thr Arg Leu
              260                 265                 270

Glu Ile Lys Gly Gly Pro Lys Ser Ala Asp Lys Thr His Thr Cys
          275                 280                 285

Pro Pro Cys Pro Ala Pro Glu Ala Ala Gly Gly Pro Ser Val Phe Leu
      290                 295                 300

Phe Pro Pro Lys Pro Lys Asp Thr Leu Met Ile Ser Arg Thr Pro Glu
305                 310                 315                 320

Val Thr Cys Val Val Val Asp Val Ser His Glu Asp Pro Glu Val Lys
                  325                 330                 335

Phe Asn Trp Tyr Val Asp Gly Val Glu Val His Asn Ala Lys Thr Lys
              340                 345                 350

Pro Arg Glu Glu Gln Tyr Asn Ser Thr Tyr Arg Val Val Ser Val Leu
          355                 360                 365

Thr Val Leu His Gln Asp Trp Leu Asn Gly Lys Glu Tyr Lys Cys Lys
      370                 375                 380

Val Ser Asn Lys Ala Leu Pro Ala Pro Ile Glu Lys Thr Ile Ser Lys
385                 390                 395                 400

Ala Lys Gly Gln Pro Arg Glu Pro Gln Val Tyr Thr Leu Pro Pro Cys
                  405                 410                 415

Arg Asp Glu Leu Thr Lys Asn Gln Val Ser Leu Trp Cys Leu Val Lys
              420                 425                 430

Gly Phe Tyr Pro Ser Asp Ile Ala Val Glu Trp Glu Ser Asn Gly Gln
          435                 440                 445

Pro Glu Asn Asn Tyr Lys Thr Thr Pro Pro Val Leu Asp Ser Asp Gly

```
                450           455           460
Ser Phe Phe Leu Tyr Ser Lys Leu Thr Val Asp Lys Ser Arg Trp Gln
465                 470                 475                 480

Gln Gly Asn Val Phe Ser Cys Ser Val Met His Glu Ala Leu His Asn
                485                 490                 495

His Tyr Thr Gln Lys Ser Leu Ser Leu Ser Pro Gly Lys
            500                 505
```

<210> SEQ ID NO 189
<211> LENGTH: 1512
<212> TYPE: DNA
<213> ORGANISM: Artificial
<220> FEATURE:
<223> OTHER INFORMATION: Full-length nucleotide sequence of NYC-0013-HC-k

<400> SEQUENCE: 189

```
atgaagcacc tgtggttctt tctgctgctg gtggccgctc ctagatgggt gctgtctggc      60
gaagtgcagc tggtggaatc tggtggcgga gttgttcagc tggcggctc tctgagactg     120
tcttgtgccg ccagcggctt caccttcgac gattatgcca tgcactgggt ccgacaggcc     180
cctggcaaag acttgaatg ggtgtccctg atcagcggcg acggcgacaa tacctactac     240
gccgatagcg tgaagggcag attcaccatc agccgggaca acaacaagaa cagcctgtac     300
ctgcagatga actccctgcg gaccgaggac accgccttct actactgtgc caaagagctg     360
atcttcggca aggtgctgca cgacttttac tactacgtga tggacgtgtg gggccagggc     420
accacagtga cagtttctag cggaggcgga ggaagtggcg gcggaggatc tggcggtggt     480
ggttctgata tccagatgac acagagcccc agcagcctgt ctgcctctgt gggagacaga     540
gtgaccatca cctgtagagc cagccagagc atcagcagct acctgaactg gtatcagcag     600
aagcccggca aggccctaa actgctgatc tatgccgcct ccagtctgca gagcggagtg     660
cctagcagat ttctggcag cggctccggc accgatttca ccctgaccat atctagcctg     720
cagcctgagg acttcgccac ctactactgc cagcagagct acagcacccc tcctatcacc     780
tttggccagg gaaccagact ggaaatcaaa ggcggagaac caagagcgc agacaagacc     840
cacacctgtc ctccatgtcc tgctccagaa gctgcaggcg gcccttccgt gtttctgttc     900
cctccaaagc ctaaggacac cctgatgatc agccggacac tgaagtgac ctgcgtggtg     960
gtggatgtgt cccacgagga tcccgaagtg aagttcaatt ggtacgtgga cggcgtggaa    1020
gtgcacaacg ccaagaccaa gcctagagag aacagtaca acagcaccta cagagtggtg    1080
tctgtgctga cagtgctgca ccaggactgg ctgaacggca agagtacaa gtgcaaggtg    1140
tccaacaagg ccctgcctgc tcctatcgag aaaaccatca gcaaggccaa gggcagcct    1200
agggaacccc aggtttacac cctgcctcca tgcagggatg agctgaccaa gaaccaggtg    1260
tccctgtggt gcctggttaa gggcttctac ccctccgata tcgccgtgga atgggagagc    1320
aatggccagc cagagaacaa ctacaagaca ccccttctg tgctggactc cgacggctca    1380
ttcttcctgt acagcaagct gaccgtggac aagagcagat ggcagcaggg caacgtgttc    1440
agctgcagcg tgatgcacga ggccctgcac aaccactaca cacagaagtc cctgtctctg    1500
agccccggca aa                                                         1512
```

<210> SEQ ID NO 190
<211> LENGTH: 504
<212> TYPE: PRT
<213> ORGANISM: Artificial
<220> FEATURE:
<223> OTHER INFORMATION: Full-length amino acid sequence of NYC-0013-HC-k

<400> SEQUENCE: 190

```
Met Lys His Leu Trp Phe Phe Leu Leu Val Ala Ala Pro Arg Trp
1               5                   10                  15

Val Leu Ser Gly Glu Val Gln Leu Val Glu Ser Gly Gly Val Val
            20                  25                  30

Gln Pro Gly Gly Ser Leu Arg Leu Ser Cys Ala Ala Ser Gly Phe Thr
            35                  40                  45

Phe Asp Asp Tyr Ala Met His Trp Val Arg Gln Ala Pro Gly Lys Gly
50                  55                  60

Leu Glu Trp Val Ser Leu Ile Ser Gly Asp Gly Asp Asn Thr Tyr Tyr
65                  70                  75                  80

Ala Asp Ser Val Lys Gly Arg Phe Thr Ile Ser Arg Asp Asn Asn Lys
                85                  90                  95

Asn Ser Leu Tyr Leu Gln Met Asn Ser Leu Arg Thr Glu Asp Thr Ala
            100                 105                 110

Phe Tyr Tyr Cys Ala Lys Glu Leu Ile Phe Gly Lys Val Leu His Asp
            115                 120                 125

Phe Tyr Tyr Val Met Asp Val Trp Gly Gln Gly Thr Thr Val Thr
130                 135                 140

Val Ser Ser Gly Gly Gly Gly Ser Gly Gly Gly Gly Ser Gly Gly Gly
145                 150                 155                 160

Gly Ser Asp Ile Gln Met Thr Gln Ser Pro Ser Ser Leu Ser Ala Ser
                165                 170                 175

Val Gly Asp Arg Val Thr Ile Thr Cys Arg Ala Ser Gln Ser Ile Ser
            180                 185                 190

Ser Tyr Leu Asn Trp Tyr Gln Gln Lys Pro Gly Lys Ala Pro Lys Leu
    195                 200                 205

Leu Ile Tyr Ala Ala Ser Ser Leu Gln Ser Gly Val Pro Ser Arg Phe
210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Ser Tyr Ser Thr
                245                 250                 255

Pro Pro Ile Thr Phe Gly Gln Gly Thr Arg Leu Glu Ile Lys Gly Gly
            260                 265                 270

Glu Pro Lys Ser Ala Asp Lys Thr His Thr Cys Pro Pro Cys Pro Ala
    275                 280                 285

Pro Glu Ala Ala Gly Gly Pro Ser Val Phe Leu Phe Pro Pro Lys Pro
290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
    355                 360                 365

Asp Trp Leu Asn Gly Lys Glu Tyr Lys Cys Lys Val Ser Asn Lys Ala
370                 375                 380

Leu Pro Ala Pro Ile Glu Lys Thr Ile Ser Lys Ala Lys Gly Gln Pro
```

```
                385                 390                 395                 400
Arg Glu Pro Gln Val Tyr Thr Leu Pro Pro Cys Arg Asp Glu Leu Thr
                    405                 410                 415

Lys Asn Gln Val Ser Leu Trp Cys Leu Val Lys Gly Phe Tyr Pro Ser
                420                 425                 430

Asp Ile Ala Val Glu Trp Glu Ser Asn Gly Gln Pro Glu Asn Asn Tyr
                435                 440                 445

Lys Thr Thr Pro Pro Val Leu Asp Ser Asp Gly Ser Phe Phe Leu Tyr
            450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys
            500

<210> SEQ ID NO 191
<211> LENGTH: 1512
<212> TYPE: DNA
<213> ORGANISM: Artificial
<220> FEATURE:
<223> OTHER INFORMATION: Full-length nucleotide sequence of NYC-0014-
      HC-k

<400> SEQUENCE: 191
atgaagcacc tgtggttctt tctgctgctg gtggccgctc ctagatgggt gctgtctggc      60
gaagtgcagc tggtggaatc tggtggcgga gttgttcagc ctggcggctc tctgagactg     120
agctgtgaag cctccggctt catcttcgac gactacgcca tgcactgggt ccgacaggca     180
cctggcaaag ccttgaatg gtgtccctg atctctggcg acggcgacat catctactac       240
gccgactctg tgaagggcag attcaccatc agccgggaca cagcaagaa cagcctgtac      300 ctgcagatga actccctgat catcgaggac acagccctgt actactgcgc caaggattgg    360
gtgttcggcg tcgtgatgac ccactactgg tacttcggcc tggatgtgtg gggccaggga    420
accacagtga cagtttctag cggaggcgga ggaagtggcg gcggaggatc tggcggtggt    480
ggttctgata tccagatgac acagagcccc agcagcctgt ctgcctctga aggcgacaga    540
gtgaccatca cctgtagagc cagccagagc atcagcacct acctgaactg gtatcagcag    600
aagcccggca aggcccctaa gctgctgatc tatggtgcct ccagtctgca gagcggcgtg    660
ccaagcagat ttctggcag cggctctggc accgacttca ccctgaccat atctagcctg     720
cagcctgagg acttcgccac ctactactgc cagcagtcct acagcacccc tcctatcaca    780
tttggccagg gcaccaaggt ggaaatcaaa ggcggagaac caagagcgc agacaagacc     840 cacacctgtc ctccatgtcc tgctccagaa gctgcaggcg gccttccgt gtttctgttc     900 cctccaaagc ctaaggacac cctgatgatc agcggacac tgaagtgac ctgcgtggtg      960 gtggatgtgt cccacgagga tcccgaagtg aagttcaatt ggtacgtgga cggcgtggaa   1020
gtgcacaacg ccaagaccaa gcctagagag gaacagtaca acagcaccta cagagtggtg   1080
tctgtgctga cagtgctgca ccaggactgg ctgaacggca agagtacaa gtgcaaggtg    1140 tccaacaagg ccctgcctgc tcctatcgag aaaaccatca gcaaggccaa gggccagcct   1200
agggaacccc aggtttacac cctgcctcca tgcagggatg agctgaccaa gaaccaggtg   1260
tccctgtggt gcctggttaa gggcttctac ccctccgata tcgccgtgga atgggagagc   1320
aatggccagc cagagaacaa ctacaagaca ccccctcctg tgctggactc cgacggctca   1380
```

-continued

```
ttcttcctgt acagcaagct gaccgtggac aagagcagat ggcagcaggg caacgtgttc    1440
agctgcagcg tgatgcacga ggccctgcac aaccactaca cacagaagtc cctgtctctg    1500
agccccggca aa                                                        1512
```

<210> SEQ ID NO 192
<211> LENGTH: 504
<212> TYPE: PRT
<213> ORGANISM: Artificial
<220> FEATURE:
<223> OTHER INFORMATION: Full-length amino acid sequence of NYC-0014-HC-k

<400> SEQUENCE: 192

```
Met Lys His Leu Trp Phe Phe Leu Leu Val Ala Ala Pro Arg Trp
1               5                   10                  15

Val Leu Ser Gly Glu Val Gln Leu Val Glu Ser Gly Gly Val Val
                20                  25                  30

Gln Pro Gly Gly Ser Leu Arg Leu Ser Cys Glu Ala Ser Gly Phe Ile
                35                  40                  45

Phe Asp Asp Tyr Ala Met His Trp Val Arg Gln Ala Pro Gly Lys Gly
50                  55                  60

Leu Glu Trp Val Ser Leu Ile Ser Gly Asp Gly Asp Ile Ile Tyr Tyr
65                  70                  75                  80

Ala Asp Ser Val Lys Gly Arg Phe Thr Ile Ser Arg Asp Asn Ser Lys
                85                  90                  95

Asn Ser Leu Tyr Leu Gln Met Asn Ser Leu Ile Ile Glu Asp Thr Ala
                100                 105                 110

Leu Tyr Tyr Cys Ala Lys Asp Trp Val Phe Gly Val Val Met Thr His
            115                 120                 125

Tyr Trp Tyr Phe Gly Leu Asp Val Trp Gly Gln Gly Thr Thr Val Thr
130                 135                 140

Val Ser Ser Gly Gly Gly Gly Ser Gly Gly Gly Gly Ser Gly Gly Gly
145                 150                 155                 160

Gly Ser Asp Ile Gln Met Thr Gln Ser Pro Ser Ser Leu Ser Ala Ser
                165                 170                 175

Glu Gly Asp Arg Val Thr Ile Thr Cys Arg Ala Ser Gln Ser Ile Ser
            180                 185                 190

Thr Tyr Leu Asn Trp Tyr Gln Gln Lys Pro Gly Lys Ala Pro Lys Leu
        195                 200                 205

Leu Ile Tyr Gly Ala Ser Ser Leu Gln Ser Gly Val Pro Ser Arg Phe
210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Ser Tyr Ser Thr
                245                 250                 255

Pro Pro Ile Thr Phe Gly Gln Gly Thr Lys Val Glu Ile Lys Gly Gly
            260                 265                 270

Glu Pro Lys Ser Ala Asp Lys Thr His Thr Cys Pro Pro Cys Pro Ala
        275                 280                 285

Pro Glu Ala Ala Gly Gly Pro Ser Val Phe Leu Phe Pro Pro Lys Pro
290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
```

```
                    325                 330                 335
Asp Gly Val Glu Val His Asn Ala Lys Thr Lys Pro Arg Glu Glu Gln
            340                 345                 350
Tyr Asn Ser Thr Tyr Arg Val Val Ser Val Leu Thr Val Leu His Gln
            355                 360                 365
Asp Trp Leu Asn Gly Lys Glu Tyr Lys Cys Lys Val Ser Asn Lys Ala
    370                 375                 380
Leu Pro Ala Pro Ile Glu Lys Thr Ile Ser Lys Ala Lys Gly Gln Pro
385                 390                 395                 400
Arg Glu Pro Gln Val Tyr Thr Leu Pro Pro Cys Arg Asp Glu Leu Thr
                405                 410                 415
Lys Asn Gln Val Ser Leu Trp Cys Leu Val Lys Gly Phe Tyr Pro Ser
            420                 425                 430
Asp Ile Ala Val Glu Trp Glu Ser Asn Gly Gln Pro Glu Asn Asn Tyr
            435                 440                 445
Lys Thr Thr Pro Pro Val Leu Asp Ser Asp Gly Ser Phe Phe Leu Tyr
    450                 455                 460
Ser Lys Leu Thr Val Asp Lys Ser Arg Trp Gln Gln Gly Asn Val Phe
465                 470                 475                 480
Ser Cys Ser Val Met His Glu Ala Leu His Asn His Tyr Thr Gln Lys
                485                 490                 495
Ser Leu Ser Leu Ser Pro Gly Lys
            500

<210> SEQ ID NO 193
<211> LENGTH: 1509
<212> TYPE: DNA
<213> ORGANISM: Artificial
<220> FEATURE:
<223> OTHER INFORMATION: Full-length nucleotide sequence of NYC-0015-
      HC-k

<400> SEQUENCE: 193
atgaagcacc tgtggttctt tctgctgctg gtggccgctc tagatgggt gctgtctggc    60 gaagtgcagc tggtggaatc tggtggcgga gttgttcagc ctggcggctc tctgagactg   120
tcttgtgccg ccagcggctt caccttcgac gattatgcca tgcactgggt ccgacaggcc   180
cctggcaaag acttgaatg gtgtccctg atctctggcg gaggcggcgg aacctactac    240
agcgattctg tgaagggcag attcaccatc agccgggaca ccagcaagga cagcctgtac   300
ctgcagatga acagcctgcg gaccgaggac acagccctgt actactgcgc caaggacatg   360
gtgttcggcg tggtcacccc ttactactac ttcgccctgg atgtgtgggg ccagggcaca   420
acagtgacag tctcttctgg cggcggagga agcggaggcg aggatccgg tggtggtgga   480 tctgacatcc agatgacaca gagccccagc agcctgtctg cctctgtggg agacagagtg   540
accatcacct gtagagccag ccagagcatc aacagctacc tgaactgta tcagcagaag   600 cccggcaagg cccctaagct gctgatctat gctgcctcca gtctgcagag cggcgtgcca   660
agcagatttt ctggcagcgg ctctggcacc gacttcaccc tgaccatatc agcctgcag   720 cctgaggact cgccaccta ctactgccag cagagctaca cgcccctcc tatcacattt    780 ggccagggaa ccagactgga aatcaaaggc ggagaaccca agagcgcaga caagacccac   840
acctgtcctc catgtcctgc tccagaagct gcaggcggcc cttccgtgtt tctgttccct   900
ccaaagccta aggacaccct gatgatcagc cggacacctg aagtgacctg cgtggtggtg   960
gatgtgtccc acgaggatcc cgaagtgaag ttcaattggt acgtggacgg cgtggaagtg  1020
```

-continued

```
cacaacgcca agaccaagcc tagagaggaa cagtacaaca gcacctacag agtggtgtct    1080
gtgctgacag tgctgcacca ggactggctg aacggcaaag agtacaagtg caaggtgtcc    1140
aacaaggccc tgcctgctcc tatcgagaaa accatcagca aggccaaggg ccagcctagg    1200 gaacccagg tttacaccct gcctccatgc agggatgagc tgaccaagaa ccaggtgtcc    1260
ctgtggtgcc tggttaaggg cttctacccc tccgatatcg ccgtggaatg ggagagcaat    1320
ggccagccag agaacaacta caagacaacc cctcctgtgc tggactccga cggctcattc    1380
ttcctgtaca gcaagctgac cgtggacaag agcagatggc agcagggcaa cgtgttcagc    1440
tgcagcgtga tgcacgaggc cctgcacaac cactacacac agaagtccct gtctctgagc    1500
cccggcaaa                                                            1509
```

<210> SEQ ID NO 194
<211> LENGTH: 503
<212> TYPE: PRT
<213> ORGANISM: Artificial
<220> FEATURE:
<223> OTHER INFORMATION: Full-length amino acid sequence of NYC-0015-HC-k

<400> SEQUENCE: 194

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Val Val
            20                  25                  30

Gln Pro Gly Gly Ser Leu Arg Leu Ser Cys Ala Ala Ser Gly Phe Thr
        35                  40                  45

Phe Asp Asp Tyr Ala Met His Trp Val Arg Gln Ala Pro Gly Lys Gly
    50                  55                  60

Leu Glu Trp Val Ser Leu Ile Ser Gly Gly Gly Gly Thr Tyr Tyr
65                  70                  75                  80

Ser Asp Ser Val Lys Gly Arg Phe Thr Ile Ser Arg Asp Thr Ser Lys
                85                  90                  95

Asp Ser Leu Tyr Leu Gln Met Asn Ser Leu Arg Thr Glu Asp Thr Ala
            100                 105                 110

Leu Tyr Tyr Cys Ala Lys Asp Met Val Phe Gly Val Val Thr Pro Tyr
        115                 120                 125

Tyr Tyr Phe Ala Leu Asp Val Trp Gly Gln Gly Thr Thr Val Thr Val
    130                 135                 140

Ser Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                165                 170                 175

Gly Asp Arg Val Thr Ile Thr Cys Arg Ala Ser Gln Ser Ile Asn Ser
            180                 185                 190

Tyr Leu Asn Trp Tyr Gln Gln Lys Pro Gly Lys Ala Pro Lys Leu Leu
        195                 200                 205

Ile Tyr Ala Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Ser Tyr Ser Ala Pro
                245                 250                 255

Pro Ile Thr Phe Gly Gln Gly Thr Arg Leu Glu Ile Lys Gly Gly Glu
```

```
            260                 265                 270
Pro Lys Ser Ala Asp Lys Thr His Thr Cys Pro Pro Cys Pro Ala Pro
                275                 280                 285

Glu Ala Ala Gly Gly Pro Ser Val Phe Leu Phe Pro Pro Lys Pro Lys
            290                 295                 300

Asp Thr Leu Met Ile Ser Arg Thr Pro Glu Val Thr Cys Val Val Val
305                 310                 315                 320

Asp Val Ser His Glu Asp Pro Glu Val Lys Phe Asn Trp Tyr Val Asp
                325                 330                 335

Gly Val Glu Val His Asn Ala Lys Thr Lys Pro Arg Glu Glu Gln Tyr
            340                 345                 350

Asn Ser Thr Tyr Arg Val Val Ser Val Leu Thr Val Leu His Gln Asp
                355                 360                 365

Trp Leu Asn Gly Lys Glu Tyr Lys Cys Lys Val Ser Asn Lys Ala Leu
            370                 375                 380

Pro Ala Pro Ile Glu Lys Thr Ile Ser Lys Ala Lys Gly Gln Pro Arg
385                 390                 395                 400

Glu Pro Gln Val Tyr Thr Leu Pro Pro Cys Arg Asp Glu Leu Thr Lys
                405                 410                 415

Asn Gln Val Ser Leu Trp Cys Leu Val Lys Gly Phe Tyr Pro Ser Asp
            420                 425                 430

Ile Ala Val Glu Trp Glu Ser Asn Gly Gln Pro Glu Asn Asn Tyr Lys
            435                 440                 445

Thr Thr Pro Pro Val Leu Asp Ser Asp Gly Ser Phe Phe Leu Tyr Ser
450                 455                 460

Lys Leu Thr Val Asp Lys Ser Arg Trp Gln Gln Gly Asn Val Phe Ser
465                 470                 475                 480

Cys Ser Val Met His Glu Ala Leu His Asn His Tyr Thr Gln Lys Ser
                485                 490                 495

Leu Ser Leu Ser Pro Gly Lys
                500

<210> SEQ ID NO 195
<211> LENGTH: 1512
<212> TYPE: DNA
<213> ORGANISM: Artificial
<220> FEATURE:
<223> OTHER INFORMATION: Full-length nucleotide sequence of NYC-0016-
      HC-k

<400> SEQUENCE: 195
atgaagcacc tgtggttctt tctgctgctg gtggccgctc ctagatgggt gctgtctggc      60
gaagtgcagc tggtggaatc tggtggcgga gttgttcagc ctggcggctc tctgagactg     120
agctgtgctg tgtccggctt caccttcgac gactacgcca tgcactgggt ccgacaggca     180
cctggcaaag gccttgaatg ggtgtccctg atcagcggag atggcggcag cacacactac     240
gccgattctg tgaagggcag attcaccatc agccgggaca cagcaagaa cagcctgtac      300 ctgcagatga actccctgcg gacaggcgac acagccctgt actactgcgc caaggacatg     360
atcttcgccg tggtcatcac cgactaccac tactacggca tggacgtgtg gggccaggga     420
accacagtga cagtttctag cggaggcgga ggaagtggcg gcggaggatc tggcggtggt     480
ggttctgata tccagatgac acagagcccc agcagcctgt ctgcctctgt gggagacaga     540
gtgaccatca cctgtagagc cagccagagc atcagcagct acctgaactg gtatcagcag     600
aagcccggca aggcccctaa actgctgatc tatgccgcct ccagtctgca gagcggagtg     660
```

```
cctagcagat tttctggcag cggctccggc accgatttca ccctgaccat atctagcctg    720
cagcctgagg acttcgccac ctactactgc cagcagagct acagcacccc tcctatcacc    780
tttggccagg gcaccagact ggaaatcaaa ggcggagaac ccaagagcgc agacaagacc    840
cacacctgtc ctccatgtcc tgctccagaa gctgcaggcg cccttccgt gtttctgttc     900 cctccaaagc ctaaggacac cctgatgatc agccggacac ctgaagtgac ctgcgtggtg    960
gtggatgtgt cccacgagga tcccgaagtg aagttcaatt ggtacgtgga cggcgtggaa   1020
gtgcacaacg ccaagaccaa gcctagagag gaacagtaca acagcaccta cagagtggtg   1080
tctgtgctga cagtgctgca ccaggactgg ctgaacggca agagtacaa gtgcaaggtg    1140 tccaacaagg ccctgcctgc tcctatcgag aaaaccatca gcaaggccaa gggccagcct   1200
agggaacccc aggtttacac cctgcctcca tgcaggatg agctgaccaa gaaccaggtg    1260
tccctgtggt gcctggttaa gggcttctac ccctccgata tcgccgtgga atgggagagc   1320
aatggccagc cagagaacaa ctacaagaca ccccctcctg tgctggactc cgacggctca   1380
ttcttcctgt acagcaagct gaccgtggac aagagcagat ggcagcaggg caacgtgttc   1440
agctgcagcg tgatgcacga ggccctgcac aaccactaca cacagaagtc cctgtctctg   1500
agccccggca aa                                                       1512
```

<210> SEQ ID NO 196
<211> LENGTH: 504
<212> TYPE: PRT
<213> ORGANISM: Artificial
<220> FEATURE:
<223> OTHER INFORMATION: Full-length amino acid sequence of NYC-0016-HC-k

<400> SEQUENCE: 196

```
Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Val Val
            20                  25                  30

Gln Pro Gly Gly Ser Leu Arg Leu Ser Cys Ala Val Ser Gly Phe Thr
        35                  40                  45

Phe Asp Asp Tyr Ala Met His Trp Val Arg Gln Ala Pro Gly Lys Gly
    50                  55                  60

Leu Glu Trp Val Ser Leu Ile Ser Gly Asp Gly Ser Thr His Tyr
65                  70                  75                  80

Ala Asp Ser Val Lys Gly Arg Phe Thr Ile Ser Arg Asp Asn Ser Lys
                85                  90                  95

Asn Ser Leu Tyr Leu Gln Met Asn Ser Leu Arg Thr Gly Asp Thr Ala
            100                 105                 110

Leu Tyr Tyr Cys Ala Lys Asp Met Ile Phe Ala Val Val Ile Thr Asp
        115                 120                 125

Tyr His Tyr Tyr Gly Met Asp Val Trp Gly Gln Gly Thr Thr Val Thr
    130                 135                 140

Val Ser Ser Gly Gly Gly Gly Ser Gly Gly Gly Gly Ser Gly Gly Gly
145                 150                 155                 160

Gly Ser Asp Ile Gln Met Thr Gln Ser Pro Ser Ser Leu Ser Ala Ser
                165                 170                 175

Val Gly Asp Arg Val Thr Ile Thr Cys Arg Ala Ser Gln Ser Ile Ser
            180                 185                 190

Ser Tyr Leu Asn Trp Tyr Gln Gln Lys Pro Gly Lys Ala Pro Lys Leu
```

```
                195                 200                 205
Leu Ile Tyr Ala Ala Ser Ser Leu Gln Ser Gly Val Pro Ser Arg Phe
210                 215                 220

Ser Gly Ser Gly Ser Gly Thr Asp Phe Thr Leu Thr Ile Ser Ser Leu
225                 230                 235                 240

Gln Pro Glu Asp Phe Ala Thr Tyr Tyr Cys Gln Gln Ser Tyr Ser Thr
                245                 250                 255

Pro Pro Ile Thr Phe Gly Gln Gly Thr Arg Leu Glu Ile Lys Gly Gly
                260                 265                 270

Glu Pro Lys Ser Ala Asp Lys Thr His Thr Cys Pro Pro Cys Pro Ala
                275                 280                 285

Pro Glu Ala Ala Gly Gly Pro Ser Val Phe Leu Phe Pro Pro Lys Pro
                290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
                340                 345                 350

Tyr Asn Ser Thr Tyr Arg Val Val Ser Val Leu Thr Val Leu His Gln
                355                 360                 365

Asp Trp Leu Asn Gly Lys Glu Tyr Lys Cys Lys Val Ser Asn Lys Ala
370                 375                 380

Leu Pro Ala Pro Ile Glu Lys Thr Ile Ser Lys Ala Lys Gly Gln Pro
385                 390                 395                 400

Arg Glu Pro Gln Val Tyr Thr Leu Pro Pro Cys Arg Asp Glu Leu Thr
                405                 410                 415

Lys Asn Gln Val Ser Leu Trp Cys Leu Val Lys Gly Phe Tyr Pro Ser
                420                 425                 430

Asp Ile Ala Val Glu Trp Glu Ser Asn Gly Gln Pro Glu Asn Asn Tyr
                435                 440                 445

Lys Thr Thr Pro Pro Val Leu Asp Ser Asp Gly Ser Phe Phe Leu Tyr
450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys
                500

<210> SEQ ID NO 197
<211> LENGTH: 719
<212> TYPE: PRT
<213> ORGANISM: Artificial
<220> FEATURE:
<223> OTHER INFORMATION: Full-length amino acid sequence of NYZ-1007-HC2

<400> SEQUENCE: 197

Met Lys His Leu Trp Phe Phe Leu Leu Leu Val Ala Ala Pro Arg Trp
1               5                   10                  15

Val Leu Ser Gly Glu Val Gln Leu Val Glu Ser Gly Gly Gly Leu Val
                20                  25                  30

Gln Pro Gly Gly Ser Leu Arg Leu Ser Cys Ala Ala Ser Gly Phe Ser
                35                  40                  45

Ile Arg Ser Tyr Asp Ile His Trp Val Arg Gln Ala Pro Gly Lys Gly
```

-continued

```
                50                  55                  60
Leu Glu Trp Val Ala Thr Ile Ser Tyr Asp Gly Ser Gln Lys Tyr Tyr
 65                  70                  75                  80

Ala Asp Ser Val Lys Gly Arg Phe Thr Ile Ser Arg Asp Glu Ser Lys
                     85                  90                  95

Asn Thr Leu Tyr Leu Gln Met Asn Ser Leu Arg Ala Glu Asp Thr Ala
                100                 105                 110

Val Tyr His Cys Ala Arg Gly Ser Ser His Tyr Glu Ala Phe Asp
                115                 120                 125

Ile Trp Gly Gln Gly Thr Leu Val Thr Val Ser Ser Gly Gly Gly
130                 135                 140

Ser Gly Gly Gly Gly Ser Gly Gly Gly Gly Ser Gln Ser Val Leu Thr
145                 150                 155                 160

Gln Pro Pro Ser Ala Ser Gly Thr Pro Gly Gln Arg Val Thr Ile Ser
                165                 170                 175

Cys Ser Gly Ser Ser Ser Asn Ile Gly Asn Trp Tyr Val Ser Trp Tyr
                180                 185                 190

Gln Gln Leu Pro Gly Thr Ala Pro Lys Leu Leu Ile Tyr Asp Asn Asn
                195                 200                 205

Lys Arg Pro Ser Gly Val Pro Asp Arg Phe Ser Gly Ser Lys Ser Gly
210                 215                 220

Thr Ser Ala Ser Leu Ala Ile Ser Gly Leu Gln Ser Glu Asp Glu Ala
225                 230                 235                 240

Asp Tyr Tyr Cys Gly Thr Trp Asp Ser Ser Leu Ser Ala Pro Trp Val
                245                 250                 255

Phe Gly Gly Gly Thr Lys Leu Thr Val Leu Gly Gly Gly Ser Glu
                260                 265                 270

Val Gln Leu Val Glu Ser Gly Gly Gly Leu Val Gln Pro Gly Gly Ser
                275                 280                 285

Leu Arg Leu Ser Cys Ala Ala Ser Gly Val Thr Phe Asn Tyr Tyr Gly
                290                 295                 300

Met Ser Trp Ile Arg Gln Ala Pro Gly Lys Gly Leu Glu Trp Val Ala
305                 310                 315                 320

Ser Ile Thr Arg Ser Gly Gly Arg Ile Tyr Tyr Pro Asp Ser Val Lys
                325                 330                 335

Gly Arg Phe Thr Ile Ser Arg Glu Asn Thr Gln Lys Thr Leu Tyr Leu
                340                 345                 350

Gln Met Asn Ser Leu Arg Ala Glu Asp Thr Ala Val Tyr Tyr Cys Thr
                355                 360                 365

Leu Asp Gly Arg Asp Gly Trp Val Ala Tyr Trp Gly Gln Gly Thr Leu
370                 375                 380

Val Thr Val Ser Ser Ala Ser Thr Lys Gly Pro Ser Val Phe Pro Leu
385                 390                 395                 400

Ala Pro Ser Ser Lys Ser Thr Ser Gly Gly Thr Ala Ala Leu Gly Cys
                405                 410                 415

Leu Val Lys Asp Tyr Phe Pro Glu Pro Val Thr Val Ser Trp Asn Ser
                420                 425                 430

Gly Ala Leu Thr Ser Gly Val His Thr Phe Pro Ala Val Leu Gln Ser
                435                 440                 445

Ser Gly Leu Tyr Ser Leu Ser Ser Val Val Thr Val Pro Ser Ser Ser
                450                 455                 460

Leu Gly Thr Gln Thr Tyr Ile Cys Asn Val Asn His Lys Pro Ser Asn
465                 470                 475                 480
```

-continued

```
Thr Lys Val Asp Lys Arg Val Glu Pro Lys Ser Cys Asp Lys Thr His
                485                 490                 495
Thr Cys Pro Pro Cys Pro Ala Pro Glu Ala Ala Gly Gly Pro Ser Val
            500                 505                 510
Phe Leu Phe Pro Pro Lys Pro Lys Asp Thr Leu Met Ile Ser Arg Thr
        515                 520                 525
Pro Glu Val Thr Cys Val Val Val Ser Val Ser His Glu Asp Pro Glu
    530                 535                 540
Val Lys Phe Asn Trp Tyr Val Asp Gly Val Glu Val His Asn Ala Lys
545                 550                 555                 560
Thr Lys Pro Arg Glu Glu Gln Tyr Asn Ser Thr Tyr Arg Val Val Ser
                565                 570                 575
Val Leu Thr Val Leu His Gln Asp Trp Leu Asn Gly Lys Glu Tyr Lys
            580                 585                 590
Cys Lys Val Ser Asn Lys Ala Leu Pro Ala Pro Ile Glu Lys Thr Ile
        595                 600                 605
Ser Lys Ala Lys Gly Gln Pro Arg Glu Pro Gln Val Tyr Val Tyr Pro
    610                 615                 620
Pro Ser Arg Asp Glu Leu Thr Lys Asn Gln Val Ser Leu Thr Cys Leu
625                 630                 635                 640
Val Lys Gly Phe Tyr Pro Ser Asp Ile Ala Val Glu Trp Glu Ser Asn
                645                 650                 655
Gly Gln Pro Glu Asn Asn Tyr Lys Thr Thr Pro Pro Val Leu Asp Ser
            660                 665                 670
Asp Gly Ser Phe Ala Leu Val Ser Lys Leu Thr Val Asp Lys Ser Arg
        675                 680                 685
Trp Gln Gln Gly Asn Val Phe Ser Cys Ser Val Met His Glu Ala Leu
    690                 695                 700
His Asn His Tyr Thr Gln Lys Ser Leu Ser Leu Ser Pro Gly Lys
705                 710                 715

<210> SEQ ID NO 198
<211> LENGTH: 719
<212> TYPE: PRT
<213> ORGANISM: Artificial
<220> FEATURE:
<223> OTHER INFORMATION: Full-length amino acid sequence of NYZ-1017-HC2

<400> SEQUENCE: 198

Met Lys His Leu Trp Phe Phe Leu Leu Leu Val Ala Ala Pro Arg Trp
1               5                   10                  15
Val Leu Ser Gly Gln Val Gln Leu Val Glu Ser Gly Gly Gly Val Val
            20                  25                  30
Gln Pro Gly Arg Ser Leu Arg Leu Ser Cys Ala Ala Ser Gly Phe Ser
        35                  40                  45
Ile Arg Ser Tyr Asp Met His Trp Val Arg Gln Ala Pro Gly Lys Gly
    50                  55                  60
Leu Glu Trp Val Ala Thr Ile Ser Tyr Asp Gly Ser Gln Lys Tyr Tyr
65                  70                  75                  80
Ala Asp Ser Val Lys Gly Arg Phe Thr Ile Ser Arg Asp Asn Ser Lys
                85                  90                  95
Asn Thr Leu Tyr Leu Gln Met Ser Ser Leu Arg Ala Glu Asp Thr Ala
            100                 105                 110
Val Tyr His Cys Ala Arg Gly Ser Ser Gly His Tyr Glu Ala Phe Asp
        115                 120                 125
```

```
Ile Trp Gly Gln Gly Thr Leu Val Thr Val Ser Ser Gly Gly Gly
        130             135             140
Ser Gly Gly Gly Gly Ser Gly Gly Gly Gly Ser Gln Ser Val Leu Thr
145                 150                 155                 160
Gln Pro Pro Ser Val Ser Ala Ala Pro Gly Gln Lys Val Thr Ile Ser
                165                 170                 175
Cys Ser Gly Ser Ser Asn Ile Gly Asn Trp Tyr Val Ser Trp Tyr
            180                 185                 190
Gln Gln Leu Pro Gly Thr Ala Pro Lys Leu Leu Ile Tyr Asp Asn Asn
        195                 200                 205
Lys Arg Pro Ser Gly Ile Pro Asp Arg Phe Ser Gly Ser Lys Ser Gly
210                 215                 220
Thr Ser Ala Thr Leu Gly Ile Thr Gly Leu Gln Thr Gly Asp Glu Ala
225                 230                 235                 240
Asp Tyr Tyr Cys Gly Thr Trp Asp Ser Ser Leu Ser Ala Pro Trp Val
            245                 250                 255
Phe Gly Gly Gly Thr Lys Val Thr Val Leu Gly Gly Gly Gly Ser Glu
                260                 265                 270
Val Gln Leu Val Glu Ser Gly Gly Gly Leu Val Gln Pro Gly Gly Ser
        275                 280                 285
Leu Arg Leu Ser Cys Ala Ala Ser Gly Val Thr Phe Asn Tyr Tyr Gly
        290                 295                 300
Met Ser Trp Ile Arg Gln Ala Pro Gly Lys Gly Leu Glu Trp Val Ala
305                 310                 315                 320
Ser Ile Thr Arg Ser Gly Gly Arg Ile Tyr Tyr Pro Asp Ser Val Lys
                325                 330                 335
Gly Arg Phe Thr Ile Ser Arg Glu Asn Thr Gln Lys Thr Leu Tyr Leu
            340                 345                 350
Gln Met Asn Ser Leu Arg Ala Glu Asp Thr Ala Val Tyr Tyr Cys Thr
        355                 360                 365
Leu Asp Gly Arg Asp Gly Trp Val Ala Tyr Trp Gly Gln Gly Thr Leu
        370                 375                 380
Val Thr Val Ser Ser Ala Ser Thr Lys Gly Pro Ser Val Phe Pro Leu
385                 390                 395                 400
Ala Pro Ser Ser Lys Ser Thr Ser Gly Gly Thr Ala Ala Leu Gly Cys
                405                 410                 415
Leu Val Lys Asp Tyr Phe Pro Glu Pro Val Thr Val Ser Trp Asn Ser
            420                 425                 430
Gly Ala Leu Thr Ser Gly Val His Thr Phe Pro Ala Val Leu Gln Ser
        435                 440                 445
Ser Gly Leu Tyr Ser Leu Ser Ser Val Val Thr Val Pro Ser Ser Ser
450                 455                 460
Leu Gly Thr Gln Thr Tyr Ile Cys Asn Val Asn His Lys Pro Ser Asn
465                 470                 475                 480
Thr Lys Val Asp Lys Arg Val Glu Pro Lys Ser Cys Asp Lys Thr His
                485                 490                 495
Thr Cys Pro Pro Cys Pro Ala Pro Glu Ala Ala Gly Gly Pro Ser Val
            500                 505                 510
Phe Leu Phe Pro Pro Lys Pro Lys Asp Thr Leu Met Ile Ser Arg Thr
        515                 520                 525
Pro Glu Val Thr Cys Val Val Val Ser Val Ser His Glu Asp Pro Glu
530                 535                 540
```

-continued

```
Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
            565                 570                 575

Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
        595                 600                 605

Ser Lys Ala Lys Gly Gln Pro Arg Glu Pro Gln Val Tyr Val Tyr Pro
        610                 615                 620

Pro Ser Arg Asp Glu Leu Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
            660                 665                 670

Asp Gly Ser Phe Ala Leu Val Ser Lys Leu Thr Val Asp Lys Ser Arg
        675                 680                 685

Trp Gln Gln Gly Asn Val Phe Ser Cys Ser Val Met His Glu Ala Leu
        690                 695                 700

His Asn His Tyr Thr Gln Lys Ser Leu Ser Leu Ser Pro Gly Lys
705                 710                 715
```